(12) United States Patent
Yamasaki et al.

(10) Patent No.: US 6,352,985 B1
(45) Date of Patent: *Mar. 5, 2002

(54) BENZIMIDAZOLE COMPOUNDS

(75) Inventors: Noritsugu Yamasaki, Hyogo; Takafumi Imoto, Ibaraki; Yoshiyuki Murai, Ibaraki; Takahiro Hiramura, Ibaraki; Teruo Oku, Osaka; Kouzou Sawada, Ibaraki, all of (JP)

(73) Assignee: Fujisawa Pharmaceutical Co., Ltd. (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/492,955

(22) Filed: Jan. 28, 2000

Related U.S. Application Data

(63) Continuation of application No. 09/091,997, filed as application No. PCT/JP96/03858 on Dec. 27, 1996, now Pat. No. 6,166,219.

(30) Foreign Application Priority Data

Dec. 28, 1995 (JP) .............................................. 7/343425
Oct. 8, 1996 (JP) .............................................. 8/287676

(51) Int. Cl.[7] ..................... C07D 235/08; C07D 235/10; C07D 401/06; C07D 405/06; A61K 31/415; A61K 31/44

(52) U.S. Cl. ................... 514/227.8; 514/94; 514/238.8; 514/255; 514/307; 514/314; 514/359; 514/363; 514/381; 514/382; 514/383; 514/394; 544/62; 544/110; 544/133; 544/139; 544/360; 544/366; 546/148; 546/152; 546/176; 546/199; 546/273.4; 548/62; 548/112; 548/127; 548/139; 548/253; 548/265.4; 548/304.4; 548/305.1; 548/306.4; 548/309.4; 548/310.4

(58) Field of Search ................................ 514/381, 255, 514/394, 382, 94, 227.8, 23.8, 307, 314, 359, 363, 383; 548/112, 253, 304.4, 62, 139, 306.4, 309.4, 305.1, 38.4, 265.4, 127; 544/360, 366, 133, 110; 546/199, 148, 176, 152, 273.4

(56) References Cited

U.S. PATENT DOCUMENTS

| | | |
|---|---|---|
| 3,152,142 A | 10/1964 | Moyle et al. |
| 4,179,505 A | 12/1979 | Raeymaekers et al. |
| 4,243,806 A | 1/1981 | Raeymaekers et al. |
| 4,243,813 A | 1/1981 | Paget et al. ............... 548/306 |
| 4,977,175 A | 12/1990 | Ohta et al. |
| 5,294,631 A | 3/1994 | Franz et al. |
| 5,328,919 A | 7/1994 | Naka et al. |
| 5,401,764 A | 3/1995 | Naka et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,703,110 A | 12/1997 | Naka et al. |
| 5,705,517 A | 1/1998 | Naka et al. |
| 6,166,912 A | 12/2000 | Yamasaki et al. ........ 548/309.4 |

FOREIGN PATENT DOCUMENTS

| | | |
|---|---|---|
| DE | 676 196 | 10/1950 |
| DE | 42 37 557 A1 | 5/1994 |
| EP | 0 260 744 A2 | 3/1988 |
| EP | 0 468 470 A1 | 1/1992 |
| EP | 0 696 583 A1 | 2/1996 |
| FR | 2291749 | 6/1976 |
| GB | 2 053 215 A | 2/1981 |
| GB | 2 177 393 A | 1/1987 |
| JP | 51-133267 | 11/1976 |
| JP | 5-222000 | 8/1993 |
| WO | WO 96/16644 | 6/1996 |

OTHER PUBLICATIONS

Garuti et al., "Synthesis and Antimycotic Activity of Some Benzyloxyimino Compounds", Pharmazie 42:378–381, 1987.

Haque et al., "Ambident Heterocyclic Reactivity:Alkylation of 4–Substituted and 2,4–Disubstituted Benzimidazoles", Aust. J. Chem. 47:1523–1535, 1994.

Primary Examiner—Floyd D. Higel
(74) Attorney, Agent, or Firm—Fish & Richardson PC

(57) ABSTRACT

A benzimidazole compound represented by the formula (I):

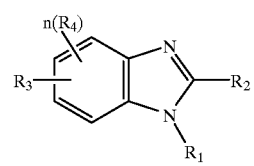

wherein $R_3$ is a carboxyl group, a esterified carboxyl group, an amidated carboxyl group, an amino group, an amido group, or a sulfonyl group, or their pharmaceutically acceptable salts. Because of their blood sugar-depressing effect or PDE5 inhibitory effect, these compounds or salts thereof are useful as medicines for treating impaired glucose tolerance, diabetes, diabetic complications, syndrome of insulin resistance, hyperlipidemia, atherosclerosis, cardiovascular disorders, hyperglycemia, or hypertension; or stenocardia, hypertension, pulmonary hypertension, congestive heart failure, glomerulopathy, tubulointerstitial disorders, renal failure, atherosclerosis, angiostenosis, distal angiopathy, cerebral apoplexy, chronic reversible obstructions, allergic rhinitis, urticaria, glaucoma, diseases characterized by enteromotility disorders, impotence, diabetic complications, nephritis, cancerous cachexia, or restenosis after PTCA.

19 Claims, 58 Drawing Sheets

FIG. 1
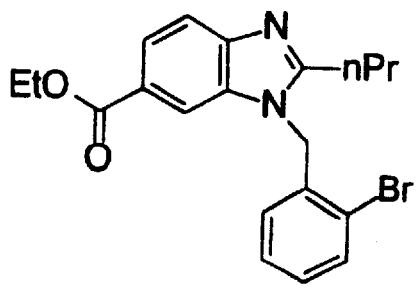
(42)
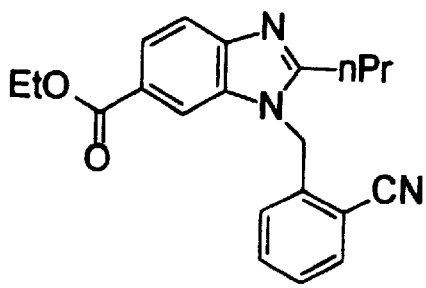
(43)
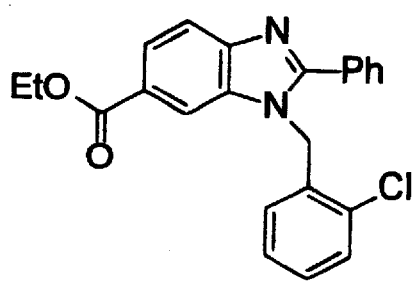
(44)
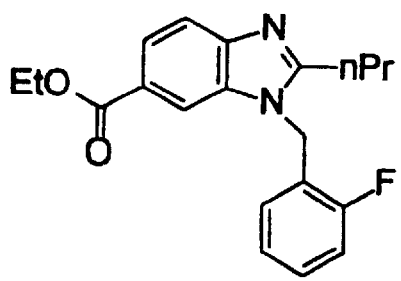
(45)
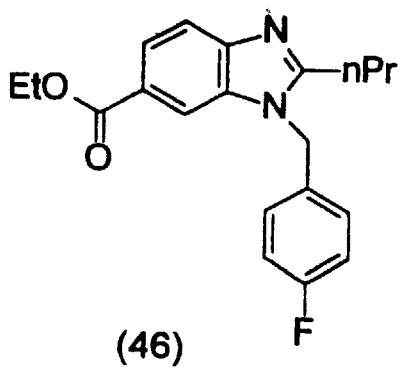
(46)
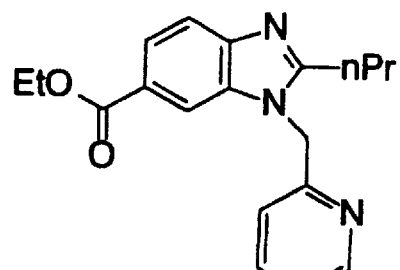
(47)

FIG. 2
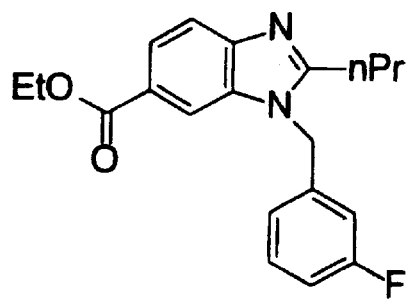
(48)
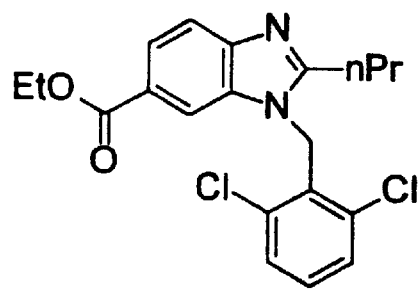
(49)
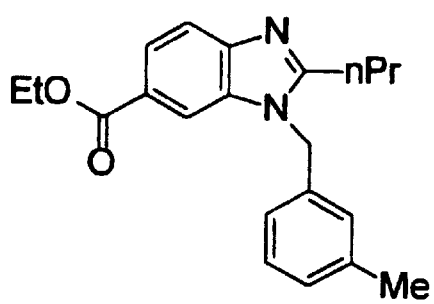
(50)
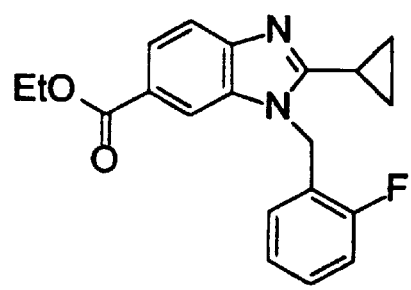
(51)
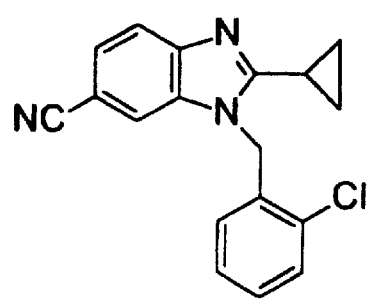
(52)
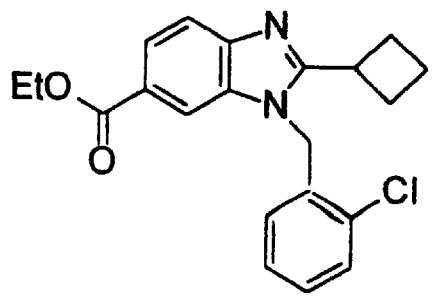
(53)

FIG. 3
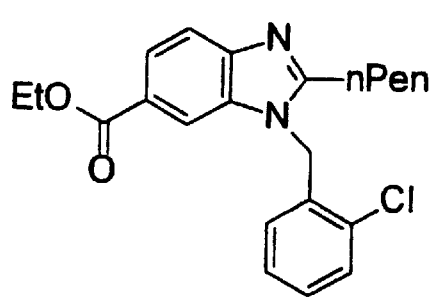
(54)
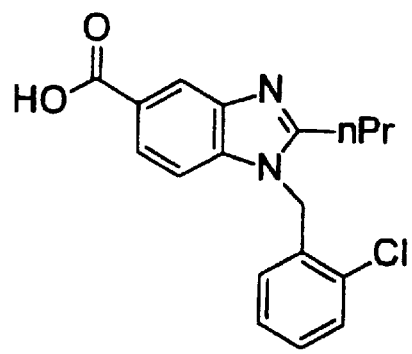
(55)
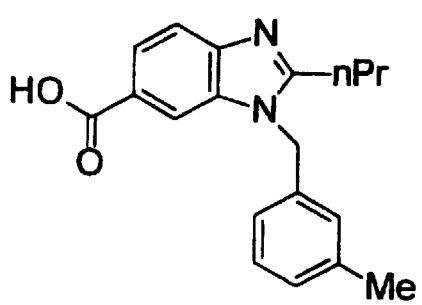
(56)
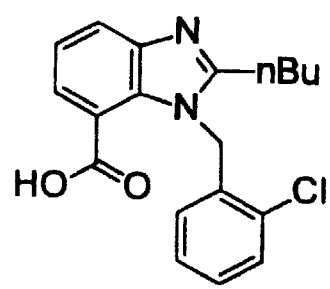
(57)
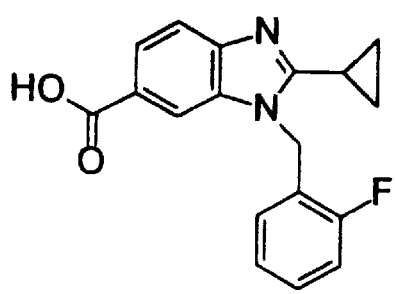
(58)
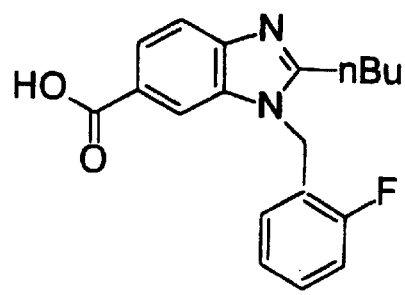
(59)

FIG. 4
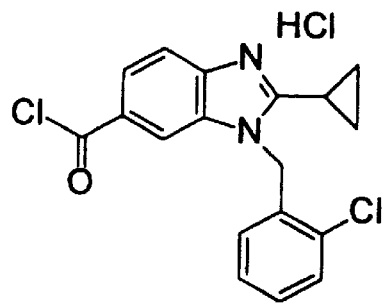
(60)
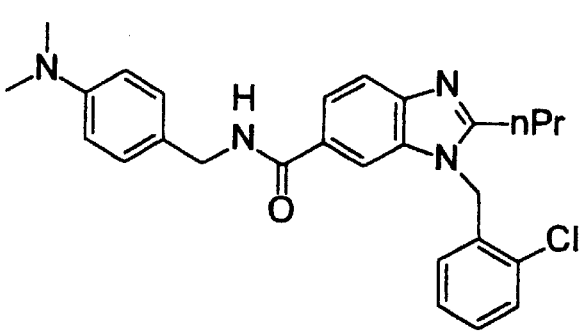
(61)
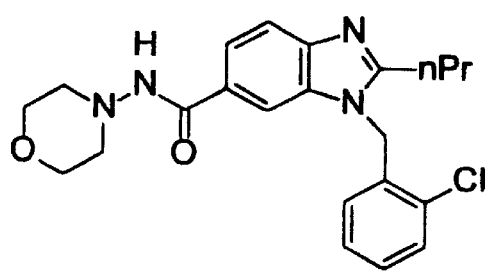
(62)
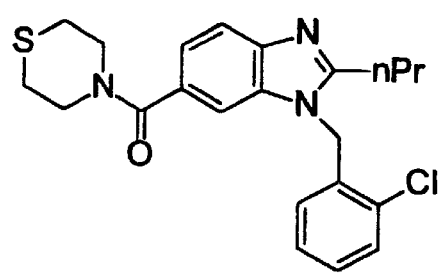
(63)
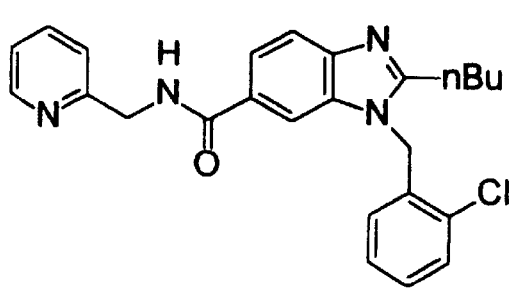
(64)
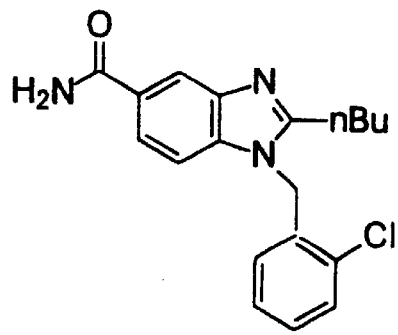
(65)

FIG. 5
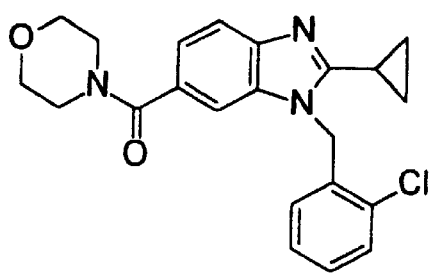
(66)
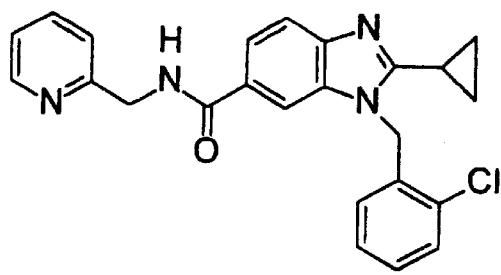
(67)
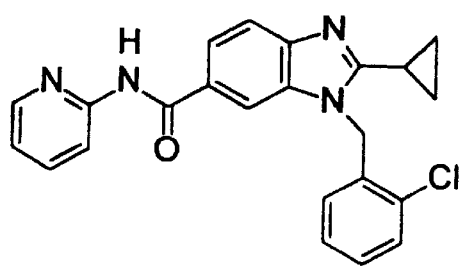
(68)
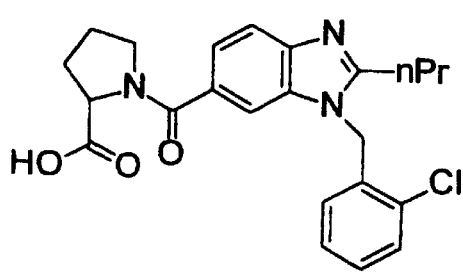
(69)
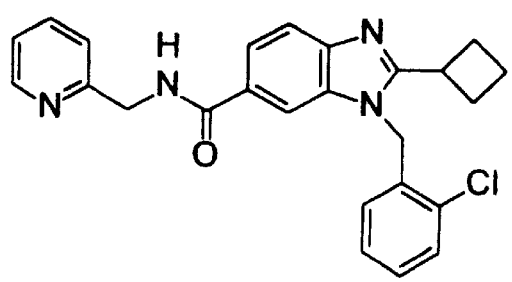
(70)
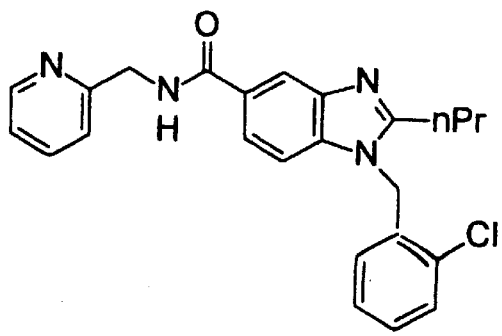
(71)

FIG. 6
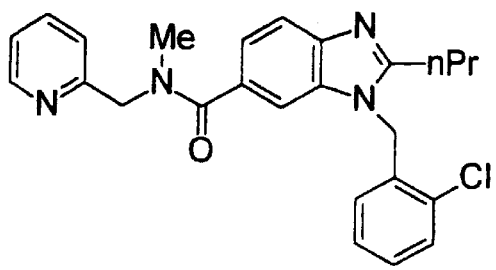
(72)
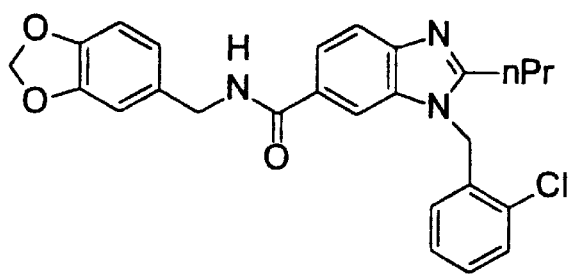
(73)
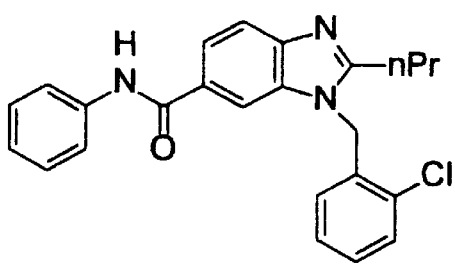
(74)
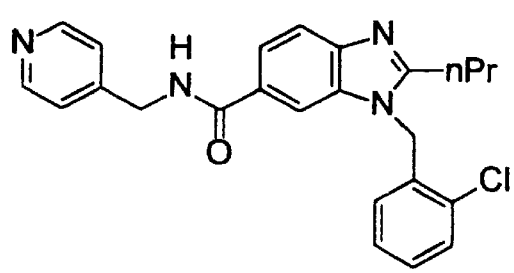
(75)
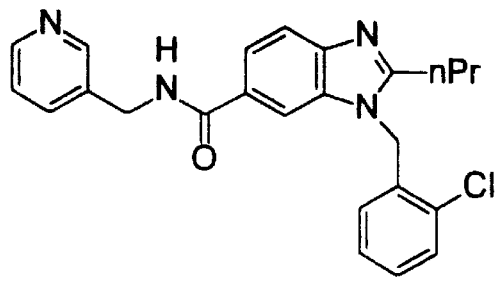
(76)
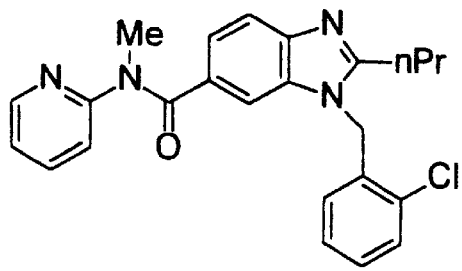
(77)

FIG. 7
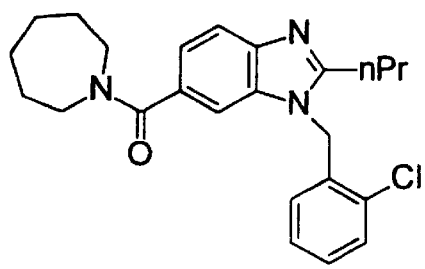
(78)
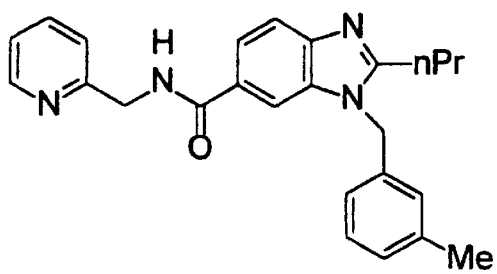
(79)
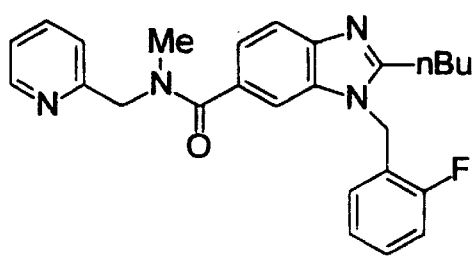
(80)
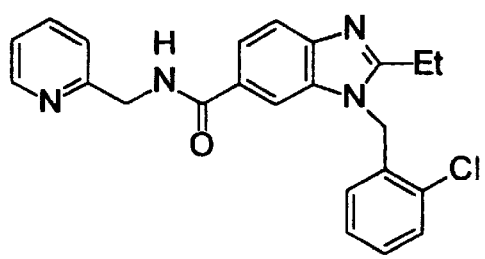
(81)
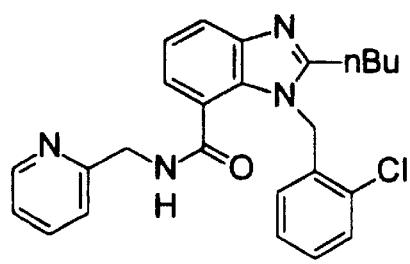
(82)
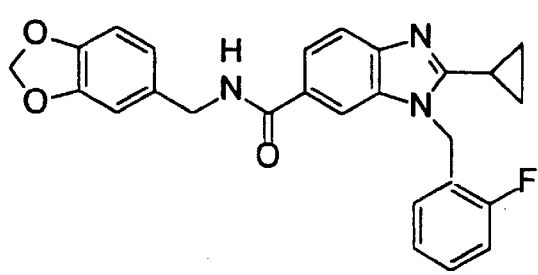
(83)

FIG. 8
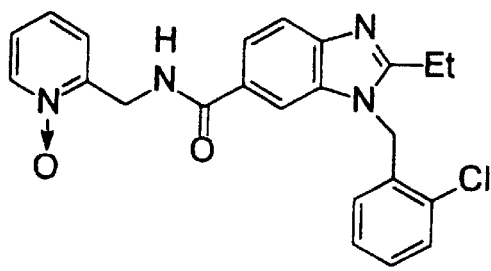
(84)
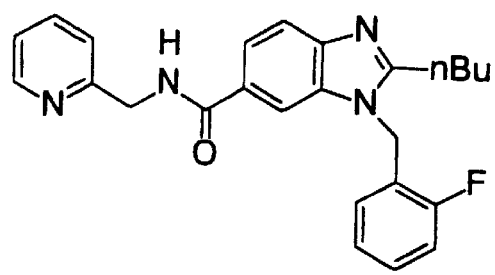
(85)
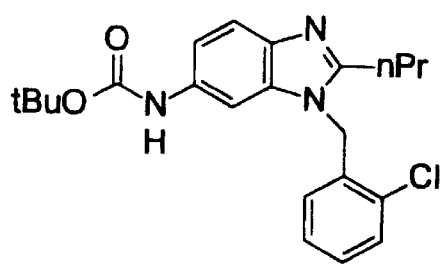
(86)
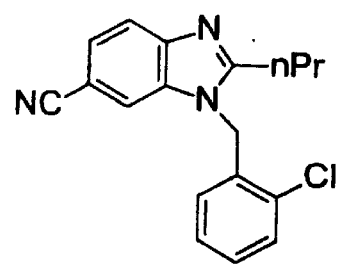
(87)
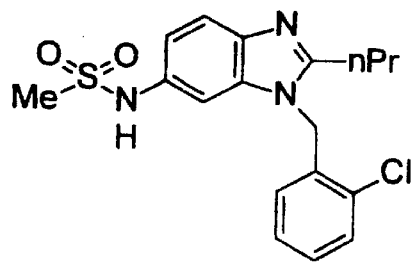
(88)
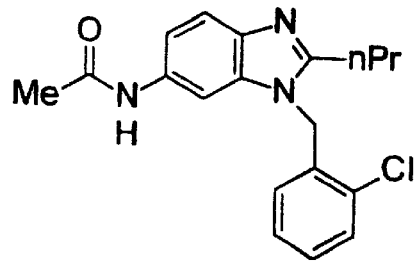
(89)

FIG. 9
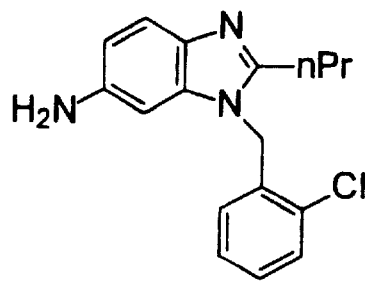
(90)
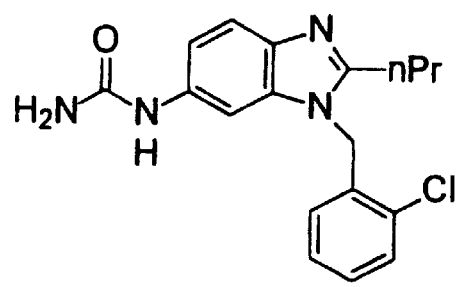
(91)
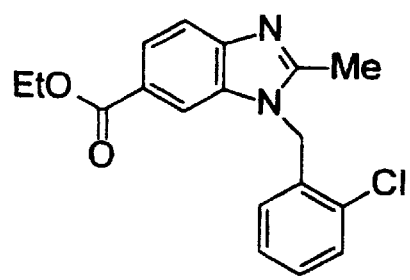
(92)
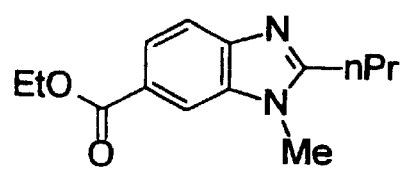
(93)
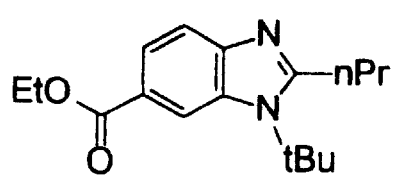
(94)
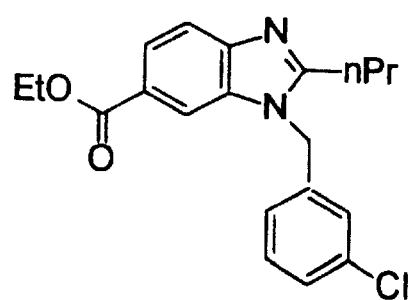
(95)

FIG. 10
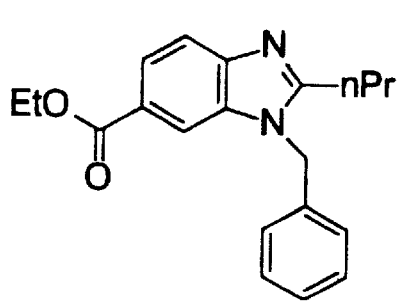
(96)
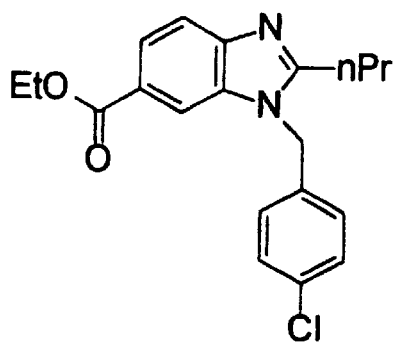
(97)
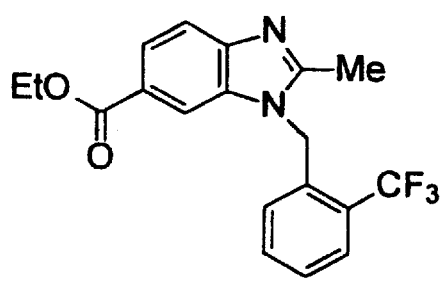
(98)
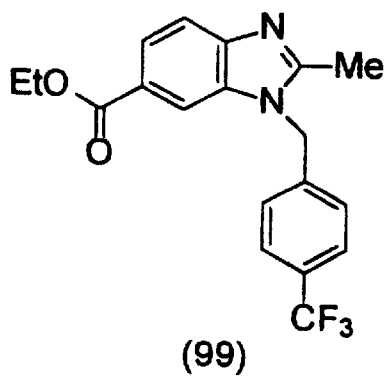
(99)
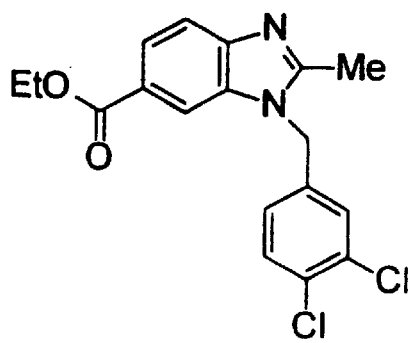
(100)
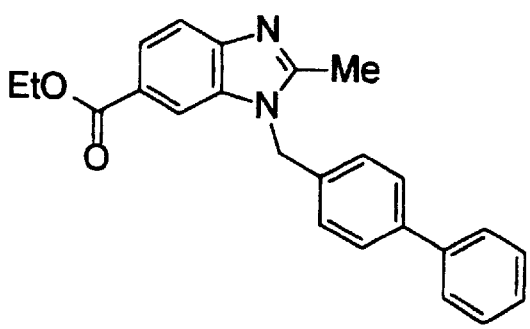
(101)

FIG. 11
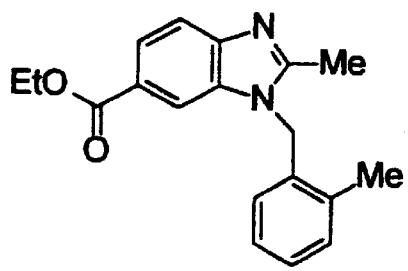
(102)
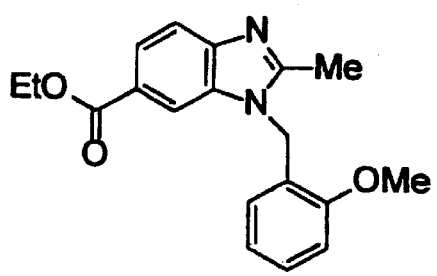
(103)
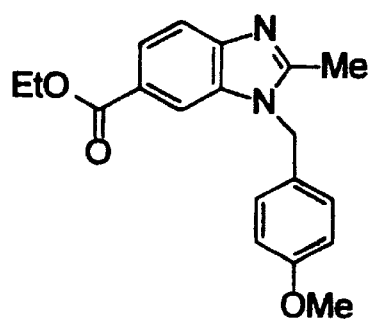
(104)
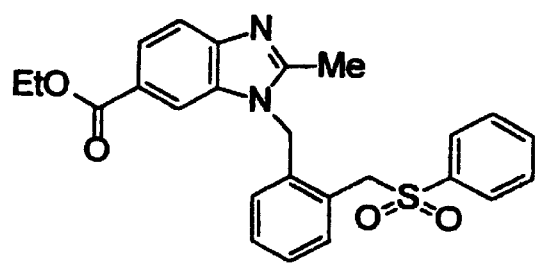
(105)
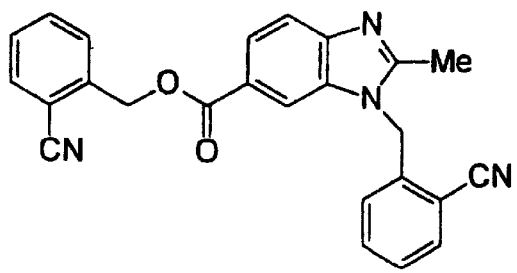
(106)
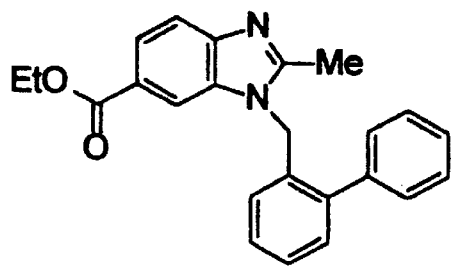
(107)

FIG. 12
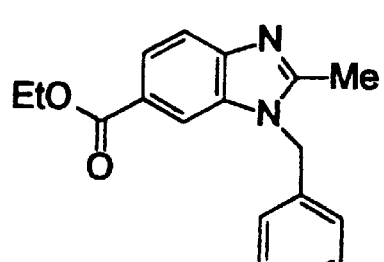
(108)
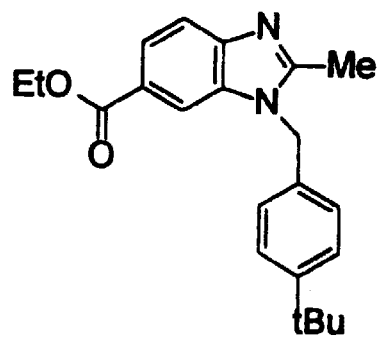
(109)
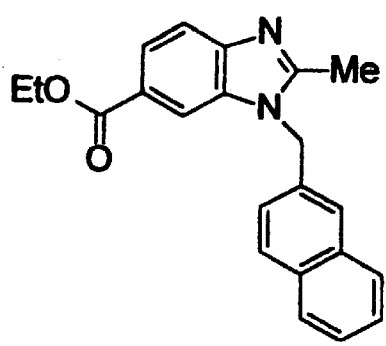
(110)
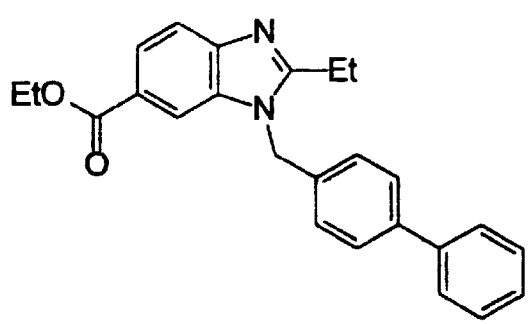
(111)
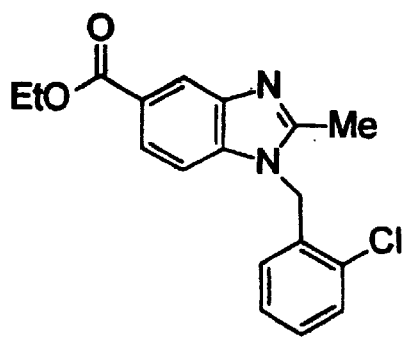
(112)
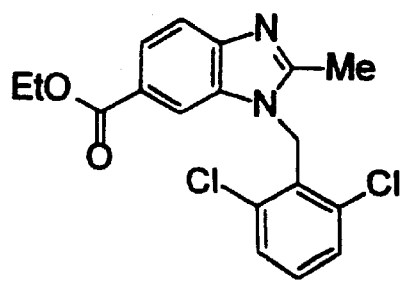
(113)

FIG. 13
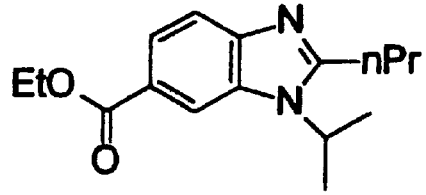
(114)
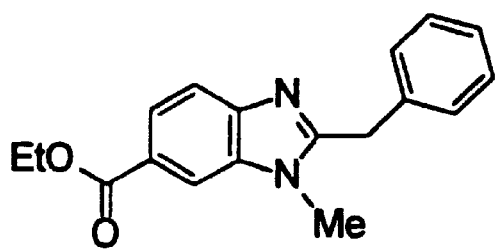
(115)
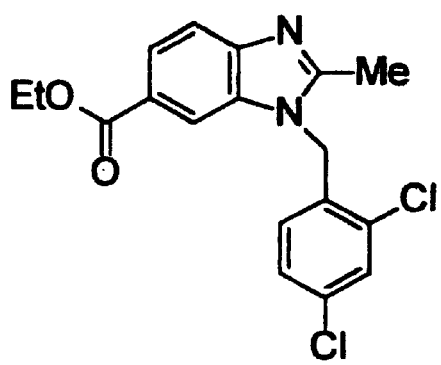
(116)
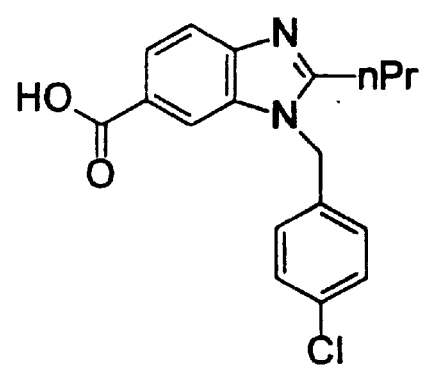
(117)
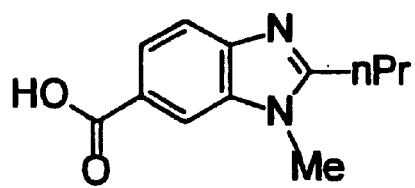
(118)
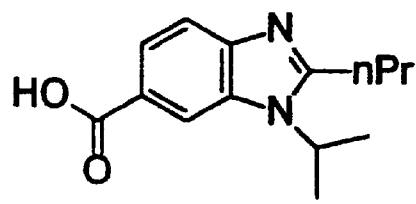
(119)

FIG. 14
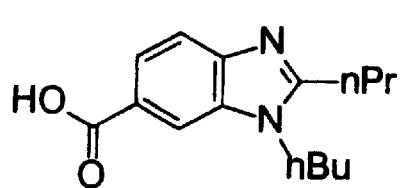
(120)
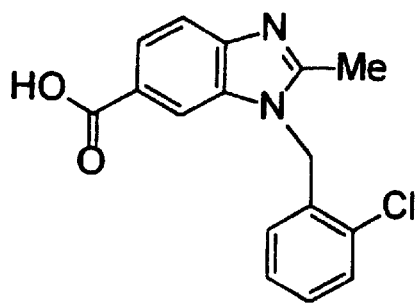
(121)
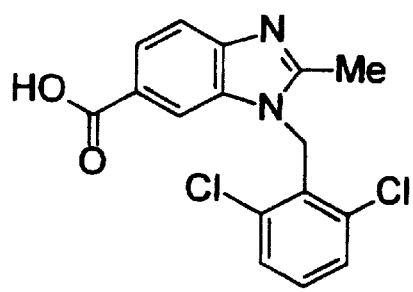
(122)
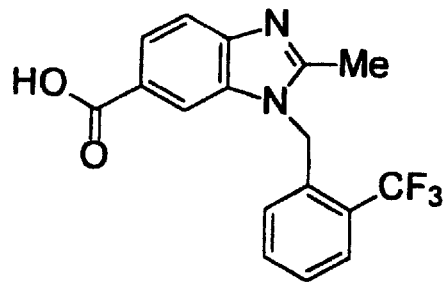
(123)
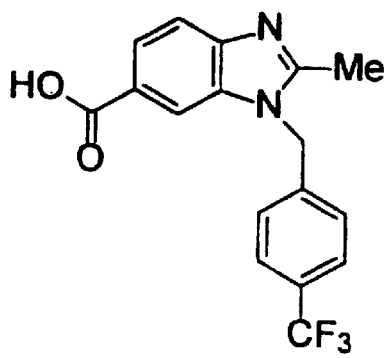
(124)
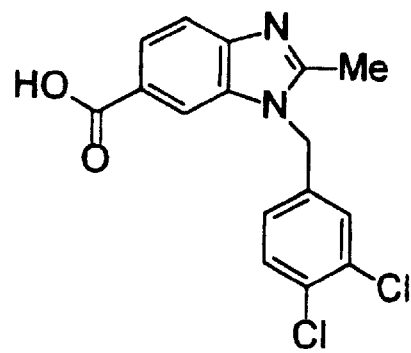
(125)

FIG. 15
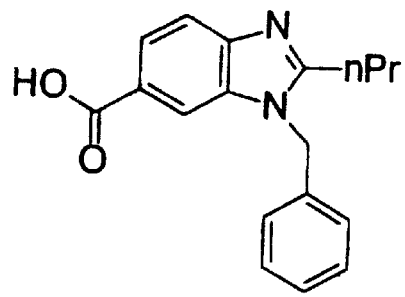
(126)
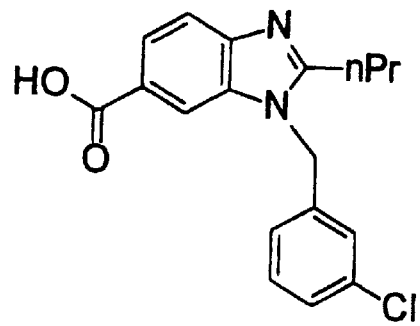
(127)
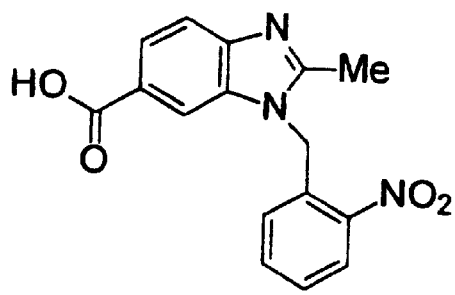
(128)
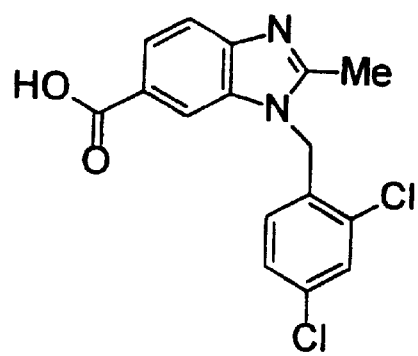
(129)
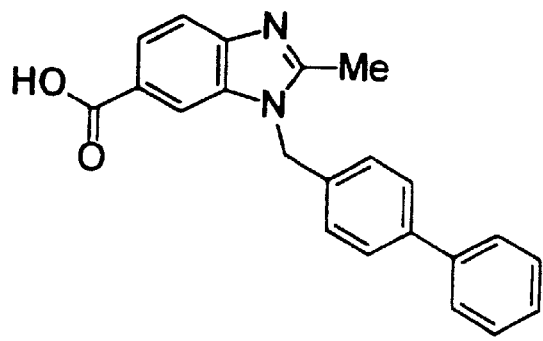
(130)
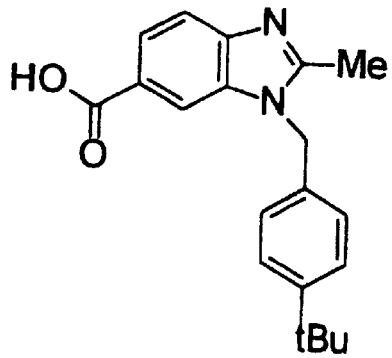
(131)

FIG. 16
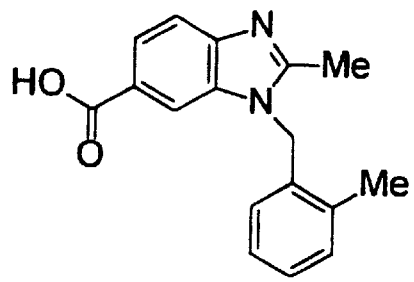
(132)
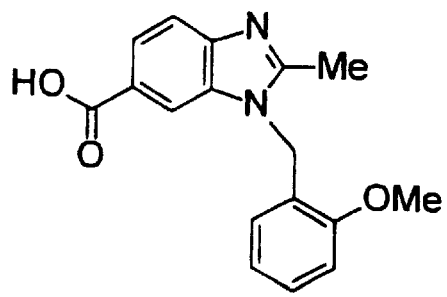
(133)
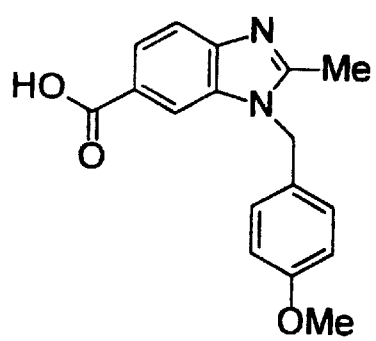
(134)
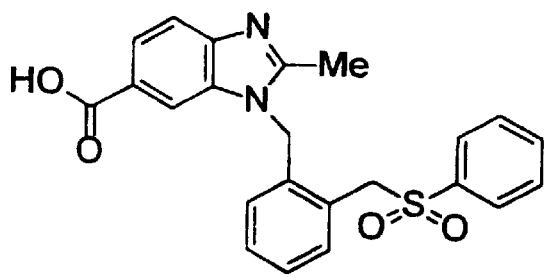
(135)
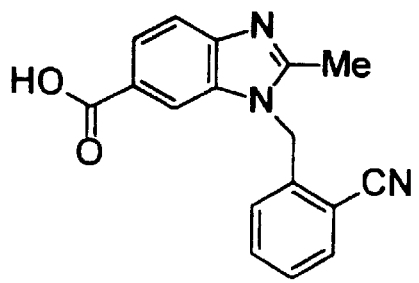
(136)
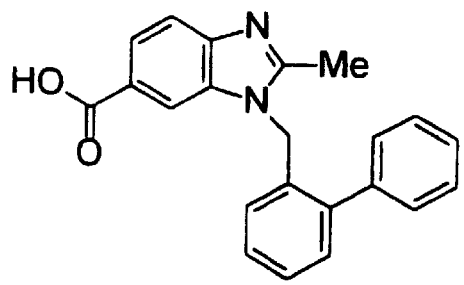
(137)

FIG. 17
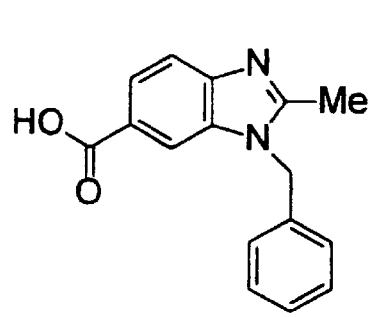
(138)
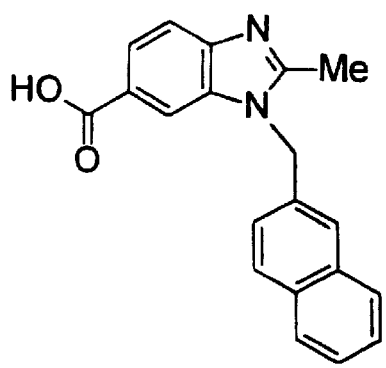
(139)
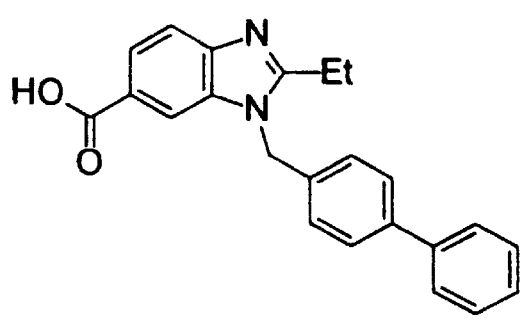
(140)
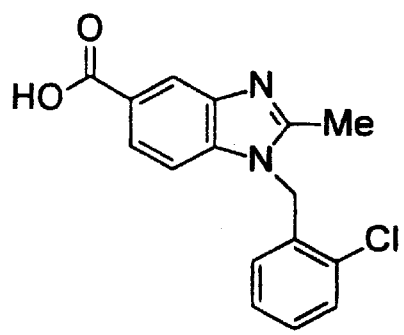
(141)
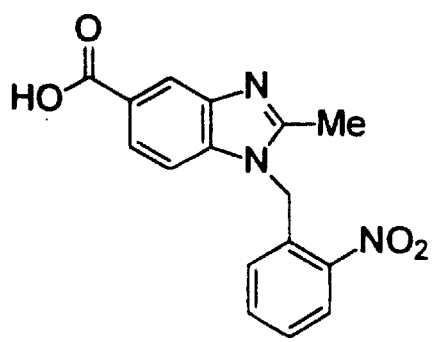
(142)
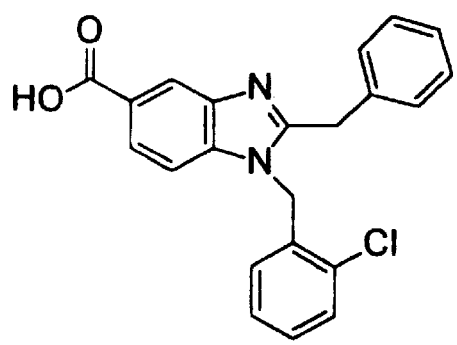
(143)

FIG. 18
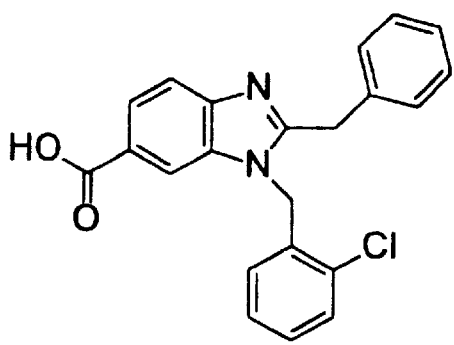
(144)
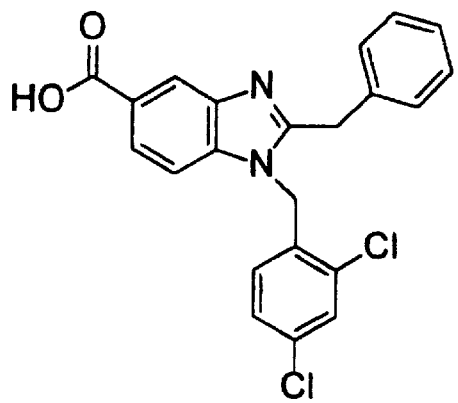
(145)
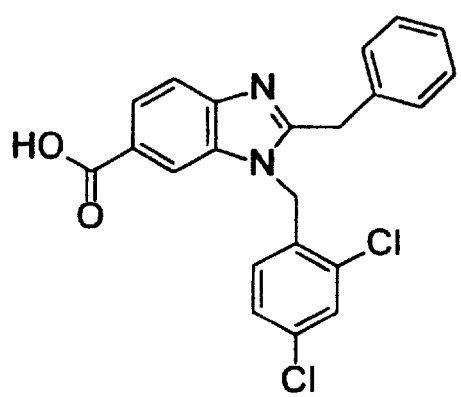
(146)
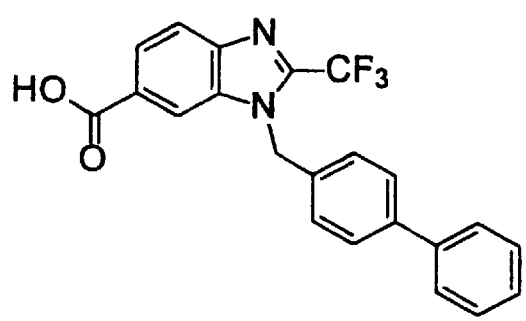
(147)
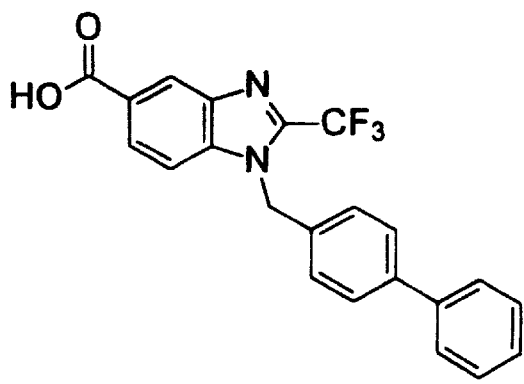
(148)
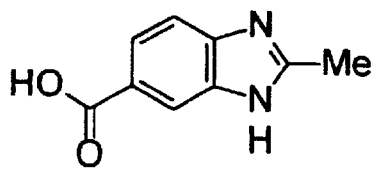
(149)

FIG. 19
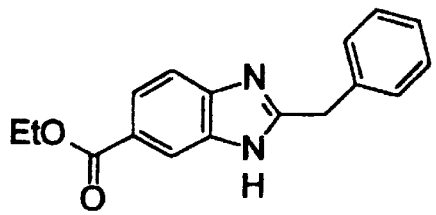
(150)
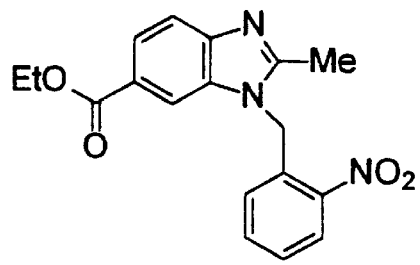
(151)
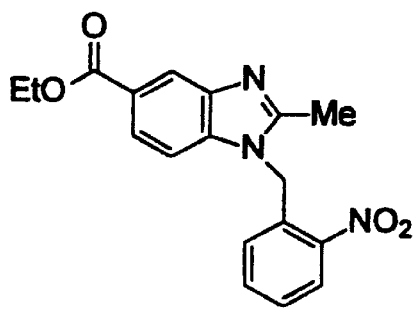
(152)
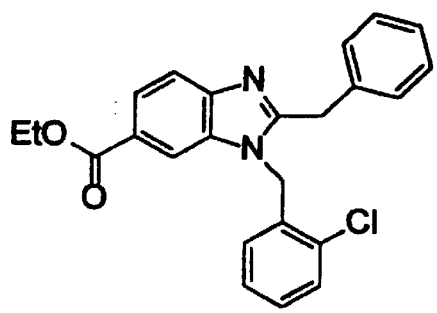
(153)
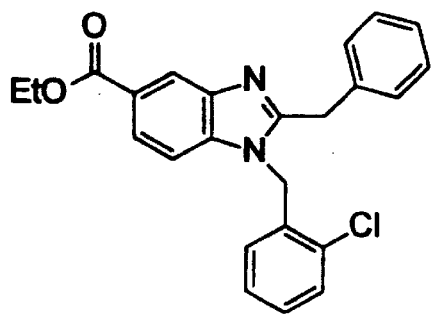
(154)
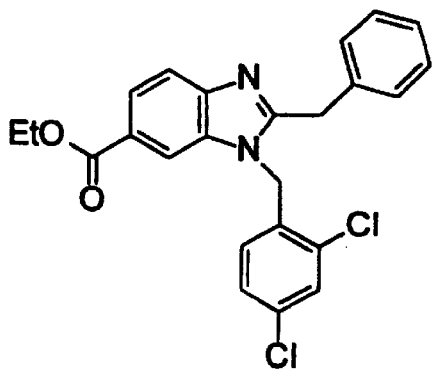
(155)

FIG. 20
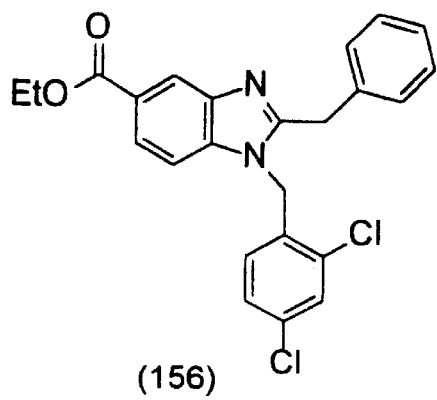
(156)
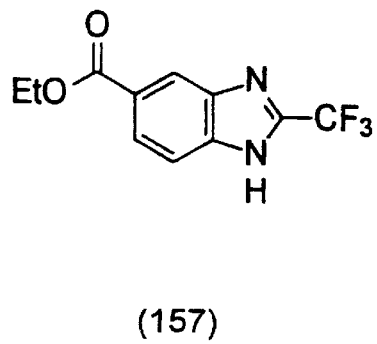
(157)
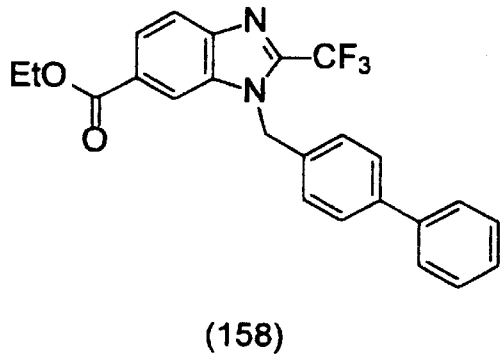
(158)
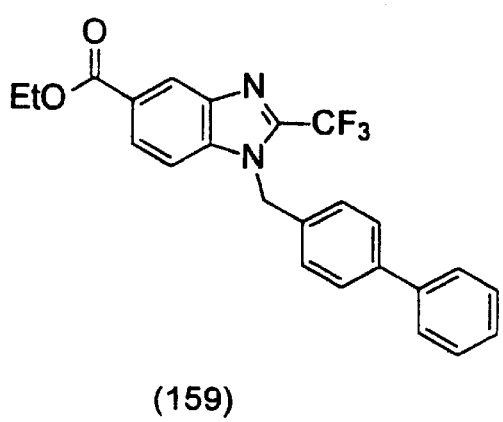
(159)
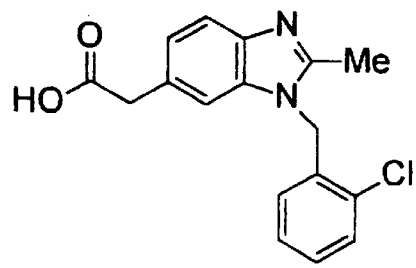
(160)
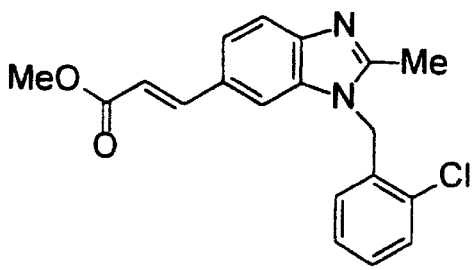
(161)

FIG. 21
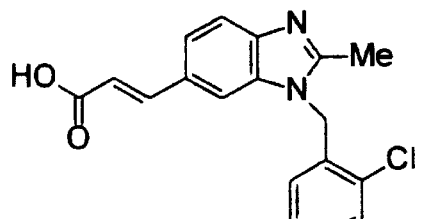
(162)
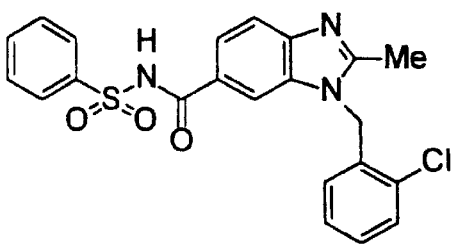
(163)
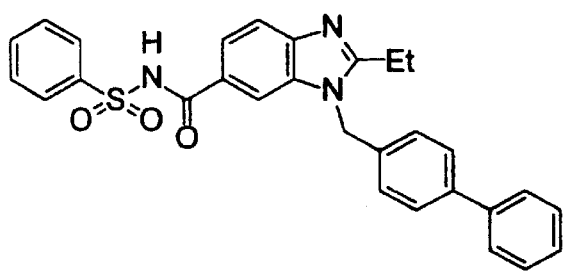
(164)
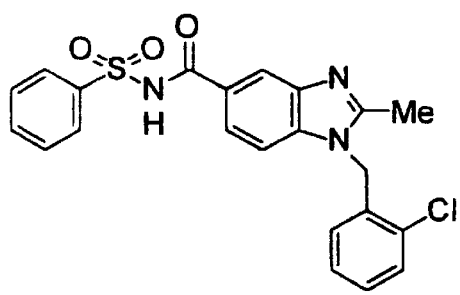
(165)
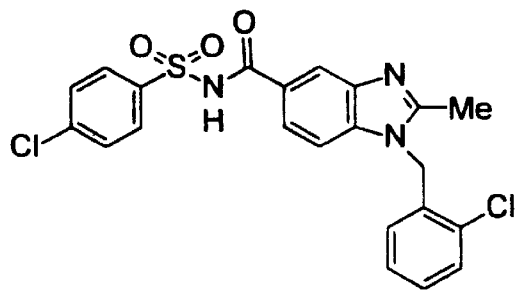
(166)
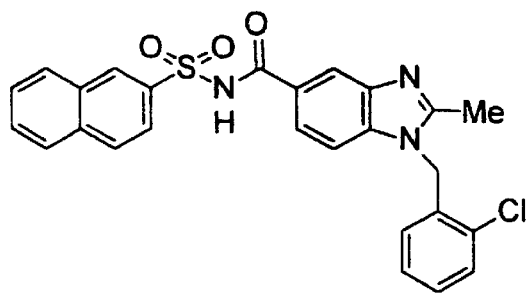
(167)

FIG. 22
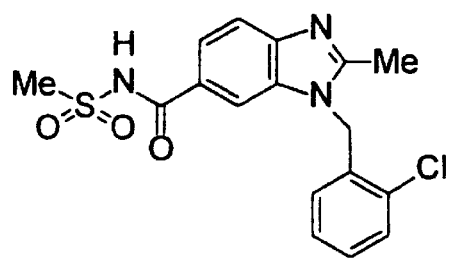
(168)
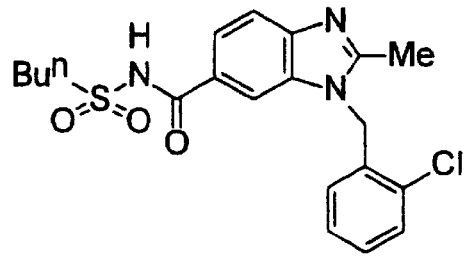
(169)
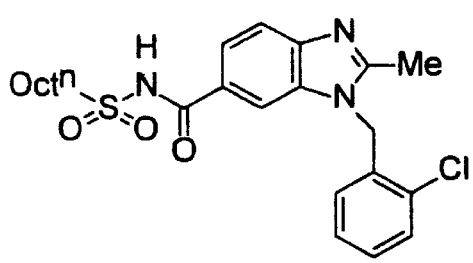
(170)
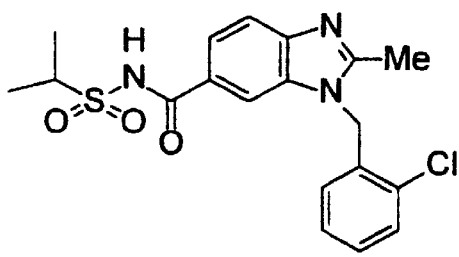
(171)
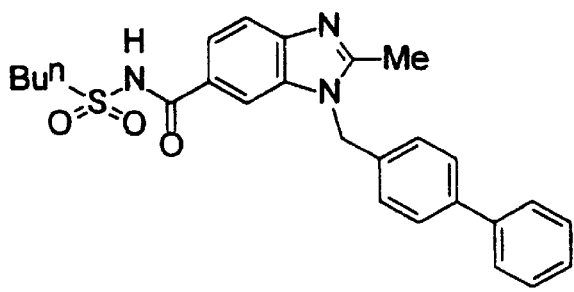
(172)
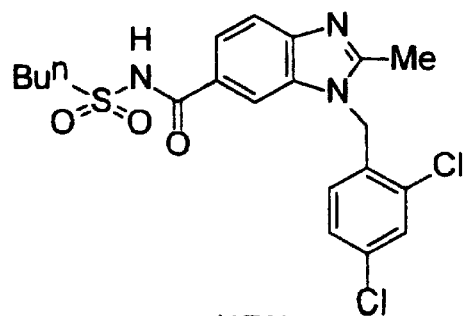
(173)

FIG. 23
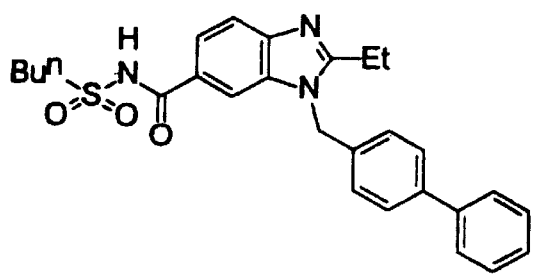
(174)
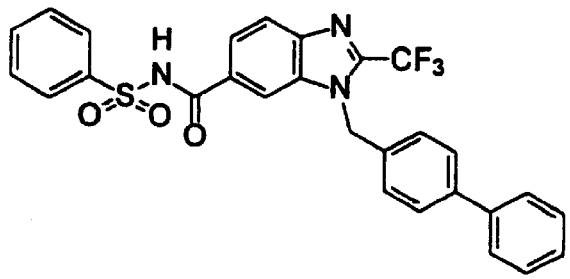
(175)
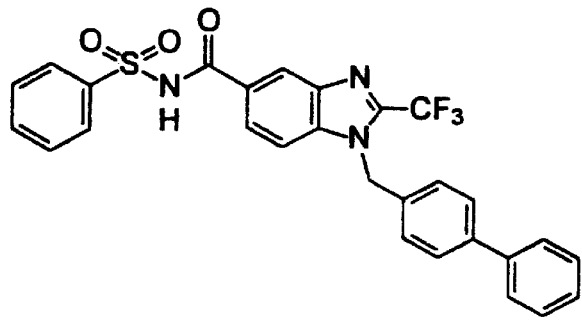
(176)
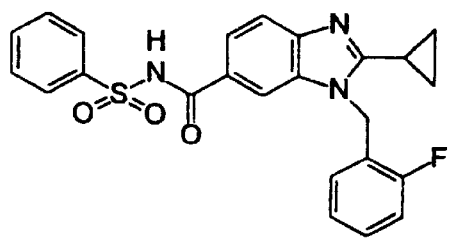
(177)
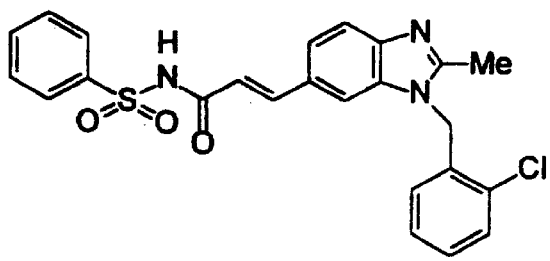
(178)
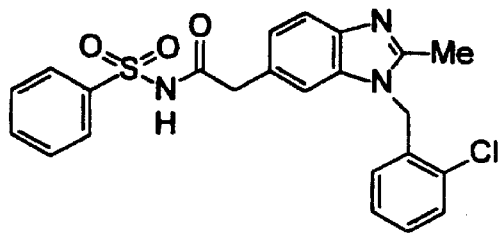
(179)

FIG. 24
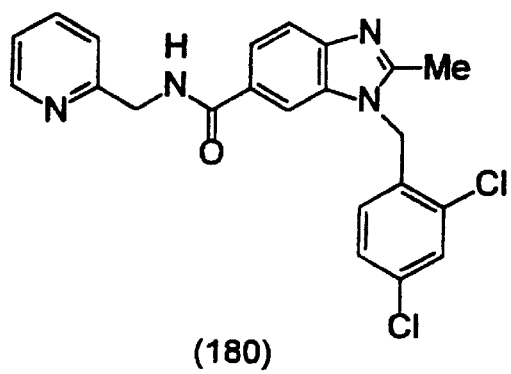
(180)
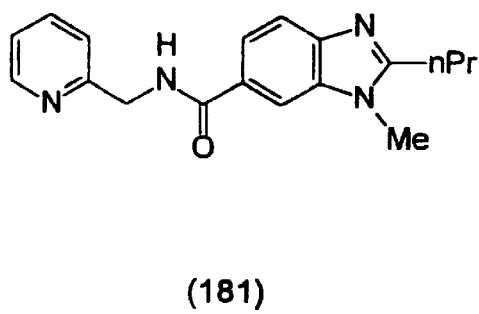
(181)
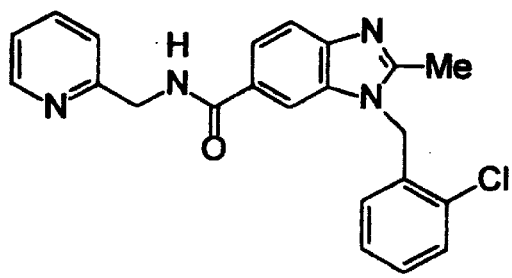
(182)
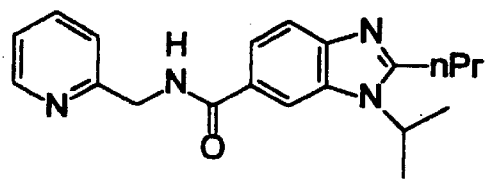
(183)
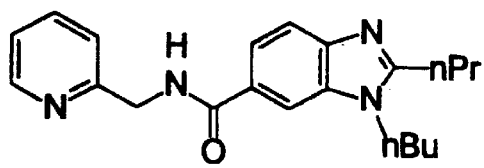
(184)
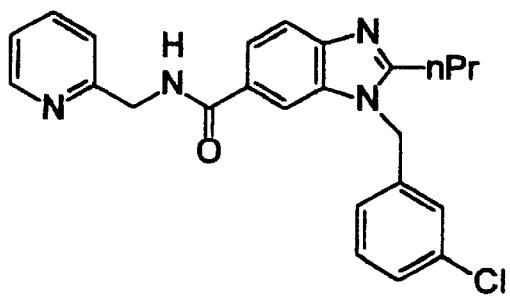
(185)

FIG. 25
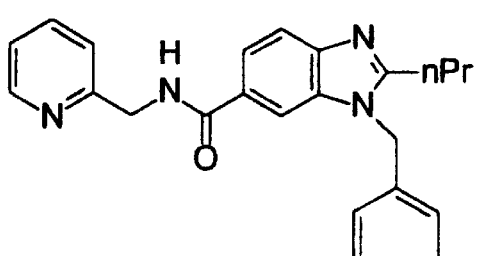
(186)
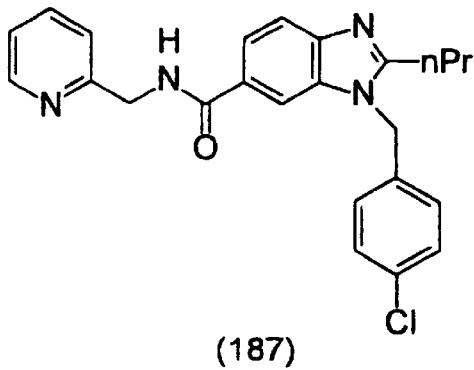
(187)
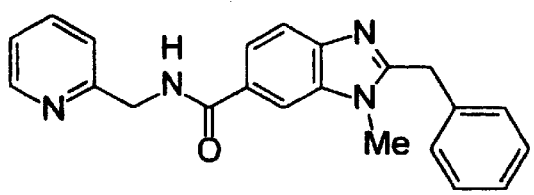
(188)
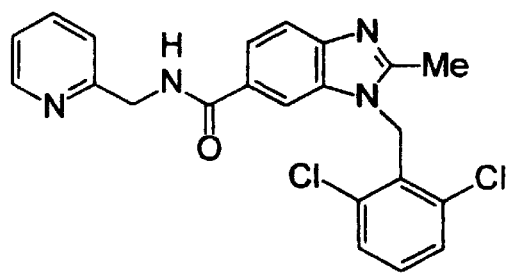
(189)
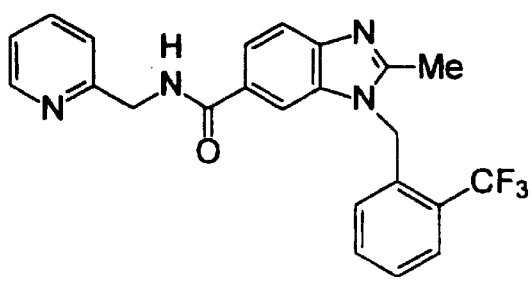
(190)
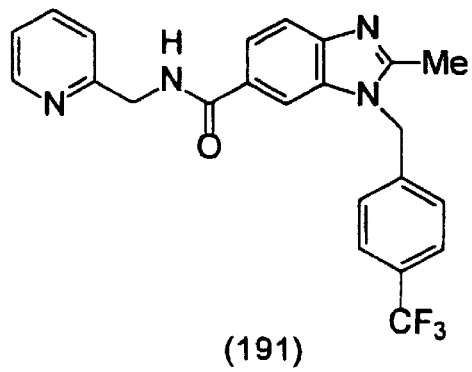
(191)

FIG. 26
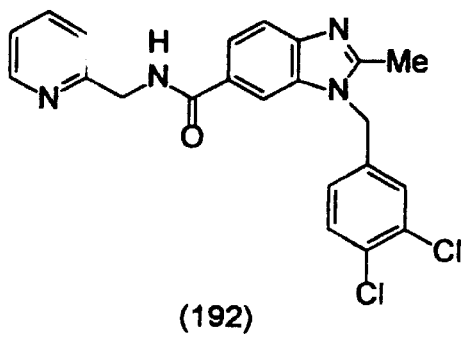
(192)
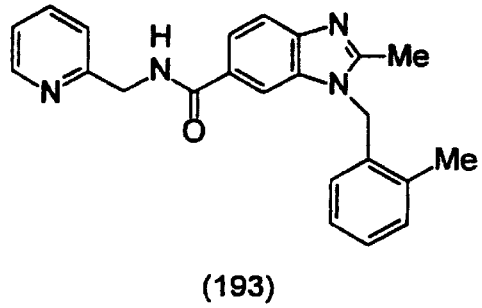
(193)
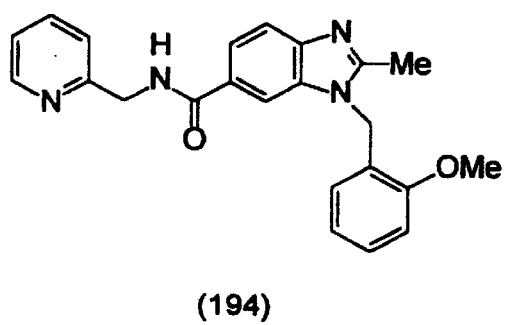
(194)
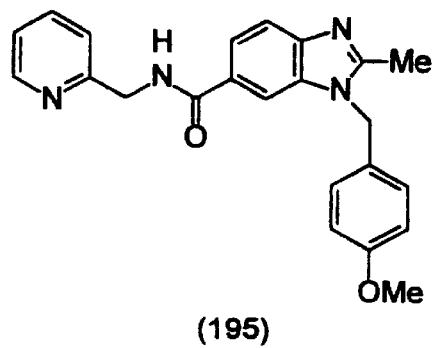
(195)
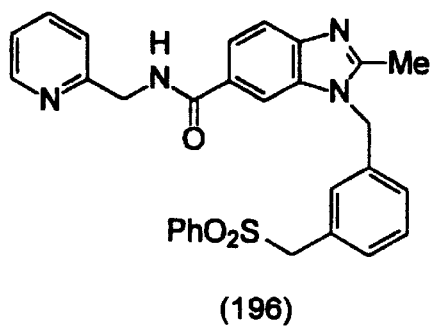
(196)
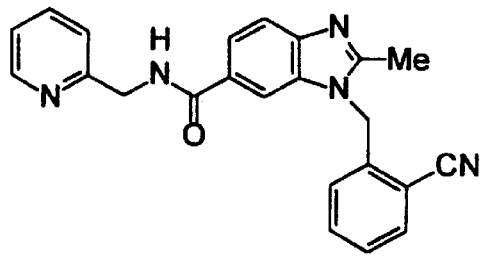
(197)

FIG. 27
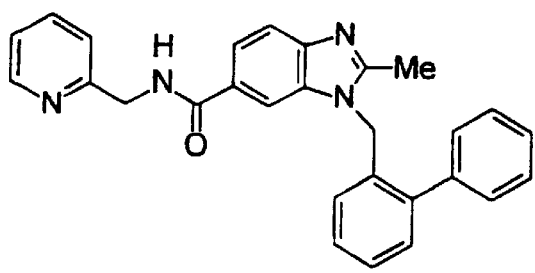
(198)
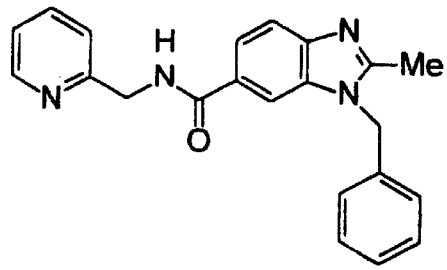
(199)
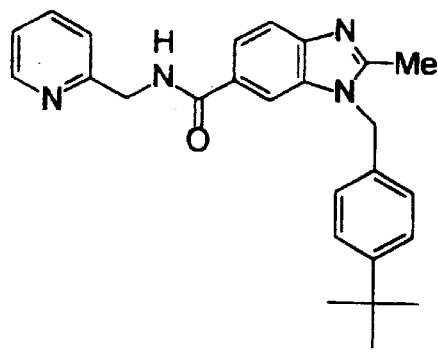
(200)
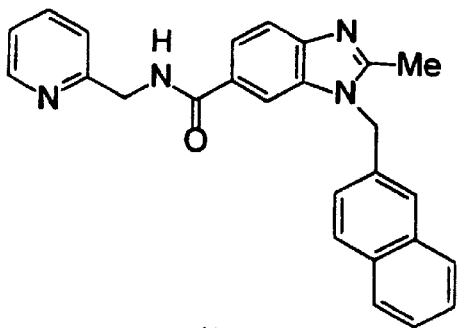
(201)
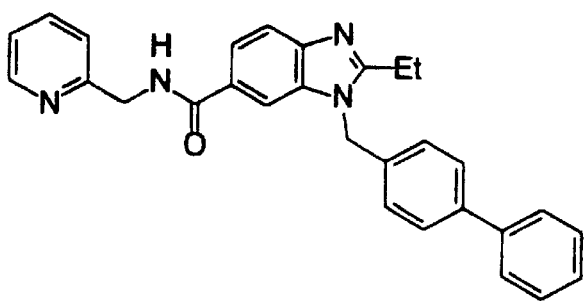
(202)
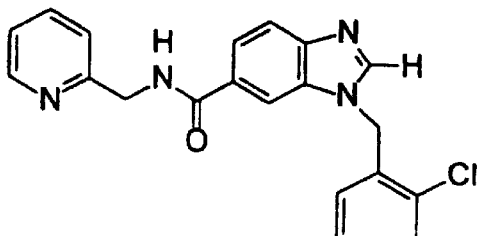
(203)

FIG. 23
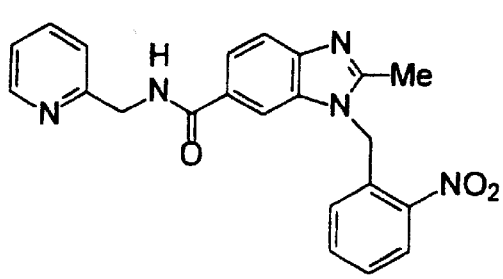
(204)
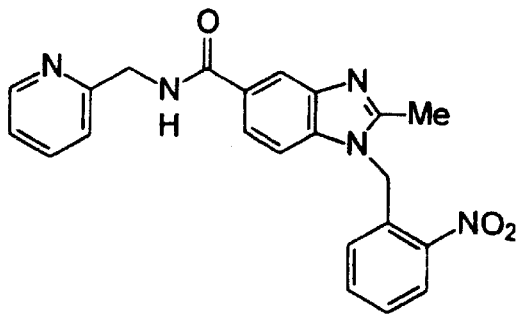
(205)
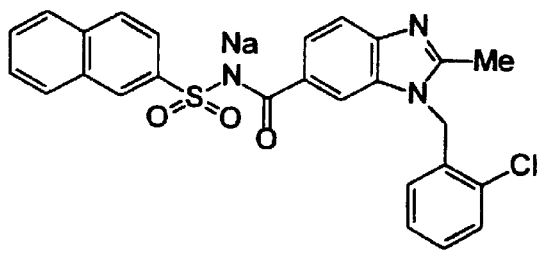
(206)
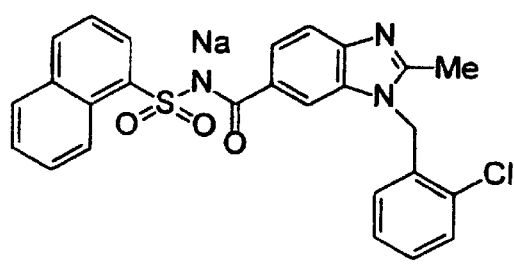
(207)
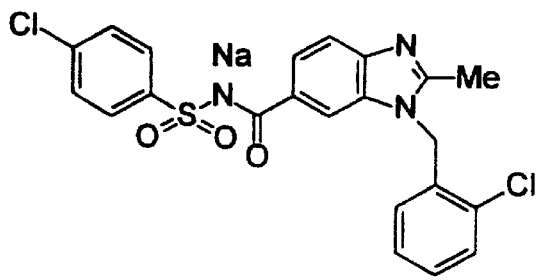
(208)
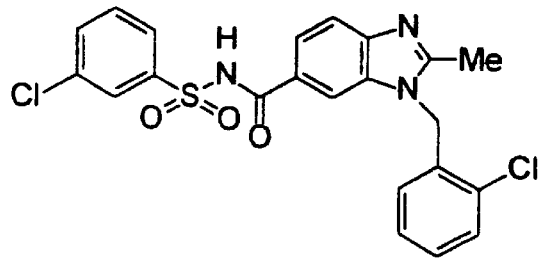
(209)

FIG. 29
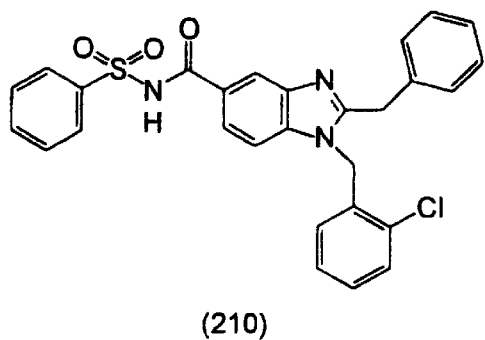
(210)
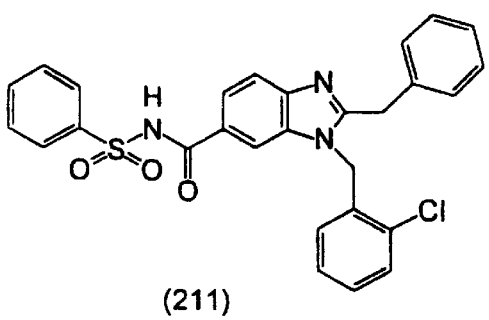
(211)
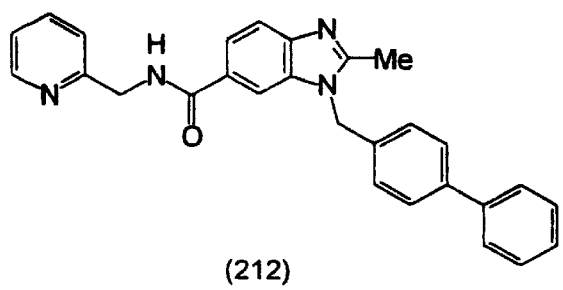
(212)
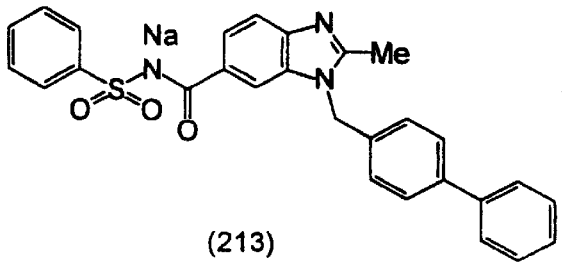
(213)
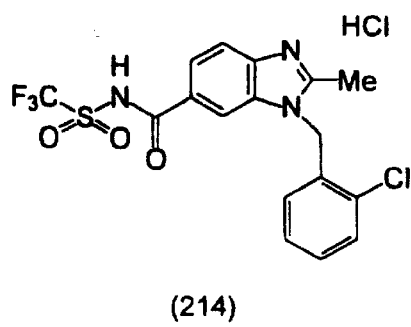
(214)
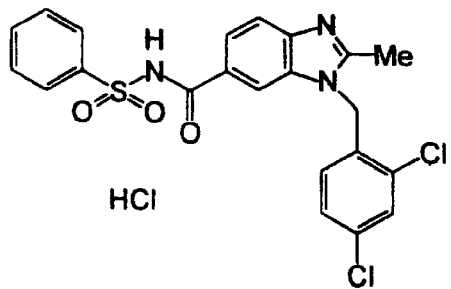
(215)

FIG. 30
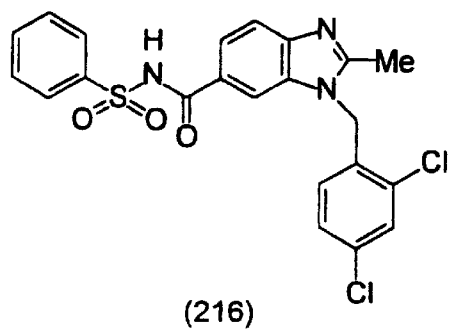
(216)
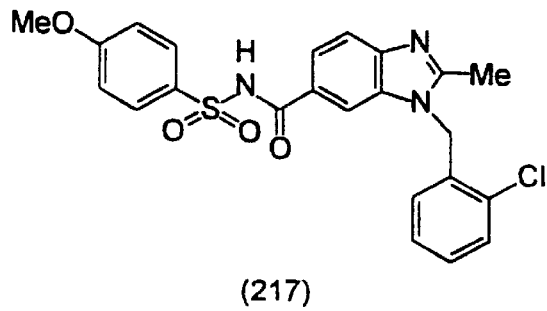
(217)
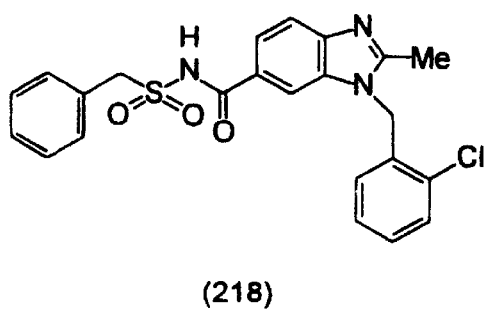
(218)
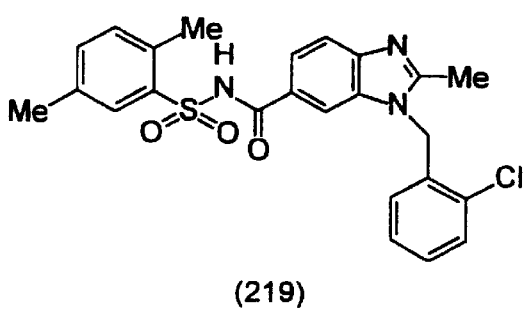
(219)
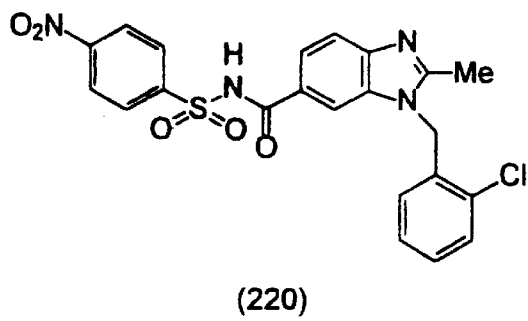
(220)
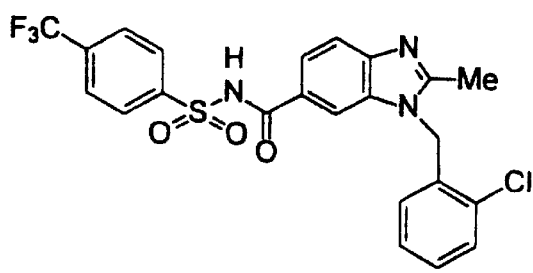
(221)

FIG. 31
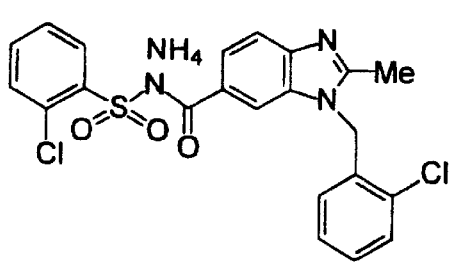
(222)
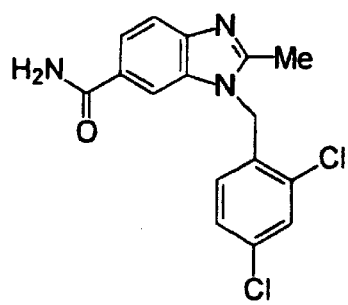
(223)
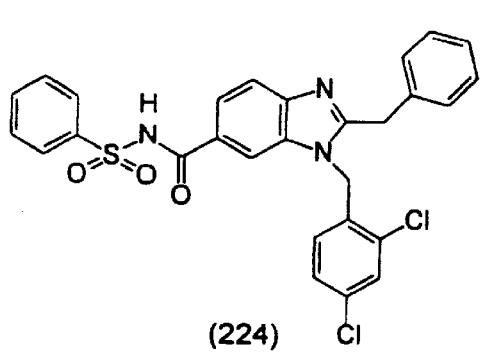
(224)
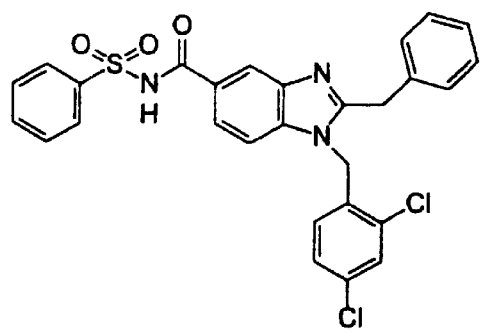
(225)
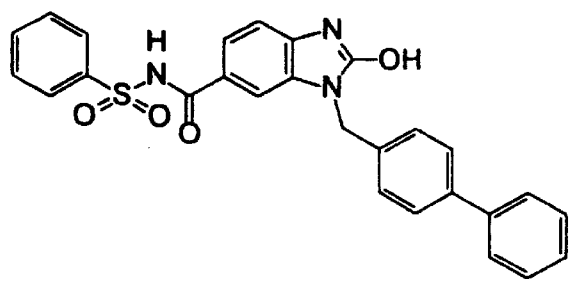
(226)
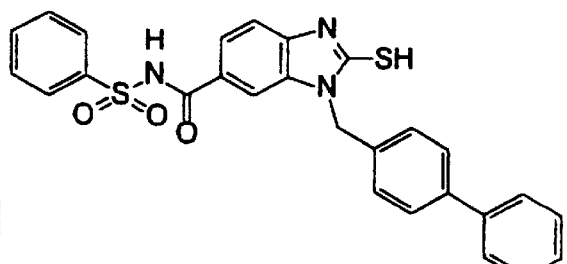
(227)

FIG. 32
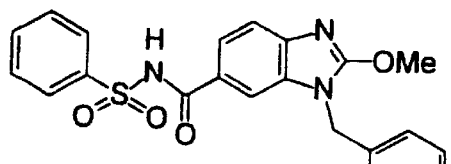
(228)
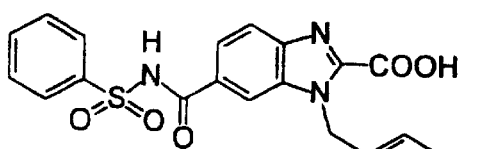
(229)
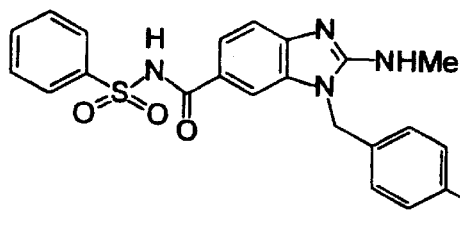
(230)
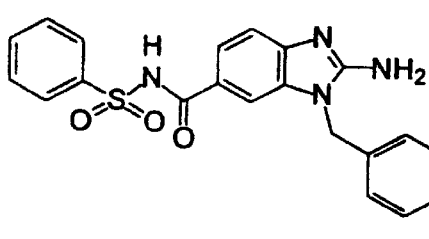
(231)
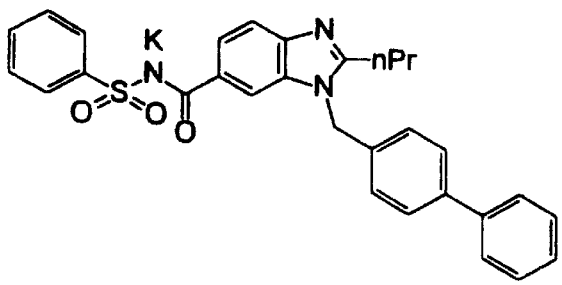
(232)
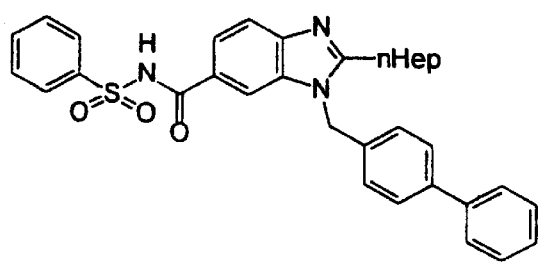
(233)

FIG. 33
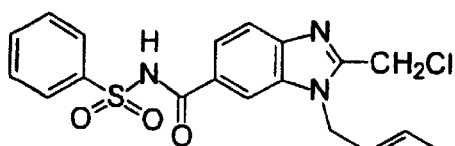
(234)
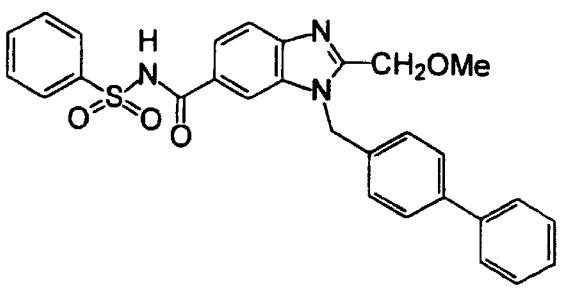
(235)
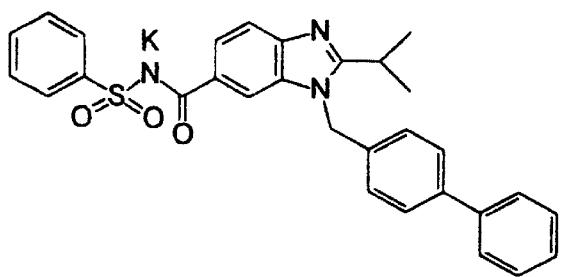
(236)
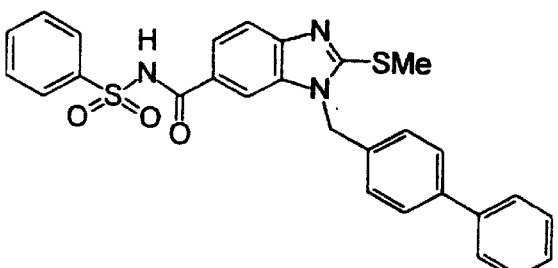
(237)
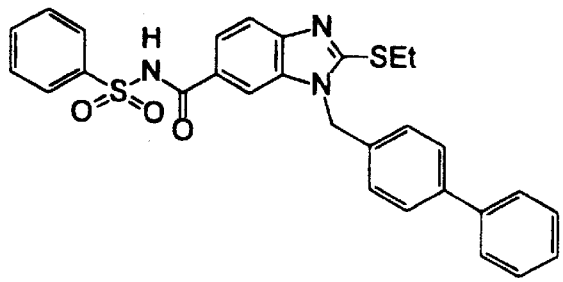
(238)
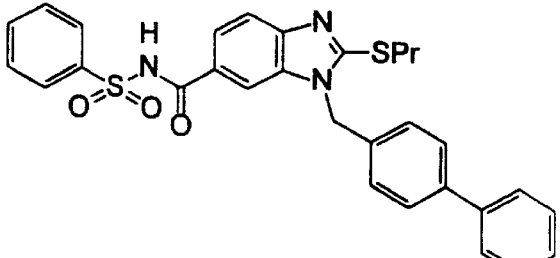
(239)

F I G. 3 4
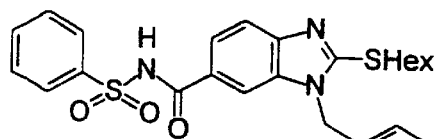
(240)
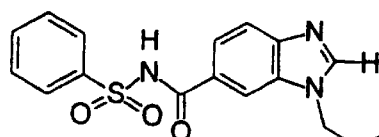
(241)
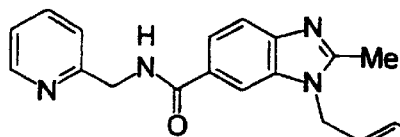
(242)
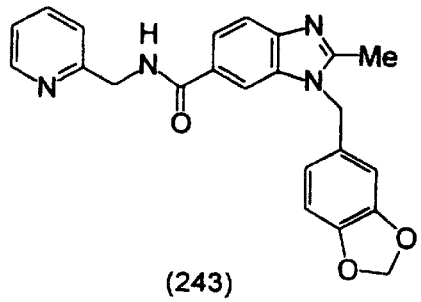
(243)
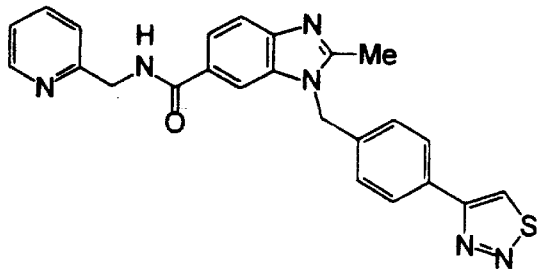
(244)
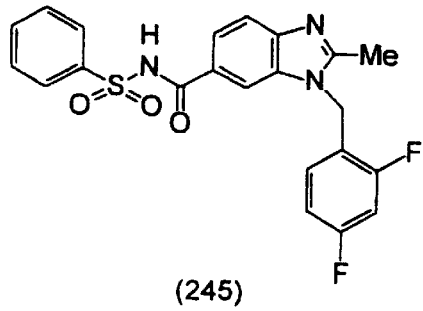
(245)

FIG. 35
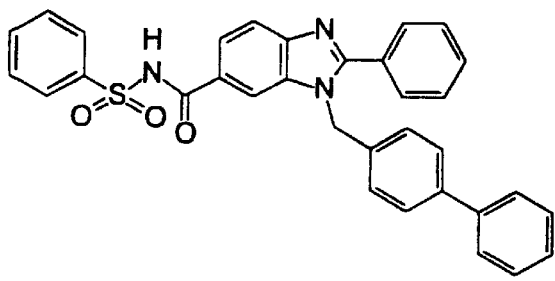
(246)
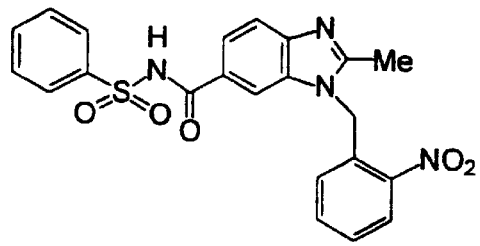
(247)
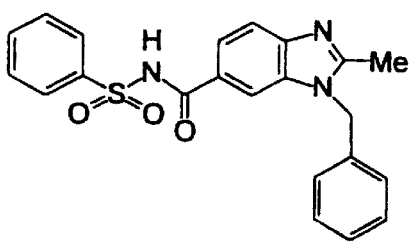
(248)
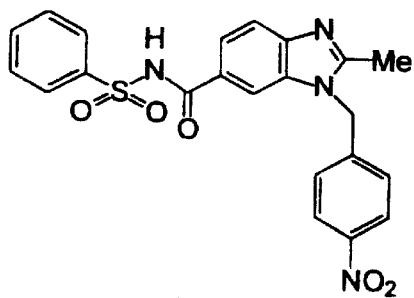
(249)
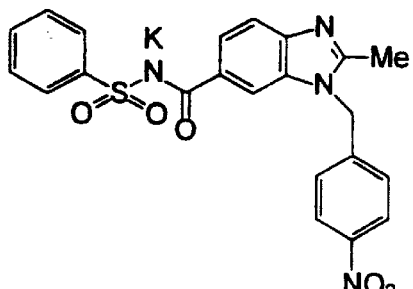
(250)
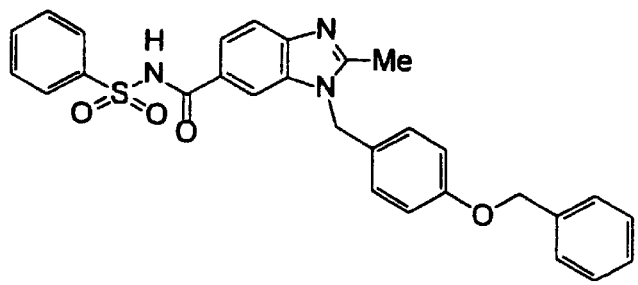
(251)

FIG. 36
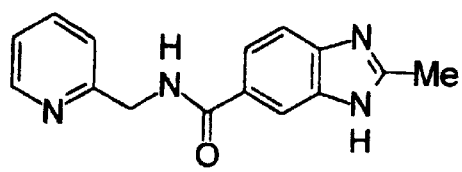
(252)
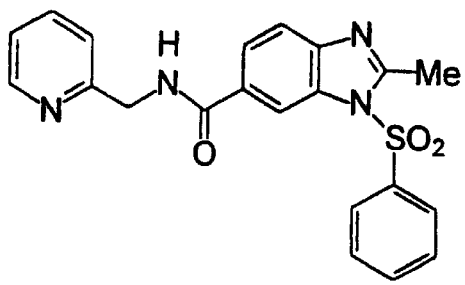
(253)
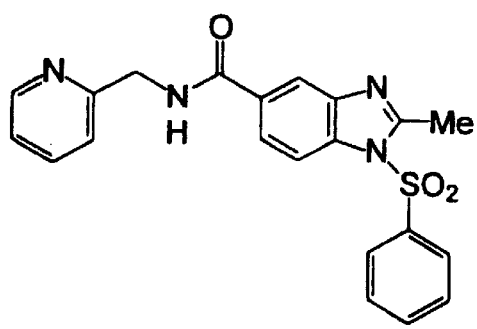
(254)
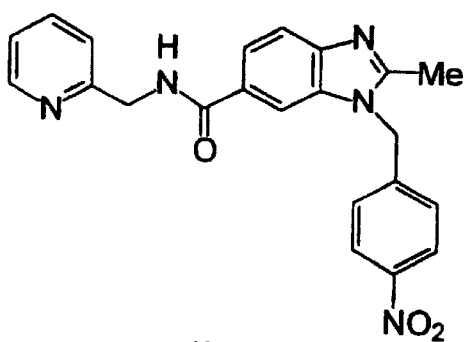
(255)
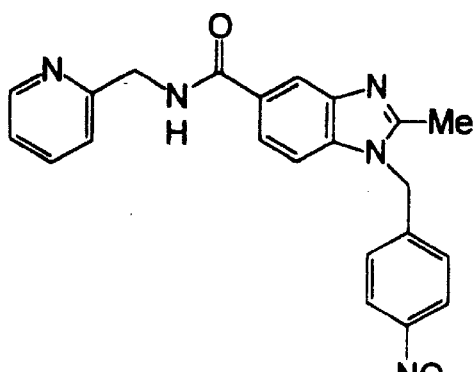
(256)
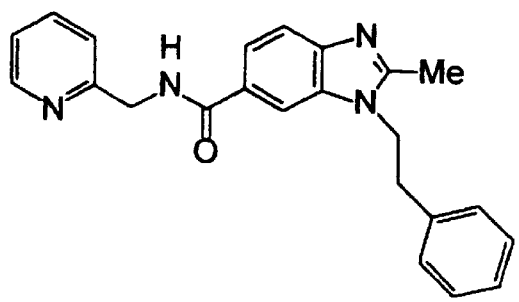
(257)

FIG. 37
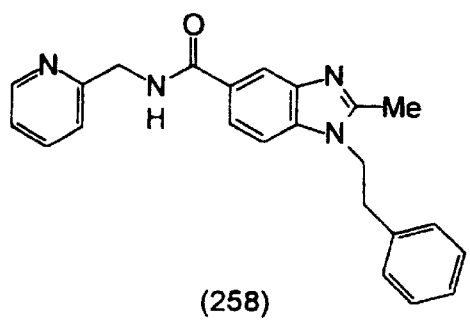
(258)
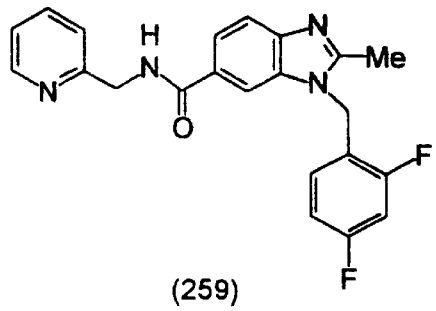
(259)
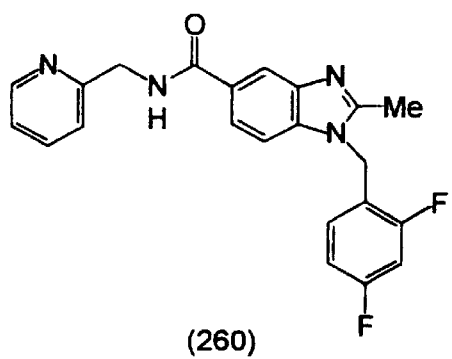
(260)
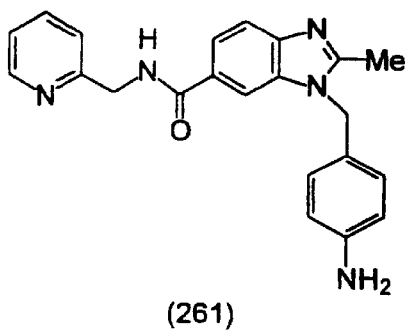
(261)
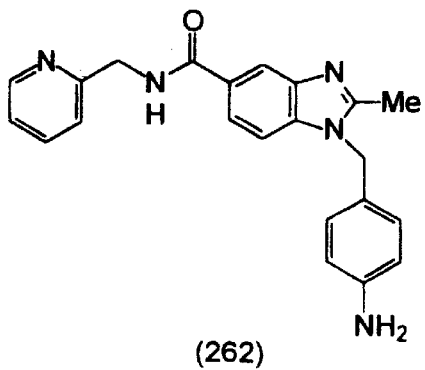
(262)
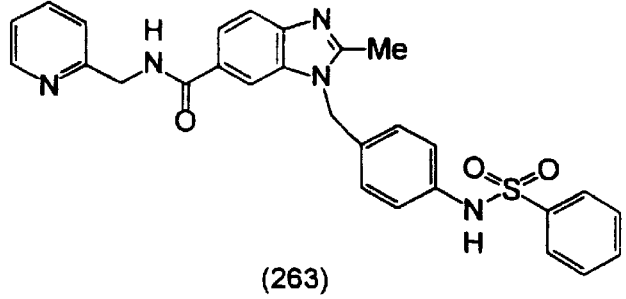
(263)

FIG. 38
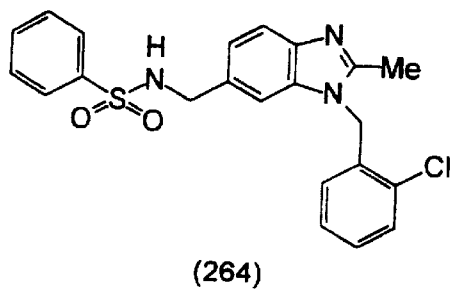
(264)
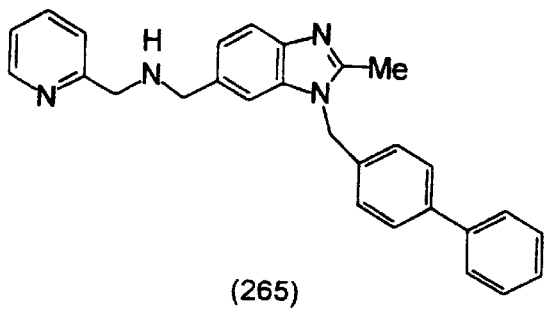
(265)
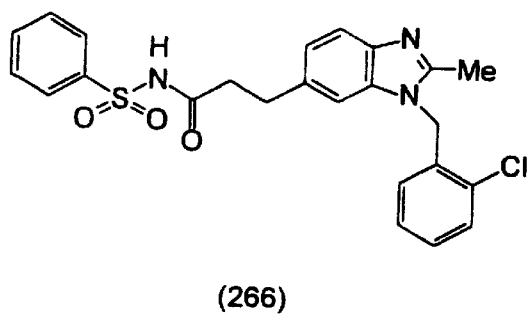
(266)
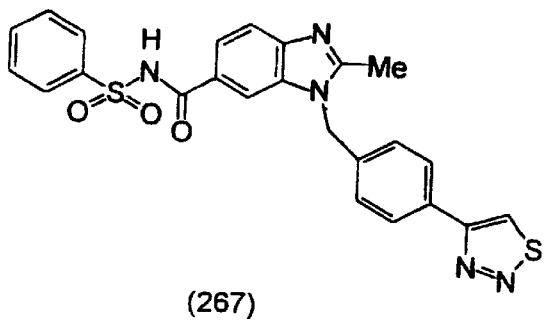
(267)
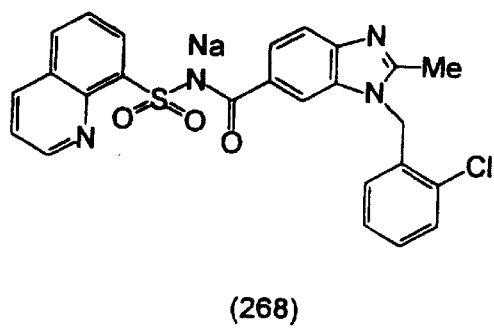
(268)
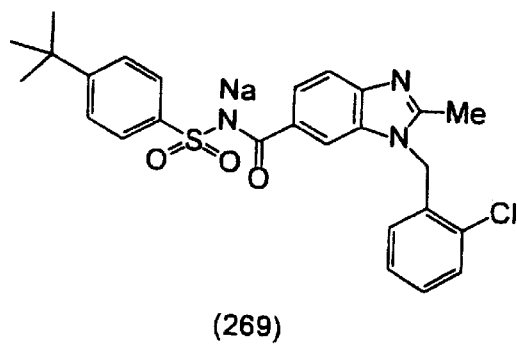
(269)

FIG. 39
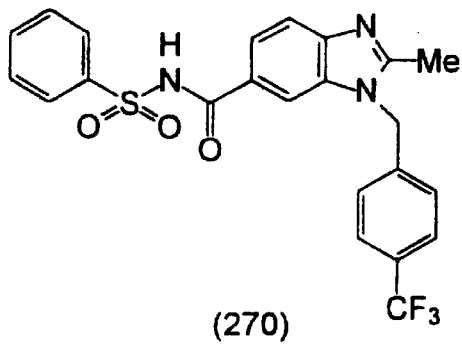
(270)
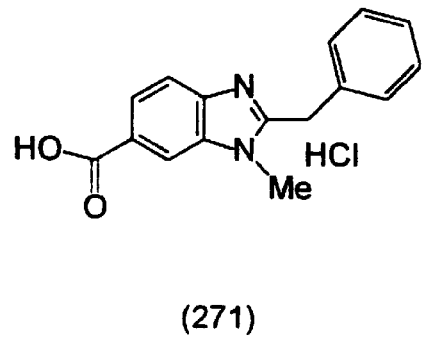
(271)
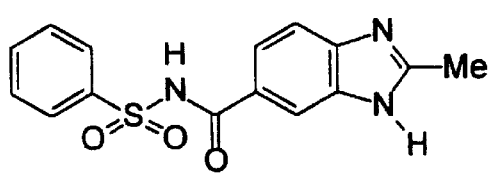
(272)
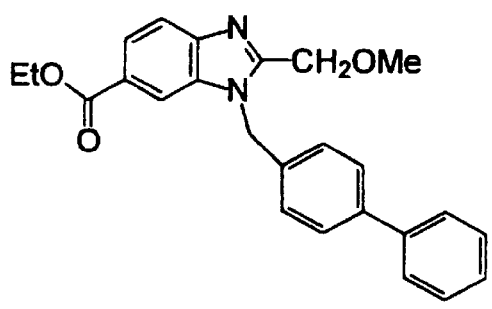
(273)
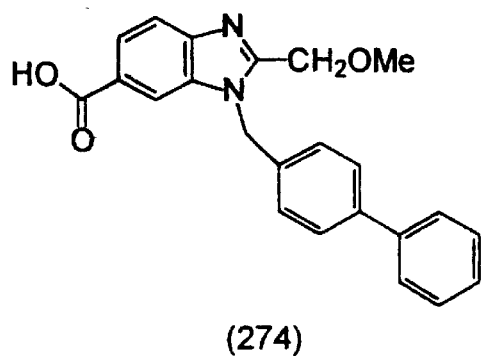
(274)
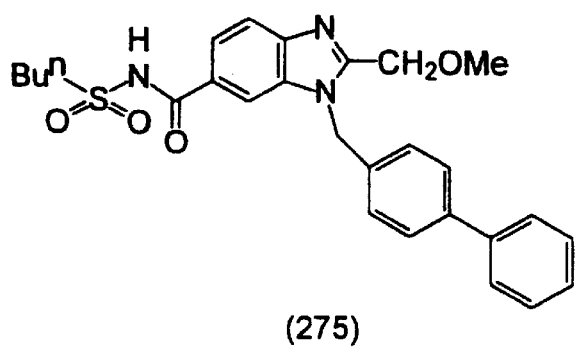
(275)

FIG. 40
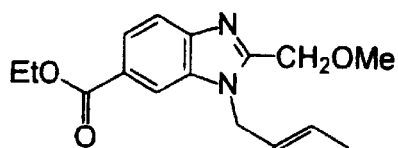
(276)
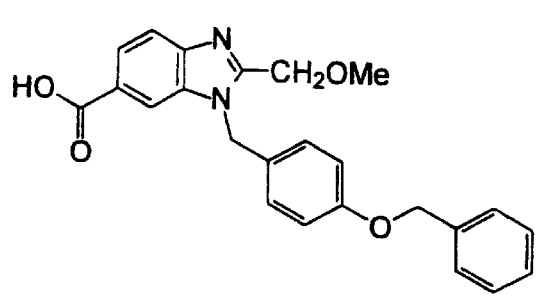
(277)
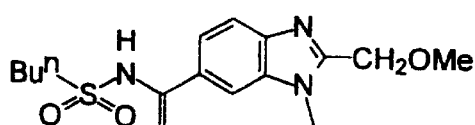
(278)
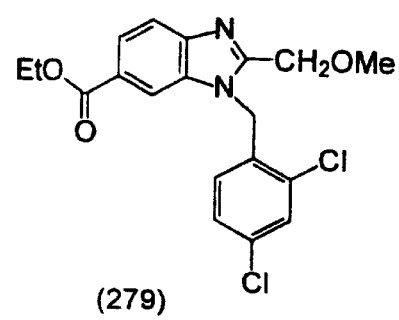
(279)
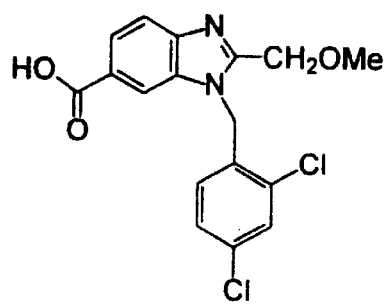
(280)
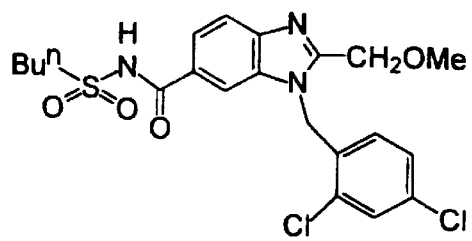
(281)

FIG. 41
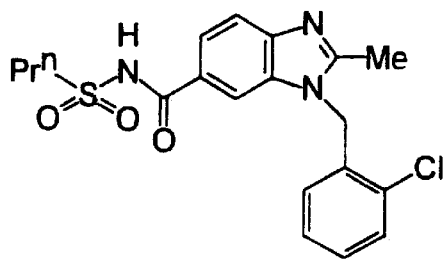
(282)
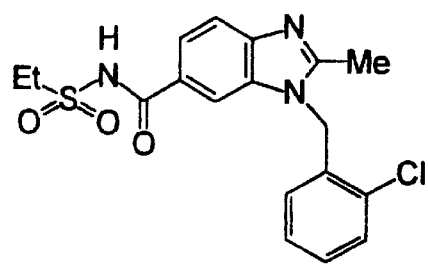
(283)
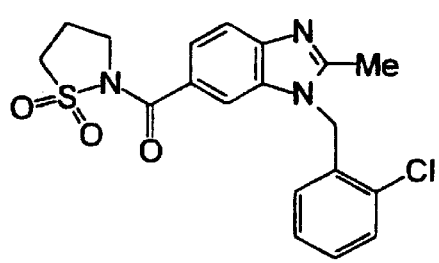
(284)
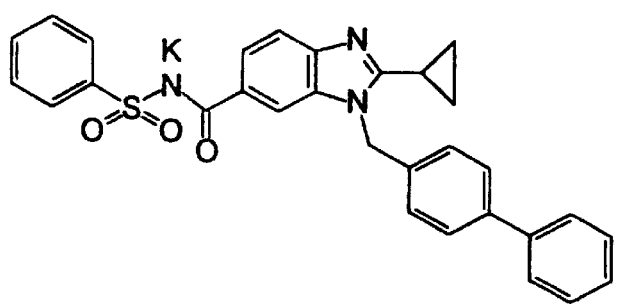
(285)
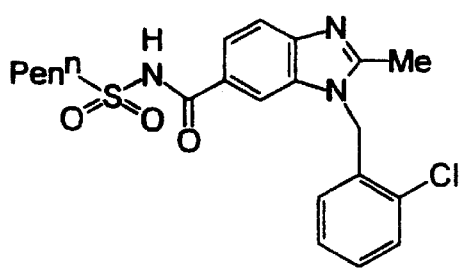
(286)
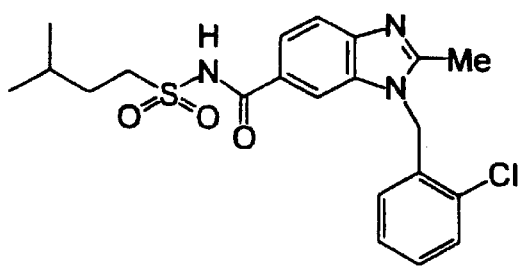
(287)

FIG. 42
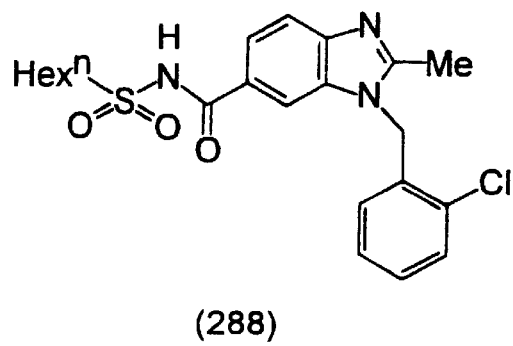
(288)
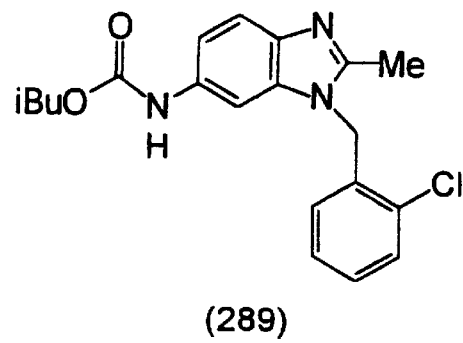
(289)
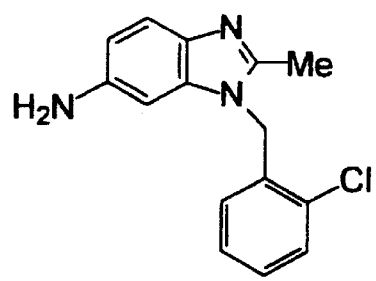
(290)
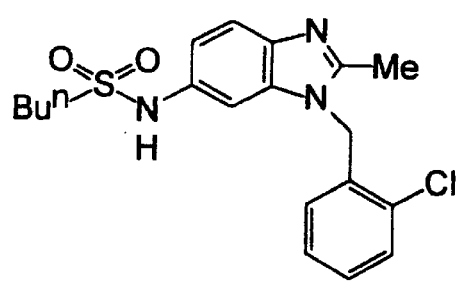
(291)
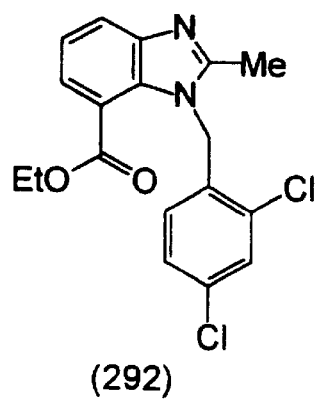
(292)
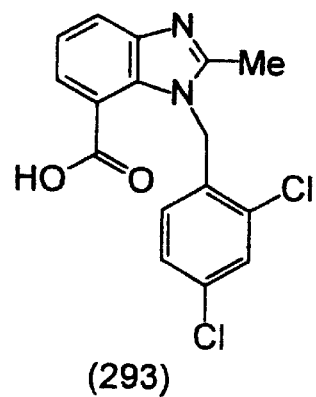
(293)

FIG. 43
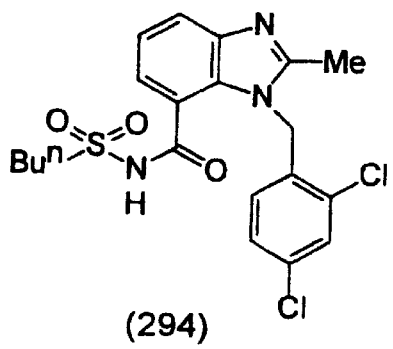
(294)
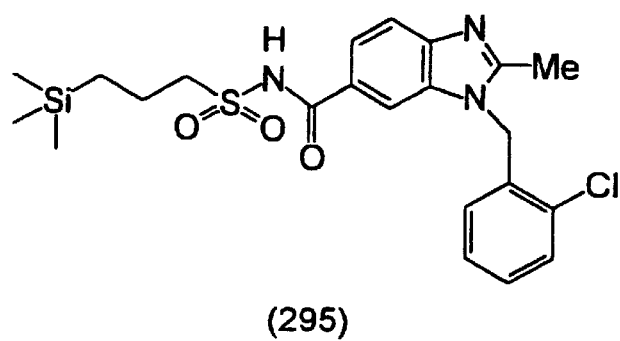
(295)
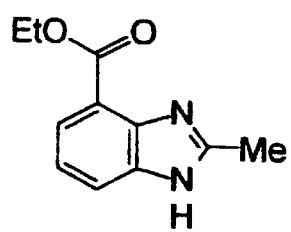
(296)
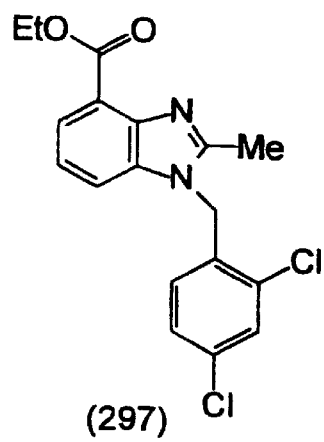
(297)
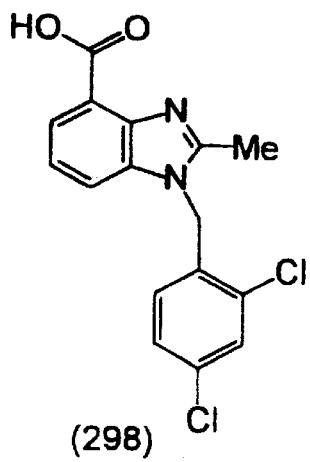
(298)
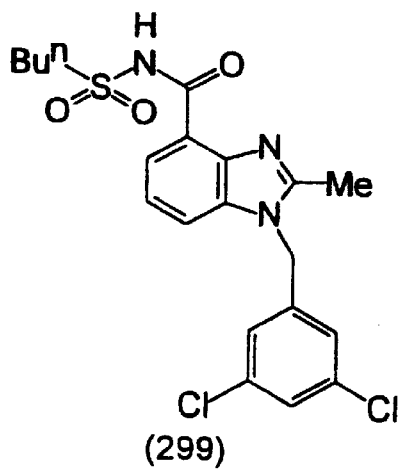
(299)

FIG. 44
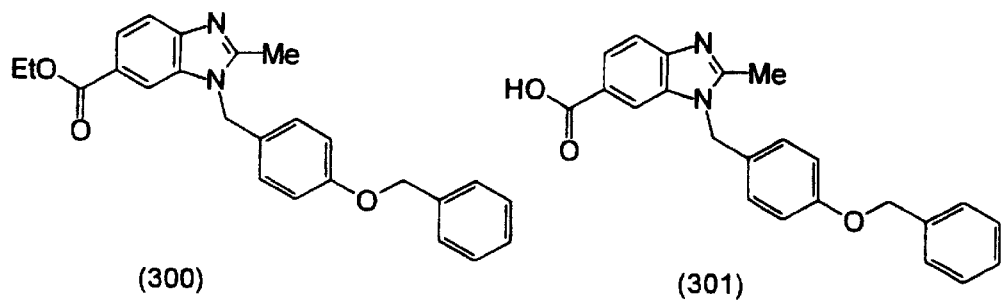
(300)  (301)
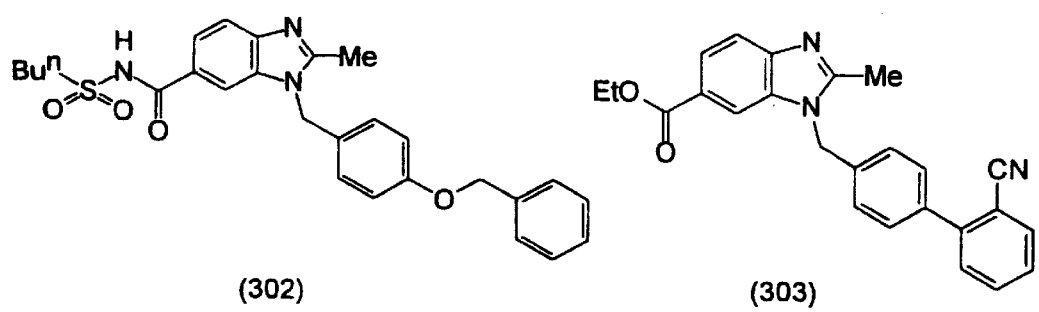
(302)  (303)
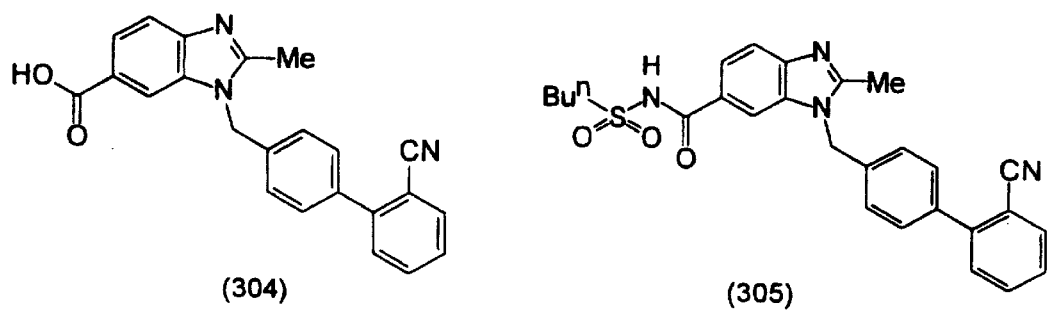
(304)  (305)

FIG. 45
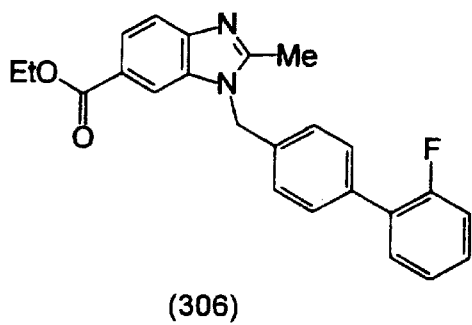
(306)
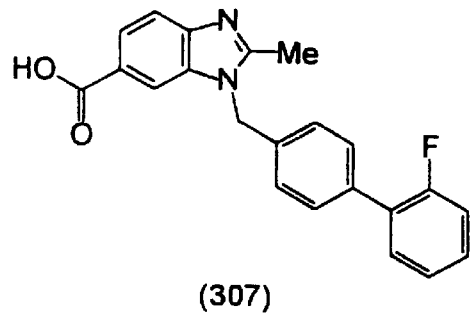
(307)
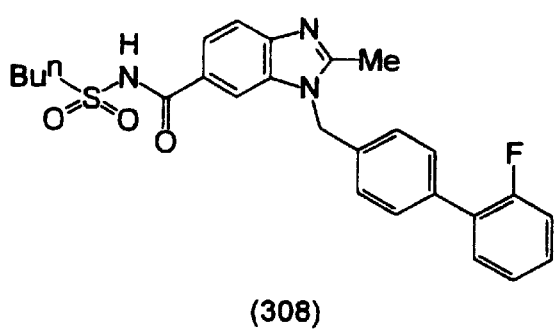
(308)
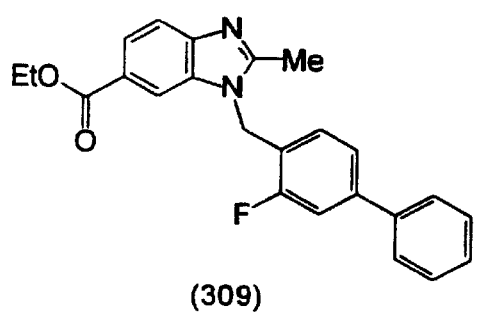
(309)
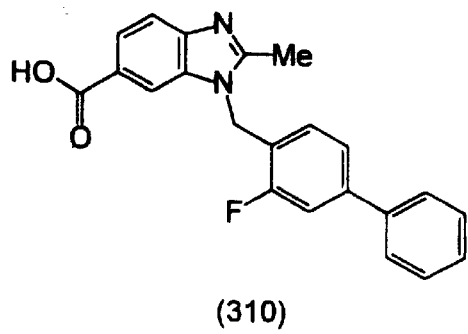
(310)
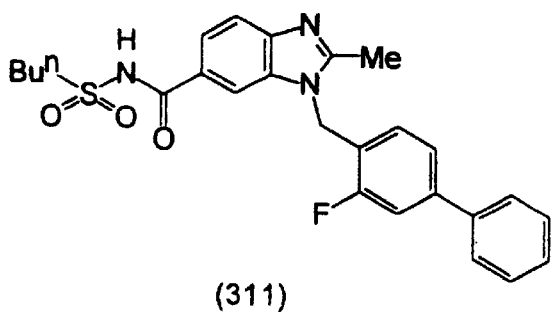
(311)

FIG. 48
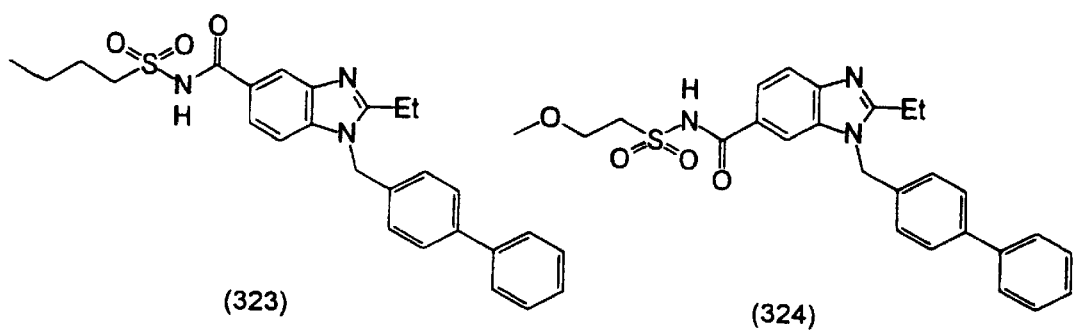
(323)  (324)
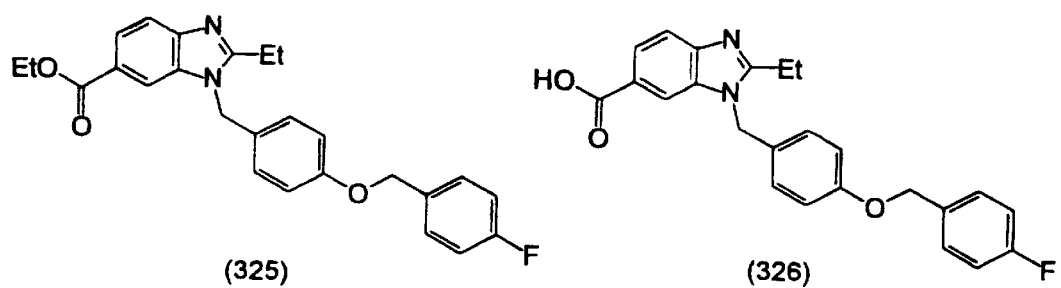
(325)  (326)
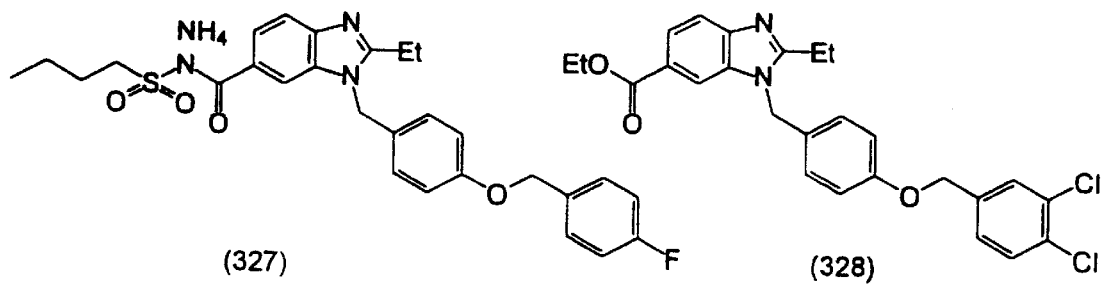
(327)  (328)

F I G. 4 9
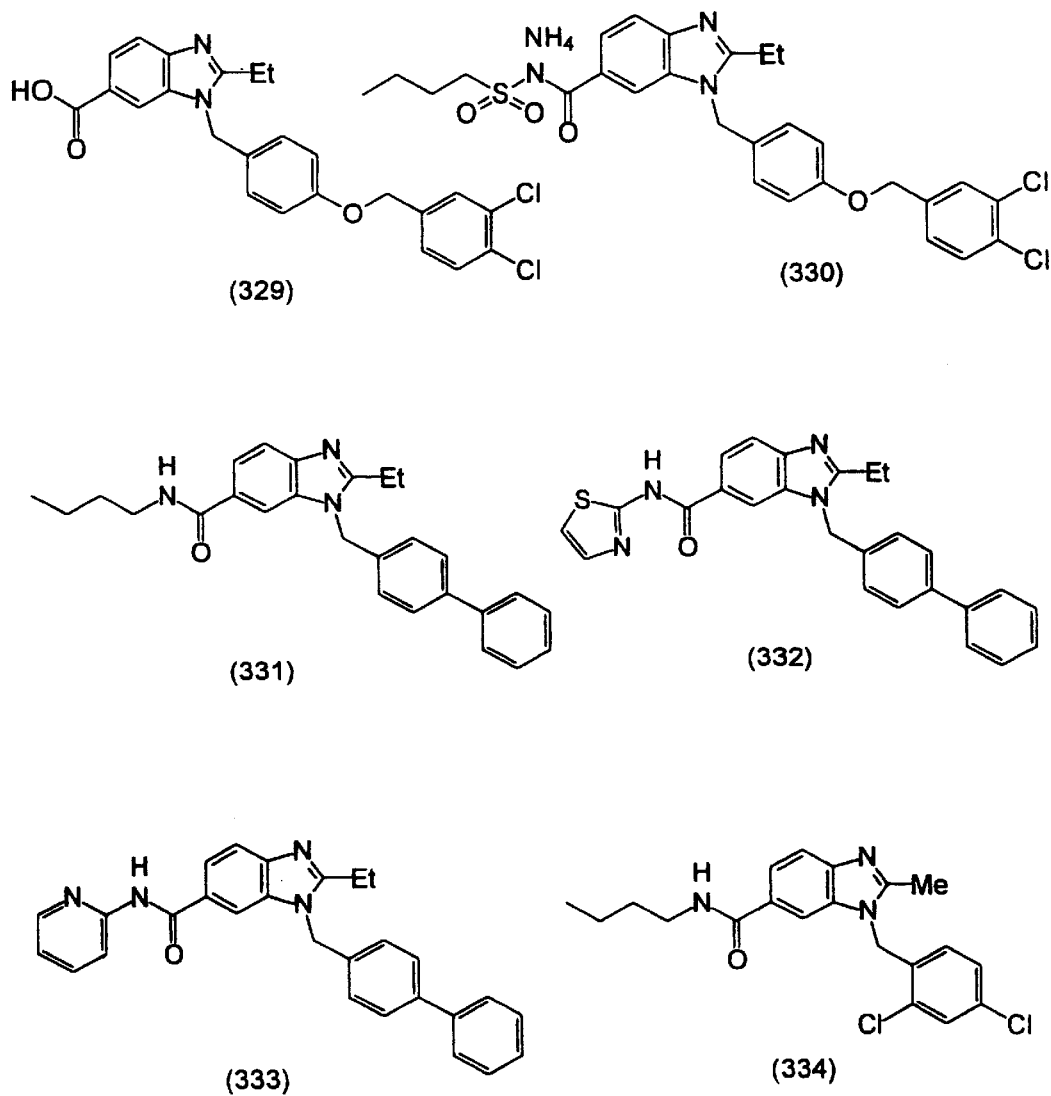

FIG. 50
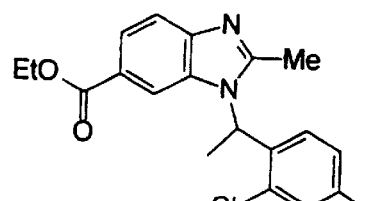
(335)
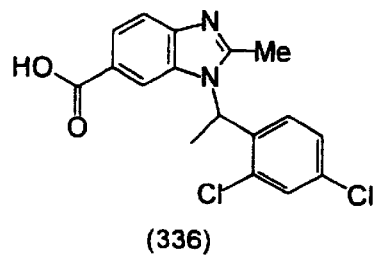
(336)
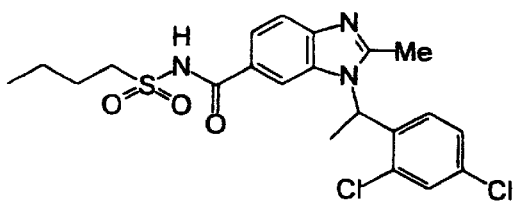
(337)
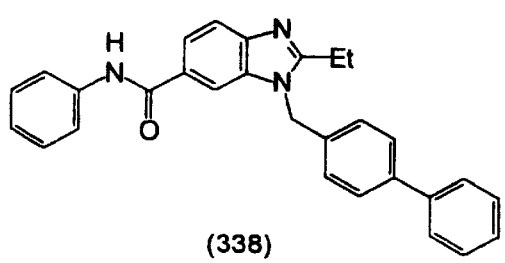
(338)
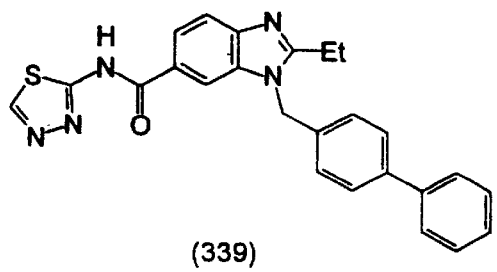
(339)
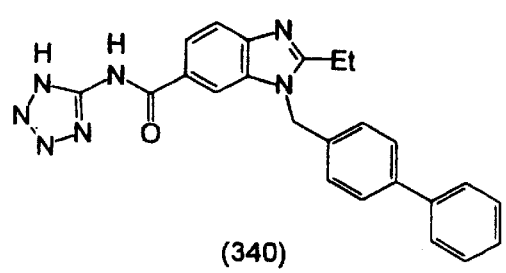
(340)

FIG. 52
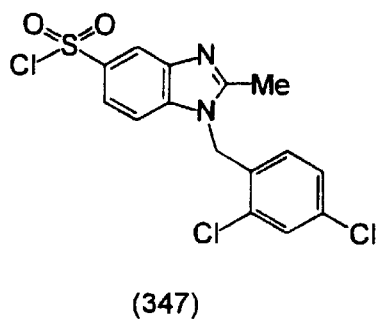
(347)
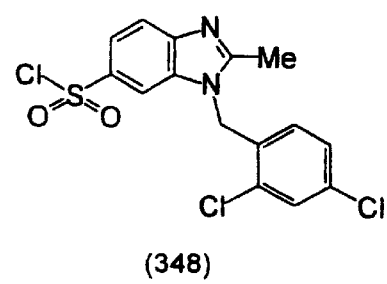
(348)
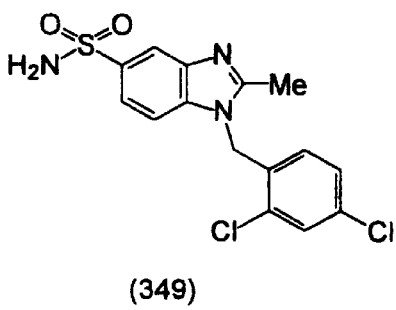
(349)
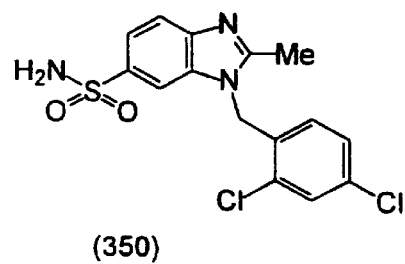
(350)
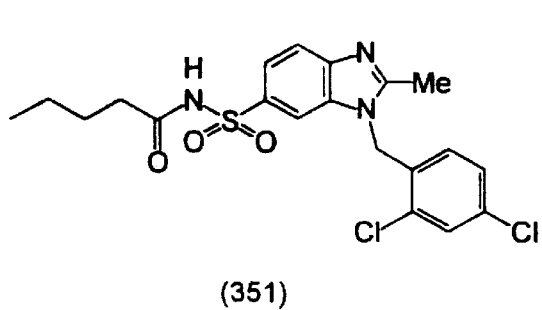
(351)
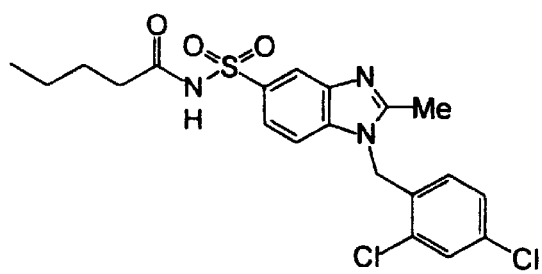
(352)

FIG. 53
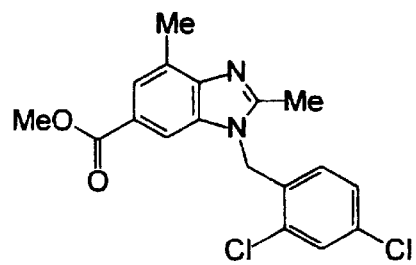
(353)
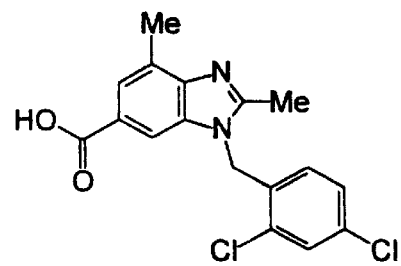
(354)
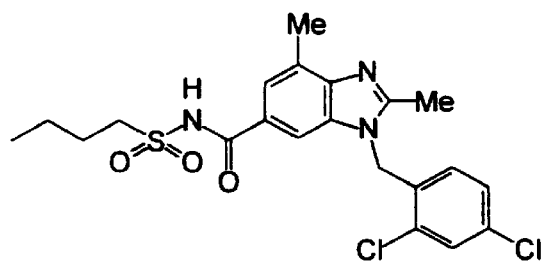
(355)
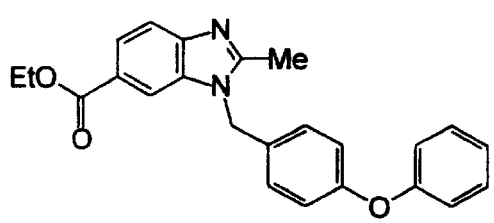
(356)
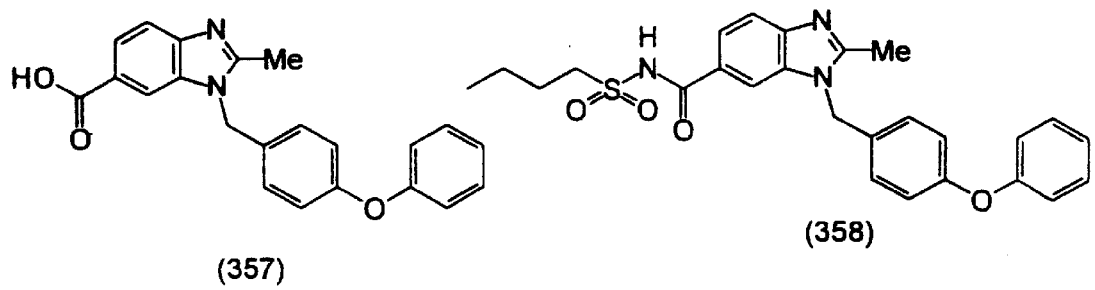
(357)                    (358)

FIG. 54
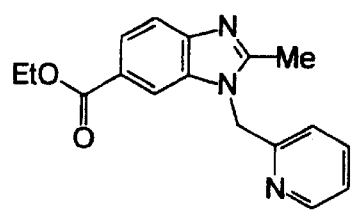
(359)
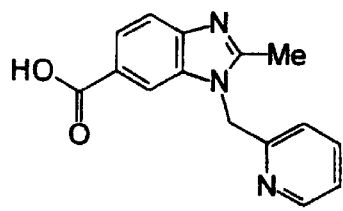
(360)
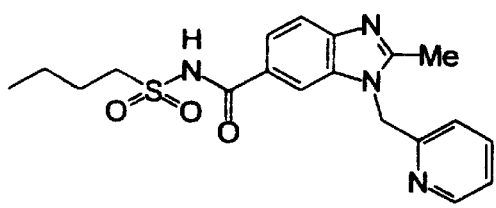
(361)
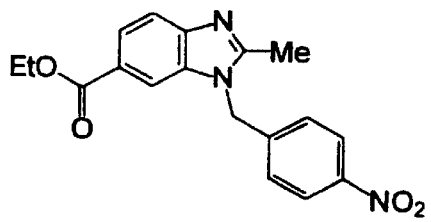
(362)
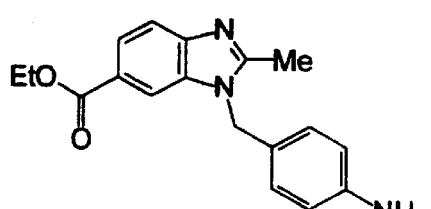
(363)
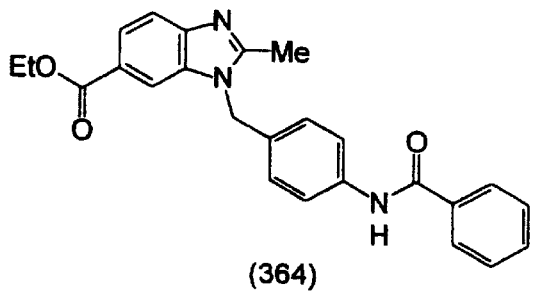
(364)

FIG. 56
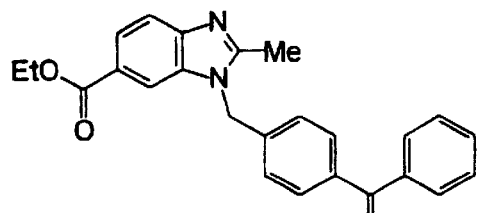
(371)
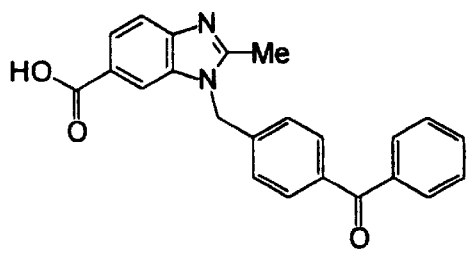
(372)
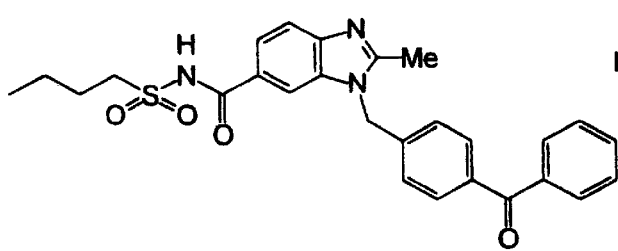
(373)
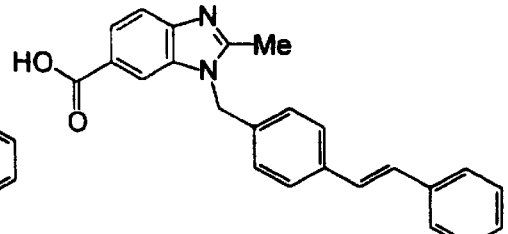
(374)
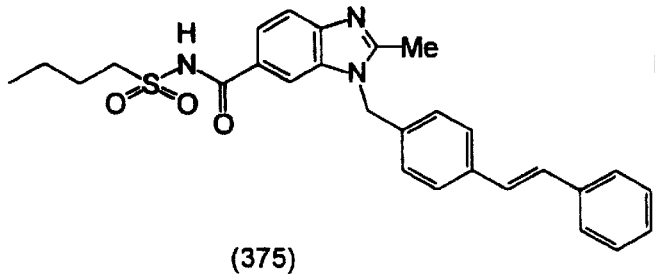
(375)
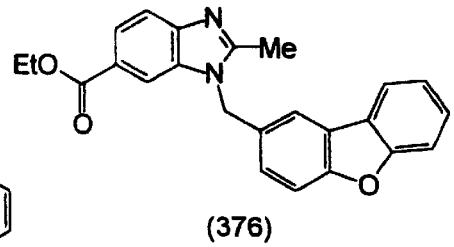
(376)

FIG. 57
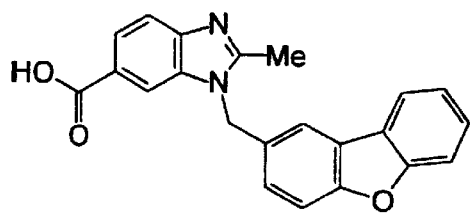
(377)
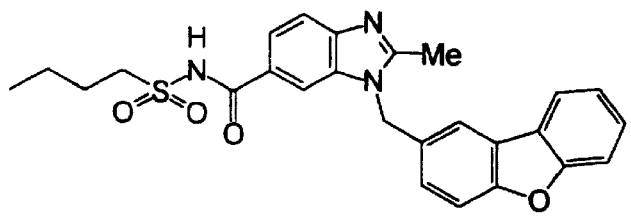
(378)
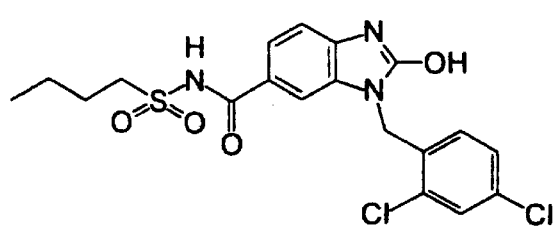
(379)
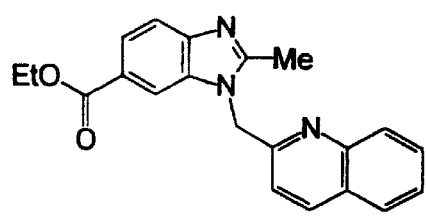
(380)
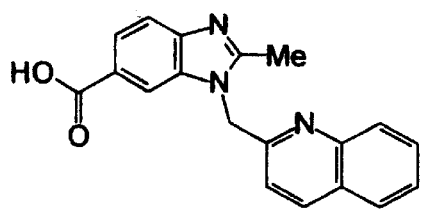
(381)
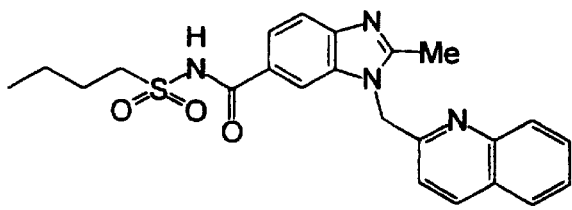
(382)

FIG. 58
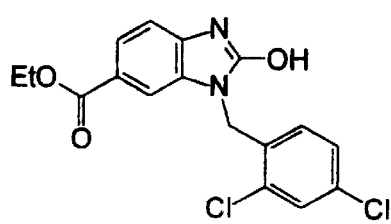
(383)
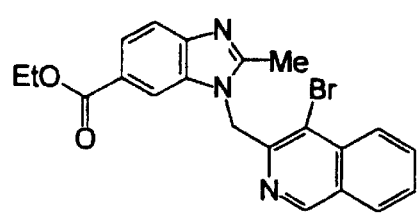
(384)
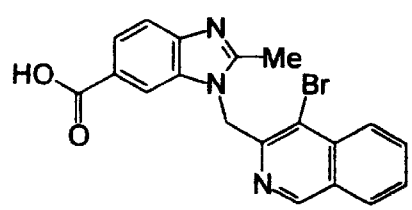
(385)
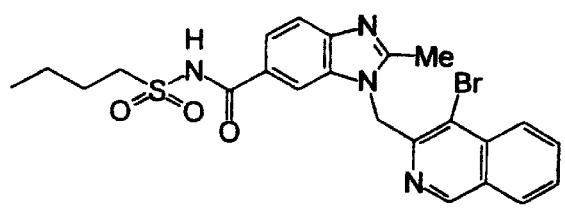
(386)

BENZIMIDAZOLE COMPOUNDS

This application is a continuation of U.S. application Ser. No. 09/091,997, filed Nov. 2, 1998, now U.S. Pat. No. 6,166,219, which is claimed priority from PCT/JP96/03858, filed Dec. 27, 1996, and Japanese Patent Application Nos. 7/43425, filed Dec. 28, 1995, and 8/287676, filed Oct. 8, 1996.

TECHNICAL FIELD

The present invention relates to novel benzimidazole derivatives, and, more precisely, to novel benzimidazole derivatives and their pharmaceutically acceptable salts having blood sugar level-depressing activity or PDE5-inhibiting activity. The present invention also relates to pharmaceutical compositions comprising, as an active ingredient, such benzimidazole derivatives or their salts.

DISCLOSURE OF THE INVENTION

The subject matter of the present invention is to provide novel benzimidazole derivatives and their pharmaceutically acceptable salts, and also pharmaceutical compositions which comprise, as an active ingredient, such benzimidazole derivatives or their pharmaceutically acceptable salts, and which are useful for preventing and treating impaired glucose tolerance, diabetes (type II diabetes), diabetic complications (e.g., diabetic nephropathy, diabetic neuropathy, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), hyperlipidemia, atherosclerosis, cardiovascular disorders (e.g., stenocardia, cardiac failure, etc.), hyperglycemia (e.g., abnormal saccharometabolism such as feeding disorders, etc.), or hypertension; or stenocardia, hypertension, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), allergic rhinitis, urticaria, glaucoma, diseases characterized by enteromotility disorders (e.g., hypersensitive enteropathy syndrome, etc.), impotence (e.g., organic impotence, psychic impotence, etc.), and diabetic complications (e.g., diabetic gangrene, diabetic arthropathy, diabetic glomerulosclerosis, diabetic dermatopathy, diabetic neuropathy, diabetic cataract, diabetic retinopathy, etc.), nephritis, cancerous cachexia, or restenosis after PTCA.

The present inventors provide pharmaceutical compositions comprising, as an active ingredient, any of benzimidazole derivatives of the following formulae (I) to (IV) and (VIII) to (XIV), and their pharmaceutically acceptable salts, which is usable for preventing and treating impaired glucose tolerance, diabetes (type II diabetes), diabetic complications such as diabetic nephropathy, diabetic neuropathy and diabetic retinopathy, syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), hyperlipidemia, atherosclerosis, cardiovascular disorders (e.g., stenocardia, cardiac failure, etc.), hyperglycemia (e.g., abnormal saccharometabolism such as feeding disorders, etc.), or hypertension; or stenocardia, hypertension, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), allergic rhinitis, urticaria, glaucoma, diseases characterized by enteromotility disorders (e.g., hypersensitive enteropathy syndrome, etc.), impotence (e.g., organic impotence, psychic impotence, etc.), and diabetic complications (e.g., diabetic gangrene, diabetic arthropathy, diabetic glomerulosclerosis, diabetic dermatopathy, diabetic neuropathy, diabetic cataract, diabetic retinopathy, etc.), nephritis, cancerous cachexia, or restenosis after PTCA.

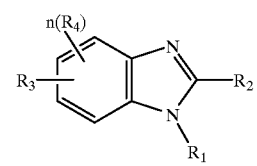

(I)

In formula (I);
$R_1$ represents a hydrogen atom, an arylsulfonyl group, or a lower alkyl group; said lower alkyl group may be substituted by an aryl group or an aryl group substituted by one or two substituents selected from a halogen atom, a haloaryl group, a lower alkyl group, a halo-lower alkyl group, a lower alkoxy group, a nitro group, an amino group, a cyano group, an aryl group, an aryl-lower alkyl group, an aryl-lower alkyloxy group, a haloaryl-lower alkyloxy group, an arylsulfonyl-lower alkyl group, an arylsulfonylamino group, a cyanoaryl group, and a heterocyclic group, or by a heterocyclic group;

$R_2$ represents a hydrogen atom, a lower cycloalkyl group, a hydroxyl group, a lower alkoxy group, a mercapto group, a lower alkylthio group, an amino group, a lower alkylamino group, a carboxyl group, an aryl group, or a lower alkyl group; said lower alkyl group may be substituted by a halogen atom, a lower alkoxy group, a cyano group, a chlorocarbonyl group, an aryl group, or a heterocyclic group;

$R_3$ represents a carboxyl group, an esterified carboxyl group, an amidated carboxyl group, an amino group, an amido group, or a sulfonyl group; said amino group and said amido group may be substituted by an acyl group or a sulfonyl group; and a halogen atom, an amino group, or an acylamino group is bonded to said sulfonyl group; or $R_3$ may be bonded to the skeleton via a lower alkylene or alkenylene group;

$R_4$ represents a neutral substituent; and n means an integer from 0 to 3.

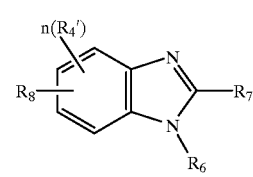

(II)

In formula (II);
$R_6$ represents an aryl-lower alkyl group or an aryl-lower alkyl group substituted by one or two substituents selected from a halogen atom, a haloaryl group, a lower alkyl group, a halo-lower alkyl group, a lower alkoxy group, a nitro group, an amino group, a cyano group, an aryl group, a cyanoaryl group, an aryl-lower alkyloxy group, an arylsulfonyl-lower alkyl group, an arylsulfonylamino group, an aryl-lower alkyl group, and a heterocyclic group;

$R_7$ represents a lower alkyl group or a lower cycloalkyl group;

$R_8$ represents a carbamoyl group, which may be substituted by a lower alkyl group, a lower alkyl group substituted by a substituted or unsubstituted aryl group or a substituted or unsubstituted heterocyclic group, an aryl group, a heterocyclic group, or a group of:

(IIa)

in which $R_9$ represents an alkyl group having up to 8 carbon atoms, a halo-lower alkyl group, an aryl-lower alkyl group, a hydroxy-lower alkyl group, a tri-lower alkylsilyl-lower alkyl group, a lower alkoxy-lower alkyl group, a lower alkylthio-lower alkyl group, a heterocyclic group, or an aryl group; said aryl group may be substituted by a halogen atom, a lower alkyl group, a halo-lower alkyl group, a lower alkoxy group, or a nitro group;

or $R_8$ may be bonded to the skeleton via a lower alkylene or alkenylene group;

$R_4'$ represents a hydrocarbon group or a halogenated hydrocarbon group; and n means an integer from 0 to 3.

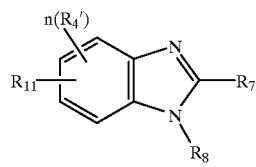

(III)

In formula (III);

$R_6$ represents an aryl-lower alkyl group or an aryl-lower alkyl group substituted by one or two substituents selected from a halogen atom, a lower alkyl group, a halo-lower alkyl group, a lower alkoxy group, a nitro group, an amino group, a cyano group, an aryl group, a haloaryl group, a cyanoaryl group, an aryl-lower alkyloxy group, an arylsulfonyl-lower alkyl group, an arylsulfonylamino group, an aryl-lower alkyl group, and a heterocyclic group;

$R_7$ represents a lower alkyl group or a lower cycloalkyl group;

$R_{11}$ represents a substitutent of a formula:

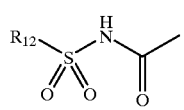

(IIIa)

in which $R_{12}$ represents an alkyl group having up to 8 carbon atoms, a halo-lower alkyl group, an aryl-lower alkyl group, a hydroxy-lower alkyl group, a tri-lower alkylsilyl-lower alkyl group, a lower alkoxy-lower alkyl group, a lower alkylthio-lower alkyl group, a heterocyclic group, or an aryl group; said aryl group may be substituted by a halogen atom, a lower alkyl group, a halo-lower alkyl group, a lower alkoxy group, or a nitro group;

or $R_{11}$ may be bonded to the skeleton via a lower alkylene or alkenylene group;

$R_4'$ represents a hydrocarbon group or a halogenated hydrocarbon group; and n means an integer from 0 to 3.

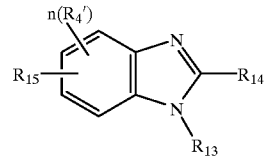

(IV)

In formula (IV);

$R_{13}$ represents an aryl-lower alkyl group or an aryl-lower alkyl group substituted by one or two substituents selected from a halogen atom, a lower alkyl group, a halo-lower alkyl group, a lower alkoxy group, a nitro group, an amino group, a cyano group, an aryl group, a haloaryl group, a cyanoaryl group, an aryl-lower alkyl group, an arylsulfonyl-lower alkyl group, an arylsulfonylamino group, and a heterocyclic group;

$R_{14}$ represents a lower alkyl group;

$R_{15}$ represents a substitutent of a formula:

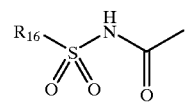

(IVa)

in which $R_{16}$ represents a lower alkyl group or an aryl group;

$R_4'$ represents a hydrocarbon group or a halogenated hydrocarbon group; and n means an integer from 0 to 3.

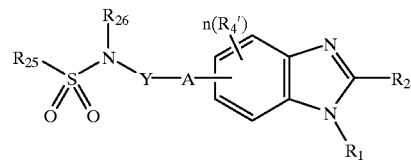

(VIII)

In formula (VIII);

$R_1$ represents a hydrogen atom, an arylsulfonyl group, or a lower alkyl group; said lower alkyl group may be substituted by an aryl group or an aryl group substituted by one or two substituents selected from a halogen atom, a haloaryl group, a lower alkyl group, a halo-lower alkyl group, a lower alkoxy group, a nitro group, an amino group, a cyano group, an aryl group, an aryl-lower alkyloxy group, an arylsulfonyl-lower alkyl group, an aryl-lower alkyl group, a haloaryl-lower alkyloxy group, an arylsulfonylamino group, an arylcarbonylamino group, an arylcarbonyl group, an arylalkenyl group, a cyanoaryl group, and a heterocyclic group, or by a heterocyclic group;

$R_2$ represents a hydrogen atom, a lower cycloalkyl group, a hydroxyl group, a hydroxy-lower alkyl group, a lower alkoxy group, a mercapto group, a lower alkylthio group, an amino group, a lower alkylamino group, a carboxyl group, an aryl group, or a lower alkyl group; said lower alkyl group may be substituted by a halogen atom, a lower alkoxy group, a cyano group, a halocarbonyl group, an aryl group, or a heterocyclic group;

$R_{25}$ represents an alkyl group having up to 8 carbon atoms, a lower cycloalkyl group, a halo-lower alkyl group, a tri-lower alkylsilyl-lower alkyl group, a lower alkoxy-lower alkyl group, a lower alkylthio-lower alkyl group, an aryl group, a heterocyclic group, an aryl-lower alkyl group, or a hydroxy-halogen alkyl group; said aryl group may be substituted by a halogen atom, a lower alkyl group, a halo-lower alkyl group, a lower alkoxy group, or a nitro group;

$R_{26}$ represents a hydrogen atom or a lower alkyl group; provided that, when $R_{25}$ and $R_{26}$ are both lower alkyl groups, they may be bonded together to form a ring;

Y represents a carbonyl group or a lower alkylene group;

A represents a single bond, or a lower alkylene or alkenylene group;

$R_4'$ represents a hydrocarbon group or a halogenated hydrocarbon group; and n means an integer from 0 to 3.

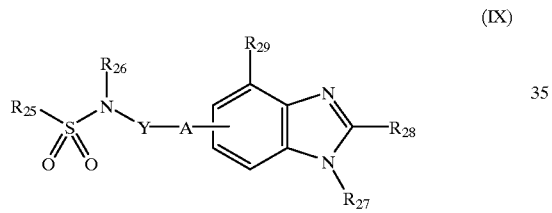

(IX)

In formula (IX);

$R_{27}$ represents a hydrogen atom, an alkyl group having up to 7 carbon atoms, a halo-lower alkyl group, an arylsulfonyl group, an aryl-lower alkyl group, a heterocyclic lower alkyl group, or a halo-heterocyclic lower alkyl group; and the aromatic ring moiety in said aryl-lower alkyl group may be substituted by one or two substituents selected from a halogen atom, a lower alkyl group, a halo-lower alkyl group, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, an aryloxy group, an arylcarbonyl group, an arylcarbonylamino group, and an aryl-lower alkyloxy group substituted by one or two halogen atoms;

$R_{28}$ represents a hydrogen atom, an alkyl group having up to 7 carbon atoms, a halo-lower alkyl group, a lower alkoxy-lower alkyl group, a lower cycloalkyl group, an aryl group, an aryl-lower alkyl group, a lower alkylamino group, a lower alkoxy group, a lower alkylthio group, a hydroxyl group, a mercapto group, an amino group, or a carboxyl group;

$R_{25}$ represents an alkyl group having up to 8 carbon atoms, a halo-lower alkyl group, a tri-lower alkylsilyl-lower alkyl group, a lower alkoxy-lower alkyl group, a lower alkylthio-lower alkyl group, an aryl group, a heterocyclic group, an aryl-lower alkyl group, or a hydroxy-lower alkyl group; and said aryl group may be substituted by a halogen atom, a lower alkyl group, a halo-lower alkyl group, a lower alkoxy group, or a nitro group;

$R_{26}$ represents a hydrogen atom or a lower alkyl group; provided that, when $R_{25}$ and $R_{26}$ are both lower alkyl groups, they may be bonded together to form a ring;

Y represents a carbonyl group or a lower alkylene group;

A represents a single bond, or a lower alkylene or alkenylene group; and $R_{29}$ represents a hydrogen atom or a lower alkyl group.

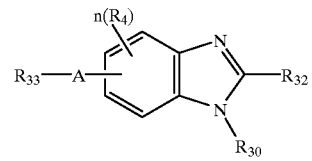

(X)

In formula (X);

$R_{30}$ represents a hydrogen atom, a lower alkyl group, a substituted or unsubstituted aryl-lower alkyl group of a formula:

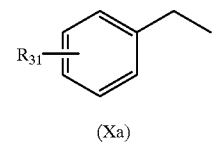

(Xa)

(Xa)

in which $R_{31}$ represents a hydrogen atom, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, or an aryloxy group, or represents an aryl-lower alkyloxy group or an aryl-lower alkyloxy group substituted by one or two halogen atoms, an arylsulfonyl group, a heterocyclic lower alkyl group, an arylcarbonylamino group, an arylcarbonyl group, an arylalkenyl group, or a lower alkylenedioxyaryl group; and the alkyl moiety in said aryl-lower alkyl group may be substituted by a lower alkyl group;

$R_{32}$ represents a hydrogen atom, a lower alkyl group, a halo-lower alkyl group, a lower cycloalkyl group, an aryl group, an aryl-lower alkyl group, a lower alkylamino group, a lower alkoxy group, a lower alkylthio group, a lower alkoxy-lower alkyl group, or a heterocyclic lower alkyl group;

$R_{33}$ represents a carboxyl group, a lower alkoxycarbonyl group, a (2-cyanoaryl)oxycarbonyl group, or a group of a formula:

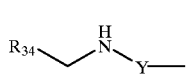
(Xb)

in which Y represents a carbonyl group or a lower alkylene group; $R_{34}$ represents a lower alkyl group or a lower alkyl group substituted by a substituted or unsubstituted aryl or heterocyclic group, or represents an aryl group or a heterocyclic group;

A represents a single bond, or a lower alkylene or alkenylene group;

$R_4'$ represents a hydrocarbon group or a halogenated hydrocarbon group. $R_4'$ may include an alkyl group, an aralkyl group, an alkynyl group, and halogenated groups of these. $R_4'$ may be either saturated or unsaturated, may be either linear or cyclic, and may even be branched, as the case may be. For the halogenated groups, the type of the halogen therein is not specifically defined, and the number of the halogen substituents therein is not also specifically defined. n means an integer from 0 to 3. Therefore, one, two or three $R_4$'s may be bonded to the skeleton, or no $R_4'$ may be bonded thereto. The position of $R_4'$ is not specifically defined and may be any of the ortho-position, the meta-position and the para-position relative to the other substituent. However, when $R_{30}$ is a hydrogen atom, n is 0, or that is, no $R_4'$ is bonded to the skeleton.

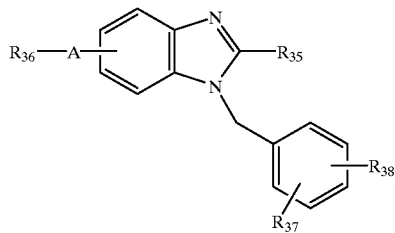
(XI)

In formula (XI);

$R_{35}$ represents a hydrogen atom, an aryl group, a lower alkoxy-lower alkyl group, a lower alkyl group, or an aryl-lower alkyl group;

$R_{36}$ represents a carboxyl group, a lower alkoxycarbonyl group, a heterocyclic lower alkylamino group, or a heterocyclic lower alkylcarbamoyl group;

$R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group; and A represents a single bond, or a lower alkylene or alkenylene group; provided that, when $R_{35}$ is a lower alkyl group, A is a lower alkylene group or a lower alkenylene group.

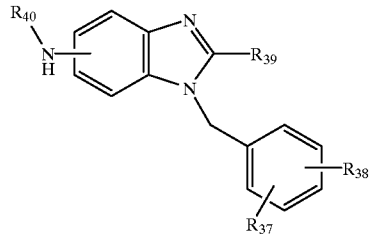
(XII)

In formula (XII);

$R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group;

$R_{39}$ represents a lower alkyl group; and $R_{40}$ represents a hydrogen atom, a lower alkoxycarbonyl group, a lower alkanoyl group, a lower alkanesulfonyl group, or a carbamoyl group.

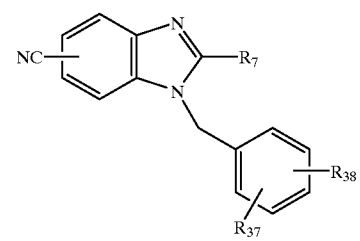
(XIII)

In formula (XIII);

$R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group; and $R_7$ represents a lower alkyl group or a lower cycloalkyl group.

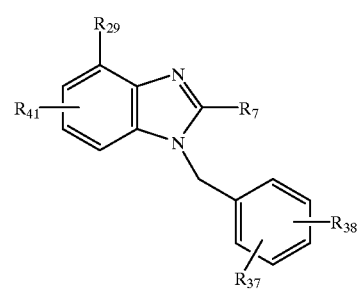
(XIV)

In formula (XIV);

$R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group;

$R_7$ represents a lower alkyl group or a lower cycloalkyl group;

$R_{41}$ represents a 2-pyridylcarbamoyl group, a 2-carboxy-1-pyrrolidinocarbonyl group, an N-methyl-N-(2-pyridylmethyl)carbamoyl group, a homopiperidinocarbonyl group, a [2-(N-oxo)-pyridylmethyl]carbamoyl group, a 4-(dimethylamino)benzylcarbamoyl group, a piperonylcarbamoyl group, an N-methyl-N-(2-pyridyl)carbamoyl group, a thiomorpholinocarbonyl group, a halosulfonyl group, an aminosulfonyl group, an acylaminosulfonyl group, a lower alkoxycarbonyl group, or a carboxyl group;

$R_{29}$ represents a hydrogen atom, or a lower alkyl group; provided that, when $R_{41}$ is a lower alkylcarbonyl group or a carboxyl group, $R_{29}$ is a lower alkyl group.

The present invention also provides novel benzimidazole derivatives of the above-mentioned (VIII) to (XIV) and their salts.

Benzimidazole derivatives to be provided by the present invention can be produced according to the following reaction formulae (a) to (f):

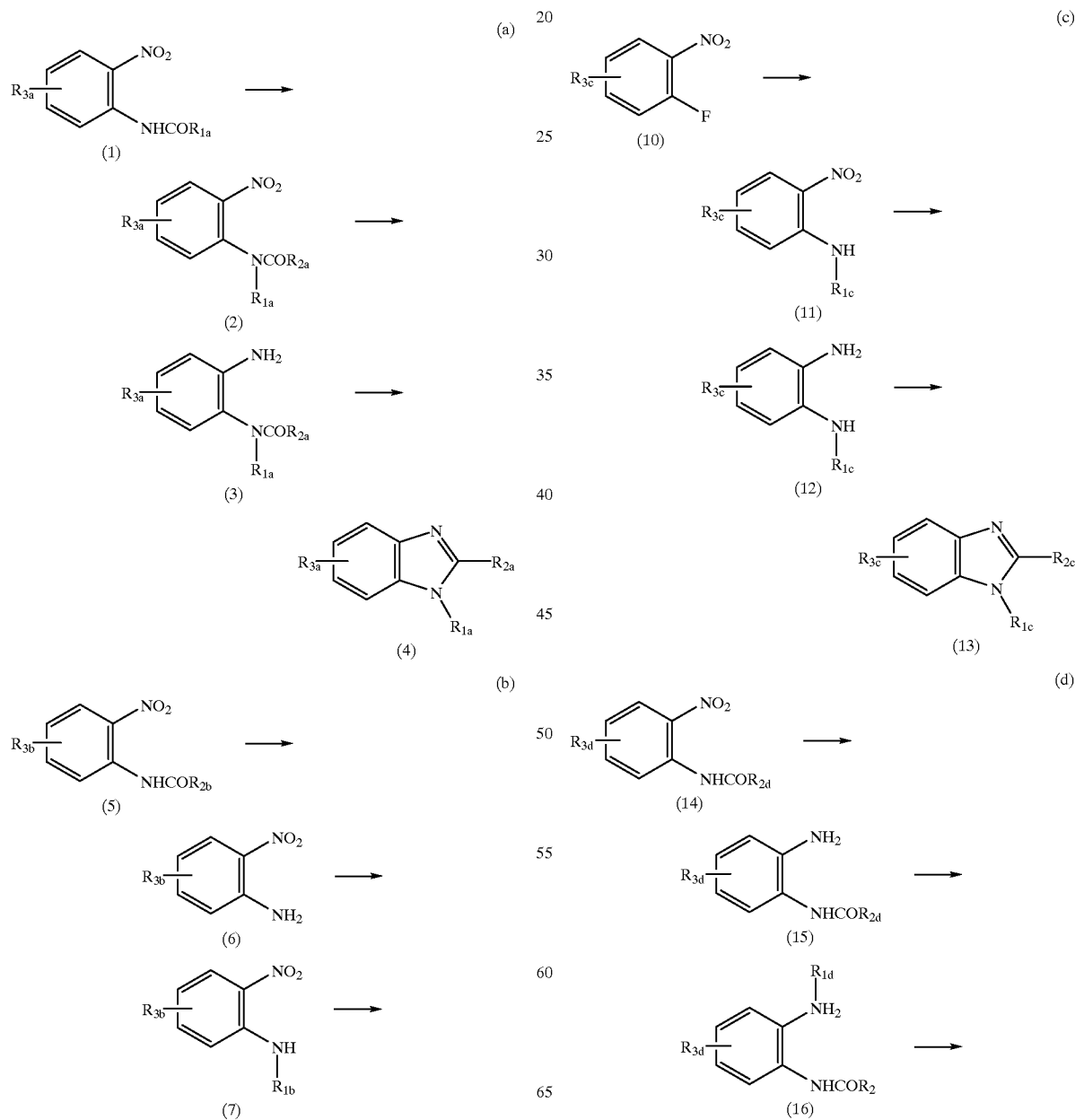

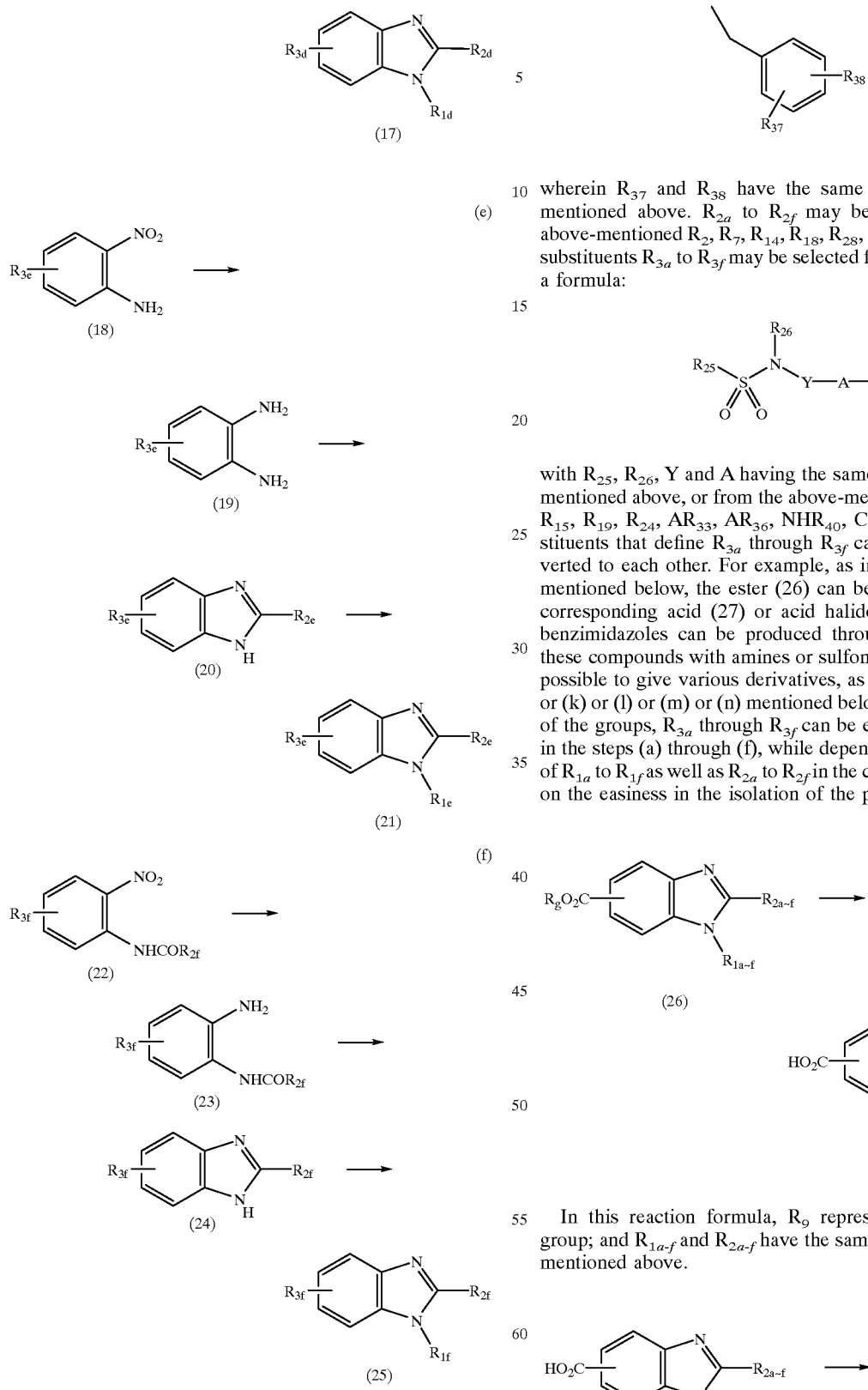

wherein $R_{37}$ and $R_{38}$ have the same meanings as those mentioned above. $R_{2a}$ to $R_{2f}$ may be selected from the above-mentioned $R_2$, $R_7$, $R_{14}$, $R_{18}$, $R_{28}$, $R_{32}$, $R_{35}$ or $R_{39}$. The substituents $R_{3a}$ to $R_{3f}$ may be selected from a substituent of a formula:

with $R_{25}$, $R_{26}$, Y and A having the same meanings as those mentioned above, or from the above-mentioned $R_3$, $R_8$, $R_{11}$, $R_{15}$, $R_{19}$, $R_{24}$, $AR_{33}$, $AR_{36}$, $NHR_{40}$, CN or $R_{41}$. The substituents that define $R_{3a}$ through $R_{3f}$ can be mutually converted to each other. For example, as in the step (g) or (h) mentioned below, the ester (26) can be converted into the corresponding acid (27) or acid halide (28). The desired benzimidazoles can be produced through the reaction of these compounds with amines or sulfonamides. It is further possible to give various derivatives, as in the step (i) or (j) or (k) or (l) or (m) or (n) mentioned below. Such conversion of the groups, $R_{3a}$ through $R_{3f}$ can be effected at any stage in the steps (a) through (f), while depending on the stability of $R_{1a}$ to $R_{1f}$ as well as $R_{2a}$ to $R_{2f}$ in the compounds and even on the easiness in the isolation of the products formed.

In this reaction formula, $R_9$ represents a lower alkyl group; and $R_{1a-f}$ and $R_{2a-f}$ have the same meanings as those mentioned above.

In the above-mentioned reaction formulae, $R_{1a}$ to $R_{1f}$ may be selected from the above-mentioned $R_1$, $R_6$, $R_{13}$, $R_{17}$, $R_{22}$, $R_{23}$, $R_{27}$, $R_{30}$, or a substituted benzyl group of a formula:

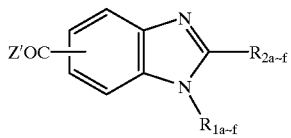

(28)

In this reaction formula, Z' represents a chlorine atom or a bromine atom; and $R_{1a-f}$ and $R_{2a-f}$ have the same meanings as those mentioned above.

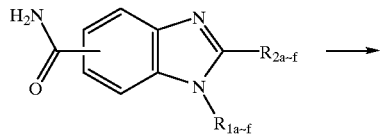

(29)

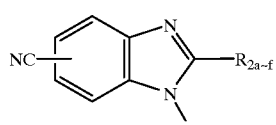

(30)

In this reaction formula, $R_{1a-f}$ and $R_{2a-f}$ have the same meanings as those mentioned above.

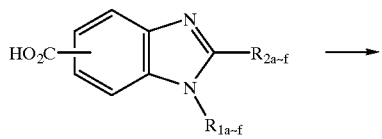

(27)

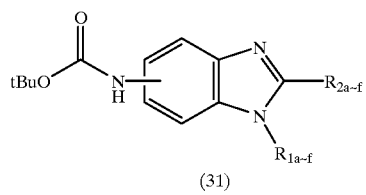

(31)

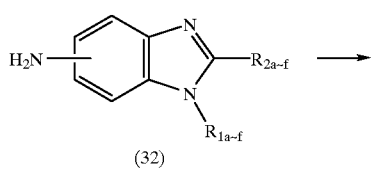

(32)

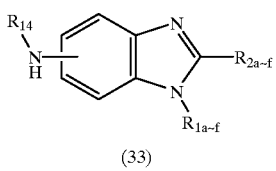

(33)

In this reaction formula, $R_{1a-f}$ and $R_{2a-f}$ have the same meanings as those mentioned above.

In the reaction step (a), a compound of formula (1) may be reacted with a base, such as sodium hydride, lithium diisopropylamide, lithium hydrogencarbonate, lithium carbonate, lithium hydroxide, sodium hydrogencarbonate, sodium carbonate, sodium hydroxide, potassium hydrogencarbonate, potassium carbonate, potassium hydroxide or the like, and with a compound to be represented by $R_{1a}Z$ (where Z represents a chlorine atom, a bromine atom, a toluenesulfonyloxy group, or a methanesulfonyloxy group) to give a compound of formula (2). The compound of formula (2) may be 1) reduced with reduced iron or zinc under an acidic condition, or 2) reduced with a transition metal catalyst, such as typically palladium, platinum, ruthenium or nickel, in a hydrogen atmosphere, or 3) reduced with a transition metal catalyst, such as typically palladium, platinum, ruthenium or nickel, in the presence of formic acid, or 4) reduced with sodium hydrosulfite, to be converted into a compound of formula (3). In the process 1), the compound of formula (3) is often cyclized in the reaction system directly into a compound of formula (4). Depending on the compound of formula (2) being reduced, the compound of formula (4) may be partly formed in any of the processes 1) to 4). The compound of formula (3) may be processed with a carboxylic acid, a sulfonic acid or an inorganic acid, such as acetic acid, p-toluenesulfonic acid, hydrochloric acid, sulfuric acid, phosphoric acid or the like, to give the compound of formula (4).

In the step (b), a compound of formula (5) is may be hydrolyzed or solvolyzed with a base, such as lithium hydrogencarbonate, lithium carbonate, lithium hydroxide, sodium hydrogencarbonate, sodium carbonate, sodium hydroxide, potassium hydrogencarbonate, potassium carbonate, potassium hydroxide or the like, or with a carboxylic acid, a sulfonic acid or inorganic acid, such as acetic acid, p-toluenesulfonic acid, hydrochloric acid, sulfuric acid, phosphoric acid or the like, into a compound of formula (6). The compound of formula (6) may be reacted with a base, such as sodium hydride, lithium diisopropylamide, lithium hydrogencarbonate, lithium carbonate, lithium hydroxide, sodium hydrogencarbonate, sodium carbonate, sodium hydroxide, potassium hydrogencarbonate, potassium carbonate, potassium hydroxide or the like, and with a compound to be represented by $R_{1b}Z$ (where Z represents a chlorine atom, a bromine atom, a toluenesulfonyloxy group, or a methanesulfonyloxy group) to give a compound of formula (7). The compound of formula (7) may be 1) reduced with reduced iron or zinc under an acidic condition, or 2) reduced with a transition metal catalyst, such as typically palladium, platinum, ruthenium or nickel, in a hydrogen atmosphere, or 3) reduced with a transition metal catalyst, such as typically palladium, platinum, ruthenium or nickel, in the presence of formic acid, or 4) reduced with sodium hydrosulfite, to be converted into a compound of formula (8). A compound of formula (9) can be produced from the compound of formula (8) and the corresponding carboxylic acid or acid chloride or acid bromide or acid anhydride.

In the step (c), a compound of formula (11) can be produced from a compound of formula (10) and a compound to be represented by $R_{1c}NH_2$. The conversion of the compound of formula (11) to a compound of formula (13) is the same as that of the compound of formula (7) to the compound of formula (9) in the step (b).

In the step (d), a compound of formula (14) may be 1) reduced with a transition metal catalyst such as typically palladium, platinum, ruthenium or nickel in a hydrogen atmosphere, or 2) reduced with sodium hydrosulfite to give a compound of formula (15). The compound of formula (15) may be reacted with a base, such as lithium hydrogencarbonate, lithium carbonate, lithium hydroxide, sodium hydrogencarbonate, sodium carbonate, sodium hydroxide, potassium hydrogencarbonate, potassium carbonate, potassium hydroxide or the like, and with a compound to be represented by $R_{1d}Z$ (where Z represents a chlorine atom, a bromine atom, a toluenesulfonyloxy group, or a methanesulfonyloxy group) to give a compound of formula (16). The compound of formula (16) may be treated with a carboxylic acid, a sulfonic acid or an inorganic acid, such as acetic acid, p-toluenesulfonic acid, hydrochloric acid, sulfuric acid, phosphoric acid or the like, to give a compound of formula (17).

In the step (e), a compound of formula (18) may be (1) reduced with reduced iron or zinc under an acidic condition, or 2) reduced with a transition metal catalyst, such as typically palladium, platinum, ruthenium or nickel, in a hydrogen atmosphere, or 3) reduced with a transition metal catalyst, such as typically palladium, platinum, ruthenium or nickel, in the presence of formic acid, or 4) reduced with sodium hydrosulfite, to be converted into a compound of formula (19). A compound of formula (20) can be produced from the compound of formula (19) and the corresponding carboxylic acid or acid anhydride or acid chloride or acid bromide. The compound of formula (20) may be reacted with a base, such as sodium hydride, lithium diisopropylamide, lithium hydrogencarbonate, lithium carbonate, lithium hydroxide, sodium hydrogencarbonate, sodium carbonate, sodium hydroxide, potassium hydrogencarbonate, potassium carbonate, potassium hydroxide or the like, and with a compound to be represented by $R_{1e}Z$ (where Z represents a chlorine atom, a bromine atom, a toluenesulfonyloxy group, or a methanesulfonyloxy group) to give a compound of formula (21).

In the process comprising the above-mentioned step, in general, the product may be obtained as a mixture comprising the compound of formula (21) where $R_{3e}$ is positioned in the 5-position and that where it is in the 6-position, or a mixture comprising the compound of formula (21) where $R_{3e}$ is positioned in the 4-position and that where it is in the 7-position. Each compound of formula (21) can be purified from the mixture as the single compound, for example, through recrystallization, column chromatography, thin-layer chromatography, high-performance liquid chromatography or the like.

In the step (f), a compound of formula (22) may be 1) reduced with reduced iron or zinc under an acidic condition, or 2) reduced with a transition metal catalyst, such as typically palladium, platinum, ruthenium or nickel, in a hydrogen atmosphere, or 3) reduced with a transition metal catalyst, such as typically palladium, platinum, ruthenium or nickel, in the presence of formic acid, or 4) reduced with sodium hydrosulfite, to be converted into a compound of formula (23). In the process 1), the compound of formula (23) is often cyclized in the reaction system directly into a compound of formula (24). Depending on the compound of formula (22) being reduced, the compound of formula (24) may be partly formed in any of the processes 1) to 4). The compound of formula (23) may be processed with a carboxylic acid, a sulfonic acid or an inorganic acid, such as acetic acid, p-toluenesulfonic acid, hydrochloric acid, sulfuric acid, phosphoric acid or the like, to give the compound of formula (24). The compound of formula (24) may be converted into a benzimidazole compound of formula (25) in the same manner as in the step (e) of converting the compound of formula (20) into the compound of formula (21). In this step, in general, the product may be obtained as a mixture comprising the compound of formula (25) where $R_{3f}$ is positioned in the 5-position and that where it is in the 6-position, or a mixture comprising the compound of formula (25) where $R_{3f}$ is positioned in the 4-position and that where it is in the 7-position. Each compound of formula (25) can be purified from the mixture as the single compound, for example, through recrystallization, column chromatography, thin-layer chromatography, high-performance liquid chromatography or the like.

In the step (g), a compound of formula (26) may be hydrolyzed with a base, such as lithium hydroxide, sodium hydroxide, potassium hydroxide or the like, to give a compound of formula (27). The compound of formula (27) may be reacted with a carbonyldiimidazole and then with amines or sulfonamides in the presence of a base to give different benzimidazole derivatives.

In the step (h), the compound of formula (27) may be processed with thionyl chloride or thionyl bromide or phosphorus trichloride or phosphorus pentachloride or phosphorus oxychloride to be converted into its acid halide of formula (28). The compound of formula (28) may be reacted with amines or sulfonamides to give different benzimidazole derivatives.

In the step (i), a compound of formula (29) may be reacted with titanium tetrachloride to give a compound of formula (30).

In the step (j), the compound of formula (27) may be reacted with an azide, such as typically diphenylphosphorylazide, in the presence of an alcohol, such as typically t-butanol, to give a compound of formula (31). The compound of formula (31) may be decomposed with an acid to give a compound of formula (32). The compound of formula (32) may be reacted with a compound to be represented by $R_{40}Z$ (where Z represents a chlorine atom or a bromine atom) to give a compound of formula (33).

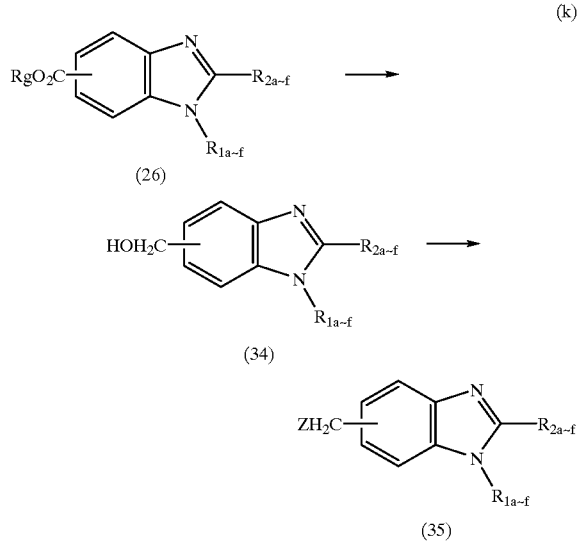

wherein $R_g$, $R_{1a-f}$, and $R_{2a-f}$ have the same meanings as those mentioned above; and Z represents a chlorine atom, a bromine atom, a toluenesulfonyloxy group, or a methanesulfonyloxy group.

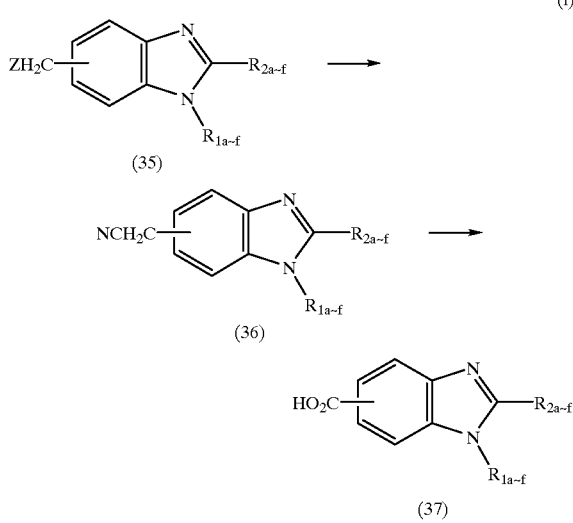

(l)

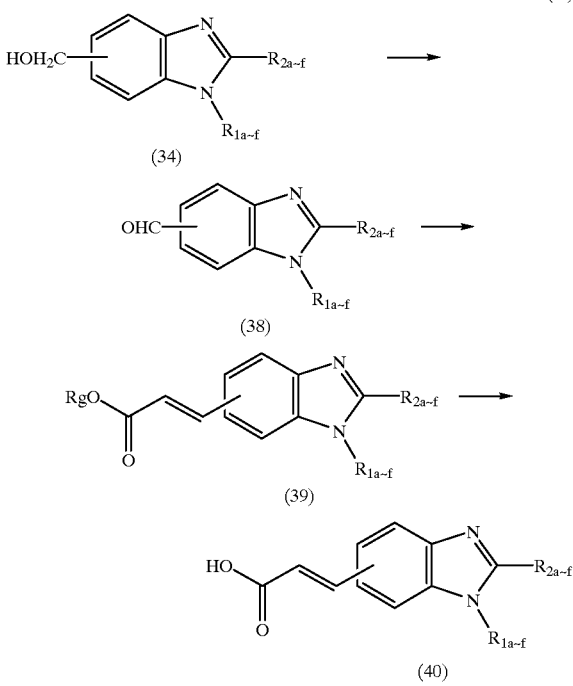

wherein $R_{1a-f}$, $R_{2a-f}$ and Z have the same meanings as those mentioned above.

(m)

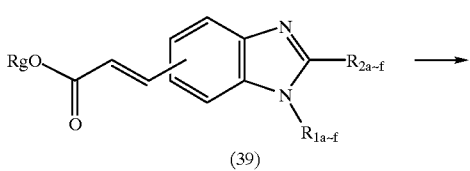

wherein $R_{1a-f}$, $R_{2a-f}$ and $R_9$ have the same meanings as those mentioned above.

(n)

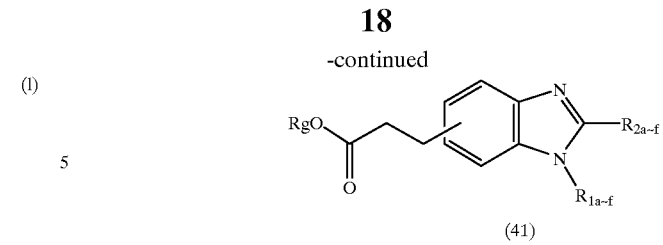

wherein $R_{1a-f}$, $R_{2a-f}$ and $R_9$ have the same meanings as those mentioned above.

In the step (k), the compound of formula (26) may be reduced into a compound of formula (34), which may be then treated with thionyl chloride, thionyl bromide, phosphorus oxychloride, phosphorus oxybromide, phosphorus trichloride, phosphorus pentachloride, methanesulfonyl chloride, toluenesulfonyl chloride or the like to be converted into a compound of formula (35).

In the step (l), the compound of formula (35) may be reacted with sodium cyanide or potassium cyanide to give a compound of formula (36), which may be then hydrolyzed with lithium hydroxide or sodium hydroxide or potassium hydroxide to give a carboxylic acid of formula (37).

In the step (m), a compound of formula (38) to be obtained by oxidizing the compound of formula (34) may be reacted with an alkyl (triphenylphosphoranilidene)acetate to give a compound of formula (39), which may then be hydrolyzed with lithium hydroxide or sodium hydroxide or potassium hydroxide to give a carboxylic acid of formula (40). The compound of formula (35), (37) or (40) may be reacted with amines or sulfonylamides to give different benzimidazole compounds.

In the step (n), the compound of formula (39) may be reduced with palladium, platinum, ruthenium or the like transition metal catalyst in a hydrogen atmosphere or in the presence of formic acid to give a compound of formula (41).

The following compounds of:

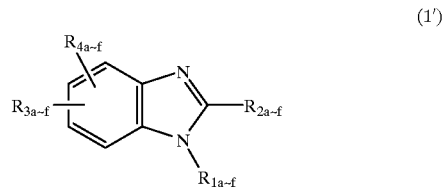

where $R_{1a-f}$, $R_{2a-f}$ and $R_{3a-f}$ have the same meanings as those mentioned above; and $R_{4a-f}$ may be selected from the above-mentioned $R_4$, $R_4'$ and $R_{29}$, can be produced according to the steps (a) to (f) while starting from the following compounds of:

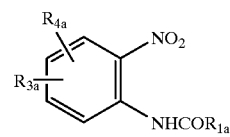

where $R_{1a}$, $R_{2a}$ and $R_{3a}$ have the same meanings as those mentioned above; and $R_{4a}$ may be selected from the above-mentioned $R_4$, $R_4'$ and $R_{29}$;

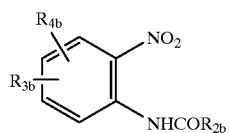

(3')

where $R_{1b}$, $R_{2b}$ and $R_{3b}$ have the same meanings as those mentioned above; and $R_{4b}$ may be selected from the above-mentioned $R_4$, $R_4'$ and $R_{29}$;

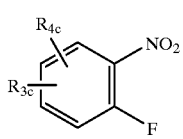

(4')

where $R_{1c}$, $R_{2c}$ and $R_{3c}$ have the same meanings as those mentioned above; and $R_{4c}$ may be selected from the above-mentioned $R_4$, $R_4'$ and $R_{29}$;

(5')

where $R_{1d}$, $R_{2d}$ and $R_{3d}$ have the same meanings as those mentioned above; and $R_{4d}$ may be selected from the above-mentioned $R_4$, $R_4'$ and $R_{29}$;

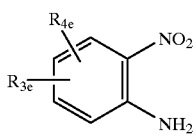

(6')

where $R_{1e}$, $R_{2e}$ and $R_{3e}$ have the same meanings as those mentioned above; and $R_{4e}$ may be selected from the above-mentioned $R_4$, $R_4'$ and $R_{29}$;

(7')

where $R_{1f}$, $R_{2f}$ and $R_{3f}$ have the same meanings as those mentioned above; and $R_{4f}$ may be selected from the above-mentioned $R_4$, $R_4'$ and $R_{29}$.

If desired, the intermediates formed in the above-mentioned steps may optionally be purified, prior to being subjected to the next step, through any conventional purification including, for example, recrystallization, column chromatography, thin-layer chromatography, high-performance liquid chromatography and the like. If also desired, the final products of the compounds of the present invention may optionally be purified through any conventional purification which is employed in the art of purifying organic compounds and which includes, for example, recrystallization, column chromatography, thin-layer chromatography, high-performance liquid chromatography and the like. To identify these compounds, employable is any of NMR spectrography, mass spectrography, IR spectrography, elementary analysis, measurement of melting point and others.

Preferred embodiments and their details of various definitions as referred to herein to be within the scope of the present invention are described below.

Unless otherwise specifically indicated herein, the terminology "lower" indicates that the group has from 1 to 6 carbon atoms. As preferred examples of the lower alkyl group as referred to herein, mentioned are linear or branched alkyl groups including a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 1,1-dimethylbutyl group, a 2,2-dimethylbutyl group, a 3,3-dimethylbutyl group, a 1-ethyl-1-methyl propyl groups, etc.

The alkyl group having up to 7 carbon atoms is a linear or branched alkyl group, including a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, etc.

The alkyl group having up to 8 carbon atoms is a linear or branched alkyl group, including a methyl group, an ethyl group, an n-propyl group, an i-propyl group, an n-butyl group, an i-butyl group, a sec-butyl group, a t-butyl group, an n-pentyl group, an i-pentyl group, a sec-pentyl group, a t-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethylbutyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methylhexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propylbutyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3- dimethylhexyl group, a 4,4-dimethylhexyl group, a 5,5-dimethylhexyl group, a 1-propylpentyl group, a 2-propylpentyl group, etc.

The lower alkylene group is an alkylene group having 6 or less carbon atoms, including a methylene group, an ethylene group, a propylene group, a butylene group, a pentylene group, a hexylene group, etc. The lower alkenylene group is an alkenylene group having 6 or less carbon atoms, including an ethenylene group, a 1-propenylene group, a 2-propenylene group, a 1-butenylene group, a 2-butenylene group, a 3-butenylene group, a 1-pentenylene group, a 2-pentenylene group, a 3-pentenylene group, a 4-pentenylene group, a 1-hexenylene group, a 2-hexenylene group, a 3-hexenylene group, a 4-hexenylene group, a 5-hexenylene group, etc.

The halogen atom includes a fluorine atom, a chlorine atom, a bromine atom and an iodine atom. Preferred are a fluorine atom, a chlorine atom and a bromine atom.

The halo-lower alkyl group is a linear or branched alkyl group having up to 8 carbon atoms, which is substituted with one or more halogen atoms selected from fluorine, chlorine, bromine and iodine atoms. Preferred is a linear or branched alkyl group having up to 8 carbon atoms, which is substituted with one or more halogen atoms selected from fluorine, chlorine and bromine atoms. It includes, for example, a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromoethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc.

The lower alkoxy group is a linear or branched alkyloxy group having up to 6 carbon atoms. It includes, for example, a methoxy group, an ethoxy group, an n-propyloxy group, an i-propyloxy group, an n-butyloxy group, an i-butyloxy group, a sec-butyloxy group, a t-butyloxy group, an n-pentyloxy group, an i-pentyloxy group, a sec-pentyloxy group, a t-pentyloxy group, a 2-methylbutoxy group, an n-hexyloxy group, an i-hexyloxy group, a t-hexyloxy group, a sec-hexyloxy group, a 2-methylpentyloxy group, a 3-methylpentyloxy group, a 1-ethylbutyloxy group, a 2-ethylbutyloxy group, a 1,1-dimethylbutyloxy group, a 2,2-dimethylbutyloxy group, a 3,3-dimethylbutyloxy group, a 1-ethyl-1-methylpropyloxy group, etc. Preferred are a methoxy group, an ethoxy group, an n-propyloxy group, an i-propyloxy group, an n-butyloxy group, an i-butyloxy group, a sec-butyloxy group, a t-butyloxy group, etc.

The lower cycloalkyl group is a cycloalkyl group having from 3 to 7 carbon atoms, and preferably includes a cyclopropyl group, a cyclobutyl group, a cyclopentyl group, a cyclohexyl group, a cycloheptyl group, etc. More preferred are a cyclopropyl group, a cyclobutyl group, etc.

The lower alkoxy-lower alkyl group is a linear or branched alkyl group having up to 8 carbon atoms, as substituted with a linear or branched alkyloxy group having up to 8 carbon atoms. For example, this includes a methoxymethyl group, a methoxyethyl group, a methoxypropyl group, a methoxybutyl group, a methoxypentyl group, a methoxyhexyl group, a methoxyheptyl group, a methoxyoctyl group, an ethoxymethyl group, an ethoxyethyl group, an ethoxybutyl group, an ehtoxypentyl group, an ehtoxyhexyl group, an ethoxyheptyl group, a ethoxyoctyl group, a propyloxymethyl group, a propyloxyethyl group, a propyloxypropyl group, a propyloxybutyl group, a propyloxypentyl group, an i-propyloxymethyl group, an i-propyloxyethyl group, an i-propyloxypropyl group, an i-propyloxybutyl group, an i-propyloxypentyl group, a butyloxymethyl group, a butyloxyethyl group, a butyloxypropyl group, a butyloxybutyl group, an i-butyloxymethyl group, an i-butyloxyethyl group, an i-butyloxypropyl group, an i-butyloxybutyl group, a sec-butyloxymethyl group, a sec-butyloxyethyl group, a sec-butyloxypropyl group, a sec-butyloxybutyl group, a t-butyloxymethyl group, a t-butyloxyethyl group, a t-butyloxypropyl group, a t-butyloxybutyl group, a pentyloxymethyl group, a pentyloxyethyl group, a pentyloxypropyl group, a pentyloxybutyl group, a hexyloxymethyl group, a hexyloxyethyl group, a hexyloxypropyl group, etc.

The tri-lower alkylsilyl-lower alkyl group is a lower alkyl group, such as that mentioned hereinabove, to which is bonded a trimethylsilyl group, a triethylsilyl group, a tripropylsilyl group or the like.

The lower alkylamino group is a linear or branched alkylamino group having up to 6 carbon atoms. This includes, for example, a methylamino group, an ethylamino group, an n-propylamino group, an i-propylamino group, an n-butylamino group, an i-butylamino group, a sec-butylamino group, a t-butylamino group, an n-pentylamino group, an i-pentylamino group, a sec-pentylamino group, a t-pentylamino group, a 2-methylbutylamino group, an n-hexylamino group, a 1-methylpentylamino group, a 2-methylpentylamino group, a 3-methylpentylamino group, a 4-methylpentylamino group, a 1-ethylbutylamino group, a 2-ethylbutylamino group, a 3-ethylbutylamino group, a 1,1-dimethylbutylamino group, a 2,2-dimethylbutylamino group, a 3,3-dimethylbutylamino group, a 1-ethyl-1-methylpropylamino group, etc. More preferred are a methylamino group, an ethylamino group, an n-propylamino group, an i-propylamino group, an n-butylamino group, an i-butylamino group, a sec-butylamino group, a t-butylamino group, etc.

The lower alkylthio group is a linear or branched alkylthio group having up to 6 carbon atoms. This includes, for example, a methylthio group, an ethylthio group, an n-propylthio group, an i-propylthio group, an n-butylthio group, an i-butylthio group, a sec-butylthio group, a t-butylthio group, an n-pentylthio group, an i-pentylthio group, a sec-pentylthio group, a t-pentylthio group, a 2-methylbutylthio group, an n-hexylthio group, an i-hexylthio group, a t-hexylthio group, a sec-hexylthio group, a 2-methylpentylthio group, a 3-methylpentylthio group, a 1-ethylbutylthio group, a 2-ethylbutylthio group, a 1,1-dimethylbutylthio group, a 2,2-dimethylbutylthio group, a 3,3-dimethylbutylthio group, a 1-ethyl-1-methylpropylthio group, etc. More preferred are a methylthio group, an ethylthio group, an n-propylthio group, an i-propylthio group, an n-butylthio group, an i-butylthio group, a sec-butylthio group, a t-butylthio group, etc.

The lower alkylthio-lower alkyl group is a linear or branched alkyl group having up to 6 carbon atoms, such as that mentioned hereinabove, as substituted with a linear or branched alkylthio group having up to 6 carbon atoms, such as that mentioned hereinabove.

The lower alkoxycarbonyl group is a linear or branched alkyloxycarbonyl group with a alkyl moiety having up to 6 carbon atoms. This includes, for example, a methoxycarbonyl group, an ethoxycarbonyl group, an n-propyloxycarbonyl group, an i-propyloxycarbonyl group, an n-butyloxycarbonyl group, an i-butyloxycarbonyl group, a sec-butyloxycarbonyl group, a t-butyloxycarbonyl group, an n-pentyloxycarbonyl group, an i-pentyloxycarbonyl group, a sec-pentyloxycarbonyl group, a t-pentyloxycarbonyl group, a 2-methylbutyloxycarbonyl group, an n-hexyloxycarbonyl group, an i-hexyloxycarbonyl group, a t-hexyloxycarbonyl group, a sec-hexyloxycarbonyl group, a 2-methylpentyloxycarbonyl group, a 3-methylpentyloxycarbonyl group, a 1-ethylbutyloxycarbonyl group, a 2-ethylbutyloxycarbonyl group, a 1,1-dimethylbutyloxycarbonyl group, a 2,2-dimethylbutyloxycarbonyl group, a 3,3-dimethylbutyloxycarbonyl group, a 1-ethyl-1-methylpropyloxycarbonyl group, etc. More preferred are a methoxycarbonyl group, an ethoxycarbonyl group, an n-propyloxycarbonyl group, an i-propyloxycarbonyl group, an n-butyloxycarbonyl group, an i-butyloxycarbonyl group, a sec-butyloxycarbonyl group, a t-butyloxycarbonyl group.

The lower alkanoyl group is a linear or branched alkylcarbonyl group having up to 6 carbon atoms. This includes, for example, a methylcarbonyl group, an ethylcarbonyl group, an n-propylcarbonyl group, an i-propylcarbonyl group, an n-butylcarbonyl group, an i-butylcarbonyl group, a sec-butylcarbonyl group, a t-butylcarbonyl group, an n-pentylcarbonyl group, an i-pentylcarbonyl group, a sec-pentylcarbonyl group, a t-pentylcarbonyl group, a 2-methylbutylcarbonyl group, an n-hexylcarbonyl group, an i-hexylcarbonyl group, a t-hexylcarbonyl group, a sec-hexylcarbonyl group, a 2-methylpentylcarbonyl group, a 3-methylpentylcarbonyl group, a 1-ethylbutylcarbonyl group, a 2-ethylbutylcarbonyl group, an 1,1-dimethylbutylcarbonyl group, a 2,2-dimethylbutylcarbonyl group, a 3,3-dimethylbutylcarbonyl group, a 1-ethyl-1-methylpropylcarbonyl group, etc. More preferred are a methylcarbonyl group, an ethylcarbonyl group, an n-propylcarbonyl group, an i-propylcarbonyl group, an n-butylcarbonyl group, an i-butylcarbonyl group, a sec-butylcarbonyl group, a t-butylcarbonyl group, etc.

The lower alkanesulfonyl group is a linear or branched alkanesulfonyl group having up to 6 carbon atoms. This includes, for example, a methanesulfonyl group, an ethanesulfonyl group, a 1-propanesulfonyl group, a 2-propanesulfonyl group, a 1-butanesulfonyl group, a 2-butanesulfonyl group, a 1,1-dimethylethanesulfonyl group, a 1-(2-methylpropane)sulfonyl group, a 1-pentanesulfonyl group, a 2-pentanesulfonyl group, a 3-pentanesulfonyl group, a 1-(3-methylbutane)sulfonyl group, a 1,1-dimethylpropanesulfonyl group, a 1-hexanesulfonyl group, a 2-hexanesulfonyl group, a 3-hexanesulfonyl group, a 1-(2-methylpentane)sulfonyl group, a 1-(3-methylpentane)sulfonyl group, a 1-(4-methylpentane)sulfonyl group, a 2-ethylbuthanesulfonyl group, a 3-ethylbutanesulfonyl group, a 1,1-dimethylbutanesulfonyl group, a 2,2-dimethylbutanesulfonyl group, a 3,3-dimethylbutanensulfonyl group, a 1-ethyl-1-methylpropanesulfonyl group, etc.

The aryl group includes, for example, a phenyl group, a naphthyl group, etc. The terminology "naphthyl" as referred to herein includes 1-naphthyl and 2-naphthyl. The benzene ring or the naphthalene ring in this group may optionally be substituted by one or more substituents selected from a halogen atom, a lower alkyl group, a cyano group, a nitro group, a trifluoromethyl groups and the like, such as those mentioned hereinabove.

The arylsulfonyl group is a sulfonyl group, to which is bonded an aryl group such as that mentioned hereinabove, and includes, for example, a benzenesulfonyl group, a toluenesulfonyl group, a naphthalenesulfonyl group, etc.

The aryl-lower alkyl group is a lower alkyl group, such as that mentioned hereinabove, to which is bonded an aryl group such as that mentioned hereinabove, and includes, for example, a benzyl group, a 1-phenylethyl group, a 2-phenylethyl group, a phenylpropyl group, a phenylbutyl group, a phenylpentyl group, a phenylhexyl group, a naphthylmethyl group, a naphthylethyl group, a naphthylpropyl group, a naphthylbutyl group, a naphthylpentyl group, a naphthylhexyl group, etc.

The aryl-lower alkyloxy group includes, for example, a benzyloxy group, a 1-phenylethyloxy group, a 2-phenylethyloxy group, a phenylpropyloxy group, a phenylbutyloxy group, a phenylpentyloxy group, a phenylhexyloxy group, a naphthylmethyloxy group, a naphthylethyloxy group, a naphthylpropyloxy group, a naphthylbutyloxy group, a naphthylpentyloxy group, etc., in which the benzene ring or the naphthalene ring may optionally be substituted.

The arylsulfonyl-lower alkyl group is a lower alkyl group, such as that mentioned hereinabove, to which is bonded an arylsulfonyl group such as that mentioned hereinabove, and includes, for example, a benzenesulfonylmethyl group, a toluenesulfonylmethyl group, a naphthalenesulfonylmethyl group, etc.

The arylsulfonylamino group is an amino group to which is bonded an arylsulfonyl group such as that mentioned hereinabove, and this includes, for example, a benzenesulfonylamino group, a toluenesulfonylamino group, a naphthalenesulfonylamino group, etc.

The aryloxy group is an aryl group, such as that mentioned hereinabove, to which is bonded an oxygen atom, and this includes, for example, a phenoxy group, a 1-naphthoxy group, a 2-naphthoxy group, etc.

The arylcarbonyl group is a carbonyl group to which is bonded an aryl group such as that mentioned hereinabove, and this includes, for example, a phenylcarbonyl group, a naphthylcarbonyl group, etc.

The arylcarbonylamino group is an amino group to which is bonded an arylcarbonyl group such as that mentioned hereinabove, and this includes, for example, a phenylcarbonylamino group, a naphthylcarbonylamino group, etc.

The aryl-lower alkenyl group is an alkenyl group having 6 or less carbon atoms, which is substituted by an aryl group such as that mentioned hereinabove, and this includes, for example, a phenylethenyl group, a naphthylethenyl group, etc.

The heterocyclic group includes, for example, a pyridyl group, a quinolyl group, an isoquinolyl group, a thiazolyl group, a thiadiazolyl group, a benzofuranyl group, a dibenzofuranyl group, a thianaphthalenyl group, a 1H-1,2,3-triazolyl group, a 1,2,4-triazolyl group, a tetrazolyl group, a furyl group, a thienyl group, a pyrrolyl group, an imidazolyl group, a pyrimidinyl group, an indolyl group, a benzimidazolyl group, etc. The heterocyclic group may optionally be substituted by one or more substituents of halogen atoms and lower alkyl groups, such as those mentioned hereinabove, and the substituted heterocyclic group of that type includes, for example, a haloisoquinolyl group, a methylisoquinolyl group, etc.

The heterocyclic lower alkyl group means a lower alkyl group, such as that mentioned hereinabove, as substituted by a heterocyclic group, such as that mentioned hereinabove. This includes, for example, a pyridylmethyl group. The halo-heterocyclic lower alkyl group is a heterocyclic lower alkyl group, such as that mentioned hereinabove, in which the heterocyclic moiety is substituted with one or more halogens.

The heterocyclic lower alkylamino group is an amino group as substituted with a heterocyclic lower alkyl group, such as that mentioned hereinabove, and this includes, for example, a pyridylmethylamino group, etc. The heterocyclic lower alkylcarbamoyl group is a carbamoyl group as substituted with a heterocyclic lower alkyl group, such as that mentioned hereinabove, and this includes, for example, a pyridylmethylcarbamoyl group, etc.

The terminology "pyridyl" as referred to herein includes 2-pyridyl, 3-pyridyl and 4-pyridyl, for which the bonding position is not specifically defined. The same shall apply to the other heterocyclic groups as referred to herein, or that is, the bonding positions of the heterocyclic groups as referred to herein are not specifically defined.

The lower alkylenedioxybenzyl group includes, for example, a methylenedioxybenzyl group, an ethylenedioxybenzyl group, a propylenedioxybenzyl group, etc.

A suitable heterocyclic group used herein means a saturated or unsaturated mono- or polycyclic hetero ring containing at least one hetero atom such as an oxygen atom, a sulfur atom, a nitrogen atom, etc.

Preferable examples thereof include the following heterocyclic groups:

7- to 12-membered, preferably 9- or 10-membered unsaturated condensed heterocyclic group (preferably bicyclic group) having 1 to 5 nitrogen atoms, such as indolyl, isoindolyl, indolidinyl, benzimidazolyl, quinolyl, isoquinolyl, indazolyl, benzotriazolyl, tetrazolopyridyl, tetrazolopyridazinyl (e.g. tetrazolo[1,5-b]pyridazinyl, etc.), dihydrotriazolopyridazinyl, or the like;

7- to 12-membered, preferably 9- or 10-membered unsaturated condensed heterocyclic group (preferably bicyclic group) having 1 to 3 sulfur atoms or S,S-dioxide thereof, such as dithianaphthalenyl (e.g. 4H-1,3-dithianaphthalenyl, 1,4-dithianaphthalenyl, etc.), benzothiophenyl or S,S-dioxide thereof (e.g. benzo[a]thiophenyl or S,S-dioxide thereof, benzo[b]thiophenyl or S,S-dioxide thereof, etc.), or the like;

3- to 8-membered, preferably 5- or 6-membered unsaturated hetero monocyclic group having 1 to 4 nitrogen atoms, such as pyrrolyl, pyrrolinyl, imidazolyl, pyrazolyl, pyridyl and its N-oxide, pyrimidyl, pyrazinyl, pyridazinyl, triazolyl (e.g. 4H-1,2,3-triazolyl, 1H-1,2,3-triazolyl, 2H-1,2,3-triazolyl, etc.), dihydrotriazinyl (e.g. 4,5-dihydro-1,2,4-triazinyl, 2,5-dihydro-1,2,4-triazinyl, etc.), or the like;

3- to 8-membered, preferably 5- or 6-membered saturated hetero monocyclic group having 1 to 4 nitrogen atoms, such as azetydinyl, pyrrolidinyl, imidazolydinyl, piperidinyl, pyrazolydinyl, piperadinyl, or the like;

7- to 12-membered, preferably 9- or 10-membered unsaturated condensed heterocyclic group (preferably bicyclic group) having 1 to 2 oxygen atoms and 1 to 3 nitrogen atoms, such as benzooxazolyl, benzooxadiazolyl, or the like;

3- to 8-membered, preferably 5- or 6-membered unsaturated hetero monocyclic group having 1 to 2 oxygen atoms and 1 to 3 nitrogen atoms, such as oxazolyl, isooxazolyl, oxadiazolyl (e.g. 1,2,4-oxadiazolyl, 1,3,4-oxadiazolyl, 1,2,5-oxadiazolyl, etc.), or the like;

3- to 8-membered, preferably 5- or 6-membered saturated hetero monocyclic group having 1 to 2 oxygen atoms and 1 to 3 nitrogen atoms, such as morpholinyl or the like;

7- to 12-membered, preferably 9- or 10-membered unsaturated condensed heterocyclic group (preferably bicyclic group) having 1 to 2 sulfur atoms and 1 to 3 nitrogen atoms, such as benzothiazolyl, benzothiadiazolyl, or the like;

3- to 8-membered, preferably 5- or 6-membered unsaturated hetero monocyclic group having 1 to 2 sulfur atoms and 1 to 3 nitrogen atoms, such as thiazolyl, 1,2-thiazolyl, thiadiazolyl (e.g. 1,2,4-thiadiazolyl, 1,3,4-thiadiazolyl, 1,2,5-thiadiazolyl, 1,2,3-thiadiazolyl, etc.), or the like;

3- to 8-membered, preferably 5- or 6-membered saturated hetero monocyclic group having 1 to 2 sulfur atoms and 1 to 3 nitrogen atoms, such as thiazolydinyl;

3- to 8-membered, preferably 5- or 6-membered unsaturated hetero monocyclic group having one sulfur atom, such as thienyl or the like; etc.

Suitable "esterified carboxyl groups" are exemplified below.

The ester portion of the esterified carboxyl group suitably include a lower alkyl ester, such as methyl ester, ethyl ester, propyl ester, isopropyl ester, butyl ester, isobutyl ester, tertiary butyl ester, pentyl ester, or hexyl ester, which may have at least one appropriate substituent. Examples of the lower alkyl ester include lower alkanoyloxy(lower)alkyl ester, such as acetoxymethyl ester, propionyloxymethyl ester, butyryloxymethyl ester, valeryloxymethyl ester, pivaloyloxymethyl ester, hexanoyloxy methyl ester, 1-(or 2-)acetoxyethyl ester, 1-(2-, or 3-)acetoxypropyl ester, 1-(2-, 3- or 4-)acetoxybutyl ester, 1-(or 2-)propionyloxyethyl ester, 1-(2-, or 3-)propionyloxypropyl ester, 1-(or 2-)butyryloxyethyl ester, 1(or 2-)isobutyryloxyethyl ester, 1-(or 2-)pivaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, or 1-(or 2-)pentanoyloxyethyl ester, lower alkanesulfonyl(lower) alkyl ester, such as 2-mesylethyl ester, mono(di, or tri)halo (lower)alkyl ester, such as 2-iodoethyl ester, 2,2,2-trichloroethyl ester, lower alkoxycarbonyloxy(lower)alkyl ester, such as methoxycarbonyloxymethyl ester, ethoxycarbonyloxymethyl ester, propoxycarbonyloxymethyl ester, tertiary-butoxycarbonyloxymethyl ester, 1-(or 2-)methoxycarbonyloxyethyl ester, 1-(or 2-)ethoxycarbonyloxyethyl ester, or 1-(or 2-)isopropoxycarbonyloxyethyl ester, phthalizilidene (lower)alkyl ester or (5-lower alkyl-2-oxo-1,3-dioxol-4-yl) (lower)alkyl ester, such as (5-methyl-2-oxo-1,3-dioxol-4-yl) methyl ester, (5-ethyl-2-oxo-1,3-dioxol-4-yl)methyl ester, or (5-propyl-2-oxo-1,3-dioxol-4-yl)ethyl ester, lower alkenyl ester, such as vinyl ester or allyl ester, lower alkynyl ester, such as ethynyl ester or propinyl ester, ar(lower)alkyl ester which may have at least one appropriate substituent, such as benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, or 4-hydroxy-3,5-di-tertiary-butylbenzyl ester, aryl ester which may have at least one appropriate substituent, such as phenyl ester, 4-chlorophenyl ester, tolyl ester, tertiary-butylphenyl ester, xylyl ester, mesityl ester, or cumenyl ester, phthalidyl ester, etc.

Preferable examples of a carboxyl groups protected by esterification include lower alkoxycarbonyl and phenyl(or nitrophenyl)($C_1$–$C_4$)alkoxycarbonyl. Most preferred are methoxycarbonyl, ethoxycarbonyl, and benzyloxycarbonyl.

Suitable amidated carboxyl groups include the following:

a carbamoyl group;

a mono- or di-lower alkyl carbamoyl group (as a lower alkyl group, those as described above can be used), such as methylcarbamoyl, dimethylcarbamoyl, isopropylcarbamoyl, n-butylcarbamoyl, t-butylcarbamoyl, N-methyl-N-(pyridylmethyl)carbamoyl, or the like;

an aryl(lower alkyl)carbamoyl (as an aryl group and a lower alkyl group, those as described above can be used), such as benzylcarbamoyl, 3,4-methylenedioxybenzylcarbamoyl, diaminobenzylcarbamoyl, or phenethylcarbamoyl;

a cyclo(lower alkyl)carbamoyl having 3 to 7 carbon atoms (as a cyclo lower alkyl group, those as described above can be used), such as cyclopropylcarbamoyl, cyclobutylcarbamoyl, cyclopentylcarbamoyl, cyclohexylcarbamoyl or the like;

an arylcabamoyl group (as an aryl group, those as described above can be used), such as phenylcarbamoyl, naphthylcarbamoyl, or the like;

a heterocyclic carbamoyl group (as a heterocyclic group, those as described above can be used), such as thiazolylcarbamoyl, thiadiazolylcarbamoyl, pyridylcarbamoyl, triazolylcarbamoyl, tetrazolylcarbamoyl, N-methyl-N-pyridinecarbamoyl, morpholinocarbamoyl, or the like;

a heterocyclic(lower alkyl)carbamoyl group (as a heterocyclic lower alkyl group, those as described above can be used), such as morpholinoethylcarbamoyl, pyridylmethylcarbamoyl, methylenedioxybenzylcarbamoyl, or the like;

an N-di-substituted carbamoyl group containing nitrogen as a member of a nitrogen-containing heterocyclic ring, such as morpholinocarbonyl, thiomorpholinocarbonyl, 1-perhydroazepinylcarbonyl, 1,1-dioxothiazolydinecarbonyl, piperidinocarbonyl, 1-piperazinylcarbonyl, 4-(2-hydroxyethyl)-1-piperazinylcarbonyl, 4-methyl-1-piperazinylcarbonyl, carboxypyrrolidinocarbonyl, or the like;

a substituted sulfonylcarbomoyl group, etc.

The substituent for the substituted sulfonyl-carbamoyl group includes the above-described groups such as the alkyl group having carbon atoms up to 8, the halo lower alkyl group, the aryl lower alkyl group, the hydroxy-lower alkyl group, the tri(lower alkyl)silyl(lower alkyl) group, the lower alkoxy-lower alkyl group, the lower alkylthio-lower alkyl group, the heterocyclic group, the aryl group, and the like. The aryl group may be sutstituted by a halogen atom, a lower alkyl group a halo lower alkyl group, a lower alkoxy group, a nitro group, or the like. Specific examples of the substituted sulfonylcarbamoyl group include naphthylsulfonylcarbamoyl, benzenesulfonylcarbamoyl, nitrobenzenesulfonylcarbamoyl, trihalobenzenesulfonylcarbamoyal, lower alkoxybenzenesulfonylcarbamoyl, halobenzenesulfonylcarbamoyl, mono- or di-(lower alkyl)-benzenesulfonylcarbamoyl, alkanesulfonylcarbamoyl having 1 to 8 carbon atoms, such as t-butylsulfonylcarbamoyl, butylsulfonylcarbamoyl, propylsulfonylcarbamoyl, isopropylsulfonylcarbamoyl, methylsulfonylcarbamoyl, octylsulfonylcarbamoyl, pentylsulfonylcarbamoyl, isopentylsulfonylcarbamoyl, hexylsulfonylcarbamoyl, or the like, trihalo(lower)alkylsulfonylcarbamoyl, phenyl(lower)alkylsulfonylcarbamoyl, tri-(lower)alkylsulfonylcarbamoyl, lower alkylthio(lower)alkylsulfonylcarbamoyl, lower alkoxy(lower)alkylsulfonylcarbamoyl, quinolinesulfonylcarbamoyl, or the like.

Suitable acyl groups include aliphatic acyl, aromatic acyl, heterocyclic acyl, and aliphatic acyl substituted with an aromatic group or a heterocyclic group, which are derived from carboxylic acid, carbonic acid, sulfonic acid, carbamic acid, and the like.

Examples of the aliphatic acyl include saturated or unsaturated non-cyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkyl sulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxy carbonyl (e.g. methoxycarbonyl, ethoxycarbonyl, propoxycarbonyl, butoxycarbonyl, tertiary-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, chlotonoyl, etc.), cycloalkanecarbonyl such as cyclo(lower)alkanecarbonyl (e.g. cyclopropanecarbonyl, cyclopentanecarbonyl, cyclohexanecarbonyl, etc.) and the like.

Examples of the aromatic acyl include $C_6$–$C_{10}$ aroyl (e.g. benzoyl, toluoyl, xyloyl, etc.), N-($C_6$–$C_{10}$)arylcarbamoyl (e.g. N-phenylcarbamoyl, N-tolylcarbamoyl, N-naphthylcarbamoyl, etc.), $C_6$–$C_{10}$ arenesulfonyl (e.g. benzenesulfonyl, tosyl, etc.), and the like.

Examples of the heterocyclic acyl include heterocyclic carbonyl, heherocyclic(lower)alkanoyl (e.g. heterocyclic acetyl, heterocyclic propanoyl, heterocyclic butanoyl, heterocyclic pentanoyl, heterocyclic hexanoyl, etc.), heterocyclic(lower)alkenoyl (e.g. heterocyclic propenoyl, heterocyclic butenoyl, heterocyclic pentenoyl, heterocyclic hexenoyl, etc.) heterocyclic glyoxyloyl, heterocyclic sulfinyl, heterocyclic sulfonyl, etc.

The aromatic group-bound aliphatic acyl includes aralkoxycarbonyl such as phenyl(lower)alkoxycarbonyl (e.g. benzyloxycarbonyl, phenethyloxycarbonyl, etc.).

These acyl groups may be substituted with one or more appropriate substituent, such as a nitro group. An example thereof is nitroaralkoxycarbonyl (e.g. nitrobenzyloxycarbonyl, etc.).

Preferred salts of the benzimidazole derivatives of the present invention are non-toxic, ordinary pharmaceutically acceptable salts thereof. For example, mentioned are salts of the derivatives with bases as well as acid-addition salts of the derivatives, which include, for example, salts thereof with inorganic bases, such as salts with alkali metals (e.g., sodium, potassium); salts with alkaline earth metals (e.g., calcium, magnesium); ammonium salts; salts with organic amines (e.g., triethylamine, pyridine, picoline, ethanolamine, triethanolamine, dicyclohexylamine, N,N'-dibenzylethylenediamine); salts with inorganic acids (e.g., hydrochloric acid, hydrobromic acid, sulfuric acid, phosphoric acid); salts with organic carboxylic acids (e.g., formic acid, acetic acid, trifluoroacetic acid, maleic acid, tartaric acid); salts with sulfonic acids (e.g., methanesulfonic acid, benzenesulfonic acid, p-toluenesulfonic acid); salts with basic or acidic amino acids (e.g., arginine, aspartic acid, glutamic acid), etc.

The compounds of the invention could contain one or more chiral centers, therefore they could be enantiomers or diastereomers. Few of the compounds containing alkenyl group could also be cis- or trans-isomers. In both cases, each of such isomers as well as the mixture thereof are within the scope of this invention.

The compounds of the invention can also exist as tautomers, and individual of such tautmers and the mixture thereof are within the scope of this invention.

The compounds of the invention and their salts can be solvate, which are also within the invention. The solvent for the solvate is preferably water or ethanol.

Specific examples of benzimidazole derivatives of formula (IX) include 6-benzenesulfonylcarbamoyl-1-(2-chlorobenzyl)-2-methylbenzimidazole, 6-benzenesulfonylcarbamoyl-1-(biphenyl-4-ylmethyl)-2-ethylbenzimidazole, 5-benzenesulfonylcarbamoyl-1-(2-chlorobenzyl)-2-methylbenzimidazole, 5-(4-chlorobenzenesulfonylcarbamoyl)-1-(2-chlorobenzyl)-2-methylbenzimidazole, 1-(2-chlorobenzyl)-2-methyl-5-(2-naphthalenesulfonylcarbamoyl)-benzimidazole, 1-(2-chlorobenzyl)-6-methanesulfonylcarbamoyl-2-methylbenzimidazole, 6-(1-butanesulfonylcarbamoyl)-1-(2-chlorobenzyl)-2-methylbenzimidazole, 1-(2-chlorobenzyl)-2-methyl-6-(1-octanesulfonylcarbamoyl)benzimidazole, 1-(2-chlorobenzyl)-2-methyl-6-(2-propanesulfonylcarbamoyl)benzimidazole, 1-(biphenyl-4-ylmethyl)-6-(1-butanesulfonylcarbamoyl)-2-methylbenzimidazole, 6-(1-butanesulfonylcarbamoyl)-1-(2,4-dichlorobenzyl)-2-methylbenzimidazole, 1-(biphenyl-4-ylmethyl)-6-(1-butanesulfonylcarbamoyl)-2-ethylbenzimidazole, 6-benzenesulfonylcarbamoyl-1-(biphenyl-4-ylmethyl)-2-trifluoromethylbenzimidazole, 5-benzenesulfonylcarbamoyl-1-(biphenyl-4-ylmethyl)-2-trifluoromethylbenzimidazole, 6-benzenesulfonylcarbamoyl-2-cyclopropyl-1-(2-fluorobenzyl)benzimidazole, N-benzenesulfonyl-3-[1-(2-chlorobenzyl)-2-methylbenzimidazol-6-yl]acrylamide, N-benzenesulfonyl-2-[1-(2-chlorobenzyl)-2-methylbenzimidazol-6-yl]acetamide, 1-(2-chlorobenzyl)-2-methyl-6-(2-naphthalenesulfonylcarbamoyl)benzimidazole, 1-(2-chlorobenzyl)-2-methyl-6-(1-naphthalenesulfonylcarbamoyl)benzimidazole, 6-(4-chlorobenzenesulfonylcarbamoyl)-1-(2-chlorobenzyl)-2-methylbenzimidazole, 6-(3-chlorobenzenesulfonylcarbamoyl)-1-(2-chlorobenzyl)-2-methylbenzimidazole, 5-benzenesulfonylcarbamoyl-2-benzyl-1-(2-chlorobenzyl)benzimidazole, 6-benzenesulfonylcarbamoyl-2-benzyl-1-(2-chlorobenzyl)benzimidazole, 6-benzenesulfonylcarbamoyl-1-(biphenyl-4-ylmethyl)-2-methylbenzimidazole, 1-(2-chlorobenzyl)-2-methyl-6-trifluoromethanesulfonylcarbamoylbenzimidazole, 6-benzenesulfonylcarbamoyl-1-(2,4-dichlorobenzyl)-2-methylbenzimidazole, 1-(2-chlorobenzyl)-6-(4-methoxybenzenesulfonylcarbamoyl)-2-methylbenzimidazole, 1-(2-chlorobenzyl)-2-methyl-6-(α-toluenesulfonylcarbamoyl)benzimidazole, 1-(2-chlorobenzyl)-6-(2,5-dimethylbenzenesulfonylcarbamoyl)-2-methylbenzimidazole, 1-(2-chlorobenzyl)-2-methyl-6-(4-nitrobenzenesulfonylcarbamoyl)benzimidazole, 1-(2-chlorobenzyl)-2-methyl-6-[4-(trifluoromethyl)benzenesulfonylcarbamoyl]benzimidazole, 6-(2-chlorobenzenesulfonylcarbamoyl)-1-(2-chlorobenzyl)-2-methylbenzimidazole, 6-benzenesulfonylcarbamoyl-2-benzyl-1-(2,4-dichlorobenzyl)benzimidazole, 5-benzenesulfonylcarbamoyl-2-benzyl-1-(2,4-dichlorobenzyl)benzimidazole, 6-benzenesulfonylcarbamoyl-1-(biphenyl-4-ylmethyl)-2-hydroxybenzimidazole, 6-benzenesulfonylcarbamoyl-1-(biphenyl-4-ylmethyl)-2-mercaptobenzimidazole, 6-benzenesulfonylcarbamoyl-1-(biphenyl-4-ylmethyl)-2-methoxybenzimidazole, 6-benzenesulfonylcarbamoyl-1-(biphenyl-4-ylmethyl)-2-carboxybenzimidazole, 6-benzenesulfonylcarbamoyl-1-(biphenyl-4-ylmethyl)-2-methylaminobenzimidazole, 2-amino-6-benzenesulfonylcarbamoyl-1-(biphenyl-4-ylmethyl)-benzimidazole, 6-benzenesulfonylcarbamoyl-1-(biphenyl-4-ylmethyl)-2-n-propylbenzimidazole, 6-benzenesulfonylcarbamoyl-1-(biphenyl-4-ylmethyl)-2-n-heptylbenzimidazole, 6-benzenesulfonylcarbamoyl-1-(biphenyl-4-ylmethyl)-2-chloromethylbenzimidazole, 6-benzenesulfonylcarbamoyl-1-(biphenyl-4-ylmethyl)-2-methoxymethylbenzimidazole, 6-benzenesulfonylcarbamoyl-1-(biphenyl-4-ylmethyl)-2-i-propylbenzimidazole, 6-benzenesulfonylcarbamoyl-1-(biphenyl-4-ylmethyl)-2-methylthiobenzimidazole, 6-benzenesulfonylcarbamoyl-1-(biphenyl-4-ylmethyl)-2-ethylthiobenzimidazole, 6-benzenesulfonylcarbamoyl-1-(biphenyl-4-ylmethyl)-2-n-propylthiobenzimidazole, 6-benzenesulfonylcarbamoyl-1-(biphenyl-4-ylmethyl)-2-n-hexylthiobenzimidazole, 6-benzenesulfonylcarbamoyl-1-(biphenyl-4-ylmethyl)benzimidazole, 6-benzenesulfonylcarbamoyl-1-(2,4-difluorobenzyl)-2-methylbenzimidazole, 6-benzenesulfonylcarbamoyl-1-(biphenyl-4-ylmethyl)-2-phenylbenzimidazole, 6-benzenesulfonylcarbamoyl-2-methyl-1-(2-nitrobenzyl)benzimidazole, 6-benzenesulfonylcarbamoyl-2-methyl-1-benzylbenzimidazole, 6-benzenesulfonylcarbamoyl-2-methyl-1-(4-nitrobenzyl)benzimidazole, 6-benzenesulfonylcarbamoyl-1-(4-benzyloxybenzyl)-2-methylbenzimidazole, 6-benzenesulfonylaminomethyl-1-(2-chlorobenzyl)-2-methylbenzimidazole, N-benzenesulfonyl-3-[1-(2-chlorobenzyl)-2-methylbenzimidazol-6-yl]propionamide, 6-benzenesulfonylcarbamoyl-2-methyl-1-[4-(1,2,3-thiadiazol-4-yl)benzyl]benzimidazole, 1-(2-chlorobenzyl)-2-methyl-6-(8-quinolinesulfonylcarbamoyl)benzimidazole, 6-(4-t-butylbenzenesulfonylcarbamoyl)-1-(2-chlorobenzyl)-2-methylbenzimidazole, 6-benzenesulfonylcarbamoyl-2-methyl-1-[4-(trifluoromethyl)benzyl]benzimidazole, 5-benzenesulfonylcarbamoyl-2-methylbenzimidaozle, 1-(biphenyl-4-ylmethyl)-6-(1-butanesulfonylcarbamoyl)-2-methoxymethylbenzimidazole, 1-(4-benzyloxybenzyl)-6-(1-butanesulfonylcarbamoyl)-2-methoxymethylbenzimidazole, 6-(1-butanesulfonylcarbamoyl)-1-(2,4-dichlorobenzyl)-2-methoxymethylbenzimidazole, 1-(2-chlorobenzyl)-2-methyl-6-(1-propanesulfonylcarbamoyl)benzimidazole, 6-ethanesulfonylcarbamoyl-1-(2-chlorobenzyl)-2-methylbenzimidazole, 6-(propanesultam-1-ylcarbonyl)-1-(2-chlorobenzyl)-2-methylbenzimidazole, 6-benzenesulfonylcarbamoyl-1-(biphenyl-4-ylmethyl)-2-cyclopropylbenzimidazole, 1-(2-chlorobenzyl)-2-methyl-6-

(1-pentanesulfonylcarbamoyl)benzimidazole, 1-(2-chlorobenzyl)-2-methyl-6-[(3-methylbutane)sulfonylcarbamoyl]benzimidazole, 1-(2-chlorobenzyl)-6-(1-hexanesulfonylcarbamoyl)-2-methylbenzimidazole, 7-(1-butanesulfonylcarbamoyl)-1-(2,4-dichlorobenzyl)-2-methylbenzimidazole, 1-(2-chlorobenzyl)-2-methyl-6-[1-[3-(trimethylsilyl)propane]sulfonylcarbamoyl]benzimidazole, 4-(1-butanesulfonylcarbamoyl)-1-(2,4-dichlorobenzyl)-2-methylbenzimidazole, 1-(4-benzyloxybenzyl)-6-(1-butanesulfonylcarbamoyl)-2-methylbenzimidazole, 6-(1-butanesulfonylcarbamoyl)-1-[(2'-cyanobiphenyl-4-yl)methyl]-2-methylbenzimidazole, 6-(1-ethanesulfonyl-carbamoyl)-1-[(2'-fluorobiphenyl-4-yl)methyl]-2-methylbenzimidazole, 6-(1-butanesulfonylcarbamoyl)-1-[(3-fluorobiphenyl-4-yl)methyl]-2-methylbenzimidazole, 1-(2-chlorobenzyl)-6-[(2-methoxyethane)-sulfonylcarbamoyl]-2-methylbenzimidazole, 1-(2-chlorobenzyl)-6-(1-hexanesulfonylcarbamoyl)-2-methylbenzimidazole, 1-(2,4-dichlorobenzyl)-2-methyl(1-pentanesulfonylcarbamoyl)benzimidazole, 1-(biphenyl-4-ylmethyl)-2-ethyl-6[1-[3-(methylthio)propane]sulfonylcarbamoyl]benzimidazole, 1-(4-biphenylmethyl)-2-ethyl-6-(1-pentanesulfonylcarbamoyl)benzimidazole, 6-(1-butanesulfonylcarbamoyl)-1-(2,4-dichlorobenzyl)-2-ethylbenzimidazole, 1-(4-biphenylmethyl)-2-ethyl-6-[1-(3-methyl)butanesulfonylcarbamoyl]benzimidazole, 5-(1-butanesulfonylcarbamoyl)-1-(2,4-dichlorobenzyl)-2-methylbenzimidazole, 1-(4biphenylmethyl)-5-(1-butanesulfonylcarbamoyl)-2-ethylbenzimidazole, 1-(4-biphenylmethyl)-2-ethyl-6-(2-methoxyethanesulfonylcarbamoyl)benzimidazole, 6-(1-butanesulfonylcarbamoyl)-2-ethyl-1-[4-(4-fluorobenzyloxy)benzyl]benzimidazole, 6-(1-butanesulfonylcarbamoyl)-1-[4-(3,4-dichlorobenzyloxy)benzyl]-2-ethylbenzimidazole, 6-(1-butanesulfonylcarbamoyl)-1-[sec-(2,4-dichlorophenethyl)]-2-methylbenzimidazole, 6-(1-butanesulfonylcarbamoyl)-1-[4-(2-pyridyl)benzyl]-2-methylbenzimidazole, 6-(1-butanesulfonylcarbamoyl)-1-(2,4-dichlorobenzyl)-2,4-dimethylbenzimidazole, 6-(1-butanesulfonylcarbamoyl)-2-methyl-1-(4-phenoxybenzyl)benzimidazole, 6-(butanesufonylcarbamoyl)-2-methyl-1-(2-pyridylmethyl)benzimidazole, 1-[(4-benzoylamino)benzyl]-6-(1-butanesulfonylcarbamoyl)-2-methylbenzimidazole, 6-(1-butanesulfonylcarbamoyl)-2-methyl-[4-(2-phenylethyl)benzyl]benzimidazole, 1-[(4-benzoyl)benzyl]-6-(1-butanesulfonylcarbamoyl)-2-methylbenzimidazole, 6-(1-butanesulfonylcarbamoyl)-2-methyl-[4-(2-phenylethenyl)benzyl]-benzimidazole, 1-(dibenzofuran-2-ylmethyl)-6-(1-butanesulfonylcarbamoyl)-2-methylbenzimidazole, 6-(1-butanesulfonylcarbamoyl)-1-(2,4-dichlorobenzyl)-2-hydroxybenzimidazole, 6-(1-butanesulfonylcarbamoyl)-2-methyl-1-(2-quinolylmethyl)benzimidazole, and 6-(1-butanesulfonylcarbamoyl)-2-methyl-1-[3-(4-bromoisoquinolyl)methyl]benzimidazole, etc.

Specific examples of compounds of formula (X) include 1-(2-cyanobenzyl)-6-ethoxycarbonyl-2-n-propylbenzimidazole, 6-ethoxycarbonyl-2-N-propyl-1-(2-pyridylmethyl)benzimidazole, 6-ethoxycarbonyl-1-methyl-2-n-propylbenzimidazole, 1-n-butyl-6-ethoxycarbonyl-2-n-propylbenzimidazole, 1-(biphenyl-4-ylmethyl)-6-ethoxycarbonyl-2-methylbenzimidazole, 6-ethoxycarbonyl-1-(2-methoxybenzyl)-2-methylbenzimidazole, 6-ethoxycarbonyl-1-(4-methoxybenzyl)-2-methylbenzimidazole, 1-[2-(benzenesulfonylmethyl)benzyl]-6-ethoxycarbonyl-2-methylbenzimidazole, 1-(2-cyanobenzyl)-6-(2-cyanobenzyloxycarbonyl)-2-methylbenzimidazole, 1-(biphenyl-2-ylmethyl)-6-ethoxycarbonyl-2-methyl-benzimidazole, 6-ethoxycarbonyl-2-methyl-1-(2-naphthylmethyl)benzimidazole, 1-(biphenyl-4-ylmethyl)-6-ethoxycarbonyl-2-ethylbenzimidazole, 6-ethoxycarbonyl-2-n-propyl-1-i-propylbenzimidazole, 2-benzyl-6-ethoxycarbonyl-1-methylbenzimidazole, 6-carboxy-1-methyl-2-n-propylbenzimidazole, 6-carboxy-2-n-propyl-1-i-propylbenzimidazole, 1-n-butyl-6-carboxy-2-n-propylbenzimidazole, 6-carboxy-2-methyl-1-(2-nitrobenzyl)benzimidazole, 1-(biphenyl-4-ylmethyl)-6-carboxy-2-methylbenzimidazole, 6-carboxy-1-(2-methoxybenzyl)-2-methylbenzimidazole, 6-carboxy-1-(4-methoxybenzyl)-2-methylbenzimidazole, 6-carboxy-2-methyl-1-[2-(benzenesulfonylmethyl)benzyl]benzimidazole, 6-carboxy-1-(2-cyanobenzyl)-2-methylbenzimidazole, 6-carboxy-1-(biphenyl-2-ylmethyl)-2-methylbenzimidazole, 6-carboxy-2-methyl-1-(2-naphthylmethyl)benzimidazole, 1-(biphenyl-4-ylmethyl)-6-carboxy-2-ethylbenzimidazole, 5-carboxy-2-methyl-1-(2-nitrobenzyl)benzimidazole, 1-(biphenyl-4-ylmethyl)-6-carboxy-2-trifluoromethylbenzimidazole, 1-(biphenyl-4-ylmethyl)-5-carboxy-2-trifluoromethylbenzimidazole, 5-ethoxycarbonyl-2-methylbenzimidazole, 2-benzyl-5-ethoxycarbonylbenzimidazole, 6-ethoxycarbonyl-2-methyl-1-(2-nitrobenzyl)benzimidazole, 5-ethoxycarbonyl-2-methyl-1-(2-nitrobenzyl)benzimidazole, 5-ethoxycarbonyl-2-trifluoromethylbenzimidazole, 1-(biphenyl-4-ylmethyl)-6-ethoxycarbonyl-2-trifluoromethylbenzimidazole, 1-(biphenyl-4-ylmethyl)-5-ethoxycarbonyl-2-trifluoromethylbenzimidazole, 1-methyl-2-n-propyl-6-[(2-pyridylmethyl)carbamoyl]benzimidazole, 2-n-propyl-1-i-propyl-6-[(2-pyridylmethyl)carbamoyl]benzimidazole, 1-n-butyl-2-n-propyl-6-[(2-pyridylmethyl)carbamoyl]benzimidazole, 2-benzyl-1-methyl-6-[(2-pyridylmethyl)carbamoyl]benzimidazole, 1-(2-methoxybenzyl)-2-methyl-6-[(2-pyridylmethyl)carbamoyl]benzimidazole, 1-(4-methoxybenzyl)-2-methyl-6-[(2-pyridylmethyl)carbamoyl]benzimidazole, 1-[2-(benzenesulfonylmethyl)benzyl]-2-methyl-6-[(2-pyridylmethyl)carbamoyl]benzimidazole, 1-(2-cyanobenzyl)-2-methyl-6-[(2-pyridylmethyl)carbamoyl]benzimidazole, 1-(biphenyl-2-ylmethyl)-2-methyl-6-[(2-pyridylmethyl)carbamoyl]benzimidazole, 2-methyl-1-(2-naphthylmethyl)-6-[(2-pyridylmethyl)carbamoyl]benzimidazole, 1-(biphenyl-4-ylmethyl)-2-ethyl-6-[(2-pyridylmethyl)carbamoyl]benzimidazole, 2-methyl-1-(2-nitrobenzyl)-6-[(2-pyridylmethyl)carbamoyl]benzimidazole, 2-methyl-1-(2-nitrobenzyl)-5-[(2-pyridylmethyl)carbamoyl]benzimidazole, 1-(biphenyl-4-ylmethyl)-2-methyl-6-[(2-pyridylmethyl)carbamoyl]benzimidazole, 1-(4-benzyloxybenzyl)-2-methyl-6-[(2-pyridylmethyl)carbamoyl]benzimidazole, 2-methyl-1-(3,4-methylenedioxybenzyl)-6-[(2-pyridylmethyl)carbamoyl]benzimidazole, 2-methyl-6-[(2-pyridylmethyl)carbamoyl]-1-[4-(1,2,3-thiadiazol-4-yl)benzyl]benzimidazole, 2-methyl-5-[(2-pyridylmethyl)carbamoyl]benzimidazole, 1-benzenesulfonyl-2-methyl-6-[(2-pyridylmethyl)carbamoyl]benzimidazole, 1-benzenesulfonyl-2-methyl-5-[(2-pyridylmethyl)carbamoyl]benzimidazole, 2-methyl-1-(4-nitrobenzyl)-6-[(2-pyridylmethyl)carbamoyl]benzimidazole, 2-methyl-1-(4-nitrobenzyl)-5-[(2-pyridylmethyl)carbamoyl]benzimidazole, 2-methyl-1-(2-phenylethyl)-6-[(2-pyridylmethyl)carbamoyl]benzimidazole, 2-methyl-1-(2-phenylethyl-5-[(2-pyridylmethyl)carbamoyl]benzimidazole, 1-(4-aminobenzyl)-2-methyl-6-[(2-pyridylmethyl)carbamoyl]

benzimidazole, 1-(4-aminobenzyl)-2-methyl-5-[(2-pyridylmethyl)carbamoyl]benzimidazole, 1-[4-(benzenesulfonylamino)benzyl]-2-methyl-6-[(2-pyridylmethyl)carbamoyl]benzimidazole, 1-(biphenyl-4-ylmethyl)-2-methyl-6-[(2-pyridylmethyl)aminomethyl]benzimidazole, 2-benzyl-6-carboxy-1-methylbenzimidazole, 4-ethoxycarbonyl-2-methylbenzimidazole, 1-(4-benzyloxybenzyl)-6-ethoxycarbonyl-2-methylbenzimidazole, 1-(4-benzyloxybenzyl)-6-carboxy-2-methylbenzimidazole, 6-ethoxycarbonyl-1-[(2'-cyanobiphenyl-4-yl)methyl]-2-methylbenzimidazole, 6-carboxy-1-[(2'-cyanobiphenyl-4-yl)methyl]-2-methylbenzimidazole, 6-ethoxycarbonyl-1-[(2'-fluorobiphenyl-4-yl)methyl]-2-methylbenzimidazole, 6-carboxy-1-[(2'-fluorobiphenyl-4-yl)methyl]-2-methylbenzimidazole, 6-ethoxycarbonyl-1-[(3-fluorobiphenyl-4-yl)methyl]-2-methylbenzimidazole, 6-carboxy-1-[(3-fluorobiphenyl-4-yl)methyl]-2-methylbenzimidazole, 1-(4-biphenylmethyl)-5-ethoxycarbonyl-2-ethylbenzimidazole, 1-(4-biphenylmethyl)-5-carboxy-2-ethylbenzimidazole, 6-ethoxycarbonyl-2-ethyl-1-[4-(4-fluorobenzyloxy)benzyl]benzimidazole, 6-carboxy-2-ethyl-1-[4-(4-fluorobenzyloxy)benzyl]benzimidazole, 1-[4-(3,4-dichlorobenzyloxy)benzyl]-6-ethoxycarbonyl-2-ethylbenzimidazole, 6-carboxy-1-[4-(3,4-dichlorobenzyloxy)benzyl]-2-ethylbenzimidazole, 1-(4-biphenylmethyl)-6-(n-butylcarbamoyl)-2-ethylbenzimidazole, 1-(4-biphenylmethyl)-2-ethyl-6-(thiazol-2-ylcarbamoyl)benzimidazole, 1-(4-biphenylmethyl)-2-ethyl-6-(2-pyridylcarbamoyl)benzimidazole, 1-[sec-(2,4-dichlorophenethyl)]-6-ethoxycarbonyl-2-methylbenzimidazole, 6-carboxy-1-[sec-(2,4-dichlorophenethyl)]-2-methylbenzimidazole, 1-(4-biphenylmethyl)-2-ethyl-6-(phenylcarbamoyl)benzimidazole, 1-(4-biphenylmethyl)-2-ethyl-6-(1,3,4-thiadiazol-2-ylcarbamoyl)benzimidazole, 1-(4-biphenylmethyl)-2-ethyl-6-(tetrazol-5-ylcarbamoyl)benzimidazole, 1-(4-biphenylmethyl)-2-ethyl-6-(1,3,4-triazol-3-ylcarbamoyl)benzimidazole, 1-(4-biphenylmethyl)-2-ethyl-(1,3,4-triazol-2-ylcarbamoyl)benzimidazole, 1-(4-biphenylmethyl)-2-ethyl-6-(3-pyridylcarbamoyl)benzimidazole, 1-(4-biphenylmethyl)-2-ethyl-6-(4-pyridylcarbamoyl)benzimidazole, 1-(2,4-dichlorobenzyl)-2,4-dimethyl-6-methoxycarbonylbenzimidazole, 6-carboxy-1-(2,4-dichlorobenzyl)-2,4-dimethylbenzimidazole, 6-ethoxycarbonyl-2-methyl-1-(4-phenoxybenzyl)benzimidazole, 6-carboxy-2-methyl-1-(4-phenoxybenzyl)benzimidazole, 6-ethoxycarbonyl-2-methyl-1-(2-pyridylmethyl)benzimidazole, 6-carboxy-2-methyl-1-(2-pyridylmethyl)benzimidazole, 6-ethoxycarbonyl-2-methyl-1-(4-nitrobenzyl)benzimidazole, 1-(4-aminobenzyl)-6-ethoxycarbonyl-2-methylbenzimidazole, 1-[(4-benzoylamino)benzyl]-6-ethoxycarbonyl-2-methylbenzimidazole, 1-[(4-benzoylamino)benzyl]-6-carboxy-2-methylbenzimidazole, 6-ethoxycarbonyl-2-methyl-1-[4-(2-phenylethenyl)benzyl]benzimidazole, 6-ethoxycarbonyl-2-methyl-1-[4-(2-phenylethyl)benzyl]benzimidazole, 6-carboxy-2-methyl-1-[4-(2-phenylethyl)benzyl]benzimidazole, 1-[(4-benzoyl)benzyl]-6-ethoxycarbonyl-2-methylbenzimidazole, 1-[(4-benzoyl)benzyl]-6-carboxy-2-methylbenzimidazole, 6-carboxy-2-methyl-[4-(2-phenylethenyl)benzyl]benzimidazole, 1-(dibenzofuran-2-ylmethyl)-6-ethoxycarbonyl-2-methylbenzimidazole, 6-carboxy-1-(dibenzofuran-2-ylmethyl)-2-methylbenzimidazole, 6-ethoxycarbonyl-2-methyl-1-(2-quinolylmethyl)benzimidazole, 6-carboxy-2-methyl-(2-quinolylmethyl)-benzimidazole, 1-(2,4-dichlorobenzyl)-2-hydroxy-6-ethoxycarbonylbenzimidazole, 6-ethoxycarbonyl-2-methyl-1-[3-(4-bromoisoquinolyl)methyl]-benzimidazole, and 6-carboxy-2-methyl-[3-(4-bromoisoquinolyl)methyl]benzimidazole, etc.

Specific examples of benzimidazole derivatives of formula (XI) include 1-(2-chlorobenzyl)-6-ethoxycarbonyl-2-phenylbenzimidazole, 2-benzyl-5-carboxy-1-(2-chlorobenzyl)benzimidazole, 2-benzyl-6-carboxy-1-(2-chlorobenzyl)benzimidazole, 2-benzyl-5-carboxy-1-(2,4-dichlorobenzyl)benzimidazole, 2-benzyl-6-carboxy-1-(2,4-dichlorobenzyl)benzimidazole, 2-benzyl-1-(2-chlorobenzyl)-6-ethoxycarbonylbenzimidazole, 2-benzyl-1-(2-chlorobenzyl)-5-ethoxycarbonylbenzimidazole, 2-benzyl-1-(2,4-dichlorobenzyl)-6-ethoxycarbonylbenzimidazole, 2-benzyl-1-(2,4-dichlorobenzyl)-5-ethoxycarbonylbenzimidazole, 1-(2-chlorobenzyl)-2-methylbenzimidazole-6-acetic acid, methyl 1-(2-chlorobenzyl)-2-methyl-benzimidazole-6-acrylate, 1-(2-chlorobenzyl)-2-methylbenzimidazole-6-acrylic acid, 1-(2-chlorobenzyl)-6-[2-(pyridylmethyl)carbamoyl]benzimidazole, 1-(biphenyl-4-ylmethyl)-6-ethoxycarbonyl-2-methoxymethylbenzimidazole, 1-(biphenyl-4-ylmethyl)-6-carboxy-2-methoxymethyl-benzimidazole, 1-(4-benzyloxybenzyl)-6-ethoxycarbonyl-2-methoxymethylbenzimidazole, 1-(4-benzyloxybenzyl)-6-carboxy-2-methoxymethylbenzimidazole, 1-(2,4-dichlorobenzyl)-6-ethoxycarbonyl-2-methoxymethylbenzimidazole, and 6-carboxy-1-(2,4-dichlorobenzyl)-2-methoxymethylbenzimidazole, etc.

Specific examples of benzimidazole derivatives of formula (XII) include 6-t-butoxycarbonylamino-1-(2-chlorobenzyl)-2-n-propylbenzimidazole, 1-(2-chlorobenzyl)-6-mesylamino-2-n-propylbenzimidazole, 6-acetylamino-1-(2-chlorobenzyl)-2-n-propylbenzimidazole, 6-amino-1-(2-chlorobenzyl)-2-n-propylbenzimidazole, 1-(2-chlorobenzyl)-2-n-propyl-6-ureidobenzimidazole, 6-t-butoxycarbonylamino-1-(2-chlorobenzyl)-2-methylbenzimidazole, 6-amino-1-(2-chlorobenzyl)-2-methylbenzimidazole, and 6-(1-butanesulfonylamino)-1-(2-chlorobenzyl)-2-methylbenzimidazole, etc.

Specific examples of benzimidazole derivatives of formula (XIII) include 1-(2-chlorobenzyl)-6-cyano-2-cyclopropylbenzimidazole, and 1-(2-chlorobenzyl)-6-cyano-2-n-propylbenzimidazole, etc. Specific examples of benzimidazole derivatives of formula (VI) include 1-(2-chlorobenzyl)-6-(4-dimethylaminophenylmethylcarbamoyl)-2-n-propylbenzimidazole, 1-(2-chlorobenzyl)-2-n-propyl-6-thiomorpholinocarbonylbenzimidazole, 1-(2-chlorobenzyl)-2-cyclopropyl-6-(2-pyridylcarbamoyl)benzimidazole, 6-(2-carboxy-1-pyrrolidinocarbonyl)-1-(2-chlorobenzyl)-2-n-propylbenzimidazole, 1-(2-chlorobenzyl)-6-[N-methyl-N-(2-pyridylmethyl)carbamoyl]-2-n-propylbenzimidazole, 1-(2-chlorobenzyl)-6-piperonylcarbamoyl-2-n-propylbenzimidazole, 1-(2-chlorobenzyl)-6-(homopiperidinocarbonyl)-2-n-propylbenzimidazole, 1-(2-chlorobenzyl)-6-[N-methyl-N-(2-pyridyl)carbamoyl]-2-n-propylbenzimidazole, 2-n-butyl-1-(2-(fluorobenzyl)-6-[N-methyl-N-(2-pyridylmethyl)carbamoyl]benzimidazole, 2-cyclopropyl-1-(2-fluorobenzyl)-6-(piperonylcarbamoyl)benzimidazole, 2-[[1-(2-chlorobenzyl)-2-ethylbenzimidazol-6-yl]carbonylaminomethyl]pyridine-1-oxide, and 1-(2,4-dichlorobenzyl)-2-methyl-6-(2-pyridylcarbamoyl)benzimidazole, etc.

The present invention further includes, within its scope, the following novel benzimidazole derivatives: 1-(2-bromobenzyl)-6-ethoxycarbonyl-2-n-propylbenzimidazole, 6-ethoxycarbonyl-1-(2-fluorobenzyl)-2-n-propylbenzimidazole, 6-ethoxycarbonyl-1-(4-fluorobenzyl)-2-n-propylbenzimidazole, 6-ethoxycarbonyl-1-(3-fluorobenzyl)-2-n-propylbenzimidazole, 1-(2,6-dichlorobenzyl)-6-ethoxycarbonyl-2-n-propylbenzimidazole, 1-(3-methylbenzyl)-6-ethoxycarbonyl-2-n-propylbenzimidazole, 2-cyclopropyl-6-ethoxycarbonyl-1-(2-fluorobenzyl)-benzimidazole, 1-(2-chlorobenzyl)-2-cyclobutyl-6-ethoxycarbonylbenzimidazole, 1-(2-chlorobenzyl)-6-ethoxycarbonyl-2-n-pentylbenzimidazole, 5-carboxy-1-(2-chlorobenzyl)-2-n-propylbenzimidazole, 6-carboxy-1-(3-methylbenzyl)-2-n-propylbenzimidazole, 2-n-butyl-7-carboxy-1-(2-chlorobenzyl)benzimidazole, 6-carboxy-1-(2-fluorobenzyl)-2-cyclopropylbenzimidazole, 2-n-butyl-6-carboxy-1-(2-fluorobenzyl)benzimidazole, 1-(2-chlorobenzyl)-6-chlorocarbonyl-2-cyclopropylbenzimidazole, 1-(2-chlorobenzyl)-6-morpholinocarbamoyl-2-n-propylbenzimidazole, 2-n-butyl-1-(2-chlorobenzyl)-6-[(2-pyridylmethyl)carbamoyl]benzimidazole, 2-n-butyl-5-carbamoyl-1-(2-chlorobenzyl)benzimidazole, 1-(2-chlorobenzyl)-2-cyclopropyl-6-morpholinocarbonylbenzimidazole, 1-(2-chlorobenzyl)-2-cyclopropyl-6-[(2-pyridylmethyl)carbamoyl]benzimidazole, 1-(2-chlorobenzyl)-2-cyclobutyl-6-[(2-pyridylmethyl)carbamoyl]benzimidazole, 1-(2-chlorobenzyl)-2-n-propyl-5-[(2-pyridylmethyl)carbamoyl]benzimidazole, 1-(2-chlorobenzyl)-6-phenylcarbamoyl-2-n-propylbenzimidazole, 1-(2-chlorobenzyl)-2-n-propyl-6-[(4-pyridylmethyl)carbamoyl]benzimidazole, 1-(2-chlorobenzyl)-2-n-propyl-6-[(3-pyridylmethyl)carbamoyl]benzimidazole, 1-(3-methylbenzyl)-2-n-propyl-6-[(2-pyridylmethyl)carbamoyl]benzimidazole, 1-(2-chlorobenzyl)-2-ethyl-6-[(2-pyridylmethyl)carbamoyl]benzimidazole, 2-n-butyl-1-(2-chlorobenzyl)-7-[(2-pyridylmethyl)carbamoyl]benzimidazole, 2-n-butyl-1-(2-fluorobenzyl)-6-(2-pyridylmethylcarbamoyl)benzimidazole, 1-(2-chlorobenzyl)-6-ethoxycarbonyl-2-methylbenzimidazole, 1-(3-chlorobenzyl)-6-ethoxycarbonyl-2-n-propylbenzimidazole, 1-benzyl-6-ethoxycarbonyl-2-n-propylbenzimidazole, 1-(4-chlorobenzyl)-6-ethoxycarbonyl-2-n-propylbenzimidazole, 6-ethoxycarbonyl-2-methyl-1-[2-(trifluoromethyl)benzyl]benzimidazole, 6-ethoxycarbonyl-2-methyl-1-[4-(trifluoromethyl)benzyl]benzimidazole, 1-(3,4-dichlorobenzyl)-6-ethoxycarbonyl-2-methylbenzimidazole, 6-ethoxycarbonyl-2-methyl-1-(2-methylbenzyl)benzimidazole, 1-benzyl-6-ethoxycarbonyl-2-methylbenzimidazole, 1-(4-t-butylbenzyl)-6-ethoxycarbonyl-2-methylbenzimidazole, 1-(2-chlorobenzyl)-5-ethoxycarbonyl-2-methylbenzimidazole, 1-(2,6-dichlorobenzyl)-6-ethoxycarbonyl-2-methylbenzimidazole, 1-(2,4-dichlorobenzyl)-6-ethoxycarbonyl-2-methylbenzimidazole, 6-carboxy-1-(4-chlorobenzyl)-2-n-propylbenzimidazole, 6-carboxy-1-(2,6-dichlorobenzyl)-2-methylbenzimidazole, 6-carboxy-2-methyl-1-[2-(trifluoromethyl)benzyl]benzinidazole, 6-carboxy-2-methyl-1-[4-(trifluoromethyl)benzyl]benzimidazole, 6-carboxy-1-(3,4-dichlorobenzyl)-2-methylbenzimidazole, 1-benzyl-6-carboxy-2-n-propylbenzimidazole, 6-carboxy-1-(3-chlorobenzyl)-2-n-propylbenzimidazole, 6-carboxy-1-(2,4-dichlorobenzyl)-2-methylbenzimidazole, 1-(4-t-butylbenzyl)-6-carboxy-2-methylbenzimidazole, 6-carboxy-2-methyl-1-(2-methylbenzyl)benzimidazole, 1-benzyl-6-carboxy-2-methylbenzimidazole, 5-carboxy-1-(2-chlorobenzyl)-2-methylbenzimidazole, 6-carboxy-1-(2-chlorobenzyl)-2-methylbenzimidazole, 1-(2,4-dichlorobenzyl)-2-methyl-6-[(2-pyridylmethyl)carbamoyl]benzimidazole, 1-(2-chlorobenzyl)-2-methyl-6-[(2-pyridylmethyl)carbamoyl]benzimidazole, 1-(3-chlorobenzyl)-2-n-propyl-6-[(2-pyridylmethyl)carbamoyl]benzimidazole, 1-benzyl-2-n-propyl-6-[(2-pyridylmethyl)carbamoyl]benzimidazole, 1-(4-chlorobenzyl)-2-propyl-6-[(2-pyridylmethyl)carbamoyl]benzimidazole, 1-(2,6-dichlorobenzyl)-2-methyl-6-[(2-pyridylmethyl)carbamoyl]benzimidazole, 2-methyl-6-[(2-pyridylmethyl)carbamoyl]-1-[2-(trifluoromethyl)benzyl]benzimidazole, 2-methyl-6-[(2-pyridylmethyl)carbamoyl]-1-[4-(trifluoromethyl)benzyl]benzimidazole, 1-(3,4-dichlorobenzyl)-2-methyl-6-[(2-pyridylmethyl)carbamoyl]benzimidazole, 2-methyl-1-(2-methylbenzyl)-6-[(2-pyridylmethyl)carbamoyl]benzimidazole, 1-benzyl-2-methyl-6-[(2-pyridylmethyl)carbamoyl]benzimidazole, 1-(4-t-butylbenzyl)-2-methyl-6-[(2-pyridylmethyl)carbamoyl]benzimidazole, 6-carbamoyl-1-(2,4-dichlorobenzyl)-2-methylbenzimidazole, 1-(2,4-difluorobenzyl)-2-methyl-6-[(2-pyridylmethyl)carbamoyl]benzimidazole, 1-(2,4-difluorobenzyl)-2-methyl-5-[(2-pyridylmethyl)carbamoyl]benzimidazole, 1-(2,4-dichlorobenzyl)-7-ethoxycarbonyl-2-methylbenzimidazole, 7-carboxy-1-(2,4-dichlorobenzyl)-2-methylbenzimidazole, 1-(2,4-dichlorobenzyl)-4-ethoxycarbonyl-2-methylbenzimidazole, 4-carboxy-1-(2,4-dichlorobenzyl)-2-methylbenzimidazole, 1-(2,4-dichlorobenzyl)-5-ethoxycarbonyl-2-methylbenzimidazole, 5-carboxy-1-(2,4-dichlorobenzyl)-2-methylbenzimidazole, and 6-(n-butylcarbamoyl)-1-(2,4-dichlorobenzyl)-2-methylbenzimidazole.

The benzimidazole derivatives and their pharmaceutically acceptable salts of the present invention that are mentioned hereinabove are effective for preventing and treating various disorders of, for example, impaired glucose tolerance, diabetes (type II diabetes), diabetic complications (e.g., diabetic nephropathy, diabetic neuropathy, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), hyperlipidemia, atherosclerosis, cardiovascular disorders (e.g., stenocardia, cardiac failure, etc.), hyperglycemia (e.g., abnormal saccharometabolism such as feeding disorders, etc.), and hypertension based on their blood sugar level-depressing activity, as well as stenocardia, hypertension, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), allergic rhinitis, urticaria, glaucoma, diseases characterized by enteromotility disorders (e.g., hypersensitive enteropathy syndrome, etc.), impotence (e.g., organic impotence, psychic impotence, etc.), and diabetic complications (e.g., diabetic gangrene, diabetic arthropathy, diabetic glomerulosclerosis, diabetic dermatopathy, diabetic neuropathy, diabetic cataract, diabetic retinopathy, etc.), nephritis, cancerous cachexia, and restenosis after PTCA based on their cGMP-PDE (especially PDE-v)-inhibiting activity, smooth muscle relaxing activity, bronchodilating activity, vasodilating activity, smooth muscle cell suppressing activity, and antiallergic activity.

In addition, we, the present inventors, have further found that the benzimidazole derivatives which we have disclosed in Japanese Patent Application Laid-Open No. 5-222000 as c-GMP phosphodiesterase inhibitors also have the above-mentioned activities, and have now confirmed that these benzimidazole derivatives are also effective for preventing and treating the above-mentioned diseases and disorders like the compounds mentioned hereinabove.

Accordingly, the present invention further includes pharmaceutical compositions comprising, as an active ingredient, any of benzimidazole derivatives of the following formula (I) and their pharmaceutically acceptable salts, which are effective for preventing and treating impaired glucose tolerance, diabetes (type II diabetes), diabetic complications (e.g., diabetic nephropathy, diabetic neuropathy, diabetic retinopathy, etc.), syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), hyperlipidemia, atherosclerosis, cardiovascular disorders (e.g., stenocardia, cardiac failure, etc.), hyperglycemia (e.g., abnormal saccharometabolism such as feeding disorders, etc.), or hypertension; or stenocardia, hypertension, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), allergic rhinitis, urticaria, glaucoma, diseases characterized by enteromotility disorders (e.g., hypersensitive enteropathy syndrome, etc.), impotence (e.g., organic impotence, psychic impotence, etc.), and diabetic complications (e.g., diabetic gangrene, diabetic arthropathy, diabetic glomerulosclerosis, diabetic dermatopathy, diabetic neuropathy, diabetic cataract, diabetic retinopathy, etc.), nephritis, cancerous cachexia, or restenosis after PTCA.

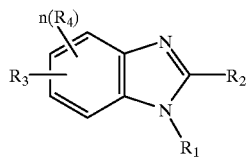

(I)

In formula (I):

$R_1$ represents a hydrogen atom, an arylsulfonyl group, or a lower alkyl group; and said lower alkyl group may be substituted by an aryl group or an aryl group substituted by one or two substituents selected from a halogen atom, a haloaryl group, a lower alkyl group, a halo-lower alkyl group, a lower alkoxy group, a nitro group, an amino group, a cyano group, an aryl group, an aryl-lower alkyl group, an aryl-lower alkyloxy group, a haloaryl-lower alkyloxy group, an arylsulfonyl-lower alkyl group, an arylsulfonylamino group, a cyanoaryl group, and a heterocyclic group, or by a heterocyclic group;

$R_2$ represents a hydrogen atom, a lower cycloalkyl group, a hydroxyl group, a lower alkoxy group, a mercapto group, a lower alkylthio group, an amino group, a lower alkylamino group, a carboxyl group, an aryl group, or a lower alkyl group; and said lower alkyl group may be substituted by a halogen atom, a lower alkoxy group, a cyano group, a chlorocarbonyl group, an aryl group, or a heterocyclic group;

$R_3$ represents a carboxyl group, an esterified carboxyl group, an amidated carboxyl group, an amino group, an amido group, or a sulfonyl group; and said amino group and said amido group may be substituted by an acyl group or a sulfonyl group; and a halogen atom, an amino group, or an acylamino group is bonded to said sulfonyl group; or $R_3$ may be bonded to the skeleton via a lower alkylene or alkenylene group; and $R_4$ represents a neutral substituent. $R_4$ includes a halogen atom, and a lower alkyl group, an aralkyl group, an alkynyl group, a lower alkyloxy group, and halogen-substituted groups of these. Where $R_4$ is a hydrocarbon group, it may be either saturated or unsaturated, or either linear or cyclic, or may even be branched. For the halogen atom and the halogen-substituted groups, the kind of the halogen is not specifically defined. For the latter, the number of halogens substituted is not specifically defined.

n means an integer from 0 to 3. Thus, one, two or three $R_4$s may be bonded to the skeleton, or no $R_4$ may be bonded thereto. The position of $R_4$ may be any of the ortho-position, the meta-position and the para-position relative to the other substituent.

Specific examples of benzimidazole derivatives of formula (I) include 2-butyl-1-(2-chlorobenzyl )-6-ethoxycarbonylbenzimidazole, 1-(4-bromo-2-fluorobenzyl)-2-butyl-6-ethoxycarbonylbenzimidazole, 2-butyl-1-(2,4-dichlorobenzyl)-6-ethoxycarbonylbenzimidazole, 2-butyl-6-ethoxycarbonyl-1-(4-methoxycarbonylbenzyl)benzimidazole, 2-butyl-6-ethoxycarbonyl-1-(2-fluorobenzyl)benzimidazole, 2-butyl-6-ethoxycarbonyl-1-(2-trifluoromethylbenzyl) benzimidazole, 1-(2-chlorobenzyl)-6-ethoxycarbonyl-2-ethylbenzimidazole, 1-(2-chlorobenzyl )-6-ethoxycarbonyl-2-propylbenzimidazole, 1-(2-chlorobenzyl)-2-cyclopropyl-6-ethoxycarbonylbenzimidazole, 1-(2-chlorobenzyl )-6-ethoxycarbonyl-2-isopropylbenzimidazole, 2-butyl-1-(2-chlorobenzyl)-5-ethoxycarbonylbenzimidazole, 2-butyl-1-(2-chlorobenzyl)-7-ethoxycarbonylbenzimidazole, 1-(2-chlorobenzyl)-5-ethoxycarbonyl-2-propylbenzimidazole, 2-butyl-1-(2-chlorobenzyl)-6-carboxybenzimidazole, 2-butyl-6-carboxy-1-(4-carboxybenzyl)benzimidazole, 6-carboxy-1-(2-chlorobenzyl)-2-ethylbenzimidazole, 6-carboxy-1-(2-chlorobenzyl)-2-propylbenzimidazole, 6-carboxy-1-(2-chlorobenzyl)-2-cyclopropylbenzimidazole, 2-butyl-5-carboxy-1-(2-chlorobenzyl)imidazole, 2-butyl-1-(2-chlorobenzyl)-6-dimethylcarbamoylbenzimidazole, 6-(benzylcarbamoyl)-2-butyl-1-(2-chlorobenzyl) benzimidazole, 2-butyl-1-(2-chlorobenzyl)-6-morpholinocarbonylbenzimidazole, 2-butyl-6-carbamoyl-(2-chlorobenzyl)-benzimidazole, 2-butyl-1-(2-chlorobenzyl)-6-(4-methylpiperazinyl) carbonylbenzimidazole, 2-butyl-1-(2-chlorobenzyl)-6-(methylcarbamoyl)benzimidazole, 6-carbamoyl-1-(2-chlorobenzyl)-2-ethylbenzimidazole, 6-carbamoyl-1-(2-chlorobenzyl)-2-propylbenzimidazole, 6-carbamoyl-1-(2-chlorobenzyl)-2-cyclopropylbenzimidazole, 2-butyl-5-carbamoyl-1-(2-chlorobenzyl)benzimidazole, 2-butyl-1-(2-chlorobenzyl)-6-(isopropylcarbonyl)benzimidazole, 1-(2-chlorobenzyl)-6-chloroformyl-2-propylbenzimidazole, 1-(2-chlorobenzyl)-6-(methylcarbamoyl)-2-propylbenzimidazole, 1-(2-chlorobenzyl)-6-(ethylcarbamoyl)-2-propylbenzimidazole, 1-(2-chlorobenzyl)-6-(isopropyl)carbamoyl-2-propylbenzimidazole, 1-(2-chlorobenzyl)-6-

(piperidinocarbonyl)-2-propylbenzimidazole, 1-(2-chlorobenzyl)-6-(morpholinocarbonyl)-2-propylbenzimidazole, 1-(2-chlorobenzyl)-6-(2-morpholinoethyl)carbamoyl-2-propylbenzimidazole, 1-(2-chlorobenzyl)-6-[4-(2-hydroxyethyl)piperazinyl]carbonyl-2-propylbenzimidazole, 1-(2-chlorobenzyl)-2-propyl-6-(2-pyridylmethyl)carbamoylbenzimidazole, 1-(2-chlorobenzyl)-2-propyl-6-[4-(4-phenyl-1,2,3,6-tetrahydropyridin-1-yl)butyl]carbamoylbenzimidazole, etc.

To use the benzimidazole derivatives of the present invention for treating diseases or disorders such as those mentioned hereinabove, they may be formulated into pharmaceutical compositions of ordinary forms, which comprise, as an active ingredient, any of the derivatives along with pharmaceutically acceptable carriers, such as organic or inorganic solid or liquid vehicles, and which are suitable for peroral administration, parenteral administration or external application. The pharmaceutical compositions may be of any solid form of tablets, granules, powders, capsules, etc., or may be of any liquid form of solutions, suspensions, syrups, emulsions, lemonades, etc.

If desired, the pharmaceutical compositions may further contain a pharmaceutical aid, a stabilizer, a wetting agent, and also any ordinary additive of, for example, lactose, citric acid, tartaric acid, stearic acid, magnesium stearate, terra alba, sucrose, corn starch, talc, gelatin, agar, pectin, peanut oil, olive oil, cacao butter, ethylene glycol, etc.

The amount of the above-mentioned derivative of the present invention to be used shall vary, depending on the age and the condition of patients, the type and the condition of diseases or disorders, and the type of the derivative to be used. In general, for peroral administration, the dose of the derivative may be from 1 to 100 mg/kg; and for intramuscular injection or intravenous injection, it may be from 0.1 to 10 mg/kg. Such a unit dose may be applied to a patient once to four times a day.

BRIEF DESCRIPTION OF THE DRAWINGS

FIG. 1 shows chemical formulae of compound (42) to compound (47).

FIG. 2 shows chemical formulae of compound (48) to compound (53).

FIG. 3 shows chemical formulae of compound (54) to compound (59).

FIG. 4 shows chemical formulae of compound (60) to compound (65).

FIG. 5 shows chemical formulae of compound (66) to compound (71).

FIG. 6 shows chemical formulae of compound (72) to compound (77).

FIG. 7 shows chemical formulae of compound (78) to compound (83).

FIG. 8 shows chemical formulae of compound (84) to compound (89).

FIG. 9 shows chemical formulae of compound (90) to compound (95).

FIG. 10 shows chemical formulae of compound (96) to compound (101).

FIG. 11 shows chemical formulae of compound (102) to compound (107).

FIG. 12 shows chemical formulae of compound (108) to compound (113).

FIG. 13 shows chemical formulae of compound (114) to compound (119).

FIG. 14 shows chemical formulae of compound (120) to compound (125).

FIG. 15 shows chemical formulae of compound (126) to compound (131).

FIG. 16 shows chemical formulae of compound (132) to compound (137).

FIG. 17 shows chemical formulae of compound (138) to compound (143).

FIG. 18 shows chemical formulae of compound (144) to compound (149).

FIG. 19 shows chemical formulae of compound (150) to compound (155).

FIG. 20 shows chemical formulae of compound (156) to compound (161).

FIG. 21 shows chemical formulae of compound (162) to compound (167).

FIG. 22 shows chemical formulae of compound (168) to compound (173).

FIG. 23 shows chemical formulae of compound (174) to compound (179).

FIG. 24 shows chemical formulae of compound (180) to compound (185).

FIG. 25 shows chemical formulae of compound (186) to compound (191).

FIG. 26 shows chemical formulae of compound (192) to compound (197).

FIG. 27 shows chemical formulae of compound (198) to compound (203).

FIG. 28 shows chemical formulae of compound (204) to compound (209).

FIG. 29 shows chemical formulae of compound (210) to compound (215).

FIG. 30 shows chemical formulae of compound (216) to compound (221).

FIG. 31 shows chemical formulae of compound (222) to compound (227).

FIG. 32 shows chemical formulae of compound (228) to compound (233).

FIG. 33 shows chemical formulae of compound (234) to compound (239).

FIG. 34 shows chemical formulae of compound (240) to compound (245).

FIG. 35 shows chemical formulae of compound (246) to compound (251).

FIG. 36 shows chemical formulae of compound (252) to compound (257).

FIG. 37 shows chemical formulae of compound (258) to compound (263).

FIG. 38 shows chemical formulae of compound (264) to compound (269).

FIG. 39 shows chemical formulae of compound (270) to compound (275).

FIG. 40 shows chemical formulae of compound (276) to compound (281).

FIG. 41 shows chemical formulae of compound (282) to compound (287).

FIG. 42 shows chemical formulae of compound (288) to compound (293).

FIG. 43 shows chemical formulae of compound (294) to compound (299).

FIG. 44 shows chemical formulae of compound (300) to compound (305).

FIG. 45 shows chemical formulae of compound (306) to compound (311).

FIG. 48 shows chemical formulae of compound (323) to compound (328).

FIG. 49 shows chemical formulae of compound (329) to compound (334).

FIG. 50 shows chemical formulae of compound (335) to compound (340).

FIG. 52 shows chemical formulae of compound (347) to compound (352).

FIG. 53 shows chemical formulae of compound (353) to compound (358).

FIG. 54 shows chemical formulae of compound (359) to compound (364).

FIG. 56 shows chemical formulae of compound (371) to compound (376).

FIG. 57 shows chemical formulae of compound (377) to compound (382).

FIG. 58 shows chemical formulae of compound (383) to compound (386).

BEST MODE FOR CARRYING OUT THE INVENTION

Figure 46:
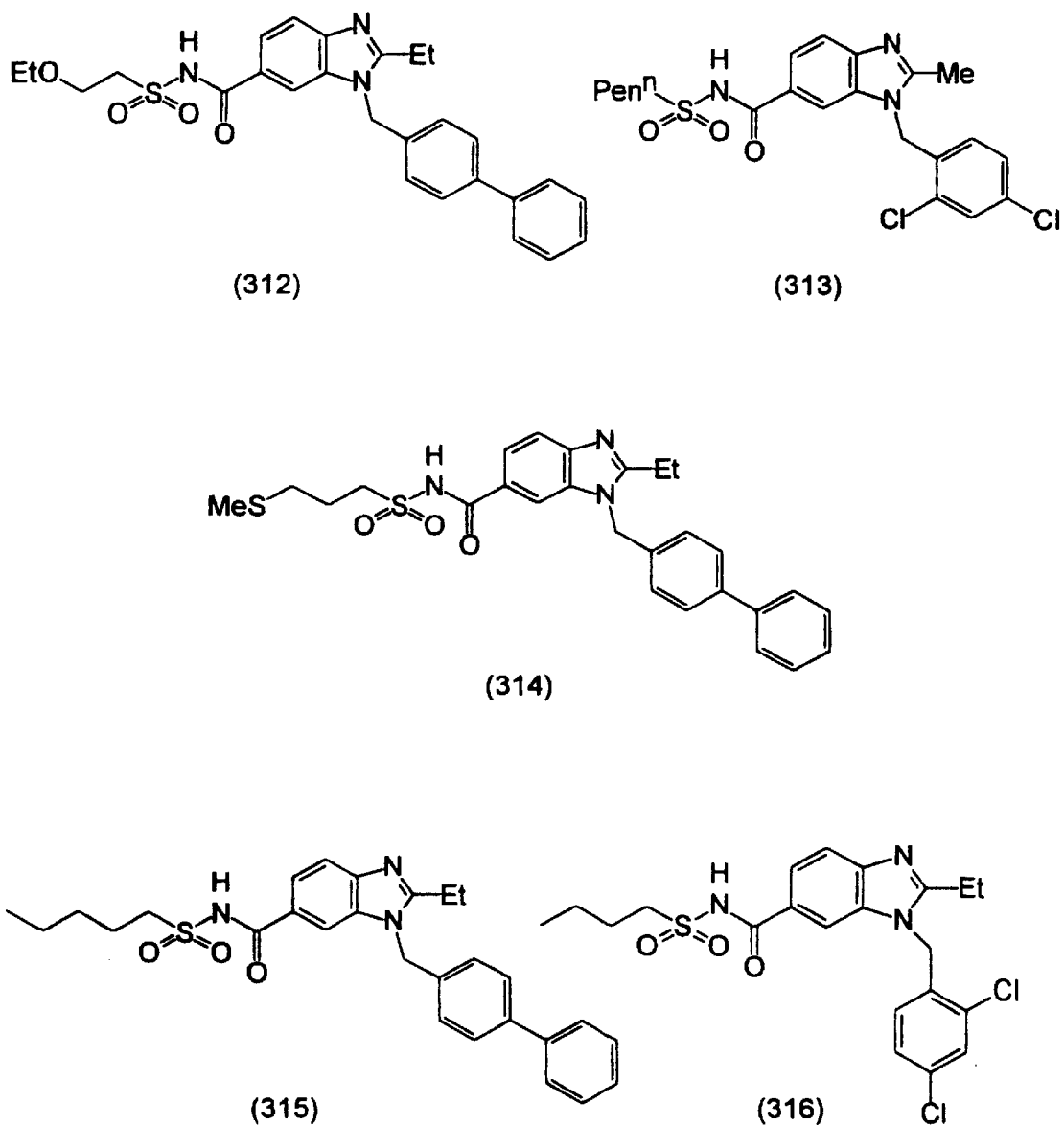
FIG. 46 shows chemical formulae of compound (312) to compound (316).
Figure 47:
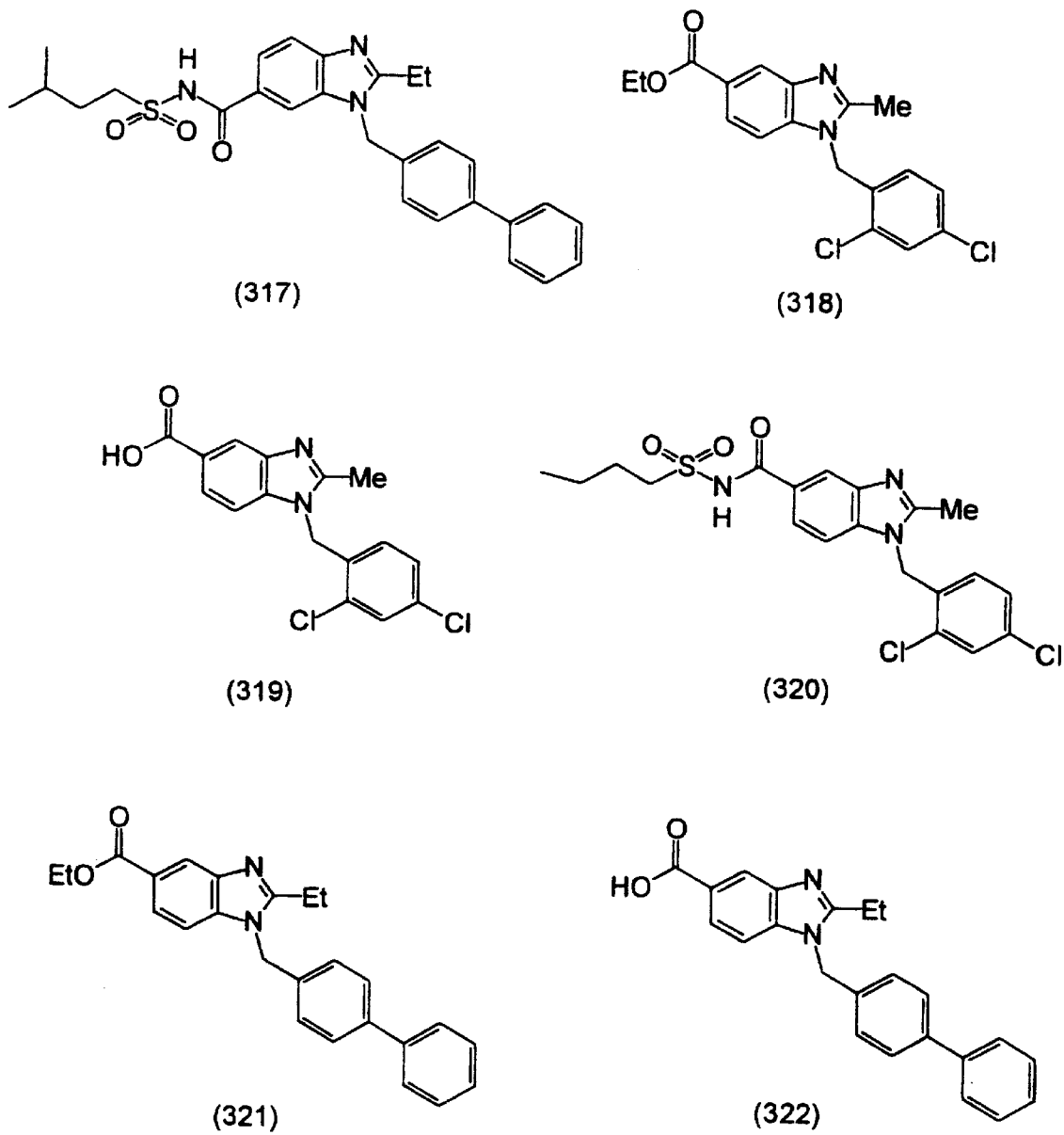
FIG. 47 shows chemical formulae of compound (317) to compound (322).
Figure 51:
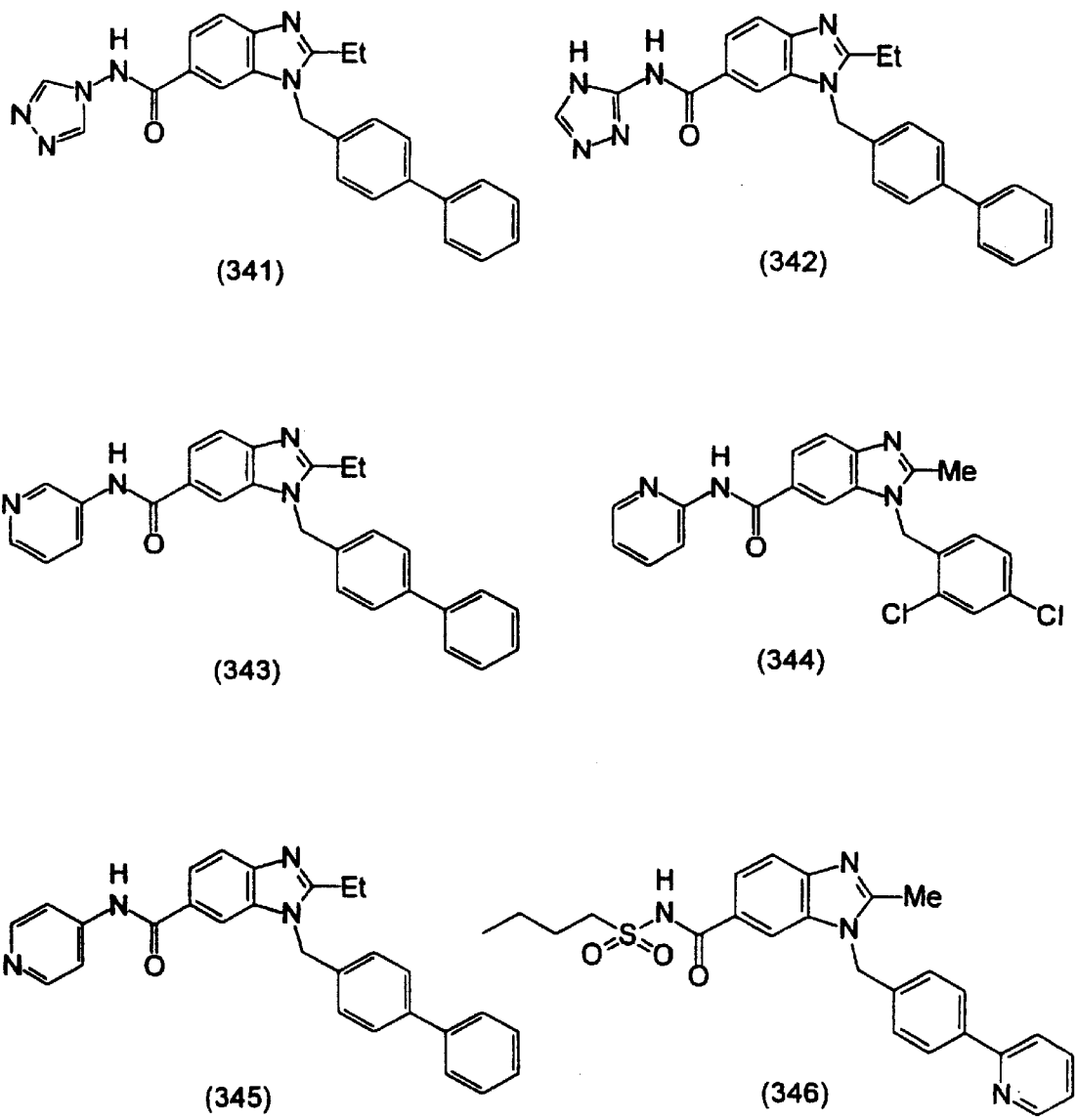
FIG. 51 shows chemical formulae of compound (341) to compound (346).
Figure 55:
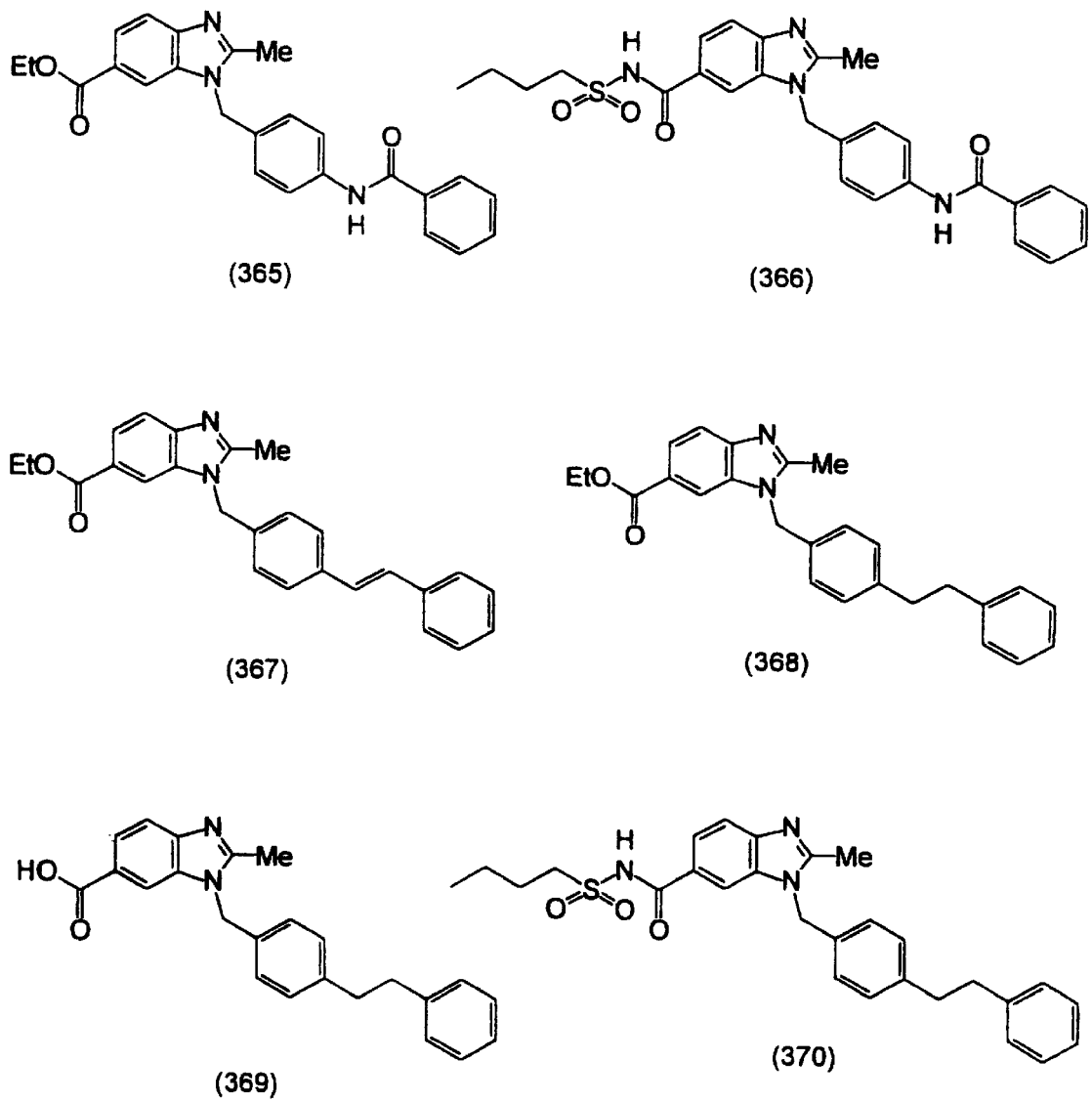
FIG. 55 shows chemical formulae of compound (365) to compound (370).

The present invention is illustrated more specifically by referring to the following Examples. However, the present invention is not limited thereto.

Production Example 1

Production of ethyl 3-[N-(2-bromobenzyl) butyrylamino]-4-nitrobenzoate

One-hundred milligrams of sodium hydride (60% water-in-oil suspension) were added to a solution of 247 mg of ethyl 3-butyrylamino-4-nitrobenzoate in 10 ml of N,N-dimethylformamide in a nitrogen atmosphere at room temperature in some divided portions. The reaction suspension was stirred at the same temperature for 1 hour, and a solution of 244 mg of 2-bromobenzyl bromide in 2 ml of N,N-dimethylformamide was gradually added dropwise thereto over a period of 10 minutes. The reaction mixture was stirred at room temperature for 1 hour, and was poured in ice water. The oily substance precipitated was extracted with methylene chloride. The organic solvent layer was washed with water, dried, and then concentrated under reduced pressure. The residue was developed through silica-gel flash column chromatography, and was eluted with a mixture of 25% ethyl acetate and n-hexane to give 540 mg of yellow oil of ethyl 3-[N-(2-bromobenzyl)butyrylamino-4-nitrobenzoate.

Properties of the compound:

$^1$H-NMR (CDCl$_3$, δ): 0.87 (3H, t, J=8 Hz), 1.48 (3H, t, J=8 Hz), 1.68 (2H, sextet, J=8 Hz), 2.03 (2H, t, J=8 Hz), 4.30–4.46 (2H, m), 4.70 (1H, d, J=15 Hz), 5.40 (1H, d, J=15 Hz), 7.08–7.34 (2H, m), 7.43 (1H, dd, J=1, 8 Hz), 7.58 (1H, dd, J=1, 8 Hz), 7.66 (1H, d, J=1 Hz), 7.96 (1H, d, J=8 Hz 8.16 (1H, dd, J=1, 8 Hz)

Production Example 2

Production of ethyl 3-[N-(2-chlorobenzyl) benzoylamino]-4-nitrobenzoate

In the same manner as in Production Example 1, 480 mg of yellow crystals of ethyl 3-[N-(2-chlorobenzyl) benzoylamino]-4-nitrobenzoate were formed from 450 mg of ethyl 3-benzoylamino-4-nitrobenzoate and 243 mg of 2-chlorobenzyl bromide.

Properties of the compound:

$^1$H-NMR (CDCl$_3$, δ): 1.35 (3H, t, J=8 Hz), 4.35 (2H, q, J=8 Hz), 4.76 (1H, bd, J=15 Hz), 5.82 (1H, bd, J=15 Hz), 7.10–8.00 (12H, m)

mp: 111–113° C.

Production Example 3

Production of ethyl 3-[N-(2-fluorobenzyl) butyrylamino]-4-nitrobenzoate

In the same manner as in Production Example 1, 394 mg of yellow oil of ethyl 3-[N-(2-fluorobenzyl)butyrylamino]-4-nitrobenzoate were formed from 300 mg of ethyl 3-butyrylamino-4-nitrobenzoate and 243 mg of 2-fluorobenzyl bromide.

Properties of the compound:

$^1$H-NMR (CDCl$_3$, δ): 0.85 (3H, t, J=8 Hz), 1.40 (3H, t, J=8 Hz), 1.65 (2H, sextet, J=8 Hz), 1.98 (2H, t, J=8 Hz), 4.30–4.45 (2H, m), 4.60 (1H, d, J=10 Hz), 5.25 (1H, d, J=10 Hz), 6.88 (2H, t, J=8 Hz), 7.08 (2H, dd, J=5, 8 Hz), 7.24 (1H, dt, J=1, 8 Hz), 7.41 (1H, dt, J=1, 8 Hz), 7.69 (1H, d, J=1 Hz), 7.96 (1H, d, J=8 Hz), 8.15 (1H, dd, J=1, 8 Hz)

Production Example 4

Production of ethyl 3-[N-(4-fluorobenzyl) butyrylamino]-4-nitrobenzoate

In the same manner as in Production Example 1, 400 mg of yellow oil of ethyl 3-[N-(4-fluorobenzyl)butyrylamino]-4-nitrobenzoate were formed from 300 mg of ethyl 3-butyrylamino-4-nitrobenzoate and 243 mg of 4-fluorobenzyl bromide.

Properties of the compound:

$^1$H-NMR (CDCl$_3$, δ): 0.86 (3H, t, J=8 Hz), 1.37 (3H t, J=8 Hz), 1.56–1.76 (2H, m), 1.96–2.04 (2H, m), 4.32–4.46 (2H, m), 4.40 (1H, d, J=14 Hz), 5.23(1H, d, J=14 Hz), 6.95 (2H, t, J=8 Hz), 7.10 (2H, dd, J=5, 8 Hz), 7.47 (1H, d, J=1 Hz), 7.95 (1H, d, J=8 Hz), 8.16 (1H, dd, J=1, 8 Hz)

Production Example 5

Production of ethyl 3-[N-(2-cyanobenzyl) butyrylamino]-4-nitrobenzoate

Potassium carbonate (296 mg) was added to a solution of 200 mg of ethyl 3-butyrylamino-4-nitrobenzoate and 154 mg of 2-cyanobenzyl bromide in N,N-dimethylformamide, and the mixture was stirred at 20° C. for 3 hours. The reaction mixture was extracted with ethyl acetate and with water. The organic layer was washed with water and with a sodium chloride aqueous solution, and was then dried over magnesium sulfate. The solvent was distilled off under reduced pressure to give 330 mg of yellow oil of ethyl 3-[N-(2-cyanobenzyl)butyrylamino]-4-nitrobenzoate.

Properties of the compound:

$^1$H-NMR (CDCl$_3$, δ): 0.86 (3H, t, J=8 Hz), 1.49 (3H, t, J=8 Hz), 1.67 (2H, sextet, J=8 Hz), 2.02 (2H, t, J=8 Hz), 4.28–4.52 (2H, m), 4.90 (1H, d, J=15 Hz), 5.28 (1H, d, J=15 Hz), 7.40 (1H, t, J=8 Hz), 7.61 (1H, dt, J=1, 8 Hz), 7.70 (1H, d, J=1 Hz), 7.74 (1H, dd, J=1, 8 Hz), 8.02 (1H, d, J=10 Hz), 8.22 (1H, dd, J=1, 10 Hz)

Production Example 6

The following compounds were produced in the same manner as in Production Example 5.

Production Example 6-1

Ethyl 3-[N-(3-fluorobenzyl)butyrylamino]-4-nitrobenzoate

Properties of the compound:
yellow oil.
$^1$H-NMR (CDCl$_3$, δ): 0.86 (3H, t, J=7.5 Hz), 1.35 (3H, t, J=7.5 Hz), 1.68 (2H, m), 2.00 (2H, t, J=7.5 Hz), 4.36 (1H, d, J=15 Hz), 4.40 (2H, m), 5.31 (1H, d, J=15 Hz), 6.85–7.28 (4H, m), 7.60 (1H, d, J=1.5 Hz), 7.97 (1H, d, J=10 Hz), 8.16 (1H, dd, J=10,1.5 Hz)

Production Example 6-2

Ethyl 4-nitro-3-[N-(2-pyridylmethyl)-n-butyrylamino]benzoate

This compound was used in the subsequent step at once.
Property of the compound:
yellow oil.

Production Example 6-3

Ethyl 3-[N-(2,6-dichlorobenzyl)butyrylamino]-4-nitrobenzoate

Properties of the compound:
$^1$H-NMR (CDCl$_3$, δ): 0.89 (3H, t, J=7.5 Hz), 1.38 (3H, t, J=7.5 Hz), 1.70 (2H, m), 2.03 (2H, t, J=7.5 Hz), 4.36 (2H, m), 4.96 (1H, d, J=13.5 Hz), 5.70(1H, d, J=13.5 Hz), 7.10–7.28 (3H, m), 7.49 (1H, d, J=1.5 Hz), 8.03 (1H, d, J=7.5 Hz), 8.14 (1H, dd, J=7.5 and 1.5 Hz)
mp: 85–89° C.

Production Example 6-4

Ethyl 3-[N-(3-methylbenzyl)propionylamino]-4-nitrobenzoate

This compound was used in the subsequent step at once.
Property of the compound:
yellow oil.

Production Example 6-5

Ethyl 3-[N-(2-fluorobenzyl) cyclopropanecarbonylamino]-4-nitrobenzoate

Properties of the compound:
yellow oil.
$^1$H-NMR (CDCl$_3$, δ): 0.60–0.71 (2H, m), 0.99–1.14 (3H, m), 1.38 (3H, t, J=7.5 Hz), 4.37 (2H, m), 4.62 (1H, d, J=12 Hz), 5.30 (1H, d, J=12 Hz), 6.92 (1H, t, J=7.5 Hz), 7.10 (1H, t, J=7.5 Hz), 7.26 (1H, m), 7.42 (1H, t, J=7.5 Hz), 7.80 (1H, s), 7.99 (1H, d, J=7.5 Hz), 8.14 (1H, dd, J=7.5 and 2 Hz)

Production Example 6-6

Ethyl 3-[N-(2-chlorobenzyl) cyclobutanecarbonylamino]-4-nitrobenzoate

Properties of the compound:
$^1$H-NMR (CDCl$_3$, δ): 1.37 (3H, t, J=7.5 Hz), 1.68–1.87 (4H, m), 2.22–2.58 (2H, m), 2.75–2.94 (1H, m), 4.23–4.46 (2H, m), 4.63 (1H, d, J=15 Hz), 5.45 (1H, d, J=15 Hz), 7.14–7.24 (3H, m), 7.35–7.45 (1H, m), 7.56 (1H, d, J=2 Hz), 7.97 (1H, d, J=9 Hz), 8.13 (1H, dd, J=9, 2 Hz)

Production Example 6-7

Ethyl 3-cyclobutanecarbonylamino-4-nitrobenzoate
Properties of the compound:
$^1$H-NMR (CDCl$_3$, δ): 1.43 (3H, t, J=7.5 Hz), 1.86–2.19 (2H, m), 2.22–2.54 (4H, m), 3.20–3.41 (1H, m), 4.43 (2H, q, J=7.5 Hz), 7.80 (1H, dd, J=10, 2 Hz), 8.26 (1H, d, J=10 Hz), 9.45 (1H, d, J=2 Hz)
mp: 94–96° C.

Production Example 7

Production of 3-acetylamino-4-nitrobenzamide

Oxalyl chloride (3.91 ml) was added dropwise to a solution of 7.00 g of 3-acetylamino-4-nitrobenzoic acid in 50 ml of dichloromethane in a nitrogen atmosphere while being cooled with ice, and the mixture was stirred for 1 hour while being cooled with ice and then at room temperature for 2.5 hours. The reaction solvent was distilled off under reduced pressure, and the residue was then dissolved in 50 ml of tetrahydrofuran. The solution was added dropwise to 28% aqueous ammonia in a nitrogen atmosphere while being cooled with ice. The reaction solution was stirred for 1 hour, and water and ethyl acetate were added thereto. Approximately 8 g of the solid material precipitated were collected through filtration. After the filtrate was separated, the organic layer was washed with water, and dried over magnesium sulfate. Then, the solvent was distilled off under reduced pressure to obtain the residue. The solid material precipitated and the residue were combined, washed with hot ethyl acetate, and collected through filtration to give 4.94 g of 3-acetylamino-4-nitrobenzamide.
Properties of the compound:
$^1$H-NMR (DMSO-d6, δ): 2.08 (3H, s), 7.68 (1H, br s), 7.78 (1H, dd, J=9, 2 Hz), 7.94–8.05 (2H, m), 8.23 (1H, brs)
Mass (FAB): 224

Production Example 8

Production of 3-[N-(2-chlorobenzyl)acetylamino]-4-nitrobenzamide

3-[N-(2-chlorobenzyl)acetylamino]-4-nitrobenzamide was produced from the compound in the same manner as in Production Example 7.
Properties of the compound:
$^1$H-NMR (DMSO-d6, δ): 1.86 (3H, s), 4.64 (1H, d, J=15 Hz), 5.06 (1H, d, J=15 Hz), 7.22–7.40 (4H, m), 7.73 (1H, br s), 7.84 (1H, d, J=2 Hz), 8.03 (1H, dd, J=9, 2 Hz), 8.14 (1H, d, J=9 Hz), 8.22 (1H, br s)

Production Example 9

Production of 3-[N-(2-chlorobenzyl)acetylamino]-4-nitrobenznitrile

Thirty milliliters of 1,4-dioxane were added dropwise to a solution of 1.70 ml of titanium tetrachloride in 4 ml of dichloromethane in a nitrogen atmosphere while being cooled with ice. Then, a solution of 2.70 g of 3-[N-(2chlorobenzyl)acetylamino]-4-nitrobenzamide in 65 ml of 1,4-dioxane was added dropwise thereto. After the mixture was stirred for 15 minutes, 3.14 g of triethylamine were added thereto, and the mixture was stirred for 2 hours while being cooled with ice. After the completion of the reaction, the solvent was distilled off under reduced pressure, and the residue was extracted with ethyl acetate and with water. The organic layer was washed with water, and was dried over magnesium sulfate. Subsequently, the solvent was distilled off under reduced pressure. The residue was purified through column chromatography [200 ml, a mixture of n-hexane and ethyl acetate at a ratio of 4:1] to give 1.21 g of 3-[N-(2-chlorobenzyl)acetylamino]-4-nitrobenznitrile.

Properties of the compound:

$^1$H-NMR (CDCl$_3$, δ): 1.92 (3H, s), 4.61 (1H, d, J=15 Hz), 5.40 (1H, d, J=15 Hz), 7.18–7.50 (5H, m), 7.80 (1H, dd, J=9, 2 Hz), 8.01 (1H, d, J=9 Hz) Mass (FAB): 300

IR (Nujol): 2250 cm$^{-1}$

Production Example 10

Production of 3-[N-(2-chlorobenzyl)amino]-4-nitrobenznitrile

One milliliter of 35% hydrochloric acid was added to a solution of 850 mg of 3-[N-(2-chlorobenzyl)acetylamino]-4-nitrobenzamide in 10 ml of 1,4-dioxane, and the mixture was heat-refluxed for 4 days. After the solvent was distilled off from the reaction solution under reduced pressure, the residue was separated by being poured in a mixture solution of water and chloroform. The organic layer was washed with water, and was dried over magnesium sulfate. The solvent was distilled off under reduced pressure. The residue was purified through column chromatography [50 ml, chloroform] to give 230 mg of 3-[N-(2-chlorobenzyl)amino]-4-nitrobenznitrile.

Properties of the compound:

$^1$H-NMR (CDCl$_3$, δ): 4.65 (2H, d, J=6 Hz), 6.93 (1H, dd, J=9, 2 Hz), 7.10 (1H, d, J=2 Hz), 7.25–7.40 (3H, m), 7.40–7.54 (1H, m), 8.30 (1H, d, J=9 Hz), 8.45 (1H, br s)

Mass (FAB): 258

IR (Nujol): 2220 cm$^{-1}$

Production Example 11

Production of 4-amino-3-[N-(2-chlorobenzyl)amino]-benznitrile

Fifty milligrams of 10% palladium on carbon were added to a mixed solution of 261 mg of 3-[N-(2-chlorobenzyl)amino]-4-nitrobenznitrile, 15 ml of methanol and 3 ml of 1,4-dioxane to conduct the catalytic reduction in a hydrogen atmosphere at 3 atm. After the completion of the reaction, the reaction solution was filtered through celite, and the filtrate was distilled off under reduced pressure. The resulting solid material was washed with ether, and was collected through filtration to give 196 mg of 4-amino-3-[N-(2-chlorobenzyl)amino]benznitrile.

Properties of the compound:

$^1$H-NMR (DMSO-d6, δ): 4.39 (2H, d, J=5 Hz), 5.57 (1H, t, J=5 Hz), 5.69 (2H, S), 6.46 (1H, d, J=2 Hz), 6.61 (1H, d, J=9 Hz), 6.88 (1H, dd, J=9, 2 Hz), 7.25–7.41 (3H, m), 7.44–7.54 (1H, m)

EXAMPLE 1

Synthesis of 1-(2-bromobenzyl)-6-ethoxycarbonyl-2-n-propylbenzimidazole (42)

A suspension obtained by adding 390 mg of ethyl 3-[N-(2-bromobenzyl)butyrylamino]-4-nitrobenzoate and 210 mg of reduced iron to a mixed solution of 1 ml of acetic acid and 2 ml of ethanol was refluxed for 1 hour while being vigorously stirred. After the completion of the reaction, the reaction solution was cooled down and filtered through celite, and the filtrate was then concentrated under reduced pressure. The residue was separated with the addition of ethyl acetate and a sodium hydrogencarbonate aqueous solution. After the organic solvent layer was dried, the solvent was distilled off under reduced pressure, and the brown residue was obtained. This residue was purified through flash column chromatography to give 160 mg of yellow crystals of 1-(2-bromobenzyl)-6-ethoxycarbonyl-2-n-propylbenzimidazole (42).

Properties of Compound (42):

$^1$H-NMR (CDCl$_3$, δ): 1.04 (3H, t, J=8 Hz), 1.40 (3H, t, J=8 Hz), 1.78–1.98 (2H, m), 2.34 (2H, t, J=8 Hz), 4.38 (2H, q, J=8 Hz), 5.45 (2H, s), 6.65 (1H, t, J=8 Hz), 7.00 (1H, t, J=8 Hz), 7.13 (1H, t, J=8 Hz), 7.28 (1H, t, J=8 Hz), 7.78 (1H, d, J=10 Hz), 7.99 (1H, d, J=10 Hz), 8.02 (1H, s)

mp: 134–135° C.

EXAMPLE 2

Synthesis of 1-(2-cyanobenzyl)-6-ethoxycarbonyl-2-n-propylbenzimidazole (43)

In the same manner as in Example 1, 160 mg of colorless crystals of 1-(2-cyanobenzyl)-6-ethoxycarbonyl-2-n-propylbenzimidazole (43) were formed from 390 mg of ethyl 3-[N-(2-cyanobenzyl)butyrylamino]-4-nitrobenzoate.

Properties of Compound (43):

$^1$H-NMR (CDCl$_3$, δ): 1.04 (3H, t, J=8 Hz), 1.40 (3H, t, J=8 Hz), 1.88 (2H, sextet, J=8 Hz), 2.80 (2H, t, J=8 Hz), 4.38 (2H, q, J=8 Hz), 5.62 (2H, s), 6.57–6.63 (1H, m), 7.38–7.50 (2H, m), 7.78 (1H, dd, J=1, 8 Hz), 7.79 (1H, d, J=8 Hz), 7.94 (1H, d, J=1 Hz), 8.03 (1H, dd, J=1, 8 Hz)

mp: 132–134° C.

EXAMPLE 3

Synthesis of 1-(2-chlorobenzyl)-6-ethoxycarbonyl-2-phenylbenzimidazole (44)

In the same manner as in Example 1, 220 mg of yellow crystals of 1-(2-chlorobenzyl)-6-ethoxycarbonyl-2-phenylbenzimidazole (44) were obtained from 460 mg of ethyl 3-[N-(2-chlorobenzyl)benzoylamino]-4-nitrobenzoate.

Properties of Compound (44):

$^1$H-NMR (CDCl$_3$, δ): 1.40 (3H, t, J=8 Hz), 4.38 (2H, q, J=8 Hz), 5.56 (2H, s), 6.72 (H, dd, J=1, 8 Hz), 7.18 (1H, dt, J=1, 8 Hz), 7.30 (1H, dt, J=1, 8 Hz), 7.45–7.55 (4H, m), 7.64 (1H, d, J=1 Hz), 7.68 (1H, d, J=1 Hz), 7.90 (1H, d, J=10 Hz), 7.95 (1H, s), 8.08 (1H, dd, J=1, 8 Hz)

mp: 140–142° C.

EXAMPLE 4

Synthesis of 6-ethoxycarbonyl-1-(2-fluorobenzyl)-2-n-propylbenzimidazole (45)

In the same manner as in Example 1, 160 mg of colorless crystals of 6-ethoxycarbonyl-1-(2-fluorobenzyl)-2-n-propylbenzimidazole (45) were formed from 390 mg of ethyl 3-[N-(2- fluorobenzyl)butyrylamino]-4-nitrobenzoate.

Properties of Compound (45):

$^1$H-NMR (CDCl$_3$, δ): 1.04 (3H, t, J=8 Hz), 1.40 (3H, t, J=8 Hz), 1.78–1.98 (2H, m), 2.34 (2H, t, J=8 Hz), 4.38 (2H, q, J=8 Hz), 5.45 (2H, s), 6.65 (1H, t, J=8 Hz), 7.00 1H, t, J=8 Hz), 7.13 (1H, t, J=8 Hz), 7.28 (1H, t, J=8 Hz), 7.78 (1H, d, J=10 Hz), 7.99 (1H, d, J=10 Hz), 8.02 (1H, s)

mp: 134–135° C.

EXAMPLE 5

Synthesis of 6-ethoxycarbonyl-1-(4-fluorobenzyl)-2-n-propylbenzimidazole (46)

In the same manner as in Example 1, 160 mg of colorless crystals of 6-ethoxycarbonyl-1-(4-fluorobenzyl)-2-n- propylbenzimidazole (46) were formed from 400 mg of ethyl 3-[N-(4-fluorobenzyl)butyryl)amino]-4-nitrobenzoate.

Properties of Compound (46):

$^1$H-NMR (CDCl$_3$, δ): 1.04 (3H, t, J=8 Hz), 1.40 (3H, t, J=8 Hz), 1.88 (2H, sextet, J=8 Hz), 2.82 (2H, t, J=8 Hz), 4.38 (2H, q, J=8 Hz), 5.38 (2H, s), 7.00 (4H, d, J=7 Hz), 7.77 (1H, d, J=8 Hz), 7.98 (1H, d, J=1 Hz), 8.00 (1H, dd, J=1, 8 Hz)

mp: 134–135° C.

EXAMPLE 6

The following compounds were formed in the same manner as in Example 1.

EXAMPLE 6-1

6-Ethoxycarbonyl-2-n-propyl-1-(2-pyridylmethyl) benzimidazole (47)

Properties of Compound (47)

$^1$H-NMR (CDCl$_3$, δ): 1.03 (3H, t, J=7.5 Hz), 1.39 (3H, t, J=7.5 Hz), 1.89 (2H, m), 2.86 (2H, t, J=7.5 Hz), 4.38 (2H, q, J=7.5 Hz), 5.50 (2H, s), 6.72 (1H, d, J=7.5 Hz), 7.24 (1H, m), 7.58 (1H, dt, J=7.5,1.5 Hz), 7.79 (1H, d, J=7.5 Hz), 7.96–8.02 (2H, m), 8.60 (1H, d, J=4 Hz)

mp: 84–85° C.

EXAMPLE 6-2

6-Ethoxycarbonyl-1-(3-fluorobenzyl)-2-n-propylbenzimidazole (48)

Properties of Compound (48)

$^1$H-NMR (CDCl$_3$, δ): 1.04 (3H, t, J=7.5 Hz), 1.39 (3H, t, J=7.5 Hz), 1.90 (2H, m), 2.81 (2H, t, J=7.5 Hz), 4.39 (2H, q, J=7.5 Hz), 5.39 (2H, s), 6.70–6.84 (2H, m), 7.00 (1H, dt, J=8.5 and 1.5 Hz), 7.78 (1H, d, J=8.5 Hz), 7.96 (1H, s), 8.00 (1H, d, J=8.5 Hz)

mp: 142–146° C.

EXAMPLE 6-3

1-(2,6-Dichlorobenzyl)-6-ethoxycarbonyl-2-n-propylbenzimidazole (49)

Properties of Compound (49)

$^1$H-NMR (CDCl$_3$, δ): 1.03 (3H, t, J=7.5 Hz), 1.38 (3H, t, J=7.5 Hz), 1.88 (2H, m), 2.93 (2H, t, J=7.5 Hz), 4.34 (2H, q, J=7.5 Hz), 5.61 (2H, s), 7.26 (1H, d, J=7.5 Hz), 7.39 (2H, d, J=7.5 Hz), 7.68 (1H, d, J=7.5 Hz), 7.84 (1H, d, J=1.5 Hz), 7.91 (2H, d, J=7.5 Hz)

mp: 153–153° C.

EXAMPLE 6-4

1-(3-Methylbenzyl)-6-ethoxycarbonyl-2-n-propylbenzimidazole (50)

Properties of Compound (50):

colorless solid.

$^1$H-NMR (CDCl$_3$, δ): 1.02 (3H, t, J=7.5 Hz), 1.41 (3H, t, J=7.5 Hz), 1.89 (2H, m), 2.29 (3H, s), 2.82 (2H, t, J=7.5 Hz), 4.38 (2H, q, J=7.5 Hz), 5.35 (2H, s), 6.79–6.86 (2H, m), 7.09 (1H, d, J=7.5 Hz), 7.20 (1H, t, J=7.5 Hz), 7.76 (1H, d, J=7.5 Hz), 7.95–8.02 (2H, m)

EXAMPLE 6-5

2-Cyclopropyl-6-ethoxycarbonyl-1-(2-fluorobenzyl) benzimidazole (51)

Properties of Compound (51):

$^1$H-NMR (CDCl$_3$, δ): 1.10 (2H, m), 1.27 (2H, m), 1.40 (3H, t, J=7.5 Hz), 1.95 (1H, m), 4.37 (2H, q, J=7.5 Hz), 5.56 (2H, s), 6.77 (1H, t, J=7.5 Hz), 7.03 (1H, t, J=7.5 Hz), 7.13 (1H, t, J=7.5 Hz), 7.29 (1H, m), 7.69 (1H, d, J=7.5 Hz), 7.96 (1H, d, J=7.5 Hz), 8.02 (1H, d, J=2 Hz)

mp: 122–126° C.

EXAMPLE 6-6

1-(2-Chlorobenzyl)-6-cyano-2-cyclopropylbenzimidazole (52)

Properties of Compound (52):

$^1$H-NMR (CDCl$_3$, δ): 1.04–1.24 (2H, m), 1.24–1.39 (2H, m), 1.83–2.01 (1H, m), 5.58 (2H, s), 6.54 (1H, d, J=9 Hz), 7.16 (1H, td, J=9, 2 Hz), 7.22–7.38 (1H, m), 7.43–7.56 (3H, m), 7.74 (1H, dd, J=9, 2 Hz)

Mass (FAB): 308 (M+1)

IR (Nujol): 2210 cm$^{-1}$

EXAMPLE 6-7

1-(2-Chlorobenzyl)-2-cyclobutyl-6-ethoxycarbonylbenzimidazole (53)

Properties of Compound (53):

$^1$H-NMR (CDCl$_3$, δ): 1.38 (3H, t, J=7.5 Hz), 1.90–2.21 (2H, m), 2.21–2.24 (2H, m), 2.46–2.70 (2H, m), 3.52–3.73 (1H, m), 4.37 (2H, q, J=7.5 Hz), 5.39 (2H, s), 6.34 (1H, dd, J=9, 2 Hz), 7.06 (1H, td, J=9, 2 Hz), 7.23 (1H, td, J=9, 2 Hz), 7.46 (1H, dd, J=9, 2 Hz), 7.83 (1H, d, J=9 Hz), 7.92 (1H, d, J=2 Hz), 8.01 (1H, dd, J=9, 2 Hz)

mp: 111–113° C.

EXAMPLE 6-8

1-(2-Chlorobenzyl)-6-ethoxycarbonyl-2-n-pentylbenzimidazole (54)

Properties of Compound (54):

$^1$H-NMR (CDCl$_3$, δ): 0.87 (3H, t, J=7.5 Hz), 1.22–1.47 (7H, m), 1.74–1.93 (2H, m), 2.80 (2H, t, J=7.5 Hz), 4.37 (2H, q, J=7.5 Hz), 5.47 (2H, s), 6.39 (1H, dd, J=9, 2 Hz), 7.08 (1H, td, J=9, 2 Hz), 7.19–7.33 (1H, m), 7.48 (1H, dd, J=9, 2 Hz), 7.79 (1H, d, J=9 Hz), 7.94 (1H, d, J=2 Hz), 8.00 (1H,dd, J=9, 2 Hz)

EXAMPLE 7

5-Carboxy-1-(2-chlorobenzyl)-2-n-propylbenzimidazole (55)

Twenty milliliters of ethanol and 10.4 g of a 10% sodium hydroxide aqueous solution were added to 2.8 g of 1-(2-chlorobenzyl)-5-ethoxycarbonyl-2-n-propylbenzimidazole, and the mixture was heat-refluxed for 4 hours. The reaction solution was cooled, and was then adjusted to a pH of 6 with 10% hydrochloric acid. The crystals were collected, washed with water, and dried under reduced pressure to give 2.46 g of a colorless solid of 5-carboxy-1-(2-chlorobenzyl)-2-n-propylbenzimidazole (55).

Properties of Compound (55):

$^1$H-NMR (DMSO-d6, δ): 0.93 (3H, t, J=7.5 Hz), 1.75 (2H, m), 2.79 (2H,t, J=7.5 Hz), 5.61 (2H, s), 6.49 (1H, d, J=7.5

Hz), 7.21 (1H, t, J=7.5 Hz),7.33 (1H, t, J=7.5 Hz), 7.46 (1H, d, J=7.5 Hz), 7.56 (1H, d, J=7.5 Hz), 7.80 (1H, d, J=7.5 Hz), 8.20 (1H, s)

EXAMPLE 8

The following compounds were formed in the same manner as in Example 7.

EXAMPLE 8-1

6-Carboxy-1-(3-methylbenzyl)-2-n-propylbenzimidazole (56)

Properties of Compound (56):
colorless solid.
$^1$H-NMR (DMSO-d6, δ): 0.97 (3H, t, J=7.5 Hz), 1.78 (2H, m), 2.23 (3H, s), 3.86 (2H, q, J=7.5 Hz), 5.53 (2H, s), 6.80 (1H, d, J=7.5 Hz), 6.91 (1H,s), 7.07 (1H, d, J=7.5 Hz), 7.21 (1H, t, J=7.5 Hz), 7.65 (1H, d, J=7.5 Hz),7.79 (1H, d, J=7.5 Hz), 8.04 (1H, s)

EXAMPLE 8-2

2-n-Butyl-7-carboxy-1-(2-chlorobenzyl)benzimidazole (57)

Properties of Compound (57):
$^1$H-NMR (DMSO-d6, δ): 0.84 (3H, t, J=7.5 Hz), 1.34 (2H, m), 1.71 (2H, m), 2.80 (2H, t, J=7.5 Hz), 5.89 (2H, s), 6.03 (1H, d, J=7.5 Hz), 7.13 (1H, t, J=7.5 Hz), 7.27 (2H, t, J=7.5 Hz), 7.48 (1H, d, J=7.5 Hz), 7.63 (1H, d, J=7.5 Hz), 7.87 (1H, d, J=7.5 Hz)

EXAMPLE 8-3

6-Carboxy-2-cyclopropyl-1-(2-fluorobenzyl)benzimidazole (58)

Properties of Compound (58):
$^1$H-NMR (DMSO-d6, δ): 1.04–1.19 (4H, m), 2.37 (1H, m), 5.79 (2H, s), 7.00 (1H, t, J=7.5 Hz), 7.15 (1H, t, J=7.5 Hz), 7.27 (1H, t, J=10.5 Hz), 7.37 (1H, m), 7.60 (1H, d, J=7.5 Hz), 7.82 (1H, d, J=7.5 Hz), 8.11 (1H, s)
mp: 224–229° C.

EXAMPLE 8-4

2-n-Butyl-6-carboxy-1-(2-fluorobenzyl)benzimidazole (59)

Properties of Compound (59):
$^1$H-NMR (DMSO-d6, δ): 0.87 (3H, t, J=7.5 Hz), 1.26–1.48 (2H, m), 1.60–1.80 (2H, m), 2.90 (2H, t, J=7.5 Hz), 5.63 (2H, s), 6.89 (1H, td, J=9, 2 Hz), 7.13 (1H, td, J=9, 2 Hz), 7.20–7.44 (2H, m), 7.64 (1H, d, J=9 Hz), 7.80 (1H, dd, J=9, 2 Hz), 8.08 (1H, d, J=2 Hz)
mp: 216–219° C.

EXAMPLE 9

Synthesis of 1-(2-chlorobenzyl)-6-chlorocarbonyl-2-cyclopropylbenzimidazole hydrochloride (60)

Oxalyl chloride (0.208 ml) was added dropwise to a suspension prepared by adding 390 mg of 6-carboxy-1-(2-chlorobenzyl)-2-cyclopropylbenzimidazole to 10 ml of methylene chloride containing 1 drop of N,N-dimethylformamide at room temperature over a period of several minutes. The mixture was stirred at the same temperature for 2 hours, and was then concentrated under reduced pressure. Isopropyl ether was added to the residue, and the mixture was pulverized to give 450 mg of 1-(2-chlorobenzyl)-6-chlorocarbonyl-2-cyclopropylbenzimidazole hydrochloride (60) as a white powder. Since this product was unstable, it was used as a starting material in the subsequent step without being purified.

EXAMPLE 10

Synthesis of 1-(2-chlorobenzyl)-6-(4-dimethylaminophenylmethylcarbamoyl)-2-n-propylbenzimidazole (61)

Four-hundred milligrams of 6-carboxy-1-(2-chlorobenzyl)-2-n-propylbenzimidazole were dissolved in 3 ml of methylene chloride containing 1 drop of N,N-dimethylformamide. Oxalyl chloride (28 mg) was added to this solution at 5° C. The thus-obtained solution was stirred at room temperature for 1 hour, and was then concentrated under reduced pressure. The residue was dissolved in 3 ml of methylene chloride, and the mixture was added to a mixed solution prepared by adding 271 mg of 4-dimethylaminobenzylamine hydrochloride and 1 ml of triethylamine to 10 ml of methylene chloride at room temperature. The resulting reaction mixture was stirred at the same temperature for 1 hour, washed with water, dried and then concentrated under reduced pressure. The residue was developed and purified through thin-layer chromatography to give 215 mg of 1-(2-chlorobenzyl)-6-(4-dimethylaminophenylmethylcarbamoyl)-2-n-propylbenzimidazole (61).

Properties of Compound (61):
colorless crystal.
$^1$H-NMR (CDCl$_3$, δ): 1.01 (3H, t, J=7 Hz), 1.88 (2H, sextet, J=7 Hz), 2.76 (2H, t, J=7 Hz), 2.95 (6H, s), 4.50 (2H, d, J=5 Hz), 5.45 (2H, s), 6.32 (1H, d, J=5 Hz), 6.36 (1H, d, J=7 Hz), 6.72 (2H, d, J=10 Hz), 7.07 (1H, dt, J=1, 8 Hz), 7.20–7.25 (3H, m), 7.46 (1H, dd, J=1, 8 Hz), 7.58 (1H, dd, J=1, 8 Hz), 7.76 (1H, d, J=8 Hz), 7.82 (1H, d, J=1 Hz)
mp: 155–156° C.

EXAMPLE 11

Synthesis of 1-(2-chlorobenzyl)-6-morpholinocarbamoyl-2-n-propylbenzimidazole (62)

In the same manner as in Example 10, 205 mg of 1-(2-chlorobenzyl)-6-morpholinocarbamoyl-2-n-propylbenzimidazole (62) were formed from 200 mg of 6-carboxy-1-(2-chlorobenzyl)-2-n-propylbenzimidazole and 124 mg of 4-aminomorpholine.

Properties of Compound (62):
colorless crystal.
$^1$H-NMR (CDCl$_3$, δ): 1.03 (3H, t, J=8 Hz), 1.88 (2H, sextet, J=8 Hz), 2.62 (4H, bs), 2.72 (2H, t, J=8 Hz), 3.85 (4H, bs), 5.42 (2H, s), 6.42 (1H, dd, J=1, 8 Hz), 7.08 (1H, dt, J=1, 8Hz), 7.20–7.28 (3H, m), 7.47 (1H, dd, J=1, 8 Hz), 7.78 (1H, dd, J=1, 8 Hz)
mp: 195–197° C.

EXAMPLE 12

Synthesis of 1-(2-chlorobenzyl)-2-n-propyl-6-thiomorpholinocarbonylbenzimidazole (63)

In the same manner as in Example 10, 160 mg of 1-(2-chlorobenzyl-2-n-propyl-6-thiomorpholinocarbonylbenzimidazole (63) were formed from 200 mg of 6-carboxy-1-(2-chlorobenzyl)-2-n-propylbenzimidazole and 125 mg of thiomorpholine.

Properties of Compound (63):

colorless crystal.

$^1$H-NMR (CDCl$_3$, δ): 1.03 (3H, t, J=8 Hz), 1.88 (2H, sextet, J=8 Hz), 2.78 (2H, t, J=8 Hz), 2.96 (4H, bt, J=5 Hz), 3.88 (4H, bt, J=5 Hz), 5.46 (2H, s), 6.34 (1H, dd, J=1, 8 Hz), 7.08 (1H, dt, J=1, 8 Hz), 7.26 (2H, dt, J=1, 8 Hz), 7.47 (1H, dd, J=1, 8 Hz), 7.58 (1H, bd, J=8 Hz), 7.76 (1H, s), 7.78 (1H, d, J=8 Hz)

mp: 160–162° C.

EXAMPLE 13

Synthesis of 2-n-butyl-1-(2-chlorobenzyl)-6-[(2-pyridylmethyl)carbamoyl]benzimidazole (64)

In the same manner as in Example 10, 230 mg of 2-n-butyl-1-(2-chlorobenzyl)-6-[(2-pyridylmethyl) carbamoyl]benzimidazole (64) were formed from 200 mg of 6-carboxy-2-n-butyl-1-(2-chlorobenzyl)-benzimidazole and 126 mg of 2-aminomethylpyridine.

Properties of Compound (64):

colorless crystal.

$^1$H-NMR (CDCl$_3$, δ): 0.92 (3H, t, J=8 Hz), 1.42 (2H, sextet, J=8 Hz), 1.82 (2H, quintet, J=8 Hz), 2.82 (2H, t, J=8 Hz), 4.76 (1H, d, J=5 Hz), 5.46 (2H, s), 6.38 (1H, dd, J=1, 8 Hz), 7.08 (1H, dt, J=1, 8 Hz), 7.18–7.26 (2H, m), 7.32 (1H, d, J=8 Hz), 7.46 (1H, dd, J=1, 8 Hz), 7.62 (1H, dt, J=1, 8 Hz), 7.72 (1H, dt, J=1, 8 Hz), 7.82 (1H, d, J=8 Hz), 7.88 (1H, d, J=1 Hz), 8.56 (1H, dd, J=1, 8 Hz)

mp: 175–176° C.

EXAMPLE 14

Synthesis of 2-n-butyl-5-carbamoyl-1-(2-chlorobenzyl)benzimidazole (65)

In the same manner as in Example 10, 170 mg of 2-n-butyl-5-carbamoyl-1-(2-chlorobenzyl)benzimidazole (65) were formed from 100 mg of 2-n-butyl-1-(2-chlorobenzyl)-5-carboxybenzimidazole.

Properties of Compound (65):

colorless crystal.

$^1$H-NMR (DMSO-d6, δ): 0.84 (3H, t, J=8 Hz), 1.35 (2H, sextet, J=8 Hz), 1.68 (2H, quintet, J=8 Hz), 2.78 (2H, t, J=8 Hz), 5.58 (2H, s), 6.50 (1H, dd, J=1, 8 Hz), 7.25 (1H, dt, J=1, 8 Hz), 7.28 (1H, bs), 7.35 (1H, dt, J=1, 8 Hz), 7.42 (1H, d, J=10 Hz), 7.56 (1H, dd, J=1, 8 Hz), 7.74 (1H, dd, J=1, 10 Hz), 7.96 (1H, bs), 8.20 (1H, d, J=1 Hz)

mp: 195–198° C.

EXAMPLE 15

Synthesis of 1-(2-chlorobenzyl)-2-cyclopropyl-6-morpholinocarbonylbenzimidazole (66)

1-(2-Chlorobenzyl)-6-chlorocarbonyl-2-cyclopropylbenzimidazole hydrochloride (140 mg) was added to a solution prepared by adding 298 mg of morpholine (30% methanol solution) to 10 ml of methylene chloride at room temperature. The reaction mixture was stirred at the same temperature for 1 hour, then washed with water, dried, and concentrated under reduced pressure. The residue was recrystallized with ether to give 20 mg of 1-(2-chlorobenzyl)-2-cyclopropyl-6-morpholinocarbonylbenzimidazole (66).

Properties of Compound (66):

colorless crystal.

$^1$H-NMR (CDCl$_3$, δ): 1.04–1.12 (2H, m), 1.25–1.32 (2H, m), 1.82–1.96 (1H, m), 3.68 (8H, bs), 5.56 (2H, s), 6.55 (1H, dd, J=1, 8 Hz), 7.13 (1H, dt, J=1, 8 Hz), 7.22–7.29 (2H, m), 7.30 (1H, d, J=1 Hz), 7.46 (1H, dd, J=1, 8 Hz), 7.77 (1H, d, J=8 Hz)

mp: 193–195° C.

EXAMPLE 16

Synthesis of 1-(2-chlorobenzyl)-2-cyclopropyl-6-[(2-pyridylmethyl)carbamoyl]benzimidazole (67)

In the same manner as in Example 15, 95 mg of 1-(2-chlorobenzyl)-2-cyclopropyl-6-[(2-pyridylmethyl) carbamoyl]benzimidazole (67) were formed from 150 mg of 1-(2-chlorobenzyl)-6-chlorocarbonyl-2-cyclopropylbenzimidazole hydrochloride and 85 mg of 2-aminomethylpyridine.

Properties of Compound (67):

colorless crystal.

$^1$H-NMR (CDCl$_3$, δ): 1.02–1.13 (2H, m), 1.24–1.32 (2H, m), 1.82–1.95 (1H, m), 4.76 (2H, d, J=5 Hz), 5.59 (2H, s), 7.11 (1H, dt, J=1, 8 Hz), 7.20–7.26 (2H, m), 7.34 (1H, d, J=8 Hz), 7.46 (1H, dd, J=1, 8 Hz), 7.60 (1H, t, J=5 Hz), 7.66 (1H, dd, J=1, 8 Hz), 7.73 (1H, s), 7.88 (1H, s)

mp: 134–135° C.

EXAMPLE 17

The following compounds were formed in the same manner as in Example 15.

EXAMPLE 17-1

1-(2-Chlorobenzyl)-2-cyclopropyl-6-(2-pyridylcarbamoyl)benzimidazole (68)

Properties of Compound (68):

$^1$H-NMR (CDCl$_3$, δ): 1.16 (2H, m), 1.32 (2H, m), 1.92 (1H, m), 5.61 (2H, s), 6.57 (1H, d, J=7.5 and 1.5 Hz), 7.15 (1H, dt, J=7.5 and 1.5 Hz), 7.22–7.31 (2H, m), 7.48 (1H, dd, J=7.5 and 1.5 Hz), 7.77 (1H, d, J=9 Hz), 8.05 (2H, m).

mp: 206–209° C.

EXAMPLE 17-2

6-(2-Carboxy-1-pyrrolidinocarbonyl)-1-(2-chlorobenzyl)-2-n-propylbenzimidazole (69)

Properties of Compound (69):

$^1$H-NMR (DMSO-d6, δ): 0.92 (3H, t, J=7.5 Hz), 1.65–1.99 (5H, m), 2.25 (1H, m), 2.77 (2H, t, J=7.5 Hz), 3.50 (2H, m), 4.40 (1H, m), 5.52 (2H, s), 6.53 (1H, d, J=7.5 Hz), 7.21–7.71 (6H, m).

mp: 96° C.

EXAMPLE 17-3

1-(2-Chlorobenzyl)-2-cyclobutyl-6-[(2-pyridylmethyl)carbamoyl]benzimidazole (70)

Properties of Compound (70):

$^1$H-NMR (CDCl$_3$, δ): 1.90–2.21 (2H, m), 2.25–2.37 (2H, m), 2.40–2.65 (2H, m), 3.64 (1H, m), 4.76 (2H, d, J=5 Hz), 5.39 (2H, s), 6.33 (1H, d, J=7.5 Hz), 7.05 (1H, t, J=7.5 Hz), 7.16–7.26 (2H, m), 7.33 (1H, d, J=7.5 Hz), 7.46 (1H, d,

J=7.5 Hz), 7.69–7.76 (3H, m), 7.73 (1H, d, J=7.5 Hz), 7.86 (1H, s), 8.55 (1H, d, J=5 Hz).

mp: 183–185° C.

EXAMPLE 17-4

(1-(2-Chlorobenzyl)-2-n-propyl-5-[(2-pyridylmethyl)carbamoyl]benzimidazole (71)

Properties of Compound (71)

$^1$H-NMR (CDCl$_3$, δ): 1.03 (3H, t, J=7.5 Hz), 1.90 (2H, m), 2.80 (2H, t, J=7.5 Hz), 4.80 (2H, d, J=5 Hz), 5.44 (2H, s), 6.40 (1H, d, J=7.5 Hz), 7.09 (1H, t, J=7.5 Hz), 7.21–7.27 (3H, m), 7.34 (1H, d, J=7.5 Hz), 7.47 (1H, d, J=7.5 Hz), 7.64–7.72 (2H, m), 7.83 (1H, dd, J=7.5 and 2 Hz), 8.30 (1H, d, J=2 Hz), 8.56 (1H, d, J=5 Hz).

mp: 115–116° C.

EXAMPLE 17-5

1-(2-Chlorobenzyl)-6-[N-methyl-N-(2-pyridylmethyl)carbamoyl]-2-n-propylbenzimidazole (72)

Properties of Compound (72):

$^1$H-NMR (DMSO-d6, δ): 1.03 (3H, t, J=7.5 Hz), 1.87 (2H, m), 2.79 (2H, t, J=7.5 Hz), 3.05 (3H, brs), 4.60 (1H, brs), 4.87 (1H, brs), 5.40 (2H, d, J=unknown), 6.38 (1H, d, J=unknown), 7.05 (1H, brs), 7.20 (3H, m), 7.35–7.49 (3H, m), 7.60–7.81 (2H, m), 8.54 (1H, brs).

mp: 99° C.

EXAMPLE 17-6

1-(2-Chlorobenzyl)-6-piperonylcarbamoyl-2-n-propylbenzimidazole (73)

Properties of Compound (73):

$^1$H-NMR (CDCl$_3$, δ): 1.01 (3H, t, J=7.5 Hz), 1.88 (2H, m), 2.78 (2H, t, J=7.5 Hz), 4.54 (2H, d, J=5 Hz), 5.45 (2H, s), 5.95 (2H, s), 6.36 (1H, d, J=7.5 Hz), 6.44 (1H, t, J=5 Hz), 6.75–6.85 (3H, m), 7.08 (1H, t, J=7.5 Hz), 7.23 (1H, t, J=7.5 Hz), 7.45 (1H, d, J=7.5 Hz), 7.67 (1H, dd, J=7.5 , 2 Hz), 7.78 (1H, d, J=7.5 Hz), 7.83 (1H, s).

mp: 131–134° C.

EXAMPLE 17-7

1-(2-chlorobenzyl)-6-phenylcarbamoyl-2-n-propylbenzimidazole (74)

Properties of Compound (74):

$^1$H-NMR (CDCl$_3$, δ): 1.03 (3H, t, J=7.5 Hz), 1.90 (2H, m), 2.81 (2H, t, J=7.5 Hz), 5.47 (2H, s), 6.40 (1H, d, J=7.5 Hz), 7.06–7.18 (2H, m), 7.26 (1H, t, J=7.5 Hz), 7.35 (2H, t, J=7.5 Hz), 7.48 (1H, d, J=7.5 Hz), 7.64 (2H, d, J=7.5 Hz), 7.72 (1H, dd, J=7.5 and 2 Hz), 7.85–7.95 (3H, m).

mp: 168° C.

EXAMPLE 17-8

1-(2-Chlorobenzyl)-2-n-propyl-6-[(4-pyridylmethyl)carbamoyl]benzimidazole (75)

Properties of Compound (75):

$^1$H-NMR (DMSO-d6, δ): 0.93 (3H, t, J=7.5 Hz), 1.76 (2H, m), 2.78 (2H, t, J=7.5 Hz), 4.49 (2H, d, J=5 Hz), 6.42 (1H, d, J=7.5 Hz), 7.22 (1H, t, J=7.5 Hz), 7.27 (2H, d, J=7.5 Hz), 7.34 (1H, t, J=7.5 Hz), 7.57 (1H, d, J=7.5 Hz), 7.69 (1H, d, J=7.5 Hz), 7.80 (1H, d, J=7.5 Hz), 7.97 (1H, s), 8.48 (2H, d, J=7.5 Hz), 9.03 (1H, t, J=5 Hz).

mp: 170–173° C.

EXAMPLE 17-9

1-(2-Chlorobenzyl)-2-n-propyl-6-[(3-pyridylmethyl)carbamoyl]benzimidazole (76)

Properties of Compound (76):

$^1$H-NMR (DMSO-d6, δ): 0.95 (3H, t, J=7.5 Hz), 1.76 (2H, m), 2.80 (2H, t, J=7.5 Hz), 4.50 (2H, d, J=5 Hz), 5.60 (2H, s), 6.42 (1H, d, J=7.5 Hz), 7.23 (1H, t, J=7.5 Hz), 7.30–7.58 (2H, m), 7.57 (1H, d, J=7.5 Hz), 7.67–7.74 (2H, m), 7.75 (1H, d, J=7.5 Hz), 7.97 (1H, s), 8.46 (1H, d, J=5 Hz), 8.56 (1H, s), 9.0 (1H, t, J=5 Hz).

mp: 193–195° C.

EXAMPLE 17-10

1-(2-Chlorobenzyl)-6-[N-methyl-N-(2-pyridyl)carbamoyl]-2-n-propylbenzimidazole (77)

Properties of Compound (77):

$^1$H-NMR (DMSO-d6, δ): 0.90 (3H, t, J=7.5 Hz), 1.70 (2H, m), 2.73 (2H, t, J=7.5 Hz), 3.40 (3H, s), 5.42 (2H, s), 6.23 (1H, d, J=7.5 Hz), 6.91 (1H, d, J=7.5 Hz), 6.98 (1H, m), 7.15–7.25 (3H, m), 7.36 (1H, t, J=7.5 Hz), 7.46–7.57 (3H, m), 8.23 (1H, m).

mp: 143–146° C.

EXAMPLE 17-11

1-(2-Chlorobenzyl)-6-(homopiperidinocarbonyl)-2-n-propylbenzimidazole (78)

Properties of Compound (78):

$^1$H-NMR (CDCl$_3$, δ): 1.03 (3H, t, J=7.5 Hz), 1.46–1.94 (10H, m), 2.80 (2H, t, J=7.5 Hz), 3.32 (2H, brs), 3.64 (2H, t, J=7.5 Hz), 5.41 (2H, s), 6.42 (1H, d, J=7.5 Hz), 7.07 (1H, t, J=7.5 Hz), 7.19–7.29 (3H, m), 7.45 (1H, d, J=7.5 Hz), 7.76 (1H, d, J=7.5 Hz).

mp: 136–137° C.

EXAMPLE 17-12

1-(3-Methylbenzyl)-2-n-propyl-6-[(2-pyridylmethyl)carbamoyl]benzimidazole (79)

Properties of Compound (79):

$^1$H-NMR (CDCl$_3$, δ): 1.02 (3H, t, J=7.5 Hz), 1.88 (2H, m), 2.26 (3H, s), 2.81 (2H, t, J=7.5 Hz), 4.76 (2H, d, J=5 Hz), 5.36 (2H, s), 6.78–6.84 (2H, m), 7.07 (1H, d, J=7.5 Hz), 7.13–7.22 (2H, m), 7.33 (1H, d, J=7.5 Hz), 7.57–7.72 (2H, m), 7.78 (1H, d, J=7.5 Hz), 7.94 (1H, s), 8.55 (1H, d, J=5 Hz).

mp: 129–131° C.

EXAMPLE 17-13

2-n-Butyl-1-(2-fluorobenzyl)-6-[N-methyl-N-(2-pyridylmethyl)carbamoyl]benzimidazole (80)

Properties of Compound (80):

$^1$H-NMR (CDCl$_3$, δ) 0.92 (3H, t, J=7.5 Hz), 1.45 (2H, m), 1.83 (2H, m), 2.86 (2H, t, J=7.5 Hz), 3.06 (3H, brs), 4.61 (1H, brs), 4.86 (1H, brs), 5.37 (2H, brd), 6.62 (1H, brd), 6.97 (1H, brs), 7.07–7.85 (8H, m), 8.57 (1H, d, J=5 Hz).

mp: 97–100° C.

EXAMPLE 17-14

1-(2-Chlorobenzyl)-2-ethyl-6-[(2-pyridylmethyl) carbamoyl]benzimidazole (81)

Properties of Compound (81):

$^1$H-NMR (CDCl$_3$, δ): 1.43 (3H, t, J=7.5 Hz), 2.84 (2H, q, J=7.5 Hz), 4.76 (2H, d, J=5 Hz), 5.45 (2H, s), 6.37 (1H, d, J=7.5 Hz), 7.07 (1H, t, J=7.5 Hz), 7.19–7.28 (2H, m), 7.33 (1H, d, J=7.5 Hz), 7.45 (1H, dd, J=7.5 and 2 Hz), 7.62–7.75 (3H, m), 7.82 (1H, d, J=7.5 Hz), 7.89 (1H, d, J=2 Hz), 8.55 (1H, d, J=5 Hz).

mp: 167–168° C.

EXAMPLE 17-15

2-n-Butyl-1-(2-chlorobenzyl)-7-[(2-pyridylmethyl) carbamoyl]benzimidazole (82)

Properties of Compound (82):

$^1$H-NMR (CDCl$_3$, δ): 0.93 (3H, t, J=7.5 Hz), 1.42 (2H, m), 1.83 (2H, m), 2.81 (2H, t, J=7.5 Hz), 4.44 (2H, d, J=5 Hz), 5.70 (2H, s), 6.13 (1H, dd, J=7.5 and 2 Hz), 6.85–6.97 (3H, m), 7.12–7.28 (4H, m), 7.34 (1H, d, J=7.5 Hz), 7.62 (1H, dt, J=7.5 and 2 Hz), 7.88 (1H, d, J=7.5 Hz), 8.40 (1H, d, J=5 Hz).

mp: 112–114° C.

EXAMPLE 17-16

2-Cyclopropyl-1-(2-fluorobenzyl)-6-(piperonylcarbamoyl)benzimidazole (83)

Properties of Compound (83):

$^1$H-NMR (DMSO-d6, δ): 1.05 (4H, m), 2.27 (1H, m), 4.38 (2H, d, J=5 Hz), 5.71 (2H, s), 5.98 (2H, s), 6.73–6.91 (4H, m), 7.14 (1H, t, J=7.5 Hz), 7.27 (1H, t, J=7.5 Hz), 7.36 (1H, m), 7.55 (1H, d, J=7.5 Hz), 7.73 (1H, dd, J=7.5 and 2 Hz), 8.04 (1H, s), 8.87 (1H, t, J=5 Hz).

mp: 170–173° C.

EXAMPLE 17-17

2-[[1-(2-chlorobenzyl)-2-ethylbenzimidazol-6-yl] carbonylaminomethyl]-pyridine-1-oxide (84)

Properties of Compound (84):

$^1$H-NMR (CDCl$_3$, δ): 1.42 (3H, t, J=7.5 Hz), 2.82 (2H, q, J=7.5 Hz), 4.81 (2H, d, J=7.5 Hz), 5.43 (2H, s), 6.31 (1H, d, J=7.5 Hz), 7.06 (1H, t, J=7.5 Hz), 7.20–7.31 (3H, m), 7.44 (1H, d, J=7.5 Hz), 7.52 (1H, dd, J=7.5 and 2 Hz), 7.65 (1H, dd, J=7.5 and 2 Hz), 7.77–7.83 (2H, m), 7.96 (1H, t, J=7.5 Hz), 8.23 (1H, dd, J=7.5 and 2 Hz).

mp: 204–207° C.

EXAMPLE 17-18

2-n-Butyl-1-(2-fluorobenzyl)-6-(2-pyridylmethylcarbamoyl)benzimidazole (85)

Properties of Compound (85):

$^1$H-NMR (CDC$_3$, δ): 0.92 (3H, t, J=7.5 Hz), 1.38–1.49 (2H, m), 1.77–1.88 (2H, m), 2.86 (2H, t, J=7.5 Hz), 4.78 (2H, d, J=5 Hz), 5.46 (2H, s), 6.67 (1H, t, J=9 Hz), 7.00 (1H, t, J=9 Hz), 7.13 (1H, t, J=9 Hz), 7.19–7.31 (2H, m), 7.33 (1H, d, J=9 Hz), 7.60 (1H, br peak), 7.65–7.74 (2H, m), 7.79 (1H, d, J=9 Hz), 7.97 (1H, d=2 Hz), 8.58 (1H, d, J=5 Hz).

mp: 154–155° C.

EXAMPLE 18

Synthesis of 6-tert-buthoxycabonylamino-1-(2-chlorobenzyl)-2-n-propylbenzimidazole (86)

Two-hundred milligrams of 6-carboxy-1-(2-chlorobenzyl)-2-n-propylbenzimidazole were suspended in 5 ml of tert-butyl alcohol, and 0.19 ml of diphenylphosphorylazide and 0.21 ml of diisopropylethylamine were added thereto at room temperature. The reaction mixture was refluxed for 4 hours, and was then separated with ethyl acetate and with water. The organic layer was washed with water, dried, and then concentrated under reduced pressure. The residue was developed and purified through column chromatography using a mixture of ethyl acetate and hexane (at a ratio of from 1:10 to 1:3), and was further recrystallized from a mixture of ethyl acetate and hexane to give 165 mg of 6-tert-buthoxycabonylamino-1-(2-chlorobenzyl)-2-n-propylbenzimidazole (86).

Properties of Compound (86):

colorless crystal.

$^1$H-NMR (CDCl$_3$, δ): 0.98 (3H, t, J=8 Hz), 1.50 (9H, s), 1.86 (2H, sextet, J=8 Hz), 2.72 (2H, t, J=8 Hz), 5.38 (2H, s), 6.40 (1H, dd, J=1, 8 Hz), 6.95 (1H, dd, J=10 Hz), 7.08 (1H, dt, J=1, 8 Hz), 7.24 (1H, dt, J=1, 8 Hz), 7.28 (1H, d, J=1 Hz), 7.45 (1H, dd, J=1, 8 Hz), 7.66 (1H, d, J=10 Hz).

mp: 166–168° C.

EXAMPLE 19

Synthesis of 1-(2-chlorobenzyl)-6-cyano-2-n-propylbenzimidazole (87)

A solution of 1 mol of titanium tetrachloride in 0.14 ml of dichloromethane and 0.36 ml of triethylamine were added to a solution of 200 mg of 6-carbamoyl-1-(2-chlorobenzyl)-2-n-propylbenzimidazole in 4 ml of tetrahydrofuran at 0° C., and the mixture was stirred at 20° C. for 2 hours. The reaction mixture was separated with ethyl acetate and with water. The organic layer was washed with water, dried, and then concentrated under reduced pressure. The residue was developed and purified through column chromatography using a mixture of ethyl acetate and hexane (at a ratio of from 1:10 to 1:3), and was further recrystallized from a mixture of ethyl acetate and hexane to give 140 mg of 1-(2-chlorobenzyl)-6-cyano-2-n-propylbenzimidazole (87).

Properties of Compound (87):

colorless crystal.

$^1$H-NMR (CDCl$_3$, δ): 1.05 (3H, t, J=8 Hz), 1.90 (2H, sextet, J=8 Hz), 2.85 (2H, t, J=8 Hz), 5.45 (2H, s), 6.42 (1H, dd, J=1, 8 Hz), 7.15 (1H, dt, J=1, 8 Hz), 7.28 (1H, dt, J=1, 8 Hz), 7.48 (1H, s), 7.50 (1H, d, J=10 Hz), 7.54 (1H, dd, J=1, 8 Hz), 7.85 (1H, d, J=10 Hz).

mp: 124–126° C.

EXAMPLE 20

Synthesis of 1-(2-chlorobenzyl)-6-mesylamino-2-n-propylbenzimidazole (88)

1-(2-Chlorobenzyl)-2-n-propylbenzimidazole (150 mg) and 61 mg of triethylamine were dissolved in 3 ml of methylene chloride, and 70 mg of methanesulfonyl chloride were added thereto at room temperature. The mixture was stirred for 1 hour, then washed with dilute hydrochloric acid, washed with water, and dried. The solvent was distilled off under reduced pressure. The residual solid was collected with ether through filtration to give 124 mg of 1-(2-chlorobenzyl)-6-mesylamino-2-n-propylbenzimidazole (88).

Properties of Compound (88):

$^1$H-NMR (CDCl$_3$—CD 3 OD, δ): 0.94 (3H, t, J=7.5 Hz), 1.76 (2H, m), 2.71 (2H, t, J=7.5 Hz), 2.81 (3H, s), 5.36 (2H, s), 6.40 (1H, d, J=7.5 Hz), 6.98–7.22 (4H, m), 7.40 (1H, d, J=7.5 Hz), 7.59 (1H, d, J=7.5 Hz).

mp: 191–193° C.

EXAMPLE 21

Synthesis of 6-acetylamino-1-(2-chlorobenzyl)-2-n-propylbenzimidazole (89)

Acetic anhydride (62 mg) was added to a solution of 150 mg of 6-amino-1-(2-chlorobenzyl)-2-n-propylbenzimidazole and 61 mg of triethylamine in 3 ml of methylene chloride at room temperature, and the mixture was stirred for 1 hour. The reaction mixture was washed with water, and was then dried. The solvent was distilled off under reduced pressure. The residue was crystallized with ether to give 143 mg of 6-acetylamino-1-(2-chlorobenzyl)-2-n-propylbenzimidazole (89).

Properties of Compound (89):

$^1$H-NMR (CDCl$_3$, δ): 1.00 (3H, t, J=7.5 Hz), 1.86 (2H, m), 2.17 (3H, s), 2.73 (2H, t, J=7.5 Hz), 5.39 (2H, s), 6.43 (1H, d, J=7.5 Hz), 6.98–7.11 (2H, m), 7.22 (1H, t, J=7.5 Hz), 7.45 (1H, d, J=7.5 Hz), 7.59 (1H, brs), 7.68 (1H, d, J=7.5 Hz), 7.84 (1H, d, J=1.5 Hz).

mp: 180–182° C.

EXAMPLE 22

Synthesis of 6-amino-1-(2-chlorobenzyl)-2-n-propylbenzimidazole (90)

Seven-hundred milligrams of 6-tert-butoxycarbonylamino-1-(2-chlorobenzyl)-2-n-propylbenzimidazole were dissolved in a mixed solvent of 10 ml of methylene chloride and 1 ml of trifluoroacetic acid, and the mixture was stirred at room temperature for 5 hours. A small amount of methylene chloride was added to the reaction solution. The mixture was washed with a sodium carbonate aqueous solution, and was dried. The solvent was then distilled off. The residue was crystallized from a mixed solvent of n-hexane and ether to give 455 mg of 6-amino-1-(2-chlorobenzyl)-2-n-propylbenzimidazole (90).

Properties of Compound (90):

$^1$H-NMR (CDCl$_3$, δ): 1.01 (3H, t, J=7.5 Hz), 1.86 (2H, m), 2.73 (2H, t, J=7.5 Hz), 5.30 (2H, s), 6.41 (1H, d, J=1.5 Hz), 6.48 (1H, d, J=7.5 Hz), 6.66 (1H, dd, J=7.5 and 1.5 Hz), 7.10 (1H, t, J=7.5 Hz), 7.25 (1H, t, J=7.5 Hz), 7.46 (1H, d, J=7.5 Hz), 7.57 (1H, d, J=7.5 Hz).

mp: 121–122° C.

EXAMPLE 23

Synthesis of 1-(2-chlorobenzyl)-2-n-propyl-6-ureidobenzimidazole (91)

1-(2-Chlorobenzyl)-2-n-propyl-6-ureidobenzimidazole (91) was formed in the same manner as in Example 21.

Properties of Compound (91):

$^1$H-NMR (DMSO-d6, δ): 0.93 (3H, t, J=7.5 Hz), 1.72 (2H, m), 2.73 (2H, t, J=7.5 Hz), 5.43 (2H, s), 5.73 (2H, s), 6.42 (1H, dd, J=7.5 and 1.5 Hz), 7.05 (1H, dd, J=7.5 and 1.5 Hz), 7.22 (1H, dt, J=7.5 and 1.5 Hz), 7.33 (1H, dt, J=7.5 and 1.5 Hz), 7.45 (1H, d, J=7.5 Hz), 7.50 (1H, s), 7.57 (1H, dd, J=7.5 and 1.5 Hz), 8.50 (1H, s).

mp: 198° C.

Production Example 12

Production of ethyl 3-acetylamino-4-nitrobenzoate

Nine milliliters of acetyl chloride were added to a mixture of 18.4 g of ethyl 3-amino-4-nitrobenzoate and 200 ml of N,N-dimethylaniline while being cooled with ice. The mixture was stirred at room temperature for 2 hours and then at 50° C. for 2 hours. The reaction solution was poured into cold 1-N hydrochloric acid, and the mixture was extracted twice with ethyl acetate. The organic layer was washed with 1-N hydrochloric acid and then with water, and was dried. The solvent was then distilled off under reduced pressure. The residue was purified through silica-gel column chromatography (eluent: a mixture of ethyl acetate and hexane at a ratio of from 1:10 to 1:4) to give 19.6 g of ethyl 3-acetylamino-4-nitrobenzoate.

Properties of the compound:

$^1$H-NMR(CDCl$_3$, δ): 1.42(3H, t, J=7.1 Hz), 2.32(3H, s), 4.43(2H, q, J=7.1 Hz), 7.82(1H, dd, J=1.8 and 8.7 Hz), 8.25(1H, d, J=8.7 Hz), 9.35(1H, d, J=1.8 Hz), 10.19(1H, s).

Production Example 13

Production of ethyl 4-nitro-3-phenylacetylaminobenzoate

In the same manner as in Production Example 12, 3.30 g of ethyl 4-nitro-3-phenylacetylaminobenzoate were formed from 2.02 g of ethyl 3-amino-4-nitrobenzoate and 1.87 g of phenylacetyl chloride.

Properties of the compound:

$^1$H-NMR(CDCl$_3$, δ): 1.41(3H, t, J=7.2 Hz), 3.85(2H, s), 4.42(2H, q, J=7.2 Hz), 7.34–7.49(5H, m), 7.79(1H, m), 8.19(1H, d, J=8.7 Hz), 9.39(1H, d, J=1.6 Hz), 10.15(1H, s).

Production Example 14

Production of ethyl 3-[N-(2-chlorobenzyl)acetylamino]-4-nitrobenzoate

A solution of 1.706 g of ethyl 3-acetylamino-4-nitrobenzoate in 12 ml of N,N-dimethylformamide were added 0.406 g of 60% sodium hydride while being cooled with ice, and the mixture was stirred at room temperature for 40 minutes. A solution of 1.806 g of 2-chlorobenzyl bromide in 10 ml of N,N-dimethylformamide was added thereto, and the mixture was stirred at room temperature for 3 hours. The reaction mixture was poured into cold 1-N hydrochloric acid, and the mixed solution was extracted twice with ethyl acetate. The organic layer was washed with 1-N hydrochloric acid and then with water, and was dried. The solvent was distilled off under reduced pressure. The residue was purified through silica-gel column chromatography (eluent: a mixture of ethyl acetate and hexane at a ratio of from 1:10 to 1:4) to give 2.08 g of oily ethyl 3-[N-(2-chlorobenzyl)acetylamino]-4-nitrobenzoate.

Properties of the compound:

$^1$H-NMR(CDCl$_3$, δ): 1.38(3H, t, J=7.1 Hz), 1.92(3H, s), 4.28–4.45(2H, m), 4.72(1H, d, J=14.5 Hz), 5.34(1H, d, J=14.5 Hz), 7.16–7.44(4H, m), 7.69(1H, d, J=1.7 Hz), 7.94(1H, d, J=8.4 Hz), 8.13(1H, dd, J=1.7 and 8.4 Hz).

Production Example 15

Production of ethyl 4-nitro-3-[N-[2-(trifluoromethyl)benzyl]acetylamino]benzoate In the same manner as in Production Example 14, 1.82 g of ethyl 4-nitro-3-[N-[2-(trifluoromethyl)-benzyl] acetylamino]benzoate were formed from 1.49 g of ethyl 3-acetylamino-4-nitrobenzoate and 1.69 g of 2-(trifluoromethyl)benzyl bromide.

Properties of the compound:
$^1$H-NMR(CDCl$_3$, δ): 1.37(3H, t, J=7.1 Hz), 1.96(3H, s), 4.29–4.42(2H, m), 4.78(1H, d, J=15.4 Hz), 5.40(1H, d, J=15.4 Hz), 7.38(1H, t, J=7.6 Hz), 7.51–7.58(2H, m), 7.61 (1H, d, J=1.7 Hz), 7.67(1H, d, J=7.8 Hz), 7.92(1H, d, J=8.4 Hz), 8.13(1H, dd, J=1.7 and 8.4 Hz).

mp: 153.5–158.0° C.

Production Example 16

Production of ethyl 4-nitro-3-[N-[4-(trifluoromethyl)benzyl]acetylaminobenzoate

In the same manner as in Production Example 14, 1.52 g of ethyl 4-nitro-3-[N-[4-(trifluoromethyl)-benzyl] acetylaminobenzoate were formed from 1.50 g of ethyl 3-acetylamino-4-nitrobenzoate and 1.71 g of 4-(trifluoromethyl)benzyl bromide.

Properties of the compound:
$^1$H-NMR(CDCl$_3$, δ): 1.36(3H, t, J=7.1 Hz), 1.91(3H, s), 4.32–4.43(2H, m), 4.42(1H, d, J=14.6 Hz), 5.33(1H, d, J=14.6 Hz), 7.30(2H, d, J=8.1 Hz), 7.54(2H, d, J=8.1 Hz), 7.61(1H, d, J=1.8 Hz), 7.96(1H, d, J=8.4 Hz), 8.12(1H, dd, J=1.8 and 8.4 Hz).

Production Example 17

Production of 2-cyanobenzyl 3-[N-(2-cyanobenzyl) acetylamino]-4-nitrobenzoate

A solution of 1.50 g of 3-acetylamino-4-nitrobenzoic acid in 10 ml of N,N-dimethylformamide was added dropwise to a slurry of 0.802 g of 60% sodium hydride and 10 ml of N,N-dimethylformamide at room temperature, and the mixture was stirred for 30 minutes. Subsequently, a solution of 3.93 g of 2-cyanobenzyl bromide in 10 ml of N,N-dimethylformamide was added dropwise thereto, and the mixture was stirred for 30 minutes. Ethyl acetate was poured into the reaction solution, and the crystals precipitated were separated through filtration. The crystals obtained were washed with ethyl acetate, and were further dissolved in chloroform. The filtrate from which the solid component was removed was concentrated to give 1.96 g of yellow crystals of 2-cyanobenzyl 3-[N-(2-cyanobenzyl) acetylamino]-4-nitrobenzoate.

Properties of the compound:
$^1$H-NMR(CDCl$_3$, δ): 1.92(3H, s), 4.92(1H, d, J=4.8 Hz), 5.24(2H, d, J=4.9 Hz), 5.44(2H, dd, J=7.9 and 2.9 Hz), 7.36(1H, t, J=7.5 Hz), 7.47(1H, d, J=7.7 Hz), 7.52(1H, t, J=7.7 Hz), 7.56–7.62(2H, m), 7.63–7.71(2H, m), 7.76(1H, d, J=7.8 Hz), 7.80(1H, d, J=1.7 Hz), 7.99(1H, d, J=8.4 Hz), 8.25(1H, dd, J=8.4 and 1.8 Hz).

Production Example 18

Production of ethyl 4-amino-3-(N-i-propylbutyrylamino)benzoate

A solution of 2.00 g of ethyl 3-butyrylamino-4-nitrobenzoate in 10 ml of N,N-dimethylformamide was added dropwise to a slurry of 0.428 g of 60% sodium hydride and 10 ml of N,N-dimethylformamide at room temperature, and the mixture was stirred for 30 minutes. A solution of 1.46 g of isopropyl iodide in 10 ml of N,N-dimethylformamide was then added dropwise thereto, and the mixture was stirred at 100° C. for 5 days. The reaction solution was poured into a mixed solution of 80 g of dilute hydrochloric acid and 80 g of ethyl acetate for separation. The resulting organic layer was washed with 50 g of water, and was then concentrated under reduced pressure. The residue was purified through silica-gel column chromatography (eluent: a mixture of hexane and ethyl acetate at a ratio of 4:1) to obtain 0.260 g of crude ethyl 4-nitro-3-(N-i-propylbutyrylamino)benzoate. Subsequently, 3 ml of ethanol and 2 ml of acetic acid were added to 0.260 g of ethyl 4-nitro-3-(N-i-propylbutyrylamino)benzoate at room temperature, and 0.519 g of reduced iron were further added thereto. The mixture was heat-refluxed for 4 hours. The solid material was removed using a filtration aid, and the filtrate was concentrated. The residue were added 30 ml of ethyl acetate and 30 ml of dilute hydrochloric acid for separation. The organic layer was washed with 30 ml of water, and was then concentrated under reduced pressure. The residue was purified through preparative thin-layer silica-gel chromatography (developing eluent: a mixture of hexane and ethyl acetate at a ratio of 1:1) to give 0.06 g of ethyl 4-amino-3-(N-i-propylbutyrylamino)benzoate.

Properties of the compound:
$^1$H-NMR(CDCl$_3$, δ): 0.82(3H, t, J=7.4 Hz), 1.01(3H, d, J=6.9 Hz), 1.24(3H, d, J=6.6 Hz), 1.38(3H, t, J=7.0 Hz), 1.54–1.62(2H, m), 1.87–2.04(2H, m), 4.34(2H, q, J=7.0 Hz), 4.45(2H, s), 4.88–4.96(1H, m), 6.78(1H, d, J=8.4 Hz), 7.64(1H, d, J=1.9 Hz), 7.87(1H, dd, J=8.4 and 1.9 Hz).

Production Example 19

Production of ethyl 3-nitro-4-phenylacetylaminobenzoate

In the same manner as in Production example 12, 6.00 g of ethyl 3-nitro-4-phenylacetylaminobenzoate were formed from 4.04 g of ethyl 4-amino-3-nitrobenzoate and 3.74 g of phenylacetyl chloride.

Production Example 20

Production of N-benzenesulfonyl-3-amino-4-nitrobenzamide

N,N'-carbonyldiimidazole (28.9 g) was added to a solution of 20.0 g of 3-acetylamino-4-nitrobenzoic acid in 300 ml of N,N-dimethylformamide, and the mixture was stirred at room temperature for 1 hour. Further, 28.00 g of benzenesulfonamide and 27.16 g of diazabicycloundecene were added thereto, and the mixture was stirred at 100° C. for 4 days. The solvent was distilled off under reduced pressure. Chloroform and a 10% sodium hydroxide aqueous solution were added to the residue, and the mixture was vigorously stirred. The aqueous layer was neutralized with 10% hydrochloric acid, and the mixture was vigorously stirred with the addition of chloroform. The crystals precipitated were separated through filtration, and were dried to 14.4 g of N-benzenesulfonyl-3-amino-4-nitrobenzamide.

Properties of the compound:
$^1$H-NMR(DMSO-d6, δ): 6.93(1H, dd, J=1.8 and 9.0 Hz), 7.43(1H, d, J=1.8 Hz), 7.52(2H, br s), 7.65(2H, t, J=7.5 Hz), 7.74(1H, t, J=7.5 Hz), 7.98–7.82(3H, m), 12.74(1H, s).

Production Example 21

Production of N-benzenesulfonyl-3-(biphenyl-4-ylmethylamino)-4-nitrobenzamide potassium salt A solution of 10.0 g of N-benzenesulfonyl-3-amino-4-nitrobenzamide in 150 ml of methanol were added 56.5 g of a 20% potassium hydrogencarbonate aqueous solution and 11.5 g of 4-bromomethylbiphenyl, and the mixture was stirred at 70° C. for 3 hours. The mixture was cooled, and the crystals precipitated were collected through filtration, and were dried to give 4.27 g of N-benzenesulfonyl-3-(biphenyl-4-ylmethylamino)-4-nitrobenzamide potassium salt.

Properties of the compound:
$^1$H-NMR(DMSO-d6, δ): 4.65(2H, d, J=5.8 Hz), 7.19(1H, d, J=8.9 Hz), 7.33–7.42(4H, m), 7.57–7.71(4H, m), 7.75–7.81(2H, m), 8.02(1H, d, J=8.9 Hz), 8.61(1H, br t).
IR(Nujol): 1598 cm$^{-1}$.

Production Example 22

Production of N-benzenesulfonyl-4-amino-3-(biphenyl-4-ylmethylamino)benzamide potassium salt.

Five-percent palladium on carbon (0.64 g) was added to a mixture containing 4.27 g of N-benzenesulfonyl-3-(biphenyl-4-ylmethylamino)-4-nitrobenzamide potassium salt, 10.7 g of a 20% potassium hydrogencarbonate aqueous solution and 200 ml of methanol, and the mixture was stirred in a hydrogen atmosphere at 35° C. for 14 hours. The crystals precipitated were dissolved in 400 ml of a mixed solution of acetone and water (at a ratio of 5:2). The solid material was separated through filtration. The filtrate was concentrated, and the crystals precipitated were separated through filtration, and were dried to give 3.15 g of N-benzenesulfonyl-4-amino-3-(biphenyl-4-ylmethylamino)benzamide potassium salt.

Properties of the compound:
$^1$H-NMR(DMSO-d6, δ): 4.31(2H, d, J=5.7 Hz), 4.85(2H, s), 4.91(1H, br t, J=5.7 Hz), 6.45(1H, d, J=7.9 Hz), 7.07(1H, s), 7.13(1H, d, J=7.9 Hz), 7.29–7.36(4H, m), 7.43–7.47(4H, m), 7.60(2H, d, J=8.1 Hz), 7.65(2H, d, J=7.6 Hz), 7.73–7.76(2H, m).
IR(Nujol): 1574 cm$^{-1}$.

Production Example 23

Production of N-(2-pyridylmethyl)-4-acetylamino-3-nitrobenzamide

Oxalyl chloride (1.25 g) was added dropwise to a solution of 1.00 g of 4-acetylamino-3-nitrobenzoic acid and 0.20 g of N,N-dimethylformamide in 15 ml of methylene chloride while being cooled with ice. The mixture was further stirred at room temperature for 1 hour. The reaction solution was concentrated, and diisopropyl ether was added thereto for crystallization. The crystals were added to a solution of 0.483 g of 2-aminomethylpyridine and 0.35 g of triethylamine in 15 ml of methylene chloride. After the mixture was stirred at room temperature for 1 hour, the organic layer was washed twice with water (100 ml×2) and then with 100 ml of a sodium hydrogencarbonate aqueous solution. The organic layer was concentrated to give 0.99 g of N-(2-pyridylmethyl)-4-acetylamino-3-nitrobenzamide.

Properties of the compound:
$^1$H-NMR(CDCl$_3$, δ): 2.33(3H, s), 4.76(2H, d, J=4.8 Hz), 7.25(1H, dd, J=5.0 and 7.2 Hz), 7.34(1H, d, J=7.9 Hz), 7.71(1H, dt, J=1.8 and 7.8 Hz), 7.84(1H, s), 8.14(1H, dd, J=2.1 and 8.8 Hz), 8.58(1H, d, J=4.9 Hz), 8.77(1H, d, J=2.1 Hz), 8.90(1H, d, J=8.0 Hz), 10.47(1H, s).

Production Example 24

Production of N-(2-pyridylmethyl)-4-acetylamino-3-aminobenzamide

Five-percent palladium on carbon (2.53 g) was added to a solution of 10.0 g of N-(2-pyridylmethyl)-4-acetylamino-3-nitrobenzamide in 150 ml of methanol, and the mixture was stirred in a hydrogen atmosphere at 60° C. for 15 hours. The solid material was separated through filtration, and the filtrate was concentrated. The resulting residue was purified through silica-gel column chromatography (eluent: a mixture of ethyl acetate and methanol at a ratio of 7:3) to give 8.02 g of N-(2-pyridylmethyl)-4-acetylamino-3-aminobenzamide.

Properties of the compound:
$^1$H-NMR(DMSO-d6, δ): 2.06(3H, s), 4.52(2H, d, J=5.9 Hz), 5.09(2H, s), 7.10(1H, dd, J=1.9 and 8.2 Hz), 7.22–7.30 (3H, m), 7.38(1H, d, J=8.2 Hz), 7.75(1H, dt, J=1.7 and 7.6 Hz), 8.50(1H, d, J=4.6 Hz), 8.84(1H, t, J=5.8 Hz), 9.19(1H, s).

Production Example 25

Production of N-(2-pyridylmethyl)-4-acetylamino-3-(4-benzyloxybenzylamino)benzamide A solution of 0.80 g of N-(2-pyridylmethyl)-4-acetylamino-3-aminobenzamide in 10 ml of N,N-dimethylformamide were added 1.31 g of 4-benzyloxybenzyl chloride and 1.18 g of sodium hydrogencarbonate, and the mixture was stirred at 90° C. for 2 hours. Chloroform and water were added to the reaction solution, and the chloroform extraction was conducted. The organic layer was washed with water, concentrated, and purified through silica-gel column chromatography to give 0.434 g of N-(2-pyridylmethyl)-4-acetylamino-3-(4-benzyloxybenzylamino)benzamide.

Properties of the compound:
$^1$H-NMR(DMSO-d6, δ): 2.07(3H, s), 4.30(2H, d, J=5.6 Hz), 4.51(2H, d, J=5.9 Hz), 5.07(2H, s), 5.68(1H, t, J=5.6 Hz), 6.97(2H, d, J=8.6 Hz), 7.14(2H, m), 7.25(2H, dd, J=3.4 and 7.4 Hz), 7.32(4H, t, 7.5 Hz), 7.38(2H, t, J=7.1 Hz), 7.44(2H, d, J=7.2 Hz), 7.72(1H, dt, J=1.8 and 7.7 Hz), 8.49(1H, dd, J=1.9 and 5.3 Hz), 8.89(1H, t, J=5.9 Hz), 9.28(1H, s).

Production Example 26

Production of N-(2-pyridylmethyl)-4-acetylamino-3-(3,4-methylenedioxybenzylamino)benzamide A solution of 0.80 g of N-(2-pyridylmethyl)-4-acetylamino-3-aminobenzamide in 10 ml of N,N-dimethylformamide were added 0.962 g of 3,4-methylenedioxybenzyl chloride and 0.710 g of sodium hydrogencarbonate, and the mixture was stirred at 80° C. for 4 hours. Chloroform and water were added to the reaction solution, and the chloroform extraction was conducted. The organic layer was washed with water, concentrated, and purified through silica-gel column chromatography (eluent: a mixture of ethyl acetate and methanol at a ratio of 9:1) to give 0.49 g of N-(2-pyridylmethyl)-4-acetylamino-3-(3,4-methylenedioxybenzylamino)benzamide.

Properties of the compound:
$^1$H-NMR(DMSO-d6, δ): 2.08(3H, s), 4.29(2H, s), 4.52 (2H, d, J=5.9 Hz), 5.27(1H, s), 5.97(2H, s), 6.84–6.88(2H, m), 6.96(1H, s), 7.10(1H, d, J=1.3 Hz), 7.13(1H, dd, J=1.6 and 8.2 Hz), 7.25–7.32(3H, m), 7.76(1H, dt, J=1.2 and 7.6 Hz), 8.51(1H, d, J=4.8 Hz), 8.90(1H, t, J=5.8 Hz), 9.28(1H, s).

Production Example 27

Production of N-(2-pyridylmethyl)-4-acetylamino-3-[4-(1,2,3-thiadiazol-4-yl)benzylamino]benzamide A solution of 0.800 g of N-(2-pyridylmethyl)-4-acetylamino-3-aminobenzamide in 10 ml of methanol were added 1.08 g of 4-(4-bromomethylphenyl)-1,2,3-thiadiazole and 0.710 g of sodium hydrogencarbonate, and the mixture was stirred at 70° C. for 1 hour. The reaction solution was concentrated, and was purified through silica-gel column chromatography (eluent: a mixture of ethyl acetate and methanol at a ratio of 9:1) to give 0.830 g of N-(2-pyridylmethyl)-4-acetylamino-3-[4-(1,2,3-thiadiazol-4-yl)benzylamino]benzamide Properties of the compound:
$^1$H-NMR(CDCl$_3$, δ): 2.11(3H, s), 4.43–5.56(2H, m), 5.92 (1H, t, J=5.9 Hz), 7.51(1H, d, J=1.4 Hz), 7.15(1H, dd, J=1.6 and 8.1 Hz), 7.22(2H, dd, J=1.9 and 8.1 Hz), 7.33(1H, d, J=8.1 Hz), 7.57(2H, d, J=8.1 Hz), 7.69(1H, dt, J=1.8 and 7.7 Hz), 8.09(2H, d, J=8.2 Hz), 8.47(1H, dd, J=1.9 and 5.2 Hz), 8.89(1H, t, J=5.9 Hz), 9.34(1H, s), 9.58(1H, s).

Production Example 28

Production of N-benzenesulfonyl-4-acetylamino-3-nitrobenzamide

N,N'-carbonyldiimidazole (14.45 g) was added to a solution of 10.00 g of 4-acetylamino-3-nitrobenzoic acid in 300 ml of N,N-dimethylformamide, and the mixture was stirred at room temperature for 1 hour. Subsequently, 14.03 g of benzenesulfonamide and 13.58 g of diazabicycloundecene were added thereto, and the mixture was stirred at 100° C. for 72 hours. The reaction mixture was separated with the addition of chloroform and water. The organic layer was then concentrated, and the resulting residue was purified through silica-gel column chromatography (eluent: a mixture of ethyl acetate and methanol at a ratio of 4:1) to give 12.67 g of N-benzenesulfonyl-4-acetylamino-3-nitrobenzamide.

Properties of the compound:
$^1$H-NMR(DMSO-d6, δ): 2.08(3H, s), 7.39–7.47(3H, m), 7.65(1H, d, J=8.5 Hz), 7.84(2H, dd, J=1.4 and 7.7 Hz), 8.11(1H, dd, J=1.9 and 8.4 Hz), 8.38(1H, d, J=1.9 Hz), 10.34(1H, s).

Production Example 29

Production of N-benzenesulfonyl-4-acetylamino-3-aminobenzamide

N-benzenesulfonyl-4-acetylamino-3-nitrobenzamide (12.67 g) was dissolved in 200 ml of methanol and 30 ml of water, and 7.59 g of potassium hydrogencarbonate were further added thereto. The mixture was hydrogenated in a hydrogen atmosphere using 2.53 g of 5% palladium on carbon as catalyst at 40° C. for 24 hours. The solid material was separated through filtration, and the filtrate was concentrated. The resulting residue was purified through silica-gel column chromatography (eluent: a mixture of ethyl acetate and methanol at a ratio of 4:1) to give 6.72 g of N-benzenesulfonyl-4-acetylamino-3-aminobenzamide.

Properties of the compound:
$^1$H-NMR(DMSO-d6, δ): 2.06(3H, s), 7.07(1H, dd, J=1.8 and 8.3 Hz), 7.17(1H, d, J=1.8 Hz), 7.44(1H, d, J=8.3 Hz), 7.61(2H, t), 7.68(1H, t), 7.96(2H, d, J=7.5 Hz), 9.19(1H, s).
IR(Nujol): 1682 cm$^{-1}$.

Production Example 30

Production of N-benzenesulfonyl-4-acetylamino-3-(2-nitrobenzylamino)benzamide

In the same manner as in Production Example 32, 0.79 g of N-benzenesulfonyl-4-acetylamino-3-(2-nitrobenzylamino)benzamide were formed from 0.60 g of N-benzenesulfonyl-4-acetylamino-3-aminobenzamide and 0.52 g of 2-nitrobenzyl bromide.

Properties of the compound:
$^1$H-NMR(DMSO-d6,δ): 2.08(3H, s), 4.72(2H, d, J=5.0 Hz), 5.92(1H, s), 6.86(1H, s), 7.13(1H, d, J=8.1 Hz), 7.31 (1H, d, J=8.0 Hz), 7.49–7.58(3H, m), 7.60(2H, d, J=7.6 Hz), 7.66(1H, t, J=7.4 Hz), 7.86(2H, d, J=7.7 Hz), 8.11(1H, d, J=8.3 Hz), 9.37(1H, s).

Production Example 31

Production of N-benzenesulfonyl-4-acetylamino-3-benzylaminobenzamide

In the same manner as in Production Example 32, 0.38 g of N-benzenesulfonyl-4-acetylamino-3-benzylaminobenzamide were formed from 0.60 g of N-benzenesulfonyl-4-acetylamino-3-aminobenzamide and 0.47 g of benzyl bromide.

Properties of the compound:
$^1$H-NMR ( DMSO-d6, δ): 2.07 ( 3H, s), 4.35(2H, d, J=5.5 Hz), 5.73(1H, s), 7.06(1H, s), 7.14(1H, d, J=8.3 Hz), 7.21–7.28(2H, m), 7.32(2H, t, J=7.3 Hz), 7.37(2H, d, J=7.6 Hz), 7.53(2H, t, J=7.4 Hz), 7.59(1H, t, J=7.0HZ), 7.88(2H, d, J=7.7 Hz), 9.29(1H, s), 12.34(1H, s)

Production Example 32

Production of N-benzenesulfonyl-4-acetylamino-3-(2,4-difluorobenzylamino)benzamide A solution of 7 ml of methanol containing 0.60 g of N-benzenesulfonyl-4-acetylamino-3-aminobenzamide, 0.656 g of 2,4-difluorobenzyl bromide and 0.423 g of potassium hydrogencarbonate was stirred at 60° C. for 1 hour. The reaction solution was concentrated, and the residue was purified through silica-gel column chromatography (eluent: a mixture of ethyl acetate and methanol at a ratio of 9:1) to give 0.370 g of N-benzenesulfonyl-4-acetylamino-3-(2,4-difluorobenzylamino)benzamide.

Properties of the compound:
$^1$H-NMR(DMSO-d6, δ): 2.05(3H, s), 4.34(2H, d, J=5.5 Hz), 5.60(1H, s), 7.02(1H, t, J=8.0 Hz), 7.06(1H, s), 7.16–7.27(3H, m), 7.38–7.51(4H, m), 7.82(2H, d, J=7.2 Hz), 9.27(1H, s), 12.35(1H, s)

Production Example 33

Production of N-benzenesulfonyl-4-acetylamino-3-(4-nitrobenzylamino)benzamide.

In the same manner as in Production Example 32, 0.52 g of N-benzenesulfonyl-4-acetylamino-3-(4-nitrobenzylamino)benzamide were formed from 0.50 g of N-benzenesulfonyl-4-acetylamino-3-aminobenzamide and 0.436 g of 4-nitrobenzyl bromide.

Properties of the compound:
$^1$H-NMR(DMSO-d6, δ): 2.09(3H, s), 4.54(2H, d, J=5.0 Hz), 6.10(1H, s), 6.89(1H, d, J=1.8 Hz), 7.14(1H, dd, J=1.8 and 8.2 Hz), 7.39(1H, d, J=8.2 Hz), 7.58–7.65(4H, m), 7.68(1H, t, J=7.6 Hz), 7.92(2H, dd, J=1.4 and 7.4 Hz), 8.20(2H, d, J=8.7 Hz), 9.36(1H, s), 12.28(1H, s)

Production Example 34

Production of N-benzenesulfonyl-4-acetylamino-3-[4-(1,2,3-thiadiazol-4-yl)benzylamino]benzamide In the same manner as in Production Example 32, 0.38 g of N-benzenesulfonyl-4-acetylamino-3-[4-(1,2,3-thiadiazol- 4-yl)benzylamino]benzamide were formed from 0.50 g of N-benzenesulfonyl-4-actylamino-3-aminobenzamide and 0.45 g of 4-(4-bromomethylphenyl)-1,2,3-thiadiazole.

Properties of the compound:

$^1$H-NMR(DMSO-d6, δ): 2.10(3H, s), 4.46(2H, d, J=5.3 Hz). 5.96(1H, s), 7.03(1H, s), 7.14(1H, dd, J=1.7 and 8.2 Hz), 7.40(1H, d, J=8.0 Hz), 7.52–7.61(4H, m), 7.65(1H, t, J=7.1 Hz), 7.93(2H, d, J=7.6 Hz), 8.10(2H, d, J=8.2 Hz), 9.35(1H, s), 9.58(1H, s), 12.31(1H, s)

Production Example 35

Production of ethyl 3-amino-2-nitrobenzoate

A mixture of 20.2 of 3-acetylamino-2-nitrobenzoic acid, 11.4 g of 97% sulfuric acid and 300 ml of ethanol was stirred for 23 hours while being heat-refluxed. One-hundred milliliters of ethanol were distilled off under reduced pressure, and the residue was cooled to room temperature. Subsequently, the reaction solution was poured into 200 ml of ice water containing 19.5 g of sodium hydrogencarbonate. The crystals precipitated were separated through filtration, and were washed with water. Further, these crystals were dispersed in 30 ml of a mixed solution of ethyl acetate and hexane at a ratio of 1:2. The crystals were separated through filtration, washed with hexane, and then dried to give 18.0 g of ethyl 3-amino-2-nitrobenzoate.

Properties of the compound:

$^1$H-NMR(CDCl$_3$, δ): 1.39(3H, t, J=7.1 Hz), 4.37(2H, q, J=7.1 Hz), 6.41(2H, br s), 6.83(1H, d, J=8.7 Hz), 8.00(1H, dd, J=1.8 and 8.7 Hz), 8.85(1H, d, J=1.8 Hz)

Production Example 36

Production of ethyl 3-acetylamino-2-nitrobenzoate

Acetyl chloride (13 ml) was added dropwise to a solution of 2.98 g of ethyl 3-amino-2-nitrobenzoate and 20 ml of N,N-dimethylaniline in an ice bath. The mixture was stirred at room temperature for 48 hours. The reaction solution was acidified with 10% hydrochloric acid, and was extracted twice with ethyl acetate. The organic layer was washed three times with water. The solvent was distilled off under reduced pressure, and the resulting residue was crystallized with hexane. The crystals were separated through filtration, washed with hexane, and dried to give 3.30 g of ethyl 3-acetylamino-2-nitrobenzoate.

Properties of the compound:

$^1$H-NMR(CDCl$_3$, δ): 1.42(3H, t), 2.33(3H, s), 4.42(2H, q), 8.27(1H, dd, J=1.9 and 8.9 Hz), 8.89(1H, d, J=1.9 Hz), 8.91(1H, d, J=8.9 Hz), 10.54(1H, br s)

Production Example 37

Production of ethyl 4-acetylamino-3-aminobenzoate

A mixture of 149.4 g of ethyl 3-acetylamino-2-nitrobenzoate, 14.9g of 5% palladium on carbon and 1,500 ml of ethanol was stirred in a hydrogen atmosphere for 15 hours. The solid material was separated though filtration, and the filtrate was concentrated. The resulting residue was dissolved in a small amount of ethanol, and diisopropyl ether was added thereto. The crystals precipitated were separated through filtration, and were dried to give 114.4 g of ethyl 4-acetylamino-3-aminobenzoate.

Properties of the compound:

$^1$H-NMR(DMSO-d6, δ): 1.27(3H, t), 2.05(3H, s), 4.23 (2H, q), 5.19(2H, s), 7.13(1H, d, J=8.2 Hz), 7.35(1H, s), 7.47(1H, d, J=8.2 Hz), 9.19(1H, s)

EXAMPLE 24

Synthesis of 1-(2-chlorobenzyl)-6-ethoxycarbonyl-2-methyl-benzimidazole (92)

Twenty milliliters of ethanol, 11 ml of acetic acid and 3.07 g of reduced iron were added to 2.07 g of ethyl 3-[N-(2-chlorobenzyl)acetylamino]-4-nitrobenzoate, and the mixture was refluxed for 4 hours. The solid material was separated through filtration, and was washed with ethanol. The filtrate was concentrated, and a sodium hydrogencarbonate aqueous solution was added to the residue. The mixture was extracted with ethyl acetate. The organic layer was dried, and the solvent was then distilled off under reduced pressure. The residue was purified through silica-gel column chromatography (eluent: a mixture of hexane and ethyl acetate at a ratio of from 100/0 to 70:30) to give 1.46 g of 1-(2-chlorobenzyl)-6-ethoxycarbonyl-2-methylbenzimidazole (92).

Properties of Compound (92):

$^1$H-NMR(CDCl$_3$, δ): 1.39(3H, t, J=7.1 Hz), 2.57(3H, s), 4.37(2H, q, J=7.1 Hz), 5.46(2H, s), 6.41(1H, d, J=7.8 Hz), 7.10(1H, t, J=7.8 Hz), 7.25(1H, t), 7.47(1H, d, J=8.0 Hz), 7.75(1H, d, J=8.4 Hz), 7.94(1H, s), 8.00(1H, dd, J=1.5 and 8.4 Hz)

EXAMPLE 25

Synthesis of 6-ethoxycarbonyl-1-methyl-2-n-propylbenzimidazole (93)

In the same manner as in Production Example 14, 1.00 g of crude ethyl 3-(N-methylbutyrylamino)-4-nitrobenzoate was obtained from 1.00 g of ethyl 3-butyrylamino-4-nitrobenzoate and 0.843 g of methyl iodide. Subsequently, 0.56 g of 6-ethoxycarbonyl-1-methyl-2-n-propylbenzimidazole (93) were formed in the same manner as in Example 24.

Properties of Compound (93):

$^1$H-NMR(CDCl$_3$, δ): 1.08(3H, t, J=7.4 Hz), 1.43(3H, t, J=7.0 Hz), 1.89–1.97(2H, m), 2.89(2H, t, J=7.7 Hz), 3.79 (3H, s), 4.38–4.44(2H, m), 7.71(1H, d, J=8.4 Hz), 7.96(1H, dd, J=8.4 and 1.5 Hz, ), 8.05(1H, d, J=1.4 Hz)

EXAMPLE 26

Synthesis of 1-n-butyl-6-ethoxycarbonyl-2-n-propylbenzimidazole (94)

A solution of 1.86 g of ethyl 3-butyrylamino-4-nitrobenzoate in 10 ml of N,N-dimethylformamide was added dropwise to a slurry of 0.428 g of 60% sodium hydride and 10 ml of N,N-dimethylformamide at room temperature, and the mixture was stirred at room temperature for 30 minutes. Subsequently, a solution of 1.97 g of n-butyl iodide in 10 ml of N,N-dimethylformamide was added dropwise thereto, and the mixture was heated at 50° C. for 13 hours. The reaction solution was poured into a mixed solution of 70 g of dilute hydrochloric acid and 70 g of ethyl acetate for extraction. The resulting organic layer was washed twice with water, dried, and then concentrated under reduced pressure to obtain 2.59 g of crude ethyl 3-(N-n-butylbutyrylamino)-4-nitrobenzoate. Then, 0.81 g of 1-n-butyl-6-ethoxycarbonyl-2-n-propylbenzimidazole (94) were formed in the same manner as in Example 24.

Properties of Compound (94):

$^1$H-NMR(CDCl$_3$, δ): 0.98(3H, t, J=7.4 Hz), 1.08(3H, t, J=7.4 Hz), 1.43(3H, t, J=7.1 Hz), 1.75–1.83(2H, m), 1.91–1.98(2H, m), 2.88(2H, t, J=7.6 Hz), 4.15(2H, t, J=7.5 Hz), 4.42(2H, q, J=7.2 Hz), 7.73(1H, d, J=8.4 Hz), 7.96(1H, dd, J=8.5 and 1.5 Hz), 8.06(1H, d, J=1.4 Hz)

EXAMPLE 27

Synthesis of 1-(3-chlorobenzyl)-6-ethoxycarbonyl-2-n-propylbenzimidazole (95)

In the same manner as in Production Example 14, crude ethyl 3-[N-(3-chlorobenzyl)butyrylamino]-4-nitrobenzoate was obtained from 1.86 g of ethyl 3-butyrylamino-4-nitrobenzoate and 1.64 g of 3-chlorobenzyl bromide. This compound was converted to 1-(3-chlorobenzyl)-6-ethoxycarbonyl-2-n-propylbenzimidazole [(95), 0.57 g] in the same manner as in Example 24 without being purified.

Properties of Compound (95):

$^1$H-NMR(CDCl$_3$, δ): 1.02(3H, t, J=7.4 Hz), 1.39(3H, t, J=7.1 Hz), 1.85–1.92(2H, m), 2.80(2H, t, J=7.5 Hz), 4.38 (2H, q, J=7.1 Hz), 5.37(2H, s), 6.86(1H, d, J=7.4 Hz), 7.04(1H, s), 7.21–7.29(2H, m), 7.77(1H, d, J=8.4 Hz), 7.96(1H, d, J=1.2 Hz), 7.99(1H, dd, J=8.5 and 1.5 Hz)

EXAMPLE 28

Synthesis of 1-benzyl-6-ethoxycarbonyl-2-n-propylbenzimidazole (96)

In the same manner as in Production Example 14, ethyl 3-[N-benzylbutyrylamino]-4-nitrobenzoate was obtained from 1.86 g of ethyl 3-butyrylamino-4-nitrobenzoate and 1.36 g of benzyl bromide. This compound was converted to 1-benzyl-6-ethoxycarbonyl-2-n-propylbenzimidazole [(96), 0.97 g] in the same manner as in Example 24 without being purified.

Properties of Compound (96):

$^1$H-NMR(CDCl$_3$, δ): 1.01(3H, t, J=7.4 Hz), 1.39(3H, t, J=7.1 Hz), 1.83–1.91(2H, m), 2.81(2H, t, J=7.5 Hz), 4.37 (2H, q, J=7.1 Hz), 5.40(2H, s), 7.03(1H, d, J=6.4 Hz), 7.28–7.33(3H, m), 7.76(1H, d, J=8.4 Hz), 7.98(1H, dd, J=8.4 and 1.2 Hz), 8.00(1H, s)

EXAMPLE 29

Synthesis of 1-(4-chlorobenzyl)-6-ethoxycarbonyl-2-n-propylbenzimidazole (97)

In the same manner as in Production Example 14, ethyl 3-[N-(4-chlorobenzyl)butyrylamino]-4-nitrobenzoate was obtained from 1.86 g of ethyl 3-butyrylamino-4-nitrobenzoate and 1.64 g of 4-chlorobenzyl bromide. This compound was converted to 1-(4-chlorobenzyl)-6-ethoxycarbonyl-2-n-propylbenzimidazole [(97), 1.06 g] in the same manner as in Example 24 without being purified.

Properties of Compound (97):

$^1$H-NMR(CDCl$_3$, δ): 1.02(3H, t, J=7.4 Hz), 1.39(3H, t, J=7.1 Hz), 1.83–1.92(2H, m), 2.80(2H, t, J=7.8 Hz), 4.38 (2H, q, J=7.5 Hz), 5.36(2H, s), 6.96(2H, d, J=8.2 Hz), 7.29(2H, d, J=8.3 Hz), 7.76(1H, d, J=8.4 Hz), 7.96(1H, d, J=1.2 Hz), 7.99(1H, dd, J=8.3 and 1.2 Hz)

EXAMPLE 30

Synthesis of 6-ethoxycarbonyl-2-methyl-1-[2-(trifluoromethyl)benzyl]benzimidazole (98)

In the same manner as in Example 24, 1.32 g of 6-ethoxycarbonyl-2-methyl-1-[2-(trifluoromethyl)benzyl]-benzimidazole (98) were formed from 1.82 g of ethyl 4-nitro-3-[N-[2-(trifluoromethyl)benzyl]acetylamino] benzoate.

Properties of Compound (98):

$^1$H-NMR(CDCl$_3$, δ): 1.38(3H, t, J=7.1 Hz), 2.53(3H, s), 4.37(2H, q, J=7.1 Hz), 5.58(2H, s), 6.47(1H, d, J=7.7 Hz), 7.36(1H, t, J=7.5 Hz), 7.41(1H, t, J=7.5 Hz), 7.75–7.97(2H, m), 7.94(1H, d, J=1.0 Hz), 8.02(1H, dd, J=1.6 and 8.6 Hz).

EXAMPLE 31

Synthesis of 6-ethoxycarbonyl-2-methyl-1-[4-(trifluoromethyl)benzyl]benzimidazole (99)

In the same manner as in Example 24, 1.22 g of 6-ethoxycarbonyl-2-methyl-1-[4-(trifluoromethyl)benzyl]-benzimidazole (99) were formed from 1.52 g of ethyl 4-nitro-3-[N-[4-(trifluoromethyl)benzyl]acetylamino] benzoate.

Properties of Compound (99):

$^1$H-NMR(CDCl$_3$, δ): 1.39(3H, t, J=7.1 Hz), 2.58(3H, s), 4.38(2H, q, J=7.1 Hz), 5.44(2H, s), 7.15(2H, d, J=8.2 Hz), 7.59(2H, d, J=8.2 Hz), 7.75(1H, d, J=8.3 Hz), 7.97(1H, s), 8.00(1H, dd, J=1.5 and 8.5 Hz)

EXAMPLE 32

Synthesis of 1-(3,4-dichlorobenzyl)-6-ethoxycarbonyl-2-methylbenzimidazole (100)

In the same manner as in Production Example 14, ethyl 3-[N-(3,4-dichlorobenzyl)acetylamino]-4-nitrobenzoate was obtained from 1.50 g of ethyl 3-acetylamino-4-nitrobenzoate and 1.74 g of 3,4-dichlorobenzyl bromide. This compound was converted to 1-(3,4-dichlorobenzyl)-6-ethoxycarbonyl-2-methylbenzimidazole [(100), 0.76 g] in the same manner as in Example 24 without being purified.

Properties of Compound (100):

$^1$H-NMR(CDCl$_3$, δ): 1.40(3H, t, J=7.1 Hz), 2.58(3H, s), 4.39(2H, q, J=7.2 Hz), 5.33(2H, s), 6.84(1H, dd, J=8.4 and 2.3 Hz), 7.16(2H, d, J=2.0 Hz), 7.39(1H, d, J=8.3 Hz), 7.74(1H, d, J=8.4 Hz), 7.96(1H, d, J=1.2 Hz), 8.00(1H, dd, J=8.4 and 1.5 Hz)

EXAMPLE 33

Synthesis of 1-(biphenyl-4-ylmethyl)-6-ethoxycarbonyl-2-methylbenzimidazole (101)

In the same manner as in Production Example 14, 1.44 g of crude ethyl 3-[N-biphenyl-4-ylmethyl)acetylamino]-4-nitrobenzoate were obtained from 1.51 g of ethyl 3-acetylamino-4-nitrobenzoate and 1.46 g of 4-chloromethylbiphenyl. Subsequently, 1.13 g of 1-(biphenyl-4-ylmethyl)-6-ethoxycarbonyl-2-methylbenzimidazole (101) were formed in the same manner as in Example 24.

Properties of Compound (101):

$^1$H-NMR(CDCl$_3$, δ): 1.39(3H, t, J=7.1 Hz), 2.62(3H, S), 4.38(2H, q, J=7.1 Hz), 5.42(2H, s), 7.11(2H, d, J=8.2 Hz), 7.34(1H, m), 7.42(2H, m), 7.54(4H, m), 7.74(1H, d, J=8.4 Hz), 7.99(1H, dd, J=1.5 and 8.4 Hz), 8.06(1H, d, J=1.5 Hz)

EXAMPLE 34

Synthesis of 6-ethoxycarbonyl-2-methyl-1-(2-methylbenzyl)benzimidazole (102)

In the same manner as in Production Example 14, ethyl 3-[N-(2-methylbenzyl)acetylamino]-4-nitrobenzoate was obtained from 1.50 g of ethyl 3-acetylamino-4-nitrobenzoate and 1.65 g of 2-methylbenzyl bromide. This compound was converted to 6-ethoxycarbonyl-2-methyl-1-(2-methylbenzyl)benzimidazole [(102), 0.81 g] in the same manner as in Example 24 without being purified.

Properties of Compound (102):

$^1$H-NMR(CDCl$_3$, δ): 1.38(3H, t, J=7.2 Hz), 2.43(3H, s), 2.54(3H, s), 4.36(2H, q, J=7.2 Hz), 5.33(2H, s), 6.35(1H, d, J=7.7 Hz), 7.03(1H, t, J=8.2 Hz), 7.18–7.25(2H, m), 7.75 (1H, d, J=8.5 Hz), 7.91(1H, d, J=1.2 Hz), 7.98(1H, dd, J=8.5 and 1.5 Hz)

EXAMPLE 35

Synthesis of 6-ethoxycarbonyl-1-(2-methoxybenzyl)-2-methylbenzimidazole (103)

In the same manner as in Production example 14, crude ethyl 3-[N-(2-methoxybenzyl)acetylamino]-4-nitrobenzoate was obtained from 1.16 g of ethyl 3-acetylamino-4-nitrobenzoate and 1.44 g of 2-methoxybenzyl chloride. Subsequently, 1.18 g of 6-ethoxycarbonyl-1-(2-methoxybenzyl)-2-methylbenzimidazole (103) were formed in the same manner as in Example 24.

Properties of Compound (103):

$^1$H-NMR(CDCl$_3$, δ): 1.39(3H, t, J=7.2 Hz), 2.60(3H, s), 3.90(3H, s), 4.37(2H, q, J=7.2 Hz), 5.36(2H, s), 6.61(1H, d, J=7.4 Hz), 6.82(1H, t, J=7.5 Hz), 6.92(1H, d, J=8.3 Hz), 7.27(1H, m), 7.71(1H, d, J=8.4 Hz), 7.96(1H, dd, J=1.5 and 8.4 Hz), 8.03(1H, d, J=1.3 Hz).

EXAMPLE 36

Synthesis of 6-ethoxycarbonyl-1-(4-methoxybenzyl)-2-methylbenzimidazole (104)

In the same manner as in Production Example 14, crude ethyl 3-[N-(4-methoxybenzyl)acetylamino]-4-nitrobenzoate was obtained from 1.60 g of ethyl 3-acetylamino-4-nitrobenzoate and 1.49 g of 4-methoxybenzyl chloride. Subsequently, 1.27 g of 6-ethoxycarbonyl-1-(4-methoxybenzyl)-2-methylbenzimidazole (104) were formed in the same manner as in Example 24.

Properties of Compound (104):

$^1$H-NMR(CDCl$_3$, δ): 1.40(3H, t, J=7.1Hz), 2.59(3H, s), 3.77(3H, s), 4.38(2H, q, J=7.1 Hz), 5.31(2H, s), 6.84(2H, m), 7.00(2H, m), 7.71(1H, d, J=8.4 Hz), 7.97(1H, dd, J=1.4 and 8.4 Hz), 8.03(1H, d, J=1.3 Hz)

EXAMPLE 37

Synthesis of 1-[2-(benzenesulfonylmethyl)benzyl]-6-ethoxycarbonyl-2-methylbenzimidazole (105)

In the same manner as in Production Example 14, ethyl 3-[N-[2-(benzenesulfonylmethyl)benzyl]acetylamino]-4-nitrobenzoate was obtained from 1.00 g of ethyl 3-acetylamino-4-nitrobenzoate and 1.93 g of 2-(benzenesulfonylmethyl)benzyl bromide. This compound was converted to 1-[2-benzenesulfonylmethyl)benzyl]-6-ethoxycarbonyl-2-methylbenzimidazole [(105), 0.89 g] in the same manner as in Example 24 without being purified.

Properties of Compound (105):

$^1$H-NMR(CDCl$_3$, δ): 1.37(3H, t, J=7.1 Hz), 2.57(3H, s), 4.36(2H, q, J=7.1 Hz), 4.50(2H, s), 5.60(2H, s), 6.38(1H, d, J=6.7 Hz), 6.88(1H, dd, J=1.5 and 7.3 Hz), 7.10–7.18(2H, m), 7.57(2H, t, J=7.6 Hz), 7.69–7.78(2H, m), 7.79(1H, dd, J=0.8 and 8.1 Hz), 7.92(1H, d, J=1.2 Hz), 7.99(1H, dd, J=1.5 and 8.4 Hz)

EXAMPLE 38

Synthesis of 1-(2-cyanobenzyl)-6-(2-cyanobenzyloxycarbonyl)-2-methylbenzimidazole (106)

In the same manner as in Example 24, 1.75 g of 1-(2-cyanobenzyl)-6-(2-cyanobenzyloxycarbonyl)-2-methylbenzimidazole (106) were formed from 3.33 g of 2-cyanobenzyl 3-[N-(2-cyanobenzyl)acetylamino]-4-nitrobenzoate.

Properties of Compound (106):

$^1$H-NMR(CDCl$_3$, δ): 2.60(3H, s), 5.55(2H, s), 5.60(2H, s), 6.68(1H, d, J=7.3 Hz), 7.41–7.48(3H, m), 7.61(2H, m), 7.72(1H, d, J=7.6 Hz), 7.76(1H, d, J=7.6 Hz), 7.77(1H, d, J=8.6 Hz), 8.02(1H, s), 8.05(1H, dd, J=8.4 and 1.5 Hz).

EXAMPLE 39

Synthesis of 1-(biphenyl-2-ylmethyl)-6-ethoxycarbonyl-2-methylbenzimidazole (107)

In the same manner as in Production Example 14, ethyl 3-[N-(biphenyl-2-ylmethyl)acetylamino]-4-nitrobenzoate was obtained from 1.00 g of ethyl 3-acetylamino-4-nitrobenzoate and 1.47 g of 2-bromomethylbiphenyl. This compound was converted to 1-(biphenyl-2-ylmethyl)-6-ethoxycarbonyl-2-methylbenzimidazole [(107), 1.31 g] in the same manner as in Example 24 without being purified.

Properties of Compound (107):

$^1$H-NMR(CDCl$_3$, δ): 1.41(3H, t, J=7.3 Hz), 2.39(3H, s), 4.38(2H, q, J=7.3 Hz), 5.27(2H, s), 6.68(1H, d, J=7.9 Hz), 7.21(1H, dt, J=9.0 and 2.1 Hz), 7.32–7.39(4H, m), 7.43(1H, dd, J=7.3 and 1.9 Hz), 7.46–7.51(2H, m), 7.68(1H, d, J=8.4 Hz), 7.87(1H, d, J=1.3 Hz), 7.95(1H, dd, J=8.4 and 1.5H

EXAMPLE 40

Synthesis of 1-benzyl-6-ethoxycarbonyl-2-methylbenzimidazole (108)

In the same manner as in Production Example 14, ethyl 3-(N-benzylacetylamino)-4-nitrobenzoate was obtained from 1.00 g of ethyl 3-acetylamino-4-nitrobenzoate and 1.02 g of benzyl bromide. This compound was converted to 1-benzyl-6-ethoxycarbonyl-2-methylbenzimidazole [(108), 0.71 g] in the same manner as in Example 24 without being purified.

Properties of Compound (108):

$^1$H-NMR(CDCl$_3$, δ): 1.39(3H, t, J=7.1 Hz), 2.58(3H, s), 4.38(2H, q, J=7.1 Hz), 5.38(2H, s), 7.05(2H, dd, J=8.3 and 1.8 Hz), 7.28–7.33(3H, m), 7.72(1H, d, J=8.4 Hz), 7.98(1H, dd, J=8.4 and 1.5 Hz), 8.02(1H, d, J=1.2 Hz)

EXAMPLE 41

Synthesis of 1-(4-tert-butylbenzyl)-6-ethoxycarbonyl-2-methylbenzimidazole (109)

In the same manner as in Production Example 14, ethyl 3-[N-(4-tert-butylbenzyl)acetylamino]-4-nitrobenzoate was obtained from 1.00 g of ethyl 3-acetylamino-4-nitrobenzoate and 1.35 g of 4-tert-butylbenzyl bromide. This compound was converted to crude 1-(4-tert-butylbenzyl)-6-ethoxycarbonyl-2-methylbenzimidazole [(109), 1.60 g] in the same manner as in Example 24 without being purified.

EXAMPLE 42

Synthesis of 6-ethoxycarbonyl-2-methyl-1-(2-naphthylmethyl)benzimidazole (110)

In the same manner as in Production example 14, ethyl 3-[N-(2-naphthylmethyl)acetylamino]-4-nitrobenzoate was obtained from 1.00 g of ethyl 3-acetylamino-4-nitrobenzoate and 1.32 g of 2-naphthylmethyl bromide. This compound was converted to crude 6-ethoxycarbonyl-2-methyl-1-(2-naphthylmethyl)benzimidazole [(110), 1.28 g] in the same manner as in Example 24 without being purified.

EXAMPLE 43

Synthesis of 1-(biphenyl-4-ylmethyl)-6-ethoxycarbonyl-2-ethylbenzimidazole (111)

In the same manner as in Production Example 14, ethyl 3-[N-(biphenyl-4-ylmethyl)propionylamino]-4-nitrobenzoate was obtained from 2.00 g of ethyl 4-nitro-3-propionylaminobenzoate and 2.28 g of 4-chloromethylbiphenyl. This compound was converted to 1-(biphenyl-4-ylmethyl)-6-ethoxycarbonyl-2-ethylbenzimidazole [(111), 2.07 g)] in the same manner as in Example 24 without being purified.

Properties of Compound (111):

$^1$H-NMR(CDCl$_3$, δ): 1.39(3H, t, J=7.2 Hz), 1.45(3H, t, J=7.5 Hz), 2.90(2H, q, J=7.5 Hz), 4.38(2H, q, J=7.2 Hz), 5.43(2H, S), 7.10(2H, d, J=8.3 Hz), 7.33–7.36(1H, m), 7.43(2H, t, J=7.4 Hz), 7.51–7.56(4H, m), 7.79(1H, d, J=8.5 Hz), 7.80(1H, dd, J=1.5 and 8.4 Hz), 8.05(1H, d, J=1.3 Hz)

EXAMPLE 44

Synthesis of 1-(2-chlorobenzyl)-5-ethoxycarbonyl-2-methyl-benzimidazole (112)

In the same manner as in Production Example 14, ethyl 4-[N-(2-chlorobenzyl)acetylamino]-3-nitrobenzoate was obtained from 3.15 g of ethyl 4-acetylamino-3-nitrobenzoate and 3.85 g of 2-chlorobenzyl bromide. This compound was converted to 1-(2-chlorobenzyl)-5-ethoxycarbonyl-2-methylbenzimidazole [(112), 2.54 g] in the same manner as in Example 24 without being purified.

Properties of Compound (112):

$^1$H-NMR(CDCl$_3$, δ): 1.41(3H, t, J=7.1 Hz), 2.59(3H, s), 4.40(2H, q, J=7.1 Hz), 5.43(1H, s), 6.43(1H, d, J=7.8 Hz), 7.10(1H, t, J=7.5 Hz), 7.19(1H, d, J=8.5 Hz), 7.25(1H, m), 7.46(1H, d, J=8.1 Hz), 7.95(1H, dd, J=1.4 and 8.4 Hz), 8.47(1H, s).

EXAMPLE 45

Synthesis of 1-(2,6-dichlorobenzyl)-6-ethoxycarbonyl-2-methyl-benzimidazole (113)

In the same manner as in Production Example 14, ethyl 3-[N-(2,6-dichlorobenzyl)acetylamino]-4-nitrobenzoate was obtained from 1.50 g of ethyl 3-acetylamino-4-nitrobenzoate and 2.14 g of 2,6-dichlorobenzyl bromide. This compound was converted to 1-(2,6-dichlorobenzyl)-6-ethoxycarbonyl-2-methylbenzimidazole [(113), 0.91 g] in the same manner as in Example 24 without being purified.

Properties of Compound (113):

$^1$H-NMR(CDCl$_3$, δ): 1.38(3H, t, J=7.1 Hz), 2.64(3H, S), 4.34(2H, q, J=7.1 Hz), 5.61(2H, s), 7.30(1H, dd, J=7.6 and 8.5 Hz), 7.40(2H, d, J=8.0 Hz), 7.66(1H, d, J=8.4 Hz), 7.87(1H, d, J=1.1 Hz), 7.91(1H, dd, J=8.4 and 1.5 Hz).

EXAMPLE 46

Synthesis of 6-ethoxycarbonyl-2-n-propyl-1-i-propylbenzimidazole (114)

Two milliliters of acetic acid were added to 0.06 g of ethyl 4-amino-3-(N-i-propylbutyrylamino)benzoate, and the mixture was stirred at 90° C. for 14 hours. The reaction solution was concentrated under reduced pressure to give 0.05 g of 6-ethoxycarbonyl-2-n-propyl-1-i-propylbenzimidazole (114).

Properties of Compound (114)

$^1$H-NMR(CDCl$_3$, δ): 1.07(3H, t, J=7.4 Hz), 1.43(3H, t, J=7.0 Hz), 1.69(6H, d, J=6.9 Hz), 1.85–1.92(2H, m), 2.91 (2H, t, J=7.7 Hz), 4.41(2H, q, J=7.3 Hz), 4.67–4.76(1H, m), 7.72(1H, d, J=8.3 Hz), 7.94(1H, dd, J=8.7 and 1.5 Hz), 8.25(1H, d, J=1.2 Hz)

EXAMPLE 47

Synthesis of 2-benzyl-6-ethoxycarbonyl-1-methylbenzimidazole (115)

A solution of 0.924 g of ethyl 4-nitro-3-phenylacetylaminobenzoate in 10 ml of N,N-dimethylformamide were added 0.166 g of 60% sodium hydride while being cooled with ice, and the mixture was stirred at room temperature for 1 hour. Methyl iodide (0.50 ml) was added thereto, and the resulting mixture was stirred at room temperature for 1 hour. The reaction solution was poured into cold 1-N hydrochloric acid, and the mixture was extracted twice with ethyl acetate. The organic layer was washed with 1-N hydrochloric acid and then with water, and was dried. The solvent was distilled off under reduced pressure. The residue was purified through silica-gel column chromatography (developing eluent: a mixture of ethyl acetate and hexane at a ratio of from 1:10 to 1:4) to obtain 0.510 g of ethyl 4-nitro-3-[N-(methyl)phenylacetylamino] benzoate. To 0.148 g of this compound were added 2 ml of ethanol, 1 ml of acetic acid and 0.240 g of reduced iron, and the mixture was refluxed for 2 hours. The solid material was separated through filtration. The filtrate was concentrated, and was then purified through preparative thin-layer silica-gel chromatography (eluent: a mixture of chloroform and ethyl acetate at a ratio of 2:1) to give 0.090 g of 2-benzyl-6-ethoxycarbonyl-1-methylbenzimidazole (115).

Properties of Compound (115):

$^1$H-NMR(CDCl$_3$, δ): 1.41(3H, t, J=7.1 Hz), 3.63(3H, s), 4.32(2H, s), 4.40(2H, q, J=7.1 Hz), 7.21–7.26(3H, m), 7.27–7.32(2H, m), 7.72(1H, d, J=8.4 Hz), 7.98(1H, dd, J=1.5 and 8.4 Hz), 8.03(1H, d, J=1.3 Hz).

EXAMPLE 48

Synthesis of 1-(2,4-dichlorobenzyl)-6-ethoxycarbonyl-2-methyl-benzimidazole (116)

A solution of 1.50 g of ethyl 3-acetylamido-4-nitrobenzoate in 8 ml of N,N-dimethylformamide was added dropwise to a slurry of 0.357 g of 60% sodium hydride and 8 ml of N,N-dimethylformamide at room temperature, and the mixture was stirred for 30 minutes. Subsequently, a solution of 1.74 g of 2,4-dichlorobenzyl chloride in 8 ml of N,N-dimethylformamide was added dropwise thereto, and the mixture was stirred for 30 minutes. The reaction solution was poured into a mixed solution of 50 g of dilute hydrochloric acid and 60 g of ethyl acetate for separation. The resulting organic layer was washed twice with 50 g of water. This organic layer was concentrated under reduced pressure to obtain 3.5 g of crude ethyl 3-[N-(2,4-dichlorobenzyl) acetylamino]-4-nitrobenzoate. This compound without being purified was dissolved in 23 ml of ethanol and 12 ml of acetic acid, and then 3.32 g of reduced iron were added thereto. The mixture was heat-refluxed for 6 hours. The solid material was removed using a filtration aid, and the filtrate was concentrated under reduced pressure. The resulting residue was separated with the addition of 60 ml of ethyl acetate and 50 ml of dilute hydrochloric acid. The organic layer was washed with 50 g of a saturated aqueous solution of sodium hydrogencarbonate and then twice with 50 g of water, and was concentrated under reduced pressure. The resulting residue was purified through silica-gel column chromatography (eluent: a mixture of hexane and ethyl acetate at a ratio of from 4:1 to 1:1) to give 0.94 g of 1-(2,4-dichlorobenzyl)-6-ethoxycarbonyl-2-methylbenzimidazole (116).

Properties of Compound (116):

$^1$H-NMR(CDCl$_3$, δ): 1.40(3H, t, J=7.1 Hz), 2.56(3H, s), 4.38(2H, q, J=7.1 Hz), 5.41(2H, s), 6.34(1H, d, J=8.4 Hz), 7.09(1H, dd, J=8.4 and 2.0 Hz), 7.49(1H, d, J=2.0Hz), 7.75(1H, d, J=8.4 Hz), 7.92(1H, s), 8.00(1H, dd, J=8.5 and 1.4 Hz)

EXAMPLE 49

Synthesis of 6-carboxy-1-(4-chlorobenzyl)-2-n-propyl-benzimidazole (117)

1.06 g of 1-(4-chlorobenzyl)-6-ethoxycarbonyl-2-n-propylbenzimidazole were added 3.57 g of a 10% sodium hydroxide aqueous solution, 5 ml of ethanol and 3.57 g of water, and the mixture was heat-refluxed for 1 hour. The reaction solution was adjusted to a pH of 6 with 10% hydrochloric acid, and was concentrated under reduced pressure. Ethanol was added to the resulting residue, and the inorganic salt was separated through filtration. The filtrate was concentrated under reduced pressure to obtain 0.80 g of the residue. This residue was purified through silica-gel column chromatography (eluent: a mixture of ethyl acetate and methanol at a ratio of 4:1) to give 0.63 g of 6-carboxy-1-(4-chlorobenzyl)-2-n-propylbenzimidazole (117).

Properties of Compound (117)

$^1$H-NMR(DMSO-d6, δ): 0.96(3H, t, J=7.3 Hz), 1.76–1.88 (2H, m), 3.10–3.23(2H, m), 5.83(2H, s), 7.27(2H, d, J=8.4 Hz), 7.44(2H, d, J=8.4 Hz), 7.89(1H, d, J=8.4 Hz), 7.89(1H, d, J=8.5 Hz), 8.28(1H, s)

EXAMPLE 50

Synthesis of 6-carboxy-1-methyl-2-n-propylbenzimidazole (118)

In the same manner as in Example 49, 0.46 g of 6-carboxy-1-methyl-2-n-propylbenzimidazole (118) were formed from 0.56 g of 6-ethoxycarbonyl-1-methyl-2-n-propylcarbonylbenzimidazole.

Properties of Compound (118):

$^1$H-NMR(DMSO-d6, δ): 1.00(3H, t, J=7.3 Hz), 1.79–1.93 (2H, m), 3.06(3H, t, J=7.4 Hz), 3.92(3H, s), 7.76(1H, d, J=8.4 Hz), 7.97(1H, d, J=8.4 Hz), 8.31(1H, s).

EXAMPLE 51

Synthesis of 6-carboxy-2-n-propyl-1-i-propylbenzimidazole (119)

In the same manner as in Example 49, 0.045 g of 6-carboxy-2-n-propyl-1-i-propylbenzimidazole (119) were formed from 0.045 g of 6-ethoxycarbonyl-2-n-propyl-1-i-propylbenzimidazole.

Properties of Compound (119):

$^1$H-NMR(CD3OD, δ): 0.98(3H, t, J=7.4 Hz), 1.61(6H, d, J=6.9 Hz), 1.74–1.82(2H, m), 2.89(2H, t, J=7.5 Hz), 3.21–3.24(2H, m), 4.78–4.83(1H, m), 7.51(1H, d, J=8.3 Hz), 7.84(1H, dd, J=8.4 and 1.5 Hz), 8.26(1H, s).

EXAMPLE 52

Synthesis of 1-n-butyl-6-carboxy-2-n-propylbenzimidazole (120)

In the same manner as in Example 49, 0.60 g of 1-n-butyl-6-carboxy-2-n-propylbenzimidazole (120) were formed from 0.81 g of 1-n-butyl-6-ethoxycarbonyl-2-n-propylbenzimidazole.

Properties of Compound (120):

$^1$H-NMR(DMSO-d6, δ): 1.02(3H, t, J=7.3 Hz), 1.17(3H, t, J=7.3 Hz), 1.33–1.41(2H, m), 1.70–1.77(2H, m), 1.85–1.93(2H, m), 3.07(2H, t, J=7.6 Hz), 4.42(2H, t, J=7.4 Hz), 7.78(1H, d, J=8.5 Hz), 7.99(1H, dd, J=8.5 and 1.0 Hz), 8.35(1H, s), 13.13(1H, s)

EXAMPLE 53

Synthesis of 6-carboxy-1-(2-chlorobenzyl)-2-methylbenzimidazole (121)

Eighty milliliters of ethanol and 37 g of a 10 % sodium hydroxide aqueous solution were added to 10.0 g of 1-(2-chlorobenzyl)-6-ethoxycarbonyl-2-methylbenzimidazole, and the mixture was refluxed for 4 hours. The reaction solution was cooled, and was then adjusted to a pH of 6 with 10% hydrochloric acid. The precipitate was collected, washed with water, and dried under reduced pressure to give 8.30 g of 6-carboxy-1-(2-chlorobenzyl)-2-methylbenzimidazole (121).

EXAMPLE 54

Synthesis of 6-carboxy-1-(2,6-dichlorobenzyl)-2-methyl-benzimidazole (122)

In the same manner as in Example 53, 0.72 g of 6-carboxy-1-(2,6-dichlorobenzyl)-2-methylbenzimidazole (122) were formed from 0.90 g of 1-(2,6-dichlorobenzyl)-6-ethoxycarbonyl-2-methylbenzimidazole.

Properties of Compound (122):

$^1$H-NMR(DMSO-d6, δ): 2.60(3H, s), 5.71(2H, s), 7.46 (1H, t, J=7.9 Hz), 7.57(3H, t, J=8.2 Hz), 7.73(2H, m), 12.57(1H, s).

EXAMPLE 55

Synthesis of 6-carboxy-2-methyl-1-[2-(trifluoromethyl)benzyl]-benzimidazole (123)

In the same manner as in Example 53, 0.98 g of 6-carboxy-2-methyl-1-[2-(trifluoromethyl)benzyl] benzimidazole (123) were formed from 1.17 g of 6-ethoxycarbonyl-2-methyl-1-[2-(trifluoromethyl)benzyl] benzimidazole.

Properties of Compound (123):

$^1$H-NMR(DMSO-d6, δ): 2.49(3H, s), 5.70(2H, s), 6.46–6.51(1H, m), 7.51(2H, m), 7.65(1H, d, J=8.4 Hz), 7.81(1H, dd, J=1.4 and 8.4 Hz), 7.82–7.87(1H, m), 7.91(1H, s).

EXAMPLE 56

Synthesis of 6-carboxy-2-methyl-1-[4-(trifluoromethyl)benzyl]-benzimidazole (124)

In the same manner as in Example 53, 1.07 g of 6-carboxy-2-methyl-1-[4-(trifluoromethyl)benzyl]- benzimidazole (124) were formed from 1.22 g of 6-ethoxycarbonyl-2-methyl-1-[4-(trifluoromethyl)benzyl]-benzimidazole.

Properties of Compound (124):
$^1$H-NMR(DMSO-d6, δ): 2.85(3H, s), 5.92(2H, s), 7.50 (2H, d, J=8.1 Hz), 7.74(2H, d, J=8.1 Hz), 7.88(1H, d, J=8.5 Hz), 8.07(1H, d, J=8.5 Hz), 8.31(1H, s), 13.3(1H, br s).

EXAMPLE 57

Synthesis of 6-carboxy-1-(3,4-dichlorobenzyl)-2-methyl-benzimidazole (125)

In the same manner as in Example 53, 0.55 g of 6-carboxy-1-(3,4-dichlorobenzyl)-2-methylbenzimidazole (125) were formed from 0.76 g of 1-(3,4-dichlorobenzyl)-6-ethoxycarbonyl-2-methylbenzimidazole.

Properties of Compound (125):
$^1$H-NMR(DMSO-d6, δ): 2.56(3H, s), 5.61(2H, s), 6.98 (1H, dd, J=8.4 and 1.9 Hz), 7.46(1H, d, J=1.9 Hz), 7.59(1H, d, J=8.3 Hz), 7.63(1H, d, J=8.4 Hz), 7.81(1H, dd, J=8.4 and 1.4 Hz), 8.07(1H, s), 12.76(1H, s)

EXAMPLE 58

Synthesis of 1-benzyl-6-carboxy-2-n-propylbenzimidazole (126)

A 10% sodium hydroxide aqueous solution (3.61 g), 5 ml of ethanol and 3 ml of water were added to 0.97 g of 1-benzyl-6-ethoxycarbonyl-2-n-propylbenzimidazole, and the mixture was heat-refluxed for 1 hour. The reaction solution was adjusted to a pH of 6 with 10% hydrochloric acid, and was concentrated under reduced pressure. Ethanol was added to the residue, and the inorganic salt was separated through filtration. The filtrate was concentrated under reduced pressure to give 0.85 g of 1-benzyl-6-carboxy-2-n-propylbenzimidazole (126).

Properties of Compound (126):
$^1$H-NMR(DMSO-d6, δ): 0.94(3H, t, J=7.4 Hz), 1.73–1.81 (2H, m), 2.85(2H, t, J=7.3 Hz), 5.59(2H, s), 7.07(2H, dd, J=1.1 and 8.3 Hz), 7.27(1H, t, J=7.3 Hz), 7.33(2H, t, J=7.4 Hz), 7.65(1H, d, J=8.4 Hz), 7.79(1H, dd, J=1.5 and 8.4 Hz), 8.04(1H, s)

EXAMPLE 59

Synthesis of 6-carboxy-1-(3-chlorobenzyl)-2-n-propyl-benzimidazole (127)

In the same manner as in Example 58, 0.35 g of 6-carboxy-1-(3-chlorobenzyl)-2-n-propylbenzimidazole (127) were formed from 0.57 g of 1-(3-chlorobenzyl)-6-ethoxycarbonyl-2-n-propylbenzimidazole.

Properties of Compound (127):
$^1$H-NMR(DMSO-d6, δ): 0.94(3H, t, J=7.3 Hz), 1.70–1.79 (2H, m), 2.83(2H, t, J=7.4 Hz), 5.59(2H, s), 6.94(1H, s), 7.15(1H, s), 7.34(2H, d, J=4.4 Hz), 7.59(1H, d, J=8.4 Hz), 7.81(1H, d, J=8.1 Hz), 8.02(1H, s)

EXAMPLE 60

Synthesis of 6-carboxy-2-methyl-1-(2-nitrobenzyl) benzimidazole (128)

In the same manner as in Example 58, 0.35 g of 6-carboxy-2-methyl-1-(2-nitrobenzyl)benzimidazole (128) were formed from 0.61 g of 6-ethoxycarbonyl-2-methyl-1-(2-nitrobenzyl)benzimidazole.

Properties of Compound (128):
$^1$H-NMR(DMSO-d6, δ): 2.51(3H, s), 5.96(2H, s), 6.33 (1H, d, J=7.0 Hz), 7.55–7.62(2H, m), 7.66(1H, d, J=8.3 Hz), 7.81(1H, d, J=8.4 Hz), 8.06(1H, s), 8.24(1H, d, J=7.0 Hz), 12.66(1H, s)

EXAMPLE 61

Synthesis of 6-carboxy-1-(2-chlorobenzyl)-2-methylbenzimidazole (121)

Ethanol (15 ml) and 10.6 g of a 5% sodium hydroxide aqueous solution were added to 1.456 g of 1-(2-chlorobenzyl)-6-ethoxycarbonyl-2-methylbenzimidazole, and the mixture was refluxed for 1 hour. The reaction solution was cooled, and was then adjusted to a pH of 6 with 10% hydrochloric acid. The precipitate was collected, washed with water, and dried under reduced pressure to give 0.645 g of 6-carboxy-1-(2-chlorobenzyl)-2-methylbenzimidazole (121).

EXAMPLE 62

Synthesis of 6-carboxy-1-(2,4-dichlorobenzyl)-2-methyl-benzimidazole (129)

A 10% sodium hydroxide aqueous solution (3.10 g) and 10 ml of ethanol were added to 0.94 g of 1-(2,4-dichlorobenzyl)-6-ethoxycarbonyl-2-methylbenzimidazole, and the mixture was heat-refluxed for 1 hour. The reaction solution was adjusted to a pH of 6 with 10% hydrochloric acid. The crystals precipitated were separated through filtration, and were dried to give 0.68 g of 6-carboxy-1-(2, 4-dichlorobenzyl)-2-methylbenzimidazole (129).

Properties of Compound (129):
$^1$H-NMR(DMSO-d6, δ): 2.52(3H, s), 5.61(2H, s), 6.54 (1H, d, J=8.4 Hz), 7.33(1H, dd, J=8.4 and 2.1 Hz), 7.64(1H, d, J=8.4 Hz), 7.74(1H, d, J=2.1 Hz), 7.81(1H, dd, J=8.4 and 1.5 Hz), 7.98(1H, s), 12.72(1H, s).

EXAMPLE 63

Synthesis of 1-(biphenyl-4-ylmethyl)-6-carboxy-2-methyl-benzimidazole (130)

In the same manner as in Example 53, 0.83 g of 1-(biphenyl-4-ylmethyl)-6-carboxy-2-methylbenzimidazole (130) were formed from 1.10 g of 1-(biphenyl-4-ylmethyl)-6-ethoxycarbonyl-2-methylbenzimidazole.

Properties of Compound (130):
$^1$H-NMR(DMSO-d6, δ): 2.53(3H, s), 5.61(2H, s), 7.18 (2H, d, J=8.2 Hz), 7.34(1H, m), 7.43(2H, m), 7.62(5H, m), 7.79(1H, dd, J=1.6 and 8.5 Hz), 8.09(1H, d, J=1.0 Hz), 12.72(1H, br s)

EXAMPLE 64

Synthesis of 1-(4-tert-butylbenzyl)-6-carboxy-2-methylbenzimidazole (131)

In the same manner as in Example 53, 0.55 g of 1-(4-tert-butylbenzyl)-6-carboxy-2-methylbenzimidazole (131) were formed from 1.34 g of 1-(4-tert-butylbenzyl)-6-ethoxycarbonyl-2-methylbenzimidazole.

Properties of Compound (131):
$^1$H-NMR(DMSO-d6, δ): 1.22(9H, s), 2.57(3H, s), 5.52 (2H, s), 7.03(2H, d, J=8.2 Hz), 7.35(1H, d, J=8.3 Hz), 7.60(1H, d, J=8.4 Hz), 7.78(1H, dd, J=8.4 and 1.5 Hz), 8.06(1H, s), 12.71(1H, s)

EXAMPLE 65

Synthesis of 6-carboxy-2-methyl-1-(2-methylbenzyl)benzimidazole (132)

In the same manner as in Example 53, 0.49 g of 6-carboxy-2-methyl-1-(2-methylbenzyl)benzimidazole (132) were formed from 0.81 g of 6-ethoxycarbonyl-2-methyl-1-(2-methylbenzyl)benzimidazole.

Properties of Compound (132):

$^1$H-NMR(DMSO-d6, δ): 2.41(3H, s), 2.48(3H, s), 5.55 (2H, s), 6.14(1H, d, J=7.6 Hz), 7.02(1H, t, J=7.4 Hz), 7.17(1H, t, J=7.3 Hz), 7.26(1H, d, J=7.4 Hz), 7.65(1H, d, J=8.4 Hz), 7.81(1H, dd, J=8.4 and 1.4 Hz), 7.97(1H, d, J=1.1 Hz), 12.71(1H, s)

EXAMPLE 66

Synthesis of 6-carboxy-1-(2-methoxybenzyl)-2-methylbenzimidazole (133)

In the same manner as in Example 53, 1.00 g of 6-carboxy-1-(2-methoxybenzyl)-2-methylbenzimidazole (133) was formed from 1.63 g of 6-ethoxycarbonyl-1-(2-methoxybenzyl)-2-methylbenzimidazole.

Properties of Compound (133):

$^1$H-NMR(DMSO-d6, δ): 2.55(3H, s), 3.81(3H, s), 5.42 (2H, s), 6.77(1H, m), 6.85(1H, m), 7.05(1H, m), 7.28(1H, m), 7.58(1H, m), 7.76(1H, m), 7.99(1H, s), 12.65(1H, br s).

EXAMPLE 67

Synthesis of 6-carboxy-1-(4-methoxybenzyl)-2-methylbenzimidazole (134)

In the same manner as in Example 53, 0.99 g of 6-carboxy-1-(4-methoxybenzyl)-2-methylbenzimidazole (134) were formed from 1.27 g of 6-ethoxycarbonyl-1-(4-methoxybenzyl)-2-methylbenzimidazole.

Properties of Compound (134):

$^1$H-NMR(DMSO-d6, δ): 2.86(3H, s), 3.71(3H, s), 5.69 (2H, s), 6.92(2H, d, J=8.4 Hz), 7.27(2H, d, J=8.4 Hz), 7.84(1H, d, J=8.5 Hz), 8.04(1H, d, J=8.5 Hz), 8.33(1H, s), 13.25(1H, br t)

EXAMPLE 68

Synthesis of 6-carboxy-2-methyl-1-[2-(benzenesulfonylmethyl)-benzyl]benzimidazole (135)

In the same manner as in Example 53, 0.74 g of 6-carboxy-2-methyl-1-[2-(benzenesulfonylmethyl)benzyl]-benzimidazole (135) were formed from 0.89 g of 6-ethoxycarbonyl-2-methyl-1-[2-(benzenesulfonylmethyl)benzyl]benzimidazole.

Properties of Compound (135):

$^1$H-NMR(DMSO-d6, δ): 2.44(3H, s), 4.99(2H, s), 5.71 (2H, s), 6.08(1H, d, J=6.5 Hz), 7.12–7.20(3H, m), 7.64–7.70 (3H, m), 7.77–7.83(2H, m), 7.89(2H, s), 7.90(1H, s), 12.71 (1H, s)

EXAMPLE 69

Synthesis of 6-carboxy-1-(2-cyanobenzyl)-2-methylbenzimidazole (136)

In the same manner as in Example 53, 1.14 g of 6-carboxy-1-(2-cyanobenzyl)-2-methylbenzimidazole (136) were formed from 2.04 g of 1-(2-cyanobenzyl)-6-(2-cyanobenzyloxycarbonyl)-2-methylbenzimidazole.

Properties of Compound (136):

$^1$H-NMR(DMSO-d6, δ): 2.54(3H, s), 5.80(2H, s), 6.78 (1H, d, J=7.8 Hz), 7.51(1H, t, J=7.4 Hz), 7.61(1H, dt, J=7.8 and 1.2 Hz), 7.64(1H, d, J=8.4 Hz), 7.80(1H, dd, J=8.4 and 1.5 Hz), 7.94(1H, d, J=6.7 Hz), 8.00(1H, d, J=1.1 Hz), 12.70(1H, s)

EXAMPLE 70

Synthesis of 6-carboxy-1-(biphenyl-2-ylmethyl)-2-methylbenzimidazole (137)

In the same manner as in Example 53, 1.07 g of 6-carboxy-1-(biphenyl-2-ylmethyl)-2-methylbenzimidazole (137) were formed from 1.31 g of 1-(biphenyl-2-ylmethyl)-6-ethoxycarbonyl-2-methylbenzimidazole.

Properties of Compound (137):

$^1$H-NMR(DMSO-d6, δ): 2.32(3H, s), 5.45(2H, s), 6.61 (1H, d, J=7.7 Hz), 7.26(1H, dt, J=7.7 and 1.4 Hz), 7.31(1H, dd, J=7.5 and 1.3 Hz), 7.36(1H, dt, J=7.5 and 0.7 Hz), 7.40–7.46(1H, m), 7.46–7.52(4H, m), 7.57(1H, d, J=8.4 Hz), 7.76(1H, dd, J=7.9 and 1.5 Hz), 7.86(1H, d, J=1.2 Hz), 12.72(1H, s)

EXAMPLE 71

Synthesis of 1-benzyl-6-carboxy-2-methylbenzimidazole (138)

In the same manner as in Example 53, 0.59 g of 1-benzyl-6-carboxy-2-methylbenzimidazole(138) were formed from 0.71 g of 1-benzyl-6-ethoxycarbonyl-2-methylbenzimidazole.

Properties of Compound (138):

$^1$H-NMR(DMSO-d6, δ): 2.56(3H, s), 5.57(2H, s), 7.11 (1H, d, J=8.0 Hz), 7.27(1H, t, J=7.2 Hz), 7.32–7.35(2H, m), 7.61(1H, d, J=8.3 Hz), 7.79(1H, dd, J=8.4 and 1.3 Hz), 8.06(1H, s), 12.75(1H, S)

EXAMPLE 72

Synthesis of 6-carboxy-2-methyl-1-(2-naphthylmethyl)benzimidazole (139)

In the same manner as in Example 53, 0.80 g of 6-carboxy-2-methyl-1-(2-naphthymethyl)benzimidazole (139) were formed from 1.28 g of 6-ethoxycarbonyl-2-methyl-1-(2-naphthylmethyl)benzimidazole.

Properties of Compound (139):

$^1$H-NMR(DMSO-d6, δ): 2.61(3H, s), 5.74(2H, s), 7.29 (1H, d, J=8.6 Hz), 7.46–7.52(2H, m), 7.59(1H, s), 7.63(1H, d, J=8.3 Hz), 7.78–7.92(4H, m), 8.09(1H, s), 12.68(1H, s).

EXAMPLE 73

Synthesis of 1-(biphenyl-4-ylmethyl)-6-carboxy-2-ethylbenzimidazole (140)

In the same manner as in Example 53, 1.70 g of 1-(biphenyl-4-ylmethyl)-6-carboxy-2-ethylbenzimidazole (140) were formed from 2.07 g of 1-(biphenyl-4-ylmethyl)-6-ethoxycarbonyl-2-ethylbenzimidazole.

Properties of Compound (140):

$^1$H-NMR(DMSO-d6, δ): 1.32(3H, t, J=7.4 Hz), 2.94(2H, q, J=7.5 Hz), 5.63(2H, s), 7.16(2H, d, J=8.2 Hz), 7.34(1H, t, J=7.4 Hz), 7.44(2H, t, J=7.5 Hz), 7.60–7.78(5H, m), 7.81(1H, dd, J=1.4 and 8.4 Hz), 8.10(1H, d, J=1.2 Hz), 12.73(1H, s).

EXAMPLE 74

Synthesis of 5-carboxy-1-(2-chlorobenzyl)-2-methylbenzimidazole (141)

In the same manner as in Example 53, 2.48 g of 5-carboxy-1-(2-chlorobenzyl)-2-methylbenzimidazole (141) were formed from 3.70 g of 1-(2-chlorobenzyl)-5-ethoxycarbonyl-2-methyl-benzimidazole.

Properties of Compound (141):
$^1$H-NMR(DMSO-d6, δ): 2.49(3H, s), 5.57(2H, s), 6.53 (1H, d, J=7.8 Hz), 7.22(1H, t, J=7.6 Hz), 7.33(1H, t, J=7.6 Hz), 7.44(1H, d, J=8.4 Hz), 7.54(1H, d, J=8.0 Hz), 7.77(1H, dd, J=1.6 and 8.5 Hz), 8.16(1H, d, J=1.3 Hz), 12.71(1H, br s).

EXAMPLE 75

Synthesis of 5-carboxy-2-methyl-1-(2-nitrobenzyl)benzimidazole (142)

In the same manner as in Example 53, 0.15 g of 5-carboxy-2-methyl-1-(2-nitrobenzyl)benzimidazole (142) were formed from 0.26 g of 5-ethoxycarbonyl-2-methyl-1-(2-nitrobenzyl)benzimidazole.

Properties of Compound (142):
$^1$H-NMR(DMSO-d6, δ): 2.49(3H, s), 5.91(2H, s), 6.36 (1H, dd, J=7.2 and 1.8 Hz), 7.52(1H, d, J=8.5 Hz), 7.55–7.62 (2H, m), 7.77(1H, dd, J=8.5 and1.5 Hz), 8.18(1H, d, J=1.3 Hz), 8.24(1H, dd, J=7.4 and 1.6 Hz), 12.69(1H, s).

EXAMPLE 76

Synthesis of 2-benzyl-5-carboxy-1-(2-chlorobenzyl)benzimidazole (143)

In the same manner as in Example 53, 0.488 g of 2-benzyl-5-carboxy-1-(2-chlorobenzyl)benzimidazole (143) were formed from 0.635 g of 2-benzyl-1-(2-chlorobenzyl)-5-ethoxycarbonyl-benzimidazole.

Properties of Compound (143):
$^1$H-NMR(DMSO-d6, δ): 4.27(2H, s), 5.57(2H, s), 6.27 (1H, d, J=7.1 Hz), 7.06(1H, t), 7.10–7.29(6H, m), 7.39(1H, d, J=8.6 Hz), 7.47(1H, d, J=7.9 Hz), 7.78(1H, dd, J=1.4 and 8.6 Hz), 8.21(1H, d, J=1.2 Hz), 12.71(1H, br s).

EXAMPLE 77

Synthesis of 2-benzyl-6-carboxy-1-(2-chlorobenzyl)benzimidazole (144)

In the same manner as in Example 53, 0.780 g of 2-benzyl-6-carboxy-1-(2-chlorobenzyl)benzimidazole (144) were formed from 1.00 g of 2-benzyl-1-(2-chlorobenzyl)-6-ethoxycarbonyl-benzimidazole.

Properties of Compound (144):
$^1$H-NMR(DMSO-d6, δ): 4.29(2H, s), 5.63(2H, s), 6.28 (1H, d, J=7.8 Hz), 7.07(1H, t, J=7.6 Hz), 7.15(1H, m), 7.19–7.29(5H, m), 7.49(1H, d, J=7.4 Hz), 7.70(1H, d, J=8.4 Hz), 7.81(1H, d, J=8.4 Hz), 7.91(1H, s), 12.73(1H, br s).

EXAMPLE 78

Synthesis of 2-benzyl-5-carboxy-1-(2,4-dichlorobenzyl)benzimidazole (145)

In the same manner as in Example 53, 0.40 g of 2-benzyl-5-carboxy-1-(2,4-dichlorobenzyl)benzimidazole (145) were formed from 0.50 g of 2-benzyl-1-(2,4-dichlorobenzyl)-5-ethoxycarbonylbenzimidazole.

Properties of Compound (145):
$^1$H-NMR(DMSO-d6, δ): 4.28(2H, s), 5.55(2H, s), 6.19 (1H, d, J=8.4 Hz), 7.08–7.22(6H, m), 7.41(1H, d, J=8.4 Hz), 7.62(1H, d, J=2.2 Hz), 7.79(1H, dd, J=1.5 and 8.6 Hz), 8.22(1H, s), 12.72(1H, br s)

EXAMPLE 79

Synthesis of 2-benzyl-6-carboxy-1-(2,4-dichlorobenzyl)benzimidazole (146)

In the same manner as in Example 53, 0.35 g of 2-benzyl-6-carboxy-1-(2,4-dichlorobenzyl)benzimidazole (146) were formed from 0.48 g of 2-benzyl-1-(2,4-dichlorobenzyl)-6-ethoxycarbonylbenzimidazole.

Properties of Compound (146):
$^1$H-NMR(DMSO-d6, δ): 4.30(2H, s), 5.61(2H, s), 6.19 (1H, d, J=8.4 Hz), 7.09–7.22(6H, m), 7.64(1H, d, J=2.1 lHz), 7.71(1H, d, J=8.4 Hz), 7.82(1H, dd, J=1.5 and 8.4 Hz), 7.94(1H, d, J=1.2 Hz), 12.78(1H, br s)

EXAMPLE 80

Synthesis of 1-(biphenyl-4-ylmethyl)-6-carboxy-2-trifluoromethylbenzimidazole (147)

In the same manner as in Example 53, 0.483 g of 1-(biphenyl-4-ylmethyl)-6-carboxy-2-trifluoromethylbenzimidazole (147) were formed from 0.690 g of 1-(biphenyl-4-ylmethyl)-6-ethoxycarbonyl-2-trifluoromethylbenzimidazole.

Properties of Compound (147):
$^1$H-NMR(DMSO-d6, δ): 5.87(2H, s), 7.18(2H, d, J=8.2 Hz), 7.35(1H, t, J=7.4 Hz), 7.44(2H, t, J=7.5 Hz), 7.60–7.67 (4H, m), 7.98(2H, d, J=0.7 Hz), 8.32(1H, s), 13.15(1H, s).

EXAMPLE 81

Synthesis of 1-(biphenyl-4-ylmethyl)-5-carboxy-2-trifluoromethylbenzimidazole (148)

In the same manner as in Example 53, 0.270 g of 1-(biphenyl-4-ylmethyl)-5-carboxy-2-trifluoromethylbenzimidazole (148) were formed from 0.38 g of 1-(biphenyl-4-ylmethyl)-5-ethoxycarbonyl-2-trifluoromethylbenzimidazole.

Properties of Compound (148):
$^1$H-NMR(DMSO-d6, δ): 5.80(2H, s), 7.19(2H, d, J=6.3 Hz), 7.35(1H, t, J=7.2 Hz), 7.43(2H, t, J=7.3 Hz), 7.82(1H, d, J=8.7 Hz), 8.04(1H, d, J=8.7 Hz), 8.45(1H, s)

EXAMPLE 82

Synthesis of 5-ethoxycarbonyl-2-methylbenzimidazole (149)

Reduced iron (6.46 g), 48 ml of ethanol and 24 ml of acetic acid were added to 3.00 g of ethyl 3-acetylamino-4-nitrobenzoate, and the mixture was heat-refluxed for 12 hours. The solid material was removed using a filtration aid, and the filtrate was concentrated under reduced pressure. To the residue were added 100 ml of ethanol and 5.2 g of 35% hydrochloric acid, and the mixture was heat-refluxed for 5 hours. The reaction solution was neutralized with 6.3 g of sodium hydrogencarbonate, and was filtrated. The filtrate was concentrated under reduced pressure. The residue was separated with the addition of 70 ml of ethyl acetate and 70 ml of water. The organic layer was washed three times with water, and the aqueous layer was extracted three times with ethyl acetate. The resulting organic layer was concentrated under reduced pressure to give 1.53 g of a powder of 5-ethoxycarbonyl-2-methylbenzimidazole (149).

Properties of Compound (149):

$^1$H-NMR(CDCl$_3$, δ): 1.41(3H, t, J=6.9 Hz), 2.67(3H, s), 4.40(2H, q, J=7.1 Hz), 7.55(1H, d, J=8.4 Hz), 7.96(1H, dd, J=8.4 and 1.5 Hz), 8.27(1H, d, J=1.4 Hz)

EXAMPLE 83

Synthesis of 2-benzyl-5-ethoxycarbonylbenzimidazole (150)

A mixture of 3.60 g of ethyl 3-nitro-4-phenylacetylaminobenzoate, 47 ml of ethanol, 23 ml of acetic acid and 6.4 g of reduced iron was heat-refluxed for 4 hours. The solid material was separated through filtration, and the filtrate was concentrated. To the residue were added 50 ml of ethanol and 5 g of 35% hydrochloric acid. The mixture was stirred for 40 hours while being heat-refluxed. The reaction solution was neutralized with sodium hydrogencarbonate, and was extracted with chloroform. The organic layer was concentrated under reduced pressure, and was purified through silica-gel column chromatography to give 2.30 g of 2-benzyl-5-ethoxycarbonylbenzimidazole (150).

Properties of Compound (150):

$^1$H-NMR(CDCl$_3$, δ): 1.39(3H, t, J=7.1 Hz), 4.26(2H, s), 4.37(2H, q, J=7.1 Hz), 7.22–7.36(5H, m), 7.50(1H, d, J=8.6 Hz), 7.94(1H, dd, J=1.5 and 8.6 Hz), 8.23(1H, d, J=1.3 Hz)

EXAMPLES 84 AND 85

Synthesis of 6-ethoxycarbonyl-2-methyl-1-(2-nitrobenzyl)benzimidazole (151) and 5-ethoxycarbonyl-2-methyl-1-(2-nitrobenzyl)benzimidazole (152)

To 1.00 g of 5-ethoxycarbonyl-2-methylbenzimidazole were added 15 ml of N,N-dimethylformamide, 1.59 g of 2-nitrobenzyl bromide and 1.23 g of sodium hydrogencarbonate, and the mixture was heated at 60° C. for 1 hour. The reaction solution was separated with the addition of 70 ml of ethyl acetate and 70 ml of water. The organic layer was then washed three times with water, and the aqueous layer was extracted three times with ethyl acetate. The resulting organic layer was concentrated under reduced pressure to obtain a mixture of 6-ethoxycarbonyl-2-methyl-1-(2-nitrobenzyl)benzimidazole and 5-ethoxycarbonyl-2-methyl-1-(2-nitrobenzyl)benzimidazole. The mixture was purified through medium-pressure silica-gel column chromatography (eluent: a mixture of hexane and ethyl acetate at a ratio of from 1:4 to 0:100) to give 0.614 g of 6-ethoxycarbonyl-2-methyl-1-(2-nitrobenzyl)benzimidazole (151) and 0.259 g of 5-ethoxycarbonyl-2-methyl-1-(2-nitrobenzyl)benzimidazole (152).

Properties of Compound (151):

$^1$H-NMR(CDCl$_3$, δ): 1.38(3H, t, J=7.2 Hz), 2.56(3H, s), 4.37(2H, q, J=7.1 Hz), 5.84(2H, s), 6.41(1H, d, J=6.8 Hz), 7.44–7.53(2H, m), 7.78(1H, d, J=8.6 Hz), 7.88(1H, s), 8.02(1H, dd, J=8.3 and 1.5 Hz), 8.30(1H, dd, J=7.9 and 1.5 Hz)

Properties of Compound (152):

$^1$H-NMR(CDCl$_3$, δ): 1.42(3H, t, J=7.0 Hz), 2.56(3H, s), 4.40(2H, q, J=7.0 Hz), 5.80(2H, s), 6.43(1H, dd, J=7.6 and 1.0 Hz), 7.14(1H, d, J=8.3 Hz), 7.45–7.53(2H, m), 7.95(1H, dd, J=8.4 and 1.5 Hz), 8.27(1H, dd, J=8.0 and 1.7 Hz), 8.48(1H, d, J=1.2 Hz)

EXAMPLES 86 AND 87

Synthesis of 2-benzyl-1-(2-chlorobenzyl)-6-ethoxycarbonylbenzimidazole (153) and 2-benzyl-1-(2-chlorobenzyl)-5-ethoxycarbonylbenzimidazole (154)

In the same manner as in Examples 84 and 85, 1.06 g of 2-benzyl-1-(2-chlorobenzyl)-6-ethoxycarbonylbenzimidazole (153) and 0.640 g of 2-benzyl-1-(2-chlorobenzyl)-5-ethoxycarbonylbenzimidazole (154) were formed from 2.37 g of 2-benzyl-5-ethoxycarbonylbenzimidazole and 3.94 g of 2-chlorobenzyl bromide.

Properties of Compound (153):

$^1$H-NMR(CDCl$_3$, δ): 1.83(3H, t, J=7.1 Hz), 4.23(2H, s), 4.35(2H, q, J=7.1 Hz), 5.36(2H, s), 6.23(1H, d, J=7.8 Hz), 6.97(1H, t, J=7.6 Hz), 7.11–7.45(7H, m), 7.85(1H, d, J=8.5 Hz), 7.91(1H, s), 8.02(1H, dd, J=1.2 and 8.6 Hz).

Properties of Compound (154):

$^1$H-NMR(CDCl$_3$, δ): 1.41(3H, t, J=7.1 Hz), 4.25(2H, s), 4.41(2H, q, J=7.1 Hz), 5.33(2H, s), 6.22(1H, d, J=6.9 Hz), 6.97(1H, t, J=7.6 Hz), 7.12–7.28(7H, m), 7.40(1H, d, J=8.0 OHz), 7.95(1H, dd, J=1.6 and 8.6 Hz), 8.60(1H, d, J=1.4 Hz)

EXAMPLES 88 AND 89

Synthesis of 2-benzyl-1-(2,4-dichlorobenzyl)-6-ethoxycarbonyl-benzimidazole (155) and 2-benzyl-1-(2,4-dichlorobenzyl)-5-ethoxycarbonyl-benzimidazole (156)

In the same manner as in Examples 84 and 85, 0.49 g of 2-benzyl-1-(2,4-dichlorobenzyl)-6-ethoxycarbonyl-benzimidazole and 0.52 g of 2-benzyl-1-(2,4-dichlorobenzyl)-5-ethoxycarbonyl-benzimidazole (156) were formed from 2.37 g of 2-benzyl-5-ethoxycarbonyl-benzimidazole and 4.45 g of 2,4-dichlorobenzyl bromide.

Properties of Compound (155):

$^1$H-NMR(CDCl$_3$, δ): 1.39(3H, t), 4.24(2H, s), 4.37(2H, q), 5.32(2H, s), 6.08(1H, d, J=8.3 Hz), 6.90(1H, d, J=8.4 Hz), 7.12–7.24(5H, m), 7.41(1H, s), 7.84(1H, d, J=8.4 Hz), 7.88(1H, s), 8.03(1H, d, J=8.4 Hz)

Properties of Compound (156):

$^1$H-NMR(CDCl$_3$, δ): 1.42(3H, t, J=7.1 Hz), 4.25(2H, s), 4.41(2H, q, J=7.1 Hz), 5.28(2H, s), 6.07(1H, d, J=8.4 Hz), 6.90(1H, dd, J=1.9 and 8.4 Hz), 7.08–7.28(6H, m), 7.40(1H, d, J=2.1 Hz), 7.96(1H, dd, J=1.3 and 8.3 Hz), 8.56(1H, d, J=0.9 Hz)

EXAMPLE 90

Synthesis of 5-ethoxycarbonyl-2-trifluoromethylbenzimidazole (157)

Five-percent palladium on carbon (0.50 g) was added to a solution of 4.00 g of ethyl 3-amino-4-nitro-benzoate in 100 ml of methanol, and the mixture was stirred in a hydrogen atmosphere at 50° C. for 16 hours. The solid material was separated through filtration, and the filtrate was concentrated to obtain ethyl 3,4-diaminobenzoate. Twenty milliliters of trifluoroacetic acid were added thereto, and the mixture was stirred at 60° C. for 2 hours. The reaction solution was concentrated, and chloroform was added thereto. The crystals precipitated were separated through filtration, and were dried to give 4.46 g of 5-ethoxycarbonyl-2-trifluoromethylbenzimidazole (157).

Properties of Compound (157):

¹H-NMR(DMSO-d6, δ): 1.36(3H, t, J=7.0 Hz), 4.36(2H, q, J=7.0 Hz), 7.82(1H, d, J=8.5 Hz), 7.99(1H, dd, J=1.5 and 8.7 Hz), 8.33(1H, s)

EXAMPLES 91 AND 92

Synthesis of 1-(biphenyl-4-ylmethyl)-6-ethoxycarbonyl-2-trifluoromethylbenzimidazole (158) and 1-(biphenyl-4-ylmethyl)-5-ethoxycarbonyl-2-trifluoromethylbenzimidazole (159)

In the same manner as in Examples 84 and 85, 0.69 g of 1-(biphenyl-4-ylmethyl)-6-ethoxycarbonyl-2-trifluoromethylbenzimidazole (158) and 0.38 g of 1-(biphenyl-4-ylmethyl)-5-ethoxycarbonyl-2-trifluoromethylbenzimidazole (159) were formed from 2.00 g of 5-ethoxycarbonyl-2-trifluoromethylbenzimidazole and 10.08 g of 4-bromomethylbiphenyl.

Properties of Compound (158):

¹H-NMR(CDCl₃, δ): 1.39(3H, t), 4.38(2H, q), 5.64(2H, s), 7.18(2H, d, J=8.2 Hz), 7.34(1H, t, J=7.4 Hz), 7.42(2H, t, J=7.4 Hz), 7.52–7.57(4H, m), 7.95(1H, d, J=8.8 Hz), 8.09 (2H, dd, J=1.4 and 8.8 Hz), 8.14(1H, d, J=1.1 Hz)

Properties of Compound (159):

¹H-NMR(CDCl₃, δ): 1.40(3H, t), 4.40(2H, q), 5.59(2H, s), 7.16(2H, d, J=8.1 Hz), 7.34(2H, t, J=6.2 Hz), 7.41(2H, t, J=7.5 Hz), 7.53(4H, m), 8.08(1H, dd, J=1.3 and 9.1 Hz), 8.65(1H, s)

Production Example 38

Production of 1-(2-chlorobenzyl)-6-hydroxymethyl-2-methylbenzimidazole

A solution of 2.66 g of 1-(2-chlorobenzyl)-6-ethoxycarbonyl-2-methylbenzimidazole in 20 ml of tetrahydrofuran was slowly added to a solution of 1.54 g of lithium aluminum hydride in 20 ml of tetrahydrofuran at a temperature of from 20 to 25° C. Further, the mixture was stirred at room temperature for 1 hour. Thirty milliliters of tetrahydrofuran were added thereto to dilute the reaction solution. Lithium ammonium hydride was decomposed and solidified with a saturated aqueous solution of sodium sulfate, and the tetrahydrofuran layer was separated. The solvent was distilled off, and the residue was purified through silica-gel column chromatography (eluent: a mixture of chloroform and methanol at a ratio of 9:1) to give 1.45 g of 1-(2-chlorobenzyl)-6-hydroxymethyl-2-methylbenzimidazole.

Properties of the compound:

¹H-NMR(CDCl₃, δ): 2.53(3H, s), 4.77(2H, s), 5.39(2H, s), 6.40(1H, d, J=7.7 Hz), 7.08(1H, t, J=7.7 Hz), 7.20–7.28 (3H, m), 7.45(1H, d, J=7.9 Hz), 7.70(1H, d, JH=8.2 Hz)

Production Example 39

Production of 1-(biphenyl-4-ylmethyl)-6-hydroxymethyl-2-methyl-benzimidazole

In the same manner as in Production Example 38, 3.72 g of 1-(biphenyl-4-ylmethyl)-6-hydroxymethyl-2-methylbenzimidazole were formed from 5.30 g of 1-(biphenyl-4-ylmethyl)-6-ethoxycarbonyl-2-methylbenzimidazole and 2.17 g of lithium aluminum hydride.

Properties of the compound:

¹H-NMR(CDCl₃, δ): 2.59(3H, s), 4.78(2H, s), 5.37(2H, s), 7.11(2H, d, J=8.3 Hz), 7.24(1H, d, J=8.3 Hz), 7.30–7.37 (2H, m), 7.42(2H, t), 7.51–7.56(4H, m), 7.70(1H, d, J=8.2 Hz).

Production Example 40

Production of 1-(2-chlorobenzyl)-6-chloromethyl-2-methylbenzimidazole hydrochloride Five milliliters of thionyl chloride were added to 3.56 g of 1-(2-chlorobenzyl)-6-hydroxymethyl-2-methylbenzimidazole, and the mixture was stirred at room temperature for 20 minutes and then at 80° C. for 20 minutes. After excess thionyl chloride was distilled off under reduced pressure, the residue was dissolved in 10 ml of chloroform, and the solution was crystallized from hexane. The crystals were separated through filtration, washed with hexane, and dried to give 4.07 g of 1-(2-chlorobenzyl)-6-chloromethyl-2-methylbenzimidazole hydrochloride.

Properties of the compound:

¹H-NMR(CDCl₃, δ): 3.01(3H, s), 4.68(2H, s), 5.61(2H, s), 6.71(1H, d, J=7.5 Hz), 7.24–7.29(1H, m), 7.38(1H, t, J=7.7 Hz), 7.44(1H, s), 7.52(2H, d, J=8.2 Hz), 7.92(1H, d, J=8.4 Hz).

Production Example 41

Production of 1-(biphenyl-4-ylmethyl)-6-chloromethyl-2-methylbenzimidazole

Two milliliters of thionyl chloride were added to a solution of 3.62 g of 1-(biphenyl-4-ylmethyl)-6-hydroxymethyl-2-methylbenzimidazole in 30 ml of chloroform at room temperature, and the mixture was stirred at 60° C. for 1 hour. A sodium hydrogencarbonate aqueous solution was added thereto to stop the reaction. The chloroform layer was washed with water, and was dried. The solvent was distilled off under reduced pressure, and the residue was crystallized from ethyl acetate. The crystals were separated through filtration, washed with ethyl acetate, and then dried to give 2.04 g of 1-(biphenyl-4-ylmethyl)-6-chloromethyl-2-methylbenzimidazole.

Properties of the compound:

¹H-NMR(CDCl₃, δ): 2.67(3H, s), 4.71(2H, s), 5.40(2H, s), 7.12(2H, d, J=8.2 Hz), 7.31–7.38(3H, m), 7.43(2H, t), 7.52–7.58(4H, m), 7.75(1H, d, J=8.2 Hz).

Production example 42

Production of 1-(2-chlorobenzyl)-6-formyl-2-methylbenzimidazole

Manganese dioxide (3.46 g) was added to a solution of 3.46 g of 1-(2-chlorobenzyl)-6-hydroxymethyl-2-methylbenzimidazole in 100 ml of toluene, and toluene was heat-refluxed for 3.5 hours while the mixture was dehydrated using a molecular sieve 4A. The solid material was separated through filtration, and was washed with chloroform. The filtrate was concentrated to give 3.35 g of 1-(2-chlorobenzyl)-6-formyl-2-methylbenzimidazole.

Properties of the compound:

¹H-NMR(CDCl₃, δ): 2.61(3H, s), 5.48(2H, s), 6.42(1H, d, J=7.8 Hz), 7.11(1H, t, J=7.6 Hz), 7.27(1H, t), 7.48(1H, d, J=8.0 Hz), 7.76(1H, s), 7.81(1H, dd, J=1.4 and 8.3 Hz), 7.86(1H, d, J=8.3 Hz), 10.02(1H, s).

IR(KBr): 1676 cm⁻¹.

mp: 124.1–125.2° C.

Production Example 43

Production of 1-(2-chlorobenzyl)-2-methylbenzimidazole-6-acetonitrile.

Potassium cyanate (0.450 g) and 0.450 g of 18-crown-6 were added to a solution of 1.20 g of 1-(2-chlorobenzyl)-6-chloromethyl-2-methylbenzimidazole in 10 ml of dimethylsulfoxide, and the mixture was stirred at room temperature for 18 hours. The reaction mixture was extracted with the addition of chloroform, water and a small amount of aqueous ammonia. The organic layer was concentrated, and the residue was purified through silica-gel column chromatography (eluent: a mixture of chloroform and methanol at a ratio of 20:1) to give 0.500 g of 1-(2-chlorobenzyl)-2-methylbenzimidazole-6-acetonitrile.

Properties of the compound:

$^1$H-NMR(CDCl$_3$, δ): 2.52(3H, s), 3.80(2H, s), 5.37(2H, s), 6.40(1H, d, J=7.6 Hz), 7.09(1H, t), 7.10–7.19(2H, m), 7.23(1H, t), 7.44(1H, d, J=7.9 Hz), 7.70(1H, d, J=8.2 Hz).

Production Example 44

Production of 6-carboxy-1-(2-chlorobenzyl)benzimidazole

To 0.490 g of 4-amino-3-(2-chlorobenzyl)aminobenzoic acid formed by the method described in U.S. Pat. No. 5,294,631 were added 0.5 ml of 98% formic acid, and the mixture was refluxed for 1 hour. The solid material precipitated was collected, washed with water, and dried to give 0.468 g of 6-carboxy-1-(2-chlorobenzyl)benzimidazole.

Properties of the compound:

$^1$H-NMR(DMSO-d6, δ): 5.69(2H, s), 7.02(1H, dd, J=1.5 and 7.7 Hz), 7.30(1H, t, J=7.5 Hz), 7.36(1H, dt, J=1.7 and 7.5 Hz), 7.53(1H, dd, J=1.3 and 7.9 Hz), 7.75(1H, d, J=8.4 Hz), 7.83(1H, dd, J=1.5 and 8.4 Hz), 8.09(1H, s), 8.54(1H, s), 12.8(1H, br s)

EXAMPLE 93

Synthesis of 1-(2-chlorobenzyl)-6-ethoxycarbonyl-2-methylbenzimidazole (92)

One-hundred grams of 2-chlorobenzyl bromide were added to a solution of 86.0 g of ethyl 4-acetylamino-3-aminobenzoate and 37.3 g of potassium carbonate in 750 ml of ethanol, and the mixture was stirred at 60° C. for 14 hours. The solid material was separated through filtration, and the filtrate was concentrated to 500 ml under reduced pressure. Then, 38.7 g of 35% hydrochloric acid were added thereto, and the mixture was stirred at 60° C. for 2 hours. The solid material was separated through filtration, and the residue was neutralized with sodium hydrogencarbonate. Ethanol was distilled off under reduced pressure. The residue was extracted three times with ethyl acetate and with water. The organic layer was washed with water, and was dried. The solvent was distilled off until the amount of the organic layer reached 300 ml. The crystals precipitated were separated through filtration, and were recrystallized from ethanol to obtain 54.3 g of 1-(2-chlorobenzyl)-6-ethoxycarbonyl-2-methylbenzimidazole(192). The filtrate was also all collected, and was concentrated. The resulting crystals were recrystallized from ethanol to give 18.1 g of 1-(2-chlorobenzyl)-6-ethoxycarbonyl-2-methylbenzimidazole (92).

Properties of Compound (92):

$^1$H-NMR(CDCl$_3$, δ): 1.39(3H, t, J=7.1 Hz), 2.57(3H, s), 4.37(2H, q, J=7.1 Hz), 5.46(2H, s), 6.41(1H, d, J=7.8 Hz), 7.10(1H, t, J=7.8 Hz), 7.25(1H, t), 7.47(1H, d, J=8.0 Hz), 7.75(1H, d, J=8.4 Hz), 7.94(1H, s), 8.00(1H, dd, J=1.5 and 8.4 Hz)

mp: 126.0–127.0° C.

EXAMPLE 94

Synthesis of 6-carboxy-1-(2-chlorobenzyl)-2-methylbenzimidazole (121)

To 60.0 g of 1-(2-chlorobenzyl)-6-ethoxycarbonyl-2-methylbenzimidazole were added 240 g of a 10% sodium hydroxide aqueous solution and 200 ml of ethanol, and the mixture was heat-refluxed for 2 hours. The reaction solution was cooled, and was then adjusted to a pH of 6 with 10% hydrochloric acid. The crystals precipitated were separated through filtration, and were dried to give 54.7 g of 6-carboxy-1-(2-chlorobenzyl)-2-methylbenzimidazole (121).

Properties of Compound (121):

$^1$H-NMR(DMSO-d6, δ): 2.51(3H, s), 5.62(2H, s), 6.54 (1H, d, J=7.7 Hz), 7.23(1H, t, J=7.5 Hz), 7.33(1H, t, J=7.7 Hz), 7.55(1H, d, J=8.0 Hz), 7.63(1H, d, J=8.4 Hz), 7.79(1H, d, J=8.4 Hz), 7.95(1H, s).

mp: 300.8–303.0° C.

EXAMPLE 95

Synthesis of 1-(2-chlorobenzyl)-2-methylbenzimidazole-6-acetic acid (160)

To 0.500 g of 1-(2-chlorobenzyl)-2-methylbenzimidazole-6-acetonitrile was added 10% hydrochloric acid, and the mixture was heat-refluxed for 15 hours. The reaction mixture was neutralized with a saturated aqueous solution of sodium hydrogencarbonate, and was extracted with chloroform. The organic layer was concentrated, and was purified through silica-gel column chromatography (eluent: a mixture of chloroform and methanol at a ratio of 9:1 to 4:1) to give 0.170 g of 1-(2-chlorobenzyl)-2-methylbenzimidazole-6-acetic acid (160).

Properties of Compound (160):

$^1$H-NMR(CDCl$_3$, δ): 2.42(3H, s), 3.56(2H, s), 5.15(2H, s), 6.33(1H, d), 6.96(1H, t), 7.03(1H, s), 7.13(2H, m), 7.35(1H, d, J=7.9 Hz), 7.62(1H, d), 8.90(1H, br s)

EXAMPLE 96

Synthesis of methyl 1-(2-chlorobenzyl)-2-methylbenzimidazole-6-acrylate

Methyl trifluorophosphoranilacetate (4.49 g) was added to a solution of 2.73 g of 1-(2-chlorobenzyl)-6-formyl-2-methylbenzimidazole in 50 ml of 1,4-dioxane, and the mixture was stirred for 6 hours while being heat-refluxed. After the reaction solution was cooled, the solvent was distilled off under reduced pressure, and the residue was purified through silica-gel chromatography (eluent: a mixture of chloroform and methanol at a ratio of 9:1) to obtain 7.43 g of crude methyl 1-(2-chlorobenzyl)-2-methylbenzimidazole-6-acrylate (161). This crude product was used in the subsequent reaction at once.

EXAMPLE 97

Synthesis of 1-(2-chlorobenzyl)-2-methylbenzimidazole-6-acrylic acid

The above-mentioned crude methyl 1-(2-chlorobenzyl)-2-methylbenzimidazole-6-acrylate (3.29 g) was dissolved in 20 ml of ethanol, and 10.1 g of a 5% sodium hydroxide aqueous solution were added thereto. The mixture was refluxed for 2 hours. The reaction solution was neutralized with a hydrochloric acid aqueous solution. The solvent was distilled off under reduced pressure, and the residue was purified through silica-gel chromatography (eluent: a mixture of chloroform and methanol at a ratio of from 9:1 to 6:1) to give 1.10 g of 1-(2-chlorobenzyl)-2-methylbenzimidazole-6-acrylic acid.

Properties of Compound (162):

$^1$H-NMR(DMSO-d6, δ): 2.56(3H, s), 5.65(2H, s), 6.54 (1H, d, J=15.9 Hz), 6.62(1H, d, J=7.6 Hz), 7.25(1H, t), 7.35(1H, t), 7.56(1H, d, J=8.1 Hz), 7.60–7.70(3H, m), 7.99(1H, s), 12.35(1H, br s)

EXAMPLE 98

Synthesis of 6-benzenesulfonylcarbamoyl-1-(2-chlorobenzyl)-2-methylbenzimidazole (163)

N,N'-carbonyldiimidazole (45.8 g) was added at a time to a solution of 45.0 g of 6-carboxy-1-(2-chlorobenzyl)-2-methylbenzimidazole in 950 ml of N,N-dimethylformamide, and the mixture was stirred at room temperature for 1 hour. Subsequently, 47.1 g of benzenesulfonamide and 35.0 g of diazabicycloundecene were added thereto, and the mixture was stirred at 100° C. for 70 hours. The reaction solution was cooled, and the solvent was distilled off under reduced pressure. To the residue were added 300 ml of water and 200 ml of methanol. Further, 60.7 g of 35% hydrochloric acid were added thereto to adjust the solution to a pH of 5.5. The crystals precipitated were separated through filtration, washed with 200 ml of a mixed solution of methanol and water (at a ratio of 1:1), and dried to obtain 38.4 g of 6-benzenesulfonylcarbamoyl-1-(2-chlorobenzyl)-2-methylbenzimidazole. Water was added to the filtrate. The crystals precipitated were separated through filtration, washed with water, and dried. The amount of the crystals was 13.3 g. The crystals were combined, and were dissolved by being heated with the addition of 3300 ml of acetone and 900 ml of water. From this solution, 200 ml of the solvent were distilled off while being heated, and the residue was cooled. The crystals precipitated were separated through filtration, and were dried to give 33.8 g of 6-benzenesulfonylcarbamoyl-1-(2-chlorobenzyl)-2-methylbenzimidazole (163).

Properties of Compound (163):

$^1$H-NMR(DMSO-d6, δ): 2.53(3H, s), 5.46(2H, s), 6.34 (1H, d, J=7.8 Hz), 7.11(1H, m), 7.27(1H, m), 7.48(1H, m), 7.52(2H, m), 7.60(1H, m), 7.69(1H,d, J=8.6 Hz), 7.90(1H, m), 8.09(2H, m), 8.11(1H, s), 11.84(1H, br s).

IR(KBr): 1684, 1448 cm$^{-1}$.

Mass(FAB): m/e 440(M+1).

mp: 273.5–274.3° C.

EXAMPLE 99

Synthesis of 6-benzenesulfonylcarbamoyl-1-(biphenyl-4-ylmethyl)-2-ethylbenzimidazole (164)

In the same manner as in Example 98, 0.473 g of 6-benzenesulfonylcarbamoyl-1-(biphenyl-4-ylmethyl)-2-ethylbenzimidazole (164) were formed from 0.600 g of 1-(biphenyl-4-ylmethyl)-2-ethyl-6-carboxybenzimidazole, 0.546 g of N,N'-carbonyldiimidazole, 0.529 g of benzenesulfonamide and 0.512 g of diazabicycloundecene.

Properties of Compound (164):

$^1$H-NMR(DMSO-d6, δ): 1.29(3H, t, J=7.4 Hz), 2.88(2H, q, J=7.4 Hz), 5.59(2H, s), 7.16(2H, d, J=8.2 Hz), 7.33–7.37 (1H, m), 7.44(2H, t, J=7.5 Hz), 7.59–7.71(8H, m), 7.74(1H, dd, J=8.4 and 1.4 Hz), 7.98–8.02(2H, m), 8.21(1H, s), 12.43(1H, s).

IR(KBr): 1684 cm$^{-1}$.

mp: 149.5–157.0° C.

EXAMPLE 100

Synthesis of 5-benzenesulfonylcarbamoyl-1-(2-chlorobenzyl)-2-methylbenzimidazole (165)

In the same manner as in Example 98, 0.480 g of 5-benzenesulfonylcarbamoyl-1-(2-chlorobenzyl)-2-methylbenzimidazole (165) were formed from 0.450 g of 5-carboxy-1-(2-chlorobenzyl)-2-methylbenzimidazole, 0.485 g of N,N'-carbonyldiimidazole, 0.470 g of benzenesulfonamide and 0.456 g of diazabicycloundecene.

Properties of Compound (165):

$^1$H-NMR(DMSO-d6, δ): 2.53(3H, s), 5.61(2H, s), 6.57 (1H, d, J=7.4 Hz), 7.22(1H, t), 7.33(1H, t), 7.50(1H, d, J=8.6 Hz), 7.54(1H, dd, J=7.9 and 0.9 Hz), 7.63(2H, t), 7.71(2H, m), 8.00(2H, d, J=7.3 Hz), 8.21(1H, d, J=1.4 Hz), 12.50(1H, br s).

IR(KBr): 1685 cm$^{-1}$.

mp: 137.0–138.5° C.

EXAMPLE 101

Synthesis of 5-(4-chlorobenzenesulfonylcarbamoyl)-1-(2-chlorobenzyl)-2-methylbenzimidazole (166)

In the same manner as in Example 98, 0.520 g of 5-(4-chlorobenzenesulfonylcarbamoyl)-1-(2-chlorobenzyl)-2-methylbenzimidazole (166) were formed from 0.450 g of 5-carboxy-1-(2-chlorobenzyl)-2-methylbenzimidazole, 0.485 g of N,N'-carbonyldiimidazole, 0.573 g of 4-chlorobenzenesulfonamide and 0.456 g of diazabicycloundecene.

Properties of Compound (166):

$^1$H-NMR(DMSO-d6, δ): 2.49(3H, s), 5.58(2H, s), 6.51 (1H, d, J=7.6 Hz), 7.21(1H, t), 7.32(1H, t), 7.45(1H, d, J=8.6 Hz), 7.53(1H, d, J=7.8 Hz), 7.69(3H, d, J=8.6 Hz), 7.99(2H, d, J=8.6 Hz), 8.18(1H, s), 12.58(1H, br s).

IR(KBr): 1619 cm$^{-1}$.

mp: 261.5–263.0° C.

EXAMPLE 102

Synthesis of 1-(2-chlorobenzyl)-2-methyl-5-(2-naphthalenesulfonylcarbamoyl)benzimidazole (167)

In the same manner as in Example 98, 0.352 g of 1-(2-chlorobenzyl)-2-methyl-5-(2-naphthalenesulfonylcarbamoyl)benzimidazole (167) were formed from 0.450 g of 5-carboxy-1-(2-chlorobenzyl)-2-methylbenzimidazole, 0.485 g of N,N'-carbonyldiimidazole, 0.620 g of 2-naphthalenesulfonamide and 0.456 g of diazabicycloundecene.

Properties of Compound (167):

$^1$H-NMR(DMSO-d6, δ): 2.48(3H, s), 5.56(2H, s), 6.49 (1H, d, J=7.7 Hz), 7.20(1H, t, J=7.6 Hz), 7.31(1H, t, J=7.7 Hz), 7.44(1H, d, J=8.6 Hz), 7.52(1H, d, J=8.0 Hz), 7.66–7.75(3H, m), 7.97(1H, d, J=8.8 Hz), 8.04(1H, d, J=8.0 Hz), 8.14(1H, d, J=8.8 Hz), 8.19(1H, s), 8.23(1H, d, J=8.0 Hz), 8.68(1H, s), 12.55(1H, br s).

IR(KBr): 1685 cm$^{-1}$.
mp: 236.5–238.0° C.

EXAMPLE 103

Synthesis of 1-(2-chlorobenzyl)-6-methanesulfonylcarbamoyl-2-methylbenzimidazole (168)

In the same manner as in Example 98, 0.564 g of 1-(2-chlorobenzyl)-6-methanesulfonylcarbamoyl-2-methylbenzimidazole (168) were formed from 0.500 g of 6-carboxy-1-(2-chlorobenzyl)-2-methylbenzimidazole, 0.539 g of N,N'-carbonyldiimidazole, 0.316 g of methanesulfonamide and 0.506 g of diazabicycloundecene.

Properties of Compound (168):
$^{1}$H-NMR(DMSO-d6, δ): 2.49(3H, s), 3.35(3H, s), 5.60 (2H, s), 6.43(1H, d, J=7.8 Hz), 7.23(1H, t), 7.34(1H, t, J=7.7 Hz), 7.57(1H, d, J=8.0 Hz), 7.68(1H, d, J=8.5 Hz), 7.81(1H, dd, J=1.7 and 8.5 Hz), 8.13(1H, d, J=1.5 Hz), 11.94(1H, br s).
IR(KBr): 1670 cm$^{-1}$.
mp: 302.0–303.0° C.

EXAMPLE 104

Synthesis of 6-(1-butanesulfonylcarbamoyl)-1-(2-chlorobenzyl)-2-methylbenzimidazole (169)

In the same manner as in Example 98, 0.595 g of 6-(1-butanesulfonylcarbamoyl)-1-(2-chlorobenzyl)-2-methylbenzimidazole (169) were formed from 0.500 g of 6-carboxy-1-(2-chlorobenzyl)-2-methylbenzimidazole, 0.539 g of N,N'-carbonyldiimidazole, 0.456 g of 1-butanesulfonamide and 0.506 g of diazabicycloundecene.

Properties of Compound (169):
$^{1}$H-NMR(DMSO-d6, δ): 0.84(3H, t, J=7.4 Hz), 1.38(2H, m), 1.65(2H, m), 2.49(3H, s), 3.49(2H, m), 5.60(2H, s), 6.44(1H, d, J=7.6 Hz), 7.23(1H, t, J=7.6 Hz), 7.35(1H, t), 7.56(1H, d, J=8.0 Hz), 7.68(1H, d, J=8.4 Hz), 7.80(1H, dd, J=1.6 and 8.4 Hz), 8.11(1H, d, J=1.4 Hz), 11.86(1H, br s).
IR(KBr): 1684 cm$^{-1}$.
mp: 214.0–217.0° C.

EXAMPLE 105

Synthesis of 1-(2-chlorobenzyl)-2-methyl-6 1-octanesulfonylcarbamoyl)benzimidazole (170)

In the same manner as in Example 98, 0.309 g of 1-(2-chlorobenzyl)-2-methyl-6-(1-octanesulfonylcarbamoyl)-benzimidazole (170) were formed from 0.400 g of 6-carboxy-1-(2-chlorobenzyl)-2-methylbenzimidazole, 0.431 g of N,N'-carbonyldiimidazole, 406 g of 1-octanesulfonamide and 0.404 g of diazabicycloundecene.

Properties of Compound (170):
$^{1}$H-NMR(DMSO-d6, δ): 0.82(3H, t, J=7.3 Hz), 1.13–1.28 (8H, m), 1.32–1.41(2H, m), 1.62–1.71(2H, m), 2.50(3H, s), 3.50(2H, t, J=8.5 Hz), 5.61(2H, s), 6.45(1H, d, J=7.7 Hz), 7.24(1H, t, J=7.5 Hz), 7.35(1H, t, J=7.5 Hz), 7.58(1H, d, J=8.0 Hz), 7.69(1H, d, J=8.4 Hz), 7.81(1H, d, J=8.5 Hz), 8.12(1H, s), 11.86(1H, s).
IR(KBr): 1674 cm$^{-1}$.
mp: 180.0–183.0° C.

EXAMPLE 106

Synthesis of 1-(2-chlorobenzyl)-2-methyl-6-(2-propanesulfonylcarbamoyl)benzimidazole (171)

In the same manner as in Example 98, 0.417 g of 1-(2-chlorobenzyl)-2-methyl-6-(2-propanesulfonylcarbamoyl)benzimidazole (171) were formed from 0.400 g of 6-carboxy-1-(2-chlorobenzyl)-2-methylbenzimidazole, 0.431 g of N,N'-carbonyldiimidazole, 0.328 g of 2-propanesulfonamide and 0.404 g of diazabicycloundecene.

Properties of Compound (171):
$^{1}$H-NMR(DMSO-d6, δ): 1.30(6H, d, J=6.9 Hz), 2.50(3H, s), 3.81–3.87(1H, m), 5.62(2H, s), 6.46(1H, d, J=7.7 Hz), 7.25(1H, t, J=7.5 Hz), 7.35(1H, t, J=7.5 Hz), 7.62(1H, d, J=7.9 Hz), 7.69(1H, d, J=8.5 Hz), 7.81(1H, d, J=8.6 Hz), 8.12(1H, s), 11.83(1H, s).
IR(KBr): 1670 cm$^{-1}$.
mp: 215.0–217.5° C.

EXAMPLE 107

Synthesis of 1-(biphenyl-4-ylmethyl)-6-(1-butanesulfonylcarbamoyl)-2-methylbenzimidazole (172)

In the same manner as in Example 98, 0.349 g of 1-(biphenyl-4-ylmethyl)-6-(1-butanesulfonylcarbamoyl)-2-methylbenzimidazole (172) were formed from 0.300 g of 1-(biphenyl-4-ylmethyl)-6-carboxy-2-methylbenzimidazole, 0.323 g of N,N'-carbonyldiimidazole, 0.273 g of 1-butanesulfonamide and 0.303 g of diazabicycloundecene.

Properties of Compound (172)
$^{1}$H-NMR(DMSO-d6, δ): 0.85(3H, t, J=7.4 Hz), 1.36–1.43 (2H, m), 1.63–1.72(2H, m), 2.57(3H, s), 3.52(2H, t, J=7.7 Hz), 5.60(2H, s), 7.21(2H, d, J=8.2 Hz), 7.35(1H, t, J=7.3 Hz), 7.44(2H, t, J=7.5 Hz), 7.60–7.68(5H, m), 7.81(1H, dd, J=1.6 and 8.4 Hz), 8.26(1H, d, J=1.4 Hz), 11.97(1H, s).
IR(KBr): 1676 cm$^{-1}$.
mp: 219.5–222.5° C.

EXAMPLE 108

Synthesis of 6-(1-butanesulfonylcarbamoyl)-1-(2,4-dichlorobenzyl)-2-methylbenzimidazole (173)

In the same manner as in Example 98, 0.459 g of 6-(1-butanesulfonylcarbamoyl)-1-(2,4-dichlorobenzyl)-2-methylbenzimidazole (173) were formed from 0.400 g of 6-carboxy-1-(2,4-dichlorobenzyl)-2-methylbenzimidazole, 0.431 g of N,N'-carbonyldiimidazole, 0.364 g of 1-butanesulfonamide and 0.404 g of diazabicycloundecene.

Properties of Compound (173):
$^{1}$H-NMR(DMSO-d6, δ): 0.85(3H, t, J=7.3 Hz), 1.36–1.42 (2H, m), 1.63–1.70(2H, m), 2.50(3H, s), 3.51(2H, t, J=7.7 Hz), 5.59(2H, s), 6.45(1H, d, J=8.4 Hz), 7.33(1H, dd, J=2.1 and 8.4 Hz), 7.69(1H, d, J=8.4 Hz), 7.76(1H, d, J=2.0 Hz), 7.81(1H, dd, J=1.7 and 8.5 Hz), 8.11(1H, d, J=1.3 Hz), 11.90(1H, s).
IR(KBr): 1670 cm$^{-1}$
mp: 222.0–223.0° C.

EXAMPLE 109

Synthesis of 1-(biphenyl-4-ylmethyl)-6-(1-butanesulfonylcarbamoyl)-2-ethylbenzimidazole (174)

In the same manner as in Example 98, 0.300 g of 1-(biphenyl-4-ylmethyl)-6-(1-butanesulfonylcarbamoyl)-2-ethylbenzimidazole (174) were formed from 0.300 g of 1-(biphenyl-4-ylmethyl)-6-carboxy-2-ethylbenzimidazole, 0.340 g of N,N'-carbonyldiimidazole, 0.300 g of butanesulfonamide and 0.320 g of diazabicycloundecene.

Properties of Compound (174):

$^1$H-NMR(DMSO-d6, δ): 0.85(3H, t, J=7.3 Hz), 1.30(3H, t, J=7.5 Hz), 1.35–1.44(2H, m), 1.64–1.72(2H, m), 2.90.(2H, q, J=7.4 Hz), 3.52(2H, t, J=7.7 Hz), 5.61(2H, s), 7.19(2H, d, J=8.3 Hz), 7.35(1H, t, J=7.3 Hz), 7.44(2H, t, J=7.5 Hz), 7.61–7.67(4H, m), 7.71(1H, d, J=8.5 Hz), 7.82(1H, dd, J=1.6 and 8.5 Hz), 8.27(1H, d, J=1.3 Hz), 12.01(1H, s).IR(Nujol): 1687,1682 cm$^{-1}$.

mp: 171.8–173.0° C.

EXAMPLE 110

Synthesis of 6-benzenesulfonylcarbamoyl-1-(biphenyl-4-ylmethyl)-2-trifluoromethylbenzimidazole (175)

In the same manner as in Example 98, 0.508 g of 6-benzenesulfonylcarbamoyl-1-(biphenyl-4-ylmethyl)-2-trifluoromethylbenzimidazole (175) were formed from 0.483 g of 1-(biphenyl-4-ylmethyl)-6-carboxy-2-trifluoromethylbenzimidazole, 0.396 g of N,N'-carbonyldiimidazole, 0.383 g of benzenesulfonamide and 0.371 g of diazabicycloundecene.

Properties of Compound (175):

$^1$H-NMR(DMSO-d6, δ): 5.81(2H, s), 7.15(2H, d, J=8.3 Hz), 7.35(1H, t, J=7.5 Hz), 7.44(2H, t, J=7.5 Hz), 7.60–7.66 (6H, m), 7.70(1H, t, J=7.4 Hz), 7.91(1H, dd, J=8.7 and 1.4 Hz), 7.96–8.01(3H, m), 8.42(1H, s), 12.65(1H, s).

IR(KBr): 1685 cm$^{-1}$.

mp: 164.5–167.0° C.

EXAMPLE 111

Synthesis of 5-benzenesulfonylcarbamoyl-1-(biphenyl-4-ylmethyl)-2-trifluoromethylbenzimidazole (176)

In the same manner as in Example 98, 0.286 g of 5-benzenesulfonylcarbamoyl-1-(biphenyl-4-ylmethyl)-2-trifluoromethylbenzimidazole (176) were formed from 0.270 g of 1-(biphenyl-4-ylmethyl)-5-carboxy-2-trifluoromethylbenzimidazole, 0.221 g of N,N'-carbonyldiimidazole, 0.214 g of benzenesulfonamide and 0.207 g of diazabicycloundecene.

Properties of Compound (176):

$^1$H-NMR(DMSO-d6, δ): 5.79(2H, s), 7.15(2H, d, J=8.1 Hz), 7.35(1H, t, J=7.5 Hz), 7.43(2H, t, J=7.5 Hz), 7.59–7.67 (6H, m), 7.72(1H, t, J=7.6 Hz), 7.83(1H, d, J=8.8 Hz), 7.94(1H, d, J=8.9 Hz), 8.02(2H, d, J=7.4 Hz), 8.49(1H, s), 12.69(1H, s).

IR(KBr): 1699 cm$^{-1}$ mp: 248.5–251.0° C.

EXAMPLE 112

Synthesis of 6-benzenesulfonylcarbamoyl-2-cyclopropyl-1-(2-fluorobenzyl)benzimidazole (177)

In the same manner as in Example 98, 0.730 g of 6-benzenesulfonylcarbamoyl-2-cyclopropyl-1-(2-fluorobenzyl)benzimidazole (177) were formed from 0.930 g of 6-carboxy-2-cyclopropyl-1-(2-fluorobenzyl) benzimidazole, 0.972 g of N,N'-carbonyldiimidazole, 0.942 g of benzenesulfonamide and 0.906 g of diazabicycloundecene.

Properties of Compound (177):

$^1$H-NMR (DMSO-d6, δ): 1.04 (4H, m), 2.15 (1H, m), 5.70 (2H, s), 6.85 (1H, t, J=7.5 Hz), 7.12 (1H, t, J=7.5 Hz), 7.22–7.38 (2H, m), 7.54–7.70 (5H, m), 7.99 (2H, d, J=7.5 Hz), 8.11 (1H, s) white powder.

EXAMPLE 113

Synthesis of N-benzenesulfonyl-3-[1-(2-chlorobenzyl)-2-methylbenzimidazol-6-yl] acrylamide (178)

In the same manner as in Example 98, 1.05 g of N-benzenesulfonyl-3-[1-(2-chlorobenzyl)-2-methylbenzimidazol-6-yl]acrylamide (178) were formed from 1.10 g of 1-(2-chlorobenzyl)-2-methylbenzimidazole-6-acrylic acid, 1.09 g of N,N'-carbonyldiimidazole, 1.06 g of benzenesulfonamide and 1.02 g of diazabicycloundecene.

Properties of Compound (178):

$^1$H-NMR(DMSO-d6, δ): 2.47(3H, s), 5.55(2H, s), 6.46–6.55(2H, m), 7.22(1H, t, J=7.6 Hz), 7.32(1H, t, J=7.7 Hz), 7.40(1H, d, J=8.4 Hz), 7.52–7.66(6H, m), 7.69(1H, t), 7.93(2H, d, J=7.9 Hz), 12.17(1H, br s).

IR(KBr): 1687 cm$^{-1}$.

Mass(FAB): m/e 466(M+1).

mp: 243.1–244.3° C.

EXAMPLE 114

Synthesis of N-benzenesulfonyl-2-[1-(2-chlorobenzyl)-2-methylbenzimidazol-6-yl]acetamide (179)

In the same manner as in Example 98, 0.09 g of N-benzenesulfonyl-2-[1-(2-chlorobenzyl)-2-methylbenzimidazol-6-yl]acetamide (179) were formed from 0.170 g of 1-(2-chlorobenzyl)-2-methylbenzimidazole-6-acetic acid, 0.175 g of N,N'-carbonyldiimidazole, 0.170 g of benzenesulfonamide and 0.164 g of diazabicycloundecene.

Properties of Compound (179):

$^1$H-NMR(DMSO-d6, δ): 2.44(3H, s), 3.57(2H, s), 5.46 (2H, s), 6.41(1H, d, J=7.7 Hz), 6.96(1H, d, J=7.0 Hz), 7.16(1H, s), 7.20(1H, t), 7.32(1H, t), 7.47(1H, d, J=8.2 Hz), 7.52–7.59(3H, m), 7.67(1H, t, J=7.5 Hz), 7.84(2H, d, J=7.4 Hz), 12.28(1H, br s).

IR(KBr) 1719 cm$^{-1}$.

mp: 236.2–237.8° C.

EXAMPLE 115

Synthesis of 1-(2,4-dichlorobenzyl)-2-methyl-6-[(2-pyridylmethyl)carbamoyl]benzimidazole (180)

Dichloromethane (150 ml) and some drops of N,N-dimethylformamide were added to 9.00 g of 6-carboxy-1-(2,4-dichlorobenzyl)-2-methylbenzimidazole, and the mixture was cooled with ice. Oxalyl chloride (6.84 g) were added dropwise thereto, and the mixed solution was stirred for some minutes. Further, this solution was stirred at room temperature for 1.5 hours, and was then concentrated to a volume of approximately ⅓ of the original volume under reduced pressure. The solid material precipitated was collected, and was added to a solution of 2.69 g of 2-aminomethylpyridine and 7.34 g of triethylamine in 200 ml of dichloromethane in some divided portions. After the mixture was stirred for 15 hours, the reaction solution was washed three times with water and then with a saturated aqueous solution of sodium hydrogencarbonate. The organic layer was concentrated under reduced pressure, and was crystallized from ethyl acetate. The crystals were separated through filtration, and were dried to give 4.35 g of 1-(2,4-dichlorobenzyl)-2-methyl-6-[(2-pyridylmethyl)carbamoyl] benzimidazole (180).

Properties of Compound (180):
$^1$H-NMR(CDCl$_3$, δ): 2.56(3H, s), 4.76(2H, d, J=4.8 Hz), 5.40(2H, s), 6.33(1H, d, J=8.4 Hz), 7.07(1H, dd, J=8.4 and 2.0 Hz), 7.22(1H, dd, J=7.4 and 4.9 Hz), 7.33(1H, d, J=7.9 Hz), 7.48(1H, d, J=2.1 Hz), 7.62–7.79(4H, m), 7.86(1H, d, J=1.1 Hz)8.57, (1H, d, J=4.9 Hz).

IR(KBr): 1645 cm$^{-1}$ mp: 204.5–206.5° C.

EXAMPLE 116

Synthesis of 1-methyl-2-n-propyl-6-[(2-pyridylmethyl)carbamoyl]benzimidazole (181)

In the same manner as in Example 115, 0.213 g of 1-methyl-2-n-propyl-6-[(2-pyridylmethyl)carbamoyl] benzimidazole (181) were formed from 0.402 g of 6-carboxy-1-methyl-2-n-propylbenzimidazole, 0.468 g of oxalyl chloride, 0.199 g of 2-aminomethylpyridine and 0.559 g of triethylamine.

Properties of Compound (181):
$^1$H-NMR(CDCl$_3$, δ): 1.08(3H, t, J=7.4 Hz) 1.92(2H, m) 2.88(2H, m) 3.76(3H, s) 4.80(2H, d, J=4.8 Hz), 7.22(1H, dd, J=2.5 and 7.5 Hz), 7.35(1H, d, J=7.8 Hz), 7.67–7.77(4H, m), 7.80(1H, s), 8.58(1H, dd, J=4.9 and 0.9 Hz).

IR(KBr): 1647 cm$^{-1}$.

mp: 140.5–141.5° C.

EXAMPLE 117

Synthesis of 1-(2-chlorobenzyl)-2-methyl-6-[(2-pyridylmethyl)carbamoyl]benzimidazole (182)

In the same manner as in Example 115, 0.164 g of 1-(2-chlorobenzyl)-2-methyl-6-[(2-pyridylmethyl) carbamoyl]-benzimidazole (182) were formed from 0.300 g of 6-carboxy-1-(2-chlorobenzyl)-2-methylbenzimidazole, 0.253 g of oxalyl chloride, 0.108 g of 2-aminomethylpyridine and 0.302 g of triethylamine.

Properties of Compound (182):
$^1$H-NMR(CDCl$_3$, δ): 2.56(3H, s), 4.76(2H, d, J=4.8 Hz), 5.45(2H, s), 6.40(1H, d, J=7.8 Hz), 7.08(1H, t, J=7.6 Hz), 7.20–7.27(2H, m), 7.33(1H, d, J=7.8 Hz), 7.45(1H, dd, J=0.9 and 8.1 Hz), 7.64(1H, s), 7.65–7.69(1H, m), 7.72(1H, dd, J=1.5 and 8.4 Hz), 7.77(1H, d, J=8.4 Hz), 7.88(1H, d, J=1.2 Hz), 8.56(1H, d, J=4.7 Hz).

IR(KBr): 1646 cm$^{-1}$.

mp: 156.5–157.5° C.

EXAMPLE 118

Synthesis of 2-n-propyl-1-i-propyl-6-[(2-pyridylmethyl)carbamoyl]benzimidazole (183)

In the same manner as in Example 115, 0.020 g of 2-n-propyl-1-i-propyl-6-[(2-pyridylmethyl)carbamoyl] benzimidazole (183) were formed from 0.095 g of 6-carboxy-2-n-propyl-1-i-propylbenzimidazole, 0.100 g of oxalyl chloride, 0.039 g of 2-aminomethylpyridine and 0.097 g of triethylamine.

Properties of Compound (183):
$^1$H-NMR(CDCl$_3$, δ): 1.08(3H, t, J=7.4 Hz), 1.69(6H, d, J=7.1 Hz), 1.87–1.93(2H, m), 2.90(2H, t, J=7.8 Hz), 4.69–4.75(1H, m), 4.80(2H, d, J=4.9 Hz), 7.23(1H, dd, J=7.3 and 2.1 Hz), 7.37(1H, d, J=7.7 Hz), 7.62–7.77(4H, m), 8.21(1H, s), 8.58(1H, d, J=4.5 Hz).

IR(KBr): 1631 cm$^{-1}$.

mp: 155.0–156.9° C.

EXAMPLE 119

Synthesis of 1-n-butyl-2-n-propyl-6-[(2-pyridylmethyl)carbamoyl]benzimidazole (184)

In the same manner as in Example 115, 0.283 g of 1-n-butyl-2-n-propyl-6-[(2-pyridylmethyl)carbamoyl] benzimidazole (184) were formed from 0.500 g of 1-n-butyl-6-carboxy-2-n-propylbenzimidazole, 0.487 g of oxalyl chloride, 0.208 g of 2-aminomethylpyridine and 0.582 g of triethylamine.

Properties of Compound (184):
$^1$H-NMR(CDCl$_3$, δ): 0.97(3H, t, J=7.3 Hz), 1.08(3H, t, J=7.4 Hz), 1.37–1.46(2H, m), 1.76–1.83(2H, m), 1.92–2.00 (2H, m), 2.86(2H, t, J=7.8 Hz), 4.15(2H, t, J=7.6 Hz), 4.81(2H, d, J=4.8 Hz), 7.23(1H, dd, J=7.3 and 2.4 Hz), 7.36(1H, d, J=7.8 Hz), 7.63–7.76(4H, m), 8.02(1H, s), 8.58(1H, d, J=4.7 Hz).

IR(KBr): 1631 cm$^{-1}$.

mp: 105.8–107.2° C.

EXAMPLE 120

Synthesis of 1-(3-chlorobenzyl)-2-n-propyl-6-[2-pyridylmethyl)carbamoyl]benzimidazole (185)

In the same manner as in Example 115, 0.311 g of 1-(3-chlorobenzyl)-2-n-propyl-6-[2-pyridylmethyl) carbamoyl]benzimidazole (185) were formed from 0.580 g of 6-carboxy-1-(3-chlorobenzyl)-2-n-propylbenzimidazole, 0.407 g of oxalyl chloride, 0.173 g of 2-aminomethylpyridine and 0.486 g of triethylamine.

Properties of Compound (185):
$^1$H-NMR(CDCl$_3$, δ): 1.03(3H, t, J=7.4 Hz), 1.85–1.93 (2H, m), 2.80(2H, t, J=7.5 Hz), 4.77(2H, d, J=4.8 Hz), 5.36(2H, s), 6.86(1H, d, J=7.4 Hz), 7.02(1H, s), 7.20–7.28 (3H, m), 7.33(1H, d, J=7.8 Hz), 7.63–7.73(3H, m), 7.79(1H, d, J=8.4 Hz), 7.91(1H, d, J=1.3 Hz), 8.57(1H, d, J=4.7 Hz).

IR(KBr): 1643 cm$^{-1}$.

mp: 157.7–158.8° C.

EXAMPLE 121

Synthesis of 1-benzyl-2-n-propyl-6-[(2-pyridylmethyl)carbamoyl]benzimidazole (186)

In the same manner as in Example 115, 0.350 g of 1-benzyl-2-n-propyl-6-[(2-pyridylmethyl)carbamoyl] benzimidazole (186) were formed from 0.850 g of 1-benzyl-6-carboxy-2-n-propylbenzimidazole, 0.949 g of oxalyl chloride, 0.404 g of 2-aminomethylpyridine and 1.132 g of triethylamine.

Properties of Compound (186):
$^1$H-NMR(CDCl$_3$, δ): 1.01(3H, t, J=7.4 Hz), 1.83–1.92 (2H, m), 2.82(2H, t, J=7.6 Hz), 4.77(2H, d, J=4.8 Hz), 5.40(2H, s), 7.03(2H, d, J=6.5 Hz), 7.21(1H, dd, J=7.1 and 2.1 Hz), 7.18–7.34(4H, m), 7.60(1H, s), 7.65–7.72(2H, m), 7.78(1H, d, J=8.4 Hz), 7.94(1H, d, J=1.2 Hz), 8.56(1H,d,J= 4.2 Hz).

IR(KBr): 1642 cm$^{-1}$
mp: 121.9–123.1° C.

EXAMPLE 122

Synthesis of 1-(4-chlorobenzyl)-2-propyl-6-[(2-pyridylmethyl)carbamoyl]-benzimidazole (187)

In the same manner as in Example 115, 0.089 g of 1-(4-chlorobenzyl)-2-propyl-6-[(2-pyridylmethyl)carbamoyl]benzimidazole (187) were formed from 0.547 g of 6-carboxy-1-(4-chlorobenzyl)-2-propylbenzimidazole, 0.384 g of oxalyl chloride, 0.163 g of 2-aminomethylpyridine and 0.458 g of triethylamine.

Properties of Compound (187):
$^1$H-NMR(CDCl$_3$, δ): 1.02(3H, t, J=7.4 Hz), 1.84–1.92 (2H, m), 2.77–2.83(2H, m), 4.76(2H, d, J=4.8 Hz), 5.36(2H, s), 6.96(2H, d, J=8.3 Hz), 7.22(1H, dd, J=6.4 and 0.4 Hz), 7.27(2H, dd, J=8.3 and 1.3 Hz), 7.33(1H, d, J=7.8 Hz), 7.62–7.73(3H, m), 7.78(1H, d, J=8.4 Hz), 7.91(1H, d, J=0.9 Hz), 8.56(1H, dd, J=4.9 and 0.8 Hz).
IR(KBr): 1643 cm$^{-1}$.
mp: 158.8–161.0° C.

EXAMPLE 123

Synthesis of 2-benzyl-1methyl-6-[(2-pyridylmethyl)carbamoyl]-benzimidazole (188)

In the same manner as in Example 115, 0.171 g of 2-benzyl-1-methyl-6-[(2-pyridylmethyl)carbamoyl]benzimidazole (188) were formed from 0.310 g of 2-benzyl-6-carboxy-1-methylbenzimidazole, 0.295 g of oxalyl chloride, 0.108 g of 2-aminomethylpyridine and 0.303 g of triethylamine.

Properties of Compound (188):
$^1$H-NMR(CDCl$_3$, δ): 3.66(3H, s), 4.35(2H, s), 4,80(2H, d, J=4.8 Hz), 7.21–7.37(7H, m), 7.66(1H, br t), 7.67–7.73(2H, m), 7.78(1H, d, J=8.4 Hz), 7.98(1H, s), 8.58(1H, d, J=4.9 Hz)
IR(KBr): 1632 cm$^{-1}$.
mp: 168.5–169.5° C.

EXAMPLE 124

Synthesis of 1-(2,6-dichlorobenzyl)-2-methyl-6-[(2-pyridylmethyl)carbamoyl]benzimidazole (189)

In the same manner as in Example 115, 0.040 g of 1-(2,6-dichlorobenzyl)-2-methyl-6-[(2-pyridylmethyl)carbamoyl]-benzimidazole (189) were formed from 0.600 g of 6-carboxy-1-(2,6-dichlorobenzyl)-2-methylbenzimidazole, 0.472 g of oxalyl chloride, 0.201 g of 2-aminomethylpyridine and 0.188 g of triethylamine.

Properties of Compound (189):
$^1$H-NMR(CDCl$_3$, δ): 2.62(3H, s), 4.76(2H, d, J=4.7 Hz), 5.62(2H, s), 7.23(1H, dd, J=7.1 and 2.2 Hz), 7.28(1H, d, J=7.8 Hz), 7.32(1H, d, J=7.9 Hz), 7.39(2H, d, J=8.1 Hz), 7.54(1H, s), 7.66–7.71(3H, m), 7.78(1H, s), 8.60(1H, d, J=4.6 Hz).
IR(KBr): 1635 cm$^{-1}$.
mp: 225.7–226.9° C.

EXAMPLE 125

Synthesis of 2-methyl-6-[(2-pyridylmethyl)carbamoyl]-1-[2-(trifluoromethyl)benzyl]benzimidazole (190)

In the same manner as in Example 115, 0.713 g of 2-methyl-6-[(2-pyridylmethyl)carbamoyl]-1-[2-(trifluoromethyl)benzyl]-benzimidazole (190) were formed from 0.970 g of 6-carboxy-2-methyl-1-[2-(trifluoromethyl)benzyl]benzimidazole, 0.736 g of oxalyl chloride, 0.261 g of 2-aminomethylpyridine and 0.726 g of triethylamine.

Properties of Compound (190):
$^1$H-NMR(CDCl$_3$, δ): 2.54(3H, s), 4.76(2H, d, J=4.8Hz), 5.59(2H, s), 6.45(1H, d, J=7.9 Hz), 7.22(1H, t, J=5.8 Hz), 7.34(2H, t, J=8.8 Hz), 7.40(1H, t, J=7.5 Hz), 7.62(1H, br s), 7.68(1H, dt, J=1.7 and 7.7 Hz), 7.72–7.82(3H, m), 7.87(1H, s), 8.56(1H, d, J=4.9 Hz).
IR(KBr): 1648 cm$^{-1}$
mp: 172–174° C.

EXAMPLE 126

Synthesis of 2-methyl-6-[(2-pyridylmethyl)carbamoyl]-1-[4-(trifluoromethyl)benzyl]benzimidazole (191)

In the same manner as in Example 115, 0.194 g of 2-methyl-6-[(2-pyridylmethyl)carbamoyl]-1-[4-(trifluoromethyl)benzyl]-benzimidazole (191) were formed from 0.970 g of 6-carboxy-2-methyl-1-[4-(trifluoromethyl)benzyl]benzimidazole, 0.736 g of oxalyl chloride, 0.261 g of 2-aminomethylpyridine and 0.726 g of triethylamine.

Properties of Compound (191):
$^1$H-NMR(CDCl$_3$, δ): 2.59(3H, s), 4.77(2H, d, J=4.7 Hz), 5.45(2H, s), 7.15(2H, d, J=8.2 Hz), 7.23(1H, m), 7.33(1H, d, J=7.9 Hz), 7.58(2H, d, J=8.2 Hz), 7.63(1H, br s), 7.67–7.74 (2H, m), 7.77(1H, d, J=8.3 Hz), 7.93(1H, s), 8.57(1H, d, J=4.9 Hz).
IR(KBr): 1637 cm$^{-1}$
mp: 188.5–190.0° C.

EXAMPLE 127

Synthesis of 1-(3,4-dichlorobenzyl)-2-methyl-6-[(2-pyridylmethyl)carbamoyl]benzimidazole (192)

In the same manner as in Example 115, 0.264 g of 1-(3,4-dichlorobenzyl)-2-methyl-6-[(2-pyridylmethyl)carbamoyl]benzimidazole (192) were formed from 0.500 g of 6-carboxy-1-(3,4-dichlorobenzyl)-2-methylbenzimidazole, 0.393 g of oxalyl chloride, 0.167 g of 2-aminomethylpyridine and 0.469 g of triethylamine.

Properties of Compound (192):
$^1$H-NMR(CDCl$_3$, δ): 2.58(3H, s), 4.77(2H, d, J=4.8 Hz), 5.33(2H, s), 6.85(1H, dd, J=8.3 and 2.2 Hz), 7.14(1H, d, J=2.1 Hz), 7.22(1H, dd, J=7.3 and 5.6 Hz), 7.33(1H, d, J=7.8 Hz), 7.38(1H, d, J=8.3 Hz), 7.65–7.77(4H, m), 7.92(1H, d, J=1.2 Hz), 8.57(1H, d, J=4.8 Hz).
IR(KBr): 1638 cm$^{-1}$.
mp: 219.0–220.7° C.

EXAMPLE 128

Synthesis of 2-methyl-1-(2-methylbenzyl)-6-[(2-pyridylmethyl)carbamoyl]benzimidazole (193)

In the same manner as in Example 115, 0.100 g of 2-methyl-1-(2-methylbenzyl)-6-[(2-pyridylmethyl)carbamoyl]benzimidazole (193) were formed fromm 0.453 g of 6-carboxy-2-methyl-1-(2-methylbenzyl)benzimidazole, 0.411 g of oxalyl chloride, 0.175 g of 2-aminomethylpyridine and 0.490 g of triethylamine.

Properties of Compound (193):
$^1$H-NMR(CDCl$_3$, δ): 2.42(3H, s), 2.54(3H, s), 4.75(2H, d, J=4.9 Hz), 5.32(2H, s), 6.33(1H, d, J=7.8 Hz), 7.01(1H, t, J=7.8 Hz), 7.17–7.24(3H, m), 7.33(1H, d, J=7.8 Hz), 7.60 (1H, s), 7.63–7.73(2H, m), 7.76(1H, d, J=8.4 Hz), 7.84(1H, d, J=1.4 Hz), 8.56(1H, d, J=4.9 Hz).

IR(KBr): 1635 cm$^{-1}$.

mp: 154.0–157.0° C.

EXAMPLE 129

Synthesis of 1-(2-methoxybenzyl)-2-methyl-6-[(2-pyridylmethyl)carbamoyl]benzimidazole (194)

In the same manner as in Example 115, 0.918 g of 1-(2-methoxybenzyl)-2-methyl-6-[(2-pyridylmethyl) carbamoyl]benzimidazole (194) were formed from 0.997 g of 6-carboxy-1-(2-methoxybenzyl)-2-methylbenzimidazole, 0.858 g of oxalyl chloride, 0.309 g of 2-aminomethylpyridine and 1.02 g of triethylamine.

Properties of Compound (194):

$^1$H-NMR(CDCl$_3$, δ): 2.60(3H, s), 3.89(3H, s), 4.77(2H, d, J=4.8 Hz), 5.36(2H, s), 6.60(1H, d, J=7.4 Hz), 6.79(1H, dt, J=0.8 and 7.4 Hz), 6.91(1H, d, J=7.4 Hz), 7.20–7.28(2H, m), 7.34(1H, d, J=7.9 Hz), 7.56(1H, br t), 7.66–7.75(3H, m), 7.95(1H, m), 8.57(1H, d, J=4.9 Hz).

IR(KBr): 1652 cm$^{-1}$.

mp: 136–138.5° C.

EXAMPLE 130

Synthesis of 1-(4-methoxybenzyl)-2-methyl-6-[(2-pyridylmethyl)carbamoyl]benzimidazole (195)

In the same manner as in Example 115, 0.697 g of 1-(4-methoxybenzyl)-2-methyl-6-[(2-pyridylmethyl) carbamoyl]benzimidazole (195) were formed from 0.985 g of 6-carboxy-1-(4-methoxybenzyl)-2-methylbenzimidazole, 0.858 g of oxalyl chloride, 0.309 g of 2-aminomethylpyridine and 1.02 g of triethylamine.

Properties of Compound (195):

$^1$H-NMR(CDCl$_3$, δ): 2.59(3H, s), 3.76(3H, s), 4.78(2H, d, J=4.8 Hz), 5.32(2H, s), 6.83(2H, m), 7.00(2H, m), 7.22(1H, dd, J=5.1 and 6.8 Hz), 7.34(1H, d, J=7.8 Hz), 7.60(1H, br t), 7.67–7.76(3H, m), 7.97(1H, d, J=1.2 Hz), 8.57(1H, d, J=4.9 Hz).

IR(KBr): 1652 cm$^{-1}$.

mp: 191.5–192.2° C.

EXAMPLE 131

Synthesis of 1-[2-(benzenesulfonylmethyl)benzyl]-2-methyl-6-[(2-pyridylmethyl)carbamoyl] benzimidazole (196)

In the same manner as in Example 115, 0.64 g of 1-[(2-(benzenesulfonylmethyl)benzyl]-2-methyl-6-[(2-pyridylmethyl)carbamoyl]benzimidazole (196) were formed from 0.74 g of 1-[2-(benzenesulfonylmethyl)benzyl]-6-carboxy-2-methylbenzimidazole, 0.45 g of oxalyl chloride, 0.19 g of 2-aminomethylpyridine and 0.53 g of triethylamine.

Properties of Compound (196):

$^1$H-NMR(CDCl$_3$, δ): 2.57(3H, s), 4.50(2H, s), 4.74(2H, d, J=4.9 Hz), 5.59(2H, s), 6.63(1H, d, J=7.7 Hz), 6.87(1H, d, J=7.4 and 1.5 Hz), 7.09–7.19(3H, m), 7.31(1H, d, J=7.8 Hz), 7.53–7.61(3H, m), 7.64(1H, dt, J=7.6 and 1.6 Hz), 7.68–7.79 (5H, m), 7.84(1H, s), 8.52(1H, d, J=4.8 Hz).

IR(neat) 1646 cm$^{-1}$ liquid.

EXAMPLE 132

Synthesis of 1-(2-cyanobenzyl)-2-methyl-6-[(2-pyridylmethyl)carbamoyl]benzimidazole (197)

In the same manner as in Example 115, 1.03 g of 1-(2-cyanobenzyl)-2-methyl-6-[(2-pyridylmethyl) carbamoyl]benzimidazole (197) were formed from 1.14 g of 6-carboxy-1-(2-cyanobenzyl)-2-methylbenzimidazole, 0.998 g of oxalyl chloride, 0.425 g of 2-aminomethylpyridine and 1.19 g of triethylamine.

Properties of Compound (197):

$^1$H-NMR(CDCl$_3$, δ): 2.58(3H, s), 4.76(2H, d, J=4.8 Hz), 5.59(2H, s), 6.64(1H, d, J=7.4 Hz), 7.21(1H, dt, J=5.6 and 1.8 Hz), 7.33(1H, d, J=7.9 Hz), 7.39–7.47(2H, m), 7.65–7.79(5H, m), 7.89(1H, s), 8.56(1H, dd, J=4.9 and 0.9 Hz).

IR(KBr): 2223, 1642 cm$^{-1}$ mp: 150.5–151.4° C.

EXAMPLE 133

Synthesis of 1-(biphenyl-2-ylmethyl)-2-methyl-6-[(2-pyridylmethyl)carbamoyl]benzimidazole (198)

In the same manner as in Example 115, 0.672 g of 1-(biphenyl-2-ylmethyl)-2-methyl-6-[(2-pyridylmethyl) carbamoyl]benzimidazole (198) were formed from 1.07 g of 1-(biphenyl-2-ylmethyl)-6-carboxy-2-methylbenzimidazole, 0.796 g of oxalyl chloride, 0.339 g of 2-aminomethylpyridine and 0.950 g of triethylamine.

Properties of Compound (198):

$^1$H-NMR(CDCl$_3$, δ): 2.38(3H, s), 4.78(2H, d, J=4.8 Hz), 5.27(2H, s), 6.64(1H, d, J=8.0 Hz), 7.17–7.24(2H, m), 7.29–7.43(6H, m), 7.48(2H, t, J=5.5 Hz), 7.49(1H, s), 7.57–7.73(3H, m), 7.80(1H, d, J=1.0 Hz), 8.58(1H, d, J=4.9 Hz).

IR(KBr): 1630, 1619 cm$^{-1}$ mp: 179.8–180.8° C.

EXAMPLE 134

Synthesis of 1-benzyl-2-methyl-6-[(2-pyridylmethyl)carbamoyl]benzimidazole (199)

In the same manner as in Example 115, 0.66 g of 1-benzyl-2-methyl-6-[(2-pyridylmethyl)carbamoyl] benzimidazole (199) were formed from 0.59 g of 1-benzyl-6-carboxy-2-methylbenzimidazole, 0.56 g of oxalyl chloride, 0.24 g of 2-aminomethylpyridine and 0.67 g of triethylamine.

Properties of Compound (199):

$^1$H-NMR(CDCl$_3$, δ): 2.58(3H, s), 4.76(2H, d, J=4.9 Hz), 5.36(2H, s), 7.02–7.06(2H, m), 7.21(1H, dd, J=6.9 and 5.0 Hz), 7.27–7.35(4H, m), 7.65–7.75(4H, m), 7.96(1H, d, J=0.8 Hz), 8.56(1H, d, J=4.8 Hz).

IR(KBr): 1640 cm$^{-1}$.

mp: 124.0–124.9° C.

EXAMPLE 135

Synthesis of 1-(4-tert-butylbenzyl)-2-methyl-6-[(2-pyridylmethyl)carbamoyl]benzimidazole (200)

In the same manner as in Example 115, 0.477 g of 1-(4-tert-butylbenzyl)-2-methyl-6-[(2-pyridylmethyl) carbamoyl]benzimidazole (200) were formed from 0.544 g of 1-(4-tert-butylbenzyl)-6-carboxy-2-methylbenzimidazole, 0.428 g of oxalyl chloride, 0.183 g of 2-aminomethylpyridine and 0.511 g of triethylamine.

Properties of Compound (200):

$^1$H-NMR(CDCl$_3$, δ): 1.27(9H, s), 2.60(3H, s), 4.77(2H, d, J=4.9 Hz), 5.34(2H, s), 6.98(2H, d, J=8.3 Hz), 7.21(1H, dd, J=7.3 and 5.1 Hz), 7.29–7.35(3H, m), 7.62(1H, br s), 7.65–7.75(3H, m), 7.96(1H, d, J=1.1 Hz), 8.57(1H, d, J =4.7 Hz).

IR(KBr): 1646 cm$^{-1}$.

mp: 140.4–142.8° C.

EXAMPLE 136

Synthesis of 2-methyl-1-(2-naphthylmethyl)-6-[(2-pyridylmethyl)carbamoyl]benzimidazole (201)

In the same manner as in Example 115, 0.47 g of 2-methyl-1-(2-naphthylmethyl)-6-[(2-pyridylmethyl)carbamoyl]benzimidazole (201) were formed from 0.80 g of 6-carboxy-2-methyl-1-(2-naphthylmethyl)benzimidazole, 0.64 g of oxalyl chloride, 0.27 g of 2-aminomethylpyridine and 0.77 g of triethylamine.

Properties of Compound (201):

$^1$H-NMR(CDCl$_3$, δ): 2.60(3H, s), 4.75(2H, d, J=4.9 Hz), 5.52(2H, s), 7.17–7.23(2H, m), 7.31(1H, d, J=7.8 Hz), 7.38(1H, s), 7.43–7.48(2H, m), 7.60–7.82(7H, m), 8.00(1H, d, J=1.0 Hz), 8.53(1H, d, J=4.7 Hz).

IR(KBr): 1640 cm$^{-1}$.

mp: 143.0–144.5° C.

EXAMPLE 137

Synthesis of 1-(biphenyl-4-ylmethyl)-2-ethyl-6-[(2-pyridylmethyl)carbamoyl]benzimidazole (202)

In the same manner as in Example 115, 0.410 g of 1-(biphenyl-4-ylmethyl)-2-ethyl-6-[(2-pyridylmethyl)carbamoyl]benzimidazole (202) were formed from 0.500 g of 1-(biphenyl-4-ylmethyl)-6-carboxy-2-ethylbenzimidazole, 0.356 g of oxalyl chloride, 0.151 g of 2-aminomethylpyridine and 0.424 g of triethylamine.

Properties of Compound (202):

$^1$H-NMR(CDCl$_3$, δ): 1.45(3H, t, J=7.7 Hz), 2.90(2H, q, J=7.4 Hz), 4.77(2H, d, J=4.7 Hz), 5.43(2H, s), 7.10(2H, d, J=8.2 Hz), 7.20(1H, dt, J=4.9 and 7.7 Hz), 7.33(2H, t, J=7.4 Hz), 7.42(2H, t, J=7.5 Hz), 7.49–7.55(4H, m), 7.61(1H, br t), 7.67(1H, dt, J=7.8 and 1.8 Hz), 7.72(1H, d, J=8.4 Hz), 7.81(1H, d, J=8.4 Hz), 7.99(1H, s), 8.56(1H, d, J=4.9 Hz).

IR(KBr): 1640 cm$^{-1}$.

mp: 123.0–124.0° C.

EXAMPLE 138

Synthesis of 1-(2-chlorobenzyl)-6-[2-(pyridylmethyl)carbamoyl]benzimidazole (203)

In the same manner as in Example 115, 0.110 g of 1-(2-chlorobenzyl)-6-[2-(pyridylmethyl)carbamoyl]benzimidazole (203) were formed from 0.461 g of 6-carboxy-1-(2-chlorobenzyl)benzimidazole, 0.728 g of oxalyl chloride, 0.174 g of 2-aminomethylpyridine and 0.486 g of triethylamine.

Properties of Compound (203):

$^1$H-NMR(CDCl$_3$, δ): 4.78(2H, d, J=4.8 Hz), 5.51(2H, s), 6.92(1H, d, J=6.5 Hz), 7.17–7.31(3H, m), 7.34(1H, d, J=7.8 Hz), 7.45(1H, dd, J=1.1 and 8.0 Hz), 7.69(1H, dt, J=1.8 and 7.7 Hz), 7.67–7.73(1H, br s), 7.76(1H, dd, J=1.5 and 8.4 Hz), 7.87(1H, d, J=8.4 Hz), 8.05(2H, s), 8.57(1H, d, J =4.9 Hz).

IR(KBr): 1646 cm$^{-1}$.

mp: 144.0–145.0° C.

EXAMPLE 139

Synthesis of 2-methyl-1-(2-nitrobenzyl)-6-[(2-pyridylmethyl)carbamoyl]benzimidazole (204)

In the same manner as in Example 115, 0.241 g of 2-methyl-1-(2-nitrobenzyl)-6-[(2-pyridylmethyl) carbamoyl]benzimidazole (204) were formed from 0.367 g of 6-carboxy-2-methyl-1(2-nitrobenzyl)benzimidazole, 0.299 g of oxalyl chloride, 0.217 g of 2-aminomethylpyridine and 0.360 g of triethylamine.

Properties of Compound (204):

$^1$H-NMR(CDCl$_3$, δ): 2.56(3H, s), 4.75(2H, d, J=4.8 Hz), 5.83(2H, s), 6.41(1H, d, J=7.8 and 1.2 Hz), 7.22(1H, dt, J=5.0 and 1.7 Hz), 7.32(1H, d, J=7.9 Hz), 7.43–7.52(2H, m), 7.64(1H, s), 7.68(1H, dt, J=7.6 and 1.7 Hz), 7.75(1H, dd, J=8.4 and 1.5 Hz), 7.80(1H, d, J=8.4 Hz), 7.82(1H, d, J=1.3 Hz), 8.28(1H, dd, J=8.0 and 1.7 Hz), 8.56(1H, d, J=4.9 Hz).

IR(KBr): 1645 cm$^{-1}$.

mp: 194.8–196.7° C.

EXAMPLE 140

Synthesis of 2-methyl-1-(2-nitrobenzyl)-5-[(2-pyridylmethyl)carbamoyl]benzimidazole (205)

In the same manner as in Example 115, 0.079 g of 2-methyl-1-(2-nitrobenzyl)-5-[(2-pyridylmethyl)carbamoyl]benzimidazole (205) were formed from 0.096 g of 5-carboxy-2-methyl-1-(2-nitrobenzyl)benzimidazole, 0.078 g of oxalyl chloride, 0.048 g of 2-aminomethylpyridine and 0.093 g of triethylamine.

Properties of Compound (205):

$^1$H-NMR(CDCl$_3$, δ): 2.57(3H, s), 4.80(2H, d, J=4.7 Hz), 5.80(2H, s), 6.43(1H, d, J=7.4 and 0.8 Hz), 7.17(1H, d, J=8.4 Hz), 7.22(1H, dt, J=5.5 and 1.8 Hz), 7.35(1H, d, J=7.8 Hz), 7.44–7.52(2H, m), 7.67(1H, s), 7.69(1H, dt, J=7.8 and 1.9 Hz), 7.82(1H, dd, J=8.4 and 1.5 Hz), 8.27(1H, dd, J=8.0 and 1.6 Hz), 8.28(1H, d, J=1.4 Hz), 8.56(1H, d, J=4.9 Hz).

IR(KBr): 1645 cm$^{-1}$.

mp: ~96° C.(decomp.)

EXAMPLE 141

Synthesis of 1-(2-chlorobenzyl)-2-methyl-6-(2-naphthalenesulfonylcarbamoyl)benzimidazole sodium salt (206)

N,N'-carbonyldiimidazole (0.541 g) was added at a time to a solution of 0.500 g of 6-carboxy-1-(2-chlorobenzyl)-2-methylbenzimidazole in 20 ml of N,N-dimethylformamide, and the mixture was stirred at room temperature for 1 hour. Subsequently, a solution of 0.689 g of 2-naphthalenesulfonamide and 0.506 g of diazabicycloundecene in 5 ml of N,N-dimethylformamide were added thereto, and the mixture was stirred at 100° C. for 48 hours. The reaction solution was cooled, and the solvent was distilled off under reduced pressure. Water and chloroform were added to the residue, and 10% hydrochloric acid was added thereto until the aqueous layer was acidified. The mixture was extracted twice with chloroform. A saturated aqueous solution of sodium hydrogencarbonate was added to the resulting organic layer, and the mixed solution was stirred. The crystals precipitated were separated through filtration, and were dissolved in a small amount of methanol. Further, ethyl acetate was added thereto for crystallization. The crystals were separated through filtration, and were dried to give 0.508 g of 1-(2-chlorobenzyl)-2-methyl-6-(2-naphthalenesulfonylcarbamoyl)benzimidazole sodium salt (206).

Properties of Compound (206):
$^1$H-NMR(DMSO-d6, δ): 2.46(3H, s), 5.51(2H, s), 6.38 (1H, d, J=7.9 Hz), 7.17(1H, t, J=7.5 Hz), 7.30(1H, t), 7.45(1H, d, J=8.5 Hz), 7.51–7.57(3H, m), 7.77–7.93(5H, m), 7.99(1H, m), 8.35(1H, s).
IR(KBr): 1594 cm$^{-1}$.
Mass(FAB): m/e 512(M+1).
mp: 352.0–354.5° C.

EXAMPLE 142

Synthesis of 1-(2-chlorobenzyl)-2-methyl-6-(1-naphthalenesulfonylcarbamoyl)benzimidazole sodium salt (207)

In the same manner as in Example 141, 0.390 g of 1-(2-chlorobenzyl)-2-methyl-6-(1-naphthalenesulfonylcarbamoyl)benzimidazole sodium salt (207) were formed from 0.600 g of 6-carboxy-1(2-chlorobenzyl)-2-methylbenzimidazole, 0.647 g of N,N'-carbonyldiimidazole, 0.829 g of 1-naphthalenesulfonamide and 0.608 g of diazabicycloundecene.

Properties of Compound (207):
$^1$H-NMR(DMSO-d6, δ): 2.46(3H, s), 5.49(2H, s), 6.39 (1H, d, J=7.8 Hz), 7.16(1H, t, J=7.5 Hz), 7.31(1H, t, J=7.3 Hz), 7.36(1H, t), 7.40–7.45(2H, m), 7.50(1H, t, J=7.7 Hz), 7.54(1H, d, J=8.0 Hz), 7.75–7.81(2H, m), 7.87(1H, d, J=7.9 Hz), 7.93(1H, d, J=8.2 Hz), 8.09(1H, d, J=7.3 Hz), 8.86(1H, d, J=8.5 Hz).
IR(KBr): 1633 cm$^{-1}$.
Mass(FAB): m/e 512(M+1).
mp: ~265° C.(decomp.)

EXAMPLE 143

Synthesis of 6-(4-chlorobenzenesulfonylcarbamoyl)-1-(2-chlorobenzyl)-2-methylbenzimidazole sodium salt (208)

In the same manner as in Example 141, 0.270 g of 6-(4-chlorobenzenesulfonylcarbamoyl)-1-(2-chlorobenzyl)-2-methylbenzimidazole sodium salt (208) were formed from 0.400 g of 6-carboxy-1-(2-chlorobenzyl)-2-methylbenzimidazole, 0.432 g of N,N'-carbonyldiimidazole, 0.510 g of 4-chlorobenzenesulfonamide and 0.404 g of diazabicycloundecene.

Properties of Compound (208):
$^1$H-NMR(DMSO-d6, δ): 2.46(3H, s), 5.52(2H, s), 6.38 (1H, d, J=7.4 Hz), 7.19(1H, t, J=7.6 Hz), 7.31(1H, t, J=7.6 Hz), 7.39(2H, d, J=8.5 Hz), 7.45(1H, d, J=8.9 Hz), 7.54(1H, d, J=8.0 Hz), 7.76–7.82(4H, m).
IR(KBr): 1592 cm$^{-1}$.
Mass(FAB): m/e 496(M+1).
mp: 360–362° C.(decomp.)

EXAMPLE 144

Synthesis of 6-(3-chlorobenzenesulfonylcarbamoyl)-1-(2-chlorobenzyl)-2-methylbenzimidazole (209)

In the same manner as in Example 141, 6-(3-chlorobenzenesulfonylcarbamoyl)-1-(2-chlorobenzyl)-2-methylbenzimidazole sodium salt was obtained from 0.450 g of 6-carboxy-1-(2-chlorobenzyl)-2-methylbenzimidazole, 0.486 g of N,N'-carbonyldiimidazole, 0.573 g of 3-chlorobenzenesulfonamide and 0.456 g of diazabicycloundecene. This salt was dissolved in a mixed solution of methanol and water, and was adjusted to a pH of from 5 to 6 with 10% hydrochloric acid. The crystals precipitated were separated through filtration, and were dried to give 0.420 g of 6-(3-chlorobenzenesulfonylcarbamoyl)-1-(2-chlorobenzyl)-2-methylbenzimidazole (209).

Properties of Compound (209):
$^1$H-NMR(DMSO-d6, δ): 2.51(3H, s), 5.63(2H, s), 6.48 (1H, d, J=7.7 Hz), 7.22(1H, t, J=7.6 Hz), 7.34(1H, t, J=7.7 Hz), 7.56(1H, t, J=8.0 Hz), 7.64(1H, t, J=8.0 Hz), 7.68(1H, d, J=8.5 Hz), 7.78(2H, t, J=8.6 Hz), 7.91(1H, d, J=7.6 Hz), 7.95(1H, d, J=1.6 Hz), 8.10(1H, s).
IR(KBr): 1687 cm$^{-1}$.
Mass(FAB): m/e 474(M+1).
mp: 254.5–257.5° C.(decomp.)

EXAMPLE 145

Synthesis of 5-benzenesulfonylcarbamoyl-2-benzyl-1-(2-chlorobenzyl)benzimidazole (210)

In the same manner as in Example 144, 0.447 g of 5-benzenesulfonylcarbamoyl-2-benzyl-1-(2-chlorobenzyl) benzimidazole (210) were formed from 0.466 g of 2-benzyl-5-carboxy-1-(2-chlorobenzyl)benzimidazole, 0.401 g of N,N'-carbonyldiimidazole, 0.389 g of benzenesulfonamide and 0.377 g of diazabicycloundecene.

Properties of Compound (210):
$^1$H-NMR(DMSO-d6, δ): 4.28(2H, s), 5.57(2H, s), 6.23 (1H, d, J=7.6 Hz), 7.04(1H, t, J=7.6 Hz), 7.10–7.26(6H, m), 7.40(1H, d, J=8.6 Hz), 7.46(1H, d, J=8.0 Hz), 7.61–7.73(4H, m), 8.00(2H, d, J=7.6 Hz), 8.23(1H, s), 12.43(1H, br s).
IR(KBr): 1685 cm$^{-1}$.
mp: 152.0–155.0° C.

EXAMPLE 146

Synthesis of 6-benzenesulfonylcarbamoyl-2-benzyl-1-(2-chlorobenzyl)benzimidazole (211)

In the same manner as in Example 144, 0.803 g of 6-benzenesulfonylcarbamoyl-2-benzyl-1-(2-chlorobenzyl) benzimidazole (211) were formed from 0.760 g of 2-benzyl-6-carboxy-1-(2-chlorobenzyl)benzimidazole, 0.654 g of N,N'-carbonyldiimidazole, 0.634 g of benzenesulfonamide and 0.614 g of diazabicycloundecene.

Properties of Compound (211):
$^1$H-NMR(DMSO-d6, δ): 4.41(2H, s), 5.71(2H, s), 6.32 (1H, d, J=7.7 Hz), 7.06(1H, t, J=7.7 Hz), 7.14–7.30(6H, m), 7.50(1H, d, J=8.0 Hz), 7.62(2H, t), 7.70(1H, t), 7.81(1H, d, J=8.6 Hz), 7.87(1H, d, J=8.5 Hz), 7.97(2H, d, J=8.2 Hz), 8.16(1H, s), 12.60(1H, br s).
IR(KBr): 1704 cm$^{-1}$.
mp: 143.0–144.5° C.

EXAMPLE 147

Synthesis of 1-(2,4-dichlorobenzyl)-2-methyl-6-[(2-pyridylmethyl)carbamoyl]benzimidazole (180)

Ten milliliters of dichloromethane and 1 drop of N,N-dimethylformamide were added to 0.627 g of 6-carboxy-1-(2,4-dichlorobenzyl)-2-methylbenzimidazole, and the mixture was cooled with ice. Oxalyl chloride (0.493 g) was added dropwise thereto, and the mixture was stirred for several minutes. Further, the mixture was stirred at room temperature for 1 hour, and was then concentrated under reduced pressure to remove oxalyl chloride. The residue was dissolved in 10 ml of dichloromethane. This solution was added dropwise to a solution of 0.167 g of 2-aminomethylpyridine and 0.469 g of triethylamine in 5 ml of methylene chloride while being cooled with ice. After the mixture was stirred for 1 hour, the reaction solution was washed three times with water and further with a saturated aqueous solution of sodium hydrogencarbonate. The organic layer was concentrated under reduced pressure, and was purified through preparative thin-layer silica-gel chromatography (eluent: a mixture of acetone and diethyl ether at a ratio of 1:1). The resulting product was further dissolved in 5 ml of ethyl acetate, and 2 ml of hexane were added thereto for crystallization. The crystals were separated through filtration, and were dried to give 0.359 g of 1-(2,4-dichlorobenzyl)-2-methyl-6-[(2-pyridylmethyl)carbamoyl] benzimidazole (180).

Properties of Compound (180):
$^1$H-NMR(CDCl$_3$, δ): 2.56(3H, s), 4.76(2H, d, J=4.8 Hz), 5.40(2H, s), 6.33(1H, d, J=8.4 Hz), 7.07(1H, dd, J=8.4 and 2.0 Hz), 7.22(1H, dd, J=7.4 and 4.9 Hz), 7.33(1H, d, J=7.9 Hz), 7.48(1H, d, J=2.1 Hz), 7.62–7.79(4H, m), 7.86(1H, d, J=1.1 Hz), 8.57, (1H, d, J=4.9 Hz).
IR(KBr): 1645 cm$^{-1}$.
mp: 204.1–206.3° C.

EXAMPLE 148

Synthesis of 1-(biphenyl-4-ylmethyl)-2-methyl-6-[(2-pyridylmethyl)carbamoyl]benzimidazole (212)

Oxalyl chloride (0.655 g) was added to a solution of 0.886 g of 1-(biphenyl-4-ylmethyl)-6-carboxy-2-methylbenzimidazole and 1 drop of N,N-dimethylformamide in 13 ml of dichloromethane while being cooled with ice, and the mixture was stirred at room temperature for 15 hours. The crystals precipitated were separated through filtration, washed with methylene chloride, and dried under reduced pressure. The crystals were added to a solution of 0.235 g of 2-aminomethylpyridine and 0.653 g of triethylamine in 15 ml of dichloromethane while being cooled, and the mixture was stirred for 1 hour. Water was added to the reaction solution to stop the reaction. The reaction solution was washed twice with water and further with a saturated aqueous solution of sodium hydrogencarbonate. The organic layer was then dried, and the solvent was concentrated under reduced pressure. The residue was recrystallized from a mixed solvent of ethyl acetate and ethanol to give 0.774 g of 1-(biphenyl-4-ylmethyl)-2-methyl-6-[(2-pyridylmethyl) carbamoyl]benzimidazole (212).

Properties of Compound (212):
$^1$H-NMR(CDCl$_3$, δ): 2.62(3H, s), 4.77(2H, d, J=4.8 Hz), 5.42(2H, s), 7.12(2H, d, J=8.5 Hz), 7.21(1H, m), 7.34(2H, m), 7.42(2H, m), 7.51–7.55(4H, m),7.62(1H, br t), 7.67(1H, dt, J=1.7 and 7.7 Hz), 7.71(1H, dd, J=1.6 and 8.4 Hz), 7.76(1H, d, J=8.4 Hz), 8.00(1H, d, J=1.2 Hz), 8.56(1H, d, J=4.8 Hz).
IR(KBr): 1642 cm$^{-1}$.
mp: 205.0–206.5° C.

EXAMPLE 149

Synthesis of 6-benzenesulfonylcarbamoyl-1-(2-chlorobenzyl)-2-methylbenzimidazole (163)

N,N'-carbonyldiimidazole (0.973 g) was added to a solution of 0.902 g of 6-carboxy-1-(2-chlorobenzyl)-2-methylbenzimidazole in 20 ml of N,N-dimethylformamide, and the mixture was stirred at room temperature for 1 hour. Subsequently, a solution of 0.943 g of benzenesulfonamide and 0.913 g of diazabicycloundecene in 5 ml of N,N-dimethylformamide was added thereto, and the mixture was stirred at 100° C. for 70 hours. The reaction solution was cooled, and the solvent was distilled off under reduced pressure. Water and chloroform were added to the residue, and 10% hydrochloric acid was added thereto while being stirred until the aqueous layer was acidified. The mixed solution was extracted twice with chloroform. The resulting organic layer was washed with a saturated aqueous solution of sodium hydrogencarbonate, and the solvent was distilled off under reduced pressure. The residue was dissolved in a small amount of chloroform, and ethyl acetate was added to the solution for crystallization. The crystals were separated through filtration, and were dried to give 0.667 g of 6-benzenesulfonylcarbamoyl-1-(2-chlorobenzyl)-2-methylbenzimidazole (163).

EXAMPLE 150

Synthesis of 6-benzenesulfonylcarbamoyl-1-(biphenyl-4-ylmethyl)-2-methylbenzimidazole sodium salt (213)

In the same manner as in Example 141, 0.365 g of 6-benzenesulfonylcarbamoyl-1-(biphenyl-4-ylmethyl)-2-methylbenzimidazole sodium salt (213) were formed from 0.637 g of 6-carboxy-1-(biphenyl-4-ylmethyl)-2-methylbenzimidazole, 0.533 g of N,N'-carbonyldiimidazole, 0.516 g of benzenesulfonamide and 0.500 g of diazabicycloundecene.

Properties of Compound (213):
$^1$H-NMR(DMSO-d6, δ): 2.52(3H, s), 5.52(2H, s), 7.13 (2H, d, J=8.1 Hz), 7.31–7.37(4H, m), 7.39–7.45(3H, m), 7.58–7.63(4H, m), 7.78–7.82(3H, m), 7.97(1H, s).
IR(Nujol): 1591 cm$^{-1}$.
mp: 289.0–290.0° C.(decomp.)

EXAMPLE 151

Synthesis of 6-benzenesulfonylcarbamoyl-1-(2-chlorobenzyl)-2-methylbenzimidazole (163)

N,N'-carbonyldiimidazole (5.41 g) was added at a time to a solution of 5.02 g of 6-carboxy-1-(2-chlorobenzyl)-2-methylbenzimidazole in 110 ml of N,N-dimethylformamide, and the mixture was stirred at room temperature for 1 hour. Subsequently, a solution of 5.24 g of benzenesulfonamide and 5.08 g of diazabicycloundecene in 20 ml of N,N-dimethylformamide was added thereto, and the mixed solution was stirred at 100° C. for 70 hours. The reaction solution was cooled, and the solvent was distilled off under reduced pressure. Water and chloroform were added to the residue, and 10% hydrochloric acid was added thereto while being stirred until the aqueous layer was acidified. The solution was extracted twice with chloroform. The organic layer was washed with a saturated aqueous solution of sodium hydrogencarbonate, and a part of the solvent was distilled off under reduced pressure. The crystals precipitated were separated through filtration, and were dried to give 4.96 g of 6-benzenesulfonylcarbamoyl-1-(2-chlorobenzyl)-2-methylbenzimidazole (163).

EXAMPLE 152

Synthesis of 1-(2-chlorobenzyl)-2-methyl-6-trifluoromethanesulfonylcarbamoylbenzimidazole hydrochloride (214)

N,N'-carbonyldiimidazole (0.647 g) was added at a time to a solution of 0.600 g of 6-carboxy-1-(2-chlorobenzyl)-2- methylbenzimidazole in 20 ml of N,N-dimethylformamide, and the mixture was stirred at room temperature for 1 hour. Subsequently, a solution of 0.596 g of trifluoromethanesulfonamide and 0.609 g of diazabicycloundecene in 5 ml of N,N-dimethylformamide was added thereto, and the mixture was stirred at 100° C. for 72 hours. The reaction solution was cooled, and the solvent was distilled off under reduced pressure. Water and ethyl acetate were added to the residue, and 10% hydrochloric acid was added thereto while being stirred until the aqueous layer was acidified. The crystals precipitated were washed with a mixed solvent of 25 ml of ethanol and 25 ml of methanol. The crystals were dried to give 0.420 g of 1-(2-chlorobenzyl)-2-methyl-6-trifluoromethanesulfonylcarbamoylbenzimidazole hydrochloride (214).

Properties of Compound (214):

$^1$H-NMR(DMSO-d6, δ): 2.84(3H, s), 5.82(2H, s), 7.08 (1H, d, J=7.5 Hz), 7.30(1H, t), 7.40(1H, t, J=7.7 Hz), 7.58(1H, d, J=8.0 Hz), 7.79(1H, d, J=8.6 Hz), 8.07–8.13(2H, m).

IR(KBr): 1634 cm$^{-1}$.

Mass(CI): m/e 432(M+1-HCl).

mp: 332–335° C.(decomp.)

EXAMPLE 153 and 154

Synthesis of 6-benzenesulfonylcarbamoyl-1-(2,4-dichlorobenzyl)-2-methylbenzimidazole hydrochloride (215) and 6-benzenesulfonylcarbamoyl-1-(2,4-dichlorobenzyl)-2-methyl-benzimidazole (216)

In the same manner as in Example 152, 0.540 g of 6-benzenesulfonylcarbamoyl-1-(2,4-dichlorobenzyl)-2-methylbenzimidazole hydrochloride (215) were formed from 0.460 g of 6-carboxy-1-(2,4-dichlorobenzyl)-2-methylbenzimidazole, 0.455 g of N,N'-carbonyldiimidazole, 0.431 g of benzenesulfonamide and 0.418 g of diazabicycloundecene.

Properties of Compound (215):

$^1$H-NMR(DMSO-d6, δ): 2.71(3H, s), 5.74(2H, s), 6.83 (1H, d, J=8.4 Hz), 7.33(1H, dd, J=2.0 and 8.4 Hz), 7.63(2H, t), 7.71(1H, t), 7.78(1H, d, J=2.0 Hz), 7.86(1H, d, J=8.7 Hz), 7.95(1H, dd, J=1.4 and 8.7 Hz), 7.99(2H, m), 8.29(1H, s).

IR(KBr): 1686 cm$^{-1}$.

mp: 236.0–238.0° C.

This compound was dissolved in a mixed solvent of a potassium hydrogencarbonate and methanol, and the solution was adjusted to a pH of from 5 to 6 with 10% hydrochloric acid. The crystals precipitated were collected, washed with water and with methanol, and dried to give 6-benzenesulfonylcarbamoyl-1-(2,4-dichlorobenzyl)-2-methylbenzimidazole (216).

Properties of Compound (216):

$^1$H-NMR(DMSO-d6, δ): 2.48(3H, s), 5.58(2H, s), 6.42 (1H, d, J=8.4 Hz), 7.31(1H, dd, J=2.2 and 8.4 Hz), 7.60–7.75 (6H, m), 7.99(2H, d, J=7.4 Hz), 8.06(1H, s), 12.40(1H, s).

IR(KBr): 1540 cm$^{-1}$.

mp: 238.2.–239.9° C.

EXAMPLE 155

Synthesis of 1-(2-chlorobenzyl)-6-(4-methoxybenzenesulfonylcarbamoyl)-2-methylbenzimidazole (217)

N,N'-carbodiimidazole (0.431 g) was added at a time to a solution of 0.400 g of 6-carboxy-1-(2-chlorobenzyl)-2-methylbenzimidazole in 15 ml of N,N-dimethylformamide, and the mixture was stirred at room temperature for 1 hour. Subsequently, a solution of 0.498 g of 4-methoxybenzenesulfonamide and 0.405 g of diazabicycloundecene in 5 ml of N,N-dimethylformamide was added thereto, and the mixed solution was stirred at 100° C. for 67 hours. The reaction solution was cooled, and the solvent was distilled off under reduced pressure. water and chloroform were added to the residue, and 10% hydrochloric acid was added thereto while being cooled until the aqueous layer was acidified. The resulting mixture was extracted twice with chloroform. The organic layer was washed with a saturated aqueous solution of sodium hydrogencarbonate, and the solvent was distilled off under reduced pressure. The residue was purified through silica-gel column chromatography (eluent: a mixture of chloroform and methanol at a ratio of 100:2 to 100:10). The resulting product was concentrated, and was crystallized from a mixed solution of ethyl acetate and diethyl ether. The crystals were separated through filtration, and were dried to give 0.450 g of 1-(2-chlorobenzyl)-6-(4-methoxybenzenesulfonylcarbamoyl)-2-methylbenzimidazole (217).

Properties of Compound (217):

$^1$H-NMR(DMSO-d6, δ): 2.46(3H, s), 3.83(3H, s), 5.58 (2H, s), 7.12(2H, d, J=9.0 Hz), 7.21(1H, t, J=7.3 Hz), 7.33(1H, t), 7.56(1H, d, J=7.0 Hz), 7.63(1H, d, J=8.5 Hz), 7.71(1H, dd, J=1.6 and 8.5 Hz), 7.91(2H, d, J=9.0 Hz), 8.05(1H, d, J=1.3 Hz).

IR(KBr): 1683 cm$^{-1}$.

Mass(FAB): m/e 470(M+).

mp: 271.0–274.0° C.

EXAMPLE 156

Synthesis of 1-(2-chlorobenzyl)-2-methyl-6-(α-toluenesulfonylcarbamoyl)benzimidazole (218)

In the same manner as in Example 155, 0.350 g of 1-(2-chlorobenzyl)-2-methyl-6-(α-toluenesulfonylcarbamoyl)benzimidazole (218) were formed from 0.450 g of 6-carboxy-1-(2-chlorobenzyl)-2-methylbenzimidazole, 0.485 g of N,N-carbonyldiimidazole, 0.512 g of α-toluenesulfonamide and 0.456 g of diazabicycloundecene.

Properties of Compound (218):

$^1$H-NMR(DMSO-d6, δ): 2.48(3H, s), 4.36(2H, s), 5.53 (2H, s), 6.40(1H, d, J=6.8 Hz), 7.15–7.28(6H, m), 7.32(1H, t), 7.49(1H, d, J=8.3 Hz), 7.55(1H, d), 7.83–7.87(2H, m).

IR(KBr): 1593 cm$^{-1}$.

Mass(FAB): m/e 454(M+1).

mp: 193–196° C.(foamed)

EXAMPLE 157

Synthesis of 1-(2-chlorobenzyl)-6-(2,5-dimethylbenzenesulfonylcarbamoyl)-2-methylbenzimidazole (219)

In the same manner as in Example 155, 0.490 g of 1-(2-chlorobenzyl)-6-(2,5-dimethylbenzenesulfonylcarbamoyl)-2-methylbenzimidazole (219) were formed from 0.500 g of 6-carboxy-1-(2-chlorobenzyl)-2-methylbenzimidazole, 0.539 g of N,N'-carbonyldiimidazole, 0.616 g of 2,5-xylenesulfonamide and 0.506 g of diazabicycloundecene.

Properties of Compound (219):
$^1$H-NMR(DMSO-d6, δ): 2.35(3H, s), 2.48(3H, s), 2.51 (3H, s), 5.58(2H, s), 6.45(1H, d, J=7.5 Hz), 7.20–7.27(2H, m), 7.31–7.39(2H, m), 7.56(1H, d, J=8.0 Hz), 7.64(1H, d, J=8.5 Hz), 7.75(1H, d, J=8.5 Hz), 7.82(1H, s), 8.06(1H, s), 12.45(1H, br s).

IR(KBr): 1690 cm$^{-1}$.

Mass(FAB): m/e 468(M+1).

mp: 266.5–267.5° C.

EXAMPLE 158

Synthesis of 1-(2-chlorobenzyl)-2-methyl-6-(4-nitrobenzenesulfonylcarbamoyl)benzimidazole (220)

N,N'-carbodiimidazole (0.432 g) was added at a time to a solution of 0.400 g of 6-carboxy-1-(2-chlorobenzyl)-2-methylbenzimidazole in 15 ml of N,N-dimethylformamide, and the solution was stirred at room temperature for 1 hour. Subsequently, a solution of 0.538 g of 4-nitrobenzenesulfonamide and 0.405 g of diazabicycloundecene in 5 ml of N,N-dimethylformamide, and the mixture was stirred at 100° C. for 84 hours. The reaction solution was cooled, and the solvent was distilled off under reduced pressure. Chloroform and hydrochloric acid were added to the residue, and the mixture was stirred to precipitate the crystals. The crystals precipitated were separated through filtration, and were dried to give 0.300 g of 1-(2-chlorobenzyl)-2-methyl-6-(4-nitrobenzenesulfonylcarbamoyl)benzimidazole (220).

Properties of Compound (220):
$^1$H-NMR(DMSO-d6, δ): 2.56(3H, s), 5.65(2H, s), 6.54 (1H, d, J=7.6 Hz), 7.23(1H, t, J=7.6 Hz), 7.34(1H, t, J=7.6 Hz), 7.56(1H, t, J=8.0 Hz), 7.68(1H, d, J=8.5 Hz), 7.83(1H, d, J=8.3 Hz), 8.07(1H, s), 8.16(2H,d,J=8.7 Hz), 8.37(2H, d, J=8.7 Hz).

IR(KBr): 1621 cm$^{-1}$.

Mass(FAB): m/e 485(M+1).

mp: 330–332° C.

EXAMPLE 159

Synthesis of 1-(2-chlorobenzyl)-2-methyl-6-[4-(trifluoromethyl)benzenesulfonylcarbamoyl] benzimidazole (221)

In the same manner as in Example 158, 0.390 g of 1-(2-chlorobenzyl)-2-methyl-6-[4-(trifluoromethyl) benzenesulfonylcarbamoyl]benzimidazole (221) were formed from 0.45 g of 6-carboxy-1-(2-chlorobenzyl)-2-methylbenzimidazole, 0.486 g of N,N'-carbonyldiimidazole, 0.676 g of 4-(trifluoromethyl)benzenesulfonamide and 0.457 g of diazabicycloundecene.

Properties of Compound (221):
$^1$H-NMR(DMSO-d6, δ): 2.52(3H, s), 5.62(2H, s), 6.47 (1H, d, J=7.2 Hz), 7.22(1H, t, J=7.5 Hz), 7.34(1H, t), 7.56(1H, d, H=8.0 Hz), 7.66(1H, d, 8.5 Hz), 7.78(1H, d), 7.97(2H, d, J=8.3 Hz), 8.06(1H, s), 8.15(2H, d, J=8.3 Hz).

IR(KBr): 1620 cm$^{-1}$.

Mass(FAB): m/e 508(M+1).

mp: 288.0–292.0° C.

EXAMPLE 160

Synthesis of 6-(2-chlorobenzenesulfonylcarbamoyl)-1-(2-chlorobenzyl)-2-methylbenzimidazole ammonium salt (222)

N,N'-carbodiimidazole (0.485 g) was added at a time to a solution of 0.450 g of 6-carboxy-1-(2-chlorobenzyl)-2-methylbenzimidazole in 15 ml of N,N-dimethylformamide and the mixture was stirred at room temperature for 1 hour. Subsequently, a solution of 0.575 g of trifluoromethanesulfonamide and 0.457 g of diazabicycloundecene in 5 ml of N,N-dimethylformamide was added thereto, and the mixture was stirred at 100° C. for 72 hours. The reaction solution was cooled, and the solvent was distilled off under reduced pressure. Water and ethyl acetate were added to the residue, and 10% hydrochloric acid was added thereto while being mixed until the aqueous layer was acidified. The crystals precipitated were separated through filtration. The crystals were dissolved in ethanol, and the solution was adjusted to a pH of 7 with aqueous ammonia. Further, diisopropyl ether was added thereto. The crystals precipitated were separated through filtration, and were dried to give 0.360 g of 6-(2-chlorobenzenesulfonylcarbamoyl)-1-(2-chlorobenzyl)-2-methylbenzimidazole ammonium salt (222).

Properties of Compound (222):
$^1$H-NMR(DMSO-d6, δ): 2.47(3H, s), 5.51(2H, s), 6.43 (1H, d, J=7.5 Hz), 7.12(4H, br s), 7.19(1H, t, J=7.6 Hz), 7.28–7.38(4H, m), 7.46(1H, d, J=8.3 Hz), 7.53(1H, d, J=7.9 Hz), 7.78–7.82(2H, m), 7.97(1H, m).

IR(KBr): 1590 cm$^{-1}$.

Mass(FAB): m/e 474(M+1-NH3).

mp: 264.0–267.0° C.

EXAMPLE 161

Synthesis of 6-carbamoyl-1-(2,4-dichlorobenzyl)-2-methylbenzimidazole (223)

Oxalyl chloride (0.437 g) was added to a solution of 0.490 g of 6-carboxy-1-(2,4-dichlorobenzyl)-2-methylbenzimidazole and 1 drop of N,N-dimethylformamide in 8 ml of methylene chloride while being cooled with ice, and the mixture was stirred at room temperature for 1.5 hours. Four milliliters of 28% aqueous ammonia were added thereto, and the solution was stirred at room temperature for 12 hours. The reaction solution was extracted with the addition of water and methylene chloride. The organic layer was concentrated, and the crystals precipitated were then collected, and were dried to give 0.240 g of 6-carbamoyl-1-(2,4-dichlorobenzyl)-2-methylbenzimidazole (223).

Properties of Compound (223):
$^1$H-NMR(DMSO-d6, δ): 2.48(3H, s), 5.54(2H, s), 6.41 (1H, d, J=8.4 Hz), 7.21–8.02(3H, m), 7.31(1H, dd, J=2.2 and 8.4 Hz), 7.60(1H, d, J=8.4 Hz), 7.75(1H, m), 7.93(1H, s).

IR(KBr): 1666 cm$^{-1}$.

mp: 112.0–114.0° C.

EXAMPLE 162

Synthesis of 6-benzensulfonylcarbamoyl-2-benzyl-1-(2,4-dichlorobenzyl)benzimidazole (224)

N,N'-carbonyldiimidazole (0.248 g) was added at a time to a solution of 0.315 g of 2-benzyl-6-carboxy-1-(2,4-dichlorobenzyl)benzimidazole in 5 ml of N,N-dimethylformamide, and the mixture was stirred at room temperature for 1 hour. Subsequently, a solution of 0.240 g of benzenesulfonamide and 0.233 g of diazabicycloundecene in 4 ml of N,N-dimethylformamide was added thereto, and the mixture was stirred at 100° C. for 62 hours. The reaction solution was cooled, and the solvent was distilled off under reduced pressure. Water and chloroform were added to the residue, and 10% hydrochloric acid was added thereto while being mixed until the aqueous layer was acidified. The solution was extracted twice with chloroform. The resulting organic layer was washed with a saturated aqueous solution of sodium hydrogencarbonate, and a part of the solvent was distilled off under reduced pressure. To the residue were added 4 ml of methanol and 4 ml of a 20% potassium hydrogencarbonate aqueous solution to form a uniform solution. This solution was then adjusted to a pH of from 5 to 6 with 10% hydrochloric acid. The crystals precipitated were separated through filtration, and were dried to give 0.310 g of 6-benzenesulfonylcarbamoyl-2-benzyl-1-(2,4-dichlorobenzyl)benzimidazole (244).

Properties of Compound (224):

$^1$H-NMR(DMSO-d6, δ): 4.32(1H, s), 5.61(2H, s), 6.16 (1H, d, J=8.4 Hz), 7.09(1H, dd, J=8.4 and 1.9 Hz), 7.18–7.10 (5H, m), 7.82–7.58(6H, m), 7.97(2H, d, J=7.6 Hz), 8.10(1H, s), 12.43(1H, br s).

IR(KBr): 1703 cm$^{-1}$.

mp: 236.0–238.0° C.

EXAMPLE 163

Synthesis of 5-benzenesulfonylcarbamoyl-2-benzyl-1(2,4-dichlorobenzyl)benzimidazole (225)

In the same manner as in Example 152, 0.270 g of 5-benzenesulfonylcarbamoyl-2-benzyl-1-(2,4-dichlorobenzyl)benzimidazole (225) were formed from 0.385 g of 2-benzyl-5-carboxy-1-(2,4-dichlorobenzyl) benzimidazole, 0.304 g of N,N'-carbonyldiimidazole, 0.294 g of benzenesulfonamide and 0.285 g of diazabicycloundecene.

Properties of Compound (225):

$^1$H-NMR(DMSO-d6, δ): 4.28(2H, s), 5.52(2H, s), 6.14 (1H, d, J=8.4 Hz), 7.21–7.06(6H, m), 7.42(1H, d, J=8.6 Hz), 7.76–7.57(5H, m), 8.05–7.95(2H, m), 8.24(1H, s), 12.43 (1H, br s).

IR(KBr): 1691 cm$^{-1}$.

mp: 107.0–110.0° C.

EXAMPLE 164

Synthesis of 6-benzenesulfonylcarbamoyl-1-(biphenyl-4-ylmethyl-2-hydroxybenzimidazole (226)

Tetramethoxymethane (0.220 g) was added to a solution of 0.400 g of N-benzenesulfonyl-4-amino-3-(biphenyl-4-ylmethylamino)benzamide in 5 ml of acetic acid, and the mixture was stirred at 80 ° C. for 2 hours. The reaction solution was concentrated, and a 20% potassium hydrogencarbonate aqueous solution was added to this reaction solution to render it basic. This solution was then adjusted to a pH of from 5 to 6 with 10% hydrochloric acid. The crystals precipitated were collected, and 10 ml of methanol, 0.50 g of 10% hydrochloric acid and 0.35% hydrochloric acid were added thereto. The mixture was stirred at 60° C. for 15 hours. A 20% potassium hydrogencarbonate aqueous solution was added to the solution to render it alkaline. This solution was then adjusted to a pH of from 5 to 6 with 10% hydrochloric acid. The crystals precipitated were separated through filtration, and were dried to give 0.219 g of 6-benzenesulfonylcarbamoyl-1-(biphenyl-4-ylmethyl-2-hydroxybenzimidazole (226).

Properties of Compound (226):

$^1$H-NMR(DMSO-d6, δ): 5.07(2H, s), 7.08(1H, d, J=8.2 Hz), 7.33–7.39(3H, m), 7.44(2H, t, J=7.5 Hz), 7.60–7.65 (7H, m), 7.66–7.72(2H, m), 7.96–7.80(2H, m), 11.46(1H, s), 12.34(1H, s).

IR(KBr): 1704, 1686 cm$^{-1}$.

Mass(FD) m/e 483(M).

mp: 268.7–273.9° C.

EXAMPLE 165

Synthesis of 6-benzenesulfonylcarbamoyl-1-(biphenyl-4-ylmethyl)-2-mercaptobenzimidazole (227)

Two milliliters of carbon disulfide were added to a solution of 0.800 g of N-benzenesulfonylcarbamoyl-4-amino-3-(biphenyl-4-ylmethylamino)benzamide, and the mixture was stirred at 50° C. for 70 hours. Chloroform and water were added thereto. The crystals precipitated were separated through filtration, and were dried to give 0.719 g of 6-benzenesulfonylcarbamoyl-1-(biphenyl-4-ylmethyl)-2-mercaptobenzimidazole (227).

Properties of Compound (227):

$^1$H-NMR(DMSO-d6, δ): 5.55(2H, s), 7.28(1H, d, J=8.4 Hz), 7.35(1H, t, J=6.3 Hz), 7.39–7.47(4H, m), 7.61–7.65 (6H, m), 7.69(1H, t, J=7.4 Hz), 7.78(1H, dd, J=8.4 and 1.4 Hz), 7.87(1H, s), 7.81–7.98(2H, m), 12.51(1H, s), 13.29(1H, s).

IR(KBr): 1701 cm$^{-1}$.

mp: 320.0–321.0° C.

EXAMPLE 166

Synthesis of 6-benzenesulfonylcarbamoyl-1-(biphenyl-4-ylmethyl)-2-methoxybenzimidazole (228)

Tetramethoxymethane (0.250 g) was added to a solution of 0.400 g of N-benzenesulfonyl-4-amino-3-(biphenyl-4-ylmethylamino)benzamide in 3 ml of acetic acid, and the mixture was stirred at 80° C. for 2 hours. Methanol was added to the reaction solution, and the crystals precipitated were collected. The crystals were washed with a mixed solvent of 1 ml of acetone and 8 ml of methanol, separated through filtration, and dried to give 0.280 g of 6-benzenesulfonylcarbamoyl-1-(biphenyl-4-ylmethyl)-2-methoxybenzimidazole (228).

Properties of Compound (228):

$^1$H-NMR(DMSO-d6, δ): 4.17(3H, s), 5.33(2H, s), 7.30 (2H, d, J=8.2 Hz), 7.35(1H, t, J=7.4 Hz), 7.44(2H, t, J=7.5 Hz), 7.50(1H, d, J=8.4 Hz), 7.60–7.65(6H, m), 7.68–7.72 (2H, m), 7.98–8.01(2H, m), 8.05(1H, d, J=1.5 Hz), 8.18(1H, s), 12.50(1H, s).

IR(KBr): 1690 cm$^{-1}$.

mp: 136.0–138.5° C.

EXAMPLE 167

Synthesis of 6-benzenesulfonylcarbamoyl-1-(biphenyl-4-ylmethyl)-2-carboxybenzimidazole (229)

Triethylamine (0.080 g) and 0.148 g of methyloxalyl chloride were added to a solution of 0.400 g of N-benzenesulfonyl-4-amino-3-(biphenyl-4-ylmethylamino) benzamide in 3 ml of N,N-dimethylformamide, and the mixture was stirred at room temperature for 2 hours. The reaction solution was concentrated, and the residue was purified through silica-gel column chromatography (eluent: a mixture of ethyl acetate and methanol at a ratio of 9:1) to obtain crude 6-benzenesulfonylcarbamoyl-1-(biphenyl-4- ylmethyl)-2-carboxybenzimidazole. This compound was dissolved in 1 ml of acetic acid and 5 ml of methanol, and the mixture was stirred at 60° C. for 15 hours. The reaction solution was neutralized with a potassium hydroxide aqueous solution. The crystals precipitated were separated through filtration, and were dried to give 0.245 g of 6-benzenesulfonylcarbamoyl-1-(biphenyl-4-ylmethyl)-2-carboxybenzimidazole (229).

Properties of Compound (229):
$^1$H-NMR(DMSO-d6, δ): 5.44(2H, s), 7.23(1H, d, J=8.4 Hz), 7.36(1H, t, J=7.6 Hz), 7.41(2H, d, J=8.1 Hz), 7.45(2H, t, J=7.5 Hz), 7.58(2H, t, J=7.8 Hz), 7.60–7.71(7H, m), 7.94(2H, d, J=8.3 Hz), 12.38(1H, s), 12.52(1H, s).

IR(KBr): 1670 cm$^{-1}$.

mp: 247.5–250.0° C.

EXAMPLE 168

Synthesis of 6-benzenesulfonylcarbamoyl-1-(biphenyl-4-ylmethyl)-2-methylaminobenzimidazole (230)

A mixture containing 0.300 g of N-benzenesulfonylcarbamoyl-4-amino-3-(biphenyl-4-ylmethylamino)benzamide, 0.200 g of methyl isothiocyanate, 5 ml of methanol and 5 ml of acetone was stirred at room temperature for 12 hours. Further, 1 ml of 97% sulfuric acid was added thereto, and the mixture was stirred at room temperature for 43 hours. A 20% potassium hydrogencarbonate aqueous solution was added to the reaction solution to render it basic. This reaction solution was then concentrated, and the residue was extracted with ethyl acetate and with water. The organic layer was concentrated, dissolved in chloroform, and precipitated with hexane. The crystals precipitated were separated through filtration, and were dried to give 0.140 g of 6-benzenesulfonylcarbamoyl-1-(biphenyl-4-ylmethyl)-2-methylaminobenzimidazole (230).

Properties of Compound (230):
$^1$H-NMR(DMSO-d6, δ): 2.98(3H, d, J=4.4 Hz), 5.34(2H, s), 7.22(2H, d, J=8.2 Hz), 7.26(1H, d, J=8.4 Hz), 7.34(1H, t, J=7.3 Hz), 7.44(2H, t, J=7.5 Hz), 7.57(2H, t, J=7.6 Hz), 7.59–7.68(6H, m), 7.76(1H, s), 7.95(2H, d, J=7.4 Hz), 12.28(1H, s).

IR(KBr): 1672 cm$^{31\ 1}$.

Mass(FAB): m/e 497(M+1).

mp: 225.0–228.0° C.

EXAMPLE 169

Synthesis of 2-amino-6-benzenesulfonylcarbamoyl-1-(biphenyl-4-ylmethyl)benzimidazole (231)

Ten milliliters of methanol, 10 ml of acetone and 0.395 g of cyanogen bromide were added to 1.500 g of N-benzenesulfonylcarbamoyl-4-amino-3-(biphenyl-4-ylmethylamino)-benzamide, and the mixture was stirred at room temperature for 100 hours and then at 50° C. for 30 hours. The reaction solution was extracted with chloroform and with water. The organic layer was washed six times with water, and was concentrated. The residue was purified through silica-gel column chromatography (eluent: a mixture of ethyl acetate and methanol at a ratio of 9:1) to give 0.135 g of 2-amino-6-benzenesulfonylcarbamoyl-1-(biphenyl-4-ylmethyl)benzimidazole (231).

Properties of Compound (231):
$^1$H-NMR(DMSO-d6, δ): 5.32(2H, s), 6.77(2H, s), 7.05 (1H, d, J=8.8 Hz), 7.21(2H, d, J=8.3 Hz), 7.31–7.38(4H, m), 7.43(2H, t, J=7.5 Hz), 7.58–7.65(6H, m), 7.79–7.82(2H, m).

IR(KBr): 1684 cm$^{-1}$.

Mass(FAB): m/e 483(M+1).

mp: 352.5–355.0° C.

EXAMPLE 170

Synthesis of 6-benzenesulfonylcarbamoyl-1-(biphenyl-4-ylmethyl)-2-n-propylbenzimidazole potassium salt (232)

Triethylamine (0.060 g) and 0.084 g of butyryl chloride were added to a solution of 0.300 g of N-benzenesulfonyl-4-amino-3-(biphenyl-4-ylmethylamino)benzamide in 2 ml of N,N-dimethylformamide, and the mixture was stirred at room temperature for 1.5 hours. The reaction solution was directly purified through silica-gel column chromatography to obtain 0.250 g of N-benzenesulfonyl-3-(biphenyl-4-ylmethylamino)-4-butyrylaminobenzamide. To this compound were added 5 ml of methanol and 0.50 g of 35% hydrochloric acid, and the mixture was stirred at 60° C. for 3 hours. Then, 20% potassium hydrogencarbonate was added thereto to stop the reaction, and the reaction solution was extracted with ethyl acetate and with water. The organic layer was concentrated, and the product was dissolved in a small amount of chloroform. Ether was added thereto for crystallization. The crystals precipitated were separated through filtration, and were dried to give 0.157 g of 6-benzenesulfonylcarbamoyl-1-(biphenyl-4-ylmethyl)-2-n-propylbenzimidazole potassium salt (232).

Properties of Compound (232):
$^1$H-NMR(DMSO-d6, δ): 0.95(3H, t, J=7.4 Hz), 1.77(2H, q, J=7.5 Hz), 2.82(2H, t, J=7.5 Hz), 5.55(2H, s), 7.11(2H, d, J=8.2 Hz), 7.32–7.38(4H, m), 7.43(2H, t, J=7.5 Hz), 7.47 (1H, d, J=8.4 Hz), 7.58–7.64(4H, m), 7.79–7.83(3H, m), 7.96(1H, s).

IR(Nujol): 1592 cm$^{-1}$.

Mass(FAB): m/e 548(M+1).

mp: 279.0–282.0° C.

EXAMPLE 171

Synthesis of 6-benzenesulfonylcarbamoyl-1-(biphenyl-4-ylmethyl)-2-n-heptylbenzimidazole (233)

In the same manner as in Example 170, 0.232 g of 6-benzenesulfonylcarbamoyl-1-(biphenyl-4-ylmethyl)-2-n-heptyl-benzimidazole (233) were formed from 0.400 g of N-benzenesulfonyl-4-amino-3-(biphenyl-4-ylmethylamino) benzamide, 0.080 g of triethylamine and 0.170 g of octanoyl chloride.

Properties of Compound (233):
$^1$H-NMR(DMSO-d6, δ): 0.79(3H, t, J=7.3 Hz), 1.12–1.24 (6H, m), 1.24–1.31(2H, m), 1.66–1.73(2H, m), 2.84(2H, t, J=7.6 Hz), 5.58(2H, s), 7.14(2H, d, J=8.1 Hz), 7.34(2H, t, J=7.6Hz), 7.43(2H, t, J=7.4 Hz), 7.52–7.66(7H, m), 7.75 (1H, d, J=8.8 Hz), 7.95(2H, d, J=7.6 Hz), 8.15(1H, s), 12.45(1H, s).IR(KBr): 1688 cm$^{-1}$.

mp: 112.0–117.5° C.

EXAMPLE 172

Synthesis of 6-benzenesulfonylcarbamoyl-1-(biphenyl-4-ylmethyl)-2-chloromethylbenzimidazole (234)

In the same manner as in Example 170, 0.913 g of 6-benzenesulfonylcarbamoyl-1-(biphenyl-4-ylmethyl)-2- chloromethyl-benzimidazole (234) were formed from 0.300 g of N-benzenesulfonyl-4-amino-3-(biphenyl-4-ylmethylamino)benzamide, 0.060 g of triethylamine and 0.102 of chloroacetyl chloride.

Properties of Compound (234):

$^1$H-NMR(DMSO-d6, δ): 5.10(2H, s), 5.71(2H, s), 7.23 (2H, d, J=8.3 Hz), 7.35(1H, t, J=7.3 Hz), 7.44(2H, t, J=7.5 Hz), 7.60–7.66(6H, m), 7.69(1H, t, J=7.5 Hz), 7.75–7.81 (2H, m), 7.98–8.01(2H, m), 8.16(1H, s), 12.52(1H, s).

IR(KBr): 1700 cm$^{-1}$.

mp: 220.5–223.5° C.

EXAMPLE 173

Synthesis of 6-benzenesulfonylcarbamoyl-1-(biphenyl-4-ylmethyl)-2-methoxymethylbenzimidazole (235)

In the same manner as in Example 170, 0.183 g of 6-benzenesulfonylcarbamoyl-1-(biphenyl-4-ylmethyl)-2-methoxy-methylbenzimidazole (235) were formed from 0.400 g of N-benzenesulfonyl-4-amino-3-(biphenyl-4-ylmethylamino)benzamide, 0.115 g of triethylamine and 0.131 g of methoxyacetyl chloride.

Properties of Compound (235):

$^1$H-NMR(DMSO-d6, δ): 3.31(3H, s), 4.72(2H, s), 5.63 (2H, s), 7.23(2H, d, J=8.3 Hz), 7.35(1H, t, J=7.4 Hz), 7.44(2H, t, J=7.5 Hz), 7.60–7.65(6H, m), 7.70(1H, t, J=7.5 Hz), 7.72–7.79(2H, m), 7.98–8.01(2H, m), 8.18(1H, s), 12.50(1H, s).

IR(KBr): 1690 cm$^{-1}$.

mp: 195.0–198.0° C.

EXAMPLE 174

Synthesis of 6-benzenesulfonylcarbamoyl-1-(biphenyl-4-ylmethyl)-2-i-propylbenzimidazole potassium salt (236)

In the same manner as in Example 170, 0.400 g of N-benzenesulfonyl-4-amino-3-(biphenyl-4-ylmethylamino) benzamide, 0.080 g of triethylamine and 0.112 g of isobutyryl chloride were reacted as starting materials. The crude product was dissolved in a mixed solvent of methanol and a 20% potassium hydrogencarbonate aqueous solution, and the pH was adjusted to 7 with 10% hydrochloric acid. The crystals precipitated were crystals of 6-benzenesulfonylcarbamoyl-1-(biphenyl-4-ylmethyl)-2-i-propylbenzimidazole potassium salt [(236), 0.167 g].

Properties of Compound (236):

$^1$H-NMR(DMSO-d6, δ): 1.26(6H, d, J=6.8 Hz), 3.25–3.40(1H, m), 5.58(2H, s), 7.09(2H, d, J=8.3 Hz), 7.32–7.37(4H, m), 7.43(2H, t, J=7.5 Hz), 7.48(1H, d, J=8.4 Hz), 7.58–7.64(4H, m), 7.79–7.83(3H, m), 7.95(1H, s).

IR(Nujol): 1592 cm$^{-1}$.

Mass(FAB): m/e 548(M+1).

mp: 310.1–312.7° C.

EXAMPLE 175

Synthesis of 6-benzenesulfonylcarbamoyl-1-(biphenyl-4-ylmethyl-2-methylthiobenzimidazole (237)

A 20% potassium hydroxide aqueous solution (0.323 g), 2 ml of water and 0.123 g of methyl iodide were added to a solution of 0.310 g of 6-benzenesulfonylcarbamoyl-1-(biphenyl-4-ylmethyl)-2-mercaptobenzimidazole in 5 ml of methanol in this order, and the mixture was stirred at room temperature for 2 hours. The reaction solution was adjusted to a pH of from 5 to 6 with 10% hydrochloric acid. The crystals precipitated were separated through filtration, and were dried to give 0.281 g of 6-benzenesulfonylcarbamoyl-1-(biphenyl-4-ylmethyl)-2-methylthio-benzimidazole (237).

Properties of Compound (237):

$^1$H-NMR(DMSO-d6, δ): 2.75(3H, s), 5.48(2H, s), 7.25 (2H, d, J=8.3 Hz), 7.35(1H, t, J=7.4 Hz), 7.44(2H, t, J=7.5 Hz), 7.60–7.66(7H, m), 7.68–7.75(2H, m), 7.82–7.99(2H, m), 8.19(1H, d, J=1.6 Hz), 12.43(1H, s).

IR(KBr): 1685 cm$^{-1}$.

mp: 218.8–220.4° C.

EXAMPLE 176

Synthesis of 6-benzenesulfonylcarbamoyl-1-(biphenyl-4-ylmethyl)-2-ethylthiobenzimidazole (238)

In the same manner as in Example 175, 0.225 g of 6-benzenesulfonylcarbamoyl-1-(biphenyl-4-ylmethyl)-2-ethylthio-benzimidazole (238) were formed from 0.240 g of 6-benzenesulfonylcarbamoyl-1-(biphenyl-4-ylmethyl)-2-mercapto-benzimidazole and 0.117 g of ethyl iodide.

Properties of Compound (238):

$^1$H-NMR(DMSO-d6, δ): 1.39(3H, t, J=7.3 Hz), 3.37(2H, q, J=7.3 Hz), 5.47(2H, s), 7.24(2H, d, J=8.1 Hz), 7.35(1H, t, J=7.1 Hz), 7.44(2H, t, J=7.6 Hz), 7.57–7.68(8H, m), 7.75(1H, d, J=8.4 Hz), 7.98(2H, d, J=7.5 Hz), 8.15(1H, s), 12.43(1H, s).

IR(KBr): 1686 cm$^{-1}$.

mp: 125.5–129.5° C.

EXAMPLE 177

Synthesis of 6-benzenesulfonylcarbamoyl-1-(biphenyl-4-ylmethyl)-2-n-propylthiobenzimidazole (239)

In the same manner as in Example 175, 0.156 g of 6-benzenesulfonylcarbamoyl-1-(biphenyl-4-ylmethyl)-2-n-propylthio-benzimidazole (239) were formed from 0.220 g of 6-benzenesulfonylcarbamoyl-1-(biphenyl-4-ylmethyl)-2-mercapto-benzimidazole and 0.117 g of n-propyl iodide.

Properties of Compound (239):

$^1$H-NMR(DMSO-d6, δ): 0.97(3H, t, J=7.4 Hz), 1.76(2H, q, J=7.2 Hz), 3.29–3.36(2H, m), 5.48(2H, s), 7.24(2H, d, J=8.3 Hz), 7.35(1H, t, J=7.3 Hz), 7.44(2H, t, J=7.4 Hz), 7.58–7.71(8H, m), 7.74(1H, dd, J=8.5 and 1.7 Hz), 7.99(2H, d, J=7.7 Hz), 8.17(1H, s), 12.43(1H, s).

IR(KBr): 1690 cm$^{-1}$.

mp: 106.0–111.5° C.

EXAMPLE 178

Synthesis of 6-benzenesulfonylcarbamoyl-1-(biphenyl-4-ylmethyl)-2-n-hexylthiobenzimidazole (240)

In the same manner as in Example 175, 0.212 g of 6-benzenesulfonylcarbamoyl-1-(biphenyl-4-ylmethyl)-2-n-hexylthio-benzimidazole (240) were formed from 0.250 g of 6-benzenesulfonylcarbamoyl-1-(biphenyl-4-ylmethyl)-2-mercapto-benzimidazole and 0.166 g of n-hexyl iodide.

Properties of Compound (240):

$^1$H-NMR(DMSO-d6, δ): 0.82(3H, t, J=7.9 Hz), 1.19–1.33 (4H, m), 1.33–1.44(2H, m), 1.68–1.75(2H, m), 3.30–3.43 (2H, m), 5.48(2H, s), 7.23(2H, d, J=8.2 Hz), 7.35(1H, t, J=7.1 Hz), 7.44(2H, t, J=7.6 Hz), 7.60–7.75(9H, m), 8.00 (2H, d, J=7.7 Hz), 8.19(1H, s), 12.44(1H, s).

IR(KBr): 1688 cm$^{-1}$.

mp: 139.5–141.0° C.(decomp.)

EXAMPLE 179

Synthesis of 6-benzenesulfonylcarbamoyl-1-(biphenyl-4-ylmethyl)-benzimidazole (241)

A mixture of 0.400 g of N-benzenesulfonyl-4-amino-3-(biphenyl-4-ylmethylamino)benzamide and 2 ml of formic acid was stirred at 90° C. for 3 hours. The reaction solution was concentrated, and was precipitated with methanol. The crystals precipitated were separated through filtration, and were dried to give 0.243 g of 6-benzenesulfonylcarbamoyl-1-(biphenyl-4-ylmethyl)benzimidazole (241).

Properties of Compound (241):

$^1$H-NMR(DMSO-d6, δ): 5.60(2H, s), 7.35(1H, t, J=7.2 Hz), 7.39(2H, d, J=8.2 Hz), 7.44(2H, t, J=7.6Hz), 7.61–7.77 (9H, m), 8.00(2H, d, J=7.7 Hz), 8.26(1H, s), 8.66(1H, s), 12.5(1H, s).

IR(KBr): 1683 cm$^{-1}$.

mp: 141.5–143.6° C.

EXAMPLE 180

Synthesis of 1-(4-benzyloxybenzyl)-2-methyl-6-[(2-pyridylmethyl)carbonyl]benzimidazole (242)

Four milliliters of acetic acid and 8 ml of ethanol were added to 0.434 g of N-(2-pyridylmethyl)-4-acetylamino-3-(4-benzyloxybenzylamino)benzamide, and the mixture was stirred at 90° C. for 7 hours. The reaction solution was concentrated under reduced pressure. Ethyl acetate and ether were added to the residue for crystallization. The crystals were separated through filtration, and were dried to give 0.375 g of 1-(4-benzyloxybenzyl)-2-methyl-6-[(2-pyridylmethyl)carbamoyl]-benzimidazole (242).

Properties of Compound (242):

$^1$H-NMR(CDCl$_3$, δ): 2.59(3H, s), 4.78(2H, d, J=4.8 Hz), 5.01(2H, s), 5.31(2H, s), 6.89(2H, d, J=8.7 Hz), 6.99(2H, d, J=8.6 Hz), 7.21(1H, dd, J=5.1 and 7.4 Hz), 7.29–7.42(6H, m), 7.62(1H, br t), 7.65–7.75(3H, m), 7.98(1H, s), 8.57(1H, d, J=4.1 Hz).

IR(KBr): 1640 cm$^{-1}$.

mp: 169.0–170.0° C.

EXAMPLE 181

Synthesis of 2-methyl-1-(3,4-methylenedioxybenzyl)-6-[(2-pyridylmethyl)carbamoyl]benzimidazole (243)

Two milliliters of acetic acid and 5 ml of methanol were added to 0.490 g of N-(2-pyridylmethyl)-4-acetylamino-3-(3,4-methylenedioxybenzylamino)benzamide, and the mixture was stirred at 70° C. for 8 hours. The reaction solution was concentrated under reduced pressure. The residue was purified through silica-gel column chromatography (eluent: a mixture of ethyl acetate and methanol at a ratio of 9:1), and was then crystallized from ethyl acetate. The crystals were separated through filtration, and were dried to give 0.270 g of 2-methyl-1-(3,4-methylenedioxybenzyl)-6-[(2-pyridylmethyl)carbamoyl]-benzimidazole (243).

Properties of Compound (243):

$^1$H-NMR(CDCl$_3$, δ): 2.59(3H, s), 4.78(2H, d, J=4.8 Hz), 5.28(2H, s), 5.93(2H, s), 6.51(1H, d, J=1.6 Hz), 6.55(1H, dd, J=1.4 and 7.9 Hz), 6.72(2H, d, J=8.0 Hz), 7.22(1H, dd, J=6.7 and 5.0 Hz), 7.34(1H, d, J=7.7 Hz), 7.62(1H, br t), 7.67–7.75 (3H, m), 7.96(1H, d, J=1.1 Hz), 8.58(1H, d, J=4.9 Hz).

IR(KBr): 1637 cm$^{-1}$.

mp: 190.5–192.0° C.

EXAMPLE 182

Synthesis of 2-methyl-6-[(2-pyridylmethyl)carbamoyl]-1-[4-(1,2,3-thiadiazol-4-yl)benzyl]benzimidazole (244)

In the same manner as in Example 180, 0.33 g of 2-methyl-6-[(2-pyridylmethyl)carbamoyl]-1-[4-(1,2,3-thiadiazol-4-yl)benzyl]benzimidazole (244) were formed from 0.50 g of N-(2-pyridylmethyl)-4-acetylamino-3-[4-(1,2,3-thiadiazol-4-yl)benzylamino]benzamide.

Properties of Compound (244):

$^1$H-NMR(CDCl$_3$, δ): 2.58(3H, s), 4.58(2H, d, J=5.9 Hz), 5.62(2H, s), 7.24(1H, dd, J=7.3 and 5.0 Hz), 7.28–7.33(3H, m), 7.64(1H, d, J=8.4 Hz), 7.73(1H, dt, J=7.7 and 1.6 Hz), 7.81(1H, dd, J=8.4 and 1.3 Hz), 8.10(1H, d, J=8.2 Hz), 8.13(1H, s), 8.49(1H, d, J=4.2 Hz), 9.04(1H, t, J=5.9 Hz), 9.58(1H, s).

IR(KBr): 1642 cm$^{-1}$.

mp: 216.0–217.0° C.

EXAMPLE 183

Synthesis of 6-benzenesulfonylcarbamoyl-1-(2,4-difluorobenzyl-2-methylbenzimidazole (245)

N-benzenesulfonyl-4-acetylamino-3-(2,4-difluorobenzylamino)benzamide (0.370 g) was dissolved in a mixed solvent of 3.3 g of 10% hydrochloric acid, 6 ml of methanol and 4 ml of water, and 0.5 g of 35% hydrochloric acid were further added thereto. The mixture was stirred at 60° C. for 3 hours. A 20% potassium hydrogencarbonate aqueous solution was added to the reaction solution to render it basic. Then, this solution was adjusted to a pH of from 5 to 6 with 10% hydrochloric acid. The crystals precipitated were separated through filtration, and were dried to give 0.182 g of 6-benzenesulfonylcarbamoyl-1-(2,4-difluorobenzyl-2-methylbenzimidazole (245).

Properties of Compound (245):

$^1$H-NMR(DMSO-d6, δ): 2.53(3H, s), 5.56(2H, s), 6.95–7.01(1H, m), 7.04(1H, dt, J=8.7 and 1.4 Hz), 7.32(1H, dt, J=10.7 and 2.1 Hz), 7.59–7.66(3H, m), 7.68–7.74(2H, m), 8.00(2H, d, J=8.1 Hz), 8.13(1H, s), 12.43(1H, s).IR (KBr): 1686 cm$^{-1}$.

mp: 234.5–235.5° C.(decomp.)

EXAMPLE 184

Synthesis of 6-benzenesulfonylcarbamoyl-1-(biphenyl-4-ylmethyl)-2-phenylbenzimidazole (246)

Triethylamine (0.115 g) and 0.200 g of benzoyl chloride were added to a solution of 0.500 g of N-benzenesulfonyl-4-amino-3-(biphenyl-4-ylmethylamino)benzamide in 5 ml of N,N-dimethylformamide. The mixture was stirred at room temperature for 15 hours. A potassium hydrogencarbonate aqueous solution was added thereto to stop the reaction. The solvent was distilled off under reduced pressure. The residue was dissolved in a mixture of water and methanol, and the solution was adjusted to a pH of from 5 to 6 with 10% hydrochloric acid. The crystals precipitated were collected, and were dried to obtain 0.393 g of crude N-benzenesulfonyl-4-benzoylamino-3-(biphenyl-4-ylmethyl-amino)benzamide. This crude product was converted to 6-benzenesulfonylcarbamoyl-1-(biphenyl-4-ylmethyl)-2-phenyl-benzimidazole [(246), 0.270 g] in the same manner as in Example 183.

Properties of Compound (246):

$^1$H-NMR(DMSO-d6, δ): 5.70(2H, s), 7.07(2H, d, J=8.2 Hz), 7.32–7.37(1H, m), 7.43(2H, t, J=5.7 Hz), 7.53–7.58 (2H, m), 7.58–7.65(7H, m), 7.68–7.72(1H, m), 7.77(2H, dd, J=7.5 and 1.5 Hz), 7.81–7.83(2H, m), 7.98–8.02(2H, m), 8.22(1H, s), 12.47(1H, s).

IR(KBr): 1690 cm$^{-1}$.

mp: 138.5–139.5° C.

EXAMPLE 185

Synthesis of 6-benzenesulfonylcarbamoyl-2-methyl-1-(2-nitrobenzyl)benzimidazole (247)

In the same manner as in Example 183, 0.237 g of 6-benzenesulfonylcarbamoyl-2-methyl-1-(2-nitrobenzyl) benzimidazole (247) were formed from 0.79 g of N-benzenesulfonyl-4-acetylamino-3-(2-nitrobenzylamino) benzamide.

Properties of Compound (247):

$^1$H-NMR(DMSO-d6, δ): 2.48(3H, s), 5.01(2H, s), 5.93 (2H, s), 6.28–6.30(1H, m), 7.55–7.62(4H, m), 7.64–7.74 (3H, m), 7.97(2H, d, J=8.0 Hz), 8.10(1H, s), 8.22–8.28(1H, m), 12.39(1H, s).

IR(KBr): 1686 cm$^{-1}$.

mp: 269.5–272.5(decomp.)

EXAMPLE 186

Synthesis of 6-benzenesulfonylcarbamoyl-2-methyl-1-benzylbenzimidazole (248)

In the same manner as in Example 183, 0.222 g of 6-benzenesulfonylcarbamoyl-2-methyl-1-benzylbenzimidazole (248) were formed from 0.38 g of N-benzenesulfonyl-4-acetylamino-3-benzylaminobenzamide.

Properties of Compound (248):

$^1$H-NMR(DMSO-d6, δ): 2.54(3H, s), 5.55(2H, s), 7.12 (2H, d, J=7.9 Hz), 7.28(1H, t, J=7.3 Hz), 7.34(2H, t, J=7.0 Hz), 7.61–7.66(3H, m), 7.69–7.76(2H, m), 8.00(2H, d, J=7.9 Hz), 8.18(1H, s), 12.43(1H, s).

IR(KBr): 1695 cm$^{-1}$.

mp: 260.0–262.0° C.(decomp.)

EXAMPLES 187 AND 188

Synthesis of 6-benzenesulfonylcarbamoyl-2-methyl-1-(4-nitrobenzyl)benzimidazole (249) and 6-benzenesulfonylcarbamoyl-2-methyl-1-(4-nitrobenzyl)benzimidazole potassium salt (250)

In the same manner as in Example 183, 0.255 g of 6-benzenesulfonylcarbamoyl-2-methyl-1-(4-nitrobenzyl) benzimidazole (249) were formed as a crystal from 0.505 g of N-benzenesulfonyl-4-acetylamino-3-(4-nitrobenzylamino)benzamide. Further, the filtrate was concentrated to form 0.136 g of 6-benzenesulfonylcarbamoyl-2-methyl-1-(4-nitrobenzyl)benzimidazole potassium salt (250) as a crystal.

Properties of Compound (249):

$^1$H-NMR(DMSO-d6, δ): 2.50(3H, s), 5.70(2H, s), 7.30 (2H, d, J=8.7 Hz), 7.52(2H, t, J=7.6 Hz), 7.57(2H, d, J=8.3 Hz), 7.76(1H, dd, J=8.4 and 1.4 Hz), 7.92(2H, d, J=7.3 Hz), 8.05(1H, s), 8.20(2H, d, J=8.7 Hz), 12.43(1H, s).

IR(KBr): 1686 cm.

mp: 164.5–167.0° C.

Properties of Compound (250):

$^1$H-NMR(DMSO-d6, δ): 2.51(3H, s), 5.68(2H, s), 7.28 (2H, d, J=8.5 Hz), 7.32–7.41(3H, m), 7.46(1H, d, J=8.4 Hz), 7.78–7.86(3H, m), 7.91(1H, s), 8.20(2H, d, J=8.5 Hz).

IR(KBr): 1594 cm$^{-1}$.

mp: 326.0–328.0° C.(decomp.)

EXAMPLE 189

Synthesis of 6-benzenesulfonylcarbamoyl-1-(4-benzyloxybenzyl)-2-methylbenzimidazole (251)

A mixture containing 0.500 g of N-benzenesulfonyl-3-amino-4-acetylaminobenzamide potassium salt, 0.470 g of 4-benzyloxybenzyl bromide, 0.925 g of a 20% potassium hydrogencarbonate aqueous solution and 3 ml of N,N-dimethylformamide was stirred at 90° C. for 1 hour. The reaction solution was concentrated, and was purified through silica-gel column chromatography (eluent: a mixture of ethyl acetate and methanol at a ratio of 9:1) to obtain crude N-benzenesulfonyl-4-acetylamino-3-(4-benzyloxybenzylamino)benzamide. This crude product was cyclized in the same manner as in Example 183 to give 0.160 g of 6-benzenesulfonylcarbamoyl-1-(4-benzyloxybenzyl)-2-methylbenzimidazole (251).

Properties of Compound (251):

$^1$H-NMR(DMSO-d6, δ): 2.54(3H, s), 5.05(2H, s), 5.44 (2H, s), 7.09(2H, d, J=8.7 Hz), 7.32(2H, d, J=7.0 Hz), 7.29–7.44(5H, m), 7.58–7.67(3H, m), 7.68–7.75(2H, m), 7.79–8.02(2H, m), 8.18(1H, s), 12.46(1H, s).

IR(KBr): 1685 cm$^{-1}$.

mp: 111.0–114.0° C.

EXAMPLE 190

Synthesis of 2-methyl-5-[(2-pyridylmethyl) carbamoyl]-benzimidazole (252)

Five-percent palladium on carbon (0.10 g) was added to a mixture of 1.00 g of crude N-(2-pyridylmethyl)-4-acetylamino-3-nitrobenzamide, 8 ml of acetic acid and 12 ml of ethanol, and the solution was stirred in a hydrogen atmosphere at 80° C. for 7 hours. The solid material was separated through filtration, and the filtrate was concentrated. Ethyl acetate was added to the residue for crystallization. The crystals were separated through filtration, and were dried to give 0.57 g of 2-methyl-5-[(2-pyridylmethyl) carbamoyl]benzimidazole (252).

Properties of Compound (252):

$^1$H-NMR(CDCl$_3$, δ): 2.52(3H, s), 4.59(2H, d, J=5.9 Hz), 7.26(1H, dd, J=7.1 and 5.1 Hz), 7.33(1H, d, J=7.8 Hz), 7.50(1H, d, J=8.4 Hz), 7.72–7.78(2H, m), 8.08(1H, s), 8.51(1H, d, J=4.8 Hz), 9.04(1H, t, J=5.8 Hz), 12.44(1H, s).

IR(KBr): 1641 cm$^{-1}$.

mp: 212.0–215.0° C.

EXAMPLES 191 AND 192

Synthesis of 1-benzenesulfonyl-2-methyl-6-[(2-pyridylmethyl)-carbamoyl]benzimidazole (253) and 1-benzenesulfonyl-2-methyl-5-[2-pyridylmethyl)carbamoyl]benzimidazole (254)

Ten milliliters of dichloromethane and 0.760 g of triethylamine were added to 1.00 g of 1-methyl-5-[(2-pyridylmethyl)carbamoyl]benzimidazole, and 0.994 g of benzenesulfonyl chloride were added dropwise thereto. The mixture was stirred for 3 hours, and the reaction solution was washed three times with water and then with a sodium hydrogencarbonate aqueous solution. The organic layer was concentrated under reduced pressure, and was purified through silica-gel column chromatography (eluent: a mixture of ethyl acetate and methanol at a ratio of 9:1) to obtain 1.380 g of a mixture of 1-benzenesulfonyl-2-methyl-6-[(2-pyridylmethyl)-carbamoyl]benzimidazole and 1-benzenesulfonyl-2-methyl-5-[2-pyridylmethyl)carbamoyl]benzimidazole. This mixture was further purified through medium-pressure silica-gel column chromatography (eluent: a mixture of ethyl acetate and methanol at a ratio of 100:3) to give 0.550 g of oily 1-benzenesulfonyl-2-methyl-6-[(2-pyridylmethyl)carbamoyl]benzimidazole (253) and 0.540 g of oily 1-benzenesulfonyl-2-methyl-5-[2-pyridylmethyl)carbamoyl]benzimidazole (254). These oily products were dissolved in 1.5 ml of methylene chloride, and were crystallized from diethyl ether.

Properties of Compound (253):

$^1$H-NMR(CDCl$_3$, δ): 2.84(3H, s), 4.81(2H, d, J=4.8 Hz), 7.24(1H, dd, J=5.1 and 7.3 Hz), 7.37(1H, d, J=7.7 Hz), 7.53(2H, dd, J=7.9 and 7.5 Hz), 7.63–7.74(2H, m), 7.85(1H, dd, J=8.4 and 1.2 Hz), 7.97(2H, dd, J=9.6 and 1.1 Hz), 8.58–8.61(2H, m).

IR(KBr): 1636 cm$^{-1}$.

mp: 163.4–164.3° C.

Properties of Compound (254):

$^1$H-NMR(CDCl$_3$, δ): 2.83(3H, s), 4.78(2H, d, J=4.7 Hz), 7.23(1H, dd, J=4.9 and 8.6 Hz), 7.34(1H, d, J=7.9 Hz), 7.53(2H, dd, J=7.5 and 8.4 Hz), 7.64–7.75(3H, m), 7.91–7.96(3H, m),8.10(1H, d, J=9.1 Hz), 8.14(1H, d, J=1.3 Hz), 8.56(1H, dd, J=4.9 and 1.0 Hz).

IR(KBr): 1657 cm$^{-1}$.

mp: 88.3–91.3° C.

EXAMPLES 193 AND 194

Synthesis of 2-methyl-1-(4-nitrobenzyl)-6-[(2-pyridylmethyl)-carbamoyl]benzimidazole (255) and 2-methyl-1-(4-nitrobenzyl)-5-[(2-pyridylmethyl)carbamoyl]benzimidazole (256)

Ten milliliters of N,N-dimethylformamide, 3.24 g of 4-nitrobenzyl bromide and 2.52 g of sodium hydrogencarbonate were added to 3.56 g of 2-methyl-5-[2-pyridylmethyl)-carbamoyl]benzimidazole, and the mixture was heated at 80° C. for 2 hours. The reaction solution was separated with the addition of chloroform and water. The organic layer was concentrated under reduced pressure, and was purified through silica-gel column chromatography (eluent: a mixture of ethyl acetate and methanol at a ratio of 4:1) to obtain a mixture of 2-methyl-1-(4-nitrobenzyl)-6-[(2-pyridylmethyl)carbamoyl]benzimidazole and 2-methyl-1-(4-nitrobenzyl)-5-[(2-pyridylmethyl)carbamoyl]-benzimidazole. This mixture was further separated into position isomers through medium-pressure silica-gel column chromatography (eluent: a mixture of ethyl acetate and methanol at a ratio of 85:15). Each of the position isomers was recrystallized from a mixed solvent of chloroform and diethyl ether to give 1.37 g of 2-methyl-1-(4-nitrobenzyl)-6-[(2-pyridylmethyl)carbamoyl]-benzimidazole (255) and 1.19 g of 2-methyl-1-(4-nitrobenzyl)-5-[(2-pyridylmethyl)carbamoyl]benzimidazole (256).

Properties of Compound (255):

$^1$H-NMR(CDCl$_3$, δ): 2.59(3H, s), 4.77(2H, d, J=4.8 Hz), 5.48(2H, s), 7.09(2H, d, J=8.7 Hz), 7.22(1H, dd, J=7.2 and 4.9 Hz), 7.33(1H, d, J=7.8 Hz), 7.66–7.70(2H, m), 7.73(1H, dd, J=8.4 and 1.5 Hz), 7.78(1H, d, J=8.4 Hz), 7.91(1H, d, J=1.2 Hz), 8.15–8.19(2H, m), 8.56(1H, d, J=4.6 Hz)

IR(KBr): 1652 cm$^{-1}$.

mp: 116.1–119.1° C.

Properties of Compound (256):

$^1$H-NMR(CDCl$_3$, δ): 2.59(3H, s), 4.79(2H, d, J=4.8 Hz), 5.46(2H, s), 7.17–7.24(4H, m), 7.35(1H, d, J=7.8 Hz), 7.69(2H, dt, J=7.6 and 1.7 Hz), 7.83(1H, d, J=8.4 Hz), 8.19(2H, d, J=8.6 Hz), 8.26(1H, d, J=1.3 Hz), 8.57(1H, d, J=4.8 Hz)

IR(KBr): 1634 cm$^{-1}$.

mp: 203.7–206.3° C.

EXAMPLES 195 AND 196

Synthesis of 2-methyl-1-(2-phenylethyl)-6-[(2-pyridylmethyl)-carbamoyl]benzimidazole (257) and 2-methyl-1-(2-phenylethyl)-5-[(2-pyridylmethyl)carbamoyl]benzimidazole (258)

In the same manner as in Examples 193 and 194, 0.30 g of 2-Methyl-1-(2-phenylethyl)-6-[(2-pyridylmethyl)carbamoyl]-benzimidazole (257) and 0.23 g of 2-methyl-1-(2-phenylethyl)-5-[(2-pyridylmethyl)carbamoyl]benzimidazole (258) were formed from 2.00 g of 2-methyl-5-[(2-pyridylmethyl)carbamoyl]benzimidazole and 15.0 g of phenetyl iodide.

Properties of Compound (257):

$^1$H-NMR(CDCl$_3$, δ): 2.17(3H, s), 3.10(2H, t, J=6.8 Hz), 4.35(2H, t, J=6.8 Hz), 4.82(2H, d, J=4.8 Hz), 6.92–6.97(2H, m), 7.21–7.28(4H, m), 7.38(1H, d, J=7.8 Hz), 7.78(1H, br t), 7.68–7.73(3H, m), 7.98(1H, d, J=0.9 Hz), 8.60(1H, dd, J=1.0 and 4.9 Hz)

IR(neat): 1633 cm$^{-1}$ liquid.

Properties of Compound (258):

$^1$H-NMR(CDCl$_3$, δ): 2.19(3H, s), 3.08(2H, t, J=6.8 Hz), 4.35(2H, t, J=6.8 Hz), 4.81(2H, d, J=4.8 Hz), 6.91–6.96(2H, m), 7.19–7.26(4H, m), 7.31(1H, d, J=8.4 Hz), 7.36(1H, d, J=7.8 Hz), 7.64–7.73(2H, m), 7.85(1H, dd, J=1.7 and 8.4 Hz), 8.19(1H, d, J=1.3 Hz), 8.58(1H, d, J=4.0 Hz)

IR(neat): 1643 cm$^{-1}$ liquid.

EXAMPLES 197 AND 198

Synthesis of 1-(2,4-difluorobenzyl)-2-methyl-6-((2-pyridylmethyl)carbamoyl]benzimidazole (259) and 1-(2,4-difluorobenzyl)-2-methyl-5-[(2-pyridylmethyl)carbamoyl]benzimidazole (260)

In the same manner as in Examples 193 and 194, 0.25 g of 1-(2,4-difluorobenzyl)-2-methyl-6-[(2-pyridylmethyl)carbamoyl]-benzimidazole (259) and 0.25 g of 1-(2,4-difluorobenzyl)-2-methyl-5-[(2-pyridylmethyl)carbamoyl]benzimidazole (260) were formed from 1.00 g of 2-methyl-5-[(2-pyridylmethyl)-carbamoyl]benzimidazole and 1.00 g of 2,4-difluorobenzyl bromide.

Properties of Compound (259):
$^1$H-NMR(CDCl$_3$, δ): 2.62(3H, s), 4.78(2H, d, J=4.7 Hz), 5.38(2H, s), 6.73–6.79(2H, m), 6.88(1H, t, J=10.0 Hz), 7.24(1H, dd, J=7.3 and 5.1 Hz), 7.35(1H, d, J=7.8 Hz), 7.67–7.76(4H, m), 7.97(1H, s), 8.58(1H, d, J=4.4 Hz).IR (KBr): 1642 cm$^{-1}$.

mp: 98.0–104.0° C.

Properties of Compound (260):
$^1$H-NMR(CDCl$_3$, δ): 2.62(3H, s), 4.79(2H, d, J=4.7 Hz), 5.35(2H, s), 6.72–6.81(2H, m), 6.89(1H, t, J=9.8 Hz), 7.22 (1H, t, J=6.2 Hz), 7.28(1H, d, J=8.4 Hz), 7.34(1H, d, J=7.8 Hz), 7.63–7.71(2H, m), 7.83(1H, d, J=8.4 Hz), 7.97(1H, s), 8.57(1H, d, J=4.7 Hz)

IR(KBr): 1647 cm$^{-1}$ mp: 143.5–144.0° C.

EXAMPLES 199 AND 200

Synthesis of 1-(4-aminobenzyl)-2-methyl-6-[(2-pyridylmethyl)-carbamoyl]benzimidazole (261) and 1-(4-aminobenzyl)-2-methyl-5-[(2-pyridylmethyl) carbamoyl]benzimidazole (262)

Thirty milliliters of methanol and 0.20 g of 5% palladium on carbon were added to 2.32 g of a mixture of 2-methyl-1-(4-nitrobenzyl)-6-[(2-pyridylmethyl)carbamoyl] benzimidazole and 2-methyl-1-(4-nitrobenzyl)-5-[(2-pyridylmethyl)carbamoyl]-benzimidazole, and the mixture was stirred in a hydrogen atmosphere at room temperature until the starting material disappeared. The solid material was separated through filtration, and the filtrate was concentrated. The resulting residue was purified through medium-pressure silica-gel column chromatography (eluent: a mixture of ethyl acetate and methanol at a ratio of 85:15) to separate 1-(4-aminobenzyl)-2-methyl-6-[(2-pyridylmethyl)carbamoyl]benzimidazole and 1-(4-aminobenzyl)-2-methyl-5-[(2-pyridylmethyl)carbamoyl] benzimidazole. Each of these compounds was crystallized from a mixed solvent of chloroform and diethyl ether. The crystals were separated through filtration, and were dried to give 0.354 g of 1-(4-aminobenzyl)-2-methyl-6-[(2-pyridylmethyl)carbamoyl]-benzimidazole (261) and 0.330 g of 1-(4-aminobenzyl)-2-methyl-5-[(2-pyridylmethyl) carbamoyl]benzimidazole (262).

Properties of Compound (261):
$^1$H-NMR(CDCl$_3$, δ): 3.00(3H, s), 4.98(2H, s), 5.88(2H, s), 7.55(2H, d, J=8.6 Hz), 7.69(2H, d, J=8.6 Hz), 7.90(1H, d, J=8.6 Hz), 7.96(1H, dt, J=7.1 and 0.6 Hz), 8.12(1H, J=8.0 Hz), 8.18(1H, dd, J=8.5 and 1.4 Hz), 8.55(1H, dt, J=8.0 and 1.7 Hz), 8.62(1H, d, J=1.1 Hz), 8.77(1H, dd, J=5.9 and 1.1 Hz)

IR(KBr): 1643 cm$^{-1}$ mp: 180.0–181.0° C.

Properties of Compound (262):
$^1$H-NMR(CDCl$_3$, δ): 3.00(3H, s), 5.01(2H, s), 5.83(2H, s), 7.47(2H, d, J=8.5 Hz), 7.78(2H, d, J=8.5 Hz), 7.78(1H, d, J=8.9 Hz), 7.97(1H, dt, J=7.2 and 0.7 Hz), 8.13(1H, J=8.1 Hz), 8.15(1H, d, J=8.9 Hz), 8.51(1H, s), 8.55(1H, dt, J=7.9 and 1.6 Hz), 8.77(1H, d, J=5.8 Hz)

IR(KBr): 1639, 1612 cm$^{-1}$ mp: 168.0–171.0° C.

EXAMPLE 201

Synthesis of 1-[4-(benzenesulfonylamino)benzyl]-2-methyl-6-[(2-pyridylmethyl)carbamoyl] benzimidazole (263)

Triethylamine (0.185 g) and benzenesulfonyl chloride (0.210 g) were added to a solution of 0.340 g of 1-(4-aminobenzyl)-2-methyl-6-[(2-pyridylmethyl)carbamoyl]-benzimidazole in 10 ml of chloroform, and the mixture was stirred at room temperature for 8 hours. Water was added thereto to stop the reaction, and the reaction mixture was extracted with chloroform. The organic layer was washed three times with water, dried, and concentrated. The residue was then purified through silica-gel column chromatography (eluent: a mixture of ethyl acetate and methanol at a ratio of 100:1 to 4:1) to give 0.300 g of 1-[4-(benzenesulfonylamino)benzyl]-2-methyl-6-[(2-pyridylmethyl)carbamoyl]benzimidazole (263).

Properties of Compound (263):
$^1$H-NMR(CDCl$_3$, δ): 2.53(3H, s), 4.78(2H, d, J=4.8 Hz), 5.28(2H, s), 6.90(2H, t, J=87.6 Hz), 6.99(2H, d, J=8.5 Hz), 7.11(1H, s), 7.23(1H, dd, J=5.5 and 7.2 Hz), 7.34(1H, d, J=7.7 Hz), 7.40(2H, t, J=8.1 Hz), 7.50(1H, t, J=7.5 Hz), 7.66–7.74(6H, m), 7.92(1H, s), 8.56(1H, d, J=4.8 Hz)

IR(KBr): 1642 cm$^{-1}$ mp: 204.4–206.5° C.

EXAMPLE 202

Synthesis of 6-benzenesulfonylaminomethyl-1-(2-chlorobenzyl)-2-methylbenzimidazole (264)

To a solution of 0.667 g of benzenesulfonic acid amide in 5 ml of N,N-dimethylformamide were added 0.127 g of 60% sodium hydride at room temperature, and the mixture was stirred for 1 hour. Further, 0.648 g of 1-(2-chlorobenzyl)-6-chloromethyl-2-methylbenzimidazole hydrochloride were added thereto, and the mixture was stirred at room temperature for 18 hours. Water was added to the reaction solution to stop the reaction, and the solvent was distilled off under reduced pressure. The residue was extracted with ethyl acetate and with water. The organic layer was concentrated, and was purified through silica-gel column chromatography (eluent: ethyl acetate) to give 0.240 g of 6-benzenesulfonylaminomethyl-1-(2-chlorobenzyl)-2-methyl-benzimidazole (264).

Properties of Compound (264):
$^1$H-NMR(DMSO-d6, δ): 2.42(3H, s), 4.02(2H, m), 4.02 (2H, m), 5.44(2H, s), 6.36(1H, d, J=7.7 Hz), 7.03(1H, d, J=8.4 Hz), 7.18(1H, s), 7.21(1H, t), 7.33(1H, t), 7.59–7.43 (5H, m), 7.73(2H, d, J=7.5 Hz), 8.08(1H, s)

IR(KBr): 1522 cm$^{-1}$ mp: 164.5–167.0° C.

EXAMPLES 203

Synthesis of 1-(biphenyl-4-ylmethyl)-2-methyl-6-[(2-pyridylmethyl)aminomethyl]benzimidazole (265)

2-Aminomethylpyridine (0.372 g) was added to a solution of 0.597 g of 1-(biphenyl-4-ylmethyl)-6-chloromethyl-2-methylbenzimidazole and 0.350 g of potassium carbonate in 3 ml of N,N-dimethylformamide, and the mixture was stirred at 60° C. for 2 hours. The reaction mixture was extracted with water and with ethyl acetate. The organic layer was washed twice with water, and the solvent was distilled off under reduced pressure. The resulting residue was purified through silica-gel column chromatography (eluent: a mixture of chloroform and methanol at a ratio of 9:1), and was recrystallized from a mixed solvent of ethyl acetate and hexane to give 0.300 g of 1-(biphenyl-4-ylmethyl)-2-methyl-6-[2-pyridylmethyl)aminomethyl] benzimidazole (265).

Properties of Compound (265):

$^1$H-NMR(CDCl$_3$, δ): 2.57(3H, s), 3.91(2H, s), 3.93(2H, s), 5.35(2H, s), 7.08–7.14(3H, m), 7.23(2H, d, J=7.3 Hz), 7.30–7.35(2H, m), 7.41(2H, t), 7.50–7.55(4H, m), 7.57(1H, dt, J=1.8 and 7.6 Hz), 7.68(1H, d, J=8.1 Hz), 8.53(1H, d, J=4.9 Hz)

IR(KBr): 1618 cm$^{-1}$ mp: 104.5–106.0° C.

EXAMPLE 204

Synthesis of N-benzenesulfonyl-3-[1-(2-chlorobenzyl)-2-methylbenzimidazole-6-yl]propionamide (266)

5% Palladium on carbon (0.500 g) was added to a solution of 0.607 g of N-benzenesulfonyl-1-(2-chlorobenzyl)-2-methylbenzimidazole-6-acrylamide in 150 ml of ethanol, and the mixture was stirred in a hydrogen atmosphere at room temperature for 43 hours. The solid material was separated through filtration, and the filtrate was concentrated. The residue was dissolved in a mixed solution of a 20% potassium hydrogencarbonate aqueous solution and methanol, and was adjusted to a pH of from 5 to 6 with 10% hydrochloric acid. The crystals precipitated were separated through filtration, and was dried to give 0.250 g of N-benzenesulfonyl-3-[1-(2-chlorobenzyl)-2-methylbenzimidazol-6-yl]propionamide (266).

Properties of Compound (266):

$^1$H-NMR(DMSO-d6, δ): 2.45(3H, s), 2.52(2H, t), 2.78 (2H, t), 5.37(2H, s), 6.88(1H, d, J=8.4 Hz), 7.08(2H, d, J=7.4 Hz), 7.22–7.34(3H, m), 7.36(1H, t, J=8.1 Hz), 7.55(2H, t), 7.67(1H, t), 7.84(2H, d, J=7.6 Hz), 12.04(1H, br s)

IR(KBr): 1715 cm$^{-1}$

Mass(FAB): m/e 468(M+1)

mp: 229.8–233.0° C.

EXAMPLE 205

Synthesis of 6-benzenesulfonylcarbamoyl-2-methyl-1-[4-(1,2,3-thiadiazol-4-yl)benzyl]benzimidazole (267)

In the same manner as in Example 183, 0.279 g of 6-benzenesulfonylcarbamoyl-2-methyl-1-[4-(1,2,3-thiadiazol-4-yl)-benzyl]benzimidazole (267) were formed from 0.382 g of N-benzenesulfonyl-4-acetylamino-3-[4-(1,2,3-thiadiazol-4-yl)-benzylamino]benzamide.

Properties of Compound (267):

$^1$H-NMR(DMSO-d6, δ): 2.56(3H, s), 5.62(2H, s), 7.28 (2H, d, J=8.2 Hz), 7.58–7.63(3H, m), 7.67(1H, t, J=7.3 Hz), 7.74(1H, dd, J=8.5 and 1.2 Hz), 7.99(2H, dd, J=8.4 and 1.2 Hz), 8.10(2H, d, J=8.2 Hz), 8.19(1H, s), 9.58(1H, s), 12.47 (1H, s)

IR(KBr): 1617, 1556 cm$^{-1}$ mp: 258.5–260.0° C.(decomp.)

EXAMPLE 206

Synthesis of 1-(2-chlorobenzyl)-2-methyl-6-(8-quinolinesulfonyl-carbamoyl)benzimidazole sodium salt (268)

In the same manner as in Example 141, 0.400 g of 1-(2-chlorobenzyl)-2-methyl-6-(8-quinolinesulfonylcarbamoyl)-benzimidazole sodium salt (268) were formed from 0.450 g of 6-carboxy-1-(2-chlorobenzyl)-2-methylbenzimidazole, 0.485 g of N,N'-carbonyldiimidazole, 0.625 g of 8-quinolinesulfonamide and 0.457 g of diazabicycloundecene.

Properties of Compound (268):

$^1$H-NMR(DMSO-d6, δ): 2.42(3H, s), 5.48(2H, s), 6.32 (1H, d, J=7.7 Hz), 7.17(1H, t, J=7.5 Hz), 7.30(1H, t, J=7.7 Hz), 7.42(1H, d, J=8.4 Hz), 7.48(1H, dd, J=4.2 and 8.2 Hz), 7.53(1H, d, J=8.0 Hz), 7.64(1H, t, J=7.7 Hz), 7.79(1H, d, J=8.5 Hz), 7.88(1H, s), 8.04(1H, d, J=8.1 Hz), 8.33–8.37 (2H, m), 8.85(1H, dd)

IR(KBr): 1594 cm$^{-1}$

Mass(FAB): m/e 513(M+1)

mp: 348–352° C. (decomp.)

EXAMPLE 207

Synthesis of 6-(4-tert-butylbenzenesulfonylcarbamoyl)-1-(2-chlorobenzyl)-2-methylbenzimidazole sodium salt (269)

In the same manner as in Example 141, 0.280 g of 6-(4-tert-butylbenzenesulfonylcarbamoyl)-1-(2-chlorobenzyl)-2-methyl-benzimidazole sodium salt (269) were obtained from 0.450 g of 6-carboxy-1-(2-chlorobenzyl)-2-methylbenzimidazole, 0.486 g of N,N'-carbonyldiimidazole, 0.640 g of 2-tert-benzenesulfonamide and 0.657 g of diazabicycloundecene.

Properties of Compound (269):

$^1$H-NMR(DMSO-d6, δ) 1.25(9H, s), 2.46(3H, s), 5.51 (2H, s), 6.37(1H, d, J=7.7 Hz), 7.18(1H, t), 7.31(1H, t), 7.34(2H, d, J=8.4 Hz), 7.44(1H, d, J=8.4 Hz), 7.54(1H, d, J=8.0 Hz), 7.69(2H, d, J=8.5 Hz), 7.78–7.82(2H, m)

IR(KBr): 1596 cm$^{-1}$

Mass(FAB): m/e 518(M+1)

mp: 359.5–362° C.

EXAMPLE 208

Synthesis of 6-benzenesulfonylcarbamoyl-2-methyl-1-[4-(trifluoromethyl)benzyl]benzimidazole (270)

In the same manner as in Production Example 32, 0.30 g of crude N-benzenesulfonyl-4-acetylamino-3-[4-(trifluoromethyl)-benzylamino]benzamide were obtained from 0.50 g of N-benzenesulfonyl-4-acetylamino-3-aminobenzamide and 0.418 g of 4-(trifluoromethyl)benzyl bromide. When this crude product was dissolved in methanol and was allowed to stand, the crystals were precipitated. The crystals were separated through filtration, and were dried to give 0.160 g of 6-benzenesulfonylcarbamoyl-2-methyl-1-[4-(trifluoromethyl)benzyl]-benzimidazole (270).

Properties of Compound (270):

$^1$H-NMR(DMSO-d6, δ): 2.51(3H, s), 5.66(2H, s), 7.28 (2H, d, J=8.1 Hz), 7.59–7.65(3H, m), 7.67–7.75(4H, m), 7.99(2H, d, J=7.5 Hz), 8.14(1H, d, J=1.0 Hz), 12.43(1H, s)

IR(KBr): 1618, 1550 cm$^{-1}$ mp: 278.5–280.0° C.

EXAMPLE 209

Synthesis of 2-benzyl-6-carboxy-1-methylbenzimidazole hydrochloride (271)

A 5% sodium hydroxide aqueous solution (2.8 g) was added to a solution of 0.340 g of 2-benzyl-6- ethoxycarbonyl-1-methylbenzimidazole in 4 ml of ethanol, and the mixture was heat-refluxed for 1.5 hours. The reaction mixture was acidified with 1-N hydrochloric acid, and was concentrated under reduced pressure. Ethanol was added to the residue to extract the organic substance. Ethanol was distilled off under reduced pressure to give 0.300 g of 2-benzyl-6-carboxy-1-methylbenzimidazole hydrochloride (271).

Properties of Compound (271):

$^1$H-NMR(DMSO-d6, δ): 4.00(3H, s), 4.62(2H, s), 7.33 (1H, m), 7.35–7.45(4H, m), 7.83(1H, d, J=8.4 Hz), 8.06(1H, d, J=8.4 Hz), 8.42(1H, s), 13.3(1H, br s)

EXAMPLE 210

Synthesis of 5-benzenesulfonylcarbamoyl-2-methylbenzimidazole (272)

A mixture of 0.500 g of N-benzenesulfonyl-4-acetylamino-3-aminobenzamide, 3.9 g of 35% hydrochloric acid, 15 ml of methanol and 12 ml of water was stirred at 60° C. for 1 hour. The reaction mixture was neutralized with a potassium hydrogencarbonate aqueous solution. The crystals precipitated were separated through filtration, and were dried to give 0.404 g of 5-benzenesulfonylcarbamoyl-2-methylbenzimidazole (272).

Properties of Compound (272):

$^1$H-NMR(DMSO-d6, δ): 2.79(3H, s), 7.64–7.68(2H, m), 7.72–7.76(1H, m), 7.81(1H, d, J=8.7 Hz), 7.94(1H, dd, J=1.6 and 8.7 Hz), 8.02–8.05(2H, m), 8.30(1H, s)

IR(KBr): 1701 cm$^{-1}$ mp: 223.0–227.5° C.

Production Example 45

Production of ethyl 3-methoxyacetylamino-4-nitrobenzoate

Ethyl 3-methoxyacetylamino-4-nitrobenzoate (18.7 g) was obtained from 15.0 g of ethyl 3-amino-4-nitrobenzoate and 15.0 g of methoxyacetyl chloride in the same manner as in Production Example 12.

Properties of the compound:

$^1$H-NMR(CDCl$_3$, δ): 1.42(3H, t, J=7.2 Hz), 3.58(3H, s), 4.11(2H, s), 4.43(2H, q, J=7.2 Hz), 7.85(1H, dd, J=1.6 and 8.7 Hz), 8.27(1H, d, J=8.7 Hz), 9.44(1H, d, J=1.6 Hz), 11.15(1H, s)

EXAMPLE 211

Synthesis of 1-(biphenyl-4-ylmethyl)-6-ethoxycarbonyl-2-methoxymethylbenzimidazole (273)

Crude ethyl 3-[N-(biphenyl-4-ylmethyl)methoxyacetylamino]-4-nitrobenzoate (2.02 g) was obtained from 2.00 g of ethyl 3-methoxyacetylamino-4-nitrobenzoate and 2.98 g of 4-biphenylmethyl bromide in the same manner as in Production Example 14. Subsequently, 1.44 g of crude 1-(biphenyl-4-ylmethyl)-6-ethoxycarbonyl-2-methoxymethylbenzimidazole (273) were obtained in the same manner as in Example 24.

EXAMPLE 212

Synthesis of 1-(biphenyl-4-ylmethyl)-6-carboxy-2-methoxymethylbenizmidazole (274)

In the same manner as in Example 53, 0.864 g of 1-(biphenyl-4-ylmethyl)-6-carboxy-2-methoxymethylbenzimidazole (274) were formed from 1.44 g of crude 1-(biphenyl-4-ylmethyl)-6-ethoxycarbonyl-2-methoxymethylbenzimidazole.

Properties of Compound (274):

$^1$H-NMR(DMSO-d6, δ): 3.35(3H, s), 4.77(2H, s), 5.68 (2H, s), 7.25(2H, d, J=8.3 Hz), 7.35(1H, t, J=7.4 Hz), 7.44(2H, t, J=7.5 Hz), 7.61–7.66(4H, m), 7.74(1H, d, J=8.6 Hz), 7.83(1H, dd, J=1.6 and 8.5 Hz), 8.08(1H, d, J=1.2 Hz), 12.83(1H, s)

EXAMPLE 213

Synthesis of 1-(biphenyl-4-ylmethyl)-6-(1-butanesulfonyl-carbamoyl)-2-methoxymethylbenzimidazole (275)

In the same manner as in Example 98, 0.429 g of 1-(biphenyl-4-ylmethyl)-6-(1-butanesulfonylcarbamoyl)-2-methoxymethylbenzimidazole (275) were formed from 0.400 g of 1-(biphenyl-4-ylmethyl)-6-carboxy-2-methoxymethylbenzimidazole, 0.348 g of N,N'-carbonyldiimidazole, 0.294 g of 1-butanesulfonamide and 0.327 g of diazabicycloundecene.

Properties of Compound (275):

$^1$H-NMR(DMSO-d6, δ): 0.84(3H, t, J=7.4 Hz), 1.35–1.42 (2H, m), 1.62–1.70(2H, m), 3.33(3H, s), 3.51(2H, t, J=7.6 Hz), 4.74(2H, s), 5.65(2H, s), 7.26(2H, d, J=8.3 Hz), 7.35 (1H, t, J=7.3 Hz), 7.44(2H, t, J=7.5 Hz), 7.62–7.67(4H, m), 7.78(1H, d, J=8.6 Hz), 7.84(1H, dd, J=1.5 and 8.4 Hz), 8.24(1H, d, J=1.5 Hz), 12.01(1H, s)

IR(KBr): 1684 cm$^{-1}$ mp: 176.0–178.5° C.

EXAMPLE 214

Synthesis of 1-(4-benzyloxybenzyl)-6-ethoxycarbonyl-2-methoxymethylbenzimidazole (276)

Crude ethyl 3-[N-4-benzyloxybenzyl)methoxyacetylamino]-4-nitrobenzoate (2.14 g) was obtained from 2.00 g of ethyl 3-methoxyacetylamino-4-nitrobenzoate and 3.30 g of 4-benzyloxybenzyl chloride in the same manner as in Production Example 14. Subsequently, 1.66 g of crude 1-(4-benzyloxybenzyl)-6-ethoxycarbonyl-2-methoxymethylbenzimidazole (276) were obtained in the same manner as in Example 24.

EXAMPLE 215

Synthesis of 1-(4-benzyloxybenzyl)-6-carboxy-2-methoxymethylbenzimidazole (277)

In the same manner as in Example 53, 2.64 g of 1-(4-benzyloxybenzyl)-6-carboxy-2-methoxymethylbenzimidazole (277) were formed from 3.75 g of crude 1-(4-benzyloxybenzyl)-6-ethoxycarbonyl-2-methoxymethylbenzimidazole.

Properties of Compound (277):

$^1$H-NMR(DMSO-d6, δ): 3.34(3H, s), 4.74(2H, s), 5.05 (2H, s), 5.53(2H, s), 6.97(2H, d, J=8.7 Hz), 7.15(2H, d, J=8.7 Hz), 7.31(1H, t, J=7.2 Hz), 7.41(2H, d, J=7.2 Hz), 7.71(1H, d, J=8.4 Hz), 7.81(1H, dd, J=1.5 and 7.4 Hz), 8.04(1H, d, J=1.1 Hz), 12.81(1H, s)

EXAMPLE 216

Synthesis of 1-(4-benzyloxybenzyl)-6-(1-butanesulfonylcarbamoyl)-2-methoxymethylbenzimidazole (278)

In the same manner as in Example 155, 0.321 g of 1-(4-benzyloxybenzyl)-6-(1-butanesulfonylcarbamoyl)-2- methoxymethylbenzimidazole (278) were formed from 0.400 g of 1-(4-benzyloxybenzyl)-6-carboxy-2-methoxymethylbenzimidazole, 0.322 g of N,N'-carbonyldiimidazole, 0.272 g of 1-butanesulfonamide and 0.302 g of diazabicycloundecene.

Properties of Compound (278):

$^1$H-NMR(DMSO-d6, δ): 0.86(3H, t, J=7.4 Hz), 1.37–1.44 (2H, m),1.65–1.71(2H, m), 3.32(3H, s), 3.52(2H, t, J=7.6 Hz), 4.71(2H, s), 5.05(2H, s), 5.51(2H, s), 6.98(2H, d, J=8.7 Hz), 7.15(2H, d, J=8.3 Hz), 7.31(1H, t, J=7.2 Hz), 7.37(2H, t, J=7.2 Hz), 7.41(2H, d, J=7.1 Hz), 7.74(1H, d, J=8.5 Hz), 7.82(1H, dd, J=1.5 and 8.5 Hz), 8.21(1H, s), 11.98(1H, s)

IR(KBr): 1685 cm$^{-1}$ mp: 72.0–74.0° C.

EXAMPLE 217

Synthesis of 1-(2,4-dichlorobenzyl)-6-ethoxycarbonyl-2-methoxymethylbenzimidazole (279)

Crude ethyl 3-[N-2,4-dichlorobenzyl) methoxyacetylamino]-4-nitrobenzoate was obtained from 2.00 g of ethyl 3-methoxyacetylamino-4-nitrobenzoate and 2.08 g of 2,4-dichlorobenzyl chloride in the same manner as in Production Example 14. Subsequently, 3.15 g of crude 1-(2,4-dichlorobenzyl)-6-ethoxycarbonyl-2-methoxymethylbenzimidazole (279) were obtained in the same manner as in Example 24.

EXAMPLE 218

Synthesis of 6-carboxy-1-(2,4-dichlorobenzyl)-2-methoxymethylbenzimidazole (280)

In the same manner as in Example 53, 1.46 g of 6-carboxy-1-(2,4-dichlorobenzyl)-2-methoxymethylbenzimidazole (280) were formed from 3.15 g of crude 1-(2,4-dichlorobenzyl)-6-ethoxycarbonyl-2-methoxymethylbenzimidazole.

Properties of Compound (280):

$^1$H-NMR(DMSO-d6, δ): 3.23(3H, s), 4.70(2H, s), 5.68 (2H, s), 6.54(1H, d, J=8.5 Hz), 7.31(1H, dd, J=2.2 and 8.5 Hz), 7.73(1H, d, J=2.1 Hz), 7.76(1H, d, J=8.5 Hz), 7.86(1H, dd, J=1.5 and 8.5 Hz), 8.00(1H, d, J=1.1 Hz), 12.85(1H, s)

EXAMPLE 219

Synthesis of 6-(1-butanesulfonylcarbamoyl)-1-(2,4-dichlorobenzyl)2-methoxymethylbenzimidazole (281)

In the same manner as in Example 98, 0.430 g of 6-(1-butanesulfonylcarbamoyl)-1-(2,4-dichlorobenzyl)-2-methoxymethylbenzimidazole (281) were formed from 0.400 g of 6-carboxy-1-(2,4-dichlorobenzyl)-2-methoxymethylbenzimidazole, 0.355 g of N,N'-carbonyldiimidazole, 0.300 g of 1-butanesulfonamide and 0.333 g of diazabicycloundecene.

Properties of Compound (281):

$^1$H-NMR(DMSO-d6, δ): 0.85(3H, t, J=7.3 Hz), 1.37–1.42 (2H, m), 1.63–1.69(2H, m), 3.21(3H, s), 3.51(2H, t, J=7.6 Hz), 4.68(2H, s), 5.65(2H, s), 6.46(1H, d, J=8.5 Hz), 7.31 (1H, dd, J=2.0 and 8.4 Hz), 7.75(1H, d, J=2.1 Hz), 7.80(1H, d, J=8.5 Hz), 7.86(1H, dd, J=1.7 and 8.6 Hz), 8.14(1H, d, J=1.2 Hz), 12.00(1H, s)

IR(KBr): 1694 cm$^{-1}$ mp: 168.5–170.5° C.

EXAMPLE 220

Synthesis of 1-(2-chlorobenzyl)-2-methyl-6-(1-propanesulfonylcarbamoyl)benzimidazole (282)

In the same manner as in Example 98, 0.459 g of 1-(2-chlorobenzyl)-2-methyl-6-(1-propanesulfonylcarbamoyl)-benzimidazole (282) were formed from 0.400 g of 6-carboxy-1-(2-chlorobenzyl)-2-methylbenzimidazole, 0.431 g of N,N'-carbonyldiimidazole, 0.328 g of 1-propanesulfonamide and 0.404 g of diazabicycloundecene.

Properties of Compound (282):

$^1$H-NMR(DMSO-d6, δ): 0.98(3H, t, J=7.4 Hz), 1.67–1.75 (2H, m), 2.50(3H, s), 3.49(2H, t, J=7.7 Hz), 5.61(2H, s), 6.45(1H, d, J=7.0 Hz), 7.24(1H, dt, J=0.8 and 7.8 Hz), 7.35(1H, dt, J=1.4 and 7.4 Hz), 7.63(1H, dd, J=0.9 and 7.9 Hz), 7.69(1H, d, J=8.5 Hz), 7.81(1H, dd, J=1.6 and 8.5 Hz), 8.12(1H, d, J=1.6 Hz), 11.90(1H, s)

IR(KBr): 1676 cm$^{-1}$ mp: 217.5–218.5° C.

EXAMPLE 221

Synthesis of 6-ethanesulfonylcarbamoyl-1-(2-chlorobenzyl)-2-methylbenzimidazole (283)

In the same manner as in Example 98, 0.459 g of 6-ethanesulfonylcarbamoyl-1-(2-chlorobenzyl)-2-methylbenzimidazole (283) were formed from 0.400 g of 6-carboxy-1-(2-chlorobenzyl)-2-methylbenzimidazole, 0.431 g of N,N'-carbonyldiimidazole, 0.290 g of ethanesulfonamide and 0.404 g of diazabicycloundecene.

Properties of Compound (283):

$^1$H-NMR(DMSO-d6, δ): 1.23(3H, t, J=7.3 Hz), 2.50(3H, s), 3.50(2H, q, J=7.3 Hz), 5.61(2H, s), 6.45(1H, d, J=6.7 Hz), 7.24(1H, dt, J=0.9 and 7.5 Hz), 7.35(1H, dt, J=1.4 and 7.5 Hz), 7.58(1H, dd, J=1.0 and 8.0 Hz), 7.69(1H, d, J=8.5 Hz), 7.81(1H, dd, J=1.6 and 8.4 Hz), 8.13(1H, d, J=1.5 Hz), 11.86(1H, s)

IR(KBr): 1673 cm$^{-1}$ mp: 256.5–258.5° C.

EXAMPLE 222

Synthesis of 6-(propanesultam-1-ylcarbonyl)-1-(2-chlorobenzyl)-2-methylbenzimidazole (284)

In the same manner as in Example 98, 0.323 g of 6-(propanesultam-1-ylcarbonyl)-1-(2-chlorobenzyl)-2-methylbenzimidazole (284) were formed from 0.400 g of 6-carboxy-1-(2-chlorobenzyl)-2-methylbenzimidazole, 0.431 g of N,N'-carbonyldiimidazole, 0.420 g of 1-(3-chloropropane)sulfonamide and 0.404 g of diazabicycloundecene.

Properties of Compound (284):

$^1$H-NMR(DMSO-d6, δ): 2.27–2.33(2H, m), 2.52(3H, s), 3.52(2H, t, J=7.0 Hz), 3.87(2H, t, J=6.6 Hz), 5.59(2H, s), 6.57(1H, d, J=7.7 Hz), 7.23(1H, t, J=7.6 Hz), 7.34(1H, t, J=6.4 Hz), 7.53–7.58(2H, m), 7.67(1H, d, J=8.4 Hz), 7.79 (1H, d, J=1.1 Hz)

IR(KBr): 1648 cm$^{-1}$ mp: 165.5–166.6° C.

EXAMPLE 223

Synthesis of 6-benzenesulfonylcarbamoyl-1-(biphenyl-4-ylmethyl)-2-cyclopropylbenzimidazole potassium salt (285)

In the same manner as in Example 170, 0.196 g of 6-benzenesulfonylcarbamoyl-1-(biphenyl-4-ylmethyl)-2- cyclopropylbenzimidazole potassium salt (285) were obtained from 0.400 g of N-benzenesulfonyl-4-amino-3-(biphenyl-4-ylmethylamino)benzamide and 0.101 g of cyclopropanecarbonyl chloride via N-benzenesulfonyl-3-(biphenyl-4-ylmethylamino)-4-cyclopropanecarbonylaminobenzamide.

Properties of Compound (285):
$^1$H-NMR(DMSO-d6, δ):1.00–1.15(4H, m), 2.23–2.31 (1H, m), 5.66(2H, s), 7.21(2H, m, J=9.1 Hz), 7.32–7.45(7H, m), 7.59–7.63(4H, m), 7.78–7.83(3H, m), 7.97(1H, s).
IR(Nujol): 1540 cm$^{-1}$
Mass(FAB): m/e 546(M+1)
mp: 220.8–224.8° C.

EXAMPLE 224

Synthesis of 1-(2-chlorobenzyl)-2-methyl-6-(1-pentanesulfonylcarbamoyl)benzimidazole (286)

In the same manner as in Example 98, 0.491 g of 1-(2-chlorobenzyl)-2-methyl-6-(1-pentanesulfonylcarbamoyl)benzimidazole (286) were formed from 0.400 g of 6-carboxy-1-(2-chlorobenzyl)-2-methylbenzimidazole, 0.431 g of N,N'-carbonyldiimidazole, 0.402 g of 1-pentanesulfonamide and 0.404 g of diazabicycloundecene.

Properties of Compound (286):
$^1$H-NMR(DMSO-d6, δ): 0.81(3H, t, J=7.2 Hz), 1.23–1.28 (2H, m), 1.32–1.37(2H, m), 1.65–1.69(2H, m), 3.50(2H, t, J=7.8 Hz), 5.61(2H, s), 6.45(1H, d, J=7.5 Hz), 7.24(IH, t, J=7.6 Hz), 7.35(1H, t, J=7.5 Hz), 7.57(1H, d, J=7.9 Hz), 7.69(1H, d, J=8.5 Hz), 7.81(1H, dd, J=1.7 and 8.4 Hz), 8.12(1H, d, J=1.2 Hz), 12.25(1H, s)
IR(KBr): 1684 cm$^{-1}$
mp: 173.3–179.80° C.

EXAMPLE 225

Synthesis of 1-(2-chlorobenzyl)-2-methyl-6-[(3-methylbutane)sulfonylcarbamoyl]benzimidazole (287)

In the same manner as in Example 98, 0.284 g of 1-(2-chlorobenzyl)-2-methyl-6-[(3-methylbutane)sulfonylcarbamoyl]-benzimidazole (287) were formed from 0.300 g of 6-carboxy-1-(2-chlorobenzyl)-2-methylbenzimidazole, 0.323 g of N,N'-carbonyldiimidazole, 0.302 g of 1-(3-methyl)butanesulfonamide and 0.303 g of diazabicycloundecene.

Properties of Compound (287):
$^1$H-NMR(DMSO-d6, δ): 0.84(6H, d, J=6.5 Hz), 1.52–1.59(2H, m), 1.61–1.70(1H, m), 3.44(2H, t, J=7.9 Hz), 5.60(2H, s), 6.45(1H, d, J=7.8 Hz), 7.24(1H, t, J=7.6 Hz), 7.35(1H, t, J=7.4 Hz), 7.57(1H, d, J=7.9 Hz), 7.66(1H, d, J=8.5 Hz), 7.81(1H, dd, J=1.6 and 8.6 Hz), 8.09(1H, s), 11.87(1H, s)
IR(KBr): 1682cm$^{-1}$
mp: 201.0–204.1° C.

EXAMPLE 226

Synthesis of 1-(2-chlorobenzyl)-6-(1-hexanesulfonylcarbamoyl)-2-methylbenzimidazole (288)

In the same manner as in Example 98, 0.379 g of 1-(2-chlorobenzyl)-6-(1-hexanesulfonylcarbamoyl)-2-methylbenzimidazole (288) were formed from 0.300 g of 6-carboxy-1-(2-chlorobenzyl)-2-methylbenzimidazole, 0.323 g of N,N'-carbonyldiimidazole, 0.335 g of 1-hexanesulfonamide and 0.303 g of diazabicycloundecene.

Properties of Compound (288):
$^1$H-NMR(DMSO-d6, δ): 0.81(3H, t, J=7.0 Hz), 1.18–1.28 (4H, m), 1.32–1.41(2H, m), 1.63–1.71(2H, m), 2.53(3H, 5), 3.50(2H, t, J=7.7 Hz), 5.64(2H, s), 6.51(1H, d, J=7.7 Hz), 7.25(1H, dt, J=1.2 and 7.8 Hz), 7.36(1H, dt, J=1.4 and 7.7 Hz), 7.58(1H, dd, J=1.0 and 8.0 Hz), 7.72(1H, d, J=8.5 Hz), 7.84(1H, dd, J=1.6 and 8.5 Hz), 8.15(1H, d, J=1.3 Hz), 11.87(1H, s)
IR(KBr): 1682 cm$^{-1}$
mp: 141.2–143.5° C.

EXAMPLE 227

Synthesis of 6-tert-butoxycarbonylamino-1-(2-chlorobenzyl)-2-methylbenzimidazole (289)

In the same manner as in Example 18, 0.760 g of 6-tert-butoxycarbonylamino-1-(2-chlorobenzyl)-2-methylbenzimidazole (289) were formed from 1.01 g of 6-carboxy-1-(2-chlorobenzyl)-2-methylbenzimidazole, 1 ml of diphenylphosphorylazide, 1 ml of diisopropylethylamine and 25 ml of tert-butyl alcohol.

Properties of Compound (289):
$^1$H-NMR(CDCl$_3$, δ): 1.49(9H, s), 2.47(3H, s), 5.37(2H, s), 6.41(1H, d, J=7.5 Hz), 6.55(1H, br s), 6.93(1H, dd, J=1.9 and 8.6 Hz), 7.08(1H, t, J=7.5 Hz), 7.22(1H, t), 7.44(1H, d, J=8.0 Hz), 7.62(2H, d, J=8.6 Hz)

EXAMPLE 228

Synthesis of 6-amino-1-(2-chlorobenzyl)-2-methylbenzimidazole (290)

In the same manner as in Example 22, 0.420 g of 6-amino-1-(2-chlorobenzyl)-2-methylbenzimidazole (290) were formed from 0.760 g of 6-tert-butoxycarbonylamino-1-(2-chlorobenzyl)-2-methylbenzimidazole.

Properties of Compound (290):
$^1$H-NMR(DMSO-d6, δ): 2.37(3H, s), 4.83(2H, br s), 5.32(2H, s), 6.33(1H, d, J=1.9 Hz), 6.42(1H, d, J=7.7 Hz), 6.46(1H, dd, J=1.9 and 8.5 Hz), 7.19–7.24(2H, m), 7.31(1H, t), 7.53(1H, d, J=7.9 Hz)

EXAMPLE 229

Synthesis of 6-(1-butanesulfonylamino)-1-(2-chlorobenzyl)-2-methylbenzimidazole (291)

In the same manner as in Example 20, 0.230 g of 6-(1-butanesulfonylamino)-1-(2-chlorobenzyl)-2-methylbenzimidazole (291) were formed from 0.300 g of 6-amino-1-(2-chlorobenzyl)-2-methylbenzimidazole, 0.216 g of 1-butanesulfonyl chloride and 0.130 g of triethylamine.

Properties of Compound (291):
$^1$H-NMR(DMSO-d6, δ): 0.74(3H, m), 1.23(2H, m), 1.55 (2H, m), 2.50(3H, s), 2.89(2H, m), 5.47(2H, s), 6.58(1H, d, J=7.4 Hz) 7.02(1H, d, J=8.5 Hz), 7.10(1H, s), 7.23(1H, t), 7.33(1H, t), 7.52(2H, m), 9.55(1H, s)
IR(KBr): 1629 cm$^{-1}$
mp: 149.5–151.0° C.

Production Example 46

Production of methyl 2-[N-(2,4-dichlorobenzyl) acetylamino]-3-nitrobenzoate

In the same manner as in Production Example 14, 0.250 g of methyl 2-[N-(2,4-dichlorobenzyl)acetylamino]-3- nitrobenzoate were formed from 1.00 g of methyl 2-acetylamino-3-nitrobenzoate and 0.985 g of 2,4-dichlorobenzyl chloride.

Properties of the compound:

$^1$H-NMR(CDCl$_3$, δ): 1.99(3H, s), 3.71(3H, s), 4.85(1H, d, J=4.5 Hz), 4.98(1H, d, J=4.5 Hz), 7.17–7.22(2H, m), 7.46 (1H, d, J=7.9 Hz), 7.63(1H, t, J=7.9 Hz), 7.98(1H, d, J=8.0 Hz), 8.09(1H, d, J=7.9 Hz)

EXAMPLE 230

Synthesis of 1-(2,4-dichlorobenzyl)-7-ethoxycarbonyl-2-methylbenzimidazole (292)

In the same manner as in Example 24, 5.15 g of 1-(2,4-dichlorobenzyl)-7-ethoxycarbonyl-2-methylbenzimidazole (292) were formed from 6.50 g of methyl 2-[N-(2,4-dichlorobenzyl)acetylamino]-3-nitrobenzoate.

Properties of Compound (292):

$^1$H-NMR(CDCl$_3$, δ): 2.53(3H, s), 3.70(3H, s), 5.72(2H, s), 6.26(1H, d, J=8.4 Hz), 7.04(1H, dd, J=2.0 and 8.4 Hz), 7.28(1H, t, J=7.9 Hz), 7.45(1H, d, J=2.0 Hz), 7.75(1H, d, J=7.8 Hz), 7.93(1H, d, J=7.9 Hz)

EXAMPLE 231

Synthesis of 7-carboxy-1-(2,4-dichlorobenzyl)-2-methylbenzimidazole (293)

In the same manner as in Example 53, 1.76 g of 7-carboxy-1-(2,4-dichlorobenzyl)-2-methylbenzimidazole (293) were formed from 2.00 g of 1-(2,4-dichlorobenzyl)-7-ethoxycarbonyl-2-methylbenzimidazole.

Properties of Compound (293):

$^1$H-NMR(DMSO-d6, δ): 2.49(3H, s), 5.81(2H, s), 6.09 (1H, d, J=8.4 Hz), 7.21–7.28(2H, m), 7.62(1H, d, J=7.8 Hz), 7.67(1H, d, J=2.2 Hz), 7.83(1H, d, J=8.0 Hz), 13.04(1H, br s)

EXAMPLE 232

Synthesis of 7-(1-butanesulfonylcarbamoyl)-1-(2,4-dichlorobenzyl)-2-methylbenzimidazole (294)

In the same manner as in Example 98, 0.325 g of 7-(1-butanesulfonylcarbamoyl)-1-(2,4-dichlorobenzyl)-2-methylbenzimidazole (294) were formed from 0.463 g of 7-carboxy-1-(2,4-dichlorobenzyl)-2-methylbenzimidazole, 0.448 g of N,N'-carbonyldiimidazole, 0.379 g of 1-butanesulfonamide and 0.421 g of diazabicycloundecene.

Properties of Compound (294):

$^1$H-NMR(DMSO-d6, δ): 0.84(3H, t, J=7.3 Hz), 1.33(2H, m), 1.44(2H, m), 2.53(3H, s), 3.16(2H, m), 5.64(2H, s), 6.03(1H, d, J=8.4 Hz), 7.25(1H, dd, J=2.1 and 8.4 Hz), 7.30(1H, t, J=7.8 Hz), 7.44(1H, d, J=7.4 Hz), 7.68(1H, d, J=2.1 Hz), 7.87(1H, d, J=7.8 Hz), 12.18(1H, br s)

IR(KBr): 1690 cm$^{-1}$ mp: 98.5–102.0° C.

EXAMPLE 233

Synthesis of 1-(2-chlorobenzyl)-2-methyl-6-[1-[3-(trimethylsilyl)propane]sulfonylcarbamoyl]benzimidazole (295)

In the same manner as in Example 149, 0.604 g of 1-(2-chlorobenzyl)-2-methyl-6-[1-[3-(trimethylsilyl)propane]sulfonyl-carbamoyl]benzimidazole (295) were formed from 0.400 g of 6-carboxy-1-(2-chlorobenzyl)-2-methylbenzimidazole, 0.431 g of N,N'-carbonyldiimidazole, 0.520 g of 1-[3-(trimethylsilyl)propane]sulfonamide and 0.404 g of diazabicycloundecene.

Properties of Compound (295):

$^1$H-NMR(DMSO-d6, δ): –0.06(9H, s), 0.61(2H, t, J=8.6 Hz), 1.66–1.73(2H, m), 2.50(3H, s), 3.51(2H, t, J=7.7 Hz), 5.61(2H, s), 6.46(1H, d, J=7.8 Hz), 7.24(1H, t, J=7.6 Hz), 7.35(1H, t, J=7.6 Hz), 7.57(1H, dd, J=7.9 and 0.9 Hz), 7.70(1H, d, J=8.5 Hz), 7.81(1H, dd, J=1.5 and 8.5 Hz), 8.12(1H, d, J=1.4 Hz), 11.98(1H, s)

IR(KBr): 1688 cm$^{-1}$ mp: 197.0–203.9° C.

EXAMPLE 234

Synthesis of 4-ethoxycarbonyl-2-methylbenzimidazole (296)

A mixture of 8.03 g of methyl 2-acetylamino-3-nitrobenzoate, 18.8 g of reduced iron, 20 ml of acetic acid and 40 ml of ethanol was heat-refluxed for 18 hours. After the solvent was concentrated, chloroform and 10% hydrochloric acid were added to the residue for extraction. The aqueous layer was acidified with a saturated aqueous solution of sodium hydrogencarbonate, and was extracted with chloroform. Chloroform was then distilled off under reduced pressure to give 1.61 g of 4-ethoxycarbonyl-2-methylbenzimidazole (296).

Properties of Compound (296):

$^1$H-NMR(CDCl$_3$, δ): 1.43(3H, t), 2.66(3H, s), 4.45(2H, q), 7.24–7.28(1H, m), 7.84–7.89(2H, m), 10.26(1H, br s)

EXAMPLE 235

Synthesis of 1-(2,4-dichlorobenzyl)-4-ethoxycarbonyl-2-methylbenzimidazole (297)

A mixture of 1.61 g of 4-ethoxycarbonyl-2-methylbenzimidazole, 3.08 g of 2,4-dichlorobenzyl chloride, 1.51 g of potassium iodide, 1.05 g of potassium carbonate and 4 ml of N,N-dimethylformamide was stirred at 80° C. for 16 hours. The reaction mixture was extracted with chloroform and with water. The chloroform layer was washed with water, dried, and concentrated. The residue was purified through silica-gel column chromatography (eluent: a mixture of hexane and ethyl acetate at a ratio of 2:8) to give 0.730 g of 1-(2,4-dichlorobenzyl)-4-ethoxycarbonyl-2-methylbenzimidazole (297).

Properties of Compound (297):

$^1$H-NMR(CDCl$_3$, δ): 1.47(3H, t, J=7.1 Hz), 2.63(3H, s), 4.52(2H, q, J=7.1 Hz), 5.39(2H, s), 6.30(1H, d, J=8.4 Hz), 7.06(1H, dd, J=2.1 and 8.4 Hz), 7.25(1H, t, J=7.9 Hz), 7.32(1H, dd, J=1.0 and 7.9 Hz), 7.48(1H, d, J=2.0 Hz), 7.93(1H, dd, J=1.0 and 7.7 Hz)

EXAMPLE 236

Synthesis of 4-carboxy-1-(2,4-dichlorobenzyl)-2-methylbenzimidazole (298)

In the same manner as in Example 53, 0.575 g of 4-carboxy-1-(2,4-dichlorobenzyl)-2-methylbenzimidazole (298) were formed from 0.730 g of 1-(2,4-dichlorobenzyl)-4-ethoxycarbonyl-2-methylbenzimidazole.

Properties of Compound (298):

$^1$H-NMR(DMSO-d6, δ): 2.65(3H, s), 5.67(2H, s), 6.73 (1H, d, J=8.3 Hz), 7.33(1H, dd, J=2.2 and 8.4 Hz), 7.39(1H, t, J=7.9 Hz), 7.74(1H, d, J=2.2 Hz), 7.76(1H, d, J=8.2 Hz), 7.85(1H, d, J=7.5 Hz)

EXAMPLE 237

Synthesis of 4-(1-butanesulfonylcarbamoyl)-1-(2,4-dichlorobenzyl)2-methylbenzimidazole (299)

In the same manner as in Example 98, 0.275 g of 4-(1-butanesulfonylcarbamoyl)-1-(2,4-dichlorobenzyl)-2-methylbenzimidazole (299) were formed from 0.350 g of 4-carboxy-1-(2,4-dichlorobenzyl)-2-methylbenzimidazole, 0.339 g of N,N'-carbonyldiimidazole, 0.287 g of 1-butanesulfonamide and 0.318 g of diazabicycloundecene.

Properties of Compound (299):

$^1$H-NMR(DMSO-d6, δ): 0.86(3H, t, J=7.3 Hz), 1.42(2H, m), 1.73(2H, m), 2.61(3H, s), 3.61(2H, m), 5.65(2H, s), 6.67(1H, d, J=8.4 Hz), 7.32(1H, dd, J=2.1 and 8.4 Hz), 7.39(1H, t, J=7.9 Hz), 7.73(1H, d, J=2.1 Hz), 7.78(1H, d, J=8.0 Hz), 7.91(1H, d, J=7.7 Hz), 12.66(1H, br s)

IR(KBr): 1699 cm$^{-1}$ mp: 180.7–183.6° C.

EXAMPLE 238

Synthesis of 1-(4-benzyloxybenzyl)-6-ethoxycarbonyl-2-methylbenzimidazole (300)

In the same manner as in Production Example 14, crude ethyl 3-[N-(4-benzyloxybenzyl)acetylamino]-4-nitrobenzoate was obtained from 2.00 g of ethyl 3-acetylamino-4-nitrobenzoate and 3.69 g of 4-benzyloxybenzyl chloride. Subsequently, 4.09 g of crude 1-(4-benzyloxybenzyl)-6-ethoxycarbonyl-2-methylbenzimidazole (300) were formed in the same manner as in Example 24.

EXAMPLE 239

Synthesis of 1-(4-benzyloxybenzyl)-6-carboxy-2-methylbenzimidazole (301)

In the same manner as in Example 53, 1.13 g of 1-(4-benzyloxybenzyl)-6-carboxy-2-methylbenzimidazole (301) were formed from 4.09 g of 1-(4-benzyloxybenzyl)-6-ethoxycarbonyl-2-methylbenzimidazole.

Properties of Compound (301):

$^1$H-NMR(DMSO-d6, δ): 2.57(3H, s), 5.05(2H, s), 5.48 (2H, s), 6.97(2H, d, J=8.6 Hz), 7.08(2H, d, J=8.5 Hz), 7.28–7.43(5H, m), 7.60(1H, d, J=8.3 Hz), 7.78(1H, d, J=7.5 Hz), 8.07(1H, s), 12.72(1H, s)

EXAMPLE 240

Synthesis of 1-(4-benzyloxybenzyl)-6-(1-butanesulfonyl-carbamoyl)-2-methylbenzimidazole (302)

In the same manner as in Example 149, 0.206 g of 1-(4-benzyloxybenzyl)-6-(1-butanesulfonylcarbamoyl)-2-methylbenzimidazole (302) were formed from 0.300 g of 6-carboxy-1-(4-benzyloxybenzyl)-2-methylbenzimidazole, 0.242 g of N,N'-carbonyldiimidazole, 0.204 g of 1-butanesulfonamide and 0.227 g of diazabicycloundecene.

Properties of Compound (302):

$^1$H-NMR(DMSO-d6, δ): 0.87(3H, t, J=7.3 Hz), 1.38–1.43 (2H, m), 1.64–1.71(2H, m), 2.54(3H, s), 3.49(2H, t, J=6.8 Hz), 5.05(2H, s), 5.45(2H, s), 6.98(2H, d, J=8.7 Hz), 7.10 (2H, d, J=8.7 Hz), 7.31(1H, t, J=7.2 Hz), 7.37(2H, t, J=7.2 Hz), 7.41(2H, d, J=7.3 Hz), 7.62(1H, d, J=8.5 Hz), 7.79(1H, dd, J=1.5 and 8.4 Hz), 8.23(1H, s), 11.93(1H, s)

IR(KBr): 1684 cm$^{-1}$ mp: 132.4–137.7° C.

EXAMPLE 241

Synthesis of 6-ethoxycarbonyl-1-[(2'-cyanobiphenyl-4-yl)methyl]-2-methylbenzimidazole (303)

In the same manner as in Production Example 14, 0.750 g of crude ethyl 3-[N-[(2'-cyanobiphenyl-4-yl)methyl] acetylamino]-4-nitrobenzoate were obtained from 1.00 g of ethyl 3-acetylamino-4-nitrobenzoate and 1.30 g of 4'-bromomethyl-2-cyanobiphenyl. Subsequently, 0.410 g of 6-ethoxycarbonyl-1-[(2'-cyanobiphenyl-4yl)methyl]-2-methylbenzimicazole were formed in the same manner as in Example 24.

Properties of Compound (303):

$^1$H-NMR(CDCl$_3$, δ): 1.40(3H, t), 2.63(3H, s), 4.39(2H, q), 5.46(2H, s), 7.17(2H, d), 7.40–7.66(5H, m), 7.73–7.78 (2H, m), 8.00(1H, dd, J=1.5 and 8.5 Hz), 8.05(1H, d, J=1.2 Hz)

EXAMPLE 242

Synthesis of 6-carboxy-1-[(2'-cyanobiphenyl-4-yl) methyl]-2-methylbenzimidazole (304)

In the same manner as in Example 53, 0.190 g of 6-carboxy-1-[(2'-cyanobiphenyl-4-yl)methyl]-2-methylbenzimidazole (304) were formed from 0.410 g of 6-ethoxycarbonyl-1-[(2'-cyanobiphenyl-4-yl)methyl]-2-methylbenzimidazole.

Properties of Compound (304):

$^1$H-NMR(DMSO-d6, δ): 2.59(3H, s), 5.67(2H, s), 7.24 (2H, d, J=8.1Hz), 7.53–7.64(5H, m), 7.75(1H, t, J=7.7 Hz), 7.80(1H, d), 7.92(1H, d, J=7.7 Hz), 8.12(1H, s), 12.74(1H, br s)

EXAMPLE 243

Synthesis of 6-(1-butanesulfonylcarbamoyl)-1-[(2'-cyanobiphenyl-4-yl)methyl]-2-methylbenzimidazole (305)

In the same manner as in Example 155, 0.155 g of 6-(1-butanesulfonylcarbamoyl)-1-[(2'-cyanobiphenyl-4-yl) methyl]-2-methylbenzimidazole (305) were formed from 0.187 g of 6-carboxy-1-[(2'-biphenyl-4-yl)methyl]-2-methylbenzimidazole, 0.160 g of N,N'-carbonyldiimidazole, 0.135 g of 1-butanesulfonamide and 0.150 g of diazabicycloundecene by being purified through silica-gel column chromatography (eluent: a mixture of chloroform and methanol at a ratio of 20:1).

Properties of Compound (305):

$^1$H-NMR(DMSO-d6, δ): 0.83(3H, t, J=7.4 Hz), 1.34(2H, m), 1.60(2H, m),2.56(3H, s), 3.27(2H, m), 5.62(2H, s), 7.23(2H, d, J=8.2 Hz), 7.53–7.57(4H, m), 7.60(1H, d, J=7.8 Hz), 7.75(1H, dt, J=1.0 and 7.8 Hz), 7.83(1H, dd, J=1.5 and 8.4 Hz), 7.92(1H, d), 8.13(1H, s), 11.92(1H, br s).

IR(KBr): 2223 cm$^{-1}$.

mp: 115–118° C.

Production Example 47

Production of 2-fluoro-4'-methylbiphenyl

Thirty milliliters of a 1.6-M-n-butyllithium hexane solution and a solution of 8.33 g of 4-bromotoluene in 30 ml of tetrahydrofuran were added in this order to 30 ml of tetrahydrofuran which had been cooled to −78° C. in a nitrogen atmosphere, and the mixture was then stirred at −78° C. for 1 hour. A solution containing 6.64 g of zinc chloride which had been dehydrated through heat-melting under reduced pressure in 30 ml of tetrahydrofuran was added thereto at −78° C., and the mixture was stirred at room temperature for 1 hour. This solution was added to a solution of 7.22 g of 2-fluoroiodobenzene and 0.52 g of tetrakis (trifluorophosphine)palladium (0) in 30 ml of tetrahydrofuran at room temperature, and the mixed solution was stirred for 24 hours. The reaction solution was diluted with 300 ml of ethyl acetate, and the dilute solution was extracted with the addition of 10% hydrochloric acid. The organic layer was washed with a saturated aqueous solution of sodium chloride, dried, and then concentrated. The residue was purified through silica-gel column chromatography (eluent: hexane) to give 6.05 g of oily 2-fluoro-4'-methylbiphenyl.

Properties of the compound:

$^1$H-NMR(CDCl$_3$, δ): 2.39(3H, s), 7.10–7.30(5H, m), 7.39–7.49(3H, m)

Production Example 48

Production of 2-fluoro-4'-bromomethylbiphenyl

A mixture of 8.70 g of 2-fluoro-4'-methylbiphenyl, 8.32 g of N-bromosuccinimide, 0.10 g of 2,2'-azobisisobutylonitrile and 150 ml of carbon tetrachloride was heat-refluxed for 5 hours. The reaction solution was washed with water, and the organic layer was concentrated. The resulting residue was purified through silica-gel column chromatography (eluent: a mixture of hexane and ethyl acetate at a ratio of 9:1) to obtain crude 2-fluoro-4'-bromomethylbiphenyl. Further, this compound was crystallized from hexane to give 4.93 g of 2-fluoro-4'-bromomethylbiphenyl.

Properties of the compound:

$^1$H-NMR(CDCl$_3$, δ): 4.55(2H, s), 7.13–7.23(2H, m), 7.33 (1H, m), 7.43(1H, m), 7.47(2H, d, J=8.1Hz), 7.54(2H, d, J=8.1 Hz)

Production Example 49

Production of ethyl 3-[N-[(2'-fluorobiphenyl-4-yl) methyl]-acetylamino]-4-nitrobenzoate Ethyl 3-[N-[2'-fluorobiphenyl-4-yl)methyl]acetylamino]-4-nitrobenzoate (1.90 g) was formed from 1.54 g of ethyl 3-acetylamino-4-nitrobenzoate and 2.26 g of 2-fluoro-4'-bromomethylbiphenyl in the same manner as in Production Example 14.

Properties of the compound:

$^1$H-NMR(CDCl$_3$, δ): 1.33(3H, t, J=7.1 Hz), 1.92(3H, s), 4.36(2H, m), 4.44(1H, d, J=4.4 Hz), 5.32(1H, d, J=4.4 Hz), 7.13(1H, m), 7.18–7.22(3H, m), 7.31(1H, m), 7.40(1H, dt, J=1.6 and 7.7 Hz), 7.44(2H, d), 7.67(1H, d, J=1.6 Hz), 7.94(1H, d, J=8.4 Hz), 8.15(1H, dd, J=1.8 and 8.4 Hz)

EXAMPLE 244

Synthesis of 6-ethoxycarbonyl-1-[(2'-fluorobiphenyl-4-yl)-methyl]-2-methylbenzimidazole (306)

In the same manner as in Example 24, 1.53 g of 6-ethoxycarbonyl-1-[(2'-fluorobiphenyl-4-yl)methyl]-2-methylbenzimidazole (306) were formed from 1.90 g of ethyl 3-[N-[2'-fluorobiphenyl-4-yl)methyl]acetylamino]-4-nitrobenzoate.

Properties of Compound (306):

$^1$H-NMR(CDCl$_3$, δ): 1.40(3H, t, J=7.1Hz), 2.62(3H, s), 4.38(2H, q, J=7.1Hz), 5.43(2H, s), 7.10–7.17(3H, m), 7.19 (1H, dt, J=1.0 and 7.5 Hz), 7.31(1H, m), 7.38(1H, dt, J=1.8 and 7.8 Hz), 7.50(2H, dd), 7.74(1H, d, J=8.5 Hz), 8.00(1H, dd, J=1.4 and 8.4 Hz), 8.06(1H, s)

EXAMPLE 245

Synthesis of 6-carboxy-1-[(2'-fluorobiphenyl-4-yl) methyl]-2-methylbenzimidazole (307)

In the same manner as in Example 53, 1.24 g of 6-carboxy-1-[(2'-fluorobiphenyl-4-yl)methyl]-2-methylbenzimidazole (307) were formed from 1.50 g of 6-ethoxycarbonyl-1-[(2'-fluorobiphenyl-4-yl)methyl]-2-methylbenzimidazole.

Properties of Compound (307):

$^1$H-NMR(DMSO-d6, δ): 2.59(3H, s), 5.63(2H, s), 7.19 (2H, d, J=8.1 Hz), 7.24–7.31(2H, m), 7.39(1H, m), 7.46–7.53(3H, m), 7.62(1H, d, J=8.4 Hz), 7.80(1H, dd, J=1.3 and 8.4 Hz), 8.10(1H, s)

EXAMPLE 246

Synthesis of 6-(1-ethanesulfonylcarbamoyl)-1-[(2'-fluorobiphenyl-4-yl)methyl]-2-methylbenzimidazole (308)

In the same manner as in Example 98, 0.340 g of 6-(1-ethanesulfonylcarbamoyl)-1-[(2'-fluorobiphenyl-4-yl) methyl]-2-methylbenzimidazole (308) were formed from 0.455 g of 6-carboxy-1-[(2'-fluorobiphenyl-4-yl)methyl]-2-methylbenzimidazole, 0.409 g of N,N'-carbonyldiimidazole, 0.346 g of 1-butanesulfonamide and 0.384 g of diazabicycloundecene.

Properties of Compound (308):

$^1$H-NMR(DMSO-d6, δ): 0.84(3H, t, J=7.3 Hz), 1.39(1H, m), 1.67(1H, m), 2.57(3H, s), 3.51(1H, t), 5.60(2H, s), 7.21(2H, d, J=8.0 Hz), 7.24–7.30(2H, m), 7.39(1H, m), 7.48(1H, t), 7.52(2H, d, J=8.0 Hz), 7.66(1H, d, J=8.5 Hz), 7.80(1H, d, J=8.5 Hz), 8.25(1H, s), 11.93(1H, br s)

Production Example 50

Production of 3-fluoro-4-methylbiphenyl

Thirty milliliters of a 1.6-M-n-butyllithium hexane solution and a solution of 9.21 g of 4-bromo-2-fluorotoluene in 30 ml of tetrahydrofuran were added in this order to 30 ml of tetrahydrofuran which had been cooled to −78° C. in a nitrogen atmosphere, and the mixture was then stirred at −78° C. for 1 hour. A solution containing 6.64 g of zinc chloride which had been dehydrated through heat-melting under reduced pressure in 30 ml of tetrahydrofuran was added thereto at −78° C., and the mixture was stirred at room temperature for 1 hour. The reaction solution was added to a solution of 6.63 g of iodobenzene and 0.52 g of tetrakis (triphenylphosphine)palladium (0) in 30 ml of tetrahydrofuran at room temperature, and the mixed solution was stirred for 24 hours. The reaction solution was diluted with 300 ml of ethyl acetate, and the dilute solution was extracted with the addition of 10% hydrochloric acid. The organic layer was washed with a saturated aqueous solution of sodium chloride, dried, and then concentrated. The residue was purified through silica-gel column chromatography (eluent: hexane) to give 6.00 g of oily 3-fluoro-4-methylbiphenyl.

Properties of the compound:

$^1$H-NMR(CDCl$_3$, δ): 2.31(3H, d, J=1.8 Hz), 7.20–7.28 (3H, m), 7.34(1H, m), 7.43(2H, t), 7.55(2H, d)

Production Example 51

Production of 4-bromomethyl-3-fluorobiphenyl

A mixture of 6.00 g of 3-fluoro-4-methylbiphenyl, 5.73 g of N-bromosuccinimide, 0.075 g of 2,2'-azobisisobutylonitrile and 120 ml of carbon tetrachloride was heat-refluxed for 5 hours. The reaction solution was washed with water, and the organic layer was concentrated. The resulting residue was purified through silica-gel column chromatography (eluent: a mixture of hexane and ethyl acetate at a ratio of 9:1) to give 8.30 g of oily 4-bromomethyl-3-fluorobiphenyl.

Properties of the compound:

$^1$H-NMR(CDCl$_3$, δ): 4.57(2H, s), 7.30(1H, d, J=11.0 Hz), 7.34–7.40(2H, m), 7.45(3H, m), 7.56(2H, d)

Production Example 52

Production of ethyl 3-[N-[(3-fluorobiphenyl-4-yl)methyl]-acetylamino]-4-nitrobenzoate In the same manner as in Production Example 14, 2.68 g of crude ethyl 3-[N-[3-fluorobiphenyl-4-yl)methyl]acetylamino]-4-nitrobenzoate were obtained from 1.54 g of ethyl 3-acetylamino-4-nitrobenzoate and 2.26 g of 3-fluoro-4-bromomethylbiphenyl.

EXAMPLE 247

Synthesis of 6-ethoxycarbonyl-1-[(3-fluorobiphenyl-4-yl)methyl]-2-methylbenzimidazole (309)

In the same manner as in Example 24, 1.34 g of 6-ethoxycarbonyl-1-[(3-fluorobiphenyl-4-yl)methyl]-2-methylbenzimidazole (309) were formed from 2.68 g of crude ethyl 3-[N-[3-fluorobiphenyl-4-yl)methyl]acetylamino]-4-nitrobenzoate.

Properties of Compound (309):

$^1$H-NMR(CDCl$_3$, δ): 1.40(3H, t, J=7.1Hz), 2.65(3H, s), 4.39(2H, q, J=7.1 Hz), 5.46(2H, s), 6.79(1H, t, J=8.0 Hz), 7.25(1H, m), 7.34–7.40(2H, m), 7.41–7.47(2H, m), 7.50–7.54(2H, m), 7.74(1H, d, J=8.5 Hz), 7.99(1H, dd, J=1.5 and 8.4 Hz), 8.07(1H, d, J=1.3 Hz)

EXAMPLE 248

Synthesis of 6-carboxy-1-[(3-fluorobiphenyl-4-yl)methyl]-2-methylbenzimidazole (310)

In the same manner as in Example 53, 1.15 g of 6-carboxy-1-[(3-fluorobiphenyl-4-yl)methyl]-2-methylbenzimidazole (310) were formed from 1.34 g of 6-ethoxycarbonyl-1-[(3-fluorobiphenyl-4-yl)methyl]-2-methylbenzimidazole.

Properties of Compound 310:

$^1$H-NMR(DMSO-d6, δ): 2.59(3H, s), 5.64(2H, s), 7.03 (1H, t, J=8.0 Hz), 7.37(1H, t, J=7.3 Hz), 7.42–7.48(3H, m), 7.56–7.68(4H, m), 7.79(1H, dd, J=1.4 and 8.4 Hz), 8.11(1H, s), 12.7(1H, br s)

EXAMPLE 249

Synthesis of 6-(1-butanesulfonylcarbamoyl)-1-[(3-fluorobiphenyl-4-yl)methyl]-2-methylbenzimidazole (311)

In the same manner as in Example 98, 0.236 g of 6-(1-butanesulfonylcarbamoyl)-1-[(3-fluorobiphenyl-4-yl)methyl]-2-methylbenzimidazole (311) were formed from 0.390 g of 6-carboxy-1-[(3-fluorobiphenyl-4-yl)methyl]-2-methylbenzimidazole, 0.351 g of N,N'-carbonyldiimidazole, 0.297 g of 1-butanesulfonamide and 0.329 g of diazabicycloundecene.

Properties of Compound (311):

$^1$H-NMR(DMSO-d6, δ): 0.84(3H, t), 1.38(2H, m), 1.65 (2H, m), 2.57(3H, s), 3.48(2H, m), 5.63(2H, s), 6.93(1H, t, J=8.1 Hz), 7.37(1H, m), 7.42–7.47(3H, m), 7.60(1H, dd, J=1.7 and 11.8 Hz), 7.62–7.68(3H, m), 7.80(1H, dd, J=1.5 and 8.4 Hz), 8.21(1H, d, J=1.3 Hz), 11.90(1H, br s).

IR(Nujol): 1681 cm$^{-1}$ mp: 227–230° C.

EXAMPLE 250

Synthesis of 1-(2-chlorobenzyl)-6-[(2-methoxyethane)sulfonylcarbamoyl]-2-methylbenzimidazole (312)

In the same manner as in Example 98, 0.149 g of 1-(2-chlorobenzyl)-6-[(2-methoxyethane)sulfonylcarbamoyl]-2-methylbenzimidazole (312) were formed from 0.300 g of 1-(biphenyl-4-ylmethyl)-6-carboxy-2-ethylbenzimidazole, 0.272 g of N,N'-carbonyldiimidazole, 0.258 g of (2-ethoxyethane)sulfonamide and 0.256 g of diazabicycloundecene.

Properties of Compound (312):

$^1$H-NMR(DMSO-d6, δ): 0.87(3H, t, J=6.9 Hz), 1.30(3H, t, J=8.0 Hz), 2.89(2H, q, J=7.6 Hz), 3.25–3.35(2H, m), 3.63–3.74(2H, m), 5.59(2H, s), 7.17(2H, d, J=8.1 Hz), 7.34(1H, t, J=7.0 Hz), 7.44(2H, t, J=7.6 Hz), 7.58–7.68(5H, m), 7.82(1H, d, J=8.4 Hz), 8.23(1H, s), 11.88(1H, s).

IR(Nujol): 1681 cm$^{-1}$.

mp: 78–81° C.

EXAMPLE 251

Synthesis of 1-(2,4-dichlorobenzyl)-2-methyl-6-(1-pentanesulfonylcarbamoyl)benzimidazole (313)

In the same manner as in Example 98, 0.196 g of 1-(2,4-dichlorobenzyl)-2-methyl-6-(1-pentanesulfonylcarbamoyl)benzimidazole (313) were formed from 0.300 g of 6-carboxy-1-(2,4-dichlorobenzyl)-2-methylbenzimidazole, 0.323 g of N,N'-carbonyldiimidazole, 0.301 g of 1-pentanesulfonamide and 0.303 g of diazabicycloundecene.

Properties of Compound (313):

$^1$H-NMR(DMSO-d6, δ): 0.81(3H, t, J=7.3 Hz), 1.22–1.30 (2H, m), 1.32–1.39(2H, m), 1.64–1.71(2H, m), 2.50(3H, s), 3.50(2H, t, J=7.8 Hz), 5.59(2H, s), 6.45(1H, d, J=8.4 Hz), 7.33(1H, dd, J=2.2 and 8.5 Hz), 7.69(1H, d, J=8.5 Hz), 7.76(1H, d, J=2.1 Hz), 7.80(1H, dd, J=1.6 and 8.5 Hz), 8.10(1H, s), 11.89(1H, s).

IR(Nujol): 1682 cm$^{-1}$.

mp: 213.2–214.6° C.

EXAMPLE 252

Synthesis of 1-(biphenyl-4-ylmethyl)-2-ethyl-6-[1-[3-(methylthio)propane]sulfonylcarbamoyl]benzimidazole (314)

In the same manner as in Example 98, 0.178 g of 1-(biphenyl-4-ylmethyl)-2-ethyl-6-[1-[3-(methylthio)propane]sulfonylcarbamoyl]benzimidazole (314) were formed from 0.300 g of 6-carboxy-1-(biphenyl-4-ylmethyl)-2-ethylbenzimidazole, 0.272 g of N,N'-carbonyldiimidazole, 0.285 g of 1-[(3-methylthio)propane]sulfonamide and 0.256 g of diazabicycloundecene.

Properties of Compound (314):
$^1$H-NMR(DMSO-d6, δ): 1.30(3H, t, J=7.5 Hz), 1.91–1.99 (2H, m), 1.97(3H, s), 2.58(2H, t, J=7.2 Hz), 2.90(2H, q, J=7.6 Hz), 3.55–3.61(2H, m), 5.60(2H, s), 7.18(2H, d, J=8.2 Hz), 7.35(1H, t, J=7.3 Hz), 7.44(2H, t, J=7.5 Hz), 7.60–7.66 (4H, m), 7.69(1H, d, J=8.5 Hz), 7.82(1H, dd, J=1.8 and 8.5 Hz), 8.24(1H, s), 11.98(1H, s).
IR(Nujol): 1671 cm$^{-1}$.
mp: 89.9–91.2° C.

EXAMPLE 253

Synthesis of 1-(4-biphenylmethyl)-2-ethyl-6-(1-pentanesulfonylcarbamoyl)benzimidazole (315)

In the same manner as in Example 98, 0.258 g of 1-(4-biphenylmethyl)-2-ethyl-6-(1-pentanesulfonylcarbamoyl)benzimidazole (315) were formed from 0.300 g of 6-carboxy-1-(4-biphenylmethyl)-2-ethylbenzimidazole, 0.272 g of N,N'-carbonyldiimidazole, 0.254 g of 1-pentanesulfonamide and 0.256 g of diazabicycloundecene.

Properties of Compound (315):
$^1$H-NMR(DMSO-d6, δ): 0.87(3H, t, J=7.2 Hz), 1.22–1.39 (4H, m), 1.30(3H, t, J=7.5 Hz), 1.66–1.73(2H, m), 2.90(2H, q, J=7.4 Hz), 3.51(2H, t, J=7.7 Hz), 5.60(2H, s), 7.18(2H, d, J=8.2 Hz), 7.34(1H, t, J=7.4 Hz), 7.44(2H, t, J=7.6 Hz), 7.60–7.67(4H, m), 7.71(1H, d, J=8.4 Hz), 7.81(1H, dd, J=1.6 and 8.4 Hz), 8.27(1H, d, J=1.1 Hz), 11.92(1H, s).
IR(Nujol): 1682 cm$^{-1}$.
mp: 175.3–178.4° C.

EXAMPLE 254

Synthesis of 6-(1-butanesulfonylcarbamoyl)-1-(2,4-dicyclobenzyl)-2-ethylbenzimidazole (316)

In the same manner as in Example 98, 0.253 g of 6-(1-butanesulfonylcarbamoyl)-1-(2,4-dicyclobenzyl)-2-ethylbenzimidazole (316) were formed from 0.300 g of 6-carboxy-1-(2,4-dichlorobenzyl)-2-ethylbenzimidazole, 0.258 g of N,N'-carbonyldiimidazole, 0.217 g of 1-butanesulfonamide and 0.262 g of diazabicycloundecene.

Properties of Compound (316):
$^1$H-NMR(DMSO-d6, δ): 0.85(3H, t, J=7.4 Hz), 1.27(3H, t, J=7.4 Hz), 1.35–1.43(2H, m), 1.63–1.70(2H, m), 2.81(2H, q, J=7.4 Hz), 3.51(2H, t, J=7.7 Hz), 5.59(2H, s), 6.41(1H, d, J=8.4 Hz), 7.32(1H, dd, J=2.0 and 8.4 Hz), 7.73(1H, d, J=8.4 Hz), 7.76(1H, d, J=2.0 Hz), 7.81(1H, dd, J=1.5 and 8.5 Hz), 8.12(1H, d, J=1.6 Hz), 11.87(1H, s).
IR(Nujol): 1694 cm$^{-1}$.
mp: 175.7–176.9° C.

EXAMPLE 255

Synthesis of 1-(4-biphenylmethyl)-2-ethyl-6-[1-(3-methyl)butanesulfonylcarbamoyl]benzimidazole (317)

In the same manner as in Example 98, 0.273 g of 1-(4-biphenylmethyl)-2-ethyl-6-[1-(3-methyl)butanesulfonylcarbamoyl]benzimidazole (317) were formed from 0.300 g of 1-(4-biphenylmethyl)-6-carboxy-2-ethylbenzimidazole, 0.272 g of N,N'-carbonyldiimidazole, 0.254 g of 1-(3-methyl)butanesulfonamide and 0.256 g of diazabicycloundecene.

Properties of Compound (317):
$^1$H-NMR(DMSO-d6, δ): 0.85(6H, d, J=6.5 Hz), 1.30(3H, t, J=7.4 Hz), 1.55–1.62(2H, m), 1.63–1.70(1H, m), 2.90(2H, q, J=7.4 Hz), 3.52(2H, t, J=7.9 Hz), 5.61(2H, s), 7.19(2H, d, J=8.3 Hz), 7.35(1H, t, J=7.4 Hz), 7.44(2H, t, J=7.5 Hz), 7.61–7.66(4H, m), 7.71(1H, d, J=8.5 Hz), 7.81(1H, dd, J=1.6 and 8.4 Hz), 8.27(1H, s), 11.95(1H, s).
IR(Nujol): 1682 cm$^{-1}$.
mp: 102.8–104.5° C.

EXAMPLE 256

Synthesis of 1-(2,4-dichlorobenzyl)-5-ethoxycarbonyl-2-methylbenzimidazole (318)

In the same manner as in Production Example 14, ethyl 4-[N-(2,4-dichlorobenzyl)acetylamino]-3-nitrobenzoate was formed from 1.525 g of ethyl 4-acetylamino-3-nitrobenzoate and 1.42 g of 2,4-dichlorobenzyl chloride. This compound was converted into 1-(2,4-dichlorobenzyl)-5-ethoxycarbonyl-2-methylbenzimidazole [(318), 1.476 g] in the same manner as in Example 24 without being purified.

Properties of Compound (318):
$^1$H-NMR(CDCl$_3$, δ): 1.42(3H, t, J=7.1 Hz), 2.57(3H, s), 4.41(2H, q, J=7.1 Hz), 5.38(2H, s), 6.35(1H, d, J=8.4 Hz), 7.09(1H, dd, J=2.0 and 8.4 Hz), 7.16(1H, d, J=8.9 Hz), 7.49(1H, d, J=2.0 Hz), 7.96(1H, dd, J=1.5 and 8.5 Hz), 8.46(1H, s)

EXAMPLE 257

Synthesis of 5-carboxy-1-(2,4-dichlorobenzyl)-2-methylbenzimidazole (319)

In the same manner as in Example 53, 1.195 g of 5-carboxy-1-(2,4-dichlorobenzyl)-2-methylbenzimidazole (319) were formed from 1.465 g of 1-(2,4-dichlorobenzyl)-5-ethoxycarbonyl-2-methylbenzimidazole.

Properties of Compound (319):
$^1$H-NMR(DMSO-d6, δ): 2.48(3H, s), 5.56(2H, s), 6.53 (1H, d, J=8.4 Hz), 7.32(1H, dd, J=2.1 and 8.4 Hz), 7.44(1H, d, J=8.4 Hz), 7.73(1H, d, J=2.2 Hz), 7.78(1H, dd, J=1.5 and 8.4 Hz), 8.15(1H, d, J=1.3 Hz)

EXAMPLE 258

Synthesis of 5-(1-butanesulfonylcarbamoyl)-1-(2,4-dichlorobenzyl)-2-methylbenzimidazole (320)

In the same manner as in Example 98, 0.690 g of 5-(1-butanesulfonylcarbamoyl)-1-(2,4-dichlorobenzyl)-2-methylbenzimidazole (320) were formed from 0.565 g of 5-carboxy-1-(2,4-dichlorobenzyl)-2-methylbenzimidazole, 0.504 g of N,N'-carbonyldiimidazole, 0.427 g of 1-butanesulfonamide and 0.473 g of diazabicycloundecene.

Properties of Compound (320):
$^1$H-NMR(DMSO-d6, δ): 0.87(3H, t, J=7.3 Hz), 1.41(2H, m), 1.68(2H, m), 2.49(3H, s), 3.52(2H, m), 5.58(2H, s), 6.53(1H, d, J=8.4 Hz), 7.33(1H, dd, J=2.1 and 8.4 Hz), 7.50(1H, d, J=8.5 Hz), 7.73(1H, d, J=2.1 Hz), 7.78(1H, dd, J=1.5 and 8.5 Hz), 8.24(1H, s), 11.97(1H, br s).
IR(Nujol): 1674 cm$^{-1}$.
mp: 135.4–139.2° C.

EXAMPLE 259

Synthesis of 1-(4-biphenylmethyl)-5-ethoxycarbonyl-2-ethylbenzimidazole (321)

In the same manner as in Production Example 14, ethyl 4-[N-(4-biphenylmethyl)propionylamino]-3-nitrobenzoate was formed from 1.50 g of 4-propionylamino-3-nitrobenzoate and 1.67 g of 4-bromomethylbiphenyl. This compound was converted into 1-(4-biphenylmethyl)-5-ethoxycarbonyl-2-ethylbenzimidazole [(321), 1.23 g] in the same manner as in Example 24 without being purified.

Properties of Compound (321):

$^1$H-NMR(CDCl$_3$, δ): 1.40(3H, t, J=7.1 Hz), 1.45(3H, t, J=7.6 Hz), 2.90(2H, q, J=7.6 Hz), 4.39(2H, q, J=7.1 Hz), 5.40(2H, s), 7.09(2H, d, J=8.2 Hz), 7.27(1H, d, J=8.8 Hz), 7.34(1H, m), 7.42(2H, t), 7.55–7.51(4H, m), 7.97(1H, dd, J=1.5 and 8.4 Hz), 8.52(1H, d, J=1.2 Hz)

EXAMPLE 260

Synthesis of 1-(4-biphenylmethyl)-5-carboxy-2-ethylbenzimidazole (322)

In the same manner as in Example 53, 0.870 g of 1-(4-biphenylmethyl)-5-carboxy-2-ethylbenzimidazole (322) were formed from 1.00 g of 1-(4-biphenylmethyl)-5-ethoxycarbonyl-2-ethylbenzimidazole.

Properties of Compound (322):

$^1$H-NMR(DMSO-d6, δ): 1.30(3H, t, J=7.4 Hz), 2.90(2H, q, J=7.4 Hz), 5.57(2H, s), 7.17(2H, d, J=8.3 Hz), 7.33(1H, m), 7.42(2H, t), 7.63–7.57(5H, m), 7.81(1H, dd, J=1.6 and 8.6 Hz), 8.18(1H, d, J=1.3 Hz), 12.67(1H, br s)

EXAMPLE 261

Synthesis of 1-(4-biphenylmethyl)-5-(1-butanesulfonylcarbamoyl)-2-ethylbenzimidazole (323)

In the same manner as in Example 98, 0.305 g of 1-(4-biphenylmethyl)-5-(1-butanesulfonylcarbamoyl)-2-ethylbenzimidazole (323) were formed from 0.400 g of 1-(4-biphenylmethyl)-5-carboxy-2-ethylbenzimidazole, 0.364 g of N,N'-carbonyldiimidazole, 0.308 g of 1-butanesulfonamide and 0.342 g of diazabicycloundecene.

Properties of Compound (323):

$^1$H-NMR(DMSO-d6, δ): 0.86(3H, t, J=7.4 Hz), 1.30(3H, t, J=7.5 Hz), 1.41(2H, m), 1.68(2H, m), 2.91(2H, q, J=7.4 Hz), 3.52(2H, m), 5.59(2H, s), 7.16(2H, d, J=8.2 Hz), 7.34(1H, t, J=7.4 Hz), 7.43(2H, t), 7.59–7.65(5H, m), 7.80 (1H, dd, J=1.6 and 8.6 Hz), 8.24(1H, d, J=1.6 Hz), 11.97(1H, br s).

IR(Nujol): 1682 cm$^{-1}$.

mp: 142.9–144.4° C.

EXAMPLE 262

Synthesis of 1-(4-biphenylmethyl)-2-ethyl-6-(2-methoxyethanesulfonylcarbamoyl)benzimidazole (324)

In the same manner as in Example 98, 0.487 g of 1-(4-biphenylmethyl)-2-ethyl-6-(2-methoxyethanesulfonylcarbamoyl)benzimidazole (324) were formed from 0.513 g of benzimidazole, 0.464 g of N,N'-carbonyldiimidazole, 0.420 g of 2-methoxyethanesulfonamide and 0.438 g of diazabicycloundecene.

Properties of Compound (324):

$^1$H-NMR(DMSO-d6, δ): 1.30(3H, t, J=7.5 Hz), 2.90(2H, q, J=7.4 Hz), 3.13(3H, s), 3.70–3.77(4H, m), 5.60(2H, s) 7.18(2H, d, J=8.2 Hz), 7.35(1H, t, J=7.1 Hz), 7.44(2H, t, J=7.5 Hz), 7.60–7.67(4H, m), 7.70(1H, d, J=8.5 Hz), 7.80 (1H, dd, J=7.4 and 1.3 Hz), 8.25(1H, s), 11.97(1H, s).

IR(Nujol): 1684 cm$^{-1}$.

mp: 94.6–97.2° C.

EXAMPLE 263

Synthesis of 6-ethoxycarbonyl-2-ethyl-1-[4-(4-fluorobenzyloxy)benzyl]benzimidazole (325)

A mixture of 0.534 g of ethyl 4-propionylamino-3-aminobenzoate, 0.374 g of potassium carbonate, 0.800 g of 4-(4-fluorobenzyloxy)benzyl bromide, 5 ml of ethyl acetate and 3 ml of water was stirred at 75° C. for 16 hours. The organic layer was concentrated, and ethanol and 0.46 g of 36% hydrochloric acid were added to the residue. The mixture was stirred for 2 hours while being heat-refluxed. The reaction mixture was neutralized with potassium carbonate, and the solvent was then concentrated under reduced pressure. The residue was extracted with ethyl acetate and with water. The organic layer was concentrated under reduced pressure, and was purified through silica-gel column chromatography (eluent: a mixture of hexane and ethyl acetate at a ratio of 1:1) to give 0.228 g of 6-ethoxycarbonyl-2-ethyl-1-[4-(4-fluorobenzyloxy)benzyl] benzimidazole (325).

Properties of Compound (325):

$^1$H-NMR(CDCl$_3$, δ): 1.40(3H, t, J=7.1 Hz), 1.42(3H, t, J=7.5 Hz), 2.86(2H, q, J=7.5 Hz), 4.38(2H, q, J=7.1 Hz), 4.97(2H, s), 5.32(2H, s), 6.88(2H, d, J=8.7 Hz), 6.98(2H, d, J=8.7 Hz), 7.05(2H, t, J=8.7 Hz), 7.37(2H, m), 7.76(2H, d, J=8.4 Hz), 7.98(1H, dd, J=1.5 and 8.5 Hz), 8.02(1H, s)

EXAMPLE 264

Synthesis of 6-carboxy-2-ethyl-1-[4-(4-fluorobenzyloxy)benzyl]benzimidazole (326)

In the same manner as in Example 53, 0.175 g of 6-carboxy-2-ethyl-1-[4-(4-fluorobenzyloxy)benzyl] benzimidazole (326) were formed from 0.225 g of 6-ethoxycarbonyl-2-ethyl-1-[4-(4-fluorobenzyloxy)benzyl] benzimidazole.

Properties of Compound (326):

$^1$H-NMR(DMSO-d6, δ): 1.28(3H, t, J=7.4 Hz), 2.89(2H, q, J=7.4 Hz), 5.01(2H, s), 5.47(2H, s), 6.95(2H, d), 7.03(2H, d), 7.18(2H, t), 7.45(2H, m), 7.62(1H, d, J=8.4 Hz), 7.77 (1H, d, J=8.4 Hz), 8.05(1H, s)

EXAMPLE 265

Synthesis of 6-(1-butanesulfonylcarbamoyl)-2-ethyl-1-[4-(4-fluorobenzyloxy)benzyl]benzimidazole ammonium salt (327)

In the same manner as in Example 98, oily 6-(1-butanesulfonylcarbamoyl)-2-ethyl-1-[4-(4-fluorobenzyloxy)benzyl]benzimidazole was obtained from 0.171 g of 6-carboxy-2-ethyl-1-[4-(4-fluorobenzyloxy) benzyl]benzimidazole, 0.137 g of N,N'-carbonyldiimidazole, 0.116 g of butanesulfonamide and 0.129 g of diazabicycloundecene. This compound was dissolved in ethyl acetate, and aqueous ammonia was added thereto. The solid material precipitated was separated through filtration, and was dried to give 0.140 g of 6-(1-butanesulfonylcarbamoyl)-2-ethyl-1-[4-(4-fluorobenzyloxy)benzyl]benzimidazole ammonium salt (327).

Properties of Compound (327):

$^1$H-NMR(DMSO-d6, δ): 0.83(3H, t), 1.25(3H, t), 1.35 (2H, m),1.61(2H, m), 2.84(2H, q), 3.27(2H, m), 5.01(2H, s), 5.42(2H, s), 6.95(2H, d, J=7.8 Hz), 7.02(2H, d, J=7.8 Hz), 7.17(2H, t), 7.44(2H, m), 7.57(1H, d, J=8.1 Hz), 7.82(1H, d, J=8.1 Hz), 8.12(1H, s).

IR(Nujol): 1614 cm$^{-1}$.

mp: 105–115° C.

EXAMPLE 266

Synthesis of 1-[4-(3,4-dichlorobenzyloxy)benzyl]-6-ethoxycarbonyl-2-ethylbenzimidazole (328)

In the same manner as in Example 263, 2.01 g of 1-[4-(3,4-dichlorobenzyloxy)benzyl]-6-ethoxycarbonyl-2-ethylbenzimidazole (328) were formed from 1.81 g of ethyl 4-propionylamino-3-aminobenzoate and 3.18 g of 4-(3,4-dichlorobenzyloxy)benzyl bromide.

Properties of Compound (328):

$^1$H-NMR(CDCl$_3$, δ): 1.40(3H, t, J=7.1 Hz), 1.42(3H, t, J=7.5 Hz), 2.86(2H, q, J=7.5 Hz), 4.38(2H, q, J=7.1 Hz), 4.97(2H, s), 5.33(2H, s), 6.87(2H, m), 6.98(2H, m), 7.22 (1H, dd, J=2.0 and 8.3 Hz), 7.44(1H, d, J=8.3 Hz), 7.50(1H, d, J=2.0 Hz), 7.76(1H, d, J=8.6 Hz), 7.97(1H, dd, J=1.6 and 8.6 Hz), 8.02(1H, d, J=1.3 Hz)

EXAMPLE 267

Synthesis of 6-carboxy-1-[4-(3,4-dichlorobenzyloxy)benzyl]-2-ethylbenzimidazole (329)

In the same manner as in Example 53, 1.82 g of 6-carboxy-1-[4-(3,4-dichlorobenzyloxy)benzyl]-2-ethylbenzimidazole (329) were formed from 2.01 g of 6-ethoxycarbonyl-2-ethyl-1-[4-(4-fluorobenzyloxy)benzyl]benzimidazole.

Properties of Compound (329):

$^1$H-NMR(DMSO-d6, δ): 1.28(3H, t), 2.88(2H, q), 5.05 (2H, s), 5.47(2H, s), 6.96(2H, d), 7.04(2H, d), 7.39(1H, m), 7.68–7.59(3H, m), 7.78(1H, d, J=8.4 Hz), 8.06(1H, s)

EXAMPLE 268

Synthesis of 6-(1-butanesulfonylcarbamoyl)-1-[4-(3,4-dichlorobenzyloxy)benzyl]-2-ethylbenzimidazole ammonium salt (330)

Oily 6-(1-butanesulfonylcarbamoyl)-1-[4-(3,4-dichlorobenzyloxy)benzyl]-2-ethylbenzimidazole was obtained from 0.500 g of 6-carboxy-1-[4-(3,4-dichlorobenzyloxy)benzyl]-2-ethylbenzimidazole, 0.356 g of N,N'-carbonyldiimidazole, 0.301 g of butanesulfonamide and 0.334 g of diazabicycloundecene in the same manner as in Example 98. This compound was dissolved in ethyl acetate, and aqueous ammonia was added thereto. The solid material precipitated was separated through filtration, and was dried to give 0.51 g of 6-(1-butanesulfonylcarbamoyl)-1-[4-(3,4-dichlorobenzyloxy)benzyl]-2-ethylbenzimidazole ammonium salt (330).

Properties of Compound (330)

$^1$H-NMR(DMSO-d6, δ): 0.82(3H, t, J=7.3 Hz), 1.26(3H, t, J=7.4 Hz), 1.31(2H, m), 1.54(2H, m), 2.84(2H, q, J=7.4 Hz), 3.07(2H, m), 5.05(2H, s), 5.41(2H, s), 6.95(2H, d, J=8.7 Hz), 7.00(2H, d, J=8.7 Hz), 7.41(1H, d, J=8.2 Hz), 7.46(1H, d, J=8.4 Hz), 7.62(1H, d, J=8.2 Hz), 7.68(1H, s), 7.81(1H, d, J=8.4 Hz), 7.97(1H, s).

IR(Nujol): 1540 cm$^{-1}$.

mp: 99.5–101.5° C.

EXAMPLE 269

Synthesis of 1-(4-biphenylmethyl)-6-(n-butylcarbamoyl)-2-ethylbenzimidazole (331)

In the same manner as in Example 15, 0.295 g of 1-(4-biphenylmethyl)-6-(n-butylcarbamoyl)-2-ethylbenzimidazole (331) were formed from 0.400 g of 1-(4-biphenylmethyl)-6-chlorocarbonyl-2-ethylbenzimidazole hydrochloride, 0.233 g of n-butylamine and 0.215 g of triethylamine.

Properties of Compound (331):

$^1$H-NMR(DMSO-d6, δ): 0.95(3H, t, J=7.3 Hz), 1.37–1.48 (2H, m), 1.45(3H, t, J=7.4 Hz), 1.57–1.63(2H, m), 2.90(2H, q, J=7.5 Hz), 3.46(2H, q, J=7.1 Hz), 5.42(2H, s), 6.16(1H, br s), 7.10(2H, d, J=8.1 Hz), 7.34(1H, t, J=7.5 Hz), 7.42(2H, t, J=7.5 Hz), 7.48–7.57(5H, m), 7.87(1H, d, J=8.4 Hz), 7.91(1H, s).

IR(Nujol): 1621 cm$^{-1}$.

mp: 170.5–173.0° C.

EXAMPLE 270

Synthesis of 1-(4-biphenylmethyl)-2-ethyl-6-(thiazol-2-ylcarbamoyl)benzimidazole (332)

In the same manner as in Example 15, 0.179 g of 1-(4-biphenylmethyl)-2-ethyl-6-(thiazol-2-ylcarbamoyl) benzimidazole (332) were obtained from 0.400 g of 1-(4-biphenylmethyl)-6-chlorocarbonyl-2-ethylbenzimidazole hydrochloride, 0.318 g of 2-aminothiazole and 0.215 g of triethylamine.

Properties of Compound (332):

$^1$H-NMR(DMSO-d6, δ): 1.48(3H, t, J=7.5 Hz), 2.95(2H, q, J=7.5 Hz), 5.41(2H, s), 6.94(1H, d, J=3.6 Hz), 7.06(2H, d, J=8.1 Hz), 7.26(1H, d, J=3.6 Hz), 7.32(1H, t, J=7.4 Hz), 7.39(2H, t, J=7.3 Hz), 7.47–7.51(4H, m), 7.87(2H, s), 8.03 (1H, s), 11.15(1H, s).

IR(Nujol): 1652 cm$^{-1}$.

mp: 225.5–227.7° C.

EXAMPLE 271

Synthesis of 1-(4-biphenylmethyl)-2-ethyl-6-(2-pyridylcarbamoyl)benzimidazole (333)

In the same manner as in Example 98, 0.116 g of 1-(4-biphenylmethyl)-2-ethyl-6-(2-pyridylcarbamoyl) benzimidazole (333) were formed from 0.300 g of 1-(4-biphenylmethyl)-6-carboxy-2-ethylbenzimidazole, 0.272 g of N,N'-carbonyldiimidazole, 0.158 g of 2-aminopyridine and 0.256 g of diazabicycloundecene.

Properties of Compound (333):

$^1$H-NMR(CDCl$_3$, δ): 1.47(3H, t, J=7.6 Hz), 2.93(2H, q, J=7.4 Hz), 5.45(2H, s), 7.06(1H, dd, J=7.4 and 4.9 Hz), 7.10(2H, d, J=8.1 Hz), 7.34(1H, t, J=7.4 Hz), 7.42(2H, t, J=7.6 Hz), 7.50–7.55(4H, m), 7.75(1H, t, J=7.9 Hz), 7.79 (1H, d, J=8.4 Hz), 7.86(1H, d, J=8.4 Hz), 7.98(1H, s), 8.30(1H, d, J=6.2 Hz), 8.38(1H, d, J=8.4 Hz), 8.62(1H,s).

IR(Nujol): 1661 cm$^{-1}$.

mp: 160.9–164.5° C.

EXAMPLE 272

Synthesis of 6-(n-butylcarbamoyl)-1-(2,4-dichlorobenzyl)-2-methyl-benzimidazole (334)

In the same manner as in Example 15, 0.156 g of 6-(n-butylcarbamoyl)-1(2,4-dichlorobenzyl)-2- methylbenzimidazole (334) were formed from 0.300 g of 6-chlorocarbonyl-1-(2,4-dichlorobenzyl)-2-ethylbenzimidazole hydrochloride, 0.181 g of triethylamine and 0.196 g of n-butylamine.

Properties of Compound (334):

$^1$H-NMR(CDCl$_3$, δ): 0.96(3H, t, J=7.3 Hz), 1.37–1.43 (2H, m), 1.55–1.62(2H, m), 2.56(3H, s), 3.46(2H, q, J=7.0 Hz), 5.40(2H, s), 6.15(1H, br s), 6.32(1H, d, J=8.5 Hz), 7.07(1H, d, J=8.4 Hz), 7.48(1H, d, J=2.0 Hz), 7.55(1H, d, J=8.4 Hz), 7.74(1H, d, J=8.4 Hz), 7.79(1H,s).

IR(Nujol): 1636 cm$^{-1}$.

mp: 146.6–147.5° C.

Production Example 53

Production of ethyl 3-[sec-(2,4-dichlorophenetyl) amino]-4-nitrobenzoate

A solution of 0.877 g of 3-fluoro-4-nitrobenzoic acid and 2.25 g of sec-(2,4-dichlorophenetyl)amine in 5 ml of toluene was heat-refluxed for 15 hours. After the solvent was distilled off, the residue was purified through silica-gel column chromatography to obtain crude 3-[sec-(2,4-dichlorophenetyl)amino]-4-nitrobenzoic acid. To this compound were added 80 ml of ethanol and 3.0 g of 97% sulfuric acid, and the mixture was heat-refluxed for 4.5 hours. After ethanol was distilled off under reduced pressure, the residue was extracted with chloroform and with a saturated aqueous solution of sodium hydrogencarbonate. The organic layer was dried, and was then concentrated under reduced pressure. The residue was purified through silica-gel column chromatography (eluent: a mixture of hexane and ethyl acetate at a ratio of 2:1) to give 1.16 g of ethyl 3-[sec-(2,4-dichlorophenetyl)amino]-4-nitrobenzoate.

Properties of the compound:

$^1$H-NMR(CDCl$_3$, δ): 1.35(3H, t, J=7.1 Hz), 1.64(3H, d, J=6.6 Hz), 4.30(2H, q, J=7.1 Hz), 5.16(1H, m), 7.18–7.31 (4H, m), 7.43(1H, d, J=2.0 Hz), 8.21(1H, d, J=8.8 Hz), 8.34(1H, d, J=5 Hz)

Production Example 54

Production of ethyl 4-amino-3-[sec-(2,4-dichlorophenetyl)amino]benzoate

A mixture of 1.14 g of ethyl 3-[sec-(2,4-dichlorophenetyl)amino]-4-nitrobenzoate, 1.60 g of reduced iron, 10 ml of ethanol and 5 ml of acetic acid was heat-refluxed for 3 hours. The solid material was separated through filtration, and the filtrate was concentrated. The residue was extracted with chloroform and with 10% hydrochloric acid. The organic layer was washed with a saturated aqueous solution of sodium hydrogencarbonate, and the solvent was distilled off under reduced pressure. The residue was purified through silica-gel column chromatography (eluent: a mixture of hexane and ethyl acetate at a ratio of 2:1) to give 0.920 g of ethyl 4-amino-3-[sec-(2,4-dichlorophenetyl)amino] benzoate.

Properties of the compound:

$^1$H-NMR(CDCl$_3$, δ): 1.31(3H, t, J=7.1 Hz), 1.52(3H, d, J=6.7 Hz), 3.56(1H, br s), 3.79(2H, br s), 4.23(2H, q, J=7.1 Hz), 4.96(1H, q, J=6.7 Hz), 6.68(1H, d, J=8.0 Hz), 7.03(1H, d, J=1.7 Hz), 7.15(1H, dd, J=2.1 and 8.4 Hz), 7.35(1H, d, J=8.4 Hz), 7.39–7.43(2H, m)

EXAMPLE 273

Synthesis of 1-[sec-(2,4-dichlorophenetyl)]-6-ethoxycarbonyl-2-methylbenzimidazole (335)

Acetyl chloride (0.243 g) was added dropwise to a solution of 0.900 g of ethyl 4-amino-3-[sec-2,4-dichlophenetyl) amino]benzoate in 2.0 ml of pyridine at room temperature. Further, the mixture was stirred at room temperature for 1 hour, and the reaction mixture was then extracted with the addition of ethyl acetate and excess 10% hydrochloric acid. The organic layer was washed with a saturated aqueous solution of sodium hydrogencarbonate, and the solvent was distilled off under reduced pressure to obtain crude ethyl 4-4-acetylamino-3-[sec-(2,4-dichlorophenetyl)amino] benzoate. This crude product was immediately dissolved in 20 ml of ethanol, and 0.4 ml of 36% hydrochloric acid were added to the solution. The mixture was heat-refluxed for 2 hours. The reaction solution was neutralized with sodium hydrogencarbonate, and the solvent was distilled off under reduced pressure. The residue was extracted with ethyl acetate and with water. The organic layer was concentrated, and the residue was purified through silica-gel column chromatography (eluent: a mixture of ethyl acetate and methanol at a ratio of 20:1) to give 0.700 g of 1-[sec-(2,4-dichlorophenetyl)]-6-ethoxycarbonyl-2-methylbenzimidazole (335).

Properties of Compound (335):

$^1$H-NMR(CDCl$_3$, δ): 1.38(3H, t, J=7.2 Hz), 2.01(3H, d, J=7.2 Hz), 2.63(3H, s), 4.29–4.40(2H, m), 5.89(1H, q, J=7.2 Hz), 7.37(1H, dd, J=2.2 and 8.4 Hz), 7.40(1H, d, J=2.0 Hz), 7.52(1H, d, J=8.4 Hz), 7.67(1H, d, J=8.4 Hz), 7.86(1H, s), 7.91(1H, dd, J=1.4 and 8.4 Hz)

EXAMPLE 274

Synthesis of 6-carboxy-1-[sec-(2,4-dichlorophenetyl)]-2-methylbenzimidazole (336)

In the same manner as in Example 53, 0.447 g of 6-carboxy-1-[sec-(2,4-dichlorophenetyl)]-2-methylbenzimidazole (336) were formed from 0.690 g of 1-[sec-(2,4-dichlorophenetyl)]-6-ethoxycarbonyl-2-methylbenzimidazole.

Properties of Compound (336):

$^1$H-NMR(DMSO-d6, δ): 1.88(3H, d, J=6.8 Hz), 2.57(3H, s), 6.01(1H, q), 7.55(1H, d), 7.60–7.67(3H, m), 7.71(1H, d), 7.89(1H, d), 12.65(1H, br s)

EXAMPLE 275

Synthesis of 6-(1-butanesulfonylcarbamoyl)-1-[sec-(2,4-dichlorophenetyl)]-2-methylbenzimidazole (337)

In the same manner as in Example 98, 6-(1-butanesulfonylcarbamoyl)-1-[sec-(2,4-dichlorophenetyl)]-2-methylbenzimidazole (336) was formed from 0.433 g of 6-carboxy-1-[sec-(2,4-dichlorophenetyl)]-2-methylbenzimidazole, 0.412 g of N,N'-carbonyldiimidazole, 0.348 g of butanesulfonamide and 0.386 g of diazabicycloundecene.

Properties of Compound (337)

$^1$H-NMR(DMSO-d6, δ): 0.84(3H, t, J=7.3 Hz), 1.34(2H, m), 1.57(2H, m), 1.89(3H, d, J=7.0 Hz), 2.49(3H, s), 3.07 (2H, m), 5.954(1H, q, J=7.0 Hz), 7.41(1H, d, J=8.7 Hz), 7.56(1H, dd, J=2.1 and 8.5 Hz), 7.61(1H, d, J=2.1 Hz), 7.74–7.79(3H, m)

EXAMPLE 276

Synthesis of 1-(4-biphenylmethyl)-2-ethyl-6-(phenylcarbamoyl)benzimidazole (338)

In the same manner as in Example 15, 0.195 g of 1-(4-biphenylmethyl)-2-ethyl-6-(phenylcarbamoyl)

benzimidazole (338) were formed from 0.300 g of 1-(4-biphenylmethyl)-6-chlorocarbonyl-2-ethylbenzimidazole hydrochloride, 0.243 g of triethylamine and 0.224 g of aniline.

Properties of Compound (338):

$^1$H-NMR(CDCl$_3$, δ): 1.47(3H, t, J=7.5 Hz), 2.93(2H, q, J=7.5 Hz), 5.44(2H, s), 7.11(2H, d, J=8.2 Hz), 7.14(1H, t, J=7.4 Hz), 7.32–7.38(3H, m), 7.42(2H, t, J=7.4 Hz), 7.51–7.54(4H, m), 7.63(2H, d, J=7.8 Hz), 7.69(1H, dd, J=8.4 and 1.6 Hz), 7.84(1H, d, J=8.4 Hz), 7.88(1H, br s), 7.97 (1H, d, J=1.5 Hz).

IR(Nujol): 1647 cm$^{-1}$.

mp: 171.7–172.1° C.

EXAMPLE 277

Synthesis of 1-(4-biphenylmethyl)-2-ethyl-6-(1,3,4-thiadiazol-2-ylcarbamoyl)benzimidazole (339)

In the same manner as in Example 98, 0.234 g of 1-(4-biphenylmethyl)-2-ethyl-6-(1,3,4-thiadiazol-2-ylcarbamoyl)benzimidazole (339) were formed from 0.300 g of 1-(4-biphenylmethyl)-6-carboxy-2-ethylbenzimidazole, 0.272 g of N,N'-carbonyldiimidazole, 0.170 g of 2-amino-1,3,4-thiadiazole and 0.256 g of diazabicycloundecene.

Properties of Compound (339):

$^1$H-NMR(CDCl$_3$, δ): 1.45(3H, t, J=7.5 Hz), 2.90(2H, q, J=7.5 Hz), 5.53(2H,s), 7.07(2H, d, J=8.3 Hz), 7.33(1H, t, J=7.5 Hz), 7.40(2H, t, J=7.3 Hz), 7.52(4H, d, J=8.2 Hz), 7.89(1H, d, J=8.5 Hz), 8.08(1H, dd, J=8.5 and 1.6 Hz), 8.34(1H, d, J=1.2 Hz), 7.60(1H, s), 12.26(1H, s).

IR(Nujol): 1654 cm$^{-1}$.

mp: 230.1–233.4° C.

EXAMPLE 278

Synthesis of 1-(4-biphenylmethyl)-2-ethyl-6-(tetrazol-5-ylcarbamoyl)benzimidazole (340)

In the same manner as in Example 98, 0.135 g of 1-(4-biphenylmethyl)-2-ethyl-6-(tetrazol-5-ylcarbamoyl) benzimidazole (340) were formed from 0.300 g of 1-(4-biphenylmethyl)-6-carboxy-2-ethylbenzimidazole, 0.272 g of N,N'-carbonyldiimidazole, 0.143 g of 5-aminotetrazole and 0.256 g of diazabicycloundecene.

Properties of Compound (340)

$^1$H-NMR(DMSO-d6, δ): 1.32(3H, t, J=7.5 Hz), 2.93(2H, q, J=7.5 Hz), 5.61(2H, s), 7.23(2H, d, J=8.1 Hz), 7.34(1H, t, J=7.4 Hz), 7.44(2H, t, J=7.6 Hz), 7.60–7.67(4H, m), 7.76(1H, d, J=8.5 Hz), 7.98(1H, d, J=8.6 Hz), 8.46(1H, s), 12.30(1H, s), 15.95(1H, s).

IR(Nujol): 1667 cm$^{-1}$.

mp: 273.1–276.0° C.

EXAMPLE 279

Synthesis of 1-(4-biphenylmethyl)-2-ethyl-6-(1,3,4-triazol-3-ylcarbamoyl)benzimidazole (341)

In the same manner as in Example 98, 0.224 g of 1-(4-biphenylmethyl)-2-ethyl-6-(1,3,4-triazol-3-ylcarbamoyl)benzimidazole (341) were formed from 0.300 g of 1-(4-biphenylmethyl)-6-carboxy-2-ethylbenzimidazole, 0.272 g of N,N'-carbonyldiimidazole, 0.141 g of 3-amino-1,3,4-triazole and 0.256 g of diazabicycloundecene.

Properties of Compound (341):

$^1$H-NMR(DMSO-d6, δ): 1.33(3H, t, J=7.4 Hz), 2.93(2H, q, J=7.4 Hz), 5.63(2H, s), 7.17(2H, d, J=8.3 Hz), 7.35(1H, t, J=7.4 Hz), 7.44(2H, t, J=7.5 Hz), 7.60–7.65(4H, m), 7.78(1H, d, J=7.4 Hz), 7.83(1H, dd, J=8.4 and 1.5 Hz), 8.17(1H, s), 8.77(2H, s), 12.04(1H, s).

IR(Nujol): 1675 cm$^{-1}$.

mp: 263.4–266.2° C.

EXAMPLE 280

Synthesis of 1-(4-biphenylmethyl)-2-ethyl-6-(1,3,4-triazol-2-ylcarbamoyl)benzimidazole (342)

In the same manner as in Example 98, 0.215 g of 1-(4-biphenylmethyl)-2-ethyl-6-(1,3,4-triazol-2-ylcarbamoyl)benzimidazole (342) were formed from 0.300 g of 1-(4-biphenylmethyl)-6-carboxy-2-ethylbenzimidazole, 0.272 g of N,N'-carbonyldiimidazole, 0.141 g of 2-amino-1,3,4-triazole and 0.256 g of diazabicycloundecene.

Properties of Compound (342):

$^1$H-NMR(DMSO-d6, δ): 1.31(3H, t, J=7.4 Hz), 2.92(2H, q, J=7.4 Hz), 5.60(2H, s), 7.23(2H, d, J=7.8 Hz), 7.34(1H, t, J=7.2 Hz), 7.44(2H, t, J=7.6 Hz), 7.60–7.66(4H, m), 7.72(1H, d, J=8.3 Hz), 7.78(1H, s), 7.95(1H, d, J=8.3 Hz), 8.43(1H, s), 11.85(1H, s), 13.57(1H, s).

IR(Nujol): 1659 cm$^{-1}$.

mp: 306.0° C.(decomp.)

EXAMPLE 281

Synthesis of 1-(4-biphenylmethyl)-2-ethyl-6-(3-pyridylcarbamoyl)benzimidazole (343)

In the same manner as in Example 98, 0.229 g of 1-(4-biphenylmethyl)-2-ethyl-6-(3-pyridylcarbamoyl) benzimidazole (343) were formed from 0.300 g of 1-(4-biphenylmethyl)-6-carboxy-2-ethylbenzimidazole, 0.272 g of N,N'-carbonyldiimidazole, 0.158 g of 3-aminopyridine and 0.256 g of diazabicycloundecene.

Properties of Compound (343):

$^1$H-NMR(CDCl$_3$, δ): 1.47(3H, t, J=7.6 Hz), 2.93(2H, q, J=7.4 Hz), 5.45(2H, s), 7.10(2H, d, J=8.1 Hz), 7.29–7.36 (2H, m), 7.42(2H, t, J=7.4 Hz), 7.53(4H, d, J=8.0 Hz), 7.71(1H, d, J=8.5 Hz), 7.86(1H, d, J=8.4 Hz), 7.97(1H, s), 7.98(1H, s), 8.27(1H, d, J=8.4 Hz), 8.38(1H, d, J=4.7 Hz), 8.68(1H, d, J=2.5 Hz).

IR(Nujol): 1644 cm$^{-1}$.

mp: 124.4–125.6° C.

EXAMPLE 282

Synthesis of 1-(2,4-dichlorobenzyl)-2-methyl-6-(2-pyridylcarbamoyl)benzimidazole (344)

In the same manner as in Example 98, 0.152 g of 1-(2,4-dichlorobenzyl)-2-methyl-6-(2-pyridylcarbamoyl) benzimidazole (344) were formed from 0.300 g of 6-carboxy-1-(2,4-dichlorobenzyl)-2-methylbenzimidazole, 0.290 g of N,N'-carbonyldiimidazole, 0.168 g of 2-aminopyridine and 0.273 g of diazabicycloundecene.

Properties of Compound (344):

$^1$H-NMR(CDCl$_3$, δ): 2.59(3H, s), 5.43(2H,s), 6.33(1H, d, J=8.4 Hz), 7.06–7.10(2H, m), 7.50(1H, d, J=2.1 Hz), 7.77 (1H, dt, J=7.8 and 1.9 Hz), 7.83(2H, s), 7.88(1H, s), 8.30 (1H, d, J=3.7 Hz), 8.39(1H, d, J=8.3 Hz), 8.78(1H, s).

IR(Nujol): 1666 cm$^{-1}$.

mp: 157.4–159.2° C.

EXAMPLE 283

Synthesis of 1-(4-biphenylmethyl)-2-ethyl-6-(4-pyridylcarbamoyl)benzimidazole (345)

In the same manner as in Example 98, 0.153 g of 1-(4-biphenylmethyl)-2-ethyl-6-(4-pyridylcarbamoyl)

benzimidazole (345) were formed from 0.300 g of 1-(4-biphenylmethyl)-6-carboxy-2-ethylbenzimidazole, 0.272 g of N,N'-carbonyldiimidazole, 0.158 g of 4-aminopyridine and 0.256 g of diazabicycloundecene.

Properties of Compound (345):

$^1$H-NMR(CDCl$_3$, δ): 1.48(3H, t, J=7.4 Hz), 2.94(2H, q, J=7.4 Hz), 5.45(2H, s), 7.10(2H, d, J=8.1 Hz), 7.35(1H, t, J=7.4 Hz), 7.42(2H, t, J=7.4 Hz), 7.50–7.60(6H, m), 7.691 (1H, d, J=7.8 Hz), 7.86(1H, d, J=8.3 Hz), 7.95(1H, s), 7.99(1H, br s), 8.54(2H, dd, J=1.5 and 4.7 Hz).

IR(Nujol): 1663 cm$^{-1}$.

mp: 123.8–124.7° C.

Production Example 55

Production of N-(1-butanesulfonyl)-4-acetylamino-3-nitrobenzamide

In the same manner as in Production Example 28, 10.75 g of N-(1-butanesulfonyl)-4-acetylamino-3-nitrobenzamide were formed from 10.0 g of 4-acetylamino-3-nitrobenzoic acid, 9.40 g of N,N'-carbonyldiimidazole, 7.92 g of 1-butanesulfonamide and 8.83 g of diazabicycloundecene.

Properties of the compound:

$^1$H-NMR(DMSO-d6, δ): 0.87(3H, t, J=7.4 Hz), 1.37–1.44 (2H, m), 1.64–1.71(2H, m), 2.12(3H, s), 3.52(2H, t, J=7.7 Hz), 7.83(1H, d, J=8.6 Hz), 8.21(1H, dd, J=8.6 and 2.1 Hz), 8.54(1H, d, J=2.2 Hz), 10.56(1H, s), 12.32(1H, s)

Production Example 56

Production of N-(1-butanesulfonyl)-3-amino-4-acetylaminobenzamide

In the same manner as in Production Example 29, 3.04 g of N-(1-butanesulfonyl)-3-amino-4-acetylaminobenzamide were formed from 10.75 g of N-(1-butanesulfonyl)-4-acetylamino-3-nitrobenzamide.

Properties of the compound:

$^1$H-NMR(DMSO-d6, δ): 0.86(3H, t, J=7.3 Hz), 1.33–1.43 (2H, m), 1.59–1.67(2H, m), 2.07(3H, s), 3.37–3.43(2H, t), 5.12(2H, br s), 7.13(1H, dd, J=8.2 and 2.0 Hz), 7.28(1H, d, J=1.9 Hz), 7.40(1H, d, J=8.3 Hz), 9.09(1H, s)

Production Example 57

Production of N-(1-butanesulfonyl)-4-acetylamino-3-[4-(2-pyridyl)benzylamino]benzamide In the same manner as in Production Example 32, crude N-(1-butanesulfonyl)-4-acetylamino-3-[4-(2-pyridyl) benzylamino]-benzamide was obtained from 0.400 g of N-(1-butanesulfonyl)-3-amino-4-acetylaminobenzamide and 0.477 g of 2-[(4-bromomethyl)phenyl]pyridine. This product was used in the subsequent reaction at once.

EXAMPLE 284

Synthesis of 6-(1-butanesulfonylcarbamoyl)-1-[4-(2-pyridyl)benzyl]-2-methylbenzimidazole (346)

In the same manner as in Example 183, 0.330 g of 6-(1-butanesulfonylcarbamoyl)-1-[4-(2-pyridyl)benzyl]-2-methylbenzimidazole (346) were obtained from the above-mentioned crude N-(1-butanesulfonyl)-4-acetylamino-3-[4-(2-pyridyl)benzylamino]-benzamide.

Properties of Compound (346):

$^1$H-NMR(DMSO-d6, δ): 0.82(3H, t), 1.37–1.46(2H, m), 1.54–1.61(2H, m), 2.54(3H, s), 3.10(2H, t, J=7.8 Hz), 5.57 (2H, s), 7.19(2H, d, J=7.5 Hz), 7.33(1H, t, J=5.2 Hz), 7.49(1H, d, J=8.4 Hz), 7.82–7.87(2H, m), 7.90(1H, d, J=8.0 Hz), 8.01–8.04(3H, m), 8.63(1H, d, J=4.2 Hz).

IR(Nujol): 1722 cm$^{-1}$.

mp: 292.4–298.4° C.

EXAMPLE 285

Synthesis of 5-chlorosulfonyl-1-(2,4-dichlorobenzyl)-2-methylbenzimidazole (347) and 6-chlorosulfonyl-1-(2,4-dichlorobenzyl)-2-methylbenzimidazole (348)

Four grams of 1-(2,4-dichlorobenzyl)-2-methylbenzimidazole were added to 20 ml of chlorosulfonic acid in an ice bath, and the mixture was stirred at room temperature for 24 hours and then at 80° C. for 1.5 hours. The reaction solution was poured into ice water, and the gum solid material precipitated was separated through filtration to obtain a mixture of 5-chlorosulfonyl-1-(2,4-dichlorobenzyl)-2-methylbenzimidazole (347) and 6-chlorosulfonyl-1-(2,4-dichlorobenzyl)-2-methylbenzimidazole (348). This mixture was used in the subsequent reaction at once.

EXAMPLE 286

Synthesis of 5-aminosulfonyl-1-(2,4-dichlorobenzyl)-2-methylbenzimidazole (349) and 6-aminosulfonyl-1-(2,4-dichlorobenzyl)-2-methylbenzimidazole (350)

The mixture of 5-chlorosulfonyl-1-(2,4-dichlorobenzyl)-2-methylbenzimidazole and 6-chlorosulfonyl-1-(2,4-dichlorobenzyl)-2-methylbenzimidazole obtained in Example 285 was immediately treated with 100 ml of 25% aqueous ammonia at room temperature for 1 hour. The solid material was separated through filtration to give 2.68 g of a mixture of 5-aminosulfonyl-1-(2,4-dichlorobenzyl)-2-methylbenzimidazole (349) and 6-aminosulfonyl-1-(2,4-dichlorobenzyl)-2-methylbenzimidazole (350) at a ratio of 1:1.

Properties of the mixture of Compound (349) and Compound (350):

$^1$H-NMR(CD$_3$OD, δ): 2.52(3/2H, s), 2.54(3/2H, s), 5.54(2H, s), 6.55(1H, d, J=6.9 Hz), 7.17(1H, d, J=8.0 Hz), 7.52(1H, s), 7.65–7.78(2H, m), 7.82(1/2H, s), 8.11(1/2H, s)

EXAMPLE 287

Synthesis of 6-(n-valerylaminosulfonyl)-1-(2,4-dichlorobenzyl)-2-methylbenzimidazole (351) and 5-(n-valerylaminosulfonyl)-1-(2,4-dichlorobenzyl)-2-methylbenzimidazole (352)

One milliliter of chloroform, 0.56 ml of triethylamine and 0.326 g of n-valeryl chloride were added to 0.500 g of a mixture of 5-aminosulfonyl-1-(2,4-dichlorobenzyl)-2-methylbenzimidazole and 6-aminosulfonyl-1-(2,4-dichlorobenzyl)-2-methylbenzimidazole at a ratio of 1:1, and the mixture was stirred at room temperature for 48 hours. Water was added thereto to stop the reaction, and the reaction solution was extracted with chloroform. The organic layer was dried, concentrated, and purified through silica-gel column chromatography (eluent: a mixture of chloroform and methanol at a ratio of 95:5) to obtain 0.360 g of a mixture of 5-(n-valerylaminosulfonyl)-1-(2,4-dichlorobenzyl)-2-methylbenzimidazole and 6-(n- valerylaminosulfonyl)-1-(2,4-dichlorobenzyl)-2-methylbenzimidazole. Further, this mixture was purified through medium-pressure silica-gel column chromatography (eluent: a mixture of hexane and ethyl acetate at a ratio of from 1:1 to 1:4) to give 0.95 g of 6-(n-valerylaminosulfonyl)-1-(2,4-dichlorobenzyl)-2-methylbenzimidazole (351) and 0.45 g of 5-(n-valerylaminosulfonyl)-1-(2,4-dichlorobenzyl)-2-methylbenzimidazole (352).

Properties of Compound (351):
$^1$H-NMR(DMSO-d6, δ): 0.74(3H, t, J=7.3 Hz), 1.09(2H, m), 1.31(2H, m), 2.10(2H, t, J=7.3 Hz), 2.53(3H, s), 5.63 (2H, s), 6.60(1H, d, J=8.4 Hz), 7.32(1H, d, J=8.3 Hz), 7.67–7.77(3H, m), 7.93(1H, s).
IR(KBr): 1726 cm$^{-1}$.
mp: 207.5–210.0° C.
Mass(FD): m/e 454(M+1)

Properties of Compound (352):
$^1$H-NMR(DMSO-d6, δ): 0.75(3H, t, J=7.3 Hz), 1.11(2H, m), 1.34(2H, m), 2.13(2H, t, J=7.4 Hz), 2.51(3H, s), 5.59 (2H, s), 6.57(1H, d, J=8.5 Hz), 7.32(1H, dd, J=2.2 and 8.4 Hz), 7.57(1H, d, J=8.6 Hz), 7.67(1H, dd, J=1.6 and 8.6 Hz), 7.73(1H, d, J=2.1 Hz), 8.08(1H, d, J=1.6 Hz).
IR(KBr): 1706 cm$^{-1}$.
mp: 213.0–216.0° C.

EXAMPLE 288

Synthesis of 2,4-dimethyl-6-methoxycarbonylbenzimidazole

Methyl 4-acetylamino-5-amino-3-methylbenzoate was obtained from methyl 4-amino-3-methylbenzoate by the method described in Journal of Medicinal Chemistry, 1993, 36, 4040–4051. Subsequently, this compound was heat-refluxed in acetic acid for 2 hours to give 2,4-dimethyl-6-methoxycarbonylbenzimidazole.

Properties of the compound:
$^1$H-NMR(CDCl$_3$, δ): 2.55(3H, s), 2.62(3H, s), 3.91(3H, s), 7.74(1H, s), 8.07(1H, s), 10.65(1H, br s)

EXAMPLE 289

Synthesis of 1-(2,4-dichlorobenzyl)-2,4-dimethyl-6-methoxycarbonylbenzimidazole (353)

A mixture containing 0.900 g of 2,4-dimethyl-6-methoxycarbonylbenzimidazole, 1.20 g of 2,4-dichlorobenzyl chloride, 0.200 g of sodium iodide, 0.610 g of potassium carbonate and 4 ml of N,N-dimethylformamide was stirred at 80° C. for 16 hours. After the organic solvent was distilled off under reduced pressure, the residue was extracted with ethyl acetate and with water. The organic layer was concentrated, and was crystallized with the addition of hexane. The crystals were separated through filtration, and were dried to give 1.08 g of 1-(2,4-dichlorobenzyl)-2,4-dimethyl-6-methoxycarbonylbenzimidazole (353).

Properties of Compound (353):
$^1$H-NMR(CDCl$_3$, δ): 2.58(3H, s), 2.71(3H, s), 3.90(3H, s), 5.39(2H, s), 6.30(1H, d, J=8.4 Hz), 7.07(1H, dd, J=8.4 and 2.0 Hz), 7.49(1H, d, J=2.0 Hz), 7.75(1H, s), 7.81(1H,s)

EXAMPLE 290

Synthesis of 6-carboxy-1-(2,4-dichlorobenzyl)-2,4-dimethylbenzimidazole (354)

In the same manner as in Example 53, 0.435 g of 6-carboxy-1-(2,4-dichlorobenzyl)-2,4-dimethylbenzimidazole (354) were formed from 0.510 g of 1-(2,4-dichlorobenzyl)-2,4-dimethyl-6-methoxycarbonylbenzimidazole.

Properties of Compound (354):
$^1$H-NMR(DMSO-d6, δ): 2.51(3H, s), 2.55(3H, s), 5.57 (2H, s), 6.49(1H, d, J=8.4 Hz), 7.31(1H, dd, J=8.4 and 2.2 Hz), 7.62(1H, s), 7.72(1H, d, J=2.0 Hz), 7.78(1H, s), 12.64 (1H, br s)

EXAMPLE 291

Synthesis of 6-(1-butanesulfonylcarbamoyl)-1-(2,4-dichlorobenzyl)-2,4-dimethylbenzimidazole (355)

In the same manner as in Example 98, 0.468 g of 6-(1-butanesulfonylcarbamoyl)-1-(2,4-dichlorobenzyl)-2,4-dimethylbenzimidazole (355) were formed from 0.417 g of 6-carboxy-1-(2,4-dichlorobenzyl)-2,4-dimethylbenzimidazole, 0.290 g of N,N'-carbonyldiimidazole, 0.246 g of 1-butenesulfonamide and 0.273 g of diazabicycloundecene.

Properties of Compound (355):
$^1$H-NMR(DMSO-d6, δ): 0.84(3H, t, J=7.4 Hz), 1.38(2H, m), 1.64(2H, m), 2.49(3H, s), 2.56(3H, s), 3.48(2H, t), 5.55(2H, s), 6.40(1H, d, J=8.5 Hz), 7.31(1H, dd, J=2.1 and 8.4 Hz), 7.64(1H, s), 7.75(1H, d, J=2.1 Hz), 7.90(1H, s), 11.79(1H, br s).
IR(Nujol): 1682 cm$^{-1}$.
mp: 180.0–181.5° C.

Production Example 58

Production of 4-phenoxybenzyl alcohol

Sodium borohydride (0.48 g) was added to a solution of 4.96 g of 4-phenoxybenzaldehyde in 20 ml of ethanol, and the mixture was stirred at room temperature for 1.5 hours. After the completion of the concentration, the residue was extracted with tert-butylmethyl ether and with water. The organic layer was concentrated to give 4.84 g of 4-phenoxybenzyl alcohol.

Properties of the compound:
$^1$H-NMR(CDCl$_3$, δ): 4..67(2H, d, J=5.7Hz), 6.99–7.01 (4H, m), 7.10(1H, t, J=7.4 Hz), 7.32–7.35(4H, m)

Production Example 59

Production of 4-phenoxybenzyl chloride

Thionyl chloride (13.34 g) was added to 4.06 g of 4-phenoxybenzyl alcohol, and the mixture was stirred at 80° C. for 3.5 hours. After the completion of the concentration, the reaction mixture was extracted with ethyl acetate and with water. The organic layer was concentrated to give 4.31 g of 4-phenoxybenzyl chloride.

Properties of the compound:
$^1$H-NMR(CDCl$_3$, δ): 4..58(2H, s), 6.96–7.03(4H, m), 7.11–7.14(1H, m), 7.32–7.37(4H, m)

EXAMPLE 292

Synthesis of 6-ethoxycarbonyl-2-methyl-1-(4-phenoxybenzyl)benzimidazole (356)

In the same manner as in Example 263, 0.49 g of ethyl 4-acetylamino-3-[(4-phenoxy)benzylamino]benzoate were obtained from 0.56 g of ethyl 4-acetylamino-3-aminobenzoate, 0.33 g of sodium carbonate, 0.12 g of sodium iodide and 0.66 g of 4-phenoxybenzyl chloride. Subsequently, this compound was converted into 6-ethoxycarbonyl-2-methyl-1-(4-phenoxybenzyl)-benzimidazole [(356), 0.44 g].

Properties of ethyl 4-acetylamino-3-[(4-phenoxy) benzylamino]benzoate:

$^1$H-NMR(CDCl$_3$, δ): 1.37(3H, t, J=7.1 Hz), 2.04(3H, s), 4.18(1H, br s), 4.31–4.36(4H, m), 6.98–7.02(4H, m), 7.09–7.12(1H, m), 7.27–7.51(8H, m)

Properties of Compound (356):

$^1$H-NMR(CDCl$_3$, δ): 1.40(3H, t, J=7.1 Hz), 2.61(3H, s), 4.39(2H, q, J=7.1 Hz), 5.35(2H, s), 6.92–6.95(2H, m), 6.97–7.00(2H, m), 7.02(2H, d, J=8.7 Hz), 7.09–7.13(1H, m), 7.31–7.34(2H, m), 7.72(1H, d, J=8.6 Hz), 7.98(1H, dd, J=1.5 and 8.4 Hz), 8.04(1H, d, J=1.2 Hz)

EXAMPLE 293

Synthesis of 6-carboxy-2-methyl-1-(4-phenoxybenzyl)benzimidazole (357)

In the same manner as in Example 53, 0.37 g of 6-carboxy-2-methyl-1-(4-phenoxybenzyl)benzimidazole (357) were formed from 0.44 g of 6-ethoxycarbonyl-2-methyl-1-(4-phenoxy)benzyl-benzimidazole.

Properties of Compound (357):

$^1$H-NMR(DMSO-d6, δ): 2.57(3H, s), 5.54(2H, s), 6.95–6.97(4H, m), 7.09–7.13(3H, m), 7.33–7.37(2H, m), 7.60(1H, d, J=8.4 Hz), 7.78(1H, d, J=8.4 Hz), 8.07(1H, s), 12.72(1H, br s)

EXAMPLE 294

Synthesis of 6-(1-butanesulfonylcarbamoyl)-2-methyl-1-(4-phenoxybenzyl)benzimidazole (358)

In the same manner as in Example 98, 0.19 g of 6-(1-butanesulfonylcarbamoyl)-2-methyl-1-(4-phenoxybenzyl) benzimidazole (358) were obtained from 0.36 g of 6-carboxy-2-methyl-1-(4-phenoxybenzyl)benzimidazole, 0.24 g of N,N'-carbonyldiimidazole, 0.21 g of 1-butanesulfonamide and 0.23 g of diazabicycloundecene.

Properties of Compound (358):

$^1$H-NMR(DMSO-d6, δ): 0.85(3H, t, J=7.4 Hz), 1.40(2H, m), 1.68(2H, m), 2.54(3H, s), 3.52(2H, t, J=7.8 Hz), 5.51 (2H, s), 6.96–6.98(4H, m), 7.11(1H, t, J=7.4 Hz), 7.17(2H, d, J=8.6 Hz), 7.34–7.37(2H, m), 7.64(1H, d, J=8.5 Hz), 7.79(1H, dd, J=1.5 and 8.5 Hz), 8.24(1H, s), 11.92(1H, br s).

IR(Nujol): 1632 cm$^{-1}$.

mp: 183.4–184.4° C.

EXAMPLE 295

Synthesis of 6-ethoxycarbonyl-2-methyl-1-(2-pyridylmethyl)benzimidazole (359)

In the same manner as in Example 263, 0.656 g of 6-ethoxycarbonyl-2-methyl-1-(2-pyridylmethyl) benzimidazole (359) were formed from 0.600 g of ethyl 4-acetylamino-3-aminobenzoate, 0.450 g of potassium carbonate, 0.122 g of sodium iodide and 0.413 g of 2-chloromethylpyridine. This compound was used in the subsequent reaction at once.

EXAMPLE 296

Synthesis of 6-carboxy-2-methyl-1-(2-pyridylmethyl)benzimidazole (360)

In the same manner as in Example 53, 0.532 g of 6-carboxy-2-methyl-1-(2-pyridylmethyl)benzimidazole (360) were formed from 0.656 g of 6-ethoxycarbonyl-2-methyl-1-(2-pyridylmethyl)benzimidazole.

Properties of Compound (360):

$^1$H-NMR(DMSO-d6, δ): 2.56(3H, s), 5.56(2H, s), 7.22 (1H, d, J=7.9 Hz), 7.28(1H, dd, J=5.0 and 7.1 Hz), 7.45(1H, d, J=8.3 Hz), 7.74–7.79(2H, m), 7.95(1H, s), 8.48(1H, d, J=8.5 Hz).

EXAMPLE 297

Synthesis of 1-(butanesulfonylcarbamoyl)-2-methyl-1-(2-pyridylmethyl)benzimidazole (361)

In the same manner as in Example 98, 0.142 g of 1-(butanesulfonylcarbamoyl)-2-methyl-1-(2-pyridylmethyl) benzimidazole (361) were formed from 0.500 g of 6-carboxy-2-methyl-1-(2-pyridylmethyl)benzimidazole, 0.394 g of N,N'-carbonyldiimidazole, 0.334 g of 1-butanesulfonamide and 0.370 g of diazabicycloundecene.

Properties of Compound (361):

$^1$H-NMR(DMSO-d6, δ): 0.83(3H, t, J=7.3 Hz), 1.28–1.36 (2H, m), 1.52–1.58(2H, m), 2.55(3H, s), 3.06(2H, t, J=7.9 Hz), 5.56(2H, s), 7.17(1H, d, J=7.8 Hz), 7.29(1H, dd, J=4.2 and 7.3 Hz), 7.43(1H, d, J=8.4 Hz), 7.77(1H, dt, J=1.8 and 7.7 Hz), 7.81(1H, dd, J=1.4 and 8.4 Hz), 7.96(1H, s), 8.50(1H, d, J=4.7 Hz)

IR(Nujol): 1674 cm$^{-1}$.

mp: 139° C. (decomp.)

EXAMPLE 298

Synthesis of 6-ethoxycarbonyl-2-methyl-1-(4-nitrobenzyl)benzimidazole (362)

In the same manner as in Example 263, 0.51 g of 6-ethoxycarbonyl-2-methyl-1-(4-nitrobenzyl) benzimidazole (362) were formed from 0.67 g of ethyl 4-acetylamino-3-aminobenzoate, 0.39 g of sodium carbonate, 0.14 g of sodium iodide and 0.78 g of 4-nitrodibenzyl bromide.

Properties of Compound (362):

$^1$H-NMR(CDCl$_3$, δ): 1.39(3H, t, J=7.1 Hz), 2.59(3H, s), 4.38(2H, q, J=7.1 Hz), 5.49(2H, s), 7.20(2H, d, J=8.6 Hz), 7.76(1H, d, J=8.5 Hz), 7.94(1H, d, J=1.1 Hz), 8.01(1H, dd, J=1.4 and 8.5 Hz), 8.20(2H, d, J=8.6 Hz).

EXAMPLE 299

Synthesis of 1-(4-aminobenzyl)-6-ethoxycarbonyl-2-methylbenzimidazole (363)

Six milliliters of ethanol and 0.8 ml of acetic acid were added to 0.50 g of 1-(4-nitrobenzyl)-6-ethoxycarbonyl-2-methylbenzimidazole and 0.47 g of reduced iron, and the mixture was refluxed for 4.5 hours. The reaction mixture was extracted with water and with ethyl acetate. The organic layer was washed with water, dried, and then concentrated under reduced pressure to give 0.46 g of 1-(4-aminobenzyl)-6-ethoxycarbonyl-2-methylbenzimidazole (363).

Properties of Compound (363):

$^1$H-NMR(CDCl$_3$, δ): 1.40(3H, t, J=7.2 Hz), 2.59(3H, s), 4.38(2H, q, J=7.2 Hz), 5.25(2H, s), 6.61(2H, d, J=8.6 Hz), 6.87(2H, d, J=8.6 Hz), 7.71(1H, d, J=8.3 Hz), 7.96(1H, dd, J=1.5 and 8.4 Hz), 8.05(1H, d, J=1.3 Hz).

EXAMPLE 300

Synthesis of 1-[(4-benzoylamino)benzyl]-6-ethoxycarbonyl-2-methylbenzimidazole (364)

A solution of 0.25 g of benzoyl chloride in 4 ml of chloroform was added to a solution of 0.45 g of 1-(4- aminobenzyl)-6-ethoxycarbonyl-2-methylbenzimidazole and 0.15 g of pyridine in 8 ml of chloroform, and the mixture was stirred at room temperature for 16 hours. The reaction mixture was extracted with water and then with chloroform. The organic layer was concentrated under reduced pressure to give 0.33 g of 1-[(4-benzoylamino)benzyl]-6-ethoxycarbonyl-2-methylbenzimidazole (364).

Properties of Compound (364)

$^1$H-NMR(CDCl$_3$, δ): 1.40(3H, t, J=71 .Hz), 2.59(3H, s), 4.38(2H, q, J=7.1 Hz), 5.37(2H, s), 7.06(2H, d, J=8.5 Hz), 7.46–7.50(2H, m), 7.53–7.57(1H, m), 7.61(2H, d, J=8.5 Hz), 7.72(1H, d, J=8.4 Hz), 7.84–7.86(2H, m), 7.89(1H, br s), 7.98(1H, dd, J=1.5 and 8.5 Hz), 8.03(1H, s).

EXAMPLE 301

Synthesis of 1-[(4-benzoylamino)benzyl]-6-carboxy-2-methylbenzimidazole (365)

In the same manner as in Example 53, 0.28 g of 1-[(4-benzoylamino)benzyl]-6-carboxy-2-methylbenzimidazole (365) were formed from 0.31 g of 1-[(4-benzoylamino)benzyl]-6-ethoxycarbonyl-2-methylbenzimidazole.

Properties of the compound (365):

$^1$H-NMR(DMSO-d6, δ): 2.58(3H, s), 5.52(2H, s), 7.12 (2H, d, J=8.5 Hz), 7.48–7.52(2H, m), 7.54–7.58(1H, m), 7.61(1H, d, J=8.4 Hz), 7.73(2H, d, J=8.6 Hz), 7.79(1H, dd, J=1.5 and 8.4 Hz), 7.90–7.92(2H, m), 8.07(1H, d, J=1.2 Hz), 10.26(1H, s), 12.73(1H, br s).

EXAMPLE 302

Synthesis of 1-[(4-benzoylamino)benzyl]-6-(1-butanesulfonylcarbamoyl)-2-methylbenzimidazole (366)

In the same manner as in Example 98, 0.14 g of 1-[(4-benzoylamino)benzyl]-6-(1-butanesulfonylcarbamoyl)-2-methylbenzimidazole (366) were obtained from 0.26 g of 1-[(4-benzoylamino)benzyl]-6-carboxy-2-methylbenzimidazole, 0.17 g of N,N'-carbonyldiimidazole, 0.14 g of 1-butanesulfonamide and 0.16 g of diazabicycloundecene.

Properties of Compound (366):

$^1$H-NMR(DMSO-d6, δ): 0.85(3H, t, J=7.4 Hz), 1.40(2H, m), 1.68(2H, m), 2.56(3H, s), 3.52(2H, t, J=7.8 Hz), 5.50 (2H, s), 7.15(2H, d, J=8.6 Hz), 7.50(2H, t, J=7.5 Hz), 7.55–7.59(1H, m), 7.64(1H, d, J=8.5 Hz), 7.74(2H, d, J=8.6 Hz), 7.79(1H, dd, J=1.6 and 8.5 Hz), 7.90–7.92(2H, m), 8.24(1H, d, J=1.3 Hz), 10.27(1H, s), 11.92(1H, br s).

IR(Nujol): 1693 cm$^{-1}$.

mp: 267.5–268.1° C.

EXAMPLE 303

Synthesis of 6-ethoxycarbonyl-2-methyl-1-[4-(2-phenylethenyl)benzyl]benzimidazole (367)

In the same manner as in Example 263, 0.320 g of 6-ethoxycarbonyl-2-methyl-1-[4-(2-phenylethenyl)benzyl] benzimidazole (367) were formed from 0.405 g of ethyl 4-acetylamino-3-aminobenzoate, 0.253 g of potassium carbonate, 0.082 g of sodium iodide and 0.500 g of 4-chloromethylstilbene.

Properties of Compound (367):

$^1$H-NMR(CDCl$_3$, δ): 1.40(3H, t, J=7.2 HJz), 2.6(3H, s), 4.38(2H, q, J=7.1 Hz), 5.38(2H, s), 7.01–7.09(4H, m), 7.26(1H, t, J=7.4 Hz), 7.35(2H, t, J=7.5 Hz), 7.45(2H, d, J=8.2 Hz), 7.49(2H, d, J=7.5 Hz), 7.73(1H, d, J=8.5 Hz), 7.99(1H, dd, J=1.5 and 8.4 Hz), 8.30(1H, d, J=1.2 Hz).

EXAMPLE 304

Synthesis of 6-ethoxycarbonyl-2-methyl-1-[4-(2-phenylethyl)-benzyl]-benzimidazole (368)

Five-percent palladium on carbon was added to a solution of 0.320 g of 6-ethoxycarbonyl-2-methyl-1-[4-(2-phenylethenyl)benzyl]benzimidazole in 10 ml of ethanol in a nitrogen atmosphere, and the mixture was stirred in a hydrogen atmosphere for 23 hours. The solid material was separated through filtration, and the filtrate was concentrated to give 6-ethoxycarbonyl-2-methyl-1-[4-(2-phenylethyl) benzyl]-benzimidazole (368). This compound was used in the subsequent reaction at once.

EXAMPLE 305

Synthesis of 6-carboxy-2-methyl-1-[4-(2-phenylethyl)benzyl]-benzimidazole (369)

In the same manner as in Example 53, 0.242 g of 6-carboxy-2-methyl-1-[4-(2-phenylethyl)benzyl]-benzimidazole (369) were formed from 0.283 g of 6-ethoxycarbonyl-2-methyl-1-[4-(2-phenylethyl)benzyl]-benzimidazole.

Properties of Compound (369)

$^1$H-NMR(DMSO-d6, δ): 2.56(3H, s), 2.82(4H, s), 5.51 (2H, s), 7.02(2H, d, J=8.1 Hz), 7.11–7.27(7H, m), 7.61(1H, d, J=8.4 Hz), 7.78(1H, dd, J=1.5 and 8.04(1H, s), 12.72(1H, s).

EXAMPLE 306

Synthesis of 6-(1-butanesulfonylcarbamoyl)-2-methyl-[4-(2-phenylethyl)benzyl]benzimidazole (370)

In the same manner as in Example 98, 0.249 g of 6-(1-butanesulfonylcarbamoyl)-2-methyl-[4-(2-phenylethyl)benzyl]benzimidazole (370) were formed from 0.225 g of 6-carboxy-2-methyl-1-[4-(2-phenylethyl) benzyl]-benzimidazole, 1.214 g of N,N'-carbonyldiimidazole, 0.167 g of 1-butanesulfonamide and 0.185 g of diazabicycloundecene.

Properties of Compound (370):

$^1$H-NMR(DMSO-d6, δ): 0.86(3H, t, J=7.4 Hz), 1.35–1.42 (2H, m), 1.63–1.71(2H, m), 2.53(3H, s), 2.83(4H, s), 3.52 (2H, t, J=7.7 Hz), 5.49(2H, s), 7.04(2H, d, J=8.0 Hz), 7.12–7.25(7H, m), 7.64(1H, d, J=8.4 Hz), 7.79(1H, dd, J=1.7 and 8.5 Hz), 8.22(1H, d, J=1.3 Hz), 11.92(1H, s).

IR(Nujol): 1682 cm$^{-1}$.

mp: 95.4–99.0° C.

Production Example 60

Production of 4-benzoylbenzyl bromide

In the same manner as in Production Example 48, 5.28 g of 4-benzoylbenzyl bromide were formed from 3.92 g of 4-methylbenzophenone, 4.28 g of N-bromosuccinimide and 0.40 g of 2,2'-azobisisobutylonitrile.

Properties of the compound:

$^1$H-NMR(CDCl$_3$, δ): 4.54(2H, s), 7.47–7.52(4H, m), 7.58–7.62(1H, m), 7.77–7.82(4H, m).

EXAMPLE 307

Synthesis of 1-[(4-benzoyl)benzyl]-6-ethoxycarbonyl-2-methylbenzimidazole (371)

In the same manner as in Example 263, 0.70 g of 1-[(4-benzoyl)benzyl]-6-ethoxycarbonyl-2-methylbenzimidazole (371) were formed from 0.56 g of ethyl 4-acetylamino-3-aminobenzoate, 0.33 g of sodium carbonate, 0.11 g of sodium iodide and 0.83 g of 4-benzoylbenzyl bromide.

Properties of Compound (371):

$^1$H-NMR(CDCl$_3$, δ): 1.40(3H, t, J=7.2 Hz), 2.61(3H, s), 4.39(2H, q, J=7.2 Hz), 5.47(2H, s), 7.14(2H, d, J=8.2 Hz), 7.45–7.48(2H, m), 7.56–7.60(1H, m), 7.74–7.77(5H, m), 7.99–8.02(2H, m).

EXAMPLE 308

Synthesis of 1-[(4-benzoyl)benzyl]-6-carboxy-2-methylbenzimidazole (372)

In the same manner as in Example 53, 0.55 g of 1-[(4-benzoyl)benzyl]-6-carboxy-2-methylbenzimidazole (372) were formed from 0.68 g of 1-[(4-benzoyl)benzyl]-6-ethoxycarbonyl]-2-methylbenzimidazole.

Properties of Compound (372):

$^1$H-NMR(DMSO-d6, δ): 2.57(3H, s), 5.71(2H, s), 7.25 (2H, d, J=8.2 Hz), 7.52(2H, t, J=7.7 Hz), 7.62–7.66(2H, m), 7.68–7.72(4H, m), 7.80(1H, dd, J=1.3 and 8.4 Hz), 8.08(1H, d, J=1.1 Hz), 12.72(1H, br s).

EXAMPLE 309

Synthesis of 1-[(4-benzoyl)benzyl]-6-(1-butanesulfonylcarbamoyl)-2-methylbenzimidazole (373)

In the same manner as in Example 98, 0.13 g of 1-[(4-benzoyl)benzyl]-6-(1-butanesulfonylcarbamoyl)-2-methylbenzimidazole (373) were formed from 0.52 g of 1-[(4-benzoyl)benzyl]-6-carboxy-2-methylbenzimidazole, 0.34 g of N,N'-carbonyldiimidazole, 0.29 g of 1-butanesulfonamide and 0.32 g of diazabicycloundecene.

Properties of Compound (373):

$^1$H-NMR(DMSO-d6, δ): 0.84(3H, t, J=7.4 Hz), 1.38(2H, m), 1.66(2H, m), 2.54(3H, s), 3.48(2H, t, J=7.7 Hz), 5.67 (2H, s), 7.27(2H, d, J=8.2 Hz), 7.51–7.55(2H, m), 7.63–7.73 (6H, m), 7.81(1H, dd, J=1.6 and 8.5 Hz), 8.21(1H, d, J=1.4 Hz).

IR(Nujol): 1660 cm$^{-1}$.

mp: 111.0–112.4° C.

Mass(FAB): m/e 490(M+1).

EXAMPLE 310

Synthesis of 6-carboxy-2-methyl-[4-(2-phenylethenyl)benzyl]benzimidazole (374)

In the same manner as in Example 53, 0.237 g of 6-carboxy-2-methyl-[4-(2-phenylethenyl)benzyl]benzimidazole (374) were formed from 0.500 g of 6-ethoxycarbonyl-2-methyl-1-[4-(2-phenylethenyl)benzyl]benzimidazole.

Properties of Compound (374):

$^1$H-NMR(DMSO-d6, δ): 2.59(3H, s), 5.58(2H, s), 7.12 (2H, d, J=8.2 Hz), 7.21(2H, s), 7.26(1H, t, J=7.4 Hz), 7.36(2H, t, J=7.6 Hz), 7.57(4H, d, J=8.0 Hz), 7.62(1H, d, J=8.4 Hz), 7.79(1H, dd, J=1.5 and 8.4 Hz), 8.07(1H, d, J=1.2 Hz), 12.73(1H, s).

EXAMPLE 311

Synthesis of 6-(1-butanesulfonylcarbamoyl)-2-methyl-[4-(2-phenylethenyl)benzyl]benzimidazole (375)

In the same manner as in Example 98, 0.239 g of 6-(1-butanesulfonylcarbamoyl)-2-methyl-[4-(2-phenylethenyl)benzyl]benzimidazole (375) were formed from 0.237 g of 6-carboxy-2-methyl-[4-(2-phenylethenyl) benzyl]benzimidazole, 0.209 g of N,N'-carbonyldiimidazole, 0.176 g of 1-butanesulfonamide and 0.195 g of diazabicycloundecene.

Properties of Compound (375):

$^1$H-NMR(DMSO-d6, δ): 0.86(3H, t, J=7.4 Hz), 1.35–1.43 (2H, m), 1.63–1.70(2H, m), 2.56(3H, s), 3.52(2H, t, J=7.6 Hz), 5.55(2H, s), 7.15(2H, d, J=8.2 Hz), 7.22(2H, s), 7.26 (1H, t, J=7.4 Hz), 7.36(2H, t, J=7.6 Hz), 7.57(1H, d, J=7.3 Hz), 7.58(1H, d, J=8.2 Hz), 7.66(1H, d, J=8.5 Hz), 7.80(1H, d, J=8.4 Hz), 8.24(1H, s), 11.93(1H, brs).

IR(Nujol): 1680 cm$^{-1}$.

mp: 140.3–143.4° C.

EXAMPLE 312

Synthesis of 1-(dibenzofuran-2-ylmethyl)-6-ethoxycarbonyl-2-methylbenzimidazole (376)

In the same manner as in Example 263, 0.47 g of 1-(dibenzofuran-2-ylmethyl)-6-ethoxycarbonyl-2-methylbenzimidazole (376) were formed from 0.480 g of ethyl 4-acetylamino-3-aminobenzoate, 0.274 g of sodium carbonate, 0.097 g of sodium iodide and 0.56 g of 2-bromomethyldibenzofuran.

Properties of Compound (376):

$^1$H-NMR(CDCl$_3$, δ): 1.38(3H, t, J=7.1 Hz), 2.62(3H, s), 4.36(2H, q, J=7.1 Hz), 5.54(2H, s), 7.19(1H, dd, J=1.6 and 8.5 Hz), 7.32(1H, t, J=7.6 Hz), 7.43–7.59(4H, m), 7.76(1H, d, J=8.4 Hz), 7.85(1H, d, J=7.1 Hz), 8.00(1H, dd, J=1.3 and 8.4 Hz), 8.07(1H, d, J=1.2 Hz).

EXAMPLE 313

Synthesis of 6-carboxy-1-(dibenzofuran-2-ylmethyl)-2-methylbenzimidazole (377)

In the same manner as in Example 53, 0.336 g of 6-carboxy-1-(dibenzofuran-2-ylmethyl)-2-methylbenzimidazole (377) were formed from 0.46 g of 6-ethoxycarbonyl-2-methylbenzimidazole.

Properties of Compound (377):

$^1$H-NMR(DMSO-d6, δ): 2.63(3H, s), 5.71(2H, s), 7.27 (1H, d, J=8.5 Hz), 7.36(1H, t, J=7.5 Hz), 7.50(1H, t), 7.61–7.68(3H, m), 7.78(1H, d, J=8.3 Hz), 7.97(1H, s), 7.07–8.11(2H, m).

EXAMPLE 314

Synthesis of 1-(dibenzofuran-2-ylmethyl)-6-(1-butanesulfonylcarbamoyl)-2-methylbenzimidazole (378)

In the same manner as in Example 98, 0.249 g of 1-(dibenzofuran-2-ylmethyl)-6-(1-butanesulfonylcarbamoyl)-2-methylbenzimidazole (378)

were formed from 0.255 g of 6-carboxy-1-(dibenzofuran-2-ylmethyl)-2-methylbenzimidazole, 0.197 g of N,N'-carbonyldiimidazole, 0.167 g of 1-butanesulfonamide and 0.185 g of diazabicycloundecene.

Properties of Compound (378):

$^1$H-NMR(DMSO-d6, δ): 0.81(3H, t, J=7.4 Hz), 1.36(2H, m), 1.65(2H, m), 2.60(3H, s), 3.50(2H, t, J=7.7 Hz), 5.69 (2H, s), 7.29(1H, dd, J=1.96 and 8.7 Hz), 7.34–7.38(1H, m), 7.48–7.52(1H, m), 7.63–7.68(3H, m), 7.81(1H, dd, J=1.7 and 8.5 Hz), 8.00(1H,.d, J=1.4 Hz), 8.94(1H, d, J=7.1 Hz), 8.28(1H, d, J=1.4 Hz), 12.70(1H, br s).

IR(Nujol): 1682 cm$^{-1}$.

mp: 224.1–229.8° C.

Production Example 61

Production of N-1-butanesulfonyl-3-acetylamino-4-nitrobenzamide

In the same manner as in Production Example 28, 6.30 g of N-1-butanesulfonyl-3-acetylamino-4-nitrobenzamide were obtained from 5.15 g of 3-acetylamino-4-nitrobenzoic acid, 5.59 g of N,N'-carbonyldiimidazole, 4.73 g of 1-butanesulfonamide and 5.25 g of diazabicycloundecene.

Properties of the compound:

$^1$H-NMR(DMSO-d6, δ): 0.87(3H, t, J=7.4 Hz), 1.40(2H, m), 1.68(2H, m), 2.07(3H, s), 3.51(2H, t), 7.83(1H, dd, J=1.8 and 8.5 Hz), 8.03(1H, d, J=8.5 Hz), 8.07(1H, d, J=1.8 Hz), 10.43(1H, s), 12.64(1H, br s).

Production Example 62

Production of N-1-butanesulfonyl-3-amino-4-nitrobenzamide

A mixture containing 6.30 g of N-1-butanesulfonyl-3-acetylamino-4-nitrobenzamide, a 10% sodium hydroxide aqueous solution, 300 ml of ethanol and 200 ml of water was stirred at room temperature for 4 hours and then at 50° C. for 3 hours. The solvent was distilled off to approximately a half volume, and the residue was adjusted to a pH of 2 with 10% hydrochloric acid. The crystals precipitated were collected, and were dried under reduced pressure to give 5.22 g of N-1-butanesulfonyl-3-amino-4-nitrobenzamide.

Properties of the compound:

$^1$H-NMR(DMSO-d6, δ): 0.87(3H, t, J=7.4 Hz), 1.40(2H, m), 1.66(2H, m), 3.49(2H, m), 6.99(1H, dd, J=1.8 and 9.0 Hz), 7.49(1H, d, J=1.8 Hz), 7.55(2H, br s), 8.04(1H, d, J=9.0 Hz), 12.28(1H, br s).

Production Example 63

Production of N-1-butanesulfonyl-3-(2,4-dichlorobenzylamino)-4-nitrobenzamide

A solution containing 1.10 g of N-1-butanesulfonyl-3-amino-4-nitrobenzamide, 0.273 g of sodium iodide, 1.54 g of potassium carbonate, 2.17 g of 2,4-dichlorobenzyl chloride and 10 ml of methanol was stirred at 60° C. for 24 hours. Further, 2.00 g of 2,4-dichlorobenzyl chloride were added thereto, and the mixture was heated at 60° C. for 36 hours. To the reaction solution were added ethyl acetate and a saturated aqueous solution of sodium hydrogencarbonate, and N-1-butanesulfonyl-3-(2,4-dichlorobenzylamino)-4-nitrobenzamide was extracted in the aqueous layer. The organic layer was concentrated to give 0.885 g of N-1-butanesulfonyl-3-(2,4-dichlorobenzylamino)-4-nitrobenzamide.

Properties of the compound:

$^1$H-NMR(DMSO-d6, δ): 0.81(3H, t, J=7.3 Hz), 1.29(2H, m), 1.49(2H, m), 2.97(2H, m), 4.66(2H, d, J=6.0 Hz), 7.22(1H, d, J=8.9 Hz), 7.27(1H, s), 7.31(1H, d, J=8.4 Hz), 7.37(1H, d, J=8.3 Hz), 7.65(1H, s), 8.04(1H, d, J=8.9 Hz), 8.57(1H, t).

Production Example 64

Production of N-1-butanesulfonyl-4-amino-3-(2,4-dichlorobenzylamino)benzamide

N-1-butanesulfonyl-3-(2,4-dichlorobenzylamino)-4-nitrobenzamide (0.505 g) was added to a mixture of 1.32 g of sodium hydrosulfite, 1 ml of ethanol, 1 ml of tetrahydrofuran and 1 ml of water at room temperature. The mixture was heat-refluxed for 40 minutes. The solvent was distilled off under reduced pressure, and water was added to the residue. The solid material precipitated was collected, and was dried. Further, the resulting material was washed with a mixed solution of 10 ml of methanol and 3 ml of water, and was dried to give 0.220 g of N-1-butanesulfonyl-4-amino-3-(2,4-dichlorobenzylamino)benzamide.

Properties of the compound:

$^1$H-NMR(DMSO-d6, δ): 0.93(3H, t, J=7.4 Hz), 1.45(2H, m), 1.83(2H, m), 3.57(2H, m), 5.45(2H, s), 6.36(1H, d, J=8.2 Hz), 7.11(1H, d, J=8.3 Hz), 7.51(1H, s), 7.75(1H, d), 7.79(1H, d), 7.88(1H, s).

EXAMPLE 315

Synthesis of 6-(1-butanesulfonylcarbamoyl)-1-(2,4-dichlorobenzyl)-2-hydroxybenzimidazole (379)

A mixture of 0.220 mg of N-1-butanesulfonyl-4-amino-3-(2,4-dichlorobenzylamino)benzamide, 0.3 ml of tetramethoxymethane and 2.0 ml of acetic acid was stirred at 60° C. for 4 hours. Acetic acid was distilled off under reduced pressure, and the residue was extracted with chloroform and with water. The chloroform layer was concentrated, and 4.0 ml of methanol and 36% hydrochloric acid (4 drops) were added to the residue. The mixture was stirred at 60° C. for 2 hours. The reaction solution was neutralized with a saturated aqueous solution of sodium hydrogencarbonate. The crystals precipitated were washed with water, and were dried to give 0.207 g of 6-(1-butanesulfonylcarbamoyl)-1-(2,4-dichlorobenzyl)-2-hydroxybenzimidazole (379).

Properties of Compound (379):

$^1$H-NMR(DMSO-d6, δ): 0.83(3H, t, J=7.3 Hz), 1.36(2H, m), 1.61(2H, m), 3.40(2H, m), 5.08(2H, s), 6.94(1H, d, J=8.3 Hz), 7.11(1H, d, J=8.2 Hz), 7.36(1H, dd, J=2.0 and 8.4 Hz), 7.58(1H, s), 7.68–7.73(2H, m), 11.47(1H, br s), 11.77 (1H, br s).

IR(Nujol): 1689 cm$^{-1}$.

mp: 254–256° C.

Mass(FD): m/e 455(M).

EXAMPLE 316

Synthesis of 6-ethoxycarbonyl-2-methyl-1-(2-quinolylmethyl)benzimidazole (380)

In accordance with Example 263, 0.87 g of 6-ethoxycarbonyl-2-methyl-1-(2-quinolylmethyl) benzimidazole (380) were formed from 2.22 g of ethyl 4-acetylamino-3-aminobenzoate, 1.27 g of sodium carbonate, 0.45 g of sodium iodide and 2.28 g of 2-bromomethylquinoline.

Properties of the compound (380):

$^1$H-NMR(DMSO-d6, δ): 1.27(3H, t, J=7.1 Hz), 2.62(3H, s), 4.26(2H, q, J=7.1 Hz), 5.85(2H, s), 7.35(1H, d, J=8.5 Hz), 7.58(1H, m), 7.63(1H, d, J=8.4 Hz), 7.73(1H, m), 7.78(1H, dd, J=1.3 and 8.4 Hz), 7.86(1H, d, J=8.4 Hz), 7.95(1H, d, J=8.0 Hz), 8.14(1H, s), 8.36(1H, d, J=8.5 Hz).

EXAMPLE 317

Synthesis of 6-carboxy-2-methyl-(2-quinolylmethyl)benzimidazole (381)

In the same manner as in Example 53, 0.46 g of 6-carboxy-2-methyl-(2-quinolylmethyl)benzimidazole (381) were formed from 0.85 g of 6-ethoxycarbonyl-2-methyl-1-(2-quinolylmethyl)benzimidazole.

Properties of Compound (381):

$^1$H-NMR(DMSO-d6, δ): 2.62(3H, s), 5.83(2H, s), 7.35 (1H, d, J=8.5 Hz), 7.57(1H, m), 7.60(1H, d, J=8.5 Hz), 7.72(1H, t, J=7.6 Hz), 7.77(1H, d, J=8.4 Hz), 7.86(1H, d, J=8.4 Hz), 7.94(1H, d, J=8.1 Hz), 8.11(1H, s), 8.35(1H, d, J=8.5 Hz).

EXAMPLE 318

Synthesis of 6-(1-butanesulfonylcarbamoyl)-2-methyl-1-(2-quinolylmethyl)benzimidazole (382)

In the same manner as in Example 98, 0.088 g of 6-(1-butanesulfonylcarbamoyl)-2-methyl-1-(2-quinolylmethyl)benzimidazole (382) were formed from 0.222 g of 6-carboxy-2-methyl-1-(2-quinolylmethyl)benzimidazole, 0.195 g of N,N'-carbonyldiimidazole, 0.165 g of 1-butanesulfonamide and 0.183 g of diazabicycloundecene.

Properties of Compound (382):

$^1$H-NMR(DMSO-d6,δ): 0.82(3H, t, J=7.3 Hz), 1.36(2H, m), 1.64(2H, m), 2.61(3H, s), 3.48(2H, t, J=7.4 Hz), 5.82 (2H,s), 7.32(1H,d, J=8.5 Hz), 7.58(1H, m), 7.65(1H, d, J=8.5 Hz), 7.73(1H, t, J=7.6Hz), 7.78(1H, m), 7.87(1H, d, J=8.5 Hz), 7.95(1H,d, J=8.1 Hz), 8.23(1H, s), 8.37(1H, d, J=8.5 Hz), 11.86(1H,brs).

IR(Nujol): 1684 cm$^{-1}$.

mp: 185.5–187.5° C.

Production Example 65

Production of ethyl 4-amino-3-(2,4-dichlorobenzylamino)benzoate

Crude ethyl 4-amino-3-(2,4-dichlorobenzylamino)benzoate was formed from 1.40 g of 3-(2,4-dichlorobenzylamino)-4-nitrobenzoate and 4.50 g of sodium hydrosulfite in the same manner as in Production Example 64. This compound was used in the subsequent reaction at once.

EXAMPLE 319

Synthesis of 1-(2,4-dichlorobenzylamino)-2-hydroxy-6-ethoxycarbonylbenzimidazole (383)

In the same manner as in Example 315, 0.400 g of 1-(2,4-dichlorobenzylamino)-2-hydroxy-6-ethoxycarbonylbenzimidazole (383) were formed from ethyl 4-amino-3-(2,4-dichlorobenzylamino)benzoate obtained in the above-mentioned Production Example 63 and 2.60 g of tetramethoxymethane.

Properties of Compound (383):

$^1$H-NMR(DMSO-d6, δ): 1.27(3H, t, J=7.1 Hz), 4.24(2H, q, J=7.1 Hz), 5.12(2H, s), 7.04(1H, d, J=8.4 Hz), 7.12(1H, d, J=8.2 Hz), 7.37(1H, dd, J=2.1 and 8.4 Hz), 7.51(1H, s), 7.67–7.72(2H, m), 11.37(1H, br s)

EXAMPLE 320

Synthesis of 6-ethoxycarbonyl-2-methyl-1-[3-(4-bromoisoquinolyl)methyl]benzimidazole (384)

In the same manner as in Example 263, 0.30 g of 6-ethoxycarbonyl-2-methyl-1-[3-(4-bromoisoquinolyl)methyl]benzimidazole (384) were formed from 0.87 g of ethyl 4-acetylamino-3-aminobenzoate, 0.53 g of sodium carbonate, 0.18 g of sodium iodide and 0.87 g of 4-bromo-3-bromomethylisoquinoline.

Properties of Compound (384):

$^1$H-NMR(DMSO-d6, δ): 1.26(3H, t, J=7.0 Hz), 2.59(3H, s), 4.24(2H, q, J=7.0 Hz), 5.93(2H, s), 7.61(1H, d, J=8.4 Hz), 7.75–7.80(2H, m) 7.99(1H, m), 8.03(1H, s), 8.13(1H, d, J=8.1 Hz), 8.23(1H, d, J=8.5 Hz), 9.12(1H, s).

EXAMPLE 321

Synthesis of 6-carboxy-2-methyl-[3-(4-bromoisoquinolyl)methyl]benzimidazole (385)

In the same manner as in Example 53, 0.118 g of 6-carboxy-2-methyl-[3-(4-bromoisoquinolyl)methyl]benzimidazole (385) were formed from 0.290 g of 6-ethoxycarbonyl-2-methyl-1-[3-(4-bromoisoquinolyl)methyl]benzimidazole. This compound was used in the subsequent reaction at once.

EXAMPLE 322

Synthesis of 6-(1-butanesulfonylcarbamoyl)-2-methyl-1-[3-(4-bromoisoquinolyl)methyl]benzimidazole (386)

In the same manner as in Example 98, 0.075 g of 6-(1-butanesulfonylcarbamoyl)-2-methyl-1-[3-(4-bromoisoquinolyl)methyl]benzimidazole (386) were formed from 0.111 g of 6-carboxy-2-methyl-1-[3-(4-bromoisoquinolyl)-methyl]benzimidazole, 0.097 g of N,N'-carbonyldiimidazole, 0.082 g of 1-butanesulfonamide and 0.091 g of diazabicycloundecene.

Properties of Compound (386):

$^1$H-NMR(DMSO-d6, δ): 0.81(3H, t, J=7.4 Hz), 1.35(2H, m), 1.62(2H, m), 2.54(3H, s), 3.46(2H, t, J=7.5 Hz), 5.91 (2H, s), 7.63(1H, d, J=8.5 Hz), 7.76(1H, dd, J=8.5 and 1.4 Hz), 7.79(1H, t, J=7.6 Hz), 8.00(1H, t, J=7.9 Hz), 8.08(1H, t, J=1.1 Hz), 8.13(1H, d, J=8.2 Hz), 8.24(1H, d, J=8.5 Hz), 9.11(1H,s), 11.81(1H, brs).

IR(Nujol): 1678 cm$^{-1}$.

mp: 258–259° C.

Mass(FAB): m/e 515, 517(M+1).

From among the compounds of the present invention, the typical compounds were selected, and were tested for pharmacological properties.

Test Example 1

Stimulatory activity of triglyceride (TG) accumulation in 3T3-L1 cells (pre-adipocytes)

Test Compound 6-benzylsulfonylcarbamoyl-2-cyclopropyl-1-(2-fluorobenzyl)benzimidazole Devices Used
1. Centrifuge: TOMY LC-122
2. Incubator: ESPEC BNA-121D
3. Mixer: Automatic Labo-Mixer
4. Water bath: TAITEC PERSONAL-11
5. Spectrophotometer: Shimadzu UV Visible Spectrophotometer UV-160A
6. 24-well plate: IWAKI GLASS CORNING Reagents Used
1. Medium: Dulbecco minimum essential medium (MEM)+5% fetal calf serum (FCS)
2. PBS (−): solution having the following composition

| NaCl | 0.8 g/liter |
|---|---|
| KCl | 0.2 |
| $Na_2HPO_4$ | 1.15 |
| $KH_2PO_4$ | 0.2 |

3. Solution of EDTA and trypsin:
   0.02% EDTA+0.25% trypsin/PBS(−)
4. Dexamethasone: made by Sigma
5. IBMX (3-isobutyl-1-methylxanthine): made by Sigma
6. Insulin: made by Sigma
7. DMSO (dimethylsulfoxide):
   made by Wako Pure Chemical Industries, Ltd.
8. TG measuring kit:
   Triglyceride-Test Wako (acetyl-acetone method): made by Wako Pure Chemical Industries, Ltd.
9. 0.1-N NaOH solution:
   prepared by diluting a 1N NaOH solution to 10 times with distilled water.
10. Bio-Rad Protein Assay Reagent: made by Bio-Rad.
11. Bovine albumin: made by Sigma Test Method Preparation of 3T3-L1 Cells 3T3-L1 cells just before a confluent state were prepared in an F75 flask. The medium was removed, and the residue was washed twice with 5 ml of PBS (−). The cells were detached using a solution of EDTA and trypsin. Ten milliliters of the medium were added thereto to form a suspension. This suspension was collected in a 50-milliliter centrifuge tube, and was subjected to centrifugation at 1,000 rpm for 5 minutes. Thus, the cells were precipitated, and the supernatant was removed. The cells were re-suspended in 20 ml of the medium, and the number of cells was counted. The suspension was adjusted such that the concentration of the cells reached $6 \times 10^4$ cells/ml, and was inoculated into a 24-well plate in an amount of 1 ml/well. In this state, the incubation was conducted in an incubator at 37° C. in 5% $CO_2$ for 2 days.

Preparation and Addition of Dexamethasone and IBMX

A solution of 1-mM dexamethasone and 500-mM IBMX was prepared in DMSO. Further, this solution was diluted to 1,000 times with the medium to form a solution of 1 μM dexamethasone and 0.5 mM IBMX. At the same time, DMSO was diluted with the medium to form a 0.1% DMSO solution as well.

Subsequently, the 24-well plate containing the incubated 3T3-L1 cells was withdrawn from the incubator. It was identified using a microscope that the cells became confluent, and the medium was removed through suction. The 2 wells of the 24-well plate were charged with the 0.1% DMSO solution in an amount of 1 ml/well, and the remaining 22 wells were charged with the solution of 1 μM dexamethasone and 0.5 mM IBMX in an amount of 1 ml/well. In this state, the incubation was conducted in an incubator at 37° C. in 5% $CO_2$ for 1 day.

Preparation and Addition of a Test Chemical Agent and Insulin

A test chemical agent was diluted with DMSO to $1 \times 10^{-2}$ M, $1 \times 10^{-3}$ M and $1 \times 10^{-4}$ M. The dilute solutions were further diluted to 500 times, and were adjusted to $2 \times 10^{-5}$ M, $2 \times 10^{-6}$ M and $2 \times 10^{-7}$ M respectively. At the same time, a 0.2% DMSO solution was also prepared. Insulin which had been adjusted to 100 μM (in 0.2% bovine serum albumin (BSA) and 3-mM HCl) and had been stored at −80° C. was naturally thawed, diluted to 50,000 times with the medium, and adjusted to 2-nM.

Subsequently, the 24-well plate to which dexamethasone and IBMX had been added the preceding day was withdrawn from the incubator. It was identified using a microscope that the shape of the cells was changed with the addition of dexamethasone and IBMX. Then, the medium was removed through suction. The 2 wells to which the 0.1% DMSO solution had been added the preceding day were charged with the 0.2% DMSO solution in an amount of 500 μl/well and the medium (this was required to check the cell state at that time). The remaining 22 wells (containing the solution of dexamethasone and IBMX) were charged with the 0.2% DMSO solution (2 wells) or the test chemical agent (20 wells) in an amount of 500 μl/well and then with the insulin solution in an amount of 500 μl/well. In this state, the incubation was conducted in an incubator at 37° C. in 5% $CO_2$ for from 4 to 5 days.

Measurement of Triglyceride (TG) and Protein

Four to five days after the addition of the test chemical agent and the insulin solution, the 24-well plate was withdrawn from the incubator. The medium was discarded by decantation, and the remaining medium was then absorbed in a paper towel to completely remove the medium. Subsequently, the residue was extracted twice with isopropyl alcohol, and TG was measured at a wavelength of 410 nm using a TG-measuring kit (acetyl-acetone method). Subsequently, isopropyl alcohol was completely vaporized from the plate in which the extraction with isopropyl alcohol was completed. This plate was then charged with a 0.1-N NaOH solution in an amount of 400 μl/well, and was allowed to stand at room temperature for 30 minutes to dissolve the cells. This solution was sampled into a tube in an amount of 50 μl. Further, a solution obtained by diluting a Bio-Rad protein assay reagent to 5 times with distilled water was added to the tube in an amount of 2.5 ml. The mixture was stirred well, and protein was measured at a measurement wavelength of 595 nm using a spectrophotometer.

Results

The stimulatory activity of the test compound for TG accumulation was calculated, when $1 \times 10^{-6}$ M of a control compound, pioglitazone, was defined as 100% and insulin (+) without the chemical agent was defined as 0%. The result is shown following.

TABLE 1

| Concentration (M) | Stimulatory activity of TG accumulation (%) |
|---|---|
| $1 \times 10^{-5}$ | 38.2% |

Test Example 2

Test for activity of decreasing plasma glucose using db/db mice

Test Compounds 6-benzenesulfonylcarbamoyl-2-cyclopropyl-1-(2-fluoro-benzyl)benzimidazole (177)
6-benzenesulfonylcarbamoyl-1-(2-chlorobenzyl)-2-methylbenzimidazole (163)
1-(biphenyl-4-ylmethyl)-6-(1-butanesulfonylcarbamoyl)-2-methylbenzimidazole (172)

Animal Used

Five-week-old female mice [C57BL/KsJ-dbm db+/db+, C57BL/KsJ-dbm +m/+m (Jackson Laboratory) were purchased, and were kept for 2 to 3 weeks. Then, these mice were used in the test.

Preparation of an Agent

A test compound was mixed with a powdered chow (CE-2, made by Nippon Clea) using a mortar. According to the amount of food intake of the mouse, the mixing ratios, 0.1%, 0.03%, and 0.01% corresponded to 100, 30, and 10 mg/kg body weight, respectively. The mixed chow was changed twice a week. The feed amount and the remaining amount were recorded, and the intake was calculated from the difference therebetween.

Test Schedule

The female db/db mice were grouped according to the body weight, the plasma glucose and the plasma triglyceride concentrations. Then, the mixture containing the test compound was administered to the mice for 14 days (from 8 to 10 weeks old). In the morning on day 7 and day 14, the blood was collected from the orbital venous plexus using heparinized glass capillary tubes (Chase Heparinized Capillary Tubes), and a plasma fraction was obtained through centrifugal separation. Plasma glucose, triglyceride, and insulin concentrations were measured on day 0 and day 14 as well as plasma glucose and triglyceride concentrations on day 7. The body weight was measured on day 0, day 7, and day 14. After the final collection of the blood, the mice were killed using $CO_2$ gas.

Measurement Method

The plasma glucose was measured by a glucose oxidase method (Glucose CII-Test Wako made by Wako Pure Chemical Industries, Ltd.) using from 10 to 15 μl of plasma. The plasma triglyceride concentration was measured by a GPO-p-chlorophenol method (Triglyceride G-Test Wako made by Wako Pure Chemical Industries, Ltd.) or a GPO-DAOS method (Triglyceride E-Test Wako) using from 10 to 15 μl of plasma. The above-mentioned measurements were conducted immediately after the blood collection. The plasma insulin concentration was measured by radio immuno assay method (Phadesef Insulin RIA Kit made by Cabi Pharmacia) using 20 μl of plasma (which can be stored at −20° C.).

Results

The difference in the plasma glucose and the plasma triglyceride concentrations betweeen the db/db mouse and the +/+ mouse was defined as 100%, and the rate (%) of decrease in the plasma glucose and the plasma triglyceride concentrations of the group to which the test compound was administered was calculated.

The results were shown in Table 2.

TABLE 2

| Compound No. | Dose (mg/kg) | Activity of decreasing plasma glucose (%) |
|---|---|---|
| (177) | 30 | 34.5 |
| (163) | 30 | 72 |
| (172) | 10 | 70–80 |

Industrial Applicability

Herein provided are novel benzimidazole derivatives and their pharmaceutically acceptable salts. These compounds and their salts have blood sugar level-depressing activity or PDE5-inhibiting activity, and are useful for preventing and treating impaired glucose tolerance, diabetes (type II diabetes), diabetic complications such as diabetic nephropathy, diabetic neuropathy and diabetic retinopathy, syndrome of insulin resistance (e.g., insulin receptor disorders, Rabson-Mendenhall syndrome, leprechaunism, Kobberling-Dunnigan syndrome, Seip syndrome, Lawrence syndrome, Cushing syndrome, acromegaly, etc.), hyperlipidemia, atherosclerosis, cardiovascular disorders (e.g., stenocardia, cardiac failure, etc.), hyperglycemia(e.g., abnormal-saccharometabolism such as feeding disorders, etc.), or hypertension; or stenocardia, hypertension, pulmonary hypertension, congestive heart failure, glomerulopathy (e.g., diabetic glomerulosclerosis, etc.), tubulointerstitial disorders (e.g., renopathy induced by FK506, cyclosporin, etc.), renal failure, atherosclerosis, angiostenosis (e.g., after percutaneous arterioplasty), distal angiopathy, cerebral apoplexy, chronic reversible obstructions (e.g., bronchitis, asthma (chronic asthma, allergic asthma), etc.), allergic rhinitis, urticaria, glaucoma, diseases characterized by enteromotility disorders (e.g., hypersensitive enteropathy syndrome, etc.), impotence (e.g., organic impotence, psychic impotence, etc.), and diabetic complications (e.g., diabetic gangrene, diabetic arthropathy, diabetic glomerulosclerosis, diabetic dermatopathy, diabetic neuropathy, diabetic cataract, diabetic retinopathy, ect.), nephritis, cancerous cachexia, or restenosis after PTCA.

What is claimed is:

1. A benzimidazole compound of the following formula, or its pharmaceutically acceptable salt:

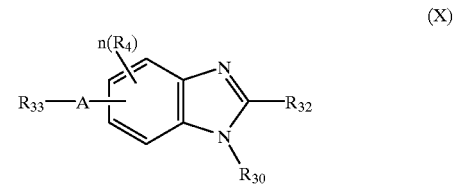

(X)

wherein
R$_{30}$ represents a hydrogen atom, a lower alkyl group, or an unsubstituted benzyl group or a benzyl group of the following formula:

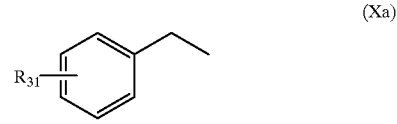

(Xa)

in which
- $R_{31}$ represents a hydrogen atom, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, an aryloxy group, an aryl-lower alkyloxy group, or an aryl-lower alkyloxy group substituted by one or two halogen atoms, an arylsulfonyl group, a heterocyclic lower alkyl group, an arylcarbonylamino group, an arylcarbonyl group, an arylalkenyl group, or a lower alkylenedioxyaryl group; the α-position of said benzyl group being unsubstituted or substituted by a lower alkyl group;
- $R_{32}$ represents a hydrogen atom, a lower alkyl group, a halo-lower alkyl group, a lower cycloalkyl group, an aryl group, an aryl-lower alkyl group, a lower alkylamino group, a lower alkoxy group, a lower alkylthio group, a lower alkoxy-lower alkyl group, or a heterocyclic lower alkyl group;
- $R_{33}$ represents a group of a formula:

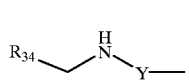

(Xb)

in which
- Y represents a carbonyl group or a lower alkylene group;
- $R_{34}$ represents an unsubstituted lower alkyl group or a lower alkyl group substituted by a substituted or unsubstituted aryl or heterocyclic group, an aryl group, or a heterocyclic group;
- A represents a single bond, a lower alkylene, or alkenylene group;
- $R_4'$ represents a hydrocarbon group or a halogenated hydrocarbon group; and
- n represents an integer from 0 to 3, provided that, when $R_{30}$, is a hydrogen atom, n is 0.

2. A benzimidazole compound of the following formula, or its pharmaceutically acceptable salt:

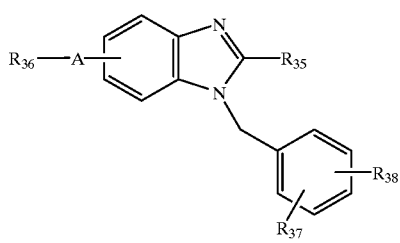

(XI)

wherein
- $R_{35}$ represents a hydrogen atom, an aryl group, a lower alkoxy-lower alkyl group, a lower alkyl group, or an aryl-lower alkyl group;
- $R_{36}$ represents a carboxyl group, a lower alkoxycarbonyl group, a heterocyclic lower alkylamino group, or a heterocyclic lower alkylcarbamoyl group;
- $R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group; and
- A represents a single bond, or a lower alkylene or alkenylene group; provided that, when $R_{35}$ is a lower alkyl group, A is a lower alkylene group or a lower alkenylene group.

3. A benzimidazole compound of the following formula, or its pharmaceutically acceptable salt:

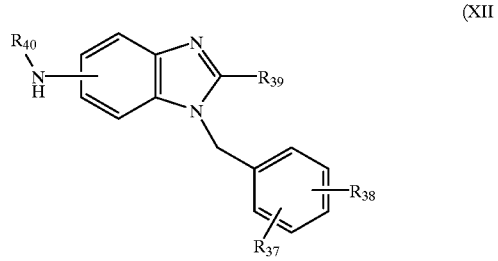

(XII)

wherein
- $R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group;
- $R_{39}$ represents a lower alkyl group; and
- $R_{40}$ represents a lower alkoxycarbonyl group, a lower alkanoyl group, a lower alkanesulfonyl group, or a carbamoyl group.

4. A benzimidazole compound of the following formula, or its pharmaceutically acceptable salt;

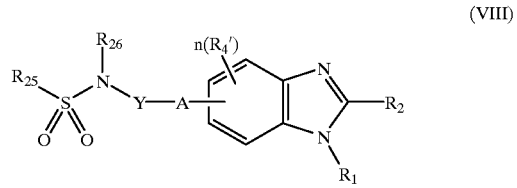

(VIII)

wherein
- $R_1$ represents a hydrogen atom, an arylsulfonyl group, or a lower alkyl group; said lower alkyl group is unsubstituted or substituted by a heterocyclic group, an aryl group or an aryl group substituted by one or two substituents selected from a halogen atom, a haloaryl group, a lower alkyl group, a halo-lower alkyl group, a lower alkoxy group, a nitro group, an amino group, a cyano group, an aryl group, an aryl-lower alkyloxy group, an arylsulfonyl-lower alkyl group, an aryl-lower alkyl group, a haloaryl-lower alkyloxy group, an arylsulfonylamino group, an arylcarbonylamino group, an arylcarbonyl group, an arylalkenyl group, a cyanoaryl group, and a heterocyclic group;
- $R_2$ represents a hydroxy-lower alkyl group, or a lower alkyl group; said lower alkyl group is substituted by a cyano group, a halocarbonyl group, or a heterocyclic group;
- $R_{25}$ represents an alkyl group having up to 8 carbon atoms, a lower cycloalkyl group, a halo-lower alkyl group, a tri-lower alkylsilyl-lower alkyl group, a lower alkoxy-lower alkyl group, a lower alkylthio-lower alkyl group, an aryl group, a heterocyclic group, an aryl-lower alkyl group, or a hydroxylower alkyl group; said aryl group is unsubstituted or substituted by a halogen atom, a lower alkyl group, a halo-lower alkyl group, a lower alkoxy group, or a nitro group;

R$_{26}$ represents a hydrogen atom or a lower alkyl group; provided that, when R$_{25}$ and R$_{26}$ are both lower alkyl groups, they are two acyclic alkyl groups or they form a ring when bonded together;

Y represents a carbonyl group or a lower alkylene group;

A represents a single bond, or a lower alkylene or alkenylene group;

R$_4$' represents a hydrocarbon group or a halogenated hydrocarbon group; and n represents an integer from 0 to 3.

5. A benzimidazole compound of the following formula, or its pharmaceutically acceptable salt:

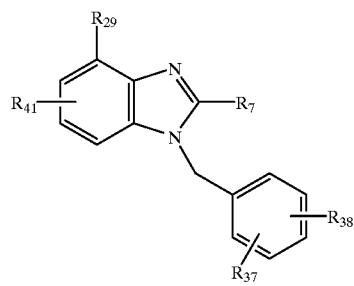

(XIV)

wherein

R$_{37}$ and R$_{38}$ each independently represent a hydrogen atom, a halogen atom, a lower alkyl group, a halo-lower alkyl group, an aryl group, an aryl-lower alkyl group, or an aryl-lower alkyloxy group;

R$_7$ represents a lower alkyl group or a lower cycloalkyl group;

R$_{41}$ represents a 2-pyridylcarbamoyl group, a 2-carboxy-1-pyrrolidinocarbonyl group, an N-methyl-N-(2-pyridylmethyl)carbamoyl group, a homopiperidinocarbonyl group, a [2-(N-oxo)-pyridylmethyl]carbamoyl group, a 4-(dimethyl-amino)benzylcarbamoyl group, a piperonylcarbamoyl group, an N-methyl-N-(2-pyridyl)carbamoyl group, a morpholinocarbonyl group, a thiomorpholinocarbonyl group, a halosulfonyl group, an aminosulfonyl group, an acylaminosulfonyl group, a lower alkoxycarbonyl group, or a carboxyl group; and R$_{29}$ represents a hydrogen atom, or a lower alkyl group; provided that, when R$_{41}$ is a lower alkoxycarbonyl group or a carboxyl group, R$_{29}$ is a lower alkyl group.

6. A pharmaceutical composition for preventing or treating a patient suffering from or at risk of suffering from impaired glucose tolerance, diabetes, diabetic complications, syndrome of insulin resistance, hyperlipidemia, atherosclerosis, cardiovascular disorders, hyperglycemia or hypertension; which comprises, as an active ingredient, a compound of the following formula or its pharmaceutically acceptable salt:

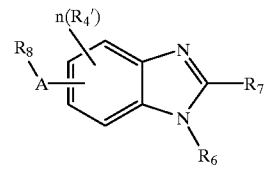

(II)

wherein

R$_6$ represents an aryl-lower alkyl group or an aryl-lower alkyl group substituted by one or two substituents selected from a halogen atom, a haloaryl group, a lower alkyl group, a halo-lower alkyl group, a lower alkoxy group, a nitro group, an amino group, a cyano group, an aryl group, a cyanoaryl group, an aryl-lower alkyloxy group, an arylsulfonyl-lower alkyl group, an arylsulfonylamino group, an aryl-lower alkyl group, and a heterocyclic group;

R$_7$ represents a lower alkyl group or a lower cycloalkyl group;

R$_8$ represents a carbamoyl group, which is unsubstituted or substituted by a lower alkyl group, a lower alkyl group substituted by a substituted or unsubstituted aryl group or a substituted or unsubstituted heterocyclic group, an aryl group, or a heterocyclic group;

A represents a single bond or a lower alkylene or alkenylene group;

R$_4$' represents a hydrocarbon group or a halogenated hydrocarbon group; and n represents an integer from 0 to 3.

7. A pharmaceutical composition comprising, a pharmaceutically acceptable excipient and a compound of formula (II):

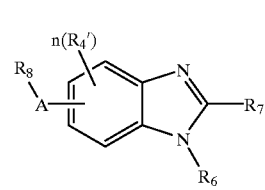

(II)

R$_4$' is a hydrocarbon group or a halogenated hydrocarbon group;

R$_6$ is an aryl-lower alkyl group or an aryl-lower alkyl group substituted by one or two substituents selected from a halogen atom, a haloaryl group, a lower alkyl group, a halo-lower alkyl group, a lower alkoxy group, a nitro group, an amino group, a cyano group, an aryl group, a cyanoaryl group, an aryl-lower alkyloxy group, an arylsulfonyl-lower alkyl group, an arylsulfonylamino group, an aryl-lower alkyl group, and a heterocyclic group;

R$_7$ is a lower alkyl group or a lower cycloalkyl group;

R$_8$ is a carbamoyl group, which is unsubstituted or substituted by a lower alkyl group, a lower alkyl group substituted by a substituted or unsubstituted aryl group or a substituted or unsubstituted heterocyclic group, an aryl group, or a heterocyclic group;

A represents a single bond or a lower alkylene or alkenylene group; and n is an integer from 0 to 3;

and having blood sugar level-depressing activity.

8. A pharmaceutical composition comprising a compound selected from the group consisting of compounds of formula VIII, X, XI, XII, and XIV

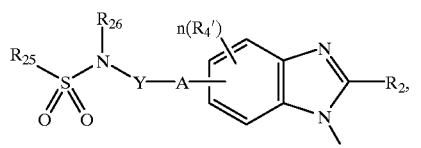
(VIII)

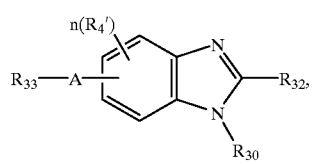
(X)

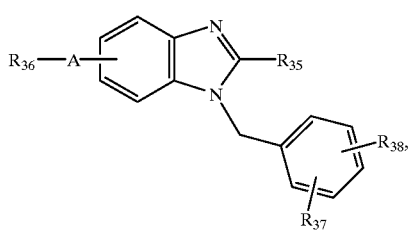
(XI)

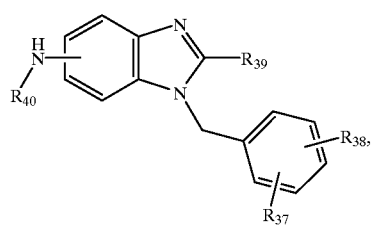
(XII)

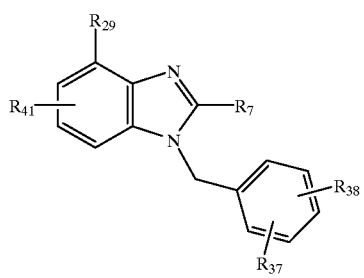
(XIV)

wherein $R_1$ represents a hydrogen atom, an arylsulfonyl group, or a lower alkyl group; said lower alkyl group is unsubstituted or substituted by a heterocyclic group, an aryl group or an aryl group substituted by one or two substituents selected from a halogen atom, a haloaryl group, a lower alkyl group, a halo-lower alkyl group, a lower alkoxy group, a nitro group, an amino group, a cyano group, an aryl group, an aryl-lower alkyloxy group, an arylsulfonyl-lower alkyl group, an aryl-lower alkyl group, a haloaryl-lower alkyloxy group, an arylsulfonylamino group, an arylcarbonylamino group, an arylcarbonyl group, an arylalkenyl group, a cyanoaryl group, and a heterocyclic group;

$R_2$ represents a hydroxy-lower alkyl group or a lower alkyl group; said lower alkyl group is substituted by a cyano group, a halocarbonyl group, or a heterocyclic group;

$R_4'$ represents a hydrocarbon group or a halogenated hydrocarbon group;

$R_7$ represents a lower alkyl group or a lower cycloalkyl group;

$R_{25}$ represents an alkyl group having up to 8 carbon atoms, a lower cycloalkyl group, a halo-lower alkyl group, a tri-lower alkylsilyl-lower alkyl group, a lower alkoxy-lower alkyl group, a lower alkylthio-lower alkyl group, an aryl group, a heterocyclic group, an aryl-lower alkyl group, or a hydroxy-lower alkyl group; said aryl group is unsubstituted or substituted by a halogen atom, a lower alkyl group, a halo-lower alkyl group, a lower alkoxy group, or a nitro group;

$R_{26}$ represents a hydrogen atom or a lower alkyl group;

provided that, when $R_{25}$ and $R_{26}$ are both lower alkyl groups, they are two acyclic alkyl groups or they form a ring when bonded together;

$R_{29}$ represents a hydrogen atom or a lower alkyl group; provided that, when $R_{41}$ is a lower alkoxycarbonyl group or a carboxyl group, $R_{29}$ is a lower alkyl group;

$R_{30}$ represents a hydrogen atom, a lower alkyl group, an unsubstitued benzyl group or a benzyl group of the following formula:

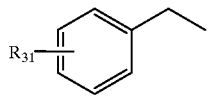
(Xa)

in which $R_{31}$ represents a hydrogen atom, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, an aryloxy group, an unsubstituted aryl-lower alkyloxy group, or an aryl-lower alkyloxy group substituted by one or two halogen atoms, an arylsulfonyl group, a heterocyclic lower alkyl group, an arylcarbonylamino group, an arylcarbonyl group, an arylalkenyl group, or a lower alkylene-dioxyaryl group; the α-position of said benzyl group being unsubstituted or substituted by a lower alkyl group;

$R_{32}$ represents a hydrogen atom, a lower alkyl group, a halo-lower alkyl group, a lower cycloalkyl group, an aryl group, an aryl-lower alkyl group, a lower alkylamino group, a lower alkoxy group, a lower alkyltlio group, a lower alkoxy-lower alkyl group, or a heterocyclic lower alkyl group;

$R_{33}$ represents a group of a formula:

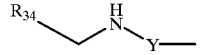
(Xb)

$R_{34}$ represents a lower alkyl group or a lower alkyl group substituted by a substituted or unsubstituted aryl or heterocyclic group, or represents an aryl group or a heterocyclic group;

R$_{35}$ represents a hydrogen atom, an aryl group, a lower alkoxy-lower alkyl group, a lower alkyl group, or an aryl-lower alkyl group;

R$_{36}$ represents a carboxyl group, a lower alkoxycarbonyl group, a heterocyclic lower alkylamino group, or a heterocyclic lower alkylcarbamoyl group;

R$_{37}$ and R$_{38}$ each independently represent a hydrogen atom, a halogen atom, a lower alkyl group, a halo-lower alkyl group, an aryl group, an aryl-lower alkyl group, or an aryl-lower alkyloxy group;

R$_{39}$ represents a lower alkyl group;

R$_{40}$ represents, a lower alkoxycarbonyl group, a lower alkanoyl group, a lower alkanesulfonyl group, or a carbamoyl group;

R$_{41}$ represents a 2-pyridylcarbamoyl group, a 2-carboxy-1-pyrrolidinocarbonyl group, an N-methyl-N-(2-pyridyl-methyl)carbamoyl group, a homopiperidinocarbonyl group, a [2-(N-oxo)-pyridylmethyl]carbamoyl group, a 4-(dimethyl-amino)benzylcarbamoyl group, a piperonylcarbamoyl (group, an N-methyl-N-(2-pyridyl)carbamoyl group, a morpholinocarbonyl group, a thiomorpholinocarbonyl group, a halosulfonyl group, an aminosulfonyl group, an acylaminosulfonyl group, a lower alkoxycarbonyl group, or a carboxyl group;

Y represents a carbonyl group or a lower alkylene group;

A represents a single bond, a lower alkylene or alkenylene group, provided that, when R$_{35}$ is a lower alkyl group, A is a lower alkylene group or a lower alkenylene group;

n represents a integer from 0 to 3, provided that, when R$_{30}$ is a hydrogen atom, n is 0;

and a pharmaceutically acceptable excipient.

9. A pharmaceutical composition comprising a pharmaceutically acceptable excipient and a compound selected from the group consisting of 1-(2-bromobenzyl)-6-ethoxycarbonyl-2-n-propylbenzimidazole, 6-ethoxycarbonyl-1-(2-fluorobenzyl)-2-n-propylbenzimidazole, 6-ethoxycarbonyl-1-(4-fluorobenzyl)-2-n-propylbenzimidazole, 6-ethoxycarbonyl-1-(3-fluorobenzyl)-2-n-propylbenzimidazole, 1-(2,6-dichlorobenzyl)-6-ethoxycarbonyl-2-n-propylbenzimidazole, 1-(3-methylbenzyl)-6-ethoxycarbonyl-2-n-propylbenzimidazole, 2-cyclopropyl-6-ethoxycarbonyl-1-(2-fluorobenzyl)benzimidazole, 1-(2-chlorobenzyl)-2-cyclobutyl-6-ethoxycarbonylbenzimidazole, 1-(2-chlorobenzyl)-6-ethoxycarbonyl-2-n-pentylbenzimidazole, 5-carboxy-1-(2-chlorobenzyl)-2-n-propylbenzimidazole, 6-carboxy-1-(3-methyl-benzyl)-2-n-propylbenzimidazole, 2-n-butyl-7-carboxy-1-(2-chlorobenzyl)-benzimidazole, 6-carboxy-1-(2-fluorobenzyl)-2-cyclopropyl-benzimidazole, 2-n-butyl-6-carboxy-1-(2-fluorobenzyl)-benzimidazole, 1-(2-chlorobenzyl)-6-chlorocarbonyl-2-cyclopropylbenzimidazole, 1-(2-chlorobenzyl)-6-morpholinocarbamoyl-2-n-propylbenzimidazole, 2-n-butyl-1-(2-chlorobenzyl)-6-[(2-pyridylmethyl)carbamoyl]benzimidazole, 2-n-butyl-5-carbamoyl-1-(2-chlorobenzyl)-benzimidazole, 1-(2-chlorobenzyl)-2-cyclopropyl-6-morpholinocarbonylbenzimidazole, 1-(2-chlorobenzyl)-2-cyclopropyl-6-[(2-pyridylmethyl)carbamoyl]benzimidazole, 1-(2-chlorobenzyl)-2-cyclobutyl-6-[(2-pyridylmethyl)carbamoyl]-benzimidazole, 1-(2-chlorobenzyl)-2-n-propyl-5-[(2-pyridyl-methyl)carbamoyl]benzimidazole, 1-(2-chlorobenzyl)-6-phenyl-carbamoyl-2-n-propylbenzimidazole, 1-(2-chlorobenzyl)-2-n-propyl-6-[(4-pyridylmethyl)carbamoyl]-benzimidazole, 1-(2-chlorobenzyl)-2-n-propyl-6-[(3-pyridylmethyl)carbamoyl]benzimidazole, 1-(3-methylbenzyl)-2-n-propyl-6-[(2-pyridyl-methyl)carbamoyl]benzimidazole, 1-(2-chlorobenzyl)-2-ethyl-6-[(2-pyridylmethyl)carbamoyl]benzimidazole, 2-n-butyl-1-(2-chlorobenzyl)-7-[(2-pyridylmethyl)carbamoyl]benzimidazole, 2-n-butyl-1-(2-fluorobenzyl)-6-(2-pyridylmethylcarbamoyl)benzimidazole, 1-(2-chlorobenzyl)-6-ethoxycarbonyl-2-methylbenzimidazole, 1-(3-chlorobenzyl)-6-ethoxycarbonyl-2-n-propyl-benzimidazole, 1-benzyl-6-ethoxycarbonyl-2-n-propylbenzimidazole, 1-(4-chlorobenzyl)-6-ethoxycarbonyl-2-n-propylbenzimidazole, 6-ethoxycarbonyl-2-methyl-1-[2-(trifluoromethyl)benzyl]-benzimidazole, 6-ethoxycarbonyl-2-methyl-1-[4-(trifluoromethyl)-benzyl]benzimidazole, 1-(3,4-dichlorobenzyl)-6-ethoxycarbonyl-2-methylbenzimidazole, 6-ethoxycarbonyl-2-methyl-1-(2-methyl-benzyl)benzimidazole, 1-benzyl-6-ethoxycarbonyl-2-methyl-benzimidazole, 1-(4-t-butylbenzyl)-6-ethoxycarbonyl-2-methyl-benzimidazole, 1-(2-chlorobenzyl)-5-ethoxycarbonyl-2-methylbenzimidazole, 1-(2,6-dichloro-benzyl)-6-ethoxycarbonyl-2-methyl-benzimidazole, 1-(2,4-dichlorobenzyl)-6-ethoxycarbonyl-2-methylbenzimidazole, 6-carboxy-1-(4-chlorobenzyl)-2-n-propyl-benzimidazole, 6-carboxy-1-(2,6-dichlorobenzyl)-2-methyl-benzimidazole, 6-carboxy-2-methyl-1-[2-(trifluoromethyl)-benzyl]-benzimidazole, 6-carboxy-2-methyl-1-[4-(trifluoromethyl)benzyl]benzimidazole, 6-carboxy-1-(3,4-dichlorobenzyl)-2-methylbenzimidazole, 1-benzyl-6-carboxy-2-n-propylbenzimidazole, 6-carboxy-1-(3-chlorobenzyl)-2-n-propylbenzimidazole, 6-carboxy-1-(2,4-dichlorobenzyl)-2-methylbenzimidazole, 1-(4-t-butyl-benzyl)-6-carboxy-2-methylbenzimidazole, 6-carboxy-2-methyl-1-(2-methylbenzyl)benzimidazole, 1-benzyl-6-carboxy-2-methylbeizimidazole, 5-carboxy-1-(2-chlorobenzyl)-2-methylbenzimidazole, 6-carboxy-1-(2-chlorobenzyl)-2-methyl-benzimidazol, 1-(2,4-dichlorobenzyl)-2-methyl-6-[(2-pyridyl-methyl)carbamoyl]benzimidazole, 1-(2-chlorobenzyl)-2-methyl-6-[(2-pyridylmethyl)carbamoyl]benzimidazole, 1-(3-chlorobenzyl)-2-n-propyl-6-[(2-pyridylmethyl)carbamoyl]benzimidazole, 1-benzyl-2-n-propyl-6-[(2-pyridyl-methyl)carbamoyl]benzimidazole, 1-(4-chlorobenzyl)-2-propyl-6-[(2-pyridylmethyl)carbamoyl]-benzimidazole, 1-(2,6-dichlorobenzyl)-2-methyl-6-[(2-pyridyl-methyl)carbamoyl]benzimidazole, 2-methyl-6-[(2-pyridylmethyl)-carbamoyl]-1-[2-(trifluoromethyl)benzyl]benzimidazole, 2-methyl-6-[(2-pyridylmethyl)carbamoyl]-1-[4-(trifluoromethyl)benzyl]benzimidazole, 1-(3,4-dichlorobenzyl)-2-methyl-6-[(2-pyridyl-methyl)carbamoyl]benzimidazole, 2-methyl-1-(2-methyl-benzyl)-6-[(2-pyridylmethyl)carbamoyl]benzimidazole, 1-benzyl-2-methyl-6-[(2-pyridylmethyl)-carbamoyl]benzimidazole, 1-(4-t-butylbenzyl)-2-methyl-6-[(2-pyridylmethyl)carbamoyl]-benzimidazole, 6-carbamoyl-1-(2,4-dichlorobenzyl)-2-methylbenzimidazole, 1-(2,4-difluorobenzyl)-2-methyl-6-[(2-pyridylmethyl)carbamoyl]-benzimidazole, 1-(2,4-difluorobenzyl)-2-methyl-5-[(2-pyridyl-methyl)carbamoyl]benzimidazole, 1-(2,4-dichlorobenzyl)-7-ethoxycarbonyl-2-methylbenzimidazole, 7-carboxy-1-(2,4-dichloro-benzyl)-2-methylbenzimidazole, 1-(2,4-dichlorobenzyl)-4-ethoxycarbonyl-2-methylbenzimidazole, 4-carboxy-1-(2,4-dichloro-benzyl)-2-methylbenzimidazole, 6-(n-butylcarbamoyl)-1-(2,4-dichlorobenzyl)-2-methyl-benzimidazole, 1-(2,4-dichlorobenzyl)-5-ethoxycarbonyl-2-methylbenzimidazole, and 5-carboxy-1-(2,4-dichlorobenzyl)-2-methylbenzimidazole; or its salts.

10. The pharmaceutical composition of claim 6, wherein diabetic complications is selected from the group consisting of diabetic nephropathy, diabetic neuropathy, diabetic retinopathy, diabetic gangrene, diabetic arthropathy, diabetic glomerulosclerosis, diabetic dermatopathy, and diabetic cataract.

11. A method for lowering the blood sugar level of a patient, which comprises administering to the patient a compound of formula (II)

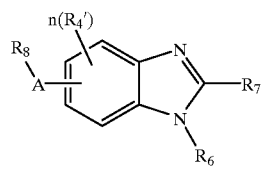
(II)

$R_4'$ is a hydrocarbon group or a halogenated hydrocarbon group;

$R_6$ is an aryl-lower alkyl group or an aryl-lower alkyl group substituted by one or two substituents selected from a halogen atom, a haloaryl group, a lower alkyl group, a halo-lower alkyl group, a lower alkoxy group, a nitro group, an amino group, a cyano group, an aryl group, a cyanoaryl group, an aryl-lower alkyloxy group, an arylsulfonyl-lower alkyl group, an arylsulfonylamino group, an aryl-lower alkyl group, and a heterocyclic group;

$R_7$ is a lower alkyl group or a lower cycloalkyl group;

$R_8$ is a carbamoyl group, which is unsubstituted or substituted by a lower alkyl group, a lower alkyl group substituted by a substituted or unsubstituted aryl group or a substituted or unsubstituted heterocyclic group, an aryl group, or a heterocyclic group;

A represents a single bond or a lower alkylene or alkenylene group; and n is an integer from 0 to 3.

12. A method for preventing or treating a patient suffering from impaired glucose tolerance, diabetes, diabetic complications, syndrome of insulin resistance, hyperlipidemia, atherosclerosis, cardiovascular disorders, hyperglycemia or hypertension; which comprises administering a compound of the following formula or its pharmaceutically acceptable salt:

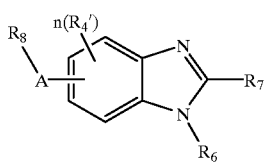
(II)

wherein $R_6$ represents an aryl-lower alkyl group or an aryl-lower alkyl group substituted by one or two substituents selected from a halogen atom, a haloaryl group, a lower alkyl group, a halolower alkyl group, a lower alkoxy group, a nitro group, an amino group, a cyano group, an aryl group, a cyanoaryl group, an aryllower alkyloxy group, an arylsulfonyl-lower alkyl group, an arylsulfonylamino group, an aryl-lower alkyl group, and a heterocyclic group;

$R_7$ represents a lower alkyl group or a lower cycloalkyl group;

$R_8$ represents a carbamoyl group, which is unsubstituted or substituted by a lower alkyl group, a lower alkyl group substituted by a substituted or unsubstituted aryl group or a substituted or unsubstituted heterocyclic group, an aryl group, or a heterocyclic group;

A represents a single bond or a lower alkylene or alkenylene group;

$R_4'$ represents a hydrocarbon group or a halogenated hydrocarbon group; and n represents an integer from 0 to 3.

13. The pharmaceutical composition of claim 12, herein diabetic complications is selected from the group consisting of diabetic nephropathy, diabetic neuropathy, diabetic retinopathy, diabetic gangrene, diabetic arthropathy, diabetic glomerulosclerosis, diabetic dermatopathy, and diabetic cataract.

14. A method of preparing a benzimidazole compound of formula X or XIV,

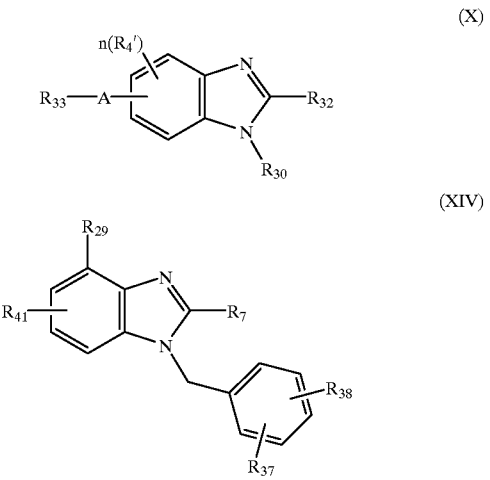

wherein $R_4'$ represents a hydrocarbon group or a halogenated hydrocarbon group;

$R_{30}$ represents a hydrogen atom, a lower alkyl group, an unsubstituted benzyl group or a benzyl group of the following formula:

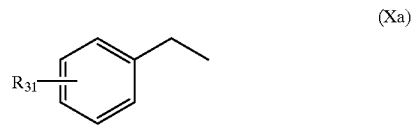
(Xa)

in which $R_{31}$ represents a hydrogen atom, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, an aryloxy group, an unsubstituted aryl-lower alkyloxy group, or an aryl-lower alkyloxy group substituted by one or two halogen atoms, an arylsulfonyl group, a hetero-cyclic lower alkyl group, an arylcarbonylamino group, an arylcarbonyl group, an arylalkenyl group, or a lower alkylenedioxyaryl group; the α-position of said benzyl group being unsubstituted or substituted by a lower alkyl group;

$R_{32}$ represents a hydrogen atom, a lower alkyl group, a halo-lower alkyl group, a lower cycloalkyl group, an aryl group, an aryl-lower alkyl group, a lower alkylamino group, a lower alkoxy group, a lower alkylthio group, a lower alkoxy-lower alkyl group, or a heterocyclic lower alkyl group;

$R_{33}$ represents a group of the following formula:

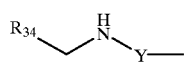
(Xb)

in which $R_{34}$ represents an aryl group, a heterocyclic group, a lower alkyl group, or a lower alkyl group substituted by a substituted or unsubstituted aryl or heterocyclic group; and Y represents a carbonyl group or a lower alkylene group;

A represents a single bond, or a lower alkylene or alkenylene group; and n means an integer from 0 to 3, provided that, when $R_{30}$ is a hydrogen atom, n is 0

$R_7$ represents a lower alkyl group or a lower cycloalkyl group;

$R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group;

$R_{41}$ represents a 2-pyridylcarbamoyl group, a 2-carboxy-1-pyrrolidinocarbonyl group, an N-methyl-N-(2-pyridyl-methyl)carbamoyl group, a homopiperidinocarbonyl group, a [2-(N-oxo)-pyridylmethyl] carbamoyl group, a 4-(dimethylamino)-benzylcarbamoyl group, a piperonylcarbamoyl group, an N-methyl-N-(2-pyridyl)carbamoyl group, a morpholinocarbonyl group, a thiomorpholinocarbonyl group, a halosulfonyl group, an aminosulfonyl group, an acylaminosulfonyl group, a lower alkoxycarbonyl group, or a carboxyl group;

$R_{29}$ represents a hydrogen atom or a lower alkyl group, provided that, when $R_{41}$ is a lower alkoxycarbonyl group or a carboxyl group, $R_{29}$ is a lower alkyl group;

said method comprising a step selected from the group consisting of steps (A), (B), (C), and (D):

(A) reacting a compound of formula (8'):

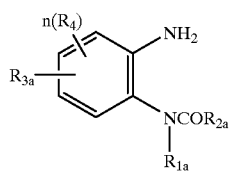
(8)' with a carboxylic acid, a sulfonic acid, or an inorganic acid to produce a benzimidazole compound of formula (9'):

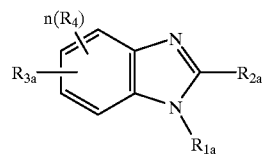
(9')

(B) reacting a compound of formula (10'):

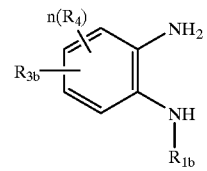
(10')

with a carboxylic acid, acid halide, or acid anhydride having a substituent $R_{2b}$, to give a benzimidazole compound of the following formula (11'):

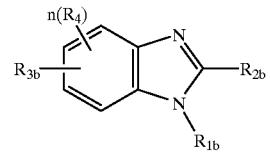
(11')

(C) reacting a compound of formula (12'):

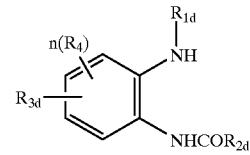
(12')

with a carboxylic acid, a sulfonic acid, or an inorganic acid to give a benzimidazole compound of the following formula (13'):

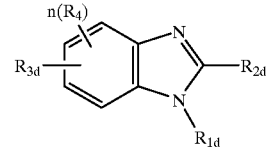
(13')

(D) reacting a compound of the following formula (14'):

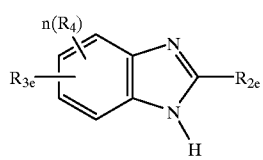

(14')

with sodium hydride, lithium diisopropylamide, lithium hydrogencarbonate, lithium carbonate, sodium hydroxide, potassium hydrogencarbonate, potassium carbonate, or potassium hydroxide and then reacting the resulting compound with $R_{1e}Z$, wherein Z is a chlorine atom, a bromine atom, a toluenesulfonyloxy group, or a methanesulfonyloxy group, to produce a benzimidazole compound of formula (15'):

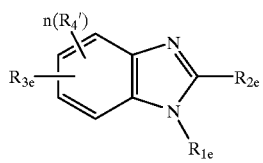

(15')

wherein each of $R_{1a}$, $R_{1b}$, $R_{1c}$, $R_{1d}$, and $R_{1e}$ is independently $R_{30}$ or the formula:

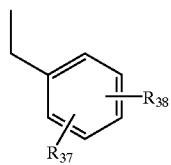

each of $R_{2a}$ $R_{2b}$, $R_{2c}$, $R_{2d}$, and $R_{2e}$ is independently $R_7$ or $R_{32}$, each of $R_{3a}$, $R_{3b}$, $R_{3c}$, $R_{3d}$, and $R_{3e}$ is independently $R_{41}$ or $R_{33}$ —A—, $R_4$ has the same meaning as $R_4'$ or $R_{29}$, and n represents an integer from 0 to 3.

15. A method of preparing a benzimidazole compound of formula X or XI,

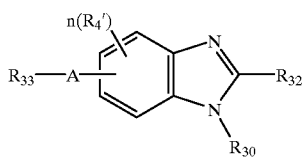

(X)

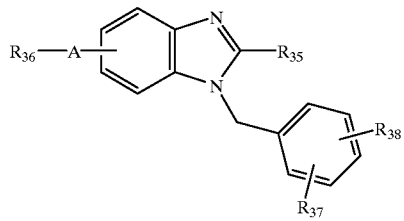

(XI)

wherein $R_4'$ represents a hydrocarbon group or a halogenated hydrocarbon group;

$R_{30}$ represents a hydrogen atom, a lower alkyl group, an unsubstituted benzyl group or a benzyl group of the following formula:

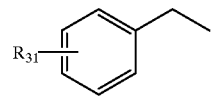

(Xa)

in which $R_{31}$ represents a hydrogen atom, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, an aryloxy group, an unsubstituted aryl-lower alkyloxy group, or an aryl-lower alkyloxy group substituted by one or two halogen atoms, an arylsulfonyl group, a hetero-cyclic lower alkyl group, an arylcarbonylamino group, an arylcarbonyl group, an arylalkenyl group, or a lower alkylenedioxyaryl group; the α-position of said benzyl group being unsubstituted or substituted by a lower alkyl group;

$R_{32}$ represents a hydrogen atom, a lower alkyl group, a halo-lower alkyl group, a lower cycloalkyl group, an aryl group, an aryl-lower alkyl group, a lower alkylamino group, a lower alkoxy group, a lower alkylthio group, a lower alkoxy-lower alkyl group, or a heterocyclic lower alkyl group;

$R_{33}$ represents a group of the following formula:

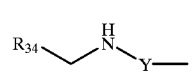

(Xb)

in which $R_{34}$ represents an aryl group, a heterocyclic group, a lower alkyl group, or a lower alkyl group substituted by a substituted or unsubstituted aryl or heterocyclic group, and Y represents a carbonyl group or a lower alkylene group; and n means an integer from 0 to 3, provided that, when $R_{30}$ is a hydrogen atom, n is 0

$R_{35}$ represents a hydrogen atom, an aryl group, a lower alkoxy-lower alkyl group, a lower alkyl group, or an aryl-lower alkyl group;

$R_{36}$ represents a carboxyl group, a lower alkoxycarbonyl group, a heterocyclic lower alkylamino group, or a heterocyclic lower alkylcarbamoyl group;

$R_{37}$ and $R_{38}$ each independently represents a hydrogen atom, a halogen atom, a lower alkyl group, a halo-lower alkyl group, an aryl group, an aryl-lower alkyl group, or an aryl-lower alkyloxy group; and A represents a single bond, or a lower alkylene or alkenylene group, provided that, when $R_{35}$ is a lower alkyl group, A is a lower alkylene group or a lower alkenylene group;

said method comprising hydrolyzing a compound of formula (16'):

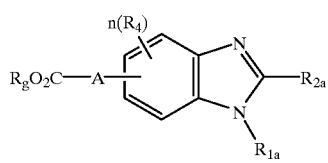

(16')

wherein $R_g$ is a lower alkyl group, with lithium hydroxide, sodium hydroxide, or potassium hydroxide to produce a benzimidazole compound of formula (17'):

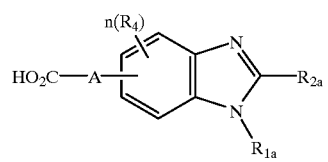

(17')

wherein $R_{1a}$ is $R_{30}$ or the following formula:

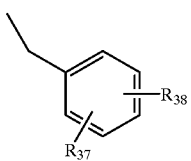

in which $R_{37}$ and $R_{38}$ have been defined above;

$R_{2a}$ is $R_{32}$ or $R_{35}$;

$R_4$ is $R_4'$; and

A and n have been defined above.

16. A method of producing a benzimidazole compound of formula X, XI, or XIV,

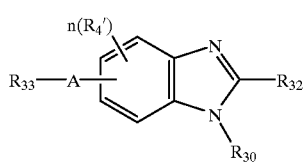

(X)

-continued

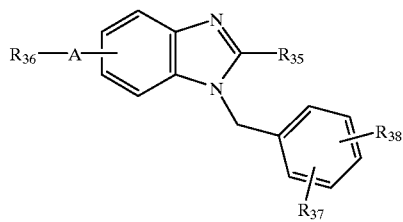

(XI)

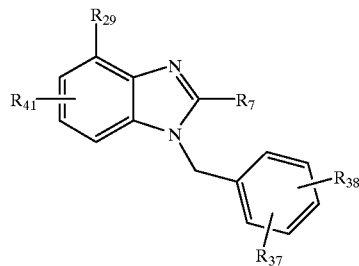

(XIV)

wherein $R_4'$ represents a hydrocarbon group or a halogenated hydrocarbon group;

$R_{30}$ represents a hydrogen atom, a lower alkyl group, an unsubstituted benzyl group or a benzyl group of the following formula:

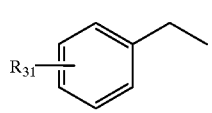

(Xa)

in which $R_{31}$ represents a hydrogen atom, a cyanoaryl group, an amino group, a lower alkoxy group, a nitro group, a cyano group, an aryl group, a haloaryl group, an arylsulfonyl-lower alkyl group, an arylsulfonylamino group, an aryl-lower alkyloxy group, an aryl-lower alkyl group, a heterocyclic group, an aryloxy group, an unsubstituted aryl-lower alkyloxy group, or an aryl-lower alkyloxy group substituted by one or two halogen atoms, an arylsulfonyl group, a hetero-cyclic lower alkyl group, an arylcarbonylamino group, an arylcarbonyl group, an arylalkenyl group, or a lower alkylenedioxyaryl group; the α-position of said benzyl group being unsubstituted or substituted by a lower alkyl group;

$R_{32}$ represents a hydrogen atom, a lower alkyl group, a halo-lower alkyl group, a lower cycloalkyl group, an aryl group, an aryl-lower alkyl group, a lower alkylamino group, a lower alkoxy group, a lower alkylthio group, a lower alkoxy-lower alkyl group, or a heterocyclic lower alkyl group;

$R_{33}$ represents a group of the following formula:

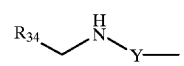

(Xb)

in which $R_{34}$ represents an aryl group, a heterocyclic group, a lower alkyl group, or a lower alkyl group substituted by a substituted or unsubstituted aryl or heterocyclic group; and Y represents a carbonyl group or a lower alkylene group;

A represents a single bond, or a lower alkylene or alkenylene group; provided that, in formula (XI), when $R_{35}$ is lower alkyl group, A is a lower alkylene group or a lower alkenylene group;

n means an integer from 0 to 3, provided that, when $R_{30}$ is a hydrogen atom, n is 0;

$R_{35}$ represents a hydrogen atom, an aryl group, a lower alkoxy-lower alkyl group, a lower alkyl group, or an aryl-lower alkyl group;

$R_{36}$ represents a carboxyl group, a lower alkoxycarbonyl group, a heterocyclic lower alkylamino group, or a heterocyclic lower alkylcarbamoyl group;

$R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group;

$R_{41}$ represents a 2-pyridylcarbamoyl group, a 2-carboxy-1pyrrolidinocarbonyl group, an N-methyl-N-(2-pyridyl-methyl)carbamoyl group, a homopiperidinocarbonyl group, a [2-(N-oxo)-pyridylmethyl] carbamoyl group, a 4-(dimethylamino)-benzylcarbamoyl group, a piperonylcarbamoyl group, an N-methyl-N-(2-pyridyl)carbamoyl group, a morpholinocarbonyl group, a thiomorpholinocarbonyl group, a halosulfonyl group, an aminosulfonyl group, an acylaminosulfonyl group, a lower alkoxycarbonyl group, or a carboxyl group;

$R_{29}$ represents a hydrogen atom or a lower alkyl group, provided that, when $R_{41}$ is a lower alkoxycarbonyl group or a carbonyl group, $R_{29}$ is a lower alkyl group;

said method comprising reacting a compound of the formula (17')

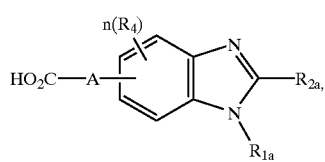

(17')

with a carbonyl diimidazole, and reacting the resulting compound with an amine or a sulfonamide to produce a benzimidazole compound of the formula (18')

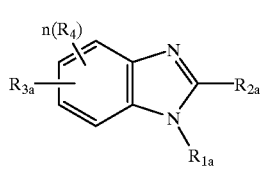

(18')

wherein
$R_{1a}$ is $R_{30}$ or the following formula:

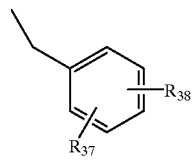

in which
$R_{37}$ and $R_{38}$ have been defined above;
$R_{2a}$ is $R_{32}$, $R_7$, or $R_{35}$;
$R_4$ is H, $R_4'$, or $R_{29}$;
$R_{3a}$ is —A—$R_{33}$, —A—$R_{36}$, or $R_{41}$; and
A and n have been defined above.

17. A method of producing a benzimidazole compound of formula XII, wherein a compound of the formula (19'):

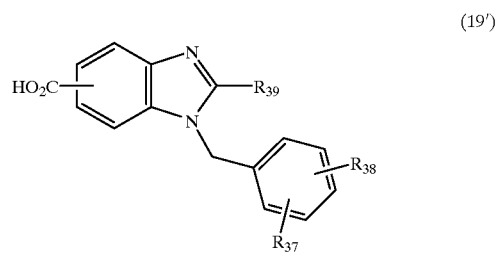

(19')

is reacted with azide in the presence of alcohol, or a compound of the formula (20'):

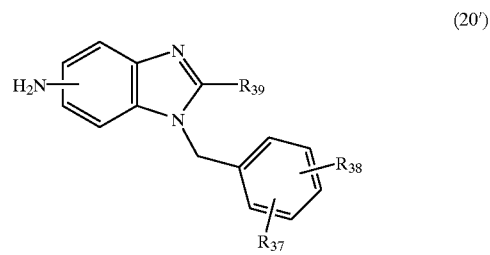

(20')

is reacted with the compound represented by $R_{40}Z$, wherein Z is a chlorine atom or a bromine atom, to give a benzimidazole compound of the formula XII:

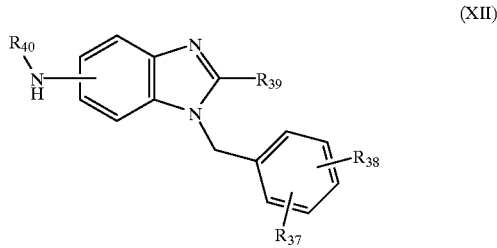

(XII)

wherein
$R_{37}$ and $R_{38}$ each independently represent a hydrogen atom, a halogen atom, a lower alkyl group, a halo-lower alkyl group, an aryl group, an aryl-lower alkyl group, or an aryl-lower alkyloxy group;
$R_{39}$ represents a lower alkyl group; and
$R_{40}$ represents a lower alkoxycarbonyl group, a lower alkanoyl group, a lower alkanesulfonyl group, or a carbamoyl group.

18. A method of preparing a benzimidazole compounds of formula VIII

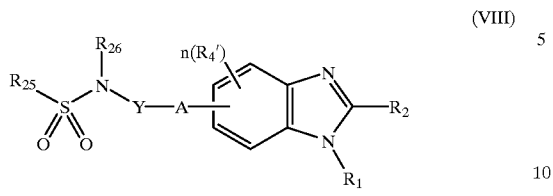

(VIII)

wherein

- $R_1$ represents a hydrogen atom, an arylsulfonyl group, or a lower alkyl group; said lower alkyl group is unsubstituted or substituted by a heterocyclic group, an unsubstituted aryl group, or an aryl group substituted by one or two substituents selected from a halogen atom, a haloaryl group, a lower alkyl group, a halo-lower alkyl group, a lower alkoxy group, a nitro group, an amino group, a cyano group, an aryl group, an aryl-lower alkyloxy group, an arylsulfonyl-lower alkyl group, an aryl-lower alkyl group, a haloaryl-lower alkyloxy group, an arylsulfonylamino group, an arylcarbonylamino group, an arylcarbonyl group, an arylalkenyl group, a cyanoaryl group, and a heterocyclic group;
- $R_2$ represents a hydrogen atom, a lower cycloalkyl group, a hydroxyl group, a hydroxy-lower alkyl group, a lower alkoxy group, a mercapto group, a lower alkylthio group, an amino group, a lower alkylamino group, a carboxyl group, an aryl group, or a lower alkyl group; said lower alkyl group is substituted by a halogen atom, a lower alkoxy group, a cyano group, a halocarbonyl group, an aryl group, or a heterocyclic group;
- $R_4'$ represents a hydrocarbon group or a halogenated hydrocarbon group; and
- $R_{25}$ represents an alkyl group having up to 8 carbon atoms, a lower cycloalkyl group, a halo-lower alkyl group, a tri-lower alkylsilyl-lower alkyl group, a lower alkoxy-lower alkyl group, a lower alkylthio-lower alkyl group, a heterocyclic group, an aryl group, an aryl-lower alkyl group, or a hydroxyl-lower alkyl group; said aryl group is unsubstituted or substituted by a halogen atom, a lower alkyl group, a halo-lower alkyl group, a lower alkoxy group or a nitro group;
- $R_{26}$ represents a hydrogen atom or a lower alkyl group;
- Provided that when $R_{25}$ and $R_{26}$ are both lower alkyl groups, they are two acyclic alkyl groups or they form a ring when bonded together;
- Y represents a carbonyl group or a lower alkylene group;
- A represents a single bond, a lower alkylene group, or alkenylene group;
- n represents an integer from 0 to 3;

said method comprising a step selected from the group consisting of steps (A), (B), (C), and (D):

(A) reacting a compound of formula (8'):

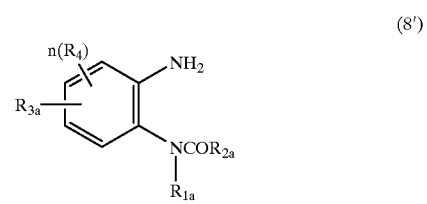

(8')

with a carboxylic acid, a sulfonic acid, or an inorganic acid to produce a benzimidazole compound of formula (9'):

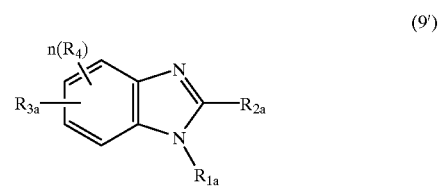

(9')

(B) reacting a compound of formula (10'):

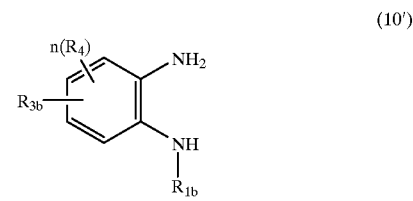

(10')

with a carboxylic acid, acid halide, or acid anhydride having a substituent $R_{2b}$ to produce a benzimidazole compound of the following formula (11'):

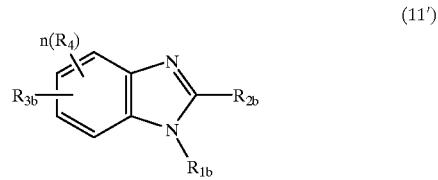

(11')

(C) reacting a compound of formula (12'):

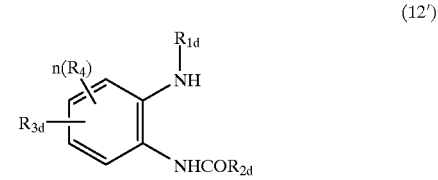

(12')

with a carboxylic acid, a sulfonic acid, or an inorganic acid to produce a benzimidazole compound of the following formula (13'):

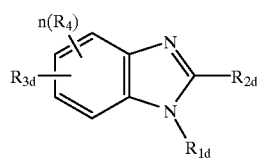

(13')

(D) reacting a compound of the following formula (14'):

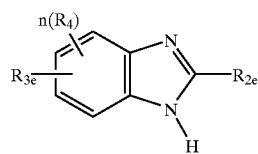

(14')

with sodium hydride, lithium diisopropylamide, lithium hydrogencarbonate, lithium carbonate, sodium hydroxide, potassium hydrogencarbonate, potassium carbonate, or potassium hydroxide and then reacting the resulting compound with $R_{1e}Z$, wherein Z is a chlorine atom, a bromine atom, a toluenesulfonyloxy group, or a methanesulfonyloxy group, to produce a benzimidazole compound of formula (15'):

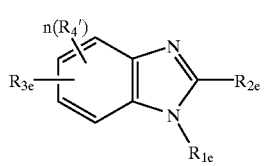

(15')

wherein each of $R_{1a}$, $R_{1b}$, $R_c$, $R_{1d}$, and $R_{1e}$ is independently $R_1$;

each of $R_{2a}$, $R_{2b}$, $R_{2c}$, $R_{2d}$, and $R_{2e}$ is independently $R_2$;

each of $R_{3a}$, $R_{3b}$, $R_{3c}$, $R_{3d}$, and $R_{3e}$ independently represents

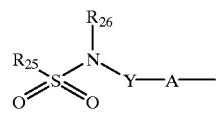

$R_{25}$, $R_{26}$, Y and A have been defined above;

$R_4$ has the same meaning as $R_4'$ defined above;

and n means an integer from 0 to 3.

19. A method of preparing a benzimidazole compounds of formula VIII

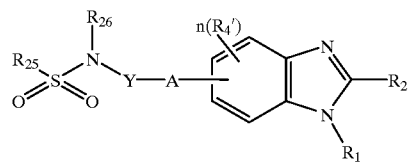

(VIII)

wherein $R_1$ represents a hydrogen atom, an arylsulfonyl group, or a lower alkyl group; said lower alkyl group is unsubstituted or substituted by a heterocyclic group, an unsubstituted aryl group, or an aryl group substituted by one or two substituents selected from a halogen atom, a haloaryl group, a lower alkyl group, a halo-lower alkyl group, a lower alkoxy group, a nitro group, an amino group, a cyano group, an aryl group, an aryl-lower alkyloxy group, an arylsulfonyl-lower alkyl group, an aryl-lower alkyl group, a haloaryl-lower alkyloxy group, an arylsulfonylamino group, an arylcarbonylamino group, an arylcarbonyl group, an arylalkenyl group, a cyanoaryl group, and a heterocyclic group;

$R_2$ represents a hydrogen atom, a lower cycloalkyl group, a hydroxyl group, a hydroxy-lower alkyl group, a lower alkoxy group, a mercapto group, a lower alkylthio group, an amino group, a lower alkylamino group, a carboxyl group, an aryl group, or a lower alkyl group; said lower alkyl group is unsubstituted or substituted by a halogen atom, a lower alkoxy group, a cyano group, a halocarbonyl group, an aryl group, or a heterocyclic group;

$R_4'$ represents a hydrocarbon group or a halogenated hydrocarbon group; and $R_{25}$ represents an alkyl group having up to 8 carbon atoms, a lower cycloalkyl group, a halo-lower alkyl group, a tri-lower alkylsilyl-lower alkyl group, a lower alkoxy-lower alkyl group, a lower alkylthio-lower alkyl group, a heterocyclic group, an aryl group, an aryl-lower alkyl group, or a hydroxyl-lower alkyl group; said aryl group is unsubstituted or substituted by a halogen atom, a lower alkyl group, a halo-lower alkyl group, a lower alkoxy group or a nitro group;

$R_{26}$ represents a hydrogen atom or a lower alkyl group;

Provided that when $R_{25}$ and $R_{26}$ are both lower alkyl groups, they are two acyclic alkyl groups or they form a ring when bonded together;

Y represents a carbonyl group or a lower alkylene group;

A represents a single bond, a lower alkylene group, or alkenylene group;

n represents an integer from 0 to 3;

said method comprising reacting a compound of the formula (17')

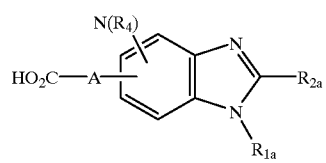

(17')

with a carbonyl diimidazole, and reacting the resulting compound with an amine or a sulfonamide to produce a benzimidazole compound of the formula (18')
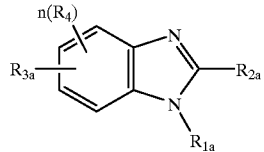
(18')
wherein
  $R_{1a}$ has the same definition as $R_1$;
  $R_{2a}$ has the same definition as $R_2$;
  $R_{3a}$ represents
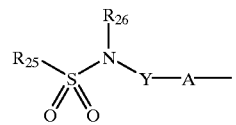
wherein
  $R_{25}$, $R_{26}$, Y and A have been defined above;
  $R_4$ has the same definition as $R_4'$; and
  A and n have been defined above.
* * * * *

UNITED STATES PATENT AND TRADEMARK OFFICE
CERTIFICATE OF CORRECTION

PATENT NO. : 6,352,985 B1
APPLICATION NO. : 09/492955
DATED : March 5, 2002
INVENTOR(S) : Yoshiyuki Murai et al.

It is certified that error appears in the above-identified patent and that said Letters Patent is hereby corrected as shown below:

Cover Page

Right Column, Yamasaki reference "6,166,912" should be --6,166,219--

In Abstract, Line 2

Delete "a esterified" and insert --an esterified--

Figure 26

A line is missing (see attached).

Column 3, Formula (III)

Delete "$R_8$" and insert --$R_6$--

Column 6, Formula ($X_a$)

$X_a$ under the formula should be deleted

Column 9, Formula (1)

Delete "$NHCOR_{1a}$" and insert --$NHCOR_{2a}$--

Column 166, Claim 1 Formula (X)

Delete "$n(R_4)$" and insert --$n(R_4')$--

Column 171, Claim 8 Formula (VIII)

Delete "$R_2$," and insert --$R_2$--

Column 171, Claim 8, Formula (X)

Delete "$R_{32}$," and insert --$R_{32}$--

Column 171, Claim 8, Formula (XI)

Delete "$R_{38}$," and insert --$R_{38}$--

UNITED STATES PATENT AND TRADEMARK OFFICE
CERTIFICATE OF CORRECTION

PATENT NO.       : 6,352,985 B1
APPLICATION NO.  : 09/492955
DATED            : March 5, 2002
INVENTOR(S)      : Yoshiyuki Murai et al.

It is certified that error appears in the above-identified patent and that said Letters Patent is hereby corrected as shown below:

Column 171, Claim 8, Formula (XII)

Delete "$R_{38},$" and insert --$R_{38}$--

Column 172, Claim 8, Line 54

Delete "alkyltlio" and insert --alkylthio--

Column 173, Claim 8, Line 20

Delete "(group" and insert --group--

Column 174, Claim 9, Line 35

Delete "methylbeizimidazole" and insert --methylbenzimidazole--

Column 175, Claim 12, Line 62

Delete "aryllower" and insert --aryl-lower--

Column 176, Claim 13, Line 11

Delete "herein" and insert --wherein--

Column 177, Claim 14, Formula (8')

Delete "(8)' " and insert --(8')--

Column 183, Claim 16, Formula (17')

Delete "$R_{2a},$" and insert --$R_{2a}$--

Column 185, Claim 18, Line 1

Delete "compounds" and insert --compound--

Column 187, Claim 18, Line 48

Delete "$R_c,$" and insert --$R_{1c}$--

UNITED STATES PATENT AND TRADEMARK OFFICE
CERTIFICATE OF CORRECTION

PATENT NO. : 6,352,985 B1
APPLICATION NO. : 09/492955
DATED : March 5, 2002
INVENTOR(S) : Yoshiyuki Murai et al.

It is certified that error appears in the above-identified patent and that said Letters Patent is hereby corrected as shown below:

<u>Column 187, Claim 18, Line 49</u>

Delete "$R_{2a}$" and insert --$R_{2a}$,--

<u>Column 187, Claim 18, Line 65</u>

Delete "compounds" and insert --compound--

Signed and Sealed this

Tenth Day of October, 2006

JON W. DUDAS
*Director of the United States Patent and Trademark Office*

FIG. 26
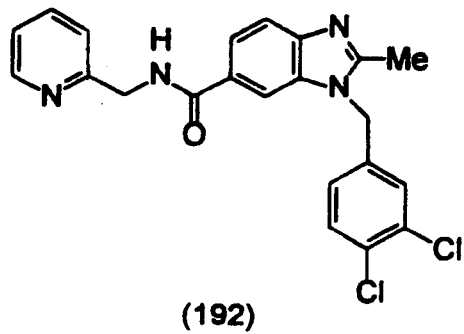
(192)
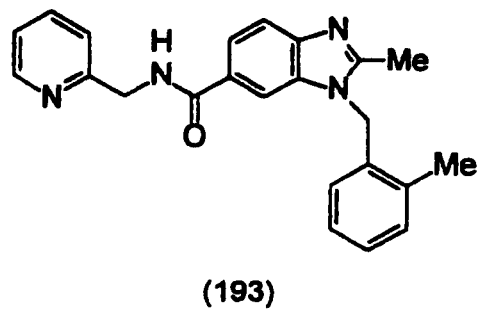
(193)
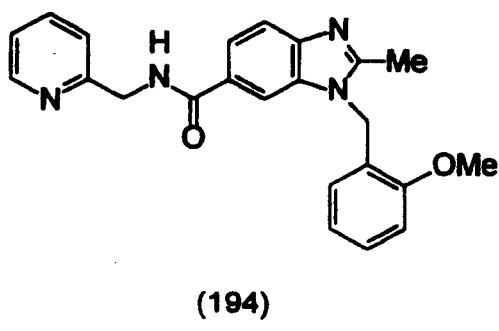
(194)
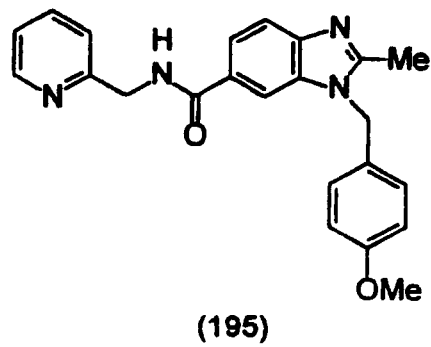
(195)
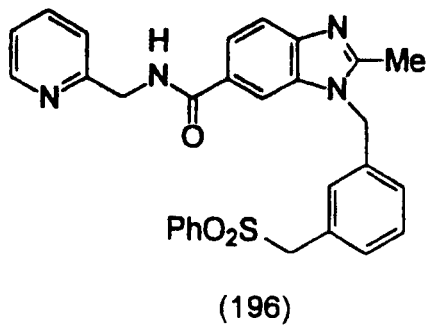
(196)
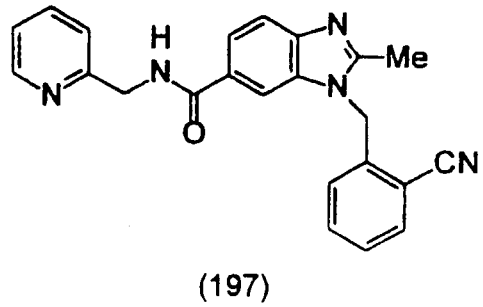
(197)